US008889716B2

(12) United States Patent
Prime et al.

(10) Patent No.: US 8,889,716 B2
(45) Date of Patent: Nov. 18, 2014

(54) TRANSGLUTAMINASE TG2 INHIBITORS, PHARMACEUTICAL COMPOSITIONS, AND METHODS OF USE THEREOF

(75) Inventors: Michael Prime, Abingdon (GB); Stephen Martin Courtney, Stanford in the Vale (GB); Richard Marston, Wantage (GB); Celia Dominguez, Los Angeles, CA (US); Douglas MacDonald, Los Angeles, CA (US); John Wityak, Carlsbad, CA (US)

(73) Assignee: CHDI Foundation, Inc., New York, NY (US)

( * ) Notice: Subject to any disclaimer, the term of this patent is extended or adjusted under 35 U.S.C. 154(b) by 65 days.

(21) Appl. No.: 13/466,018

(22) Filed: May 7, 2012

(65) Prior Publication Data

US 2012/0302539 A1    Nov. 29, 2012

Related U.S. Application Data

(60) Provisional application No. 61/484,621, filed on May 10, 2011.

(51) Int. Cl.
| | |
|---|---|
| A61K 31/445 | (2006.01) |
| C07D 211/96 | (2006.01) |
| C07D 409/12 | (2006.01) |
| C07D 205/04 | (2006.01) |
| C07D 405/12 | (2006.01) |
| C07D 405/14 | (2006.01) |
| C07D 207/48 | (2006.01) |
| C07D 401/14 | (2006.01) |
| C07D 401/12 | (2006.01) |

(52) U.S. Cl.
CPC ............ *C07D 205/04* (2013.01); *C07D 211/96* (2013.01); *C07D 409/12* (2013.01); *C04D 413/12* (2013.01); *C07D 405/12* (2013.01); *C07D 405/14* (2013.01); *C07D 207/48* (2013.01); *C07D 401/14* (2013.01); *C07D 401/12* (2013.01)
USPC ............... 514/329; 514/210.01; 514/253.12; 514/316; 514/320; 514/323; 514/325; 514/326; 514/434; 546/196; 546/201; 546/203; 546/207; 546/208

(58) Field of Classification Search
USPC ............ 514/210.01, 235.5, 253.12, 316, 320, 514/323, 324, 325, 326, 329, 434; 546/196, 546/201, 202, 203, 205, 207, 208
See application file for complete search history.

(56) References Cited

U.S. PATENT DOCUMENTS

| | | | |
|---|---|---|---|
| 4,247,549 A | 1/1981 | Ohnmacht et al. | |
| 4,970,297 A | 11/1990 | Castelhano et al. | |
| 5,565,567 A | 10/1996 | Share | |
| 6,344,358 B1 | 2/2002 | Matsuoka et al. | |
| 6,451,816 B1 * | 9/2002 | Biedermann et al. | 514/318 |
| 6,699,891 B1 | 3/2004 | Kawanishi et al. | |
| 6,710,043 B1 | 3/2004 | Yamada et al. | |
| 7,417,058 B2 | 8/2008 | Halazy et al. | |
| 7,910,741 B2 | 3/2011 | Nishizawa et al. | |
| 8,012,995 B1 | 9/2011 | Arkinstall et al. | |
| 8,471,063 B2 * | 6/2013 | Oertel | 564/123 |
| 2004/0077632 A1 | 4/2004 | Halazy et al. | |
| 2004/0176462 A1 | 9/2004 | Kawanishi et al. | |
| 2006/0160864 A1 | 7/2006 | Shiraishi et al. | |
| 2006/0178399 A1 | 8/2006 | Nishizawa et al. | |
| 2010/0240711 A1 | 9/2010 | Takada et al. | |
| 2011/0117073 A1 | 5/2011 | Singh et al. | |
| 2011/0230476 A1 | 9/2011 | Niu et al. | |
| 2011/0230487 A1 | 9/2011 | Ly et al. | |
| 2012/0302539 A1 | 11/2012 | Prime et al. | |
| 2013/0116216 A1 | 5/2013 | Dominguez et al. | |

FOREIGN PATENT DOCUMENTS

| | | |
|---|---|---|
| EP | 1814551 | 8/2007 |
| EP | 2316458 | 5/2011 |
| SG | 174488 A1 | 10/2011 |
| WO | WO-00/42011 | 7/2000 |
| WO | WO-00/72834 A2 | 12/2000 |
| WO | WO-01/23378 A1 | 4/2001 |
| WO | WO 2010 001366 | 1/2010 |
| WO | WO-2011/035159 A1 | 3/2011 |
| WO | WO 2011035159 | 3/2011 |
| WO | WO 2011 060321 | 5/2011 |
| WO | WO-2011/116161 A2 | 9/2011 |

OTHER PUBLICATIONS

Caccamo et al. "Potential of transglutaminase . . . " Exp. Opin. ther Targets 14(9) p. 989-1003 (2010).*
Cheng et al. "Pd2(dba)3 promoted . . . " Tetra hedrwon Lett. 51, p. 4886-4889 (2010).*
Duval et al. "Structure-activity . . . " Bioorg. Med. Chem. Lett. 15, p. 1885-1889 (2005).*
Enzyme Active site "Structural biochemistry . . . " Wikipedia p. 1-9 (2014).*

(Continued)

*Primary Examiner* — Celia Chang

(57) ABSTRACT

Certain compounds and pharmaceutically acceptable salts are provided herein. Also provided are pharmaceutical compositions comprising at least one compound or pharmaceutically acceptable salt therein and one or more pharmaceutically acceptable vehicle. Methods of treating patients suffering from certain disease states responsive to the inhibition of transglutaminase TG2 activity are described. These disease states include neurodegenerative disorders such as Huntington's disease. Also described are methods of treatment include administering at least one compound or pharmaceutically acceptable salt thereof as a single active agent or administering at least one compound or pharmaceutically acceptable salt thereof in combination with one or more other therapeutic agents.

14 Claims, No Drawings

(56) References Cited

OTHER PUBLICATIONS

Improper Markush, Fed. Reg. V.76(27) 7162-75, and traingin slides 1, 64-67 (2011).*

Prime et al. "Irreversible 4-Aminopiperidine Transglutaminase 2 Inhibitors forHuntington's Disease" ACS Med. Chem. Lett. 2012, 3, 731-735.

* cited by examiner

TRANSGLUTAMINASE TG2 INHIBITORS, PHARMACEUTICAL COMPOSITIONS, AND METHODS OF USE THEREOF

This application claims the benefit under 35 U.S.C. §119 (e) of U.S. Provisional Application No. 61/484,621, filed May 10, 2011 the contents of which is incorporated by reference in its entirety.

Provided herein are certain transglutaminase TG2 inhibitors, pharmaceutical compositions thereof, and methods of their use.

Transglutaminases (TGases, EC 2.3.2.13) are calcium-dependent enzymes that catalyze the intermolecular cross-linking of certain proteins through the formation of γ-glutamyl-ε-lysine side chain bridges. In mammals, eight types of TGases have been characterized to date and are found in tissue, plasma and epidermis. Tissue TGases are involved in diverse biological processes such as endocytosis, apoptosis and cell growth regulation. The plasma-soluble form of TGase, Factor XIIIa, stabilizes blood clots by catalyzing the cross-linking of fibrin during hemostasis. Epidermal TGase plays a role in the synthesis of the cornified envelope of epidermal keratinocytes.

Several members of the transglutaminase family have been linked to disease, including tissue transglutaminase (TG2), and the skin transglutaminases, TG1 and TG3. TG2 is a cytoplasmic enzyme present in many cells, including those in the blood vessel wall. Aberrant TG2 activity is believed to play a role in neurological disorders such as Alzheimer's, Parkinson's and Huntington's disease. Expression of TG1 and TG2 have been correlated with various types of malignancies, including glioblastomas, lung and breast cancers, suggesting an important role for TG2 in tumor proliferation and survival.

Provided is a compound of Formula I

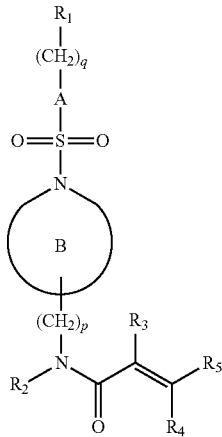

Formula I or a pharmaceutically acceptable salt thereof, wherein

A is optionally substituted aryl, optionally substituted heteroaryl or optionally substituted heterocycloalkyl;

B is an optionally substituted mono- or bicyclic heterocycloalkyl;

$R_1$ is chosen from H, —$NO_2$, —$R^a$, —$COR^b$, —$CO_2R^b$, —$(CH_2)_xCONR^cR^d$, —$(CH_2)_xNR^cCOR^d$, —$NR^cCO_2R^d$, —$NR^cCONR^cR^d$, —$OCOR^b$, —$OR^b$, —$NR^bR^c$, and —$OCONR^cR^d$, wherein $R^a$ is chosen from optionally substituted alkyl and optionally substituted cycloalkyl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl;

for each occurrence, $R^c$ is independently chosen from H and optionally substituted $C_1$-$C_6$ alkyl;

$R^d$ is chosen from H, optionally substituted $C_1$-$C_6$ alkyl, optionally substituted cycloalkyl, optionally substituted aryl, optionally substituted aralkyl, optionally substituted heterocycloalkyl, and optionally substituted heteroaryl; or $R^c$ and $R^d$, and the nitrogen to which they are attached, form an optionally substituted heterocycloalkyl group;

x is 0, 1, or 2; and where, for $R^a$, $R^b$, $R^c$, and $R^d$, each optionally substituted group independently, is unsubstituted or substituted with one or more substituents independently chosen from $C_1$-$C_4$ alkyl optionally substituted with one or more groups chosen from halo and heterocycloalkyl, cycloalkyl optionally substituted with one or more groups chosen from halo, $C_1$-$C_4$ alkyl and $C_1$-$C_4$ haloalkyl, aryl optionally substituted with one or more groups chosen from halo, $C_1$-$C_4$ alkyl, $C_1$-$C_4$ alkoxy, and $C_1$-$C_4$ haloalkyl, heterocycloalkyl optionally substituted with one or more groups chosen from halo, $C_1$-$C_4$ alkyl and $C_1$-$C_4$ haloalkyl, heteroaryl optionally substituted with one or more groups chosen from halo, $C_1$-$C_4$ alkyl and $C_1$-$C_4$ haloalkyl, —C(O)(heterocycloalkyl) optionally substituted with one or more groups chosen from halo, $C_1$-$C_4$ alkyl and $C_1$-$C_4$ haloalkyl, —$OC_1$-$C_4$ alkyl optionally substituted with one or more groups chosen from halo, $C_1$-$C_4$ alkyl and $C_1$-$C_4$ haloalkyl, and halo;

$R_2$ is chosen from H and optionally substituted alkyl;

$R_3$, $R_4$, and $R_5$ are independently chosen from H, fluoro, chloro, and optionally substituted alkyl;

p is chosen from 0, 1, 2, and 3; and q is chosen from 0 and 1.

Also provided are pharmaceutical compositions comprising a compound described herein, or a pharmaceutically acceptable salt thereof, and a pharmaceutically acceptable excipient.

Also provided are methods of inhibiting transglutaminase TG2 activity, the methods comprising: contacting transglutaminase TG2 in vitro with an amount of a compound or a pharmaceutically acceptable salt thereof described herein, sufficient to inhibit an activity of the transglutaminase TG2.

Also provided are methods of treating a disease state in which inhibition of transglutaminase TG2 is desired, the methods comprising: administering to a subject in need thereof, a therapeutically effective amount of a compound described herein, or a pharmaceutically acceptable salt thereof, so as to inhibit the activity of the transglutaminase TG2, thereby treating the disease state.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or In some embodiments, from 1 to 3, heteroatoms chosen from N, O, and S, with the remaining ring atoms being carbon; and
bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —NH($C_1$-$C_4$ alkyl),
—$N(C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —NHC(O)(phenyl), —$N(C_1$-$C_4$ alkyl)C(O)($C_1$-$C_4$ alkyl), —$N(C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2(C_1$-$C_4$ alkyl), —$SO_2$(phenyl), —$SO_2(C_1$-$C_4$ haloalkyl), —$SO_2NH_2$,
—$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

The term "substituted alkoxy" refers to alkoxy wherein the alkyl constituent is substituted (i.e., —O— (substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O) (optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)—H, —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O— (substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of transglutaminase TG2 activity.

The term "inhibition" indicates a significant decrease in the baseline activity of a biological activity or process. "Inhibition of transglutaminase TG2 activity" refers to a decrease in the activity of TG2 as a direct or indirect response to the presence of at least one compound or pharmaceutically acceptable salt thereof described herein, relative to the activity of TG2 in the absence of at least one compound or pharmaceutically acceptable salt thereof. The decrease in activity may be due to the direct interaction of the compound with TG2, or due to the interaction of the compounds or salts described herein with one or more other factors that in turn affect TG2 activity. For example, the presence of the compound or pharmaceutically acceptable salt thereof may decrease TG2 activity by directly binding to the TG2, by causing (directly or indirectly) another factor to decrease TG2 activity, or by (directly or indirectly) decreasing the amount of TG2 present in the cell or organism.

In some embodiments, the compounds and pharmaceutical acceptable salts thereof described herein inhibit TG2.

In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

"Treatment" or "treating" means any treatment of a disease state in a patient, including:
 a) preventing the disease, that is, causing the clinical symptoms of the disease not to develop;
 b) inhibiting the disease;
 c) slowing or arresting the development of clinical symptoms; and/or
 d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I

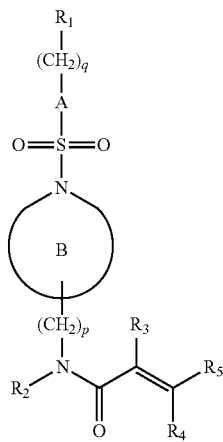

Formula I or a pharmaceutically acceptable salt thereof, wherein
A is optionally substituted aryl, optionally substituted heteroaryl or optionally substituted heterocycloalkyl;
B is an optionally substituted mono- or bicyclic heterocycloalkyl;
$R_1$ is chosen from H, $-NO_2$, $-R^a$, $-COR^b$, $-CO_2R^b$, $-(CH_2)_xCONR^cR^d$, $-(CH_2)_xNR^cCOR^d$, $-NR^cCO_2R^d$, $-NR^cCONR^cR^d$, $-OCOR^b$, $OR^b$, $-NR^bR^c$, and $-OCONR^cR^d$, wherein
 $R^a$ is chosen from optionally substituted alkyl and optionally substituted cycloalkyl;
 $R^b$ is chosen from H, optionally substituted $C_1$-$C_6$ alkyl, optionally substituted cycloalkyl, optionally substituted heterocycloalkyl, optionally substituted aryl, and optionally substituted heteroaryl;
 for each occurrence, $R^c$ is independently chosen from H and optionally substituted $C_1$-$C_6$ alkyl;
 $R^d$ is chosen from H, optionally substituted $C_1$-$C_6$ alkyl, optionally substituted cycloalkyl, optionally substituted aryl, optionally substituted aralkyl, optionally substituted heterocycloalkyl, and optionally substituted heteroaryl; or
 $R^c$ and $R^d$, and the nitrogen to which they are attached, form an optionally substituted heterocycloalkyl group;
 x is 0, 1, or 2; and
  where, for $R^a$, $R^b$, $R^c$, and $R^d$, each optionally substituted group independently, is unsubstituted or substituted with one or more substituents independently chosen from
   $C_1$-$C_4$ alkyl optionally substituted with one or more groups chosen from halo and heterocycloalkyl,
   cycloalkyl optionally substituted with one or more groups chosen from halo, $C_1$-$C_4$ alkyl and $C_1$-$C_4$ haloalkyl,
   aryl optionally substituted with one or more groups chosen from halo, $C_1$-$C_4$ alkyl, $C_1$-$C_4$ alkoxy, and $C_1$-$C_4$ haloalkyl,
   heterocycloalkyl optionally substituted with one or more groups chosen from halo, $C_1$-$C_4$ alkyl and $C_1$-$C_4$ haloalkyl,
   heteroaryl optionally substituted with one or more groups chosen from halo, $C_1$-$C_4$ alkyl and $C_1$-$C_4$ haloalkyl,
   $-C(O)$(heterocycloalkyl) optionally substituted with one or more groups chosen from halo, $C_1$-$C_4$ alkyl and $C_1$-$C_4$ haloalkyl,
   $-OC_1$-$C_4$ alkyl optionally substituted with one or more groups chosen from halo, $C_1$-$C_4$ alkyl and $C_1$-$C_4$ haloalkyl, and
   halo;
$R_2$ is chosen from H and optionally substituted alkyl;
$R_3$, $R_4$, and $R_5$ are independently chosen from H, fluoro, chloro, and optionally substituted alkyl;
p is chosen from 0, 1, 2, and 3; and
q is chosen from 0 and 1.

In some embodiments, A is optionally substituted phenylene. In some embodiments, A is phenylene substituted with one or more groups chosen from lower alkyl, lower alkoxy, and halo. In some embodiments, A is phenylene. In some embodiments, A is para-phenylene.

In some embodiments, A is chosen from 2-oxo-1,2,3,4-tetrahydroquinolindiyl, chromanediyl, and indolinediyl, each of which is optionally substituted.

In some embodiments, A is optionally substituted heterocycloalkyl. In some embodiments, A is chosen from optionally substituted piperidinediyl and optionally substituted piperazinediyl. In some embodiments, A is piperidinediyl. In some embodiments, A is piperidin-1,4-diyl. In some embodiments, A is piperidin-1,4-diyl wherein the 4-position is bound to the sulfonyl. In some embodiments, A is piperazinediyl. In some embodiments, A is piperazine-1,4-diyl. In some embodiments, A is piperazine-1,4-diyl wherein the 4-position is bound to the sulfonyl.

In some embodiments, A is optionally substituted heteroaryl. In some embodiments, A is chosen from benzo[d]thiazolediyl, thiophenediyl, furandiyl, thiazolediyl, pyridinediyl, 1H-pyrrolediyl, and 1H-pyrazolediyl, each of which is optionally substituted. In some embodiments, A is chosen from benzo[d]thiazolediyl, thiophenediyl, furandiyl, thiazolediyl, pyridinediyl, 1H-pyrrolediyl, and 1H-pyrazolediyl, each of which is optionally substituted with one or more groups independently chosen from lower alkoxy, lower alkyl, and halo.

In some embodiments, $R_1$ is $-NO_2$.

In some embodiments, $R_1$ is $R^a$. In some embodiments, $R^a$ is optionally substituted cycloalkyl. In some embodiments, $R^a$ is cycloalkyl.

In some embodiments, $R_1$ is chosen from $-(CH_2)_xNR^c-COR^d$, $-NR^cCO_2R^d$, and $-NR^cCONR^cR^d$, wherein
for each occurrence, $R^c$ is independently chosen from H and methyl;
$R^d$ is chosen from optionally substituted $C_1$-$C_6$ alkyl, optionally substituted cycloalkyl, optionally substituted aralkyl, and optionally substituted heterocycloalkyl;
x is 0 or 1; and
where each optionally substituted group is unsubstituted or substituted with one or more substituents independently chosen from $C_1$-$C_4$ alkyl and aryl.

In some embodiments, $R^d$ is methyl, cyclopropyl, adamantyl, cyclohexylethyl, benzyl, phenylethyl, naphthalenylethyl, tetrahydropyranyl, or benzofuranyl, each of which is optionally substituted.

In some embodiments, $R_1$ is chosen from $-COR^b$, $-CO_2R^b$, and $-OCOR^b$, wherein
$R^b$ is chosen from optionally substituted $C_1$-$C_6$ alkyl, optionally substituted heterocycloalkyl, optionally substituted aryl, and optionally substituted heteroaryl; and
where each optionally substituted group is unsubstituted or substituted with one or more substituents independently chosen from aryl and $-C_1$-$C_4$ haloalkyl.

In some embodiments, $R^b$ is methyl, benzyl, phenyl, pyridinyl, or phenylethyl, each of which is optionally substituted.

In some embodiments, $R_1$ is chosen from $-(CH_2)_xCONR^cR^d$ and $-OCONR^cR^d$, wherein
$R^c$ is H or methyl;
$R^d$ is chosen from optionally substituted $C_1$-$C_6$ alkyl, optionally substituted cycloalkyl, optionally substituted aryl, optionally substituted aralkyl, optionally substituted heterocycloalkyl, and optionally substituted heteroaryl; or
$R^c$ and $R^d$, and the nitrogen to which they are attached, form an optionally substituted heterocycloalkyl group;
x is 0 or 1; and
where each optionally substituted group is unsubstituted or substituted with one or more substituents independently chosen from $C_1$-$C_4$ alkyl, cycloalkyl, aryl, heterocycloalkyl, heteroaryl optionally substituted with one, two, or three $C_1$-$C_4$ alkyl, $-C(O)$(heterocycloalkyl), $-OC_1$-$C_4$ alkyl, $-C_1$-$C_4$ haloalkyl, and halo.

In some embodiments, $R^d$ is cyclopropyl, cyclohexyl, indanyl, cyclopropylmethyl, cyclohexylethyl, benzyl, phenylethyl, naphthalenylmethyl, naphthalenylethyl, quinolinylethyl, dihydrobenzofuranylethyl, chromanylethyl, benzo[1,3]dioxolylethyl, phenylpropyl, biphenylethyl, piperidylethyl, pyranylethyl, morpholinylethyl, or benzofuranyl, each of which is optionally substituted.

In some embodiments, $R^c$ and $R^d$, and the nitrogen to which they are attached, form a piperidyl, decahydroisoquinolinyl, piperazinyl, or dihydroisoquinolinyl, each of which is optionally substituted.

In some embodiments, each optionally substituted group is substituted with one or more substituents independently chosen from methyl, t-butyl, cyclopropyl, cyclohexyl, phenyl, biphenyl, piperidyl, pyranyl, morpholinyl, 6-methyl-pyridin-2-yl, pyrrolidine-1-carbonyl, methoxy, trifluoromethyl, fluoro, and chloro.

In some embodiments, $R_2$ is H.

In some embodiments, $R_3$, $R_4$, and $R_5$ are H. In some embodiments, one of $R_3$, $R_4$, and $R_5$ is fluoro or chloro and the others are hydrogen.

In some embodiments, p is 0. In some embodiments, p is 1. In some embodiments, p is 2. In some embodiments, p is 3.

In some embodiments, q is 0. In some embodiments, q is 1.

Also provided is a compound of Formula II

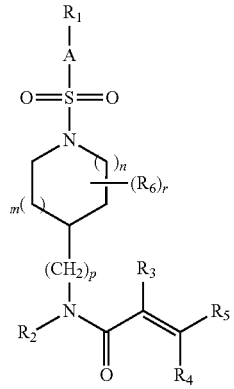

Formula II or a pharmaceutically acceptable salt thereof, wherein A, $R_1$, $R_2$, $R_3$, $R_4$, $R_5$, and p are as described for compounds of Formula I and wherein
m is chosen from 0, 1, 2, and 3;
n is chosen from 0 and 1;
for each occurrence, $R_6$ is independently chosen from optionally substituted lower alkyl; and
r is chosen from 0, 1, 2, 3, and 4.

In some embodiments, m and n are 1. In some embodiments, m is 1 and n is 0.

In some embodiments, for each occurrence, $R_6$ is independently chosen from methyl and hydroxymethyl.

In some embodiments, r is 0 or 1.

Also provided is a compound of Formula III

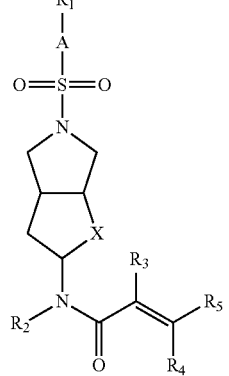

Formula III or a pharmaceutically acceptable salt thereof, wherein A, $R_1$, $R_2$, $R_3$, $R_4$, and $R_5$ are as described for compounds of Formula I and wherein X is —$CH_2$—, —O—, or —S—.

In some embodiments, X is —O—. In some embodiments, X is —S—. In some embodiments, X is —$CH_2$—.

Also provided is a compound of Formula IV

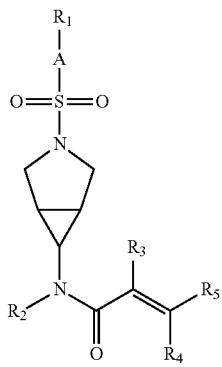

Formula IV or a pharmaceutically acceptable salt thereof, wherein A, $R_1$, $R_2$, $R_3$, $R_4$, and $R_5$ are as described for compounds of Formula I.

Also provided is a compound of Formula V

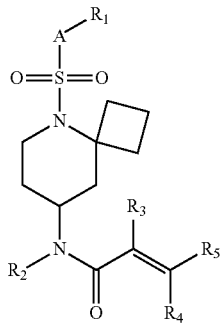

Formula V or a pharmaceutically acceptable salt thereof, wherein A, $R_1$, $R_2$, $R_3$, $R_4$, and $R_5$ are as described for compounds of Formula I.

Also provided is a compound of Formula VI

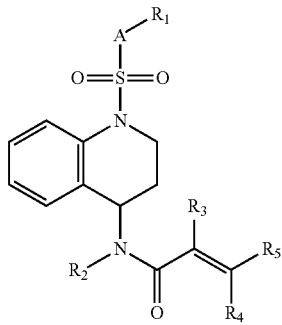

Formula VI or a pharmaceutically acceptable salt thereof, wherein A, $R_1$, $R_2$, $R_3$, $R_4$, and $R_5$ are as described for compounds of Formula I.

Also provided is a compound of Formula VII

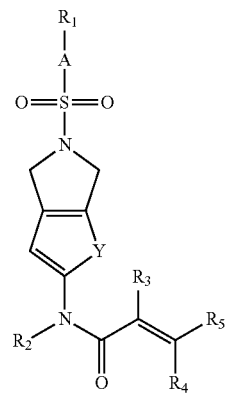

Formula VII or a pharmaceutically acceptable salt thereof, wherein A, $R_1$, $R_2$, $R_3$, $R_4$, and $R_5$ are as described for compounds of Formula I and wherein Y is —O— or —S—.

In some embodiments, Y is —O—. In some embodiments, Y is —S—.

Also provided is a compound, or pharmaceutically acceptable salt thereof, chosen from:

N-{(3S)-1-[(4-cyclohexylphenyl)sulfonyl]piperidin-3-yl}prop-2-enamide

N-(4-{[(3S)-3-(acryloylamino)piperidin-1-yl]sulfonyl}phenyl)cyclopropanecarboxamide N-(4-{[(3S)-3-(acryloylamino)piperidin-1-yl]sulfonyl}phenyl)tricyclo[3.3.1.1~3,7~]decane-1-carboxamide benzyl(4-{[(3S)-3-(acryloylamino)piperidin-1-yl]sulfonyl}phenyl)carbamate N-[(3S)-1-{[4-(piperidin-1-ylcarbonyl)phenyl]sulfonyl}piperidin-3-yl]prop-2-enamide benzyl 4-{[(3S)-3-(acryloylamino)piperidin-1-yl]sulfonyl}piperidine-1-carboxylate N-{(3S)-1-[(4-nitrophenyl)sulfonyl]piperidin-3-yl}prop-2-enamide N-(4-{[(3S)-3-(acryloylamino)piperidin-1-yl]sulfonyl}phenyl)tetrahydro-2H-pyran-4-carboxamide N-[(3S)-1-({4-[(3-phenylpropanoyl)amino]phenyl}sulfonyl)piperidin-3-yl]prop-2-enamide N-(4-{[(3S)-3-(acryloylamino)piperidin-1-yl]sulfonyl}phenyl)-2-phenylcyclopropanecarboxamide N-(4-{[(3S)-3-(acryloylamino)piperidin-1-yl]sulfonyl}phenyl)-N-methyltetrahydro-2H -pyran-4-carboxamide 4-{[(3S)-3-(acryloylamino)piperidin-1-yl]sulfonyl}-N-benzyl-N-methylbenzamide 4-{[(3S)-3-(acryloylamino)piperidin-1-yl]sulfonyl}-N-(cyclopropylmethyl)benzamide N-[(3S)-1-{[3-(piperidin-1-ylcarbonyl)phenyl]sulfonyl}piperidin-3-yl]prop-2-enamide N-(4-{[(3S)-3-(acryloylamino)piperidin-1-yl]sulfonyl}phenyl)-N-methylcyclopropanecarboxamide N-{(3S)-1-[(4-{[4-(6-methylpyridin-2-yl)piperazin-1-yl]carbonyl}phenyl)sulfonyl]piperidin-3-yl}prop-2-enamide 4-{[(3S)-3-(acryloylamino)piperidin-1-yl]sulfonyl}-N-[2-(morpholin-4-yl)ethyl]benzamide 4-{[(3S)-3-(acryloylamino)piperidin-1-yl]sulfonyl}-N-(2-phenylethyl)benzamide
4-{[(3S)-3-(acryloylamino)piperidin-1-yl]sulfonyl}-N-methyl-N-(2-phenylethyl)benzamide
N-[(3S)-1-{[4-(3,4-dihydroisoquinolin-2(1H)-ylcarbonyl)phenyl]sulfonyl}piperidin-3-yl]prop-2-enamide
4-{[(3S)-3-(acryloylamino)piperidin-1-yl]sulfonyl}-N-(2-cyclohexylethyl)benzamide
4-{[(3S)-3-(acryloylamino)piperidin-1-yl]sulfonyl}-N-cyclohexylbenzamide
N-{(3S)-1-[(4-{[4-(pyrrolidin-1-ylcarbonyl)piperidin-1-yl]carbonyl}phenyl)sulfonyl]piperidin-3-yl}prop-2-enamide
4-{[(3S)-3-(acryloylamino)piperidin-1-yl]sulfonyl}-N-(3,5-dimethylbenzyl)benzamide
4-{[(3S)-3-(acryloylamino)piperidin-1-yl]sulfonyl}-N-benzylbenzamide
4-{[(3S)-3-(acryloylamino)piperidin-1-yl]sulfonyl}-N-(3,4-difluorobenzyl)benzamide
4-{[(3S)-3-(acryloylamino)piperidin-1-yl]sulfonyl}-N-[4-(trifluoromethyl)benzyl]benzamide
4-{[(3S)-3-(acryloylamino)piperidin-1-yl]sulfonyl}-N-(naphthalen-1-ylmethyl)benzamide
4-{[(3S)-3-(acryloylamino)piperidin-1-yl]sulfonyl}-N-[2-(3,4-dimethylphenyl)ethyl]benzamide
4-{[(3S)-3-(acryloylamino)piperidin-1-yl]sulfonyl}-N-[2-(4-methoxyphenyl)ethyl]benzamide
4-{[(3S)-3-(acryloylamino)piperidin-1-yl]sulfonyl}-N-(2,3-dihydro-1H-inden-2-yl)benzamide
4-{[(3S)-3-(acryloylamino)piperidin-1-yl]sulfonyl}-N-[2-(3-methylphenyl)ethyl]benzamide
N-[(3S)-1-({4-[(acetylamino)methyl]phenyl}sulfonyl)piperidin-3-yl]prop-2-enamide
N-{(3S)-1-[(4-{[3-(naphthalen-1-yl)propanoyl]amino}phenyl)sulfonyl]piperidin-3-yl}prop-2-enamide
N-[(3S)-1-({4-[(3-cyclohexylpropanoyl)amino]phenyl}sulfonyl)piperidin-3-yl]prop-2-enamide
N-{(3S)-1-[(1-benzoylpiperidin-4-yl)sulfonyl]piperidin-3-yl}prop-2-enamide
N-[(3S)-1-{[1-(piperidin-1-ylcarbonyl)piperidin-4-yl]sulfonyl}piperidin-3-yl]prop-2-enamide
N-[(3S)-1-{[1-(pyridin-2-ylcarbonyl)piperidin-4-yl]sulfonyl}piperidin-3-yl]prop-2-enamide
N-(4-{[(3S)-3-(acryloylamino)piperidin-1-yl]sulfonyl}phenyl)-4-tert-butylcyclohexanecarboxamide
N-(4-{[(3S)-3-(acryloylamino)piperidin-1-yl]sulfonyl}phenyl)-1-benzofuran-2-carboxamide
benzyl(3-{[(3S)-3-(acryloylamino)piperidin-1-yl]sulfonyl}phenyl)carbamate
N-[(3S)-1-({3-[(3-phenylpropanoyl)amino]phenyl}sulfonyl)piperidin-3-yl]prop-2-enamide
N-(3-{[(3S)-3-(acryloylamino)piperidin-1-yl]sulfonyl}phenyl)tetrahydro-2H-pyran-4-carboxamide
4-{[(3S)-3-(acryloylamino)piperidin-1-yl]sulfonyl}-N-(3-phenylpropyl)benzamide
4-{[(3S)-3-(acryloylamino)piperidin-1-yl]sulfonyl}-N-[2-(3-chlorophenyl)ethyl]benzamide
4-{[(3S)-3-(acryloylamino)piperidin-1-yl]sulfonyl}-N-[2-(2-methoxyphenyl)ethyl]benzamide
4-{[(3S)-3-(acryloylamino)piperidin-1-yl]sulfonyl}-N-[2-(2,3-dihydro-1-benzofuran-7-yl)ethyl]benzamide
4-{[(3S)-3-(acryloylamino)piperidin-1-yl]sulfonyl}-N-[2-(tetrahydro-2H-pyran-4-yl)ethyl]benzamide
4-{[(3S)-3-(acryloylamino)piperidin-1-yl]sulfonyl}-N-[2-(4,4-difluoropiperidin-1-yl)ethyl]benzamide
N-[(3S)-1-({1-[3-(trifluoromethyl)benzoyl]piperidin-4-yl}sulfonyl)piperidin-3-yl]prop-2-enamide
N-[(3S)-1-{[1-(3-phenylpropanoyl)piperidin-4-yl]sulfonyl}piperidin-3-yl]prop-2-enamide
N-[(3S)-1-({4-[2-(benzylamino)-2-oxoethyl]phenyl}sulfonyl)piperidin-3-yl]prop-2-enamide
4-{[(3S)-3-(acryloylamino)piperidin-1-yl]sulfonyl}-N-(4-tert-butylbenzyl)benzamide
4-{[(3S)-3-(acryloylamino)piperidin-1-yl]sulfonyl}-N-(4-phenylbutyl)benzamide
4-{[(3S)-3-(acryloylamino)piperidin-1-yl]sulfonyl}-N-[2-(4-chlorophenyl)ethyl]benzamide
4-{[(3S)-3-(acryloylamino)piperidin-1-yl]sulfonyl}-N-[2-(quinolin-7-yl)ethyl]benzamide
4-{[(3S)-3-(acryloylamino)piperidin-1-yl]sulfonyl}-N-[2-(naphthalen-2-yl)ethyl]benzamide
4-{[(3S)-3-(acryloylamino)piperidin-1-yl]sulfonyl}-N-(3,4-dihydro-2H-chromen-6-ylmethyl)benzamide
4-{[(3S)-3-(acryloylamino)piperidin-1-yl]sulfonyl}-N-[2-(4-tert-butylphenyl)ethyl]benzamide
4-{[(3S)-3-(acryloylamino)piperidin-1-yl]sulfonyl}-N-[2-(biphenyl-4-yl)ethyl]benzamide
4-{[(3S)-3-(acryloylamino)piperidin-1-yl]sulfonyl}-N-[2-(1,3-benzodioxol-5-yl)ethyl]benzamide
4-{[(3S)-3-(acryloylamino)piperidin-1-yl]sulfonyl}-N-[(1R)-2-phenylcyclopropyl]benzamide
benzyl(4-{[(3S)-3-(acryloylamino)piperidin-1-yl]sulfonyl}phenyl)methylcarbamate
4-{[(3S)-3-(acryloylamino)piperidin-1-yl]sulfonyl}-N-[2-(3,4-dimethoxyphenyl)ethyl]benzamide
4-{[(3S)-3-(acryloylamino)piperidin-1-yl]sulfonyl}-N-{2-[4-(trifluoromethyl)phenyl]ethyl}benzamide
4-{[(3S)-3-(acryloylamino)piperidin-1-yl]sulfonyl}-N-(2-phenylethyl)piperidine-1-carboxamide
N-(4-{[(3S)-3-(acryloylamino)piperidin-1-yl]sulfonyl}phenyl)furan-2-carboxamide
N-{(3S)-1-[(4-{[3-(tricyclo[3.3.1.1~3,7~]dec-1-yl)propanoyl]amino}phenyl)sulfonyl]piperidin-3-yl}prop-2-enamide
4-{[(3S)-3-(acryloylamino)piperidin-1-yl]sulfonyl}-N-[2-(tricyclo[3.3.1.1~3,7~]dec-1-yl)ethyl]benzamide
N-[(3S)-1-{[1-(cyclopropylcarbonyl)-2,3-dihydro-1H-indol-5-yl]sulfonyl}piperidin-3-yl]prop-2-enamide
N-[(3S)-1-({2-chloro-4-[(3-phenylpropanoyl)amino]phenyl}sulfonyl)piperidin-3-yl]prop-2-enamide
N-(4-{[(3S)-3-(acryloylamino)piperidin-1-yl]sulfonyl}phenyl)-5,6-dihydro-4H-cyclopenta[b]thiophene-2-carboxamide
N-(4-{[(3S)-3-(acryloylamino)piperidin-1-yl]sulfonyl}phenyl)-4,5,6,7-tetrahydro-1H-indole-2-carboxamide
N-[(3S)-1-({2-methoxy-4-[(3-phenylpropanoyl)amino]phenyl}sulfonyl)piperidin-3-yl]prop-2-enamide
N-(4-{[(3S)-3-(acryloylamino)piperidin-1-yl]sulfonyl}phenyl)-5-(pyrrolidin-1-ylmethyl)furan-2-carboxamide
N-(4-{[(3S)-3-(acryloylamino)piperidin-1-yl]sulfonyl}phenyl)-1-benzothiophene-2-carboxamide
N-(4-{[(3S)-3-(acryloylamino)piperidin-1-yl]sulfonyl}phenyl)-3-methyl-1-benzofuran-2-carboxamide
N-(4-{[(3S)-3-(acryloylamino)piperidin-1-yl]sulfonyl}phenyl)-1H-indole-2-carboxamide
4-{[(3S)-3-(acryloylamino)piperidin-1-yl]sulfonyl}-N-(tricyclo[3.3.1.1~3,7~]dec-1-ylmethyl)benzamide
4-{[(3S)-3-(acryloylamino)piperidin-1-yl]sulfonyl}-N-(1,2,3,4-tetrahydronaphthalen-1-yl)benzamide
N-(4-{[(3S)-3-(acryloylamino)piperidin-1-yl]sulfonyl}phenyl)-4,5,6,7-tetrahydro-1-benzothiophene-2-carboxamide N-(4-{[(3S)-3-(acryloylamino)piperidin-1-yl]
sulfonyl}phenyl)-5-phenylfuran-2-carboxamide
N-(4-{[(3S)-3-(acryloylamino)piperidin-1-yl]
sulfonyl}phenyl)-4-phenylthiophene-2-carboxamide
N-[(3S)-1-({5-[5-(trifluoromethyl)-1,2-oxazol-3-yl]
thiophen-2-yl}sulfonyl)piperidin-3-yl]prop-2-enamide
5-{[(3S)-3-(acryloylamino)piperidin-1-yl]sulfonyl}-N-(2-
phenylethyl)furan-2-carboxamide
N-{(3S)-1-[(6-phenoxypyridin-3-yl)sulfonyl]piperidin-3-
yl}prop-2-enamide
N-[(3S)-1-{[6-(morpholin-4-yl)pyridin-3-yl]
sulfonyl}piperidin-3-yl]prop-2-enamide
N-{(3S)-1-[(6-phenylpyridin-3-yl)sulfonyl]piperidin-3-
yl}prop-2-enamide
N-[(3S)-1-({3-chloro-4-[(3-phenylpropanoyl)amino]
phenyl}sulfonyl)piperidin-3-yl]prop-2-enamide
4-{[(3S)-3-(acryloylamino)piperidin-1-yl]sulfonyl}-2-
fluoro-N-(2-phenylethyl)benzamide
N-[(3S)-1-{[5-(pyridin-2-yl)thiophen-2-yl]
sulfonyl}piperidin-3-yl]prop-2-enamide
4-{[(3S)-3-(acryloylamino)piperidin-1-yl]sulfonyl}-2-
methoxy-N-(2-phenylethyl)benzamide
N-[(3S)-1-(1,3-benzothiazol-6-ylsulfonyl)piperidin-3-yl]
prop-2-enamide
N-{(3S)-1-[(4-methyl-2-phenyl-1,3-thiazol-5-yl)sulfonyl]
piperidin-3-yl}prop-2-enamide
N-[(3S)-1-{[5-(2-methyl-1,3-thiazol-4-yl)thiophen-2-yl]
sulfonyl}piperidin-3-yl]prop-2-enamide
N-[(3S)-1-{[5-(1,2-oxazol-5-yl)thiophen-2-yl]
sulfonyl}piperidin-3-yl]prop-2-enamide
N-[(3S)-1-(2,3-dihydro-1,4-benzodioxin-6-ylsulfonyl)piperidin-3-yl]prop-2-enamide
5-{[(3S)-3-(acryloylamino)piperidin-1-yl]sulfonyl}-N-(2-
phenylethyl)furan-3-carboxamide
N-[(3S)-1-({4-[(phenylacetyl)amino]benzyl}sulfonyl)piperidin-3-yl]prop-2-enamide
N-[(3S)-1-{[4-(morpholin-4-ylsulfonyl)phenyl]
sulfonyl}piperidin-3-yl]prop-2-enamide
N-[(3S)-1-{[5-(1,3-oxazol-5-yl)thiophen-2-yl]
sulfonyl}piperidin-3-yl]prop-2-enamide
4-{[(3S)-3-(acryloylamino)piperidin-1-yl]sulfonyl}-2-methyl-N-(2-phenylethyl)benzamide
N-{(3S)-1-[(4-phenoxyphenyl)sulfonyl]piperidin-3-
yl}prop-2-enamide
N-[(3S)-1-({4-[(6-methylpyrazin-2-yl)oxy]
phenyl}sulfonyl)piperidin-3-yl]prop-2-enamide
N-[(3S)-1-({3-[(6-methylpyrazin-2-yl)oxy]
phenyl}sulfonyl)piperidin-3-yl]prop-2-enamide
5-{[(3S)-3-(acryloylamino)piperidin-1-yl]sulfonyl}-1-methyl-N-(2-phenylethyl)-1H-pyrrole-2-carboxamide
N-[(3S)-1-{[4-(isoquinolin-3-ylamino)phenyl]
sulfonyl}piperidin-3-yl]prop-2-enamide
N-{(3S)-1-[(3-chloro-4-methylphenyl)sulfonyl]piperidin-3-
yl}prop-2-enamide
N-[(3S)-1-{[5-(1,2-oxazol-5-yl)furan-2-yl]
sulfonyl}piperidin-3-yl]prop-2-enamide
N-{(3S)-1-[(4-{[3-chloro-5-(trifluoromethyl)pyridin-2-yl]
oxy}phenyl)sulfonyl]piperidin-3-yl}prop-2-enamide
N-[(3S)-1-{[4-(1H-pyrazol-1-yl)phenyl]sulfonyl}piperidin-3-yl]prop-2-enamide
N-{(3S)-1-[(4-methoxy-3-methylphenyl)sulfonyl]piperidin-3-yl}prop-2-enamide
N-[(3S)-1-{[6-(2-phenylethoxy)pyridin-3-yl]
sulfonyl}piperidin-3-yl]prop-2-enamide
N-[(3S)-1-({5-[(acetylamino)methyl]thiophen-2-
yl}sulfonyl)piperidin-3-yl]prop-2-enamide
N-{(3S)-1-[(5-methyl-1-phenyl-1H-pyrazol-4-yl)sulfonyl]
piperidin-3-yl}prop-2-enamide
N-[(3S)-1-{[4-(1-methyl-1H-pyrazol-5-yl)phenyl]
sulfonyl}piperidin-3-yl]prop-2-enamide
N-[(3S)-1-{[3-(1-methyl-1H-pyrazol-5-yl)phenyl]
sulfonyl}piperidin-3-yl]prop-2-enamide
N-{(3S)-1-[(2,2-dimethyl-3,4-dihydro-2H-chromen-6-yl)
sulfonyl]piperidin-3-yl}prop-2-enamide
N-{(3S)-1-[(5-phenylthiophen-2-yl)sulfonyl]piperidin-3-
yl}prop-2-enamide
N-[(3S)-1-{[4-(cyclopentyloxy)phenyl]sulfonyl}piperidin-3-yl]prop-2-enamide
N-[(3S)-1-{[5-(pyrrolidin-1-ylcarbonyl)-1H-pyrrol-3-yl]
sulfonyl}piperidin-3-yl]prop-2-enamide
N-[(3S)-1-{[4-(2-methyl-1,3-thiazol-4-yl)phenyl]
sulfonyl}piperidin-3-yl]prop-2-enamide
N-[(3S)-1-{[4-(pyridin-2-yloxy)phenyl]sulfonyl}piperidin-3-yl]prop-2-enamide
N-{(3S)-1-[(2-oxo-1,2,3,4-tetrahydroquinolin-6-yl)sulfonyl]piperidin-3-yl}prop-2-enamide
N-{(3S)-1-[(4-cyclohexylphenyl)sulfonyl]piperidin-3-
yl}prop-2-enamide
N-(4-{[(3S)-3-(acryloylamino)piperidin-1-yl]
sulfonyl}phenyl)cyclopropanecarboxamide
N-(4-{[(3S)-3-(acryloylamino)piperidin-1-yl]
sulfonyl}phenyl)tricyclo[3.3.1.1~3,7~]decane-1-carboxamide
benzyl(4-{[(3S)-3-(acryloylamino)piperidin-1-yl]
sulfonyl}phenyl)carbamate
N-[(3S)-1-{[4-(piperidin-1-ylcarbonyl)phenyl]
sulfonyl}piperidin-3-yl]prop-2-enamide
benzyl 4-{[(3S)-3-(acryloylamino)piperidin-1-yl]
sulfonyl}piperidine-1-carboxylate
N-{(3S)-1-[(4-nitrophenyl)sulfonyl]piperidin-3-yl}prop-2-
enamide
N-(4-{[(3S)-3-(acryloylamino)piperidin-1-yl]
sulfonyl}phenyl)tetrahydro-2H-pyran-4-carboxamide
N-[(3S)-1-({4-[(3-phenylpropanoyl)amino]
phenyl}sulfonyl)piperidin-3-yl]prop-2-enamide
N-(4-{[(3S)-3-(acryloylamino)piperidin-1-yl]
sulfonyl}phenyl)-2-phenylcyclopropanecarboxamide
N-(4-{[(3S)-3-(acryloylamino)piperidin-1-yl]
sulfonyl}phenyl)-N-methyltetrahydro-2H-pyran-4-carboxamide
4-{[(3S)-3-(acryloylamino)piperidin-1-yl]sulfonyl}-N-benzyl-N-methylbenzamide
4-{[(3S)-3-(acryloylamino)piperidin-1-yl]sulfonyl}-N-(cyclopropylmethyl)benzamide
N-[(3S)-1-{[3-(piperidin-1-ylcarbonyl)phenyl]
sulfonyl}piperidin-3-yl]prop-2-enamide
N-(4-{[(3S)-3-(acryloylamino)piperidin-1-yl]
sulfonyl}phenyl)-N-methylcyclopropanecarboxamide
N-{(3S)-1-[(4-{[4-(6-methylpyridin-2-yl)piperazin-1-yl]
carbonyl}phenyl)sulfonyl]piperidin-3-yl}prop-2-enamide
4-{[(3S)-3-(acryloylamino)piperidin-1-yl]sulfonyl}-N-[2-
(morpholin-4-yl)ethyl]benzamide
4-{[(3S)-3-(acryloylamino)piperidin-1-yl]sulfonyl}-N-(2-
phenylethyl)benzamide
4-{[(3S)-3-(acryloylamino)piperidin-1-yl]sulfonyl}-N-methyl-N-(2-phenylethyl)benzamide
N-[(3S)-1-{[4-(3,4-dihydroisoquinolin-2(1H)-ylcarbonyl)
phenyl]sulfonyl}piperidin-3-yl]prop-2-enamide
4-{[(3S)-3-(acryloylamino)piperidin-1-yl]sulfonyl}-N-(2-
cyclohexylethyl)benzamide
4-{[(3S)-3-(acryloylamino)piperidin-1-yl]sulfonyl}-N-cyclohexylbenzamide N-{(3S)-1-[(4-{[4-(pyrrolidin-1-ylcarbonyl)piperidin-1-yl]carbonyl}phenyl)sulfonyl]piperidin-3-yl}prop-2-enamide
4-{[(3S)-3-(acryloylamino)piperidin-1-yl]sulfonyl}-N-(3,5-dimethylbenzyl)benzamide
4-{[(3S)-3-(acryloylamino)piperidin-1-yl]sulfonyl}-N-benzylbenzamide
4-{[(3S)-3-(acryloylamino)piperidin-1-yl]sulfonyl}-N-(3,4-difluorobenzyl)benzamide
4-{[(3S)-3-(acryloylamino)piperidin-1-yl]sulfonyl}-N-[4-(trifluoromethyl)benzyl]benzamide
4-{[(3S)-3-(acryloylamino)piperidin-1-yl]sulfonyl}-N-(naphthalen-1-ylmethyl)benzamide
4-{[(3S)-3-(acryloylamino)piperidin-1-yl]sulfonyl}-N-[2-(3,4-dimethylphenyl)ethyl]benzamide
4-{[(3S)-3-(acryloylamino)piperidin-1-yl]sulfonyl}-N-[2-(4-methoxyphenyl)ethyl]benzamide
4-{[(3S)-3-(acryloylamino)piperidin-1-yl]sulfonyl}-N-(2,3-dihydro-1H-inden-2-yl)benzamide
4-{[(3S)-3-(acryloylamino)piperidin-1-yl]sulfonyl}-N-[2-(3-methylphenyl)ethyl]benzamide
N-[(3S)-1-({4-[(acetylamino)methyl]phenyl}sulfonyl)piperidin-3-yl]prop-2-enamide
N-{(3S)-1-[(4-{[3-(naphthalen-1-yl)propanoyl]amino}phenyl)sulfonyl]piperidin-3-yl}prop-2-enamide
N-[(3S)-1-({4-[(3-cyclohexylpropanoyl)amino]phenyl}sulfonyl)piperidin-3-yl]prop-2-enamide
N-{(3S)-1-[(1-benzoylpiperidin-4-yl)sulfonyl]piperidin-3-yl}prop-2-enamide
N-[(3S)-1-{[1-(piperidin-1-ylcarbonyl)piperidin-4-yl]sulfonyl}piperidin-3-yl]prop-2-enamide
N-[(3S)-1-{[1-(pyridin-2-ylcarbonyl)piperidin-4-yl]sulfonyl}piperidin-3-yl]prop-2-enamide
N-(4-{[(3S)-3-(acryloylamino)piperidin-1-yl]sulfonyl}phenyl)-4-tert-butylcyclohexanecarboxamide
N-(4-{[(3S)-3-(acryloylamino)piperidin-1-yl]sulfonyl}phenyl)-1-benzofuran-2-carboxamide
benzyl(3-{[(3S)-3-(acryloylamino)piperidin-1-yl]sulfonyl}phenyl)carbamate
N-[(3S)-1-({3-[(3-phenylpropanoyl)amino]phenyl}sulfonyl)piperidin-3-yl]prop-2-enamide
N-(3-{[(3S)-3-(acryloylamino)piperidin-1-yl]sulfonyl}phenyl)tetrahydro-2H-pyran-4-carboxamide
4-{[(3S)-3-(acryloylamino)piperidin-1-yl]sulfonyl}-N-(3-phenylpropyl)benzamide
4-{[(3S)-3-(acryloylamino)piperidin-1-yl]sulfonyl}-N-[2-(3-chlorophenyl)ethyl]benzamide
4-{[(3S)-3-(acryloylamino)piperidin-1-yl]sulfonyl}-N-[2-(2-methoxyphenyl)ethyl]benzamide
4-{[(3S)-3-(acryloylamino)piperidin-1-yl]sulfonyl}-N-[2-(2,3-dihydro-1-benzofuran-7-yl)ethyl]benzamide
4-{[(3S)-3-(acryloylamino)piperidin-1-yl]sulfonyl}-N-[2-(tetrahydro-2H-pyran-4-yl)ethyl]benzamide
4-{[(3S)-3-(acryloylamino)piperidin-1-yl]sulfonyl}-N-[2-(4,4-difluoropiperidin-1-yl)ethyl]benzamide
N-[(3S)-1-({1-[3-(trifluoromethyl)benzoyl]piperidin-4-yl}sulfonyl)piperidin-3-yl]prop-2-enamide
N-[(3S)-1-{[1-(3-phenylpropanoyl)piperidin-4-yl]sulfonyl}piperidin-3-yl]prop-2-enamide
N-[(3S)-1-({4-[2-(benzylamino)-2-oxoethyl]phenyl}sulfonyl)piperidin-3-yl]prop-2-enamide
4-{[(3S)-3-(acryloylamino)piperidin-1-yl]sulfonyl}-N-(4-tert-butylbenzyl)benzamide
4-{[(3S)-3-(acryloylamino)piperidin-1-yl]sulfonyl}-N-(4-phenylbutyl)benzamide
4-{[(3S)-3-(acryloylamino)piperidin-1-yl]sulfonyl}-N-[2-(4-chlorophenyl)ethyl]benzamide
4-{[(3S)-3-(acryloylamino)piperidin-1-yl]sulfonyl}-N-[2-(quinolin-7-yl)ethyl]benzamide
4-{[(3S)-3-(acryloylamino)piperidin-1-yl]sulfonyl}-N-[2-(naphthalen-2-yl)ethyl]benzamide
4-{[(3S)-3-(acryloylamino)piperidin-1-yl]sulfonyl}-N-(3,4-dihydro-2H-chromen-6-ylmethyl)benzamide
4-{[(3S)-3-(acryloylamino)piperidin-1-yl]sulfonyl}-N-[2-(4-tert-butylphenyl)ethyl]benzamide
4-{[(3S)-3-(acryloylamino)piperidin-1-yl]sulfonyl}-N-[2-(biphenyl-4-yl)ethyl]benzamide
4-{[(3S)-3-(acryloylamino)piperidin-1-yl]sulfonyl}-N-[2-(1,3-benzodioxol-5-yl)ethyl]benzamide
4-{[(3S)-3-(acryloylamino)piperidin-1-yl]sulfonyl}-N-[(1R)-2-phenylcyclopropyl]benzamide
benzyl(4-{[(3S)-3-(acryloylamino)piperidin-1-yl]sulfonyl}phenyl)methylcarbamate
4-{[(3S)-3-(acryloylamino)piperidin-1-yl]sulfonyl}-N-[2-(3,4-dimethoxyphenyl)ethyl]benzamide
4-{[(3S)-3-(acryloylamino)piperidin-1-yl]sulfonyl}-N-{2-[4-(trifluoromethyl)phenyl]ethyl}benzamide
4-{[(3S)-3-(acryloylamino)piperidin-1-yl]sulfonyl}-N-(2-phenylethyl)piperidine-1-carboxamide
N-(4-{[(3S)-3-(acryloylamino)piperidin-1-yl]sulfonyl}phenyl)furan-2-carboxamide
N-{(3S)-1-[(4-{[3-(tricyclo[3.3.1.1~3,7~]dec-1-yl)propanoyl]amino}phenyl)sulfonyl]piperidin-3-yl}prop-2-enamide
4-{[(3S)-3-(acryloylamino)piperidin-1-yl]sulfonyl}-N-[2-(tricyclo[3.3.1.1~3,7~]dec-1-yl)ethyl]benzamide
N-[(3S)-1-{[1-(cyclopropylcarbonyl)-2,3-dihydro-1H-indol-5-yl]sulfonyl}piperidin-3-yl]prop-2-enamide
N-[(3S)-1-({2-chloro-4-[(3-phenylpropanoyl)amino]phenyl}sulfonyl)piperidin-3-yl]prop-2-enamide
N-(4-{[(3S)-3-(acryloylamino)piperidin-1-yl]sulfonyl}phenyl)-5,6-dihydro-4H-cyclopenta[b]thiophene-2-carboxamide
N-(4-{[(3S)-3-(acryloylamino)piperidin-1-yl]sulfonyl}phenyl)-4,5,6,7-tetrahydro-1H-indole-2-carboxamide
N-[(3S)-1-({2-methoxy-4-[(3-phenylpropanoyl)amino]phenyl}sulfonyl)piperidin-3-yl]prop-2-enamide
N-(4-{[(3S)-3-(acryloylamino)piperidin-1-yl]sulfonyl}phenyl)-5-(pyrrolidin-1-ylmethyl)furan-2-carboxamide
N-(4-{[(3S)-3-(acryloylamino)piperidin-1-yl]sulfonyl}phenyl)-1-benzothiophene-2-carboxamide
N-(4-{[(3S)-3-(acryloylamino)piperidin-1-yl]sulfonyl}phenyl)-3-methyl-1-benzofuran-2-carboxamide
N-(4-{[(3S)-3-(acryloylamino)piperidin-1-yl]sulfonyl}phenyl)-1H-indole-2-carboxamide
4-{[(3S)-3-(acryloylamino)piperidin-1-yl]sulfonyl}-N-(tricyclo[3.3.1.1~3,7~]dec-1-ylmethyl)benzamide
4-{[(3S)-3-(acryloylamino)piperidin-1-yl]sulfonyl}-N-(1,2,3,4-tetrahydronaphthalen-1-yl)benzamide
N-(4-{[(3S)-3-(acryloylamino)piperidin-1-yl]sulfonyl}phenyl)-4,5,6,7-tetrahydro-1-benzothiophene-2-carboxamide
N-(4-{[(3S)-3-(acryloylamino)piperidin-1-yl]sulfonyl}phenyl)-5-phenylfuran-2-carboxamide
N-(4-{[(3S)-3-(acryloylamino)piperidin-1-yl]sulfonyl}phenyl)-4-phenylthiophene-2-carboxamide
N-[(3S)-1-({5-[5-(trifluoromethyl)-1,2-oxazol-3-yl]thiophen-2-yl}sulfonyl)piperidin-3-yl]prop-2-enamide
5-{[(3S)-3-(acryloylamino)piperidin-1-yl]sulfonyl}-N-(2-phenylethyl)furan-2-carboxamide
N-{(3S)-1-[(6-phenoxypyridin-3-yl)sulfonyl]piperidin-3-yl}prop-2-enamide N-[(3S)-1-{[6-(morpholin-4-yl)pyridin-3-yl]
  sulfonyl}piperidin-3-yl]prop-2-enamide
N-{(3S)-1-[(6-phenylpyridin-3-yl)sulfonyl]piperidin-3-
  yl}prop-2-enamide
N-[(3S)-1-({3-chloro-4-[(3-phenylpropanoyl)amino]
  phenyl}sulfonyl)piperidin-3-yl]prop-2-enamide
4-{[(3S)-3-(acryloylamino)piperidin-1-yl]sulfonyl}-2-
  fluoro-N-(2-phenylethyl)benzamide
N-[(3S)-1-{[5-(pyridin-2-yl)thiophen-2-yl]
  sulfonyl}piperidin-3-yl]prop-2-enamide
4-{[(3S)-3-(acryloylamino)piperidin-1-yl]sulfonyl}-2-
  methoxy-N-(2-phenylethyl)benzamide
N-[(3S)-1-(1,3-benzothiazol-6-ylsulfonyl)piperidin-3-yl]
  prop-2-enamide
N-{(3S)-1-[(4-methyl-2-phenyl-1,3-thiazol-5-yl)sulfonyl]
  piperidin-3-yl}prop-2-enamide
N-[(3S)-1-{[5-(2-methyl-1,3-thiazol-4-yl)thiophen-2-yl]
  sulfonyl}piperidin-3-yl]prop-2-enamide
N-[(3S)-1-{[5-(1,2-oxazol-5-yl)thiophen-2-yl]
  sulfonyl}piperidin-3-yl]prop-2-enamide
N-[(3S)-1-(2,3-dihydro-1,4-benzodioxin-6-ylsulfonyl)pip-
  eridin-3-yl]prop-2-enamide
5-{[(3S)-3-(acryloylamino)piperidin-1-yl]sulfonyl}-N-(2-
  phenylethyl)furan-3-carboxamide
N-[(3S)-1-({4-[(phenylacetyl)amino]benzyl}sulfonyl)pip-
  eridin-3-yl]prop-2-enamide
N-[(3S)-1-{[4-(morpholin-4-ylsulfonyl)phenyl]
  sulfonyl}piperidin-3-yl]prop-2-enamide
N-[(3S)-1-{[5-(1,3-oxazol-5-yl)thiophen-2-yl]
  sulfonyl}piperidin-3-yl]prop-2-enamide
4-{[(3S)-3-(acryloylamino)piperidin-1-yl]sulfonyl}-2-me-
  thyl-N-(2-phenylethyl)benzamide
N-{(3S)-1-[(4-phenoxyphenyl)sulfonyl]piperidin-3-
  yl}prop-2-enamide
N-[(3S)-1-({4-[(6-methylpyrazin-2-yl)oxy]
  phenyl}sulfonyl)piperidin-3-yl]prop-2-enamide
N-[(3S)-1-({3-[(6-methylpyrazin-2-yl)oxy]
  phenyl}sulfonyl)piperidin-3-yl]prop-2-enamide
5-{[(3S)-3-(acryloylamino)piperidin-1-yl]sulfonyl}-1-me-
  thyl-N-(2-phenylethyl)-1H-pyrrole-2-carboxamide
N-[(3S)-1-{[4-(isoquinolin-3-ylamino)phenyl]
  sulfonyl}piperidin-3-yl]prop-2-enamide
N-{(3S)-1-[(3-chloro-4-methylphenyl)sulfonyl]piperidin-3-
  yl}prop-2-enamide
N-[(3S)-1-{[5-(1,2-oxazol-5-yl)furan-2-yl]
  sulfonyl}piperidin-3-yl]prop-2-enamide
N-{(3S)-1-[(4-{[3-chloro-5-(trifluoromethyl)pyridin-2-yl]
  oxy}phenyl)sulfonyl]piperidin-3-yl}prop-2-enamide
N-[(3S)-1-{[4-(1H-pyrazol-1-yl)phenyl]sulfonyl}piperidin-
  3-yl]prop-2-enamide
N-{(3S)-1-[(4-methoxy-3-methylphenyl)sulfonyl]piperidin-
  3-yl}prop-2-enamide
N-[(3S)-1-{[6-(2-phenylethoxy)pyridin-3-yl]
  sulfonyl}piperidin-3-yl]prop-2-enamide
N-[(3S)-1-({5-[(acetylamino)methyl]thiophen-2-
  yl}sulfonyl)piperidin-3-yl]prop-2-enamide
N-{(3S)-1-[(5-methyl-1-phenyl-1H-pyrazol-4-yl)sulfonyl]
  piperidin-3-yl}prop-2-enamide
N-[(3S)-1-{[4-(1-methyl-1H-pyrazol-5-yl)phenyl]
  sulfonyl}piperidin-3-yl]prop-2-enamide
N-[(3S)-1-{[3-(1-methyl-1H-pyrazol-5-yl)phenyl]
  sulfonyl}piperidin-3-yl]prop-2-enamide
N-{(3S)-1-[(2,2-dimethyl-3,4-dihydro-2H-chromen-6-yl)
  sulfonyl]piperidin-3-yl}prop-2-enamide
N-{(3S)-1-[(5-phenylthiophen-2-yl)sulfonyl]piperidin-3-
  yl}prop-2-enamide
N-[(3S)-1-{[4-(cyclopentyloxy)phenyl]sulfonyl}piperidin-
  3-yl]prop-2-enamide
N-[(3S)-1-{[5-(pyrrolidin-1-ylcarbonyl)-1H-pyrrol-3-yl]
  sulfonyl}piperidin-3-yl]prop-2-enamide
N-[(3S)-1-{[4-(2-methyl-1,3-thiazol-4-yl)phenyl]
  sulfonyl}piperidin-3-yl]prop-2-enamide
N-[(3S)-1-{[4-(pyridin-2-yloxy)phenyl]sulfonyl}piperidin-
  3-yl]prop-2-enamide
N-{(3S)-1-[(2-oxo-1,2,3,4-tetrahydroquinolin-6-yl)sulfo-
  nyl]piperidin-3-yl}prop-2-enamide
N-({1-[(4-cyclohexylphenyl)sulfonyl]piperidin-4-
  yl}methyl)prop-2-enamide
N-[4-({4-[(acryloylamino)methyl]piperidin-1-yl}sulfonyl)
  phenyl]cyclopropanecarboxamide
N-[4-({4-[(acryloylamino)methyl]piperidin-1-yl}sulfonyl)
  phenyl]tricyclo[3.3.1.1~3,7~]decane-1-carboxamide
benzyl       [4-({4-[(acryloylamino)methyl]piperidin-1-
  yl}sulfonyl)phenyl]carbamate
N-[(1-{[4-(piperidin-1-ylcarbonyl)phenyl]
  sulfonyl}piperidin-4-yl)methyl]prop-2-enamide
benzyl       4-({4-[(acryloylamino)methyl]piperidin-1-
  yl}sulfonyl)piperidine-1-carboxylate
N-({1-[(4-nitrophenyl)sulfonyl]piperidin-4-yl}methyl)
  prop-2-enamide
N-[4-({4-[(acryloylamino)methyl]piperidin-1-yl}sulfonyl)
  phenyl]tetrahydro-2H-pyran-4-carboxamide
N-{[1-({4-[(3-phenylpropanoyl)amino]phenyl}sulfonyl)pi-
  peridin-4-yl]methyl}prop-2-enamide
N-[4-({4-[(acryloylamino)methyl]piperidin-1-yl}sulfonyl)
  phenyl]-2-phenylcyclopropanecarboxamide
N-[4-({4-[(acryloylamino)methyl]piperidin-1-yl}sulfonyl)
  phenyl]-N-methyltetrahydro-2H-pyran-4-carboxamide
4-({4-[(acryloylamino)methyl]piperidin-1-yl}sulfonyl)-N-
  benzyl-N-methylbenzamide
4-({4-[(acryloylamino)methyl]piperidin-1-yl}sulfonyl)-N-
  (cyclopropylmethyl)benzamide
N-[(1-{[3-(piperidin-1-ylcarbonyl)phenyl]
  sulfonyl}piperidin-4-yl)methyl]prop-2-enamide
N-[4-({4-[(acryloylamino)methyl]piperidin-1-yl}sulfonyl)
  phenyl]-N-methylcyclopropanecarboxamide
N-({1-[(4-{[4-(6-methylpyridin-2-yl)piperazin-1-yl]
  carbonyl}phenyl)sulfonyl]piperidin-4-yl}methyl)prop-2-
  enamide
4-({4-[(acryloylamino)methyl]piperidin-1-yl}sulfonyl)-N-
  [2-(morpholin-4-yl)ethyl]benzamide
4-({4-[(acryloylamino)methyl]piperidin-1-yl}sulfonyl)-N-
  (2-phenylethyl)benzamide
4-({4-[(acryloylamino)methyl]piperidin-1-yl}sulfonyl)-N-
  methyl-N-(2-phenylethyl)benzamide
N-[(1-{[4-(3,4-dihydroisoquinolin-2(1H)-ylcarbonyl)phe-
  nyl]sulfonyl}piperidin-4-yl)methyl]prop-2-enamide
4-({4-[(acryloylamino)methyl]piperidin-1-yl}sulfonyl)-N-
  (2-cyclohexylethyl)benzamide
4-({4-[(acryloylamino)methyl]piperidin-1-yl}sulfonyl)-N-
  cyclohexylbenzamide
N-({1-[(4-{[4-(pyrrolidin-1-ylcarbonyl)piperidin-1-yl]
  carbonyl}phenyl)sulfonyl]piperidin-4-yl}methyl)prop-2-
  enamide
4-({4-[(acryloylamino)methyl]piperidin-1-yl}sulfonyl)-N-
  (3,5-dimethylbenzyl)benzamide
4-({4-[(acryloylamino)methyl]piperidin-1-yl}sulfonyl)-N-
  benzylbenzamide
4-({4-[(acryloylamino)methyl]piperidin-1-yl}sulfonyl)-N-
  (3,4-difluorobenzyl)benzamide
4-({4-[(acryloylamino)methyl]piperidin-1-yl}sulfonyl)-N-
  [4-(trifluoromethyl)benzyl]benzamide 4-({4-[(acryloylamino)methyl]piperidin-1-yl}sulfonyl)-N-(naphthalen-1-ylmethyl)benzamide
4-({4-[(acryloylamino)methyl]piperidin-1-yl}sulfonyl)-N-[2-(3,4-dimethylphenyl)ethyl]benzamide
4-({4-[(acryloylamino)methyl]piperidin-1-yl}sulfonyl)-N-[2-(4-methoxyphenyl)ethyl]benzamide
4-({4-[(acryloylamino)methyl]piperidin-1-yl}sulfonyl)-N-(2,3-dihydro-1H-inden-2-yl)benzamide
4-({4-[(acryloylamino)methyl]piperidin-1-yl}sulfonyl)-N-[2-(3-methylphenyl)ethyl]benzamide
N-{[1-({4-[(acetylamino)methyl]phenyl}sulfonyl)piperidin-4-yl]methyl}prop-2-enamide
N-({1-[(4-{[3-(naphthalen-1-yl)propanoyl]amino}phenyl)sulfonyl]piperidin-4-yl}methyl)prop-2-enamide
N-{[1-({4-[(3-cyclohexylpropanoyl)amino]phenyl}sulfonyl)piperidin-4-yl]methyl}prop-2-enamide
N-({1-[(1-benzoylpiperidin-4-yl)sulfonyl]piperidin-4-yl}methyl)prop-2-enamide
N-[(1-{[1-(piperidin-1-ylcarbonyl)piperidin-4-yl]sulfonyl}piperidin-4-yl)methyl]prop-2-enamide
N-[(1-{[1-(pyridin-2-ylcarbonyl)piperidin-4-yl]sulfonyl}piperidin-4-yl)methyl]prop-2-enamide
N-[4-({4-[(acryloylamino)methyl]piperidin-1-yl}sulfonyl)phenyl]-4-tert-butylcyclohexanecarboxamide
N-[4-({4-[(acryloylamino)methyl]piperidin-1-yl}sulfonyl)phenyl]-1-benzofuran-2-carboxamide
benzyl [3-({4-[(acryloylamino)methyl]piperidin-1-yl}sulfonyl)phenyl]carbamate
N-{[1-({3-[(3-phenylpropanoyl)amino]phenyl}sulfonyl)piperidin-4-yl]methyl}prop-2-enamide
N-[3-({4-[(acryloylamino)methyl]piperidin-1-yl}sulfonyl)phenyl]tetrahydro-2H-pyran-4-carboxamide
4-({4-[(acryloylamino)methyl]piperidin-1-yl}sulfonyl)-N-(3-phenylpropyl)benzamide
4-({4-[(acryloylamino)methyl]piperidin-1-yl}sulfonyl)-N-[2-(3-chlorophenyl)ethyl]benzamide
4-({4-[(acryloylamino)methyl]piperidin-1-yl}sulfonyl)-N-[2-(2-methoxyphenyl)ethyl]benzamide
4-({4-[(acryloylamino)methyl]piperidin-1-yl}sulfonyl)-N-[2-(2,3-dihydro-1-benzofuran-7-yl)ethyl]benzamide
4-({4-[(acryloylamino)methyl]piperidin-1-yl}sulfonyl)-N-[2-(tetrahydro-2H-pyran-4-yl)ethyl]benzamide
4-({4-[(acryloylamino)methyl]piperidin-1-yl}sulfonyl)-N-[2-(4,4-difluoropiperidin-1-yl)ethyl]benzamide
N-{[1-({1-[3-(trifluoromethyl)benzoyl]piperidin-4-yl}sulfonyl)piperidin-4-yl]methyl}prop-2-enamide
N-[(1-{[1-(3-phenylpropanoyl)piperidin-4-yl]sulfonyl}piperidin-4-yl)methyl]prop-2-enamide
N-{[1-({4-[2-(benzylamino)-2-oxoethyl]phenyl}sulfonyl)piperidin-4-yl]methyl}prop-2-enamide
4-({4-[(acryloylamino)methyl]piperidin-1-yl}sulfonyl)-N-(4-tert-butylbenzyl)benzamide
4-({4-[(acryloylamino)methyl]piperidin-1-yl}sulfonyl)-N-(4-phenylbutyl)benzamide
4-({4-[(acryloylamino)methyl]piperidin-1-yl}sulfonyl)-N-[2-(4-chlorophenyl)ethyl]benzamide
4-({4-[(acryloylamino)methyl]piperidin-1-yl}sulfonyl)-N-[2-(quinolin-7-yl)ethyl]benzamide
4-({4-[(acryloylamino)methyl]piperidin-1-yl}sulfonyl)-N-[2-(naphthalen-2-yl)ethyl]benzamide
4-({4-[(acryloylamino)methyl]piperidin-1-yl}sulfonyl)-N-(3,4-dihydro-2H-chromen-6-ylmethyl)benzamide
4-({4-[(acryloylamino)methyl]piperidin-1-yl}sulfonyl)-N-[2-(4-tert-butylphenyl)ethyl]benzamide
4-({4-[(acryloylamino)methyl]piperidin-1-yl}sulfonyl)-N-[2-(biphenyl-4-yl)ethyl]benzamide
4-({4-[(acryloylamino)methyl]piperidin-1-yl}sulfonyl)-N-[2-(1,3-benzodioxol-5-yl)ethyl]benzamide
4-({4-[(acryloylamino)methyl]piperidin-1-yl}sulfonyl)-N-[(1R)-2-phenylcyclopropyl]benzamide
benzyl [4-({4-[(acryloylamino)methyl]piperidin-1-yl}sulfonyl)phenyl]methylcarbamate
4-({4-[(acryloylamino)methyl]piperidin-1-yl}sulfonyl)-N-[2-(3,4-dimethoxyphenyl)ethyl]benzamide
4-({4-[(acryloylamino)methyl]piperidin-1-yl}sulfonyl)-N-{2-[4-(trifluoromethyl)phenyl]ethyl}benzamide
4-({4-[(acryloylamino)methyl]piperidin-1-yl}sulfonyl)-N-(2-phenylethyl)piperidine-1-carboxamide
N-[4-({4-[(acryloylamino)methyl]piperidin-1-yl}sulfonyl)phenyl]furan-2-carboxamide
N-({1-[(4-{[3-(tricyclo[3.3.1.1~3,7~]dec-1-yl)propanoyl]amino}phenyl)sulfonyl]piperidin-4-yl}methyl)prop-2-enamide
4-({4-[(acryloylamino)methyl]piperidin-1-yl}sulfonyl)-N-[2-(tricyclo[3.3.1.1~3,7~]dec-1-yl)ethyl]benzamide
N-[(1-{[1-(cyclopropylcarbonyl)-2,3-dihydro-1H-indol-5-yl]sulfonyl}piperidin-4-yl)methyl]prop-2-enamide
N-{[1-({2-chloro-4-[(3-phenylpropanoyl)amino]phenyl}sulfonyl)piperidin-4-yl]methyl}prop-2-enamide
N-[4-({4-[(acryloylamino)methyl]piperidin-1-yl}sulfonyl)phenyl]-5,6-dihydro-4H-cyclopenta[b]thiophene-2-carboxamide
N-[4-({4-[(acryloylamino)methyl]piperidin-1-yl}sulfonyl)phenyl]-4,5,6,7-tetrahydro-1H-indole-2-carboxamide
N-{[1-({2-methoxy-4-[(3-phenylpropanoyl)amino]phenyl}sulfonyl)piperidin-4-yl]methyl}prop-2-enamide
N-[4-({4-[(acryloylamino)methyl]piperidin-1-yl}sulfonyl)phenyl]-5-(pyrrolidin-1-ylmethyl)furan-2-carboxamide
N-[4-({4-[(acryloylamino)methyl]piperidin-1-yl}sulfonyl)phenyl]-1-benzothiophene-2-carboxamide
N-[4-({4-[(acryloylamino)methyl]piperidin-1-yl}sulfonyl)phenyl]-3-methyl-1-benzofuran-2-carboxamide
N-[4-({4-[(acryloylamino)methyl]piperidin-1-yl}sulfonyl)phenyl]-1H-indole-2-carboxamide
4-({4-[(acryloylamino)methyl]piperidin-1-yl}sulfonyl)-N-(tricyclo[3.3.1.1~3,7~]dec-1-ylmethyl)benzamide
4-({4-[(acryloylamino)methyl]piperidin-1-yl}sulfonyl)-N-(1,2,3,4-tetrahydronaphthalen--yl)benzamide
N-[4-({4-[(acryloylamino)methyl]piperidin-1-yl}sulfonyl)phenyl]-4,5,6,7-tetrahydro-1-benzothiophene-2-carboxamide
N-[4-({4-[(acryloylamino)methyl]piperidin-1-yl}sulfonyl)phenyl]-5-phenylfuran-2-carboxamide
N-[4-({4-[(acryloylamino)methyl]piperidin-1-yl}sulfonyl)phenyl]-4-phenylthiophene-2-carboxamide
N-{[1-({5-[5-(trifluoromethyl)-1,2-oxazol-3-yl]thiophen-2-yl}sulfonyl)piperidin-4-yl]methyl}prop-2-enamide
5-({4-[(acryloylamino)methyl]piperidin-1-yl}sulfonyl)-N-(2-phenylethyl)furan-2-carboxamide
N-({1-[(6-phenoxypyridin-3-yl)sulfonyl]piperidin-4-yl}methyl)prop-2-enamide
N-[(1-{[6-(morpholin-4-yl)pyridin-3-yl]sulfonyl}piperidin-4-yl)methyl]prop-2-enamide
N-({1-[(6-phenylpyridin-3-yl)sulfonyl]piperidin-4-yl}methyl)prop-2-enamide
N-{[1-({3-chloro-4-[(3-phenylpropanoyl)amino]phenyl}sulfonyl)piperidin-4-yl]methyl}prop-2-enamide
4-({4-[(acryloylamino)methyl]piperidin-1-yl}sulfonyl)-2-fluoro-N-(2-phenylethyl)benzamide
N-[(1-{[5-(pyridin-2-yl)thiophen-2-yl]sulfonyl}piperidin-4-yl)methyl]prop-2-enamide
4-({4-[(acryloylamino)methyl]piperidin-1-yl}sulfonyl)-2-methoxy-N-(2-phenylethyl)benzamide N-{[1-(1,3-benzothiazol-6-ylsulfonyl)piperidin-4-yl]methyl}prop-2-enamide
N-({1-[(4-methyl-2-phenyl-1,3-thiazol-5-yl)sulfonyl]piperidin-4-yl}methyl)prop-2-enamide
N-[(1-{[5-(2-methyl-1,3-thiazol-4-yl)thiophen-2-yl]sulfonyl}piperidin-4-yl)methyl]prop-2-enamide
N-[(1-{[5-(1,2-oxazol-5-yl)thiophen-2-yl]sulfonyl}piperidin-4-yl)methyl]prop-2-enamide
N-{[1-(2,3-dihydro-1,4-benzodioxin-6-ylsulfonyl)piperidin-4-yl]methyl}prop-2-enamide
5-({4-[(acryloylamino)methyl]piperidin-1-yl}sulfonyl)-N-(2-phenylethyl)furan-3-carboxamide
N-{[1-({4-[(phenylacetyl)amino]benzyl}sulfonyl)piperidin-4-yl]methyl}prop-2-enamide
N-[(1-{[4-(morpholin-4-ylsulfonyl)phenyl]sulfonyl}piperidin-4-yl)methyl]prop-2-enamide
N-[(1-{[5-(1,3-oxazol-5-yl)thiophen-2-yl]sulfonyl}piperidin-4-yl)methyl]prop-2-enamide
4-({4-[(acryloylamino)methyl]piperidin-1-yl}sulfonyl)-2-methyl-N-(2-phenylethyl)benzamide
N-({1-[(4-phenoxyphenyl)sulfonyl]piperidin-4-yl}methyl)prop-2-enamide
N-{[1-({4-[(6-methylpyrazin-2-yl)oxy]phenyl}sulfonyl)piperidin-4-yl]methyl}prop-2-enamide
N-{[1-({3-[(6-methylpyrazin-2-yl)oxy]phenyl}sulfonyl)piperidin-4-yl]methyl}prop-2-enamide
5-({4-[(acryloylamino)methyl]piperidin-1-yl}sulfonyl)-1-methyl-N-(2-phenylethyl)-1H-pyrrole-2-carboxamide
N-[(1-{[4-(isoquinolin-3-ylamino)phenyl]sulfonyl}piperidin-4-yl)methyl]prop-2-enamide
N-({1-[(3-chloro-4-methylphenyl)sulfonyl]piperidin-4-yl}methyl)prop-2-enamide
N-[(1-{[5-(1,2-oxazol-5-yl)furan-2-yl]sulfonyl}piperidin-4-yl)methyl]prop-2-enamide
N-({1-[(4-{[3-chloro-5-(trifluoromethyl)pyridin-2-yl]oxy}phenyl)sulfonyl]piperidin-4-yl}methyl)prop-2-enamide
N-[(1-{[4-(1H-pyrazol-1-yl)phenyl]sulfonyl}piperidin-4-yl)methyl]prop-2-enamide
N-({1-[(4-methoxy-3-methylphenyl)sulfonyl]piperidin-4-yl}methyl)prop-2-enamide
N-[(1-{[6-(2-phenylethoxy)pyridin-3-yl]sulfonyl}piperidin-4-yl)methyl]prop-2-enamide
N-{[1-({5-[(acetylamino)methyl]thiophen-2-yl}sulfonyl)piperidin-4-yl]methyl}prop-2-enamide
N-({1-[(5-methyl-1-phenyl-1H-pyrazol-4-yl)sulfonyl]piperidin-4-yl}methyl)prop-2-enamide
N-[(1-{[4-(1-methyl-1H-pyrazol-5-yl)phenyl]sulfonyl}piperidin-4-yl)methyl]prop-2-enamide
N-[(1-{[3-(1-methyl-1H-pyrazol-5-yl)phenyl]sulfonyl}piperidin-4-yl)methyl]prop-2-enamide
N-({1-[(2,2-dimethyl-3,4-dihydro-2H-chromen-6-yl)sulfonyl]piperidin-4-yl}methyl)prop-2-enamide
N-({1-[(5-phenylthiophen-2-yl)sulfonyl]piperidin-4-yl}methyl)prop-2-enamide
N-[(1-{[4-(cyclopentyloxy)phenyl]sulfonyl}piperidin-4-yl)methyl]prop-2-enamide
N-[(1-{[5-(pyrrolidin-1-ylcarbonyl)-1H-pyrrol-3-yl]sulfonyl}piperidin-4-yl)methyl]prop-2-enamide
N-[(1-{[4-(2-methyl-1,3-thiazol-4-yl)phenyl]sulfonyl}piperidin-4-yl)methyl]prop-2-enamide
N-[(1-{[4-(pyridin-2-yloxy)phenyl]sulfonyl}piperidin-4-yl)methyl]prop-2-enamide
N-({1-[(2-oxo-1,2,3,4-tetrahydroquinolin-6-yl)sulfonyl]piperidin-4-yl}methyl)prop-2-enamide
N-{1-[(4-cyclohexylphenyl)sulfonyl]piperidin-4-yl}prop-2-enamide
N-(4-{[4-(acryloylamino)piperidin-1-yl]sulfonyl}phenyl)cyclopropanecarboxamide
N-(4-{[4-(acryloylamino)piperidin-1-yl]sulfonyl}phenyl)tricyclo[3.3.1.1~3,7~]decane-1-carboxamide
benzyl(4-{[4-(acryloylamino)piperidin-1-yl]sulfonyl}phenyl)carbamate
N-(1-{[4-(piperidin-1-ylcarbonyl)phenyl]sulfonyl}piperidin-4-yl)prop-2-enamide
benzyl 4-{[4-(acryloylamino)piperidin-1-yl]sulfonyl}piperidine-1-carboxylate
N-{1-[(4-nitrophenyl)sulfonyl]piperidin-4-yl}prop-2-enamide
N-(4-{[4-(acryloylamino)piperidin-1-yl]sulfonyl}phenyl)tetrahydro-2H-pyran-4-carboxamide
N-[1-({4-[(3-phenylpropanoyl)amino]phenyl}sulfonyl)piperidin-4-yl]prop-2-enamide
N-(4-{[4-(acryloylamino)piperidin-1-yl]sulfonyl}phenyl)-2-phenylcyclopropanecarboxamide
N-(4-{[4-(acryloylamino)piperidin-1-yl]sulfonyl}phenyl)-N-methyltetrahydro-2H-pyran-4-carboxamide
4-{[4-(acryloylamino)piperidin-1-yl]sulfonyl}-N-benzyl-N-methylbenzamide
4-{[4-(acryloylamino)piperidin-1-yl]sulfonyl}-N-(cyclopropylmethyl)benzamide
N-(1-{[3-(piperidin-1-ylcarbonyl)phenyl]sulfonyl}piperidin-4-yl)prop-2-enamide
N-(4-{[4-(acryloylamino)piperidin-1-yl]sulfonyl}phenyl)-N-methylcyclopropanecarboxamide
N-{1-[(4-{[4-(6-methylpyridin-2-yl)piperazin-1-yl]carbonyl}phenyl)sulfonyl]piperidin-4-yl}prop-2-enamide
4-{[4-(acryloylamino)piperidin-1-yl]sulfonyl}-N-[2-(morpholin-4-yl)ethyl]benzamide
4-{[4-(acryloylamino)piperidin-1-yl]sulfonyl}-N-(2-phenylethyl)benzamide
4-{[4-(acryloylamino)piperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}piperidin-4-yl)prop-2-enamide
4-{[4-(acryloylamino)piperidin-1-yl]sulfonyl}-N-(2-cyclohexylethyl)benzamide
4-{[4-(acryloylamino)piperidin-1-yl]sulfonyl}-N-cyclohexylbenzamide
N-{1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)piperidin-1-yl]sulfonyl}-N-(3,5-dimethylbenzyl)benzamide
4-{[4-(acryloylamino)piperidin-1-yl]sulfonyl}-N-benzylbenzamide
4-{[4-(acryloylamino)piperidin-1-yl]sulfonyl}-N-(3,4-difluorobenzyl)benzamide
4-{[4-(acryloylamino)piperidin-1-yl]sulfonyl}-N-[4-(trifluoromethyl)benzyl]benzamide
4-{[4-(acryloylamino)piperidin-1-yl]sulfonyl}-N-(naphthalen-1-ylmethyl)benzamide
4-{[4-(acryloylamino)piperidin-1-yl]sulfonyl}-N-[2-(3,4-dimethylphenyl)ethyl]benzamide
4-{[4-(acryloylamino)piperidin-1-yl]sulfonyl}-N-[2-(4-methoxyphenyl)ethyl]benzamide
4-{[4-(acryloylamino)piperidin-1-yl]sulfonyl}-N-(2,3-dihydro-1H-inden-2-yl)benzamide
4-{[4-(acryloylamino)piperidin-1-yl]sulfonyl}-N-[2-(3-methylphenyl)ethyl]benzamide
N-[1-({4-[(acetylamino)methyl]phenyl}sulfonyl)piperidin-4-yl]prop-2-enamide N-{1-[(4-{[3-(naphthalen-1-yl)propanoyl]amino}phenyl)sulfonyl]piperidin-4-yl}prop-2-enamide
N-[1-({4-[(3-cyclohexylpropanoyl)amino]phenyl}sulfonyl)piperidin-4-yl]prop-2-enamide
N-{1-[(1-benzoylpiperidin-4-yl)sulfonyl]piperidin-4-yl}prop-2-enamide
N-(1-{[1-(piperidin-1-ylcarbonyl)piperidin-4-yl]sulfonyl}piperidin-4-yl)prop-2-enamide
N-(1-{[1-(pyridin-2-ylcarbonyl)piperidin-4-yl]sulfonyl}piperidin-4-yl)prop-2-enamide
N-(4-{[4-(acryloylamino)piperidin-1-yl]sulfonyl}phenyl)-4-tert-butylcyclohexanecarboxamide
N-(4-{[4-(acryloylamino)piperidin-1-yl]sulfonyl}phenyl)-1-benzofuran-2-carboxamide
benzyl(3-{[4-(acryloylamino)piperidin-1-yl]sulfonyl}phenyl)carbamate
N-[1-({3-[(3-phenylpropanoyl)amino]phenyl}sulfonyl)piperidin-4-yl]prop-2-enamide
N-(3-{[4-(acryloylamino)piperidin-1-yl]sulfonyl}phenyl)tetrahydro-2H-pyran-4-carboxamide
4-{[4-(acryloylamino)piperidin-1-yl]sulfonyl}-N-(3-phenylpropyl)benzamide
4-{[4-(acryloylamino)piperidin-1-yl]sulfonyl}-N-[2-(3-chlorophenyl)ethyl]benzamide
4-{[4-(acryloylamino)piperidin-1-yl]sulfonyl}-N-[2-(2-methoxyphenyl)ethyl]benzamide
4-{[4-(acryloylamino)piperidin-1-yl]sulfonyl}-N-[2-(2,3-dihydro-1-benzofuran-7-yl)ethyl]benzamide
4-{[4-(acryloylamino)piperidin-1-yl]sulfonyl}-N-[2-(tetrahydro-2H-pyran-4-yl)ethyl]benzamide
4-{[4-(acryloylamino)piperidin-1-yl]sulfonyl}-N-[2-(4,4-difluoropiperidin-1-yl)ethyl]benzamide
N-[1-({1-[3-(trifluoromethyl)benzoyl]piperidin-4-yl}sulfonyl)piperidin-4-yl]prop-2-enamide
N-(1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)piperidin-4-yl]prop-2-enamide
4-{[4-(acryloylamino)piperidin-1-yl]sulfonyl}-N-(4-tert-butylbenzyl)benzamide
4-{[4-(acryloylamino)piperidin-1-yl]sulfonyl}-N-(4-phenylbutyl)benzamide
4-{[4-(acryloylamino)piperidin-1-yl]sulfonyl}-N-[2-(4-chlorophenyl)ethyl]benzamide
4-{[4-(acryloylamino)piperidin-1-yl]sulfonyl}-N-[2-(quinolin-7-yl)ethyl]benzamide
4-{[4-(acryloylamino)piperidin-1-yl]sulfonyl}-N-[2-(naphthalen-2-yl)ethyl]benzamide
4-{[4-(acryloylamino)piperidin-1-yl]sulfonyl}-N-(3,4-dihydro-2H-chromen-6-ylmethyl)benzamide
4-{[4-(acryloylamino)piperidin-1-yl]sulfonyl}-N-[2-(4-tert-butylphenyl)ethyl]benzamide
4-{[4-(acryloylamino)piperidin-1-yl]sulfonyl}-N-[2-(biphenyl-4-yl)ethyl]benzamide
4-{[4-(acryloylamino)piperidin-1-yl]sulfonyl}-N-[2-(1,3-benzodioxol-5-yl)ethyl]benzamide
4-{[4-(acryloylamino)piperidin-1-yl]sulfonyl}-N-[(1R)-2-phenylcyclopropyl]benzamide
benzyl(4-{[4-(acryloylamino)piperidin-1-yl]sulfonyl}phenyl)methylcarbamate
4-{[4-(acryloylamino)piperidin-1-yl]sulfonyl}-N-[2-(3,4-dimethoxyphenyl)ethyl]benzamide
4-{[4-(acryloylamino)piperidin-1-yl]sulfonyl}-N-{2-[4-(trifluoromethyl)phenyl]ethyl}benzamide
4-{[4-(acryloylamino)piperidin-1-yl]sulfonyl}-N-(2-phenylethyl)piperidine-1-carboxamide
N-(4-{[4-(acryloylamino)piperidin-1-yl]sulfonyl}phenyl)furan-2-carboxamide
N-{1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)piperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}piperidin-4-yl)prop-2-enamide
N-[1-({2-chloro-4-[(3-phenylpropanoyl)amino]phenyl}sulfonyl)piperidin-4-yl]prop-2-enamide
N-(4-{[4-(acryloylamino)piperidin-1-yl]sulfonyl}phenyl)-5,6-dihydro-4H-cyclopenta[b]thiophene-2-carboxamide
N-(4-{[4-(acryloylamino)piperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)piperidin-4-yl]prop-2-enamide
N-(4-{[4-(acryloylamino)piperidin-1-yl]sulfonyl}phenyl)-5-(pyrrolidin-1-ylmethyl)furan-2-carboxamide
N-(4-{[4-(acryloylamino)piperidin-1-yl]sulfonyl}phenyl)-1-benzothiophene-2-carboxamide
N-(4-{[4-(acryloylamino)piperidin-1-yl]sulfonyl}phenyl)-3-methyl-1-benzofuran-2-carboxamide
N-(4-{[4-(acryloylamino)piperidin-1-yl]sulfonyl}phenyl)-1H-indole-2-carboxamide
4-{[4-(acryloylamino)piperidin-1-yl]sulfonyl}-N-(tricyclo[3.3.1.1~3,7~]dec-1-ylmethyl)benzamide
4-{[4-(acryloylamino)piperidin-1-yl]sulfonyl}-N-(1,2,3,4-tetrahydronaphthalen-1-yl)benzamide
N-(4-{[4-(acryloylamino)piperidin-1-yl]sulfonyl}phenyl)-4,5,6,7-tetrahydro-1-benzothiophene-2-carboxamide
N-(4-{[4-(acryloylamino)piperidin-1-yl]sulfonyl}phenyl)-5-phenylfuran-2-carboxamide
N-(4-{[4-(acryloylamino)piperidin-1-yl]sulfonyl}phenyl)-4-phenylthiophene-2-carboxamide
N-[1-({5-[5-(trifluoromethyl)-1,2-oxazol-3-yl]thiophen-2-yl}sulfonyl)piperidin-4-yl]prop-2-enamide
5-{[4-(acryloylamino)piperidin-1-yl]sulfonyl}-N-(2-phenylethyl)furan-2-carboxamide
N-{1-[(6-phenoxypyridin-3-yl)sulfonyl]piperidin-4-yl}prop-2-enamide
N-(1-{[6-(morpholin-4-yl)pyridin-3-yl]sulfonyl}piperidin-4-yl)prop-2-enamide
N-{1-[(6-phenylpyridin-3-yl)sulfonyl]piperidin-4-yl}prop-2-enamide
N-[1-({3-chloro-4-[(3-phenylpropanoyl)amino]phenyl}sulfonyl)piperidin-4-yl]prop-2-enamide
4-{[4-(acryloylamino)piperidin-1-yl]sulfonyl}-2-fluoro-N-(2-phenylethyl)benzamide
N-(1-{[5-(pyridin-2-yl)thiophen-2-yl]sulfonyl}piperidin-4-yl)prop-2-enamide
4-{[4-(acryloylamino)piperidin-1-yl]sulfonyl}-2-methoxy-N-(2-phenylethyl)benzamide
N-[1-(1,3-benzothiazol-6-ylsulfonyl)piperidin-4-yl]prop-2-enamide
N-{1-[(4-methyl-2-phenyl-1,3-thiazol-5-yl)sulfonyl]piperidin-4-yl}prop-2-enamide
N-(1-{[5-(2-methyl-1,3-thiazol-4-yl)thiophen-2-yl]sulfonyl}piperidin-4-yl)prop-2-enamide
N-(1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)piperidin-4-yl]prop-2-enamide
5-{[4-(acryloylamino)piperidin-1-yl]sulfonyl}-N-(2-phenylethyl)furan-3-carboxamide
N-[1-({4-[(phenylacetyl)amino]benzyl}sulfonyl)piperidin-4-yl]prop-2-enamide N-(1-{[4-(morpholin-4-ylsulfonyl)phenyl]
sulfonyl}piperidin-4-yl)prop-2-enamide
N-(1-{[5-(1,3-oxazol-5-yl)thiophen-2-yl]
sulfonyl}piperidin-4-yl)prop-2-enamide
4-{[4-(acryloylamino)piperidin-1-yl]sulfonyl}-2-methyl-N-
(2-phenylethyl)benzamide
N-{1-[(4-phenoxyphenyl)sulfonyl]piperidin-4-yl}prop-2-
enamide
N-[1-({4-[(6-methylpyrazin-2-yl)oxy]phenyl}sulfonyl)pip-
eridin-4-yl]prop-2-enamide
N-[1-({3-[(6-methylpyrazin-2-yl)oxy]phenyl}sulfonyl)pip-
eridin-4-yl]prop-2-enamide
5-{[4-(acryloylamino)piperidin-1-yl]sulfonyl}-1-methyl-N-
(2-phenylethyl)-1H-pyrrole-2-carboxamide
N-(1-{[4-(isoquinolin-3-ylamino)phenyl]
sulfonyl}piperidin-4-yl)prop-2-enamide
N-{1-[(3-chloro-4-methylphenyl)sulfonyl]piperidin-4-
yl}prop-2-enamide
N-(1-{[5-(1,2-oxazol-5-yl)furan-2-yl]sulfonyl}piperidin-4-
yl)prop-2-enamide
N-{1-[(4-{[3-chloro-5-(trifluoromethyl)pyridin-2-yl]
oxy}phenyl)sulfonyl]piperidin-4-yl}prop-2-enamide
N-(1-{[4-(1H-pyrazol-1-yl)phenyl]sulfonyl}piperidin-4-yl)
prop-2-enamide
N-{1-[(4-methoxy-3-methylphenyl)sulfonyl]piperidin-4-
yl}prop-2-enamide
N-(1-{[6-(2-phenylethoxy)pyridin-3-yl]sulfonyl}piperidin-
4-yl)prop-2-enamide
N-[1-({5-[(acetylamino)methyl]thiophen-2-yl}sulfonyl)pip-
eridin-4-yl]prop-2-enamide
N-{1-[(5-methyl-1-phenyl-1H-pyrazol-4-yl)sulfonyl]piperi-
din-4-yl}prop-2-enamide
N-(1-{[4-(1-methyl-1H-pyrazol-5-yl)phenyl]
sulfonyl}piperidin-4-yl)prop-2-enamide
N-(1-{[3-(1-methyl-1H-pyrazol-5-yl)phenyl]
sulfonyl}piperidin-4-yl)prop-2-enamide
N-{1-[(2,2-dimethyl-3,4-dihydro-2H-chromen-6-yl)sulfo-
nyl]piperidin-4-yl}prop-2-enamide
N-{1-[(5-phenylthiophen-2-yl)sulfonyl]piperidin-4-
yl}prop-2-enamide
N-(1-{[4-(cyclopentyloxy)phenyl]sulfonyl}piperidin-4-yl)
prop-2-enamide
N-(1-{[5-(pyrrolidin-1-ylcarbonyl)-1H-pyrrol-3-yl]
sulfonyl}piperidin-4-yl)prop-2-enamide
N-(1-{[4-(2-methyl-1,3-thiazol-4-yl)phenyl]
sulfonyl}piperidin-4-yl)prop-2-enamide
N-(1-{[4-(pyridin-2-yloxy)phenyl]sulfonyl}piperidin-4-yl)
prop-2-enamide
N-{1-[(2-oxo-1,2,3,4-tetrahydroquinolin-6-yl)sulfonyl]pip-
eridin-4-yl}prop-2-enamide
N-{1-[(4-cyclohexylphenyl)sulfonyl]-3,3,5,5-tetramethylpi-
peridin-4-yl}prop-2-enamide
N-(4-{[4-(acryloylamino)-3,3,5,5-tetramethylpiperidin-1-
yl]sulfonyl}phenyl)cyclopropanecarboxamide
N-(4-{[4-(acryloylamino)-3,3,5,5-tetramethylpiperidin-1-
yl]sulfonyl}phenyl)tricyclo[3.3.1.1~3,7~]decane-1-car-
boxamide
benzyl(4-{[4-(acryloylamino)-3,3,5,5-tetramethylpiperidin-
1-yl]sulfonyl}phenyl)carbamate
N-(3,3,5,5-tetramethyl-1-{[4-(piperidin-1-ylcarbonyl)phe-
nyl]sulfonyl}piperidin-4-yl)prop-2-enamide
benzyl 4-{[4-(acryloylamino)-3,3,5,5-tetramethylpiperidin-
1-yl]sulfonyl}piperidine-1-carboxylate
N-{3,3,5,5-tetramethyl-1-[(4-nitrophenyl)sulfonyl]piperi-
din-4-yl}prop-2-enamide
N-(4-{[4-(acryloylamino)-3,3,5,5-tetramethylpiperidin-1-
yl]sulfonyl}phenyl)tetrahydro-2H-pyran-4-carboxamide
N-[3,3,5,5-tetramethyl-1-({4-[(3-phenylpropanoyl)amino]
phenyl}sulfonyl)piperidin-4-yl]prop-2-enamide
N-(4-{[4-(acryloylamino)-3,3,5,5-tetramethylpiperidin-1-
yl]sulfonyl}phenyl)-2-phenylcyclopropanecarboxamide
N-(4-{[4-(acryloylamino)-3,3,5,5-tetramethylpiperidin-1-
yl]sulfonyl}phenyl)-N-methyltetrahydro-2H-pyran-4-
carboxamide
4-{[4-(acryloylamino)-3,3,5,5-tetramethylpiperidin-1-yl]
sulfonyl}-N-benzyl-N-methylbenzamide
4-{[4-(acryloylamino)-3,3,5,5-tetramethylpiperidin-1-yl]
sulfonyl}-N-(cyclopropylmethyl)benzamide
N-(3,3,5,5-tetramethyl-1-{[3-(piperidin-1-ylcarbonyl)phe-
nyl]sulfonyl}piperidin-4-yl)prop-2-enamide
N-(4-{[4-(acryloylamino)-3,3,5,5-tetramethylpiperidin-1-
yl]sulfonyl}phenyl)-N-methylcyclopropanecarboxamide
N-{3,3,5,5-tetramethyl-1-[(4-{[4-(6-methylpyridin-2-yl)
piperazin-1-yl]carbonyl}phenyl)sulfonyl]piperidin-4-
yl}prop-2-enamide
4-{[4-(acryloylamino)-3,3,5,5-tetramethylpiperidin-1-yl]
sulfonyl}-N-[2-(morpholin-4-yl)ethyl]benzamide
4-{[4-(acryloylamino)-3,3,5,5-tetramethylpiperidin-1-yl]
sulfonyl}-N-(2-phenylethyl)benzamide
4-{[4-(acryloylamino)-3,3,5,5-tetramethylpiperidin-1-yl]
sulfonyl}-N-methyl-N-(2-phenylethyl)benzamide
N-(1-{[4-(3,4-dihydroisoquinolin-2(1H)-ylcarbonyl)phe-
nyl]sulfonyl}-3,3,5,5-tetramethylpiperidin-4-yl)prop-2-
enamide
4-{[4-(acryloylamino)-3,3,5,5-tetramethylpiperidin-1-yl]
sulfonyl}-N-(2-cyclohexylethyl)benzamide
4-{[4-(acryloylamino)-3,3,5,5-tetramethylpiperidin-1-yl]
sulfonyl}-N-cyclohexylbenzamide
N-{3,3,5,5-tetramethyl-1-[(4-{[4-(pyrrolidin-1-ylcarbonyl)
piperidin-1-yl]carbonyl}phenyl)sulfonyl]piperidin-4-
yl}prop-2-enamide
4-{[4-(acryloylamino)-3,3,5,5-tetramethylpiperidin-1-yl]
sulfonyl}-N-(3,5-dimethylbenzyl)benzamide
4-{[4-(acryloylamino)-3,3,5,5-tetramethylpiperidin-1-yl]
sulfonyl}-N-benzylbenzamide
4-{[4-(acryloylamino)-3,3,5,5-tetramethylpiperidin-1-yl]
sulfonyl}-N-(3,4-difluorobenzyl)benzamide
4-{[4-(acryloylamino)-3,3,5,5-tetramethylpiperidin-1-yl]
sulfonyl}-N-[4-(trifluoromethyl)benzyl]benzamide
4-{[4-(acryloylamino)-3,3,5,5-tetramethylpiperidin-1-yl]
sulfonyl}-N-(naphthalen-1-ylmethyl)benzamide
4-{[4-(acryloylamino)-3,3,5,5-tetramethylpiperidin-1-yl]
sulfonyl}-N-[2-(3,4-dimethylphenyl)ethyl]benzamide
4-{[4-(acryloylamino)-3,3,5,5-tetramethylpiperidin-1-yl]
sulfonyl}-N-[2-(4-methoxyphenyl)ethyl]benzamide
4-{[4-(acryloylamino)-3,3,5,5-tetramethylpiperidin-1-yl]
sulfonyl}-N-(2,3-dihydro-1H-inden-2-yl)benzamide
4-{[4-(acryloylamino)-3,3,5,5-tetramethylpiperidin-1-yl]
sulfonyl}-N-[2-(3-methylphenyl)ethyl]benzamide
N-[1-({4-[(acetylamino)methyl]phenyl}sulfonyl)-3,3,5,5-
tetramethylpiperidin-4-yl]prop-2-enamide
N-{3,3,5,5-tetramethyl-1-[(4-{[3-(naphthalen-1-yl)pro-
panoyl]amino}phenyl)sulfonyl]piperidin-4-yl}prop-2-
enamide
N-[1-({4-[(3-cyclohexyl propanoyl)amino]
phenyl}sulfonyl)-3,3,5,5-tetramethylpiperidin-4-yl]prop-
2-enamide
N-{1-[(1-benzoylpiperidin-4-yl)sulfonyl]-3,3,5,5-tetram-
ethylpiperidin-4-yl}prop-2-enamide
N-(3,3,5,5-tetramethyl-1-{[1-(piperidin-1-ylcarbonyl)pip-
eridin-4-yl]sulfonyl}piperidin-4-yl)prop-2-enamide
N-(3,3,5,5-tetramethyl-1-{[1-(pyridin-2-ylcarbonyl)piperi-
din-4-yl]sulfonyl}piperidin-4-yl)prop-2-enamide N-(4-{[4-(acryloylamino)-3,3,5,5-tetramethylpiperidin-1-yl]sulfonyl}phenyl)-4-tert-butylcyclohexanecarboxamide
N-(4-{[4-(acryloylamino)-3,3,5,5-tetramethylpiperidin-1-yl]sulfonyl}phenyl)-1-benzofuran-2-carboxamide
benzyl(3-{[4-(acryloylamino)-3,3,5,5-tetramethylpiperidin-1-yl]sulfonyl}phenyl)carbamate
N-[3,3,5,5-tetramethyl-1-({3-[(3-phenylpropanoyl)amino]phenyl}sulfonyl)piperidin-4-yl]prop-2-enamide
N-(3-{[4-(acryloylamino)-3,3,5,5-tetramethylpiperidin-1-yl]sulfonyl}phenyl)tetrahydro-2H-pyran-4-carboxamide
4-{[4-(acryloylamino)-3,3,5,5-tetramethylpiperidin-1-yl]sulfonyl}-N-(3-phenylpropyl)benzamide
4-{[4-(acryloylamino)-3,3,5,5-tetramethylpiperidin-1-yl]sulfonyl}-N-[2-(3-chlorophenyl)ethyl]benzamide
4-{[4-(acryloylamino)-3,3,5,5-tetramethylpiperidin-1-yl]sulfonyl}-N-[2-(2-methoxyphenyl)ethyl]benzamide
4-{[4-(acryloylamino)-3,3,5,5-tetramethylpiperidin-1-yl]sulfonyl}-N-[2-(2,3-dihydro-1-benzofuran-7-yl)ethyl]benzamide
4-{[4-(acryloylamino)-3,3,5,5-tetramethylpiperidin-1-yl]sulfonyl}-N-[2-(tetrahydro-2H-pyran-4-yl)ethyl]benzamide
4-{[4-(acryloylamino)-3,3,5,5-tetramethylpiperidin-1-yl]sulfonyl}-N-[2-(4,4-difluoropiperidin-1-yl)ethyl]benzamide
N-[3,3,5,5-tetramethyl-1-({1-[3-(trifluoromethyl)benzoyl]piperidin-4-yl}sulfonyl)piperidin-4-yl]prop-2-enamide
N-(3,3,5,5-tetramethyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-3,3,5,5-tetramethylpiperidin-4-yl]prop-2-enamide
4-{[4-(acryloylamino)-3,3,5,5-tetramethylpiperidin-1-yl]sulfonyl}-N-(4-tert-butylbenzyl)benzamide
4-{[4-(acryloylamino)-3,3,5,5-tetramethylpiperidin-1-yl]sulfonyl}-N-(4-phenylbutyl)benzamide
4-{[4-(acryloylamino)-3,3,5,5-tetramethylpiperidin-1-yl]sulfonyl}-N-[2-(4-chlorophenyl)ethyl]benzamide
4-{[4-(acryloylamino)-3,3,5,5-tetramethylpiperidin-1-yl]sulfonyl}-N-[2-(quinolin-7-yl)ethyl]benzamide
4-{[4-(acryloylamino)-3,3,5,5-tetramethylpiperidin-1-yl]sulfonyl}-N-[2-(naphthalen-2-yl)ethyl]benzamide
4-{[4-(acryloylamino)-3,3,5,5-tetramethylpiperidin-1-yl]sulfonyl}-N-(3,4-dihydro-2H-chromen-6-ylmethyl)benzamide
4-{[4-(acryloylamino)-3,3,5,5-tetramethylpiperidin-1-yl]sulfonyl}-N-[2-(4-tert-butylphenyl)ethyl]benzamide
4-{[4-(acryloylamino)-3,3,5,5-tetramethylpiperidin-1-yl]sulfonyl}-N-[2-(biphenyl-4-yl)ethyl]benzamide
4-{[4-(acryloylamino)-3,3,5,5-tetramethylpiperidin-1-yl]sulfonyl}-N-[2-(1,3-benzodioxol-5-yl)ethyl]benzamide
4-{[4-(acryloylamino)-3,3,5,5-tetramethylpiperidin-1-yl]sulfonyl}-N-[(1R)-2-phenylcyclopropyl]benzamide
benzyl(4-{[4-(acryloylamino)-3,3,5,5-tetramethylpiperidin-1-yl]sulfonyl}phenyl)methylcarbamate
4-{[4-(acryloylamino)-3,3,5,5-tetramethylpiperidin-1-yl]sulfonyl}-N-[2-(3,4-dimethoxyphenyl)ethyl]benzamide
4-{[4-(acryloylamino)-3,3,5,5-tetramethylpiperidin-1-yl]sulfonyl}-N-{2-[4-(trifluoromethyl)phenyl]ethyl}benzamide
4-{[4-(acryloylamino)-3,3,5,5-tetramethylpiperidin-1-yl]sulfonyl}-N-(2-phenylethyl)piperidine-1-carboxamide
N-(4-{[4-(acryloylamino)-3,3,5,5-tetramethylpiperidin-1-yl]sulfonyl}phenyl)furan-2-carboxamide
N-{3,3,5,5-tetramethyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-3,3,5,5-tetramethylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-3,3,5,5-tetramethylpiperidin-4-yl)prop-2-enamide
N-[1-({2-chloro-4-[(3-phenylpropanoyl)amino]phenyl}sulfonyl)-3,3,5,5-tetramethylpiperidin-4-yl]prop-2-enamide
N-(4-{[4-(acryloylamino)-3,3,5,5-tetramethylpiperidin-1-yl]sulfonyl}phenyl)-5,6-dihydro-4H-cyclopenta[b]thiophene-2-carboxamide
N-(4-{[4-(acryloylamino)-3,3,5,5-tetramethylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-3,3,5,5-tetramethylpiperidin-4-yl]prop-2-enamide
N-(4-{[4-(acryloylamino)-3,3,5,5-tetramethylpiperidin-1-yl]sulfonyl}phenyl)-5-(pyrrolidin-1-ylmethyl)furan-2-carboxamide
N-(4-{[4-(acryloylamino)-3,3,5,5-tetramethylpiperidin-1-yl]sulfonyl}phenyl)-1-benzothiophene-2-carboxamide
N-(4-{[4-(acryloylamino)-3,3,5,5-tetramethylpiperidin-1-yl]sulfonyl}phenyl)-3-methyl-1-benzofuran-2-carboxamide
N-(4-{[4-(acryloylamino)-3,3,5,5-tetramethylpiperidin-1-yl]sulfonyl}phenyl)-1H-indole-2-carboxamide
4-{[4-(acryloylamino)-3,3,5,5-tetramethylpiperidin-1-yl]sulfonyl}-N-(tricyclo[3.3.1.1~3,7~]dec-1-ylmethyl)benzamide
4-{[4-(acryloylamino)-3,3,5,5-tetramethylpiperidin-1-yl]sulfonyl}-N-(1,2,3,4-tetrahydronaphthalen-1-yl)benzamide
N-(4-{[4-(acryloylamino)-3,3,5,5-tetramethylpiperidin-1-yl]sulfonyl}phenyl)-4,5,6,7-tetrahydro-1-benzothiophene-2-carboxamide
N-(4-{[4-(acryloylamino)-3,3,5,5-tetramethylpiperidin-1-yl]sulfonyl}phenyl)-5-phenylfuran-2-carboxamide
N-(4-{[4-(acryloylamino)-3,3,5,5-tetramethylpiperidin-1-yl]sulfonyl}phenyl)-4-phenylthiophene-2-carboxamide
N-[3,3,5,5-tetramethyl-1-({5-[5-(trifluoromethyl)-1,2-oxazol-3-yl]thiophen-2-yl}sulfonyl)piperidin-4-yl]prop-2-enamide
5-{[4-(acryloylamino)-3,3,5,5-tetramethylpiperidin-1-yl]sulfonyl}-N-(2-phenylethyl)furan-2-carboxamide
N-{3,3,5,5-tetramethyl-1-[(6-phenoxypyridin-3-yl)sulfonyl]piperidin-4-yl}prop-2-enamide
N-(3,3,5,5-tetramethyl-1-{[6-(morpholin-4-yl)pyridin-3-yl]sulfonyl}piperidin-4-yl)prop-2-enamide
N-{3,3,5,5-tetramethyl-1-[(6-phenylpyridin-3-yl)sulfonyl]piperidin-4-yl}prop-2-enamide
N-[1-({3-chloro-4-[(3-phenylpropanoyl)amino]phenyl}sulfonyl)-3,3,5,5-tetramethylpiperidin-4-yl]prop-2-enamide
4-{[4-(acryloylamino)-3,3,5,5-tetramethylpiperidin-1-yl]sulfonyl}-2-fluoro-N-(2-phenylethyl)benzamide
N-(3,3,5,5-tetramethyl-1-{[5-(pyridin-2-yl)thiophen-2-yl]sulfonyl}piperidin-4-yl)prop-2-enamide
4-{[4-(acryloylamino)-3,3,5,5-tetramethylpiperidin-1-yl]sulfonyl}-2-methoxy-N-(2-phenylethyl)benzamide
N-[1-(1,3-benzothiazol-6-ylsulfonyl)-3,3,5,5-tetramethylpiperidin-4-yl]prop-2-enamide
N-{3,3,5,5-tetramethyl-1-[(4-methyl-2-phenyl-1,3-thiazol-5-yl)sulfonyl]piperidin-4-yl}prop-2-enamide
N-(3,3,5,5-tetramethyl-1-{[5-(2-methyl-1,3-thiazol-4-yl)thiophen-2-yl]sulfonyl}piperidin-4-yl)prop-2-enamide N-(3,3,5,5-tetramethyl-1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)-3,3,5,5-tetramethylpiperidin-4-yl]prop-2-enamide
5-{[4-(acryloylamino)-3,3,5,5-tetramethylpiperidin-1-yl]sulfonyl}-N-(2-phenylethyl)furan-3-carboxamide
N-[3,3,5,5-tetramethyl-1-({4-[(phenylacetyl)amino]benzyl}sulfonyl)piperidin-4-yl]prop-2-enamide
N-(3,3,5,5-tetramethyl-1-{[4-(morpholin-4-ylsulfonyl)phenyl]sulfonyl}piperidin-4-yl)prop-2-enamide
N-(3,3,5,5-tetramethyl-1-{[5-(1,3-oxazol-5-yl)thiophen-2-yl]sulfonyl}piperidin-4-yl)prop-2-enamide
4-{[4-(acryloylamino)-3,3,5,5-tetramethylpiperidin-1-yl]sulfonyl}-2-methyl-N-(2-phenylethyl)benzamide
N-{3,3,5,5-tetramethyl-1-[(4-phenoxyphenyl)sulfonyl]piperidin-4-yl}prop-2-enamide
N-[3,3,5,5-tetramethyl-1-({4-[(6-methylpyrazin-2-yl)oxy]phenyl}sulfonyl)piperidin-4-yl]prop-2-enamide
N-[3,3,5,5-tetramethyl-1-({3-[(6-methylpyrazin-2-yl)oxy]phenyl}sulfonyl)piperidin-4-yl]prop-2-enamide
5-{[4-(acryloylamino)-3,3,5,5-tetramethylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-3,3,5,5-tetramethylpiperidin-4-yl)prop-2-enamide
N-{1-[(3-chloro-4-methylphenyl)sulfonyl]-3,3,5,5-tetramethylpiperidin-4-yl}prop-2-enamide
N-(3,3,5,5-tetramethyl-1-{[5-(1,2-oxazol-5-yl)furan-2-yl]sulfonyl}piperidin-4-yl)prop-2-enamide
N-{1-[(4-{[3-chloro-5-(trifluoromethyl)pyridin-2-yl]oxy}phenyl)sulfonyl]-3,3,5,5-tetramethylpiperidin-4-yl}prop-2-enamide
N-(3,3,5,5-tetramethyl-1-{[4-(1H-pyrazol-1-yl)phenyl]sulfonyl}piperidin-4-yl)prop-2-enamide
N-{1-[(4-methoxy-3-methylphenyl)sulfonyl]-3,3,5,5-tetramethylpiperidin-4-yl}prop-2-enamide
N-(3,3,5,5-tetramethyl-1-{[6-(2-phenylethoxy)pyridin-3-yl]sulfonyl}piperidin-4-yl)prop-2-enamide
N-[1-({5-[(acetylamino)methyl]thiophen-2-yl}sulfonyl)-3,3,5,5-tetramethylpiperidin-4-yl]prop-2-enamide
N-{3,3,5,5-tetramethyl-1-[(5-methyl-1-phenyl-1H-pyrazol-4-yl)sulfonyl]piperidin-4-yl}prop-2-enamide
N-(3,3,5,5-tetramethyl-1-{[4-(1-methyl-1H-pyrazol-5-yl)phenyl]sulfonyl}piperidin-4-yl)prop-2-enamide
N-(3,3,5,5-tetramethyl-1-{[3-(1-methyl-1H-pyrazol-5-yl)phenyl]sulfonyl}piperidin-4-yl)prop-2-enamide
N-{1-[(2,2-dimethyl-3,4-dihydro-2H-chromen-6-yl)sulfonyl]-3,3,5,5-tetramethylpiperidin-4-yl}prop-2-enamide
N-{3,3,5,5-tetramethyl-1-[(5-phenylthiophen-2-yl)sulfonyl]piperidin-4-yl}prop-2-enamide
N-(1-{[4-(cyclopentyloxy)phenyl]sulfonyl}-3,3,5,5-tetramethylpiperidin-4-yl)prop-2-enamide
N-(3,3,5,5-tetramethyl-1-{[5-(pyrrolidin-1-ylcarbonyl)-1H-pyrrol-3-yl]sulfonyl}piperidin-4-yl)prop-2-enamide
N-(3,3,5,5-tetramethyl-1-{[4-(2-methyl-1,3-thiazol-4-yl)phenyl]sulfonyl}piperidin-4-yl)prop-2-enamide
N-(3,3,5,5-tetramethyl-1-{[4-(pyridin-2-yloxy)phenyl]sulfonyl}piperidin-4-yl)prop-2-enamide
N-{3,3,5,5-tetramethyl-1-[(2-oxo-1,2,3,4-tetrahydroquinolin-6-yl)sulfonyl]piperidin-4-yl}prop-2-enamide
N-{1-[(4-cyclohexylphenyl)sulfonyl]-2,2,6,6-tetramethylpiperidin-4-yl}prop-2-enamide
N-(4-{[4-(acryloylamino)-2,2,6,6-tetramethylpiperidin-1-yl]sulfonyl}phenyl)cyclopropanecarboxamide
N-(4-{[4-(acryloylamino)-2,2,6,6-tetramethylpiperidin-1-yl]sulfonyl}phenyl)tricyclo[3.3.1.1~3,7~]decane-1-carboxamide
benzyl(4-{[4-(acryloylamino)-2,2,6,6-tetramethylpiperidin-1-yl]sulfonyl}phenyl)carbamate
N-(2,2,6,6-tetramethyl-1-{[4-(piperidin-1-ylcarbonyl)phenyl]sulfonyl}piperidin-4-yl)prop-2-enamide
benzyl 4-{[4-(acryloylamino)-2,2,6,6-tetramethylpiperidin-1-yl]sulfonyl}piperidine-1-carboxylate
N-{2,2,6,6-tetramethyl-1-[(4-nitrophenyl)sulfonyl]piperidin-4-yl}prop-2-enamide
N-(4-{[4-(acryloylamino)-2,2,6,6-tetramethylpiperidin-1-yl]sulfonyl}phenyl)tetrahydro-2H-pyran-4-carboxamide
N-[2,2,6,6-tetramethyl-1-({4-[(3-phenylpropanoyl)amino]phenyl}sulfonyl)piperidin-4-yl]prop-2-enamide
N-(4-{[4-(acryloylamino)-2,2,6,6-tetramethylpiperidin-1-yl]sulfonyl}phenyl)-2-phenylcyclopropanecarboxamide
N-(4-{[4-(acryloylamino)-2,2,6,6-tetramethylpiperidin-1-yl]sulfonyl}phenyl)-N-methyltetrahydro-2H-pyran-4-carboxamide
4-{[4-(acryloylamino)-2,2,6,6-tetramethylpiperidin-1-yl]sulfonyl}-N-benzyl-N-methylbenzamide
4-{[4-(acryloylamino)-2,2,6,6-tetramethylpiperidin-1-yl]sulfonyl}-N-(cyclopropylmethyl)benzamide
N-(2,2,6,6-tetramethyl-1-{[3-(piperidin-1-ylcarbonyl)phenyl]sulfonyl}piperidin-4-yl)prop-2-enamide
N-(4-{[4-(acryloylamino)-2,2,6,6-tetramethylpiperidin-1-yl]sulfonyl}phenyl)-N-methylcyclopropanecarboxamide
N-{2,2,6,6-tetramethyl-1-[(4-{[4-(6-methylpyridin-2-yl)piperazin-1-yl]carbonyl}phenyl)sulfonyl]piperidin-4-yl}prop-2-enamide
4-{[4-(acryloylamino)-2,2,6,6-tetramethylpiperidin-1-yl]sulfonyl}-N-[2-(morpholin-4-yl)ethyl]benzamide
4-{[4-(acryloylamino)-2,2,6,6-tetramethylpiperidin-1-yl]sulfonyl}-N-(2-phenylethyl)benzamide
4-{[4-(acryloylamino)-2,2,6,6-tetramethylpiperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-2,2,6,6-tetramethylpiperidin-4-yl)prop-2-enamide
4-{[4-(acryloylamino)-2,2,6,6-tetramethylpiperidin-1-yl]sulfonyl}-N-(2-cyclohexylethyl)benzamide
4-{[4-(acryloylamino)-2,2,6,6-tetramethylpiperidin-1-yl]sulfonyl}-N-cyclohexylbenzamide
N-{2,2,6,6-tetramethyl-1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)-2,2,6,6-tetramethylpiperidin-1-yl]sulfonyl}-N-(3,5-dimethylbenzyl)benzamide
4-{[4-(acryloylamino)-2,2,6,6-tetramethylpiperidin-1-yl]sulfonyl}-N-benzylbenzamide
4-{[4-(acryloylamino)-2,2,6,6-tetramethylpiperidin-1-yl]sulfonyl}-N-(3,4-difluorobenzyl)benzamide
4-{[4-(acryloylamino)-2,2,6,6-tetramethylpiperidin-1-yl]sulfonyl}-N-[4-(trifluoromethyl)benzyl]benzamide
4-{[4-(acryloylamino)-2,2,6,6-tetramethylpiperidin-1-yl]sulfonyl}-N-(naphthalen-1-ylmethyl)benzamide
4-{[4-(acryloylamino)-2,2,6,6-tetramethylpiperidin-1-yl]sulfonyl}-N-[2-(3,4-dimethylphenyl)ethyl]benzamide
4-{[4-(acryloylamino)-2,2,6,6-tetramethylpiperidin-1-yl]sulfonyl}-N-[2-(4-methoxyphenyl)ethyl]benzamide
4-{[4-(acryloylamino)-2,2,6,6-tetramethylpiperidin-1-yl]sulfonyl}-N-(2,3-dihydro-1H-inden-2-yl)benzamide
4-{[4-(acryloylamino)-2,2,6,6-tetramethylpiperidin-1-yl]sulfonyl}-N-[2-(3-methylphenyl)ethyl]benzamide
N-[1-({4-[(acetylamino)methyl]phenyl}sulfonyl)-2,2,6,6-tetramethylpiperidin-4-yl]prop-2-enamide
N-{2,2,6,6-tetramethyl-1-[(4-{[3-(naphthalen-1-yl)propanoyl]amino}phenyl)sulfonyl]piperidin-4-yl}prop-2-enamide N-[1-({4-[(3-cyclohexylpropanoyl)amino]phenyl}sulfonyl)-2,2,6,6-tetramethylpiperidin-4-yl]prop-2-enamide N-{1-[(1-benzoylpiperidin-4-yl)sulfonyl]-2,2,6,6-tetramethylpiperidin-4-yl}prop-2-enamide N-(2,2,6,6-tetramethyl-1-{[1-(piperidin-1-ylcarbonyl)piperidin-4-yl]sulfonyl}piperidin-4-yl)prop-2-enamide N-(2,2,6,6-tetramethyl-1-{[1-(pyridin-2-ylcarbonyl)piperidin-4-yl]sulfonyl}piperidin-4-yl)prop-2-enamide N-(4-{[4-(acryloylamino)-2,2,6,6-tetramethylpiperidin-1-yl]sulfonyl}phenyl)-4-tert-butylcyclohexanecarboxamide N-(4-{[4-(acryloylamino)-2,2,6,6-tetramethylpiperidin-1-yl]sulfonyl}phenyl)-1-benzofuran-2-carboxamide benzyl(3-{[4-(acryloylamino)-2,2,6,6-tetramethylpiperidin-1-yl]sulfonyl}phenyl)carbamate N-[2,2,6,6-tetramethyl-1-({3-[(3-phenylpropanoyl)amino]phenyl}sulfonyl)piperidin-4-yl]prop-2-enamide N-(3-{[4-(acryloylamino)-2,2,6,6-tetramethylpiperidin-1-yl]sulfonyl}phenyl)tetrahydro-2H-pyran-4-carboxamide 4-{[4-(acryloylamino)-2,2,6,6-tetramethylpiperidin-1-yl]sulfonyl}-N-(3-phenylpropyl)benzamide 4-{[4-(acryloylamino)-2,2,6,6-tetramethylpiperidin-1-yl]sulfonyl}-N-[2-(3-chlorophenyl)ethyl]benzamide 4-{[4-(acryloylamino)-2,2,6,6-tetramethylpiperidin-1-yl]sulfonyl}-N-[2-(2-methoxyphenyl)ethyl]benzamide 4-{[4-(acryloylamino)-2,2,6,6-tetramethylpiperidin-1-yl]sulfonyl}-N-[2-(2,3-dihydro-1-benzofuran-7-yl)ethyl]benzamide 4-{[4-(acryloylamino)-2,2,6,6-tetramethylpiperidin-1-yl]sulfonyl}-N-[2-(tetrahydro-2H-pyran-4-yl)ethyl]benzamide 4-{[4-(acryloylamino)-2,2,6,6-tetramethylpiperidin-1-yl]sulfonyl}-N-[2-(4,4-difluoropiperidin-1-yl)ethyl]benzamide N-[2,2,6,6-tetramethyl-1-({1-[3-(trifluoromethyl)benzoyl]piperidin-4-yl}sulfonyl)piperidin-4-yl]prop-2-enamide N-(2,2,6,6-tetramethyl-1-{[1-(3-phenylpropanoyl)piperidin-4-yl]sulfonyl}piperidin-4-yl)prop-2-enamide N-[1-({4-[2-(benzylamino)-2-oxoethyl]phenyl}sulfonyl)-2,2,6,6-tetramethylpiperidin-4-yl]prop-2-enamide 4-{[4-(acryloylamino)-2,2,6,6-tetramethylpiperidin-1-yl]sulfonyl}-N-(4-tert-butylbenzyl)benzamide 4-{[4-(acryloylamino)-2,2,6,6-tetramethylpiperidin-1-yl]sulfonyl}-N-(4-phenylbutyl)benzamide 4-{[4-(acryloylamino)-2,2,6,6-tetramethylpiperidin-1-yl]sulfonyl}-N-[2-(4-chlorophenyl)ethyl]benzamide 4-{[4-(acryloylamino)-2,2,6,6-tetramethylpiperidin-1-yl]sulfonyl}-N-[2-(quinolin-7-yl)ethyl]benzamide 4-{[4-(acryloylamino)-2,2,6,6-tetramethylpiperidin-1-yl]sulfonyl}-N-[2-(naphthalen-2-yl)ethyl]benzamide 4-{[4-(acryloylamino)-2,2,6,6-tetramethylpiperidin-1-yl]sulfonyl}-N-(3,4-dihydro-2H-chromen-6-ylmethyl)benzamide 4-{[4-(acryloylamino)-2,2,6,6-tetramethylpiperidin-1-yl]sulfonyl}-N-[2-(4-tert-butylphenyl)ethyl]benzamide 4-{[4-(acryloylamino)-2,2,6,6-tetramethylpiperidin-1-yl]sulfonyl}-N-[2-(biphenyl-4-yl)ethyl]benzamide 4-{[4-(acryloylamino)-2,2,6,6-tetramethylpiperidin-1-yl]sulfonyl}-N-[2-(1,3-benzodioxol-5-yl)ethyl]benzamide 4-{[4-(acryloylamino)-2,2,6,6-tetramethylpiperidin-1-yl]sulfonyl}-N-[(1R)-2-phenylcyclopropyl]benzamide benzyl(4-{[4-(acryloylamino)-2,2,6,6-tetramethylpiperidin-1-yl]sulfonyl}phenyl)methylcarbamate 4-{[4-(acryloylamino)-2,2,6,6-tetramethylpiperidin-1-yl]sulfonyl}-N-[2-(3,4-dimethoxyphenyl)ethyl]benzamide 4-{[4-(acryloylamino)-2,2,6,6-tetramethylpiperidin-1-yl]sulfonyl}-N-{2-[4-(trifluoromethyl)phenyl]ethyl}benzamide 4-{[4-(acryloylamino)-2,2,6,6-tetramethylpiperidin-1-yl]sulfonyl}-N-(2-phenylethyl)piperidine-1-carboxamide N-(4-{[4-(acryloylamino)-2,2,6,6-tetramethylpiperidin-1-yl]sulfonyl}phenyl)furan-2-carboxamide N-{2,2,6,6-tetramethyl-1-[(4-{[3-(tricyclo[3.3.1.1~3,7~]dec-1-yl)propanoyl]amino}phenyl)sulfonyl]piperidin-4-yl}prop-2-enamide 4-{[4-(acryloylamino)-2,2,6,6-tetramethylpiperidin-1-yl]sulfonyl}-N-[2-(tricyclo[3.3.1.1~3,7~]dec-1-yl)ethyl]benzamide N-(1-{[1-(cyclopropylcarbonyl)-2,3-dihydro-1H-indol-5-yl]sulfonyl}-2,2,6,6-tetramethylpiperidin-4-yl)prop-2-enamide N-[1-({2-chloro-4-[(3-phenylpropanoyl)amino]phenyl}sulfonyl)-2,2,6,6-tetramethylpiperidin-4-yl]prop-2-enamide N-(4-{[4-(acryloylamino)-2,2,6,6-tetramethylpiperidin-1-yl]sulfonyl}phenyl)-5,6-dihydro-4H-cyclopenta[b]thiophene-2-carboxamide N-(4-{[4-(acryloylamino)-2,2,6,6-tetramethylpiperidin-1-yl]sulfonyl}phenyl)-4,5,6,7-tetrahydro-1H-indole-2-carboxamide N-[1-({2-methoxy-4-[(3-phenylpropanoyl)amino]phenyl}sulfonyl)-2,2,6,6tetramethylpiperidin-4-yl]prop-2-enamide N-(4-{[4-(acryloylamino)-2,2,6,6-tetramethylpiperidin-1-yl]sulfonyl}phenyl)-5-(pyrrolidin-1-ylmethyl)furan-2-carboxamide N-(4-{[4-(acryloylamino)-2,2,6,6-tetramethylpiperidin-1-yl]sulfonyl}phenyl)-1-benzothiophene-2-carboxamide N-(4-{[4-(acryloylamino)-2,2,6,6-tetramethylpiperidin-1-yl]sulfonyl}phenyl)-3-methyl-1-benzofuran-2-carboxamide N-(4-{[4-(acryloylamino)-2,2,6,6-tetramethylpiperidin-1-yl]sulfonyl}phenyl)-1H-indole-2-carboxamide 4-{[4-(acryloylamino)-2,2,6,6-tetramethylpiperidin-1-yl]sulfonyl}-N-(tricyclo[3.3.1.1~3,7~]dec-1-ylmethyl)benzamide 4-{[4-(acryloylamino)-2,2,6,6-tetramethylpiperidin-1-yl]sulfonyl}-N-(1,2,3,4-tetrahydronaphthalen-1-yl)benzamide N-(4-{[4-(acryloylamino)-2,2,6,6-tetramethylpiperidin-1-yl]sulfonyl}phenyl)-4,5,6,7-tetrahydro-1-benzothiophene-2-carboxamide N-(4-{[4-(acryloylamino)-2,2,6,6-tetramethylpiperidin-1-yl]sulfonyl}phenyl)-5-phenylfuran-2-carboxamide N-(4-{[4-(acryloylamino)-2,2,6,6-tetramethylpiperidin-1-yl]sulfonyl}phenyl)-4-phenylthiophene-2-carboxamide N-[2,2,6,6-tetramethyl-1-({5-[5-(trifluoromethyl)-1,2-oxazol-3-yl]thiophen-2-yl}sulfonyl)piperidin-4-yl]prop-2-enamide 5-{[4-(acryloylamino)-2,2,6,6-tetramethylpiperidin-1-yl]sulfonyl}-N-(2-phenylethyl)furan-2-carboxamide N-{2,2,6,6-tetramethyl-1-[(6-phenoxypyridin-3-yl)sulfonyl]piperidin-4-yl}prop-2-enamide N-(2,2,6,6-tetramethyl-1-{[6-(morpholin-4-yl)pyridin-3-yl]sulfonyl}piperidin-4-yl)prop-2-enamide N-{2,2,6,6-tetramethyl-1-[(6-phenylpyridin-3-yl)sulfonyl]piperidin-4-yl}prop-2-enamide N-[1-({3-chloro-4-[(3-phenylpropanoyl)amino]phenyl}sulfonyl)-2,2,6,6-tetramethylpiperidin-4-yl]prop-2-enamide 4-{[4-(acryloylamino)-2,2,6,6-tetramethylpiperidin-1-yl]sulfonyl}-2-fluoro-N-(2-phenylethyl)benzamide N-(2,2,6,6-tetramethyl-1-{[5-(pyridin-2-yl)thiophen-2-yl]sulfonyl}piperidin-4-yl)prop-2-enamide
4-{[4-(acryloylamino)-2,2,6,6-tetramethylpiperidin-1-yl]sulfonyl}-2-methoxy-N-(2-phenylethyl)benzamide
N-[1-(1,3-benzothiazol-6-ylsulfonyl)-2,2,6,6-tetramethylpiperidin-4-yl]prop-2-enamide
N-{2,2,6,6-tetramethyl-1-[(4-methyl-2-phenyl-1,3-thiazol-5-yl)sulfonyl]piperidin-4-yl}prop-2-enamide
N-(2,2,6,6-tetramethyl-1-{[5-(2-methyl-1,3-thiazol-4-yl)thiophen-2-yl]sulfonyl}piperidin-4-yl)prop-2-enamide
N-(2,2,6,6-tetramethyl-1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)-2,2,6,6-tetramethylpiperidin-4-yl]prop-2-enamide
5-{[4-(acryloylamino)-2,2,6,6-tetramethylpiperidin-1-yl]sulfonyl}-N-(2-phenylethyl)furan-3-carboxamide
N-[2,2,6,6-tetramethyl-1-({4-[(phenylacetyl)amino]benzyl}sulfonyl)piperidin-4-yl]prop-2-enamide
N-(2,2,6,6-tetramethyl-1-{[4-(morpholin-4-ylsulfonyl)phenyl]sulfonyl}piperidin-4-yl)prop-2-enamide
N-(2,2,6,6-tetramethyl-1-{[5-(1,3-oxazol-5-yl)thiophen-2-yl]sulfonyl}piperidin-4-yl)prop-2-enamide
4-{[4-(acryloylamino)-2,2,6,6-tetramethylpiperidin-1-yl]sulfonyl}-2-methyl-N-(2-phenylethyl)benzamide
N-{2,2,6,6-tetramethyl-1-[(4-phenoxyphenyl)sulfonyl]piperidin-4-yl}prop-2-enamide
N-[2,2,6,6-tetramethyl-1-({4-[(6-methylpyrazin-2-yl)oxy]phenyl}sulfonyl)piperidin-4-yl]prop-2-enamide
N-[2,2,6,6-tetramethyl-1-({3-[(6-methylpyrazin-2-yl)oxy]phenyl}sulfonyl)piperidin-4-yl]prop-2-enamide
5-{[4-(acryloylamino)-2,2,6,6-tetramethylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-2,2,6,6-tetramethylpiperidin-4-yl)prop-2-enamide
N-{1-[(3-chloro-4-methylphenyl)sulfonyl]-2,2,6,6-tetramethylpiperidin-4-yl}prop-2-enamide
N-(2,2,6,6-tetramethyl-1-{[5-(1,2-oxazol-5-yl)furan-2-yl]sulfonyl}piperidin-4-yl)prop-2-enamide
N-{1-[(4-{[3-chloro-5-(trifluoromethyl)pyridin-2-yl]oxy}phenyl)sulfonyl]-2,2,6,6-tetramethylpiperidin-4-yl}prop-2-enamide
N-(2,2,6,6-tetramethyl-1-{[4-(1H-pyrazol-1-yl)phenyl]sulfonyl}piperidin-4-yl)prop-2-enamide
N-{1-[(4-methoxy-3-methylphenyl)sulfonyl]-2,2,6,6-tetramethylpiperidin-4-yl}prop-2-enamide
N-(2,2,6,6-tetramethyl-1-{[6-(2-phenylethoxy)pyridin-3-yl]sulfonyl}piperidin-4-yl)prop-2-enamide
N-[1-({5-[(acetylamino)methyl]thiophen-2-yl}sulfonyl)-2,2,6,6-tetramethylpiperidin-4-yl]prop-2-enamide
N-{2,2,6,6-tetramethyl-1-[(5-methyl-1-phenyl-1H-pyrazol-4-yl)sulfonyl]piperidin-4-yl}prop-2-enamide
N-(2,2,6,6-tetramethyl-1-{[4-(1-methyl-1H-pyrazol-5-yl)phenyl]sulfonyl}piperidin-4-yl)prop-2-enamide
N-(2,2,6,6-tetramethyl-1-{[3-(1-methyl-1H-pyrazol-5-yl)phenyl]sulfonyl}piperidin-4-yl)prop-2-enamide
N-{1-[(2,2-dimethyl-3,4-dihydro-2H-chromen-6-yl)sulfonyl]-2,2,6,6-tetramethylpiperidin-4-yl}prop-2-enamide
N-{2,2,6,6-tetramethyl-1-[(5-phenylthiophen-2-yl)sulfonyl]piperidin-4-yl}prop-2-enamide
N-(1-{[4-(cyclopentyloxy)phenyl]sulfonyl}-2,2,6,6-tetramethylpiperidin-4-yl)prop-2-enamide
N-(2,2,6,6-tetramethyl-1-{[5-(pyrrolidin-1-ylcarbonyl)-1H-pyrrol-3-yl]sulfonyl}piperidin-4-yl)prop-2-enamide
N-(2,2,6,6-tetramethyl-1-{[4-(2-methyl-1,3-thiazol-4-yl)phenyl]sulfonyl}piperidin-4-yl)prop-2-enamide
N-(2,2,6,6-tetramethyl-1-{[4-(pyridin-2-yloxy)phenyl]sulfonyl}piperidin-4-yl)prop-2-enamide
N-{2,2,6,6-tetramethyl-1-[(2-oxo-1,2,3,4-tetrahydroquinolin-6-yl)sulfonyl]piperidin-4-yl}prop-2-enamide
N-{1-[(4-cyclohexylphenyl)sulfonyl]-3,5-dimethylpiperidin-4-yl}prop-2-enamide
N-(4-{[4-(acryloylamino)-3,5-dimethylpiperidin-1-yl]sulfonyl}phenyl)cyclopropanecarboxamide
N-(4-{[4-(acryloylamino)-3,5-dimethylpiperidin-1-yl]sulfonyl}phenyl)tricyclo[3.3.1.1~3,7~]decane-1-carboxamide
benzyl(4-{[4-(acryloylamino)-3,5-dimethylpiperidin-1-yl]sulfonyl}phenyl)carbamate
N-(3,5-dimethyl-1-{[4-(piperidin-1-ylcarbonyl)phenyl]sulfonyl}piperidin-4-yl)prop-2-enamide
benzyl 4-{[4-(acryloylamino)-3,5-dimethylpiperidin-1-yl]sulfonyl}piperidine-1-carboxylate
N-{3,5-dimethyl-1-[(4-nitrophenyl)sulfonyl]piperidin-4-yl}prop-2-enamide
N-(4-{[4-(acryloylamino)-3,5-dimethylpiperidin-1-yl]sulfonyl}phenyl)tetrahydro-2H-pyran-4-carboxamide
N-[3,5-dimethyl-1-({4-[(3-phenylpropanoyl)amino]phenyl}sulfonyl)piperidin-4-yl]prop-2-enamide
N-(4-{[4-(acryloylamino)-3,5-dimethylpiperidin-1-yl]sulfonyl}phenyl)-2-phenylcyclopropanecarboxamide
N-(4-{[4-(acryloylamino)-3,5-dimethylpiperidin-1-yl]sulfonyl}phenyl)-N-methyltetrahydro-2H-pyran-4-carboxamide
4-{[4-(acryloylamino)-3,5-dimethylpiperidin-1-yl]sulfonyl}-N-benzyl-N-methylbenzamide
4-{[4-(acryloylamino)-3,5-dimethylpiperidin-1-yl]sulfonyl}-N-(cyclopropylmethyl)benzamide
N-(3,5-dimethyl-1-{[3-(piperidin-1-ylcarbonyl)phenyl]sulfonyl}piperidin-4-yl)prop-2-enamide
N-(4-{[4-(acryloylamino)-3,5-dimethylpiperidin-1-yl]sulfonyl}phenyl)-N-methylcyclopropanecarboxamide
N-{3,5-dimethyl-1-[(4-{[4-(6-methylpyridin-2-yl)piperazin-1-yl]carbonyl}phenyl)sulfonyl]piperidin-4-yl}prop-2-enamide
4-{[4-(acryloylamino)-3,5-dimethylpiperidin-1-yl]sulfonyl}-N-[2-(morpholin-4-yl)ethyl]benzamide
4-{[4-(acryloylamino)-3,5-dimethylpiperidin-1-yl]sulfonyl}-N-(2-phenylethyl)benzamide
4-{[4-(acryloylamino)-3,5-dimethylpiperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-3,5-dimethylpiperidin-4-yl)prop-2-enamide
4-{[4-(acryloylamino)-3,5-dimethylpiperidin-1-yl]sulfonyl}-N-(2-cyclohexylethyl)benzamide
4-{[4-(acryloylamino)-3,5-dimethylpiperidin-1-yl]sulfonyl}-N-cyclohexylbenzamide
N-{3,5-dimethyl-1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)-3,5-dimethylpiperidin-1-yl]sulfonyl}-N-(3,5-dimethylbenzyl)benzamide
4-{[4-(acryloylamino)-3,5-dimethylpiperidin-1-yl]sulfonyl}-N-benzylbenzamide
4-{[4-(acryloylamino)-3,5-dimethylpiperidin-1-yl]sulfonyl}-N-(3,4-difluorobenzyl)benzamide
4-{[4-(acryloylamino)-3,5-dimethylpiperidin-1-yl]sulfonyl}-N-[4-(trifluoromethyl)benzyl]benzamide
4-{[4-(acryloylamino)-3,5-dimethylpiperidin-1-yl]sulfonyl}-N-(naphthalen-1-ylmethyl)benzamide
4-{[4-(acryloylamino)-3,5-dimethylpiperidin-1-yl]sulfonyl}-N-[2-(3,4-dimethylphenyl)ethyl]benzamide 4-{[4-(acryloylamino)-3,5-dimethylpiperidin-1-yl]sulfonyl}-N-[2-(4-methoxyphenyl)ethyl]benzamide
4-{[4-(acryloylamino)-3,5-dimethylpiperidin-1-yl]sulfonyl}-N-(2,3-dihydro-1H-inden-2-yl)benzamide
4-{[4-(acryloylamino)-3,5-dimethylpiperidin-1-yl]sulfonyl}-N-[2-(3-methylphenyl)ethyl]benzamide
N-[1-({4-[(acetylamino)methyl]phenyl}sulfonyl)-3,5-dimethylpiperidin-4-yl]prop-2-enamide
N-{3,5-dimethyl-1-[(4-{[3-(naphthalen-1-yl)propanoyl]amino}phenyl)sulfonyl]piperidin-4-yl}prop-2-enamide
N-[1-({4-[(3-cyclohexylpropanoyl)amino]phenyl}sulfonyl)-3,5-dimethylpiperidin-4-yl]prop-2-enamide
N-{1-[(1-benzoylpiperidin-4-yl)sulfonyl]-3,5-dimethylpiperidin-4-yl}prop-2-enamide
N-(3,5-dimethyl-1-{[1-(piperidin-1-ylcarbonyl)piperidin-4-yl]sulfonyl}piperidin-4-yl)prop-2-enamide
N-(3,5-dimethyl-1-{[1-(pyridin-2-ylcarbonyl)piperidin-4-yl]sulfonyl}piperidin-4-yl)prop-2-enamide
N-(4-{[4-(acryloylamino)-3,5-dimethylpiperidin-1-yl]sulfonyl}phenyl)-4-tert-butylcyclohexanecarboxamide
N-(4-{[4-(acryloylamino)-3,5-dimethylpiperidin-1-yl]sulfonyl}phenyl)-1-benzofuran-2-carboxamide
benzyl(3-{[4-(acryloylamino)-3,5-dimethylpiperidin-1-yl]sulfonyl}phenyl)carbamate
N-[3,5-dimethyl-1-({3-[(3-phenylpropanoyl)amino]phenyl}sulfonyl)piperidin-4-yl]prop-2-enamide
N-(3-{[4-(acryloylamino)-3,5-dimethylpiperidin-1-yl]sulfonyl}phenyl)tetrahydro-2H-pyran-4-carboxamide
4-{[4-(acryloylamino)-3,5-dimethylpiperidin-1-yl]sulfonyl}-N-(3-phenylpropyl)benzamide
4-{[4-(acryloylamino)-3,5-dimethylpiperidin-1-yl]sulfonyl}-N-[2-(3-chlorophenyl)ethyl]benzamide
4-{[4-(acryloylamino)-3,5-dimethylpiperidin-1-yl]sulfonyl}-N-[2-(2methoxyphenyl)ethyl]benzamide
4-{[4-(acryloylamino)-3,5-dimethylpiperidin-1-yl]sulfonyl}-N-[2-(2,3-dihydro-1-benzofuran-7-yl)ethyl]benzamide
4-{[4-(acryloylamino)-3,5-dimethylpiperidin-1-yl]sulfonyl}-N-[2-(tetrahydro-2H-pyran-4-yl)ethyl]benzamide
4-{[4-(acryloylamino)-3,5-dimethylpiperidin-1-yl]sulfonyl}-N-[2-(4,4-difluoropiperidin-1-yl)ethyl]benzamide
N-[3,5-dimethyl-1-({1-[3-(trifluoromethyl)benzoyl]piperidin-4-yl}sulfonyl)piperidin-4-yl]prop-2-enamide
N-(3,5-dimethyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-3,5-dimethylpiperidin-4-yl]prop-2-enamide
4-{[4-(acryloylamino)-3,5-dimethylpiperidin-1-yl]sulfonyl}-N-(4-tert-butylbenzyl)benzamide
4-{[4-(acryloylamino)-3,5-dimethylpiperidin-1-yl]sulfonyl}-N-(4-phenylbutyl)benzamide
4-{[4-(acryloylamino)-3,5-dimethylpiperidin-1-yl]sulfonyl}-N-[2-(4-chlorophenyl)ethyl]benzamide
4-{[4-(acryloylamino)-3,5-dimethylpiperidin-1-yl]sulfonyl}-N-[2-(quinolin-7-yl)ethyl]benzamide
4-{[4-(acryloylamino)-3,5-dimethylpiperidin-1-yl]sulfonyl}-N-[2-(naphthalen-2-yl)ethyl]benzamide
4-{[4-(acryloylamino)-3,5-dimethylpiperidin-1-yl]sulfonyl}-N-(3,4-dihydro-2H-chromen-6-ylmethyl)benzamide
4-{[4-(acryloylamino)-3,5-dimethylpiperidin-1-yl]sulfonyl}-N-[2-(4-tert-butylphenyl)ethyl]benzamide
4-{[4-(acryloylamino)-3,5-dimethylpiperidin-1-yl]sulfonyl}-N-[2-(biphenyl-4-yl)ethyl]benzamide
4-{[4-(acryloylamino)-3,5-dimethylpiperidin-1-yl]sulfonyl}-N-[2-(1,3-benzodioxol-5-yl)ethyl]benzamide
4-{[4-(acryloylamino)-3,5-dimethylpiperidin-1-yl]sulfonyl}-N-[(1R)-2-phenylcyclopropyl]benzamide
benzyl(4-{[4-(acryloylamino)-3,5-dimethylpiperidin-1-yl]sulfonyl}phenyl)methylcarbamate
4-{[4-(acryloylamino)-3,5-dimethylpiperidin-1-yl]sulfonyl}-N-[2-(3,4-dimethoxyphenyl)ethyl]benzamide
4-{[4-(acryloylamino)-3,5-dimethylpiperidin-1-yl]sulfonyl}-N-{2-[4-(trifluoromethyl)phenyl]ethyl}benzamide
4-{[4-(acryloylamino)-3,5-dimethylpiperidin-1-yl]sulfonyl}-N-(2-phenylethyl)piperidine-1-carboxamide
N-(4-{[4-(acryloylamino)-3,5-dimethylpiperidin-1-yl]sulfonyl}phenyl)furan-2-carboxamide
N-{3,5-dimethyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-3,5-dimethylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-3,5-dimethylpiperidin-4-yl)prop-2-enamide
N-[1-({2-chloro-4-[(3-phenylpropanoyl)amino]phenyl}sulfonyl)-3,5-dimethylpiperidin-4-yl]prop-2-enamide
N-(4-{[4-(acryloylamino)-3,5-dimethylpiperidin-1-yl]sulfonyl}phenyl)-5,6-dihydro-4H-cyclopenta[b]thiophene-2-carboxamide
N-(4-{[4-(acryloylamino)-3,5-dimethylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-3,5-dimethylpiperidin-4-yl]prop-2-enamide
N-(4-{[4-(acryloylamino)-3,5-dimethylpiperidin-1-yl]sulfonyl}phenyl)-5-(pyrrolidin-1-ylmethyl)furan-2-carboxamide
N-(4-{[4-(acryloylamino)-3,5-dimethylpiperidin-1-yl]sulfonyl}phenyl)-1-benzothiophene-2-carboxamide
N-(4-{[4-(acryloylamino)-3,5-dimethylpiperidin-1-yl]sulfonyl}phenyl)-3-methyl-1-benzofuran-2-carboxamide
N-(4-{[4-(acryloylamino)-3,5-dimethylpiperidin-1-yl]sulfonyl}phenyl)-1H-indole-2-carboxamide
4-{[4-(acryloylamino)-3,5-dimethylpiperidin-1-yl]sulfonyl}-N-(tricyclo[3.3.1.1~3,7~]dec-1-ylmethyl)benzamide
4-{[4-(acryloylamino)-3,5-dimethylpiperidin-1-yl]sulfonyl}-N-(1,2,3,4-tetrahydronaphthalen-1-yl)benzamide
N-(4-{[4-(acryloylamino)-3,5-dimethylpiperidin-1-yl]sulfonyl}phenyl)-4,5,6,7-tetrahydro-1-benzothiophene-2-carboxamide
N-(4-{[4-(acryloylamino)-3,5-dimethylpiperidin-1-yl]sulfonyl}phenyl)-5-phenylfuran-2-carboxamide
N-(4-{[4-(acryloylamino)-3,5-dimethylpiperidin-1-yl]sulfonyl}phenyl)-4-phenylthiophene-2-carboxamide
N-[3,5-dimethyl-1-({5-[5-(trifluoromethyl)-1,2-oxazol-3-yl]thiophen-2-yl}sulfonyl)piperidin-4-yl]prop-2-enamide
5-{[4-(acryloylamino)-3,5-dimethylpiperidin-1-yl]sulfonyl}-N-(2-phenylethyl)furan-2-carboxamide
N-{3,5-dimethyl-1-[(6-phenoxypyridin-3-yl)sulfonyl]piperidin-4-yl}prop-2-enamide
N-(3,5-dimethyl-1-{[6-(morpholin-4-yl)pyridin-3-yl]sulfonyl}piperidin-4-yl)prop-2-enamide
N-{3,5-dimethyl-1-[(6-phenylpyridin-3-yl)sulfonyl]piperidin-4-yl}prop-2-enamide
N-[1-({3-chloro-4-[(3-phenylpropanoyl)amino]phenyl}sulfonyl)-3,5-dimethylpiperidin-4-yl]prop-2-enamide 4-{[4-(acryloylamino)-3,5-dimethylpiperidin-1-yl]sulfonyl}-2-fluoro-N-(2-phenylethyl)benzamide
N-(3,5-dimethyl-1-{[5-(pyridin-2-yl)thiophen-2-yl]sulfonyl}piperidin-4-yl)prop-2-enamide
4-{[4-(acryloylamino)-3,5-dimethylpiperidin-1-yl]sulfonyl}-2-methoxy-N-(2-phenylethyl)benzamide
N-[1-(1,3-benzothiazol-6-ylsulfonyl)-3,5-dimethylpiperidin-4-yl]prop-2-enamide
N-{3,5-dimethyl-1-[(4-methyl-2-phenyl-1,3-thiazol-5-yl)sulfonyl]piperidin-4-yl}prop-2-enamide
N-(3,5-dimethyl-1-{[5-(2-methyl-1,3-thiazol-4-yl)thiophen-2-yl]sulfonyl}piperidin-4-yl)prop-2-enamide
N-(3,5-dimethyl-1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)-3,5-dimethylpiperidin-4-yl]prop-2-enamide
5-{[4-(acryloylamino)-3,5-dimethylpiperidin-1-yl]sulfonyl}-N-(2-phenylethyl)furan-3-carboxamide
N-[3,5-dimethyl-1-({4-[(phenylacetyl)amino]benzyl}sulfonyl)piperidin-4-yl]prop-2-enamide
N-(3,5-dimethyl-1-{[4-(morpholin-4-ylsulfonyl)phenyl]sulfonyl}piperidin-4-yl)prop-2-enamide
N-(3,5-dimethyl-1-{[5-(1,3-oxazol-5-yl)thiophen-2-yl]sulfonyl}piperidin-4-yl)prop-2-enamide
4-{[4-(acryloylamino)-3,5-dimethylpiperidin-1-yl]sulfonyl}-2-methyl-N-(2-phenylethyl)benzamide
N-{3,5-dimethyl-1-[(4-phenoxyphenyl)sulfonyl]piperidin-4-yl}prop-2-enamide
N-[3,5-dimethyl-1-({4-[(6-methylpyrazin-2-yl)oxy]phenyl}sulfonyl)piperidin-4-yl]prop-2-enamide
N-[3,5-dimethyl-1-({3-[(6-methylpyrazin-2-yl)oxy]phenyl}sulfonyl)piperidin-4-yl]prop-2-enamide
5-{[4-(acryloylamino)-3,5-dimethylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-3,5-dimethylpiperidin-4-yl)prop-2-enamide
N-{1-[(3-chloro-4-methylphenyl)sulfonyl]-3,5-dimethylpiperidin-4-yl}prop-2-enamide
N-(3,5-dimethyl-1-{[5-(1,2-oxazol-5-yl)furan-2-yl]sulfonyl}piperidin-4-yl)prop-2-enamide
N-{1-[(4-{[3-chloro-5-(trifluoromethyl)pyridin-2-yl]oxy}phenyl)sulfonyl]-3,5-dimethylpiperidin-4-yl}prop-2-enamide
N-(3,5-dimethyl-1-{[4-(1H-pyrazol-1-yl)phenyl]sulfonyl}piperidin-4-yl)prop-2-enamide
N-{1-[(4-methoxy-3-methylphenyl)sulfonyl]-3,5-dimethylpiperidin-4-yl}prop-2-enamide
N-(3,5-dimethyl-1-{[6-(2-phenylethoxy)pyridin-3-yl]sulfonyl}piperidin-4-yl)prop-2-enamide
N-[1-({5-[(acetylamino)methyl]thiophen-2-yl}sulfonyl)-3,5-dimethylpiperidin-4-yl]prop-2-enamide
N-{3,5-dimethyl-1-[(5-methyl-1-phenyl-1H-pyrazol-4-yl)sulfonyl]piperidin-4-yl}prop-2-enamide
N-(3,5-dimethyl-1-{[4-(1-methyl-1H-pyrazol-5-yl)phenyl]sulfonyl}piperidin-4-yl)prop-2-enamide
N-(3,5-dimethyl-1-{[3-(1-methyl-1H-pyrazol-5-yl)phenyl]sulfonyl}piperidin-4-yl)prop-2-enamide
N-{1-[(2,2-dimethyl-3,4-dihydro-2H-chromen-6-yl)sulfonyl]-3,5-dimethylpiperidin-4-yl}prop-2-enamide
N-{3,5-dimethyl-1-[(5-phenylthiophen-2-yl)sulfonyl]piperidin-4-yl}prop-2-enamide
N-(1-{[4-(cyclopentyloxy)phenyl]sulfonyl}-3,5-dimethylpiperidin-4-yl)prop-2-enamide
N-(3,5-dimethyl-1-{[5-(pyrrolidin-1-ylcarbonyl)-1H-pyrrol-3-yl]sulfonyl}piperidin-4-yl)prop-2-enamide
N-(3,5-dimethyl-1-{[4-(2-methyl-1,3-thiazol-4-yl)phenyl]sulfonyl}piperidin-4-yl)prop-2-enamide
N-(3,5-dimethyl-1-{[4-(pyridin-2-yloxy)phenyl]sulfonyl}piperidin-4-yl)prop-2-enamide
N-{3,5-dimethyl-1-[(2-oxo-1,2,3,4-tetrahydroquinolin-6-yl)sulfonyl]piperidin-4-yl}prop-2-enamide
N-{1-[(4-cyclohexylphenyl)sulfonyl]-2,6-dimethylpiperidin-4-yl}prop-2-enamide
N-(4-{[4-(acryloylamino)-2,6-dimethylpiperidin-1-yl]sulfonyl}phenyl)cyclopropanecarboxamide
N-(4-{[4-(acryloylamino)-2,6-dimethylpiperidin-1-yl]sulfonyl}phenyl)tricyclo[3.3.1.1~3,7~]decane-1-carboxamide
benzyl(4-{[4-(acryloylamino)-2,6-dimethylpiperidin-1-yl]sulfonyl}phenyl)carbamate
N-(2,6-dimethyl-1-{[4-(piperidin-1-ylcarbonyl)phenyl]sulfonyl}piperidin-4-yl)prop-2-enamide
benzyl 4-{[4-(acryloylamino)-2,6-dimethylpiperidin-1-yl]sulfonyl}piperidine-1-carboxylate
N-{2,6-dimethyl-1-[(4-nitrophenyl)sulfonyl]piperidin-4-yl}prop-2-enamide
N-(4-{[4-(acryloylamino)-2,6-dimethylpiperidin-1-yl]sulfonyl}phenyl)tetrahydro-2H-pyran-4-carboxamide
N-[2,6-dimethyl-1-({4-[(3-phenylpropanoyl)amino]phenyl}sulfonyl)piperidin-4-yl]prop-2-enamide
N-(4-{[4-(acryloylamino)-2,6-dimethylpiperidin-1-yl]sulfonyl}phenyl)-2-phenylcyclopropanecarboxamide
N-(4-{[4-(acryloylamino)-2,6-dimethylpiperidin-1-yl]sulfonyl}phenyl)-N-methyltetrahydro-2H-pyran-4-carboxamide
4-{[4-(acryloylamino)-2,6-dimethylpiperidin-1-yl]sulfonyl}-N-benzyl-N-methylbenzamide
4-{[4-(acryloylamino)-2,6-dimethylpiperidin-1-yl]sulfonyl}-N-(cyclopropylmethyl)benzamide
N-(2,6-dimethyl-1-{[3-(piperidin-1-ylcarbonyl)phenyl]sulfonyl}piperidin-4-yl)prop-2-enamide
N-(4-{[4-(acryloylamino)-2,6-dimethylpiperidin-1-yl]sulfonyl}phenyl)-N-methylcyclopropanecarboxamide
N-{2,6-dimethyl-1-[(4-{[4-(6-methylpyridin-2-yl)piperazin-1-yl]carbonyl}phenyl)sulfonyl]piperidin-4-yl}prop-2-enamide
4-{[4-(acryloylamino)-2,6-dimethylpiperidin-1-yl]sulfonyl}-N-[2-(morpholin-4-yl)ethyl]benzamide
4-{[4-(acryloylamino)-2,6-dimethylpiperidin-1-yl]sulfonyl}-N-(2-phenylethyl)benzamide
4-{[4-(acryloylamino)-2,6-dimethylpiperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-2,6-dimethylpiperidin-4-yl)prop-2-enamide
4-{[4-(acryloylamino)-2,6-dimethylpiperidin-1-yl]sulfonyl}-N-(2-cyclohexylethyl)benzamide
4-{[4-(acryloylamino)-2,6-dimethylpiperidin-1-yl]sulfonyl}-N-cyclohexylbenzamide
N-{2,6-dimethyl-1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)-2,6-dimethylpiperidin-1-yl]sulfonyl}-N-(3,5-dimethylbenzyl)benzamide
4-{[4-(acryloylamino)-2,6-dimethylpiperidin-1-yl]sulfonyl}-N-benzylbenzamide
4-{[4-(acryloylamino)-2,6-dimethylpiperidin-1-yl]sulfonyl}-N-(3,4-difluorobenzyl)benzamide
4-{[4-(acryloylamino)-2,6-dimethylpiperidin-1-yl]sulfonyl}-N-[4-(trifluoromethyl)benzyl]benzamide
4-{[4-(acryloylamino)-2,6-dimethylpiperidin-1-yl]sulfonyl}-N-(naphthalen-1-ylmethyl)benzamide 4-{[4-(acryloylamino)-2,6-dimethylpiperidin-1-yl]sulfonyl}-N-[2-(3,4-dimethylphenyl)ethyl]benzamide
4-{[4-(acryloylamino)-2,6-dimethylpiperidin-1-yl]sulfonyl}-N-[2-(4-methoxyphenyl)ethyl]benzamide
4-{[4-(acryloylamino)-2,6-dimethylpiperidin-1-yl]sulfonyl}-N-(2,3-dihydro-1H-inden-2-yl)benzamide
4-{[4-(acryloylamino)-2,6-dimethylpiperidin-1-yl]sulfonyl}-N-[2-(3-methylphenyl)ethyl]benzamide
N-[1-({4-[(acetylamino)methyl]phenyl}sulfonyl)-2,6-dimethylpiperidin-4-yl]prop-2-enamide
N-{2,6-dimethyl-1-[(4-{[3-(naphthalen-1-yl)propanoyl]amino}phenyl)sulfonyl]piperidin-4-yl}prop-2-enamide
N-[1-({4-[(3-cyclohexylpropanoyl)amino]phenyl}sulfonyl)-2,6-dimethylpiperidin-4-yl]prop-2-enamide
N-{1-[(1-benzoylpiperidin-4-yl)sulfonyl]-2,6-dimethylpiperidin-4-yl}prop-2-enamide
N-(2,6-dimethyl-1-{[1-(piperidin-1-ylcarbonyl)piperidin-4-yl]sulfonyl}piperidin-4-yl)prop-2-enamide
N-(2,6-dimethyl-1-{[1-(pyridin-2-ylcarbonyl)piperidin-4-yl]sulfonyl}piperidin-4-yl)prop-2-enamide
N-(4-{[4-(acryloylamino)-2,6-dimethylpiperidin-1-yl]sulfonyl}phenyl)-4-tert-butylcyclohexanecarboxamide
N-(4-{[4-(acryloylamino)-2,6-dimethylpiperidin-1-yl]sulfonyl}phenyl)-1-benzofuran-2-carboxamide
benzyl(3-{[4-(acryloylamino)-2,6-dimethylpiperidin-1-yl]sulfonyl}phenyl)carbamate
N-[2,6-dimethyl-1-({3-[(3-phenylpropanoyl)amino]phenyl}sulfonyl)piperidin-4-yl]prop-2-enamide
N-(3-{[4-(acryloylamino)-2,6-dimethylpiperidin-1-yl]sulfonyl}phenyl)tetrahydro-2H-pyran-4-carboxamide
4-{[4-(acryloylamino)-2,6-dimethylpiperidin-1-yl]sulfonyl}-N-(3-phenylpropyl)benzamide
4-{[4-(acryloylamino)-2,6-dimethylpiperidin-1-yl]sulfonyl}-N-[2-(3-chlorophenyl)ethyl]benzamide
4-{[4-(acryloylamino)-2,6-dimethylpiperidin-1-yl]sulfonyl}-N-[2-(2-methoxyphenyl)ethyl]benzamide
4-{[4-(acryloylamino)-2,6-dimethylpiperidin-1-yl]sulfonyl}-N-[2-(2,3-dihydro-1-benzofuran-7-yl)ethyl]benzamide
4-{[4-(acryloylamino)-2,6-dimethylpiperidin-1-yl]sulfonyl}-N-[2-(tetrahydro-2H-pyran-4-yl)ethyl]benzamide
4-{[4-(acryloylamino)-2,6-dimethylpiperidin-1-yl]sulfonyl}-N-[2-(4,4-difluoropiperidin-1-yl)ethyl]benzamide
N-[2,6-dimethyl-1-({1-[3-(trifluoromethyl)benzoyl]piperidin-4-yl}sulfonyl)piperidin-4-yl]prop-2-enamide
N-(2,6-dimethyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-2,6-dimethylpiperidin-4-yl]prop-2-enamide
4-{[4-(acryloylamino)-2,6-dimethylpiperidin-1-yl]sulfonyl}-N-(4-tert-butylbenzyl)benzamide
4-{[4-(acryloylamino)-2,6-dimethylpiperidin-1-yl]sulfonyl}-N-(4-phenylbutyl)benzamide
4-{[4-(acryloylamino)-2,6-dimethylpiperidin-1-yl]sulfonyl}-N-[2-(4-chlorophenyl)ethyl]benzamide
4-{[4-(acryloylamino)-2,6-dimethylpiperidin-1-yl]sulfonyl}-N-[2-(quinolin-7-yl)ethyl]benzamide
4-{[4-(acryloylamino)-2,6-dimethylpiperidin-1-yl]sulfonyl}-N-[2-(naphthalen-2-yl)ethyl]benzamide
4-{[4-(acryloylamino)-2,6-dimethylpiperidin-1-yl]sulfonyl}-N-(3,4-dihydro-2H-chromen-6-ylmethyl)benzamide
4-{[4-(acryloylamino)-2,6-dimethylpiperidin-1-yl]sulfonyl}-N-[2-(4-tert-butylphenyl)ethyl]benzamide
4-{[4-(acryloylamino)-2,6-dimethylpiperidin-1-yl]sulfonyl}-N-[2-(biphenyl-4-yl)ethyl]benzamide
4-{[4-(acryloylamino)-2,6-dimethylpiperidin-1-yl]sulfonyl}-N-[2-(1,3-benzodioxol-5-yl)ethyl]benzamide
4-{[4-(acryloylamino)-2,6-dimethylpiperidin-1-yl]sulfonyl}-N-[(1R)-2-phenylcyclopropyl]benzamide
benzyl(4-{[4-(acryloylamino)-2,6-dimethylpiperidin-1-yl]sulfonyl}phenyl)methylcarbamate
4-{[4-(acryloylamino)-2,6-dimethylpiperidin-1-yl]sulfonyl}-N-[2-(3,4-dimethoxyphenyl)ethyl]benzamide
4-{[4-(acryloylamino)-2,6-dimethylpiperidin-1-yl]sulfonyl}-N-{2-[4-(trifluoromethyl)phenyl]ethyl}benzamide
4-{[4-(acryloylamino)-2,6-dimethylpiperidin-1-yl]sulfonyl}-N-(2-phenylethyl)piperidine-1-carboxamide
N-(4-{[4-(acryloylamino)-2,6-dimethylpiperidin-1-yl]sulfonyl}phenyl)furan-2-carboxamide
N-{2,6-dimethyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-2,6-dimethylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-2,6-dimethylpiperidin-4-yl)prop-2-enamide
N-[1-({2-chloro-4-[(3-phenylpropanoyl)amino]phenyl}sulfonyl)-2,6-dimethylpiperidin-4-yl]prop-2-enamide
N-(4-{[4-(acryloylamino)-2,6-dimethylpiperidin-1-yl]sulfonyl}phenyl)-5,6-dihydro-4H-cyclopenta[b]thiophene-2-carboxamide
N-(4-{[4-(acryloylamino)-2,6-dimethylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-2,6-dimethylpiperidin-4-yl]prop-2-enamide
N-(4-{[4-(acryloylamino)-2,6-dimethylpiperidin-1-yl]sulfonyl}phenyl)-5-(pyrrolidin-1-ylmethyl)furan-2-carboxamide
N-(4-{[4-(acryloylamino)-2,6-dimethylpiperidin-1-yl]sulfonyl}phenyl)-1-benzothiophene-2-carboxamide
N-(4-{[4-(acryloylamino)-2,6-dimethylpiperidin-1-yl]sulfonyl}phenyl)-3-methyl-1-benzofuran-2-carboxamide
N-(4-{[4-(acryloylamino)-2,6-dimethylpiperidin-1-yl]sulfonyl}phenyl)-1H-indole-2-carboxamide
4-{[4-(acryloylamino)-2,6-dimethylpiperidin-1-yl]sulfonyl}-N-(tricyclo[3.3.1.1~3,7~]dec-1-ylmethyl)benzamide
4-{[4-(acryloylamino)-2,6-dimethylpiperidin-1-yl]sulfonyl}-N-(1,2,3,4-tetrahydronaphthalen-1-yl)benzamide
N-(4-{[4-(acryloylamino)-2,6-dimethylpiperidin-1-yl]sulfonyl}phenyl)-4,5,6,7-tetrahydro-1-benzothiophene-2-carboxamide
N-(4-{[4-(acryloylamino)-2,6-dimethylpiperidin-1-yl]sulfonyl}phenyl)-5-phenylfuran-2-carboxamide
N-(4-{[4-(acryloylamino)-2,6-dimethylpiperidin-1-yl]sulfonyl}phenyl)-4-phenylthiophene-2-carboxamide
N-[2,6-dimethyl-1-({5-[5-(trifluoromethyl)-1,2-oxazol-3-yl]thiophen-2-yl}sulfonyl)piperidin-4-yl]prop-2-enamide
5-{[4-(acryloylamino)-2,6-dimethylpiperidin-1-yl]sulfonyl}-N-(2-phenylethyl)furan-2-carboxamide
N-{2,6-dimethyl-1-[(6-phenoxypyridin-3-yl)sulfonyl]piperidin-4-yl}prop-2-enamide
N-(2,6-dimethyl-1-{[6-(morpholin-4-yl)pyridin-3-yl]sulfonyl}piperidin-4-yl)prop-2-enamide
N-{2,6-dimethyl-1-[(6-phenylpyridin-3-yl)sulfonyl]piperidin-4-yl}prop-2-enamide N-[1-({3-chloro-4-[(3-phenylpropanoyl)amino]
phenyl}sulfonyl)-2,6-dimethylpiperidin-4-yl]prop-2-enamide
4-{[4-(acryloylamino)-2,6-dimethylpiperidin-1-yl]sulfonyl}-2-fluoro-N-(2-phenylethyl)benzamide
N-(2,6-dimethyl-1-{[5-(pyridin-2-yl)thiophen-2-yl]
sulfonyl}piperidin-4-yl)prop-2-enamide
4-{[4-(acryloylamino)-2,6-dimethylpiperidin-1-yl]sulfonyl}-2-methoxy-N-(2-phenylethyl)benzamide
N-[1-(1,3-benzothiazol-6-ylsulfonyl)-2,6-dimethylpiperidin-4-yl]prop-2-enamide
N-{2,6-dimethyl-1-[(4-methyl-2-phenyl-1,3-thiazol-5-yl)
sulfonyl]piperidin-4-yl}prop-2-enamide
N-(2,6-dimethyl-1-{[5-(2-methyl-1,3-thiazol-4-yl)
thiophen-2-yl]sulfonyl}piperidin-4-yl)prop-2-enamide
N-(2,6-dimethyl-1-{[5-(1,2-oxazol-5-yl)thiophen-2-yl]
sulfonyl}piperidin-4-yl)prop-2-enamide
N-[1-(2,3-dihydro-1,4-benzodioxin-6-ylsulfonyl)-2,6-dimethylpiperidin-4-yl]prop-2-enamide
5-{[4-(acryloylamino)-2,6-dimethylpiperidin-1-yl]sulfonyl}-N-(2-phenylethyl)furan-3-carboxamide
N-[2,6-dimethyl-1-({4-[(phenylacetyl)amino]
benzyl}sulfonyl)piperidin-4-yl]prop-2-enamide
N-(2,6-dimethyl-1-{[4-(morpholin-4-ylsulfonyl)phenyl]
sulfonyl}piperidin-4-yl)prop-2-enamide
N-(2,6-dimethyl-1-{[5-(1,3-oxazol-5-yl)thiophen-2-yl]
sulfonyl}piperidin-4-yl)prop-2-enamide
4-{[4-(acryloylamino)-2,6-dimethylpiperidin-1-yl]sulfonyl}-2-methyl-N-(2-phenylethyl)benzamide
N-{2,6-dimethyl-1-[(4-phenoxyphenyl)sulfonyl]piperidin-4-yl}prop-2-enamide
N-[2,6-dimethyl-1-({4-[(6-methylpyrazin-2-yl)oxy]
phenyl}sulfonyl)piperidin-4-yl]prop-2-enamide
N-[2,6-dimethyl-1-({3-[(6-methylpyrazin-2-yl)oxy]
phenyl}sulfonyl)piperidin-4-yl]prop-2-enamide
5-{[4-(acryloylamino)-2,6-dimethylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-2,6-dimethylpiperidin-4-yl)prop-2-enamide
N-{1-[(3-chloro-4-methylphenyl)sulfonyl]-2,6-dimethylpiperidin-4-yl}prop-2-enamide
N-(2,6-dimethyl-1-{[5-(1,2-oxazol-5-yl)furan-2-yl]
sulfonyl}piperidin-4-yl)prop-2-enamide
N-{1-[(4-{[3-chloro-5-(trifluoromethyl)pyridin-2-yl]
oxy}phenyl)sulfonyl]-2,6-dimethylpiperidin-4-yl}prop-2-enamide
N-(2,6-dimethyl-1-{[4-(1H-pyrazol-1-yl)phenyl]
sulfonyl}piperidin-4-yl)prop-2-enamide
N-{1-[(4-methoxy-3-methylphenyl)sulfonyl]-2,6-dimethylpiperidin-4-yl}prop-2-enamide
N-(2,6-dimethyl-1-{[6-(2-phenylethoxy)pyridin-3-yl]
sulfonyl}piperidin-4-yl)prop-2-enamide
N-[1-({5-[(acetylamino)methyl]thiophen-2-yl}sulfonyl)-2,6-dimethylpiperidin-4-yl]prop-2-enamide
N-{2,6-dimethyl-1-[(5-methyl-1-phenyl-1H-pyrazol-4-yl)
sulfonyl]piperidin-4-yl}prop-2-enamide
N-(2,6-dimethyl-1-{[4-(1-methyl-1H-pyrazol-5-yl)phenyl]
sulfonyl}piperidin-4-yl)prop-2-enamide
N-(2,6-dimethyl-1-{[3-(1-methyl-1H-pyrazol-5-yl)phenyl]
sulfonyl}piperidin-4-yl)prop-2-enamide
N-{1-[(2,2-dimethyl-3,4-dihydro-2H-chromen-6-yl)sulfonyl]-2,6-dimethylpiperidin-4-yl}prop-2-enamide
N-{2,6-dimethyl-1-[(5-phenylthiophen-2-yl)sulfonyl]piperidin-4-yl}prop-2-enamide
N-(1-{[4-(cyclopentyloxy)phenyl]sulfonyl}-2,6-dimethylpiperidin-4-yl)prop-2-enamide
N-(2,6-dimethyl-1-{[5-(pyrrolidin-1-ylcarbonyl)-1H-pyrrol-3-yl]sulfonyl}piperidin-4-yl)prop-2-enamide
N-(2,6-dimethyl-1-{[4-(2-methyl-1,3-thiazol-4-yl)phenyl]
sulfonyl}piperidin-4-yl)prop-2-enamide
N-(2,6-dimethyl-1-{[4-(pyridin-2-yloxy)phenyl]
sulfonyl}piperidin-4-yl)prop-2-enamide
N-{2,6-dimethyl-1-[(2-oxo-1,2,3,4-tetrahydroquinolin-6-yl)
sulfonyl]piperidin-4-yl}prop-2-enamide
N-{1-[(4-cyclohexylphenyl)sulfonyl]-3-methylpiperidin-4-yl}prop-2-enamide
N-(4-{[4-(acryloylamino)-3-methylpiperidin-1-yl]
sulfonyl}phenyl)cyclopropanecarboxamide
N-(4-{[4-(acryloylamino)-3-methylpiperidin-1-yl]
sulfonyl}phenyl)tricyclo[3.3.1.1~3,7~]decane-1-carboxamide
benzyl(4-{[4-(acryloylamino)-3-methylpiperidin-1-yl]
sulfonyl}phenyl)carbamate
N-(3-methyl-1-{[4-(piperidin-1-ylcarbonyl)phenyl]
sulfonyl}piperidin-4-yl)prop-2-enamide
benzyl 4-{[4-(acryloylamino)-3-methylpiperidin-1-yl]
sulfonyl}piperidine-1-carboxylate
N-{3-methyl-1-[(4-nitrophenyl)sulfonyl]piperidin-4-yl}prop-2-enamide
N-(4-{[4-(acryloylamino)-3-methylpiperidin-1-yl]
sulfonyl}phenyl)tetrahydro-2H-pyran-4-carboxamide
N-[3-methyl-1-({4-[(3-phenylpropanoyl)amino]
phenyl}sulfonyl)piperidin-4-yl]prop-2-enamide
N-(4-{[4-(acryloylamino)-3-methylpiperidin-1-yl]
sulfonyl}phenyl)-2-phenylcyclopropanecarboxamide
N-(4-{[4-(acryloylamino)-3-methylpiperidin-1-yl]
sulfonyl}phenyl)-N-methyltetrahydro-2H-pyran-4-carboxamide
4-{[4-(acryloylamino)-3-methylpiperidin-1-yl]sulfonyl}-N-benzyl-N-methylbenzamide
4-{[4-(acryloylamino)-3-methylpiperidin-1-yl]sulfonyl}-N-(cyclopropylmethyl)benzamide
N-(3-methyl-1-{[3-(piperidin-1-ylcarbonyl)phenyl]
sulfonyl}piperidin-4-yl)prop-2-enamide
N-(4-{[4-(acryloylamino)-3-methylpiperidin-1-yl]
sulfonyl}phenyl)-N-methylcyclopropanecarboxamide
N-{3-methyl-1-[(4-{[4-(6-methylpyridin-2-yl)piperazin-1-yl]carbonyl}phenyl)sulfonyl]piperidin-4-yl}prop-2-enamide
4-{[4-(acryloylamino)-3-methylpiperidin-1-yl]sulfonyl}-N-[2-(morpholin-4-yl)ethyl]benzamide
4-{[4-(acryloylamino)-3-methylpiperidin-1-yl]sulfonyl}-N-(2-phenylethyl)benzamide
4-{[4-(acryloylamino)-3-methylpiperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-3-methylpiperidin-4-yl)prop-2-enamide
4-{[4-(acryloylamino)-3-methylpiperidin-1-yl]sulfonyl}-N-(2-cyclohexylethyl)benzamide
4-{[4-(acryloylamino)-3-methylpiperidin-1-yl]sulfonyl}-N-cyclohexylbenzamide
N-{3-methyl-1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)-3-methylpiperidin-1-yl]sulfonyl}-N-(3,5-dimethylbenzyl)benzamide
4-{[4-(acryloylamino)-3-methylpiperidin-1-yl]sulfonyl}-N-benzylbenzamide
4-{[4-(acryloylamino)-3-methylpiperidin-1-yl]sulfonyl}-N-(3,4-difluorobenzyl)benzamide
4-{[4-(acryloylamino)-3-methylpiperidin-1-yl]sulfonyl}-N-[4-(trifluoromethyl)benzyl]benzamide 4-{[4-(acryloylamino)-3-methylpiperidin-1-yl]sulfonyl}-N-(naphthalen-1-ylmethyl)benzamide
4-{[4-(acryloylamino)-3-methylpiperidin-1-yl]sulfonyl}-N-[2-(3,4-dimethylphenyl)ethyl]benzamide
4-{[4-(acryloylamino)-3-methylpiperidin-1-yl]sulfonyl}-N-[2-(4-methoxyphenyl)ethyl]benzamide
4-{[4-(acryloylamino)-3-methylpiperidin-1-yl]sulfonyl}-N-(2,3-dihydro-1H-inden-2-yl)benzamide
4-{[4-(acryloylamino)-3-methylpiperidin-1-yl]sulfonyl}-N-[2-(3-methylphenyl)ethyl]benzamide
N-[1-({4-[(acetylamino)methyl]phenyl}sulfonyl)-3-methylpiperidin-4-yl]prop-2-enamide
N-{3-methyl-1-[(4-{[3-(naphthalen-1-yl)propanoyl]amino}phenyl)sulfonyl]piperidin-4-yl}prop-2-enamide
N-[1-({4-[(3-cyclohexylpropanoyl)amino]phenyl}sulfonyl)-3-methylpiperidin-4-yl]prop-2-enamide
N-{1-[(1-benzoylpiperidin-4-yl)sulfonyl]-3-methylpiperidin-4-yl}prop-2-enamide
N-(3-methyl-1-{[1-(piperidin-1-ylcarbonyl)piperidin-4-yl]sulfonyl}piperidin-4-yl)prop-2-enamide
N-(3-methyl-1-{[1-(pyridin-2-ylcarbonyl)piperidin-4-yl]sulfonyl}piperidin-4-yl)prop-2-enamide
N-(4-{[4-(acryloylamino)-3-methylpiperidin-1-yl]sulfonyl}phenyl)-4-tert-butylcyclohexanecarboxamide
N-(4-{[4-(acryloylamino)-3-methylpiperidin-1-yl]sulfonyl}phenyl)-1-benzofuran-2-carboxamide
benzyl(3-{[4-(acryloylamino)-3-methylpiperidin-1-yl]sulfonyl}phenyl)carbamate
N-[3-methyl-1-({3-[(3-phenylpropanoyl)amino]phenyl}sulfonyl)piperidin-4-yl]prop-2-enamide
N-(3-{[4-(acryloylamino)-3-methylpiperidin-1-yl]sulfonyl}phenyl)tetrahydro-2H-pyran-4-carboxamide
4-{[4-(acryloylamino)-3-methylpiperidin-1-yl]sulfonyl}-N-(3-phenylpropyl)benzamide
4-{[4-(acryloylamino)-3-methylpiperidin-1-yl]sulfonyl}-N-[2-(3-chlorophenyl)ethyl]benzamide
4-{[4-(acryloylamino)-3-methylpiperidin-1-yl]sulfonyl}-N-[2-(2-methoxyphenyl)ethyl]benzamide
4-{[4-(acryloylamino)-3-methylpiperidin-1-yl]sulfonyl}-N-[2-(2,3-dihydro-1-benzofuran-7-yl)ethyl]benzamide
4-{[4-(acryloylamino)-3-methylpiperidin-1-yl]sulfonyl}-N-[2-(tetrahydro-2H-pyran-4-yl)ethyl]benzamide
4-{[4-(acryloylamino)-3-methylpiperidin-1-yl]sulfonyl}-N-[2-(4,4-difluoropiperidin-1-yl)ethyl]benzamide
N-[3-methyl-1-({1-[3-(trifluoromethyl)benzoyl]piperidin-4-yl}sulfonyl)piperidin-4-yl]prop-2-enamide
N-(3-methyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-3-methylpiperidin-4-yl]prop-2-enamide
4-{[4-(acryloylamino)-3-methylpiperidin-1-yl]sulfonyl}-N-(4-tert-butylbenzyl)benzamide
4-{[4-(acryloylamino)-3-methylpiperidin-1-yl]sulfonyl}-N-(4-phenylbutyl)benzamide
4-{[4-(acryloylamino)-3-methylpiperidin-1-yl]sulfonyl}-N-[2-(4-chlorophenyl)ethyl]benzamide
4-{[4-(acryloylamino)-3-methylpiperidin-1-yl]sulfonyl}-N-[2-(quinolin-7-yl)ethyl]benzamide
4-{[4-(acryloylamino)-3-methylpiperidin-1-yl]sulfonyl}-N-[2-(naphthalen-2-yl)ethyl]benzamide
4-{[4-(acryloylamino)-3-methylpiperidin-1-yl]sulfonyl}-N-(3,4-dihydro-2H-chromen-6-ylmethyl)benzamide
4-{[4-(acryloylamino)-3-methylpiperidin-1-yl]sulfonyl}-N-[2-(4-tert-butylphenyl)ethyl]benzamide
4-{[4-(acryloylamino)-3-methylpiperidin-1-yl]sulfonyl}-N-[2-(biphenyl-4-yl)ethyl]benzamide
4-{[4-(acryloylamino)-3-methylpiperidin-1-yl]sulfonyl}-N-[2-(1,3-benzodioxol-5-yl)ethyl]benzamide
4-{[4-(acryloylamino)-3-methylpiperidin-1-yl]sulfonyl}-N-[(1R)-2-phenylcyclopropyl]benzamide
benzyl(4-{[4-(acryloylamino)-3-methylpiperidin-1-yl]sulfonyl}phenyl)methylcarbamate
4-{[4-(acryloylamino)-3-methylpiperidin-1-yl]sulfonyl}-N-[2-(3,4-dimethoxyphenyl)ethyl]benzamide
4-{[4-(acryloylamino)-3-methylpiperidin-1-yl]sulfonyl}-N-{2-[4-(trifluoromethyl)phenyl]ethyl}benzamide
4-{[4-(acryloylamino)-3-methylpiperidin-1-yl]sulfonyl}-N-(2-phenylethyl)piperidine-1-carboxamide
N-(4-{[4-(acryloylamino)-3-methylpiperidin-1-yl]sulfonyl}phenyl)furan-2-carboxamide
N-{3-methyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-3-methylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-3-methylpiperidin-4-yl)prop-2-enamide
N-[1-({2-chloro-4-[(3-phenylpropanoyl)amino]phenyl}sulfonyl)-3-methylpiperidin-4-yl]prop-2-enamide
N-(4-{[4-(acryloylamino)-3-methylpiperidin-1-yl]sulfonyl}phenyl)-5,6-dihydro-4H-cyclopenta[b]thiophene-2-carboxamide
N-(4-{[4-(acryloylamino)-3-methylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-3-methylpiperidin-4-yl]prop-2-enamide
N-(4-{[4-(acryloylamino)-3-methylpiperidin-1-yl]sulfonyl}phenyl)-5-(pyrrolidin-1-ylmethyl)furan-2-carboxamide
N-(4-{[4-(acryloylamino)-3-methylpiperidin-1-yl]sulfonyl}phenyl)-1-benzothiophene-2-carboxamide
N-(4-{[4-(acryloylamino)-3-methylpiperidin-1-yl]sulfonyl}phenyl)-3-methyl-1-benzofuran-2-carboxamide
N-(4-{[4-(acryloylamino)-3-methylpiperidin-1-yl]sulfonyl}phenyl)-1H-indole-2-carboxamide
4-{[4-(acryloylamino)-3-methylpiperidin-1-yl]sulfonyl}-N-(tricyclo[3.3.1.1~3,7~]dec-1-ylmethyl)benzamide
4-{[4-(acryloylamino)-3-methylpiperidin-1-yl]sulfonyl}-N-(1,2,3,4-tetrahydronaphthalen-1-yl)benzamide
N-(4-{[4-(acryloylamino)-3-methylpiperidin-1-yl]sulfonyl}phenyl)-4,5,6,7-tetrahydro-1-benzothiophene-2-carboxamide
N-(4-{[4-(acryloylamino)-3-methylpiperidin-1-yl]sulfonyl}phenyl)-5-phenylfuran-2-carboxamide
N-(4-{[4-(acryloylamino)-3-methylpiperidin-1-yl]sulfonyl}phenyl)-4-phenylthiophene-2-carboxamide
N-[3-methyl-1-({5-[5-(trifluoromethyl)-1,2-oxazol-3-yl]thiophen-2-yl}sulfonyl)piperidin-4-yl]prop-2-enamide
5-{[4-(acryloylamino)-3-methylpiperidin-1-yl]sulfonyl}-N-(2-phenylethyl)furan-2-carboxamide
N-{3-methyl-1-[(6-phenoxypyridin-3-yl)sulfonyl]piperidin-4-yl}prop-2-enamide
N-(3-methyl-1-{[6-(morpholin-4-yl)pyridin-3-yl]sulfonyl}piperidin-4-yl)prop-2-enamide
N-{3-methyl-1-[(6-phenylpyridin-3-yl)sulfonyl]piperidin-4-yl}prop-2-enamide
N-[1-({3-chloro-4-[(3-phenylpropanoyl)amino]phenyl}sulfonyl)-3-methylpiperidin-4-yl]prop-2-enamide
4-{[4-(acryloylamino)-3-methylpiperidin-1-yl]sulfonyl}-2-fluoro-N-(2-phenylethyl)benzamide
N-(3-methyl-1-{[5-(pyridin-2-yl)thiophen-2-yl]sulfonyl}piperidin-4-yl)prop-2-enamide 4-{[4-(acryloylamino)-3-methylpiperidin-1-yl]sulfonyl}-2-methoxy-N-(2-phenylethyl)benzamide
N-[1-(1,3-benzothiazol-6-ylsulfonyl)-3-methylpiperidin-4-yl]prop-2-enamide
N-{3-methyl-1-[(4-methyl-2-phenyl-1,3-thiazol-5-yl)sulfonyl]piperidin-4-yl}prop-2-enamide
N-(3-methyl-1-{[5-(2-methyl-1,3-thiazol-4-yl)thiophen-2-yl]sulfonyl}piperidin-4-yl)prop-2-enamide
N-(3-methyl-1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)-3-methylpiperidin-4-yl]prop-2-enamide
5-{[4-(acryloylamino)-3-methylpiperidin-1-yl]sulfonyl}-N-(2-phenylethyl)furan-3-carboxamide
N-[3-methyl-1-({4-[(phenylacetyl)amino]benzyl}sulfonyl)piperidin-4-yl]prop-2-enamide
N-(3-methyl-1-{[4-(morpholin-4-ylsulfonyl)phenyl]sulfonyl}piperidin-4-yl)prop-2-enamide
N-(3-methyl-1-{[5-(1,3-oxazol-5-yl)thiophen-2-yl]sulfonyl}piperidin-4-yl)prop-2-enamide
4-{[4-(acryloylamino)-3-methylpiperidin-1-yl]sulfonyl}-2-methyl-N-(2-phenylethyl)benzamide
N-{3-methyl-1-[(4-phenoxyphenyl)sulfonyl]piperidin-4-yl}prop-2-enamide
N-[3-methyl-1-({4-[(6-methylpyrazin-2-yl)oxy]phenyl}sulfonyl)piperidin-4-yl]prop-2-enamide
N-[3-methyl-1-({3-[(6-methylpyrazin-2-yl)oxy]phenyl}sulfonyl)piperidin-4-yl]prop-2-enamide
5-{[4-(acryloylamino)-3-methylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-3-methylpiperidin-4-yl)prop-2-enamide
N-{1-[(3-chloro-4-methylphenyl)sulfonyl]-3-methylpiperidin-4-yl}prop-2-enamide
N-(3-methyl-1-{[5-(1,2-oxazol-5-yl)furan-2-yl]sulfonyl}piperidin-4-yl)prop-2-enamide
N-{1-[(4-{[3-chloro-5-(trifluoromethyl)pyridin-2-yl]oxy}phenyl)sulfonyl]-3-methylpiperidin-4-yl}prop-2-enamide
N-(3-methyl-1-{[4-(1H-pyrazol-1-yl)phenyl]sulfonyl}piperidin-4-yl)prop-2-enamide
N-{1-[(4-methoxy-3-methylphenyl)sulfonyl]-3-methylpiperidin-4-yl}prop-2-enamide
N-(3-methyl-1-{[6-(2-phenylethoxy)pyridin-3-yl]sulfonyl}piperidin-4-yl)prop-2-enamide
N-[1-({5-[(acetylamino)methyl]thiophen-2-yl}sulfonyl)-3-methylpiperidin-4-yl]prop-2-enamide
N-{3-methyl-1-[(5-methyl-1-phenyl-1H-pyrazol-4-yl)sulfonyl]piperidin-4-yl}prop-2-enamide
N-(3-methyl-1-{[4-(1-methyl-1H-pyrazol-5-yl)phenyl]sulfonyl}piperidin-4-yl)prop-2-enamide
N-(3-methyl-1-{[3-(1-methyl-1H-pyrazol-5-yl)phenyl]sulfonyl}piperidin-4-yl)prop-2-enamide
N-{1-[(2,2-dimethyl-3,4-dihydro-2H-chromen-6-yl)sulfonyl]-3-methylpiperidin-4-yl}prop-2-enamide
N-{3-methyl-1-[(5-phenylthiophen-2-yl)sulfonyl]piperidin-4-yl}prop-2-enamide
N-(1-{[4-(cyclopentyloxy)phenyl]sulfonyl}-3-methylpiperidin-4-yl)prop-2-enamide
N-(3-methyl-1-{[5-(pyrrolidin-1-ylcarbonyl)-1H-pyrrol-3-yl]sulfonyl}piperidin-4-yl)prop-2-enamide
N-(3-methyl-1-{[4-(2-methyl-1,3-thiazol-4-yl)phenyl]sulfonyl}piperidin-4-yl)prop-2-enamide
N-(3-methyl-1-{[4-(pyridin-2-yloxy)phenyl]sulfonyl}piperidin-4-yl)prop-2-enamide
N-{3-methyl-1-[(2-oxo-1,2,3,4-tetrahydroquinolin-6-yl)sulfonyl]piperidin-4-yl}prop-2-enamide
N-{1-[(4-cyclohexylphenyl)sulfonyl]-2-methylpiperidin-4-yl}prop-2-enamide
N-(4-{[4-(acryloylamino)-2-methylpiperidin-1-yl]sulfonyl}phenyl)cyclopropanecarboxamide
N-(4-{[4-(acryloylamino)-2-methylpiperidin-1-yl]sulfonyl}phenyl)tricyclo[3.3.1.1~3,7~]decane-1-carboxamide
benzyl(4-{[4-(acryloylamino)-2-methylpiperidin-1-yl]sulfonyl}phenyl)carbamate
N-(2-methyl-1-{[4-(piperidin-1-ylcarbonyl)phenyl]sulfonyl}piperidin-4-yl)prop-2-enamide
benzyl 4-{[4-(acryloylamino)-2-methylpiperidin-1-yl]sulfonyl}piperidine-1-carboxylate
N-{2-methyl-1-[(4-nitrophenyl)sulfonyl]piperidin-4-yl}prop-2-enamide
N-(4-{[4-(acryloylamino)-2-methylpiperidin-1-yl]sulfonyl}phenyl)tetrahydro-2H-pyran-4-carboxamide
N-[2-methyl-1-({4-[(3-phenylpropanoyl)amino]phenyl}sulfonyl)piperidin-4-yl]prop-2-enamide
N-(4-{[4-(acryloylamino)-2-methylpiperidin-1-yl]sulfonyl}phenyl)-2-phenylcyclopropanecarboxamide
N-(4-{[4-(acryloylamino)-2-methylpiperidin-1-yl]sulfonyl}phenyl)-N-methyltetrahydro-2H-pyran-4-carboxamide
4-{[4-(acryloylamino)-2-methylpiperidin-1-yl]sulfonyl}-N-benzyl-N-methylbenzamide
4-{[4-(acryloylamino)-2-methylpiperidin-1-yl]sulfonyl}-N-(cyclopropylmethyl)benzamide
N-(2-methyl-1-{[3-(piperidin-1-ylcarbonyl)phenyl]sulfonyl}piperidin-4-yl)prop-2-enamide
N-(4-{[4-(acryloylamino)-2-methylpiperidin-1-yl]sulfonyl}phenyl)-N-methylcyclopropanecarboxamide
N-{2-methyl-1-[(4-{[4-(6-methylpyridin-2-yl)piperazin-1-yl]carbonyl}phenyl)sulfonyl]piperidin-4-yl}prop-2-enamide
4-{[4-(acryloylamino)-2-methylpiperidin-1-yl]sulfonyl}-N-[2-(morpholin-4-yl)ethyl]benzamide
4-{[4-(acryloylamino)-2-methylpiperidin-1-yl]sulfonyl}-N-(2-phenylethyl)benzamide
4-{[4-(acryloylamino)-2-methylpiperidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-2-methylpiperidin-4-yl)prop-2-enamide
4-{[4-(acryloylamino)-2-methylpiperidin-1-yl]sulfonyl}-N-(2-cyclohexylethyl)benzamide
4-{[4-(acryloylamino)-2-methylpiperidin-1-yl]sulfonyl}-N-cyclohexylbenzamide
N-{2-methyl-1-[(4-{[4-(pyrrolidin-1-ylcarbonyl)piperidin-1-yl]carbonyl}phenyl)sulfonyl]piperidin-4-yl}prop-2-enamide
4-{[4-(acryloylamino)-2-methylpiperidin-1-yl]sulfonyl}-N-(3,5-dimethylbenzyl)benzamide
4-{[4-(acryloylamino)-2-methylpiperidin-1-yl]sulfonyl}-N-benzylbenzamide
4-{[4-(acryloylamino)-2-methylpiperidin-1-yl]sulfonyl}-N-(3,4-difluorobenzyl)benzamide
4-{[4-(acryloylamino)-2-methylpiperidin-1-yl]sulfonyl}-N-[4-(trifluoromethyl)benzyl]benzamide
4-{[4-(acryloylamino)-2-methylpiperidin-1-yl]sulfonyl}-N-(naphthalen-1-ylmethyl)benzamide
4-{[4-(acryloylamino)-2-methylpiperidin-1-yl]sulfonyl}-N-[2-(3,4-dimethylphenyl)ethyl]benzamide
4-{[4-(acryloylamino)-2-methylpiperidin-1-yl]sulfonyl}-N-[2-(4-methoxyphenyl)ethyl]benzamide
4-{[4-(acryloylamino)-2-methylpiperidin-1-yl]sulfonyl}-N-(2,3-dihydro-1H-inden-2-yl)benzamide 4-{[4-(acryloylamino)-2-methylpiperidin-1-yl]sulfonyl}-N-[2-(3-methylphenyl)ethyl]benzamide
N-[1-({4-[(acetylamino)methyl]phenyl}sulfonyl)-2-methylpiperidin-4-yl]prop-2-enamide
N-{2-methyl-1-[(4-{[3-(naphthalen-1-yl)propanoyl]amino}phenyl)sulfonyl]piperidin-4-yl}prop-2-enamide
N-[1-({4-[(3-cyclohexylpropanoyl)amino]phenyl}sulfonyl)-2-methylpiperidin-4-yl]prop-2-enamide
N-{1-[(1-benzoylpiperidin-4-yl)sulfonyl]-2-methylpiperidin-4-yl}prop-2-enamide
N-(2-methyl-1-{[1-(piperidin-1-ylcarbonyl)piperidin-4-yl]sulfonyl}piperidin-4-yl)prop-2-enamide
N-(2-methyl-1-{[1-(pyridin-2-ylcarbonyl)piperidin-4-yl]sulfonyl}piperidin-4-yl)prop-2-enamide
N-(4-{[4-(acryloylamino)-2-methylpiperidin-1-yl]sulfonyl}phenyl)-4-tert-butylcyclohexanecarboxamide
N-(4-{[4-(acryloylamino)-2-methylpiperidin-1-yl]sulfonyl}phenyl)-1-benzofuran-2-carboxamide
benzyl(3-{[4-(acryloylamino)-2-methylpiperidin-1-yl]sulfonyl}phenyl)carbamate
N-[2-methyl-1-({3-[(3-phenylpropanoyl)amino]phenyl}sulfonyl)piperidin-4-yl]prop-2-enamide
N-(3-{[4-(acryloylamino)-2-methylpiperidin-1-yl]sulfonyl}phenyl)tetrahydro-2H-pyran-4-carboxamide
4-{[4-(acryloylamino)-2-methylpiperidin-1-yl]sulfonyl}-N-(3-phenylpropyl)benzamide
4-{[4-(acryloylamino)-2-methylpiperidin-1-yl]sulfonyl}-N-[2-(3-chlorophenyl)ethyl]benzamide
4-{[4-(acryloylamino)-2-methylpiperidin-1-yl]sulfonyl}-N-[2-(2-methoxyphenyl)ethyl]benzamide
4-{[4-(acryloylamino)-2-methylpiperidin-1-yl]sulfonyl}-N-[2-(2,3-dihydro-1-benzofuran-7-yl)ethyl]benzamide
4-{[4-(acryloylamino)-2-methylpiperidin-1-yl]sulfonyl}-N-[2-(tetrahydro-2H-pyran-4-yl)ethyl]benzamide
4-{[4-(acryloylamino)-2-methylpiperidin-1-yl]sulfonyl}-N-[2-(4,4-difluoropiperidin-1-yl)ethyl]benzamide
N-[3-methyl-1-({1-[3-(trifluoromethyl)benzoyl]piperidin-4-yl}sulfonyl)piperidin-4-yl]prop-2-enamide
N-(2-methyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-2-methylpiperidin-4-yl]prop-2-enamide
4-{[4-(acryloylamino)-2-methylpiperidin-1-yl]sulfonyl}-N-(4-tert-butylbenzyl)benzamide
4-{[4-(acryloylamino)-2-methylpiperidin-1-yl]sulfonyl}-N-(4-phenylbutyl)benzamide
4-{[4-(acryloylamino)-2-methylpiperidin-1-yl]sulfonyl}-N-[2-(4-chlorophenyl)ethyl]benzamide
4-{[4-(acryloylamino)-2-methylpiperidin-1-yl]sulfonyl}-N-[2-(quinolin-7-yl)ethyl]benzamide
4-{[4-(acryloylamino)-2-methylpiperidin-1-yl]sulfonyl}-N-[2-(naphthalen-2-yl)ethyl]benzamide
4-{[4-(acryloylamino)-2-methylpiperidin-1-yl]sulfonyl}-N-(3,4-dihydro-2H-chromen-6-ylmethyl)benzamide
4-{[4-(acryloylamino)-2-methylpiperidin-1-yl]sulfonyl}-N-[2-(4-tert-butylphenyl)ethyl]benzamide
4-{[4-(acryloylamino)-2-methylpiperidin-1-yl]sulfonyl}-N-[2-(biphenyl-4-yl)ethyl]benzamide
4-{[4-(acryloylamino)-2-methylpiperidin-1-yl]sulfonyl}-N-[2-(1,3-benzodioxol-5-yl)ethyl]benzamide
4-{[4-(acryloylamino)-2-methylpiperidin-1-yl]sulfonyl}-N-[(1R)-2phenylcyclopropyl]benzamide
benzyl(4-{[4-(acryloylamino)-2-methylpiperidin-1-yl]sulfonyl}phenyl)methylcarbamate
4-{[4-(acryloylamino)-2-methylpiperidin-1-yl]sulfonyl}-N-[2-(3,4-dimethoxyphenyl)ethyl]benzamide
4-{[4-(acryloylamino)-2-methylpiperidin-1-yl]sulfonyl}-N-{2-[4-(trifluoromethyl)phenyl]ethyl}benzamide
4-{[4-(acryloylamino)-2-methylpiperidin-1-yl]sulfonyl}-N-(2-phenylethyl)piperidine-1-carboxamide
N-(4-{[4-(acryloylamino)-2-methylpiperidin-1-yl]sulfonyl}phenyl)furan-2-carboxamide
N-{2-methyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-2-methylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-2-methylpiperidin-4-yl)prop-2-enamide
N-[1-({2-chloro-4-[(3-phenylpropanoyl)amino]phenyl}sulfonyl)-2-methylpiperidin-4-yl]prop-2-enamide
N-(4-{[4-(acryloylamino)-2-methylpiperidin-1-yl]sulfonyl}phenyl)-5,6-dihydro-4H-cyclopenta[b]thiophene-2-carboxamide
N-(4-{[4-(acryloylamino)-2-methylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-2-methylpiperidin-4-yl]prop-2-enamide
N-(4-{[4-(acryloylamino)-2-methylpiperidin-1-yl]sulfonyl}phenyl)-5-(pyrrolidin-1-ylmethyl)furan-2-carboxamide
N-(4-{[4-(acryloylamino)-2-methylpiperidin-1-yl]sulfonyl}phenyl)-1-benzothiophene-2-carboxamide
N-(4-{[4-(acryloylamino)-2-methylpiperidin-1-yl]sulfonyl}phenyl)-3-methyl-1-benzofuran-2-carboxamide
N-(4-{[4-(acryloylamino)-2-methylpiperidin-1-yl]sulfonyl}phenyl)-1H-indole-2-carboxamide
4-{[4-(acryloylamino)-2-methylpiperidin-1-yl]sulfonyl}-N-(tricyclo[3.3.1.1~3,7~]dec-1-ylmethyl)benzamide
4-{[4-(acryloylamino)-2-methylpiperidin-1-yl]sulfonyl}-N-(1,2,3,4-tetrahydronaphthalen-1-yl)benzamide
N-(4-{[4-(acryloylamino)-2-methylpiperidin-1-yl]sulfonyl}phenyl)-4,5,6,7-tetrahydro-1-benzothiophene-2-carboxamide
N-(4-{[4-(acryloylamino)-2-methylpiperidin-1-yl]sulfonyl}phenyl)-5-phenylfuran-2-carboxamide
N-(4-{[4-(acryloylamino)-2-methylpiperidin-1-yl]sulfonyl}phenyl)-4-phenylthiophene-2-carboxamide
N-[3-methyl-1-({5-[5-(trifluoromethyl)-1,2-oxazol-3-yl]thiophen-2-yl}sulfonyl)piperidin-4-yl]prop-2-enamide
5-{[4-(acryloylamino)-2-methylpiperidin-1-yl]sulfonyl}-N-(2-phenylethyl)furan-2-carboxamide
N-{2-methyl-1-[(6-phenoxypyridin-3-yl)sulfonyl]piperidin-4-yl}prop-2-enamide
N-(2-methyl-1-{[6-(morpholin-4-yl)pyridin-3-yl]sulfonyl}piperidin-4-yl)prop-2-enamide
N-{2-methyl-1-[(6-phenylpyridin-3-yl)sulfonyl]piperidin-4-yl}prop-2-enamide
N-[1-({3-chloro-4-[(3-phenylpropanoyl)amino]phenyl}sulfonyl)-2-methylpiperidin-4-yl]prop-2-enamide
4-{[4-(acryloylamino)-2-methylpiperidin-1-yl]sulfonyl}-2-fluoro-N-(2-phenylethyl)benzamide
N-(2-methyl-1-{[5-(pyridin-2-yl)thiophen-2-yl]sulfonyl}piperidin-4-yl)prop-2-enamide
4-{[4-(acryloylamino)-2-methylpiperidin-1-yl]sulfonyl}-2-methoxy-N-(2-phenylethyl)benzamide
N-[1-(1,3-benzothiazol-6-ylsulfonyl)-2-methylpiperidin-4-yl]prop-2-enamide
N-{2-methyl-1-[(4-methyl-2-phenyl-1,3-thiazol-5-yl)sulfonyl]piperidin-4-yl}prop-2-enamide
N-(2-methyl-1-{[5-(2-methyl-1,3-thiazol-4-yl)thiophen-2-yl]sulfonyl}piperidin-4-yl)prop-2-enamide N-(2-methyl-1-{[5-(1,2-oxazol-5-yl)thiophen-2-yl]
  sulfonyl}piperidin-4-yl)prop-2-enamide
N-[1-(2,3-dihydro-1,4-benzodioxin-6-ylsulfonyl)-2-meth-
  ylpiperidin-4-yl]prop-2-enamide
5-{[4-(acryloylamino)-2-methylpiperidin-1-yl]sulfonyl}-N-
  (2-phenylethyl)furan-3-carboxamide
N-[2-methyl-1-({4-[(phenylacetyl)amino]benzyl}sulfonyl)
  piperidin-4-yl]prop-2-enamide
N-(2-methyl-1-{[4-(morpholin-4-ylsulfonyl)phenyl]
  sulfonyl}piperidin-4-yl)prop-2-enamide
N-(2-methyl-1-{[5-(1,3-oxazol-5-yl)thiophen-2-yl]
  sulfonyl}piperidin-4-yl)prop-2-enamide
4-{[4-(acryloylamino)-2-methylpiperidin-1-yl]sulfonyl}-2-
  methyl-N-(2-phenylethyl)benzamide
N-{2-methyl-1-[(4-phenoxyphenyl)sulfonyl]piperidin-4-
  yl}prop-2-enamide
N-[2-methyl-1-({4-[(6-methylpyrazin-2-yl)oxy]
  phenyl}sulfonyl)piperidin-4-yl]prop-2-enamide
N-[2-methyl-1-({3-[(6-methylpyrazin-2-yl)oxy]
  phenyl}sulfonyl)piperidin-4-yl]prop-2-enamide
5-{[4-(acryloylamino)-2-methylpiperidin-1-yl]sulfonyl}-1-
  methyl-N-(2-phenylethyl)-1H-pyrrole-2-carboxamide
N-(1-{[4-(isoquinolin-3-ylamino)phenyl]sulfonyl}-2-meth-
  ylpiperidin-4-yl)prop-2-enamide
N-{1-[(3-chloro-4-methylphenyl)sulfonyl]-2-methylpiperi-
  din-4-yl}prop-2-enamide
N-(2-methyl-1-{[5-(1,2-oxazol-5-yl)furan-2-yl]
  sulfonyl}piperidin-4-yl)prop-2-enamide
N-{1-[(4-{[3-chloro-5-(trifluoromethyl)pyridin-2-yl]
  oxy}phenyl)sulfonyl]-2-methylpiperidin-4-yl}prop-2-
  enamide
N-(2-methyl-1-{[4-(1H-pyrazol-1-yl)phenyl]
  sulfonyl}piperidin-4-yl)prop-2-enamide
N-{1-[(4-methoxy-3-methylphenyl)sulfonyl]-2-methylpip-
  eridin-4-yl}prop-2-enamide
N-(2-methyl-1-{[6-(2-phenylethoxy)pyridin-3-yl]
  sulfonyl}piperidin-4-yl)prop-2-enamide
N-[1-({5-[(acetylamino)methyl]thiophen-2-yl}sulfonyl)-2-
  methylpiperidin-4-yl]prop-2-enamide
N-{2-methyl-1-[(5-methyl-1-phenyl-1H-pyrazol-4-yl)sulfo-
  nyl]piperidin-4-yl}prop-2-enamide
N-(2-methyl-1-{[4-(1-methyl-1H-pyrazol-5-yl)phenyl]
  sulfonyl}piperidin-4-yl)prop-2-enamide
N-(2-methyl-1-{[3-(1-methyl-1H-pyrazol-5-yl)phenyl]
  sulfonyl}piperidin-4-yl)prop-2-enamide
N-{1-[(2,2-dimethyl-3,4-dihydro-2H-chromen-6-yl)sulfo-
  nyl]-2-methylpiperidin-4-yl}prop-2-enamide
N-{2-methyl-1-[(5-phenylthiophen-2-yl)sulfonyl]piperidin-
  4-yl}prop-2-enamide
N-(1-{[4-(cyclopentyloxy)phenyl]sulfonyl}-2-methylpip-
  eridin-4-yl)prop-2-enamide
N-(2-methyl-1-{[5-(pyrrolidin-1-ylcarbonyl)-1H-pyrrol-3-
  yl]sulfonyl}piperidin-4-yl)prop-2-enamide
N-(2-methyl-1-{[4-(2-methyl-1,3-thiazol-4-yl)phenyl]
  sulfonyl}piperidin-4-yl)prop-2-enamide
N-(2-methyl-1-{[4-(pyridin-2-yloxy)phenyl]
  sulfonyl}piperidin-4-yl)prop-2-enamide
N-{2-methyl-1-[(2-oxo-1,2,3,4-tetrahydroquinolin-6-yl)sul-
  fonyl]piperidin-4-yl}prop-2-enamide
N-{1-[(4-cyclohexylphenyl)sulfonyl]-4-methylpiperidin-4-
  yl}prop-2-enamide
N-(4-{[4-(acryloylamino)-4-methylpiperidin-1-yl]
  sulfonyl}phenyl)cyclopropanecarboxamide
N-(4-{[4-(acryloylamino)-4-methylpiperidin-1-yl]
  sulfonyl}phenyl)tricyclo[3.3.1.1~3,7~]decane-1-car-
  boxamide
benzyl(4-{[4-(acryloylamino)-4-methylpiperidin-1-yl]
  sulfonyl}phenyl)carbamate
N-(4-methyl-1-{[4-(piperidin-1-ylcarbonyl)phenyl]
  sulfonyl}piperidin-4-yl)prop-2-enamide
benzyl 4-{[4-(acryloylamino)-4-methylpiperidin-1-yl]
  sulfonyl}piperidine-1-carboxylate
N-{4-methyl-1-[(4-nitrophenyl)sulfonyl]piperidin-4-
  yl}prop-2-enamide
N-(4-{[4-(acryloylamino)-4-methylpiperidin-1-yl]
  sulfonyl}phenyl)tetrahydro-2H-pyran-4-carboxamide
N-[4-methyl-1-({4-[(3-phenylpropanoyl)amino]
  phenyl}sulfonyl)piperidin-4-yl]prop-2-enamide
N-(4-{[4-(acryloylamino)-4-methylpiperidin-1-yl]
  sulfonyl}phenyl)-2-phenylcyclopropanecarboxamide
N-(4-{[4-(acryloylamino)-4-methylpiperidin-1-yl]
  sulfonyl}phenyl)-N-methyltetrahydro-2H-pyran-4-car-
  boxamide
4-{[4-(acryloylamino)-4-methylpiperidin-1-yl]sulfonyl}-N-
  benzyl-N-methylbenzamide
4-{[4-(acryloylamino)-4-methylpiperidin-1-yl]sulfonyl}-N-
  (cyclopropylmethyl)benzamide
N-(4-methyl-1-{[3-(piperidin-1-ylcarbonyl)phenyl]
  sulfonyl}piperidin-4-yl)prop-2-enamide
N-(4-{[4-(acryloylamino)-4-methylpiperidin-1-yl]
  sulfonyl}phenyl)-N-methylcyclopropanecarboxamide
N-{4-methyl-1-[(4-{[4-(6-methylpyridin-2-yl)piperazin-1-
  yl]carbonyl}phenyl)sulfonyl]piperidin-4-yl}prop-2-ena-
  mide
4-{[4-(acryloylamino)-4-methylpiperidin-1-yl]sulfonyl}-N-
  [2-(morpholin-4-yl)ethyl]benzamide
4-{[4-(acryloylamino)-4-methylpiperidin-1-yl]sulfonyl}-N-
  (2-phenylethyl)benzamide
4-{[4-(acryloylamino)-4-methylpiperidin-1-yl]sulfonyl}-N-
  methyl-N-(2-phenylethyl)benzamide
N-(1-{[4-(3,4-dihydroisoquinolin-2(1H)-ylcarbonyl)phe-
  nyl]sulfonyl}-4-methylpiperidin-4-yl)prop-2-enamide
4-{[4-(acryloylamino)-4-methylpiperidin-1-yl]sulfonyl}-N-
  (2-cyclohexylethyl)benzamide
4-{[4-(acryloylamino)-4-methylpiperidin-1-yl]sulfonyl}-N-
  cyclohexylbenzamide
N-{4-methyl-1-[(4-{[4-(pyrrolidin-1-ylcarbonyl)piperidin-
  1-yl]carbonyl}phenyl)sulfonyl]piperidin-4-yl}prop-2-
  enamide
4-{[4-(acryloylamino)-4-methylpiperidin-1-yl]sulfonyl}-N-
  (3,5-dimethylbenzyl)benzamide
4-{[4-(acryloylamino)-4-methylpiperidin-1-yl]sulfonyl}-N-
  benzylbenzamide
4-{[4-(acryloylamino)-4-methylpiperidin-1-yl]sulfonyl}-N-
  (3,4-difluorobenzyl)benzamide
4-{[4-(acryloylamino)-4-methylpiperidin-1-yl]sulfonyl}-N-
  [4-(trifluoromethyl)benzyl]benzamide
4-{[4-(acryloylamino)-4-methylpiperidin-1-yl]sulfonyl}-N-
  (naphthalen-1-ylmethyl)benzamide
4-{[4-(acryloylamino)-4-methylpiperidin-1-yl]sulfonyl}-N-
  [2-(3,4-dimethylphenyl)ethyl]benzamide
4-{[4-(acryloylamino)-4-methylpiperidin-1-yl]sulfonyl}-N-
  [2-(4-methoxyphenyl)ethyl]benzamide
4-{[4-(acryloylamino)-4-methylpiperidin-1-yl]sulfonyl}-N-
  (2,3-dihydro-1H-inden-2-yl)benzamide
4-{[4-(acryloylamino)-4-methylpiperidin-1-yl]sulfonyl}-N-
  [2-(3-methylphenyl)ethyl]benzamide
N-[1-({4-[(acetylamino)methyl]phenyl}sulfonyl)-4-meth-
  ylpiperidin-4-yl]prop-2-enamide
N-{4-methyl-1-[(4-{[3-(naphthalen-1-yl)propanoyl]
  amino}phenyl)sulfonyl]piperidin-4-yl}prop-2-enamide
N-[1-({4-[(3-cyclohexylpropanoyl)amino]
  phenyl}sulfonyl)-4-methylpiperidin-4-yl]prop-2-enamide N-{1-[(1-benzoylpiperidin-4-yl)sulfonyl]-4-methylpiperidin-4-yl}prop-2-enamide
N-(4-methyl-1-{[1-(piperidin-1-ylcarbonyl)piperidin-4-yl]sulfonyl}piperidin-4-yl)prop-2-enamide
N-(4-methyl-1-{[1-(pyridin-2-ylcarbonyl)piperidin-4-yl]sulfonyl}piperidin-4-yl)prop-2-enamide
N-(4-{[4-(acryloylamino)-4-methylpiperidin-1-yl]sulfonyl}phenyl)-4-tert-butylcyclohexanecarboxamide
N-(4-{[4-(acryloylamino)-4-methylpiperidin-1-yl]sulfonyl}phenyl)-1-benzofuran-2-carboxamide
benzyl(3-{[4-(acryloylamino)-4-methylpiperidin-1-yl]sulfonyl}phenyl)carbamate
N-[4-methyl-1-({3-[(3-phenylpropanoyl)amino]phenyl}sulfonyl)piperidin-4-yl]prop-2-enamide
N-(3-{[4-(acryloylamino)-4-methylpiperidin-1-yl]sulfonyl}phenyl)tetrahydro-2H-pyran-4-carboxamide
4-{[4-(acryloylamino)-4-methylpiperidin-1-yl]sulfonyl}-N-(3-phenylpropyl)benzamide
4-{[4-(acryloylamino)-4-methylpiperidin-1-yl]sulfonyl}-N-[2-(3-chlorophenyl)ethyl]benzamide
4-{[4-(acryloylamino)-4-methylpiperidin-1-yl]sulfonyl}-N-[2-(2-methoxyphenyl)ethyl]benzamide
4-{[4-(acryloylamino)-4-methylpiperidin-1-yl]sulfonyl}-N-[2-(2,3-dihydro-1-benzofuran-7-yl)ethyl]benzamide
4-{[4-(acryloylamino)-4-methylpiperidin-1-yl]sulfonyl}-N-[2-(tetrahydro-2H-pyran-4-yl)ethyl]benzamide
4-{[4-(acryloylamino)-4-methylpiperidin-1-yl]sulfonyl}-N-[2-(4,4-difluoropiperidin-1-yl)ethyl]benzamide
N-[4-methyl-1-({1-[3-(trifluoromethyl)benzoyl]piperidin-4-yl}sulfonyl)piperidin-4-yl]prop-2-enamide
N-(4-methyl-1-{[1-(3-phenylpropanoyl)piperidin-4-yl]sulfonyl}piperidin-4-yl)prop-2-enamide
N-[1-({4-[2-(benzylamino)-2-oxoethyl]phenyl}sulfonyl)-4-methylpiperidin-4-yl]prop-2-enamide
4-{[4-(acryloylamino)-4-methylpiperidin-1-yl]sulfonyl}-N-(4-tert-butylbenzyl)benzamide
4-{[4-(acryloylamino)-4-methylpiperidin-1-yl]sulfonyl}-N-(4-phenylbutyl)benzamide
4-{[4-(acryloylamino)-4-methylpiperidin-1-yl]sulfonyl}-N-[2-(4-chlorophenyl)ethyl]benzamide
4-{[4-(acryloylamino)-4-methylpiperidin-1-yl]sulfonyl}-N-[2-(quinolin-7-yl)ethyl]benzamide
4-{[4-(acryloylamino)-4-methylpiperidin-1-yl]sulfonyl}-N-[2-(naphthalen-2-yl)ethyl]benzamide
4-{[4-(acryloylamino)-4-methylpiperidin-1-yl]sulfonyl}-N-(3,4-dihydro-2H-chromen-6-ylmethyl)benzamide
4-{[4-(acryloylamino)-4-methylpiperidin-1-yl]sulfonyl}-N-[2-(4-tert-butylphenyl)ethyl]benzamide
4-{[4-(acryloylamino)-4-methylpiperidin-1-yl]sulfonyl}-N-[2-(biphenyl-4-yl)ethyl]benzamide
4-{[4-(acryloylamino)-4-methylpiperidin-1-yl]sulfonyl}-N-[2-(1,3-benzodioxol-5-yl)ethyl]benzamide
4-{[4-(acryloylamino)-4-methylpiperidin-1-yl]sulfonyl}-N-[(1R)-2-phenylcyclopropyl]benzamide
benzyl(4-{[4-(acryloylamino)-4-methylpiperidin-1-yl]sulfonyl}phenyl)methylcarbamate
4-{[4-(acryloylamino)-4-methylpiperidin-1-yl]sulfonyl}-N-[2-(3,4-dimethoxyphenyl)ethyl]benzamide
4-{[4-(acryloylamino)-4-methylpiperidin-1-yl]sulfonyl}-N-{2-[4-(trifluoromethyl)phenyl]ethyl}benzamide
4-{[4-(acryloylamino)-4-methylpiperidin-1-yl]sulfonyl}-N-(2-phenylethyl)piperidine-1-carboxamide
N-(4-{[4-(acryloylamino)-4-methylpiperidin-1-yl]sulfonyl}phenyl)furan-2-carboxamide
N-{4-methyl-1-[(4-{[3-(tricyclo[3.3.1.1~3,7~]dec-1-yl)propanoyl]amino}phenyl)sulfonyl]piperidin-4-yl}prop-2-enamide
4-{[4-(acryloylamino)-4-methylpiperidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-4-methylpiperidin-4-yl)prop-2-enamide
N-[1-({2-chloro-4-[(3-phenylpropanoyl)amino]phenyl}sulfonyl)-4-methylpiperidin-4-yl]prop-2-enamide
N-(4-{[4-(acryloylamino)-4-methylpiperidin-1-yl]sulfonyl}phenyl)-5,6-dihydro-4H-cyclopenta[b]thiophene-2-carboxamide
N-(4-{[4-(acryloylamino)-4-methylpiperidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-4-methylpiperidin-4-yl]prop-2-enamide
N-(4-{[4-(acryloylamino)-4-methylpiperidin-1-yl]sulfonyl}phenyl)-5-(pyrrolidin-1-ylmethyl)furan-2-carboxamide
N-(4-{[4-(acryloylamino)-4-methylpiperidin-1-yl]sulfonyl}phenyl)-1-benzothiophene-2-carboxamide
N-(4-{[4-(acryloylamino)-4-methylpiperidin-1-yl]sulfonyl}phenyl)-3-methyl-1-benzofuran-2-carboxamide
N-(4-{[4-(acryloylamino)-4-methylpiperidin-1-yl]sulfonyl}phenyl)-1H-indole-2-carboxamide
4-{[4-(acryloylamino)-4-methylpiperidin-1-yl]sulfonyl}-N-(tricyclo[3.3.1.1~3,7~]dec-1-ylmethyl)benzamide
4-{[4-(acryloylamino)-4-methylpiperidin-1-yl]sulfonyl}-N-(1,2,3,4-tetrahydronaphthalen-1-yl)benzamide
N-(4-{[4-(acryloylamino)-4-methylpiperidin-1-yl]sulfonyl}phenyl)-4,5,6,7-tetrahydro-1-benzothiophene-2-carboxamide
N-(4-{[4-(acryloylamino)-4-methylpiperidin-1-yl]sulfonyl}phenyl)-5-phenylfuran-2-carboxamide
N-(4-{[4-(acryloylamino)-4-methylpiperidin-1-yl]sulfonyl}phenyl)-4-phenylthiophene-2-carboxamide
N-[4-methyl-1-({5-[5-(trifluoromethyl)-1,2-oxazol-3-yl]thiophen-2-yl}sulfonyl)piperidin-4-yl]prop-2-enamide
5-{[4-(acryloylamino)-4-methylpiperidin-1-yl]sulfonyl}-N-(2-phenylethyl)furan-2-carboxamide
N-{4-methyl-1-[(6-phenoxypyridin-3-yl)sulfonyl]piperidin-4-yl}prop-2-enamide
N-(4-methyl-1-{[6-(morpholin-4-yl)pyridin-3-yl]sulfonyl}piperidin-4-yl)prop-2-enamide
N-{4-methyl-1-[(6-phenylpyridin-3-yl)sulfonyl]piperidin-4-yl}prop-2-enamide
N-[1-({3-chloro-4-[(3-phenylpropanoyl)amino]phenyl}sulfonyl)-4-methylpiperidin-4-yl]prop-2-enamide
4-{[4-(acryloylamino)-4-methylpiperidin-1-yl]sulfonyl}-2-fluoro-N-(2-phenylethyl)benzamide
N-(4-methyl-1-{[5-(pyridin-2-yl)thiophen-2-yl]sulfonyl}piperidin-4-yl)prop-2-enamide
4-{[4-(acryloylamino)-4-methylpiperidin-1-yl]sulfonyl}-2-methoxy-N-(2-phenylethyl)benzamide
N-[1-(1,3-benzothiazol-6-ylsulfonyl)-4-methylpiperidin-4-yl]prop-2-enamide
N-{4-methyl-1-[(4-methyl-2-phenyl-1,3-thiazol-5-yl)sulfonyl]piperidin-4-yl}prop-2-enamide
N-(4-methyl-1-{[5-(2-methyl-1,3-thiazol-4-yl)thiophen-2-yl]sulfonyl}piperidin-4-yl)prop-2-enamide
N-(4-methyl-1-{[5-(1,2-oxazol-5-yl)thiophen-2-yl]sulfonyl}piperidin-4-yl)prop-2-enamide
N-[1-(2,3-dihydro-1,4-benzodioxin-6-ylsulfonyl)-4-methylpiperidin-4-yl]prop-2-enamide
5-{[4-(acryloylamino)-4-methylpiperidin-1-yl]sulfonyl}-N-(2-phenylethyl)furan-3-carboxamide
N-[4-methyl-1-({4-[(phenylacetyl)amino]benzyl}sulfonyl)piperidin-4-yl]prop-2-enamide N-(4-methyl-1-{[4-(morpholin-4-ylsulfonyl)phenyl]sulfonyl}piperidin-4-yl)prop-2-enamide
N-(4-methyl-1-{[5-(1,3-oxazol-5-yl)thiophen-2-yl]sulfonyl}piperidin-4-yl)prop-2-enamide
4-{[4-(acryloylamino)-4-methylpiperidin-1-yl]sulfonyl}-2-methyl-N-(2-phenylethyl)benzamide
N-{4-methyl-1-[(4-phenoxyphenyl)sulfonyl]piperidin-4-yl}prop-2-enamide
N-[4-methyl-1-({4-[(6-methylpyrazin-2-yl)oxy]phenyl}sulfonyl)piperidin-4-yl]prop-2-enamide
N-[4-methyl-1-({3-[(6-methylpyrazin-2-yl)oxy]phenyl}sulfonyl)piperidin-4-yl]prop-2-enamide
5-{[4-(acryloylamino)-4-methylpiperidin-1-yl]sulfonyl}-1-methyl-N-(2-phenylethyl)-1H-pyrrole-2-carboxamide
N-(1-{[4-(isoquinolin-3-ylamino)phenyl]sulfonyl}-4-methylpiperidin-4-yl)prop-2-enamide
N-{1-[(3-chloro-4-methylphenyl)sulfonyl]-4-methylpiperidin-4-yl}prop-2-enamide
N-(4-methyl-1-{[5-(1,2-oxazol-5-yl)furan-2-yl]sulfonyl}piperidin-4-yl)prop-2-enamide
N-{1-[(4-{[3-chloro-5-(trifluoromethyl)pyridin-2-yl]oxy}phenyl)sulfonyl]-4-methylpiperidin-4-yl}prop-2-enamide
N-(4-methyl-1-{[4-(1H-pyrazol-1-yl)phenyl]sulfonyl}piperidin-4-yl)prop-2-enamide
N-{1-[(4-methoxy-3-methylphenyl)sulfonyl]-4-methylpiperidin-4-yl}prop-2-enamide
N-(4-methyl-1-{[6-(2-phenylethoxy)pyridin-3-yl]sulfonyl}piperidin-4-yl)prop-2-enamide
N-[1-({5-[(acetylamino)methyl]thiophen-2-yl}sulfonyl)-4-methylpiperidin-4-yl]prop-2-enamide
N-{4-methyl-1-[(5-methyl-1-phenyl-1H-pyrazol-4-yl)sulfonyl]piperidin-4-yl}prop-2-enamide
N-(4-methyl-1-{[4-(1-methyl-1H-pyrazol-5-yl)phenyl]sulfonyl}piperidin-4-yl)prop-2-enamide
N-(4-methyl-1-{[3-(1-methyl-1H-pyrazol-5-yl)phenyl]sulfonyl}piperidin-4-yl)prop-2-enamide
N-{1-[(2,2-dimethyl-3,4-dihydro-2H-chromen-6-yl)sulfonyl]-4-methylpiperidin-4-yl}prop-2-enamide
N-{4-methyl-1-[(5-phenylthiophen-2-yl)sulfonyl]piperidin-4-yl}prop-2-enamide
N-(1-{[4-(cyclopentyloxy)phenyl]sulfonyl}-4-methylpiperidin-4-yl)prop-2-enamide
N-(4-methyl-1-{[5-(pyrrolidin-1-ylcarbonyl)-1H-pyrrol-3-yl]sulfonyl}piperidin-4-yl)prop-2-enamide
N-(4-methyl-1-{[4-(2-methyl-1,3-thiazol-4-yl)phenyl]sulfonyl}piperidin-4-yl)prop-2-enamide
N-(4-methyl-1-{[4-(pyridin-2-yloxy)phenyl]sulfonyl}piperidin-4-yl)prop-2-enamide
N-{4-methyl-1-[(2-oxo-1,2,3,4-tetrahydroquinolin-6-yl)sulfonyl]piperidin-4-yl}prop-2-enamide
N-{5-[(4-cyclohexylphenyl)sulfonyl]-5-azaspiro[3.5]non-8-yl}prop-2-enamide
N-(4-{[8-(acryloylamino)-5-azaspiro[3.5]non-5-yl]sulfonyl}phenyl)cyclopropanecarboxamide
N-(4-{[8-(acryloylamino)-5-azaspiro[3.5]non-5-yl]sulfonyl}phenyl)tricyclo[3.3.1.1~3,7~]decane-1-carboxamide
benzyl(4-{[8-(acryloylamino)-5-azaspiro[3.5]non-5-yl]sulfonyl}phenyl)carbamate
N-(5-{[4-(piperidin-1-ylcarbonyl)phenyl]sulfonyl}-5-azaspiro[3.5]non-8-yl)prop-2-enamide
benzyl 4-{[8-(acryloylamino)-5-azaspiro[3.5]non-5-yl]sulfonyl}piperidine-1-carboxylate
N-{5-[(4-nitrophenyl)sulfonyl]-5-azaspiro[3.5]non-8-yl}prop-2-enamide
N-(4-{[8-(acryloylamino)-5-azaspiro[3.5]non-5-yl]sulfonyl}phenyl)tetrahydro-2H-pyran-4-carboxamide
N-[5-({4-[(3-phenylpropanoyl)amino]phenyl}sulfonyl)-5-azaspiro[3.5]non-8-yl]prop-2-enamide
N-(4-{[8-(acryloylamino)-5-azaspiro[3.5]non-5-yl]sulfonyl}phenyl)-2-phenylcyclopropanecarboxamide
N-(4-{[8-(acryloylamino)-5-azaspiro[3.5]non-5-yl]sulfonyl}phenyl)-N-methyltetrahydro-2H-pyran-4-carboxamide
4-{[8-(acryloylamino)-5-azaspiro[3.5]non-5-yl]sulfonyl}-N-benzyl-N-methylbenzamide
4-{[8-(acryloylamino)-5-azaspiro[3.5]non-5-yl]sulfonyl}-N-(cyclopropylmethyl)benzamide
N-(5-{[3-(piperidin-1-ylcarbonyl)phenyl]sulfonyl}-5-azaspiro[3.5]non-8-yl)prop-2-enamide
N-(4-{[8-(acryloylamino)-5-azaspiro[3.5]non-5-yl]sulfonyl}phenyl)-N-methylcyclopropanecarboxamide
N-{5-[(4-{[4-(6-methylpyridin-2-yl)piperazin-1-yl]carbonyl}phenyl)sulfonyl]-5-azaspiro[3.5]non-8-yl}prop-2-enamide
4-{[8-(acryloylamino)-5-azaspiro[3.5]non-5-yl]sulfonyl}-N-[2-(morpholin-4-yl)ethyl]benzamide
4-{[8-(acryloylamino)-5-azaspiro[3.5]non-5-yl]sulfonyl}-N-(2-phenylethyl)benzamide
4-{[8-(acryloylamino)-5-azaspiro[3.5]non-5-yl]sulfonyl}-N-methyl-N-(2-phenylethyl)benzamide
N-(5-{[4-(3,4-dihydroisoquinolin-2(1H)-ylcarbonyl)phenyl]sulfonyl}-5-azaspiro[3.5]non-8-yl)prop-2-enamide
4-{[8-(acryloylamino)-5-azaspiro[3.5]non-5-yl]sulfonyl}-N-(2-cyclohexylethyl)benzamide
4-{[8-(acryloylamino)-5-azaspiro[3.5]non-5-yl]sulfonyl}-N-cyclohexylbenzamide
N-{5-[(4-{[4-(pyrrolidin-1-ylcarbonyl)piperidin-1-yl]carbonyl}phenyl)sulfonyl]-5-azaspiro[3.5]non-8-yl}prop-2-enamide
4-{[8-(acryloylamino)-5-azaspiro[3.5]non-5-yl]sulfonyl}-N-(3,5-dimethylbenzyl)benzamide
4-{[8-(acryloylamino)-5-azaspiro[3.5]non-5-yl]sulfonyl}-N-benzylbenzamide
4-{[8-(acryloylamino)-5-azaspiro[3.5]non-5-yl]sulfonyl}-N-(3,4-difluorobenzyl)benzamide
4-{[8-(acryloylamino)-5-azaspiro[3.5]non-5-yl]sulfonyl}-N-[4-(trifluoromethyl)benzyl]benzamide
4-{[8-(acryloylamino)-5-azaspiro[3.5]non-5-yl]sulfonyl}-N-(naphthalen-1-ylmethyl)benzamide
4-{[8-(acryloylamino)-5-azaspiro[3.5]non-5-yl]sulfonyl}-N-[2-(3,4-dimethylphenyl)ethyl]benzamide
4-{[8-(acryloylamino)-5-azaspiro[3.5]non-5-yl]sulfonyl}-N-[2-(4-methoxyphenyl)ethyl]benzamide
4-{[8-(acryloylamino)-5-azaspiro[3.5]non-5-yl]sulfonyl}-N-(2,3-dihydro-1H-inden-2-yl)benzamide
4-{[8-(acryloylamino)-5-azaspiro[3.5]non-5-yl]sulfonyl}-N-[2-(3-methylphenyl)ethyl]benzamide
N-[5-({4-[(acetylamino)methyl]phenyl}sulfonyl)-5-azaspiro[3.5]non-8-yl]prop-2-enamide
N-{5-[(4-{[3-(naphthalen-1-yl)propanoyl]amino}phenyl)sulfonyl]-5-azaspiro[3.5]non-8-yl}prop-2-enamide
N-[5-({4-[(3-cyclohexylpropanoyl)amino]phenyl}sulfonyl)-5-azaspiro[3.5]non-8-yl]prop-2-enamide
N-{5-[(1-benzoylpiperidin-4-yl)sulfonyl]-5-azaspiro[3.5]non-8-yl}prop-2-enamide
N-(5-{[1-(piperidin-1-yl carbonyl)piperidin-4-yl]sulfonyl}-5-azaspiro[3.5]non-8-yl)prop-2-en amide
N-(5-{[1-(pyridin-2-ylcarbonyl)piperidin-4-yl]sulfonyl}-5-azaspiro[3.5]non-8-yl)prop-2-enamide N-(4-{[8-(acryloylamino)-5-azaspiro[3.5]non-5-yl]
sulfonyl}phenyl)-4-tert-butylcyclohexanecarboxamide
N-(4-{[8-(acryloylamino)-5-azaspiro[3.5]non-5-yl]
sulfonyl}phenyl)-1-benzofuran-2-carboxamide
benzyl(3-{[8-(acryloylamino)-5-azaspiro[3.5]non-5-yl]
sulfonyl}phenyl)carbamate
N-[5-({3-[(3-phenylpropanoyl)amino]phenyl}sulfonyl)-5-
azaspiro[3.5]non-8-yl]prop-2-enamide
N-(3-{[8-(acryloylamino)-5-azaspiro[3.5]non-5-yl]
sulfonyl}phenyl)tetrahydro-2H-pyran-4-carboxamide
4-{[8-(acryloylamino)-5-azaspiro[3.5]non-5-yl]sulfonyl}-
N-(3-phenylpropyl)benzamide
4-{[8-(acryloylamino)-5-azaspiro[3.5]non-5-yl]sulfonyl}-
N-[2-(3-chlorophenyl)ethyl]benzamide
4-{[8-(acryloylamino)-5-azaspiro[3.5]non-5-yl]sulfonyl}-
N-[2-(2-methoxyphenyl)ethyl]benzamide
4-{[8-(acryloylamino)-5-azaspiro[3.5]non-5-yl]sulfonyl}-
N-[2-(2,3-dihydro-1-benzofuran-7-yl)ethyl]benzamide
4-{[8-(acryloylamino)-5-azaspiro[3.5]non-5-yl]sulfonyl}-
N-[2-(tetrahydro-2H-pyran-4-yl)ethyl]benzamide
4-{[8-(acryloylamino)-5-azaspiro[3.5]non-5-yl]sulfonyl}-
N-[2-(4,4-difluoropiperidin-1-yl)ethyl]benzamide
N-[5-({1-[3-(trifluoromethyl)benzoyl]piperidin-4-
yl}sulfonyl)-5-azaspiro[3.5]non-8-yl]prop-2-enamide
N-(5-{[1-(3-phenylpropanoyl)piperidin-4-yl]sulfonyl}-5-
azaspiro[3.5]non-8-yl)prop-2-enamide
N-[5-({4-[2-(benzylamino)-2-oxoethyl]phenyl}sulfonyl)-5-
azaspiro[3.5]non-8-yl]prop-2-enamide
4-{[8-(acryloylamino)-5-azaspiro[3.5]non-5-yl]sulfonyl}-
N-(4-tert-butylbenzyl)benzamide
4-{[8-(acryloylamino)-5-azaspiro[3.5]non-5-yl]sulfonyl}-
N-(4-phenylbutyl)benzamide
4-{[8-(acryloylamino)-5-azaspiro[3.5]non-5-yl]sulfonyl}-
N-[2-(4-chlorophenyl)ethyl]benzamide
4-{[8-(acryloylamino)-5-azaspiro[3.5]non-5-yl]sulfonyl}-
N-[2-(quinolin-7-yl)ethyl]benzamide
4-{[8-(acryloylamino)-5-azaspiro[3.5]non-5-yl]sulfonyl}-
N-[2-(naphthalen-2-yl)ethyl]benzamide
4-{[8-(acryloylamino)-5-azaspiro[3.5]non-5-yl]sulfonyl}-
N-(3,4-dihydro-2H-chromen-6-ylmethyl)benzamide
4-{[8-(acryloylamino)-5-azaspiro[3.5]non-5-yl]sulfonyl}-
N-[2-(4-tert-butylphenyl)ethyl]benzamide
4-{[8-(acryloylamino)-5-azaspiro[3.5]non-5-yl]sulfonyl}-
N-[2-(biphenyl-4-yl)ethyl]benzamide
4-{[8-(acryloylamino)-5-azaspiro[3.5]non-5-yl]sulfonyl}-
N-[2-(1,3-benzodioxol-5-yl)ethyl]benzamide
4-{[8-(acryloylamino)-5-azaspiro[3.5]non-5-yl]sulfonyl}-
N-[(1R)-2-phenylcyclopropyl]benzamide
benzyl(4-{[8-(acryloylamino)-5-azaspiro[3.5]non-5-yl]
sulfonyl}phenyl)methylcarbamate
4-{[8-(acryloylamino)-5-azaspiro[3.5]non-5-yl]sulfonyl}-
N-[2-(3,4-dimethoxyphenyl)ethyl]benzamide
4-{[8-(acryloylamino)-5-azaspiro[3.5]non-5-yl]sulfonyl}-
N-{2-[4-(trifluoromethyl)phenyl]ethyl}benzamide
4-{[8-(acryloylamino)-5-azaspiro[3.5]non-5-yl]sulfonyl}-
N-(2-phenylethyl)piperidine-1-carboxamide
N-(4-{[8-(acryloylamino)-5-azaspiro[3.5]non-5-yl]
sulfonyl}phenyl)furan-2-carboxamide
N-{5-[(4-{[3-(tricyclo[3.3.1.1~3,7~]dec-1-yl)propanoyl]
amino}phenyl)sulfonyl]-5-azaspiro[3.5]non-8-yl}prop-2-
enamide
4-{[8-(acryloylamino)-5-azaspiro[3.5]non-5-yl]sulfonyl}-
N-[2-(tricyclo[3.3.1.1~3,7~]dec-1-yl)ethyl]benzamide
N-(5-{[1-(cyclopropylcarbonyl)-2,3-dihydro-1H-indol-5-
yl]sulfonyl}-5-azaspiro[3.5]non-8-yl)prop-2-enamide
N-[5-({2-chloro-4-[(3-phenylpropanoyl)amino]
phenyl}sulfonyl)-5-azaspiro[3.5]non-8-yl]prop-2-enam-
ide
N-(4-{[8-(acryloylamino)-5-azaspiro[3.5]non-5-yl]
sulfonyl}phenyl)-5,6-dihydro-4H-cyclopenta[b]
thiophene-2-carboxamide
N-(4-{[8-(acryloylamino)-5-azaspiro[3.5]non-5-yl]
sulfonyl}phenyl)-4,5,6,7-tetrahydro-1H-indole-2-car-
boxamide
N-[5-({2-methoxy-4-[(3-phenylpropanoyl)amino]
phenyl}sulfonyl)-5-azaspiro[3.5]non-8-yl]prop-2-enam-
ide
N-(4-{[8-(acryloylamino)-5-azaspiro[3.5]non-5-yl]
sulfonyl}phenyl)-5-(pyrrolidin-1-ylmethyl)furan-2-car-
boxamide
N-(4-{[8-(acryloylamino)-5-azaspiro[3.5]non-5-yl]
sulfonyl}phenyl)-1-benzothiophene-2-carboxamide
N-(4-{[8-(acryloylamino)-5-azaspiro[3.5]non-5-yl]
sulfonyl}phenyl)-3-methyl-1-benzofuran-2-carboxamide
N-(4-{[8-(acryloylamino)-5-azaspiro[3.5]non-5-yl]
sulfonyl}phenyl)-1H-indole-2-carboxamide
4-{[8-(acryloylamino)-5-azaspiro[3.5]non-5-yl]sulfonyl}-
N-(tricyclo[3.3.1.1~3,7~]dec-1-ylmethyl)benzamide
4-{[8-(acryloylamino)-5-azaspiro[3.5]non-5-yl]sulfonyl}-
N-(1,2,3,4-tetrahydronaphthalen-1-yl)benzamide
N-(4-{[8-(acryloylamino)-5-azaspiro[3.5]non-5-yl]
sulfonyl}phenyl)-4,5,6,7-tetrahydro-1-benzothiophene-2-
carboxamide
N-(4-{[8-(acryloylamino)-5-azaspiro[3.5]non-5-yl]
sulfonyl}phenyl)-5-phenylfuran-2-carboxamide
N-(4-{[8-(acryloylamino)-5-azaspiro[3.5]non-5-yl]
sulfonyl}phenyl)-4-phenylthiophene-2-carboxamide
N-[5-({5-[5-(trifluoromethyl)-1,2-oxazol-3-yl]thiophen-2-
yl}sulfonyl)-5-azaspiro[3.5]non-8-yl]prop-2-enamide
5-{[8-(acryloylamino)-5-azaspiro[3.5]non-5-yl]sulfonyl}-
N-(2-phenylethyl)furan-2-carboxamide
N-{5-[(6-phenoxypyridin-3-yl)sulfonyl]-5-azaspiro[3.5]
non-8-yl}prop-2-enamide
N-(5-{[6-(morpholin-4-yl)pyridin-3-yl]sulfonyl}-5-aza-
spiro[3.5]non-8-yl)prop-2-enamide
N-{5-[(6-phenylpyridin-3-yl)sulfonyl]-5-azaspiro[3.5]non-
8-yl}prop-2-enamide
N-[5-({3-chloro-4-[(3-phenylpropanoyl)amino]
phenyl}sulfonyl)-5-azaspiro[3.5]non-8-yl]prop-2-enam-
ide
4-{[8-(acryloylamino)-5-azaspiro[3.5]non-5-yl]sulfonyl}-
2-fluoro-N-(2-phenylethyl)benzamide
N-(5-{[5-(pyridin-2-yl)thiophen-2-yl]sulfonyl}-5-azaspiro
[3.5]non-8-yl)prop-2-enamide
4-{[8-(acryloylamino)-5-azaspiro[3.5]non-5-yl]sulfonyl}-
2-methoxy-N-(2-phenylethyl)benzamide
N-[5-(1,3-benzothiazol-6-ylsulfonyl)-5-azaspiro[3.5]non-8-
yl]prop-2-enamide
N-{5-[(4-methyl-2-phenyl-1,3-thiazol-5-yl)sulfonyl]-5-aza-
spiro[3.5]non-8-yl}prop-2-enamide
N-(5-{[5-(2-methyl-1,3-thiazol-4-yl)thiophen-2-yl]sulfo-
nyl}-5-azaspiro[3.5]non-8-yl)prop-2-enamide
N-(5-{[5-(1,2-oxazol-5-yl)thiophen-2-yl]sulfonyl}-5-aza-
spiro[3.5]non-8-yl)prop-2-enamide
N-[5-(2,3-dihydro-1,4-benzodioxin-6-ylsulfonyl)-5-aza-
spiro[3.5]non-8-yl]prop-2-enamide
5-{[8-(acryloylamino)-5-azaspiro[3.5]non-5-yl]sulfonyl}-
N-(2-phenylethyl)furan-3-carboxamide
N-[5-({4-[(phenylacetyl)amino]benzyl}sulfonyl)-5-aza-
spiro[3.5]non-8-yl]prop-2-enamide
N-(5-{[4-(morpholin-4-ylsulfonyl)phenyl]sulfonyl}-5-aza-
spiro[3.5]non-8-yl)prop-2-enamide N-(5-{[5-(1,3-oxazol-5-yl)thiophen-2-yl]sulfonyl}-5-azaspiro[3.5]non-8-yl)prop-2-enamide
4-{[8-(acryloylamino)-5-azaspiro[3.5]non-5-yl]sulfonyl}-2-methyl-N-(2-phenylethyl)benzamide
N-{5-[(4-phenoxyphenyl)sulfonyl]-5-azaspiro[3.5]non-8-yl}prop-2-enamide
N-[5-({4-[(6-methylpyrazin-2-yl)oxy]phenyl}sulfonyl)-5-azaspiro[3.5]non-8-yl]prop-2-enamide
N-[5-({3-[(6-methylpyrazin-2-yl)oxy]phenyl}sulfonyl)-5-azaspiro[3.5]non-8-yl]prop-2-enamide
5-{[8-(acryloylamino)-5-azaspiro[3.5]non-5-yl]sulfonyl}-1-methyl-N-(2-phenylethyl)-1H-pyrrole-2-carboxamide
N-(5-{[4-(isoquinolin-3-ylamino)phenyl]sulfonyl}-5-azaspiro[3.5]non-8-yl)prop-2-enamide
N-{5-[(3-chloro-4-methylphenyl)sulfonyl]-5-azaspiro[3.5]non-8-yl}prop-2-enamide
N-(5-{[5-(1,2-oxazol-5-yl)furan-2-yl]sulfonyl}-5-azaspiro[3.5]non-8-yl)prop-2-enamide
N-{5-[(4-{[3-chloro-5-(trifluoromethyl)pyridin-2-yl]oxy}phenyl)sulfonyl]-5-azaspiro[3.5]non-8-yl}prop-2-enamide
N-(5-{[4-(1H-pyrazol-1-yl)phenyl]sulfonyl}-5-azaspiro[3.5]non-8-yl)prop-2-enamide
N-{5-[(4-methoxy-3-methylphenyl)sulfonyl]-5-azaspiro[3.5]non-8-yl}prop-2-enamide
N-(5-{[6-(2-phenylethoxy)pyridin-3-yl]sulfonyl}-5-azaspiro[3.5]non-8-yl)prop-2-enamide
N-[5-({5-[(acetylamino)methyl]thiophen-2-yl}sulfonyl)-5-azaspiro[3.5]non-8-yl]prop-2-enamide
N-{5-[(5-methyl-1-phenyl-1H-pyrazol-4-yl)sulfonyl]-5-azaspiro[3.5]non-8-yl}prop-2-enamide
N-(5-{[4-(1-methyl-1H-pyrazol-5-yl)phenyl]sulfonyl}-5-azaspiro[3.5]non-8-yl)prop-2-enamide
N-(5-{[3-(1-methyl-1H-pyrazol-5-yl)phenyl]sulfonyl}-5-azaspiro[3.5]non-8-yl)prop-2-enamide
N-{5-[(2,2-dimethyl-3,4-dihydro-2H-chromen-6-yl)sulfonyl]-5-azaspiro[3.5]non-8-yl}prop-2-enamide
N-{5-[(5-phenylthiophen-2-yl)sulfonyl]-5-azaspiro[3.5]non-8-yl}prop-2-enamide
N-(5-{[4-(cyclopentyloxy)phenyl]sulfonyl}-5-azaspiro[3.5]non-8-yl)prop-2-enamide
N-(5-{[5-(pyrrolidin-1-ylcarbonyl)-1H-pyrrol-3-yl]sulfonyl}-5-azaspiro[3.5]non-8-yl)prop-2-enamide
N-(5-{[4-(2-methyl-1,3-thiazol-4-yl)phenyl]sulfonyl}-5-azaspiro[3.5]non-8-yl)prop-2-enamide
N-(5-{[4-(pyridin-2-yloxy)phenyl]sulfonyl}-5-azaspiro[3.5]non-8-yl)prop-2-enamide
N-{5-[(2-oxo-1,2,3,4-tetrahydroquinolin-6-yl)sulfonyl]-5-azaspiro[3.5]non-8-yl}prop-2-enamide
N-{1-[(4-cyclohexylphenyl)sulfonyl]-1,2,3,4-tetrahydroquinolin-4-yl}prop-2-enamide
N-(4-{[4-(acryloylamino)-3,4-dihydroquinolin-1(2H)-yl]sulfonyl}phenyl)cyclopropanecarboxamide
N-(4-{[4-(acryloylamino)-3,4-dihydroquinolin-1(2H)-yl]sulfonyl}phenyl)tricyclo[3.3.1.1~3,7~]decane-1-carboxamide
benzyl(4-{[4-(acryloylamino)-3,4-dihydroquinolin-1(2H)-yl]sulfonyl}phenyl)carbamate
N-(1-{[4-(piperidin-1-ylcarbonyl)phenyl]sulfonyl}-1,2,3,4-tetrahydroquinolin-4-yl)prop-2-enamide
benzyl 4-{[4-(acryloylamino)-3,4-dihydroquinolin-1(2H)-yl]sulfonyl}piperidine-1-carboxylate
N-{1-[(4-nitrophenyl)sulfonyl]-1,2,3,4-tetrahydroquinolin-4-yl}prop-2-enamide
N-(4-{[4-(acryloylamino)-3,4-dihydroquinolin-1(2H)-yl]sulfonyl}phenyl)tetrahydro-2H-pyran-4-carboxamide
N-[1-({4-[(3-phenylpropanoyl)amino]phenyl}sulfonyl)-1,2,3,4-tetrahydroquinolin-4-yl]prop-2-enamide
N-(4-{[4-(acryloylamino)-3,4-dihydroquinolin-1(2H)-yl]sulfonyl}phenyl)-2-phenylcyclopropanecarboxamide
N-(4-{[4-(acryloylamino)-3,4-dihydroquinolin-1(2H)-yl]sulfonyl}phenyl)-N-methyltetrahydro-2H-pyran-4-carboxamide
4-{[4-(acryloylamino)-3,4-dihydroquinolin-1(2H)-yl]sulfonyl}-N-benzyl-N-methylbenzamide
4-{[4-(acryloylamino)-3,4-dihydroquinolin-1(2H)-yl]sulfonyl}-N-(cyclopropylmethyl)benzamide
N-(1-{[3-(piperidin-1-ylcarbonyl)phenyl]sulfonyl}-1,2,3,4-tetrahydroquinolin-4-yl)prop-2-enamide
N-(4-{[4-(acryloylamino)-3,4-dihydroquinolin-1(2H)-yl]sulfonyl}phenyl)-N-methylcyclopropanecarboxamide
N-{1-[(4-{[4-(6-methylpyridin-2-yl)piperazin-1-yl]carbonyl}phenyl)sulfonyl]-1,2,3,4-tetrahydroquinolin-4-yl}prop-2-enamide
4-{[4-(acryloylamino)-3,4-dihydroquinolin-1(2H)-yl]sulfonyl}-N-[2-(morpholin-4-yl)ethyl]benzamide
4-{[4-(acryloylamino)-3,4-dihydroquinolin-1(2H)-yl]sulfonyl}-N-(2-phenylethyl)benzamide
4-{[4-(acryloylamino)-3,4-dihydroquinolin-1(2H)-yl]sulfonyl}-N-methyl-N-(2-phenylethyl)benzamide
N-(1-{[4-(3,4-dihydroisoquinolin-2(1H)-ylcarbonyl)phenyl]sulfonyl}-1,2,3,4-tetrahydroquinolin-4-yl)prop-2-enamide
4-{[4-(acryloylamino)-3,4-dihydroquinolin-1(2H)-yl]sulfonyl}-N-(2-cyclohexylethyl)benzamide
4-{[4-(acryloylamino)-3,4-dihydroquinolin-1(2H)-yl]sulfonyl}-N-cyclohexylbenzamide
N-{1-[(4-{[4-(pyrrolidin-1-ylcarbonyl)piperidin-1-yl]carbonyl}phenyl)sulfonyl]-1,2,3,4-tetrahydroquinolin-4-yl}prop-2-enamide
4-{[4-(acryloylamino)-3,4-dihydroquinolin-1(2H)-yl]sulfonyl}-N-(3,5-dimethylbenzyl)benzamide
4-{[4-(acryloylamino)-3,4-dihydroquinolin-1(2H)-yl]sulfonyl}-N-benzylbenzamide
4-{[4-(acryloylamino)-3,4-dihydroquinolin-1(2H)-yl]sulfonyl}-N-(3,4-difluorobenzyl)benzamide
4-{[4-(acryloylamino)-3,4-dihydroquinolin-1(2H)-yl]sulfonyl}-N-[4-(trifluoromethyl)benzyl]benzamide
4-{[4-(acryloylamino)-3,4-dihydroquinolin-1(2H)-yl]sulfonyl}-N-(naphthalen-1-ylmethyl)benzamide
4-{[4-(acryloylamino)-3,4-dihydroquinolin-1(2H)-yl]sulfonyl}-N-[2-(3,4-dimethylphenyl)ethyl]benzamide
4-{[4-(acryloylamino)-3,4-dihydroquinolin-1(2H)-yl]sulfonyl}-N-[2-(4-methoxyphenyl)ethyl]benzamide
4-{[4-(acryloylamino)-3,4-dihydroquinolin-1(2H)-yl]sulfonyl}-N-(2,3-dihydro-1H-inden-2-yl)benzamide
4-{[4-(acryloylamino)-3,4-dihydroquinolin-1(2H)-yl]sulfonyl}-N-[2-(3-methylphenyl)ethyl]benzamide
N-[1-({4-[(acetylamino)methyl]phenyl}sulfonyl)-1,2,3,4-tetrahydroquinolin-4-yl]prop-2-enamide
N-{1-[(4-{[3-(naphthalen-1-yl)propanoyl]amino}phenyl)sulfonyl]-1,2,3,4-tetrahydroquinolin-4-yl}prop-2-enamide
N-[1-({4-[(3-cyclohexylpropanoyl)amino]phenyl}sulfonyl)-1,2,3,4-tetrahydroquinolin-4-yl]prop-2-enamide
N-{1-[(1-benzoylpiperidin-4-yl)sulfonyl]-1,2,3,4-tetrahydroquinolin-4-yl}prop-2-enamide
N-(1-{[1-(piperidin-1-ylcarbonyl)piperidin-4-yl]sulfonyl}-1,2,3,4-tetrahydroquinolin-4-yl)prop-2-enamide
N-(1-{[1-(pyridin-2-ylcarbonyl)piperidin-4-yl]sulfonyl}-1,2,3,4-tetrahydroquinolin-4-yl)prop-2-enamide N-(4-{[4-(acryloylamino)-3,4-dihydroquinolin-1(2H)-yl] sulfonyl}phenyl)-4-tert-butylcyclohexanecarboxamide
N-(4-{[4-(acryloylamino)-3,4-dihydroquinolin-1(2H)-yl] sulfonyl}phenyl)-1-benzofuran-2-carboxamide
benzyl(3-{[4-(acryloylamino)-3,4-dihydroquinolin-1(2H)-yl]sulfonyl}phenyl)carbamate
N-[1-({3-[(3-phenylpropanoyl)amino]phenyl}sulfonyl)-1,2,3,4-tetrahydroquinolin-4-yl]prop-2-enamide
N-(3-{[4-(acryloylamino)-3,4-dihydroquinolin-1(2H)-yl] sulfonyl}phenyl)tetrahydro-2H-pyran-4-carboxamide
4-{[4-(acryloylamino)-3,4-dihydroquinolin-1(2H)-yl]sulfonyl}-N-(3-phenylpropyl)benzamide
4-{[4-(acryloylamino)-3,4-dihydroquinolin-1(2H)-yl]sulfonyl}-N-[2-(3-chlorophenyl)ethyl]benzamide
4-{[4-(acryloylamino)-3,4-dihydroquinolin-1(2H)-yl]sulfonyl}-N-[2-(2-methoxyphenyl)ethyl]benzamide
4-{[4-(acryloylamino)-3,4-dihydroquinolin-1(2H)-yl]sulfonyl}-N-[2-(2,3-dihydro-1-benzofuran-7-yl)ethyl]benzamide
4-{[4-(acryloylamino)-3,4-dihydroquinolin-1(2H)-yl]sulfonyl}-N-[2-(tetrahydro-2H-pyran-4-yl)ethyl]benzamide
4-{[4-(acryloylamino)-3,4-dihydroquinolin-1(2H)-yl]sulfonyl}-N-[2-(4,4-difluoropiperidin-1-yl)ethyl]benzamide
N-[1-({1-[3-(trifluoromethyl)benzoyl]piperidin-4-yl}sulfonyl)-1,2,3,4-tetrahydroquinolin-4-yl]prop-2-enamide
N-(1-{[1-(3-phenylpropanoyl)piperidin-4-yl]sulfonyl}-1,2,3,4-tetrahydroquinolin-4-yl)prop-2-enamide
N-[1-({4-[2-(benzylamino)-2-oxoethyl]phenyl}sulfonyl)-1,2,3,4-tetrahydroquinolin-4-yl]prop-2-enamide
4-{[4-(acryloylamino)-3,4-dihydroquinolin-1(2H)-yl]sulfonyl}-N-(4-tert-butylbenzyl)benzamide
4-{[4-(acryloylamino)-3,4-dihydroquinolin-1(2H)-yl]sulfonyl}-N-(4-phenylbutyl)benzamide
4-{[4-(acryloylamino)-3,4-dihydroquinolin-1(2H)-yl]sulfonyl}-N-[2-(4-chlorophenyl)ethyl]benzamide
4-{[4-(acryloylamino)-3,4-dihydroquinolin-1(2H)-yl]sulfonyl}-N-[2-(quinolin-7-yl)ethyl]benzamide
4-{[4-(acryloylamino)-3,4-dihydroquinolin-1(2H)-yl]sulfonyl}-N-[2-(naphthalen-2-yl)ethyl]benzamide
4-{[4-(acryloylamino)-3,4-dihydroquinolin-1(2H)-yl]sulfonyl}-N-(3,4-dihydro-2H-chromen-6-ylmethyl)benzamide
4-{[4-(acryloylamino)-3,4-dihydroquinolin-1(2H)-yl]sulfonyl}-N-[2-(4-tert-butylphenyl)ethyl]benzamide
4-{[4-(acryloylamino)-3,4-dihydroquinolin-1(2H)-yl]sulfonyl}-N-[2-(biphenyl-4-yl)ethyl]benzamide
4-{[4-(acryloylamino)-3,4-dihydroquinolin-1(2H)-yl]sulfonyl}-N-[2-(1,3-benzodioxol-5-yl)ethyl]benzamide
4-{[4-(acryloylamino)-3,4-dihydroquinolin-1(2H)-yl]sulfonyl}-N-[(1R)-2-phenylcyclopropyl]benzamide
benzyl(4-{[4-(acryloylamino)-3,4-dihydroquinolin-1(2H)-yl]sulfonyl}phenyl)methylcarbamate
4-{[4-(acryloylamino)-3,4-dihydroquinolin-1(2H)-yl]sulfonyl}-N-[2-(3,4-dimethoxyphenyl)ethyl]benzamide
4-{[4-(acryloylamino)-3,4-dihydroquinolin-1(2H)-yl]sulfonyl}-N-{2-[4-(trifluoromethyl)phenyl]ethyl}benzamide
4-{[4-(acryloylamino)-3,4-dihydroquinolin-1(2H)-yl]sulfonyl}-N-(2-phenylethyl)piperidine-1-carboxamide
N-(4-{[4-(acryloylamino)-3,4-dihydroquinolin-1(2H)-yl] sulfonyl}phenyl)furan-2-carboxamide
N-{1-[(4-{[3-(tricyclo[3.3.1.1~3,7~]dec-1-yl)propanoyl]amino}phenyl)sulfonyl]-1,2,3,4-tetrahydroquinolin-4-yl}prop-2-enamide
4-{[4-(acryloylamino)-3,4-dihydroquinolin-1(2H)-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-1,2,3,4-tetrahydroquinolin-4-yl)prop-2-enamide
N-[1-({2-chloro-4-[(3-phenylpropanoyl)amino]phenyl}sulfonyl)-1,2,3,4-tetrahydroquinolin-4-yl]prop-2-enamide
N-(4-{[4-(acryloylamino)-3,4-dihydroquinolin-1(2H)-yl] sulfonyl}phenyl)-5,6-dihydro-4H-cyclopenta[b]thiophene-2-carboxamide
N-(4-{[4-(acryloylamino)-3,4-dihydroquinolin-1(2H)-yl] sulfonyl}phenyl)-4,5,6,7-tetrahydro-1H-indole-2-carboxamide
N-[1-({2-methoxy-4-[(3-phenylpropanoyl)amino]phenyl}sulfonyl)-1,2,3,4-tetrahydroquinolin-4-yl]prop-2-enamide
N-(4-{[4-(acryloylamino)-3,4-dihydroquinolin-1(2H)-yl] sulfonyl}phenyl)-5-(pyrrolidin-1-ylmethyl)furan-2-carboxamide
N-(4-{[4-(acryloylamino)-3,4-dihydroquinolin-1(2H)-yl] sulfonyl}phenyl)-1-benzothiophene-2-carboxamide
N-(4-{[4-(acryloylamino)-3,4-dihydroquinolin-1(2H)-yl] sulfonyl}phenyl)-3-methyl-1-benzofuran-2-carboxamide
N-(4-{[4-(acryloylamino)-3,4-dihydroquinolin-1(2H)-yl] sulfonyl}phenyl)-1H-indole-2-carboxamide
4-{[4-(acryloylamino)-3,4-dihydroquinolin-1(2H)-yl]sulfonyl}-N-(tricyclo[3.3.1.1~3,7~]dec-1-ylmethyl)benzamide
4-{[4-(acryloylamino)-3,4-dihydroquinolin-1(2H)-yl]sulfonyl}-N-(1,2,3,4-tetrahydronaphthalen-1-yl)benzamide
N-(4-{[4-(acryloylamino)-3,4-dihydroquinolin-1(2H)-yl] sulfonyl}phenyl)-4,5,6,7-tetrahydro-1-benzothiophene-2-carboxamide
N-(4-{[4-(acryloylamino)-3,4-dihydroquinolin-1(2H)-yl] sulfonyl}phenyl)-5-phenylfuran-2-carboxamide
N-(4-{[4-(acryloylamino)-3,4-dihydroquinolin-1(2H)-yl] sulfonyl}phenyl)-4-phenylthiophene-2-carboxamide
N-[1-({5-[5-(trifluoromethyl)-1,2-oxazol-3-yl]thiophen-2-yl}sulfonyl)-1,2,3,4-tetrahydroquinolin-4-yl]prop-2-enamide
5-{[4-(acryloylamino)-3,4-dihydroquinolin-1(2H)-yl]sulfonyl}-N-(2-phenylethyl)furan-2-carboxamide
N-{1-[(6-phenoxypyridin-3-yl)sulfonyl]-1,2,3,4-tetrahydroquinolin-4-yl}prop-2-enamide
N-(1-{[6-(morpholin-4-yl)pyridin-3-yl]sulfonyl}-1,2,3,4-tetrahydroquinolin-4-yl)prop-2-enamide
N-{1-[(6-phenylpyridin-3-yl)sulfonyl]-1,2,3,4-tetrahydroquinolin-4-yl}prop-2-enamide
N-[1-({3-chloro-4-[(3-phenylpropanoyl)amino]phenyl}sulfonyl)-1,2,3,4-tetrahydroquinolin-4-yl]prop-2-enamide
4-{[4-(acryloylamino)-3,4-dihydroquinolin-1(2H)-yl]sulfonyl}-2-fluoro-N-(2-phenylethyl)benzamide
N-(1-{[5-(pyridin-2-yl)thiophen-2-yl]sulfonyl}-1,2,3,4-tetrahydroquinolin-4-yl)prop-2-enamide
4-{[4-(acryloylamino)-3,4-dihydroquinolin-1(2H)-yl]sulfonyl}-2-methoxy-N-(2-phenylethyl)benzamide
N-[1-(1,3-benzothiazol-6-ylsulfonyl)-1,2,3,4-tetrahydroquinolin-4-yl]prop-2-enamide
N-{1-[(4-methyl-2-phenyl-1,3-thiazol-5-yl)sulfonyl]-1,2,3,4-tetrahydroquinolin-4-yl}prop-2-enamide
N-(1-{[5-(2-methyl-1,3-thiazol-4-yl)thiophen-2-yl]sulfonyl}-1,2,3,4-tetrahydroquinolin-4-yl)prop-2-enamide
N-(1-{[5-(1,2-oxazol-5-yl)thiophen-2-yl]sulfonyl}-1,2,3,4-tetrahydroquinolin-4-yl)prop-2-enamide
N-[1-(2,3-dihydro-1,4-benzodioxin-6-ylsulfonyl)-1,2,3,4-tetrahydroquinolin-4-yl]prop-2-enamide 5-{[4-(acryloylamino)-3,4-dihydroquinolin-1(2H)-yl]sulfonyl}-N-(2-phenylethyl)furan-3-carboxamide
N-[1-({4-[(phenylacetyl)amino]benzyl}sulfonyl)-1,2,3,4-tetrahydroquinolin-4-yl]prop-2-enamide
N-(1-{[4-(morpholin-4-ylsulfonyl)phenyl]sulfonyl}-1,2,3,4-tetrahydroquinolin-4-yl)prop-2-enamide
N-(1-{[5-(1,3-oxazol-5-yl)thiophen-2-yl]sulfonyl}-1,2,3,4-tetrahydroquinolin-4-yl)prop-2-enamide
4-{[4-(acryloylamino)-3,4-dihydroquinolin-1(2H)-yl]sulfonyl}-2-methyl-N-(2-phenylethyl)benzamide
N-{1-[(4-phenoxyphenyl)sulfonyl]-1,2,3,4-tetrahydroquinolin-4-yl}prop-2-enamide
N-[1-({4-[(6-methylpyrazin-2-yl)oxy]phenyl}sulfonyl)-1,2,3,4-tetrahydroquinolin-4-yl]prop-2-enamide
N-[1-({3-[(6-methylpyrazin-2-yl)oxy]phenyl}sulfonyl)-1,2,3,4-tetrahydroquinolin-4-yl]prop-2-enamide
5-{[4-(acryloylamino)-3,4-dihydroquinolin-1(2H)-yl]sulfonyl}-1-methyl-N-(2-phenylethyl)-1H-pyrrole-2-carboxamide
N-(1-{[4-(isoquinolin-3-ylamino)phenyl]sulfonyl}-1,2,3,4-tetrahydroquinolin-4-yl)prop-2-enamide
N-{1-[(3-chloro-4-methylphenyl)sulfonyl]-1,2,3,4-tetrahydroquinolin-4-yl}prop-2-enamide
N-(1-{[5-(1,2-oxazol-5-yl)furan-2-yl]sulfonyl}-1,2,3,4-tetrahydroquinolin-4-yl)prop-2-enamide
N-{1-[(4-{[3-chloro-5-(trifluoromethyl)pyridin-2-yl]oxy}phenyl)sulfonyl]-1,2,3,4-tetrahydroquinolin-4-yl}prop-2-enamide
N-(1-{[4-(1H-pyrazol-1-yl)phenyl]sulfonyl}-1,2,3,4-tetrahydroquinolin-4-yl)prop-2-enamide
N-{1-[(4-methoxy-3-methylphenyl)sulfonyl]-1,2,3,4-tetrahydroquinolin-4-yl}prop-2-enamide
N-(1-{[6-(2-phenylethoxy)pyridin-3-yl]sulfonyl}-1,2,3,4-tetrahydroquinolin-4-yl)prop-2-enamide
N-[1-({5-[(acetylamino)methyl]thiophen-2-yl}sulfonyl)-1,2,3,4-tetrahydroquinolin-4-yl]prop-2-enamide
N-{1-[(5-methyl-1-phenyl-1H-pyrazol-4-yl)sulfonyl]-1,2,3,4-tetrahydroquinolin-4-yl}prop-2-enamide
N-(1-{[4-(1-methyl-1H-pyrazol-5-yl)phenyl]sulfonyl}-1,2,3,4-tetrahydroquinolin-4-yl)prop-2-enamide
N-(1-{[3-(1-methyl-1H-pyrazol-5-yl)phenyl]sulfonyl}-1,2,3,4-tetrahydroquinolin-4-yl)prop-2-enamide
N-{1-[(2,2-dimethyl-3,4-dihydro-2H-chromen-6-yl)sulfonyl]-1,2,3,4-tetrahydroquinolin-4-yl}prop-2-enamide
N-{1-[(5-phenylthiophen-2-yl)sulfonyl]-1,2,3,4-tetrahydroquinolin-4-yl}prop-2-enamide
N-(1-{[4-(cyclopentyloxy)phenyl]sulfonyl}-1,2,3,4-tetrahydroquinolin-4-yl)prop-2-enamide
N-(1-{[5-(pyrrolidin-1-ylcarbonyl)-1H-pyrrol-3-yl]sulfonyl}-1,2,3,4-tetrahydroquinolin-4-yl)prop-2-enamide
N-(1-{[4-(2-methyl-1,3-thiazol-4-yl)phenyl]sulfonyl}-1,2,3,4-tetrahydroquinolin-4-yl)prop-2-enamide
N-(1-{[4-(pyridin-2-yloxy)phenyl]sulfonyl}-1,2,3,4-tetrahydroquinolin-4-yl)prop-2-enamide
N-{1-[(2-oxo-1,2,3,4-tetrahydroquinolin-6-yl)sulfonyl]-1,2,3,4-tetrahydroquinolin-4-yl}prop-2-enamide
N-{2-[(4-cyclohexylphenyl)sulfonyl]octahydrocyclopenta[c]pyrrol-5-yl}prop-2-enamide
N-(4-{[5-(acryloylamino)hexahydrocyclopenta[c]pyrrol-2(1H)-yl]sulfonyl}phenyl)cyclopropanecarboxamide
N-(4-{[5-(acryloylamino)hexahydrocyclopenta[c]pyrrol-2(1H)-yl]sulfonyl}phenyl)tricyclo[3.3.1.1~3,7~]decane-1-carboxamide
benzyl(4-{[5-(acryloylamino)hexahydrocyclopenta[c]pyrrol-2(1H)-yl]sulfonyl}phenyl)carbamate
N-(2-{[4-(piperidin-1-ylcarbonyl)phenyl]sulfonyl}octahydrocyclopenta[c]pyrrol-5-yl)prop-2-enamide
benzyl 4-{[5-(acryloylamino)hexahydrocyclopenta[c]pyrrol-2(1H)-yl]sulfonyl}piperidine-1-carboxylate
N-{2-[(4-nitrophenyl)sulfonyl]octahydrocyclopenta[c]pyrrol-5-yl}prop-2-enamide
N-(4-{[5-(acryloylamino)hexahydrocyclopenta[c]pyrrol-2(1H)-yl]sulfonyl}phenyl)tetrahydro-2H-pyran-4-carboxamide
N-[2-({4-[(3-phenylpropanoyl)amino]phenyl}sulfonyl)octahydrocyclopenta[c]pyrrol-5-yl]prop-2-enamide
N-(4-{[5-(acryloylamino)hexahydrocyclopenta[c]pyrrol-2(1H)-yl]sulfonyl}phenyl)-2-phenylcyclopropanecarboxamide
N-(4-{[5-(acryloylamino)hexahydrocyclopenta[c]pyrrol-2(1H)-yl]sulfonyl}phenyl)-N-methyltetrahydro-2H-pyran-4-carboxamide
4-{[5-(acryloylamino)hexahydrocyclopenta[c]pyrrol-2(1H)-yl]sulfonyl}-N-benzyl-N-methylbenzamide
4-{[5-(acryloylamino)hexahydrocyclopenta[c]pyrrol-2(1H)-yl]sulfonyl}-N-(cyclopropylmethyl)benzamide
N-(2-{[3-(piperidin-1-ylcarbonyl)phenyl]sulfonyl}octahydrocyclopenta[c]pyrrol-5-yl)prop-2-enamide
N-(4-{[5-(acryloylamino)hexahydrocyclopenta[c]pyrrol-2(1H)-yl]sulfonyl}phenyl)-N-methylcyclopropanecarboxamide
N-{2-[(4-{[4-(6-methylpyridin-2-yl)piperazin-1-yl]carbonyl}phenyl)sulfonyl]octahydrocyclopenta[c]pyrrol-5-yl}prop-2-enamide
4-{[5-(acryloylamino)hexahydrocyclopenta[c]pyrrol-2(1H)-yl]sulfonyl}-N-[2-(morpholin-4-yl)ethyl]benzamide
4-{[5-(acryloylamino)hexahydrocyclopenta[c]pyrrol-2(1H)-yl]sulfonyl}-N-(2-phenylethyl)benzamide
4-{[5-(acryloylamino)hexahydrocyclopenta[c]pyrrol-2(1H)-yl]sulfonyl}-N-methyl-N-(2-phenylethyl)benzamide
N-(2-{[4-(3,4-dihydroisoquinolin-2(1H)-ylcarbonyl)phenyl]sulfonyl}octahydrocyclopenta[c]pyrrol-5-yl)prop-2-enamide
4-{[5-(acryloylamino)hexahydrocyclopenta[c]pyrrol-2(1H)-yl]sulfonyl}-N-(2-cyclohexylethyl)benzamide
4-{[5-(acryloylamino)hexahydrocyclopenta[c]pyrrol-2(1H)-yl]sulfonyl}-N-cyclohexylbenzamide
N-{2-[(4-{[4-(pyrrolidin-1-ylcarbonyl)piperidin-1-yl]carbonyl}phenyl)sulfonyl]octahydrocyclopenta[c]pyrrol-5-yl}prop-2-enamide
4-{[5-(acryloylamino)hexahydrocyclopenta[c]pyrrol-2(1H)-yl]sulfonyl}-N-(3,5-dimethylbenzyl)benzamide
4-{[5-(acryloylamino)hexahydrocyclopenta[c]pyrrol-2(1H)-yl]sulfonyl}-N-benzylbenzamide
4-{[5-(acryloylamino)hexahydrocyclopenta[c]pyrrol-2(1H)-yl]sulfonyl}-N-(3,4-difluorobenzyl)benzamide
4-{[5-(acryloylamino)hexahydrocyclopenta[c]pyrrol-2(1H)-yl]sulfonyl}-N-[4-(trifluoromethyl)benzyl]benzamide
4-{[5-(acryloylamino)hexahydrocyclopenta[c]pyrrol-2(1H)-yl]sulfonyl}-N-(naphthalen-1-ylmethyl)benzamide
4-{[5-(acryloylamino)hexahydrocyclopenta[c]pyrrol-2(1H)-yl]sulfonyl}-N-[2-(3,4-dimethylphenyl)ethyl]benzamide
4-{[5-(acryloylamino)hexahydrocyclopenta[c]pyrrol-2(1H)-yl]sulfonyl}-N-[2-(4-methoxyphenyl)ethyl]benzamide 4-{[5-(acryloylamino)hexahydrocyclopenta[c]pyrrol-2(1H)-yl]sulfonyl}-N-(2,3-dihydro-1H-inden-2-yl)benzamide 4-{[5-(acryloylamino)hexahydrocyclopenta[c]pyrrol-2(1H)-yl]sulfonyl}-N-[2-(3-methylphenyl)ethyl]benzamide N-[2-({4-[(acetylamino)methyl]phenyl}sulfonyl)octahydrocyclopenta[c]pyrrol-5-yl]prop-2-enamide N-{2-[(4-{[3-(naphthalen-1-yl)propanoyl]amino}phenyl)sulfonyl]octahydrocyclopenta[c]pyrrol-5-yl}prop-2-enamide N-[2-({4-[(3-cyclohexylpropanoyl)amino]phenyl}sulfonyl)octahydrocyclopenta[c]pyrrol-5-yl]prop-2-enamide N-{2-[(1-benzoylpiperidin-4-yl)sulfonyl]octahydrocyclopenta[c]pyrrol-5-yl}prop-2-enamide N-(2-{[1-(piperidin-1-ylcarbonyl)piperidin-4-yl]sulfonyl}octahydrocyclopenta[c]pyrrol-5-yl)prop-2-enamide N-(2-{[1-(pyridin-2-ylcarbonyl)piperidin-4-yl]sulfonyl}octahydrocyclopenta[c]pyrrol-5-yl)prop-2-enamide N-(4-{[5-(acryloylamino)hexahydrocyclopenta[c]pyrrol-2(1H)-yl]sulfonyl}phenyl)-4-tert-butylcyclohexanecarboxamide N-(4-{[5-(acryloylamino)hexahydrocyclopenta[c]pyrrol-2(1H)-yl]sulfonyl}phenyl)-1-benzofuran-2-carboxamide benzyl(3-{[5-(acryloylamino)hexahydrocyclopenta[c]pyrrol-2(1H)-yl]sulfonyl}phenyl)carbamate N-[2-({3-[(3-phenylpropanoyl)amino]phenyl}sulfonyl)octahydrocyclopenta[c]pyrrol-5-yl]prop-2-enamide N-(3-{[5-(acryloylamino)hexahydrocyclopenta[c]pyrrol-2(1H)-yl]sulfonyl}phenyl)tetrahydro-2H-pyran-4-carboxamide 4-{[5-(acryloylamino)hexahydrocyclopenta[c]pyrrol-2(1H)-yl]sulfonyl}-N-(3-phenylpropyl)benzamide 4-{[5-(acryloylamino)hexahydrocyclopenta[c]pyrrol-2(1H)-yl]sulfonyl}-N-[2-(3-chlorophenyl)ethyl]benzamide 4-{[5-(acryloylamino)hexahydrocyclopenta[c]pyrrol-2(1H)-yl]sulfonyl}-N-[2-(2-methoxyphenyl)ethyl]benzamide 4-{[5-(acryloylamino)hexahydrocyclopenta[c]pyrrol-2(1H)-yl]sulfonyl}-N-[2-(2,3-dihydro-1-benzofuran-7-yl)ethyl]benzamide 4-{[5-(acryloylamino)hexahydrocyclopenta[c]pyrrol-2(1H)-yl]sulfonyl}-N-[2-(tetrahydro-2H-pyran-4-yl)ethyl]benzamide 4-{[5-(acryloylamino)hexahydrocyclopenta[c]pyrrol-2(1H)-yl]sulfonyl}-N-[2-(4,4-difluoropiperidin-1-yl)ethyl]benzamide N-[2-({1-[3-(trifluoromethyl)benzoyl]piperidin-4-yl}sulfonyl)octahydrocyclopenta[c]pyrrol-5-yl]prop-2-enamide N-(2-{[1-(3-phenylpropanoyl)piperidin-4-yl]sulfonyl}octahydrocyclopenta[c]pyrrol-5-yl)prop-2-enamide N-[2-({4-[2-(benzylamino)-2-oxoethyl]phenyl}sulfonyl)octahydrocyclopenta[c]pyrrol-5-yl]prop-2-enamide 4-{[5-(acryloylamino)hexahydrocyclopenta[c]pyrrol-2(1H)-yl]sulfonyl}-N-(4-tert-butylbenzyl)benzamide 4-{[5-(acryloylamino)hexahydrocyclopenta[c]pyrrol-2(1H)-yl]sulfonyl}-N-(4-phenylbutyl)benzamide 4-{[5-(acryloylamino)hexahydrocyclopenta[c]pyrrol-2(1H)-yl]sulfonyl}-N-[2-(4-chlorophenyl)ethyl]benzamide 4-{[5-(acryloylamino)hexahydrocyclopenta[c]pyrrol-2(1H)-yl]sulfonyl}-N-[2-(quinolin-7-yl)ethyl]benzamide 4-{[5-(acryloylamino)hexahydrocyclopenta[c]pyrrol-2(1H)-yl]sulfonyl}-N-[2-(naphthalen-2-yl)ethyl]benzamide 4-{[5-(acryloylamino)hexahydrocyclopenta[c]pyrrol-2(1H)-yl]sulfonyl}-N-(3,4-dihydro-2H-chromen-6-ylmethyl)benzamide 4-{[5-(acryloylamino)hexahydrocyclopenta[c]pyrrol-2(1H)-yl]sulfonyl}-N-[2-(4-tert-butylphenyl)ethyl]benzamide 4-{[5-(acryloylamino)hexahydrocyclopenta[c]pyrrol-2(1H)-yl]sulfonyl}-N-[2-(biphenyl-4-yl)ethyl]benzamide 4-{[5-(acryloylamino)hexahydrocyclopenta[c]pyrrol-2(1H)-yl]sulfonyl}-N-[2-(1,3-benzodioxol-5-yl)ethyl]benzamide 4-{[5-(acryloylamino)hexahydrocyclopenta[c]pyrrol-2(1H)-yl]sulfonyl}-N-[(1R)-2-phenylcyclopropyl]benzamide benzyl(4-{[5-(acryloylamino)hexahydrocyclopenta[c]pyrrol-2(1H)-yl]sulfonyl}phenyl)methylcarbamate 4-{[5-(acryloylamino)hexahydrocyclopenta[c]pyrrol-2(1H)-yl]sulfonyl}-N-[2-(3,4-dimethoxyphenyl)ethyl]benzamide 4-{[5-(acryloylamino)hexahydrocyclopenta[c]pyrrol-2(1H)-yl]sulfonyl}-N-{2-[4-(trifluoromethyl)phenyl]ethyl}benzamide 4-{[5-(acryloylamino)hexahydrocyclopenta[c]pyrrol-2(1H)-yl]sulfonyl}-N-(2-phenylethyl)piperidine-1-carboxamide N-(4-{[5-(acryloylamino)hexahydrocyclopenta[c]pyrrol-2(1H)-yl]sulfonyl}phenyl)furan-2-carboxamide N-{2-[(4-{[3-(tricyclo[3.3.1.1~3,7~]dec-1-yl)propanoyl]amino}phenyl)sulfonyl]octahydrocyclopenta[c]pyrrol-5-yl}prop-2-enamide 4-{[5-(acryloylamino)hexahydrocyclopenta[c]pyrrol-2(1H)-yl]sulfonyl}-N-[2-(tricyclo[3.3.1.1~3,7~]dec-1-yl)ethyl]benzamide N-(2-{[1-(cyclopropylcarbonyl)-2,3-dihydro-1H-indol-5-yl]sulfonyl}octahydrocyclopenta[c]pyrrol-5-yl)prop-2-enamide N-[2-({2-chloro-4-[(3-phenylpropanoyl)amino]phenyl}sulfonyl)octahydrocyclopenta[c]pyrrol-5-yl]prop-2-enamide N-(4-{[5-(acryloylamino)hexahydrocyclopenta[c]pyrrol-2(1H)-yl]sulfonyl}phenyl)-5,6-dihydro-4H-cyclopenta[b]thiophene-2-carboxamide N-(4-{[5-(acryloylamino)hexahydrocyclopenta[c]pyrrol-2(1H)-yl]sulfonyl}phenyl)-4,5,6,7-tetrahydro-1H-indole-2-carboxamide N-[2-({2-methoxy-4-[(3-phenylpropanoyl)amino]phenyl}sulfonyl)octahydrocyclopenta[c]pyrrol-5-yl]prop-2-enamide N-(4-{[5-(acryloylamino)hexahydrocyclopenta[c]pyrrol-2(1H)-yl]sulfonyl}phenyl)-5-(pyrrolidin-1-ylmethyl)furan-2-carboxamide N-(4-{[5-(acryloylamino)hexahydrocyclopenta[c]pyrrol-2(1H)-yl]sulfonyl}phenyl)-1-benzothiophene-2-carboxamide N-(4-{[5-(acryloylamino)hexahydrocyclopenta[c]pyrrol-2(1H)-yl]sulfonyl}phenyl)-3-methyl-1-benzofuran-2-carboxamide N-(4-{[5-(acryloylamino)hexahydrocyclopenta[c]pyrrol-2(1H)-yl]sulfonyl}phenyl)-1H-indole-2-carboxamide 4-{[5-(acryloylamino)hexahydrocyclopenta[c]pyrrol-2(1H)-yl]sulfonyl}-N-(tricyclo[3.3.1.1~3,7~]dec-1-ylmethyl)benzamide 4-{[5-(acryloylamino)hexahydrocyclopenta[c]pyrrol-2 (1H)-yl]sulfonyl}-N-(1,2,3,4-tetrahydronaphthalen-1-yl) benzamide
N-(4-{[5-(acryloylamino)hexahydrocyclopenta[c]pyrrol-2 (1H)-yl]sulfonyl}phenyl)-4,5,6,7-tetrahydro-1-benzothiophene-2-carboxamide
N-(4-{[5-(acryloylamino)hexahydrocyclopenta[c]pyrrol-2 (1H)-yl]sulfonyl}phenyl)-5-phenylfuran-2-carboxamide
N-(4-{[5-(acryloylamino)hexahydrocyclopenta[c]pyrrol-2 (1H)-yl]sulfonyl}phenyl)-4-phenylthiophene-2-carboxamide
N-[2-({5-[5-(trifluoromethyl)-1,2-oxazol-3-yl]thiophen-2-yl}sulfonyl)octahydrocyclopenta[c]pyrrol-5-yl]prop-2-enamide
5-{[5-(acryloylamino)hexahydrocyclopenta[c]pyrrol-2 (1H)-yl]sulfonyl}-N-(2-phenylethyl)furan-2-carboxamide
N-{2-[(6-phenoxypyridin-3-yl)sulfonyl]octahydrocyclopenta[c]pyrrol-5-yl}prop-2-enamide
N-(2-{[6-(morpholin-4-yl)pyridin-3-yl]sulfonyl}octahydrocyclopenta[c]pyrrol-5-yl)prop-2-enamide
N-{2-[(6-phenylpyridin-3-yl)sulfonyl]octahydrocyclopenta[c]pyrrol-5-yl}prop-2-enamide
N-[2-({3-chloro-4-[(3-phenylpropanoyl)amino]phenyl}sulfonyl)octahydrocyclopenta[c]pyrrol-5-yl]prop-2-enamide
4-{[5-(acryloylamino)hexahydrocyclopenta[c]pyrrol-2 (1H)-yl]sulfonyl}-2-fluoro-N-(2-phenylethyl)benzamide
N-(2-{[5-(pyridin-2-yl)thiophen-2-yl]sulfonyl}octahydrocyclopenta[c]pyrrol-5-yl)prop-2-enamide
4-{[5-(acryloylamino)hexahydrocyclopenta[c]pyrrol-2 (1H)-yl]sulfonyl}-2-methoxy-N-(2-phenylethyl)benzamide
N-[2-(1,3-benzothiazol-6-ylsulfonyl)octahydrocyclopenta[c]pyrrol-5-yl]prop-2-enamide
N-{2-[(4-methyl-2-phenyl-1,3-thiazol-5-yl)sulfonyl]octahydrocyclopenta[c]pyrrol-5-yl}prop-2-enamide
N-(2-{[5-(2-methyl-1,3-thiazol-4-yl)thiophen-2-yl]sulfonyl}octahydrocyclopenta[c]pyrrol-5-yl)prop-2-enamide
N-(2-{[5-(1,2-oxazol-5-yl)thiophen-2-yl]sulfonyl}octahydrocyclopenta[c]pyrrol-5-yl)prop-2-enamide
N-[2-(2,3-dihydro-1,4-benzodioxin-6-ylsulfonyl)octahydrocyclopenta[c]pyrrol-5-yl]prop-2-enamide
5-{[5-(acryloylamino)hexahydrocyclopenta[c]pyrrol-2 (1H)-yl]sulfonyl}-N-(2-phenylethyl)furan-3-carboxamide
N-[2-({4-[(phenylacetyl)amino]benzyl}sulfonyl)octahydrocyclopenta[c]pyrrol-5-yl]prop-2-enamide
N-(2-{[4-(morpholin-4-ylsulfonyl)phenyl]sulfonyl}octahydrocyclopenta[c]pyrrol-5-yl)prop-2-enamide
N-(2-{[5-(1,3-oxazol-5-yl)thiophen-2-yl]sulfonyl}octahydrocyclopenta[c]pyrrol-5-yl)prop-2-enamide
4-{[5-(acryloylamino)hexahydrocyclopenta[c]pyrrol-2 (1H)-yl]sulfonyl}-2-methyl-N-(2-phenylethyl)benzamide
N-{2-[(4-phenoxyphenyl)sulfonyl]octahydrocyclopenta[c]pyrrol-5-yl}prop-2-enamide
N-[2-({4-[(6-methylpyrazin-2-yl)oxy]phenyl}sulfonyl)octahydrocyclopenta[c]pyrrol-5-yl]prop-2-enamide
N-[2-({3-[(6-methylpyrazin-2-yl)oxy]phenyl}sulfonyl)octahydrocyclopenta[c]pyrrol-5-yl]prop-2-enamide
5-{[5-(acryloylamino)hexahydrocyclopenta[c]pyrrol-2 (1H)-yl]sulfonyl}-1-methyl-N-(2-phenylethyl)-1H-pyrrole-2-carboxamide
N-(2-{[4-(isoquinolin-3-ylamino)phenyl]sulfonyl}octahydrocyclopenta[c]pyrrol-5-yl)prop-2-enamide
N-{2-[(3-chloro-4-methylphenyl)sulfonyl]octahydrocyclopenta[c]pyrrol-5-yl}prop-2-enamide
N-(2-{[5-(1,2-oxazol-5-yl)furan-2-yl]sulfonyl}octahydrocyclopenta[c]pyrrol-5-yl)prop-2-enamide
N-{2-[(4-{[3-chloro-5-(trifluoromethyl)pyridin-2-yl]oxy}phenyl)sulfonyl]octahydrocyclopenta[c]pyrrol-5-yl}prop-2-enamide
N-(2-{[4-(1H-pyrazol-1-yl)phenyl]sulfonyl}octahydrocyclopenta[c]pyrrol-5-yl)prop-2-enamide
N-{2-[(4-methoxy-3-methylphenyl)sulfonyl]octahydrocyclopenta[c]pyrrol-5-yl}prop-2-enamide
N-(2-{[6-(2-phenylethoxy)pyridin-3-yl]sulfonyl}octahydrocyclopenta[c]pyrrol-5-yl)prop-2-enamide
N-[2-({5-[(acetylamino)methyl]thiophen-2-yl}sulfonyl)octahydrocyclopenta[c]pyrrol-5-yl]prop-2-enamide
N-{2-[(5-methyl-1-phenyl-1H-pyrazol-4-yl)sulfonyl]octahydrocyclopenta[c]pyrrol-5-yl}prop-2-enamide
N-(2-{[4-(1-methyl-1H-pyrazol-5-yl)phenyl]sulfonyl}octahydrocyclopenta[c]pyrrol-5-yl)prop-2-enamide
N-(2-{[3-(1-methyl-1H-pyrazol-5-yl)phenyl]sulfonyl}octahydrocyclopenta[c]pyrrol-5-yl)prop-2-enamide
N-{2-[(2,2-dimethyl-3,4-dihydro-2H-chromen-6-yl)sulfonyl]octahydrocyclopenta[c]pyrrol-5-yl}prop-2-enamide
N-{2-[(5-phenylthiophen-2-yl)sulfonyl]octahydrocyclopenta[c]pyrrol-5-yl}prop-2-enamide
N-(2-{[4-(cyclopentyloxy)phenyl]sulfonyl}octahydrocyclopenta[c]pyrrol-5-yl)prop-2-enamide
N-(2-{[5-(pyrrolidin-1-ylcarbonyl)-1H-pyrrol-3-yl]sulfonyl}octahydrocyclopenta[c]pyrrol-5-yl)prop-2-enamide
N-(2-{[4-(2-methyl-1,3-thiazol-4-yl)phenyl]sulfonyl}octahydrocyclopenta[c]pyrrol-5-yl)prop-2-enamide
N-(2-{[4-(pyridin-2-yloxy)phenyl]sulfonyl}octahydrocyclopenta[c]pyrrol-5-yl)prop-2-enamide
N-{2-[(2-oxo-1,2,3,4-tetrahydroquinolin-6-yl)sulfonyl]octahydrocyclopenta[c]pyrrol-5-yl}prop-2-enamide
N-{5-[(4-cyclohexylphenyl)sulfonyl]hexahydro-2H-furo[2,3-c]pyrrol-2-yl}prop-2-enamide
N-(4-{[2-(acryloylamino)hexahydro-5H-furo[2,3-c]pyrrol-5-yl]sulfonyl}phenyl)cyclopropanecarboxamide
N-(4-{[2-(acryloylamino)hexahydro-5H-furo[2,3-c]pyrrol-5-yl]sulfonyl}phenyl)tricyclo[3.3.1.1~3,7~]decane-1-carboxamide
benzyl(4-{[2-(acryloylamino)hexahydro-5H-furo[2,3-c]pyrrol-5-yl]sulfonyl}phenyl)carbamate
N-(5-{[4-(piperidin-1-ylcarbonyl)phenyl]sulfonyl}hexahydro-2H-furo[2,3-c]pyrrol-2-yl)prop-2-enamide
benzyl 4-{[2-(acryloylamino)hexahydro-5H-furo[2,3-c]pyrrol-5-yl]sulfonyl}piperidine-1-carboxylate
N-{5-[(4-nitrophenyl)sulfonyl]hexahydro-2H-furo[2,3-c]pyrrol-2-yl}prop-2-enamide N-(4-{[2-(acryloylamino)hexahydro-5H-furo[2,3-c]pyrrol-5-yl]sulfonyl}phenyl)tetrahydro-2H-pyran-4-carboxamide N-[5-({4-[(3-phenylpropanoyl)amino]phenyl}sulfonyl)hexahydro-2H-furo[2,3-c]pyrrol-2-yl]prop-2-enamide N-(4-{[2-(acryloylamino)hexahydro-5H-furo[2,3-c]pyrrol-5-yl]sulfonyl}phenyl)-2-phenylcyclopropanecarboxamide N-(4-{[2-(acryloylamino)hexahydro-5H-furo[2,3-c]pyrrol-5-yl]sulfonyl}phenyl)-N-methyltetrahydro-2H-pyran-4-carboxamide 4-{[2-(acryloylamino)hexahydro-5H-furo[2,3-c]pyrrol-5-yl]sulfonyl}-N-benzyl-N-methylbenzamide 4-{[2-(acryloylamino)hexahydro-5H-furo[2,3-c]pyrrol-5-yl]sulfonyl}-N-(cyclopropylmethyl)benzamide N-(5-{[3-(piperidin-1-ylcarbonyl)phenyl]sulfonyl}hexahydro-2H-furo[2,3-c]pyrrol-2-yl)prop-2-enamide N-(4-{[2-(acryloylamino)hexahydro-5H-furo[2,3-c]pyrrol-5-yl]sulfonyl}phenyl)-N-methylcyclopropanecarboxamide N-{5-[(4-{[4-(6-methylpyridin-2-yl)piperazin-1-yl]carbonyl}phenyl)sulfonyl]hexahydro-2H-furo[2,3-c]pyrrol-2-yl}prop-2-enamide 4-{[2-(acryloylamino)hexahydro-5H-furo[2,3-c]pyrrol-5-yl]sulfonyl}-N-[2-(morpholin-4-yl)ethyl]benzamide 4-{[2-(acryloylamino)hexahydro-5H-furo[2,3-c]pyrrol-5-yl]sulfonyl}-N-(2-phenylethyl)benzamide 4-{[2-(acryloylamino)hexahydro-5H-furo[2,3-c]pyrrol-5-yl]sulfonyl}-N-methyl-N-(2-phenylethyl)benzamide N-(5-{[4-(3,4-dihydroisoquinolin-2(1H)-ylcarbonyl)phenyl]sulfonyl}hexahydro-2H-furo[2,3-c]pyrrol-2-yl)prop-2-enamide 4-{[2-(acryloylamino)hexahydro-5H-furo[2,3-c]pyrrol-5-yl]sulfonyl}-N-(2-cyclohexylethyl)benzamide 4-{[2-(acryloylamino)hexahydro-5H-furo[2,3-c]pyrrol-5-yl]sulfonyl}-N-cyclohexylbenzamide N-{5-[(4-{[4-(pyrrolidin-1-ylcarbonyl)piperidin-1-yl]carbonyl}phenyl)sulfonyl]hexahydro-2H-furo[2,3-c]pyrrol-2-yl}prop-2-enamide 4-{[2-(acryloylamino)hexahydro-5H-furo[2,3-c]pyrrol-5-yl]sulfonyl}-N-(3,5-dimethylbenzyl)benzamide 4-{[2-(acryloylamino)hexahydro-5H-furo[2,3-c]pyrrol-5-yl]sulfonyl}-N-benzylbenzamide 4-{[2-(acryloylamino)hexahydro-5H-furo[2,3-c]pyrrol-5-yl]sulfonyl}-N-(3,4-difluorobenzyl)benzamide 4-{[2-(acryloylamino)hexahydro-5H-furo[2,3-c]pyrrol-5-yl]sulfonyl}-N-[4-(trifluoromethyl)benzyl]benzamide 4-{[2-(acryloylamino)hexahydro-5H-furo[2,3-c]pyrrol-5-yl]sulfonyl}-N-(naphthalen-1-ylmethyl)benzamide 4-{[2-(acryloylamino)hexahydro-5H-furo[2,3-c]pyrrol-5-yl]sulfonyl}-N-[2-(3,4-dimethylphenyl)ethyl]benzamide 4-{[2-(acryloylamino)hexahydro-5H-furo[2,3-c]pyrrol-5-yl]sulfonyl}-N-[2-(4-methoxyphenyl)ethyl]benzamide 4-{[2-(acryloylamino)hexahydro-5H-furo[2,3-c]pyrrol-5-yl]sulfonyl}-N-(2,3-dihydro-1H-inden-2-yl)benzamide 4-{[2-(acryloylamino)hexahydro-5H-furo[2,3-c]pyrrol-5-yl]sulfonyl}-N-[2-(3-methylphenyl)ethyl]benzamide N-[5-({4-[(acetylamino)methyl]phenyl}sulfonyl)hexahydro-2H-furo[2,3-c]pyrrol-2-yl]prop-2-enamide N-{5-[(4-{[3-(naphthalen-1-yl)propanoyl]amino}phenyl)sulfonyl]hexahydro-2H-furo[2,3-c]pyrrol-2-yl}prop-2-enamide N-[5-({4-[(3-cyclohexylpropanoyl)amino]phenyl}sulfonyl)hexahydro-2H-furo[2,3-c]pyrrol-2-yl]prop-2-enamide N-{5-[(1-benzoylpiperidin-4-yl)sulfonyl]hexahydro-2H-furo[2,3-c]pyrrol-2-yl}prop-2-enamide N-(5-{[1-(piperidin-1-ylcarbonyl)piperidin-4-yl]sulfonyl}hexahydro-2H-furo[2,3-c]pyrrol-2-yl)prop-2-enamide N-(5-{[1-(pyridin-2-ylcarbonyl)piperidin-4-yl]sulfonyl}hexahydro-2H-furo[2,3-c]pyrrol-2-yl)prop-2-enamide N-(4-{[2-(acryloylamino)hexahydro-5H-furo[2,3-c]pyrrol-5-yl]sulfonyl}phenyl)-4-tert-butylcyclohexanecarboxamide N-(4-{[2-(acryloylamino)hexahydro-5H-furo[2,3-c]pyrrol-5-yl]sulfonyl}phenyl)-1-benzofuran-2-carboxamide benzyl(3-{[2-(acryloylamino)hexahydro-5H-furo[2,3-c]pyrrol-5-yl]sulfonyl}phenyl)carbamate N-[5-({3-[(3-phenylpropanoyl)amino]phenyl}sulfonyl)hexahydro-2H-furo[2,3-c]pyrrol-2-yl]prop-2-enamide N-(3-{[2-(acryloylamino)hexahydro-5H-furo[2,3-c]pyrrol-5-yl]sulfonyl}phenyl)tetrahydro-2H-pyran-4-carboxamide 4-{[2-(acryloylamino)hexahydro-5H-furo[2,3-c]pyrrol-5-yl]sulfonyl}-N-(3-phenylpropyl)benzamide 4-{[2-(acryloylamino)hexahydro-5H-furo[2,3-c]pyrrol-5-yl]sulfonyl}-N-[2-(3-chlorophenyl)ethyl]benzamide 4-{[2-(acryloylamino)hexahydro-5H-furo[2,3-c]pyrrol-5-yl]sulfonyl}-N-[2-(2-methoxyphenyl)ethyl]benzamide 4-{[2-(acryloylamino)hexahydro-5H-furo[2,3-c]pyrrol-5-yl]sulfonyl}-N-[2-(2,3-dihydro-1-benzofuran-7-yl)ethyl]benzamide 4-{[2-(acryloylamino)hexahydro-5H-furo[2,3-c]pyrrol-5-yl]sulfonyl}-N-[2-(tetrahydro-2H-pyran-4-yl)ethyl]benzamide 4-{[2-(acryloylamino)hexahydro-5H-furo[2,3-c]pyrrol-5-yl]sulfonyl}-N-[2-(4,4-difluoropiperidin-1-yl)ethyl]benzamide N-[5-({1-[3-(trifluoromethyl)benzoyl]piperidin-4-yl}sulfonyl)hexahydro-2H-furo[2,3-c]pyrrol-2-yl]prop-2-enamide N-(5-{[1-(3-phenylpropanoyl)piperidin-4-yl]sulfonyl}hexahydro-2H-furo[2,3-c]pyrrol-2-yl)prop-2-enamide N-[5-({4-[2-(benzylamino)-2-oxoethyl]phenyl}sulfonyl)hexahydro-2H-furo[2,3-c]pyrrol-2-yl]prop-2-enamide 4-{[2-(acryloylamino)hexahydro-5H-furo[2,3-c]pyrrol-5-yl]sulfonyl}-N-(4-tert-butylbenzyl)benzamide 4-{[2-(acryloylamino)hexahydro-5H-furo[2,3-c]pyrrol-5-yl]sulfonyl}-N-(4-phenylbutyl)benzamide 4-{[2-(acryloylamino)hexahydro-5H-furo[2,3-c]pyrrol-5-yl]sulfonyl}-N-[2-(4-chlorophenyl)ethyl]benzamide 4-{[2-(acryloylamino)hexahydro-5H-furo[2,3-c]pyrrol-5-yl]sulfonyl}-N-[2-(quinolin-7-yl)ethyl]benzamide 4-{[2-(acryloylamino)hexahydro-5H-furo[2,3-c]pyrrol-5-yl]sulfonyl}-N-[2-(naphthalen-2-yl)ethyl]benzamide 4-{[2-(acryloylamino)hexahydro-5H-furo[2,3-c]pyrrol-5-yl]sulfonyl}-N-(3,4-dihydro-2H-chromen-6-ylmethyl)benzamide 4-{[2-(acryloylamino)hexahydro-5H-furo[2,3-c]pyrrol-5-yl]sulfonyl}-N-[2-(4-tert-butylphenyl)ethyl]benzamide 4-{[2-(acryloylamino)hexahydro-5H-furo[2,3-c]pyrrol-5-yl]sulfonyl}-N-[2-(biphenyl-4-yl)ethyl]benzamide 4-{[2-(acryloylamino)hexahydro-5H-furo[2,3-c]pyrrol-5-yl]sulfonyl}-N-[2-(1,3-benzodioxol-5-yl)ethyl]benzamide 4-{[2-(acryloylamino)hexahydro-5H-furo[2,3-c]pyrrol-5-yl]sulfonyl}-N-[(1R)-2-phenylcyclopropyl]benzamide benzyl(4-{[2-(acryloylamino)hexahydro-5H-furo[2,3-c]pyrrol-5-yl]sulfonyl}phenyl)methylcarbamate 4-{[2-(acryloylamino)hexahydro-5H-furo[2,3-c]pyrrol-5-yl]sulfonyl}-N-[2-(3,4-dimethoxyphenyl)ethyl]benzamide 4-{[2-(acryloylamino)hexahydro-5H-furo[2,3-c]pyrrol-5-yl]sulfonyl}-N-{2-[4-(trifluoromethyl)phenyl]ethyl}benzamide 4-{[2-(acryloylamino)hexahydro-5H-furo[2,3-c]pyrrol-5-yl]sulfonyl}-N-(2-phenylethyl)piperidine-1-carboxamide N-(4-{[2-(acryloylamino)hexahydro-5H-furo[2,3-c]pyrrol-5-yl]sulfonyl}phenyl)furan-2-carboxamide N-{5-[(4-{[3-(tricyclo[3.3.1.1~3,7~]dec-1-yl)propanoyl]amino}phenyl)sulfonyl]hexahydro-2H-furo[2,3-c]pyrrol-2-yl}prop-2-enamide 4-{[2-(acryloylamino)hexahydro-5H-furo[2,3-c]pyrrol-5-yl]sulfonyl}-N-[2-(tricyclo[3.3.1.1~3,7~]dec-1-yl)ethyl]benzamide N-(5-{[1-(cyclopropylcarbonyl)-2,3-dihydro-1H-indol-5-yl]sulfonyl}hexahydro-2H-furo[2,3-c]pyrrol-2-yl)prop-2-enamide N-[5-({2-chloro-4-[(3-phenylpropanoyl)amino]phenyl}sulfonyl)hexahydro-2H-furo[2,3-c]pyrrol-2-yl]prop-2-enamide N-(4-{[2-(acryloylamino)hexahydro-5H-furo[2,3-c]pyrrol-5-yl]sulfonyl}phenyl)-5,6-dihydro-4H-cyclopenta[b]thiophene-2-carboxamide N-(4-{[2-(acryloylamino)hexahydro-5H-furo[2,3-c]pyrrol-5-yl]sulfonyl}phenyl)-4,5,6,7-tetrahydro-1H-indole-2-carboxamide N-[5-({2-methoxy-4-[(3-phenylpropanoyl)amino]phenyl}sulfonyl)hexahydro-2H-furo[2,3-c]pyrrol-2-yl]prop-2-enamide N-(4-{[2-(acryloylamino)hexahydro-5H-furo[2,3-c]pyrrol-5-yl]sulfonyl}phenyl)-5-(pyrrolidin-1-ylmethyl)furan-2-carboxamide N-(4-{[2-(acryloylamino)hexahydro-5H-furo[2,3-c]pyrrol-5-yl]sulfonyl}phenyl)-1-benzothiophene-2-carboxamide N-(4-{[2-(acryloylamino)hexahydro-5H-furo[2,3-c]pyrrol-5-yl]sulfonyl}phenyl)-3-methyl-1-benzofuran-2-carboxamide N-(4-{[2-(acryloylamino)hexahydro-5H-furo[2,3-c]pyrrol-5-yl]sulfonyl}phenyl)-1H-indole-2-carboxamide 4-{[2-(acryloylamino)hexahydro-5H-furo[2,3-c]pyrrol-5-yl]sulfonyl}-N-(tricyclo[3.3.1.1~3,7~]dec-1-ylmethyl)benzamide 4-{[2-(acryloylamino)hexahydro-5H-furo[2,3-c]pyrrol-5-yl]sulfonyl}-N-(1,2,3,4-tetrahydronaphthalen-1-yl)benzamide N-(4-{[2-(acryloylamino)hexahydro-5H-furo[2,3-c]pyrrol-5-yl]sulfonyl}phenyl)-4,5,6,7-tetrahydro-1-benzothiophene-2-carboxamide N-(4-{[2-(acryloylamino)hexahydro-5H-furo[2,3-c]pyrrol-5-yl]sulfonyl}phenyl)-5-phenylfuran-2-carboxamide N-(4-{[2-(acryloylamino)hexahydro-5H-furo[2,3-c]pyrrol-5-yl]sulfonyl}phenyl)-4-phenylthiophene-2-carboxamide N-[5-({5-[5-(trifluoromethyl)-1,2-oxazol-3-yl]thiophen-2-yl}sulfonyl)hexahydro-2H-furo[2,3-c]pyrrol-2-yl]prop-2-enamide 5-{[2-(acryloylamino)hexahydro-5H-furo[2,3-c]pyrrol-5-yl]sulfonyl}-N-(2-phenylethyl)furan-2-carboxamide N-{5-[(6-phenoxypyridin-3-yl)sulfonyl]hexahydro-2H-furo[2,3-c]pyrrol-2-yl}prop-2-enamide N-(5-{[6-(morpholin-4-yl)pyridin-3-yl]sulfonyl}hexahydro-2H-furo[2,3-c]pyrrol-2-yl)prop-2-enamide N-{5-[(6-phenylpyridin-3-yl)sulfonyl]hexahydro-2H-furo[2,3-c]pyrrol-2-yl}prop-2-enamide N-[5-({3-chloro-4-[(3-phenylpropanoyl)amino]phenyl}sulfonyl)hexahydro-2H-furo[2,3-c]pyrrol-2-yl]prop-2-enamide 4-{[2-(acryloylamino)hexahydro-5H-furo[2,3-c]pyrrol-5-yl]sulfonyl}-2-fluoro-N-(2-phenylethyl)benzamide N-(5-{[5-(pyridin-2-yl)thiophen-2-yl]sulfonyl}hexahydro-2H-furo[2,3-c]pyrrol-2-yl)prop-2-enamide 4-{[2-(acryloylamino)hexahydro-5H-furo[2,3-c]pyrrol-5-yl]sulfonyl}-2-methoxy-N-(2-phenylethyl)benzamide N-[5-(1,3-benzothiazol-6-ylsulfonyl)hexahydro-2H-furo[2,3-c]pyrrol-2-yl]prop-2-enamide N-{5-[(4-methyl-2-phenyl-1,3-thiazol-5-yl)sulfonyl]hexahydro-2H-furo[2,3-c]pyrrol-2-yl}prop-2-enamide N-(5-{[5-(2-methyl-1,3-thiazol-4-yl)thiophen-2-yl]sulfonyl}hexahydro-2H-furo[2,3-c]pyrrol-2-yl)prop-2-enamide N-(5-{[5-(1,2-oxazol-5-yl)thiophen-2-yl]sulfonyl}hexahydro-2H-furo[2,3-c]pyrrol-2-yl)prop-2-enamide N-[5-(2,3-dihydro-1,4-benzodioxin-6-ylsulfonyl)hexahydro-2H-furo[2,3-c]pyrrol-2-yl]prop-2-enamide 5-{[2-(acryloylamino)hexahydro-5H-furo[2,3-c]pyrrol-5-yl]sulfonyl}-N-(2-phenylethyl)furan-3-carboxamide N-[5-({4-[(phenylacetyl)amino]benzyl}sulfonyl)hexahydro-2H-furo[2,3-c]pyrrol-2-yl]prop-2-enamide N-(5-{[4-(morpholin-4-ylsulfonyl)phenyl]sulfonyl}hexahydro-2H-furo[2,3-c]pyrrol-2-yl)prop-2-enamide N-(5-{[5-(1,3-oxazol-5-yl)thiophen-2-yl]sulfonyl}hexahydro-2H-furo[2,3-c]pyrrol-2-yl)prop-2-enamide 4-{[2-(acryloylamino)hexahydro-5H-furo[2,3-c]pyrrol-5-yl]sulfonyl}-2-methyl-N-(2-phenylethyl)benzamide N-{5-[(4-phenoxyphenyl)sulfonyl]hexahydro-2H-furo[2,3-c]pyrrol-2-yl}prop-2-enamide N-[5-({4-[(6-methylpyrazin-2-yl)oxy]phenyl}sulfonyl)hexahydro-2H-furo[2,3-c]pyrrol-2-yl]prop-2-enamide N-[5-({3-[(6-methylpyrazin-2-yl)oxy]phenyl}sulfonyl)hexahydro-2H-furo[2,3-c]pyrrol-2-yl]prop-2-enamide 5-{[2-(acryloylamino)hexahydro-5H-furo[2,3-c]pyrrol-5-yl]sulfonyl}-1-methyl-N-(2-phenylethyl)-1H-pyrrole-2-carboxamide N-(5-{[4-(isoquinolin-3-ylamino)phenyl]sulfonyl}hexahydro-2H-furo[2,3-c]pyrrol-2-yl)prop-2-enamide N-{5-[(3-chloro-4-methylphenyl)sulfonyl]hexahydro-2H-furo[2,3-c]pyrrol-2-yl}prop-2-enamide N-(5-{[5-(1,2-oxazol-5-yl)furan-2-yl]sulfonyl}hexahydro-2H-furo[2,3-c]pyrrol-2-yl)prop-2-enamide N-{5-[(4-{[3-chloro-5-(trifluoromethyl)pyridin-2-yl]oxy}phenyl)sulfonyl]hexahydro-2H-furo[2,3-c]pyrrol-2-yl}prop-2-enamide N-(5-{[4-(1H-pyrazol-1-yl)phenyl]sulfonyl}hexahydro-2H-furo[2,3-c]pyrrol-2-yl)prop-2-enamide N-{5-[(4-methoxy-3-methylphenyl)sulfonyl]hexahydro-2H-furo[2,3-c]pyrrol-2-yl}prop-2-enamide N-(5-{[6-(2-phenylethoxy)pyridin-3-yl]sulfonyl}hexahydro-2H-furo[2,3-c]pyrrol-2-yl)prop-2-enamide N-[5-({5-[(acetylamino)methyl]thiophen-2-yl}sulfonyl)hexahydro-2H-furo[2,3-c]pyrrol-2-yl]prop-2-enamide N-{5-[(5-methyl-1-phenyl-1H-pyrazol-4-yl)sulfonyl]hexahydro-2H-furo[2,3-c]pyrrol-2-yl}prop-2-enamide N-(5-{[4-(1-methyl-1H-pyrazol-5-yl)phenyl]sulfonyl}hexahydro-2H-furo[2,3-c]pyrrol-2-yl)prop-2-enamide N-(5-{[3-(1-methyl-1H-pyrazol-5-yl)phenyl]sulfonyl}hexahydro-2H-furo[2,3-c]pyrrol-2-yl)prop-2-enamide N-{5-[(2,2-dimethyl-3,4-dihydro-2H-chromen-6-yl)sulfonyl]hexahydro-2H-furo[2,3-c]pyrrol-2-yl}prop-2-enamide N-{5-[(5-phenylthiophen-2-yl)sulfonyl]hexahydro-2H-furo[2,3-c]pyrrol-2-yl}prop-2-enamide N-(5-{[4-(cyclopentyloxy)phenyl]sulfonyl}hexahydro-2H-furo[2,3-c]pyrrol-2-yl)prop-2-enamide N-(5-{[5-(pyrrolidin-1-ylcarbonyl)-1H-pyrrol-3-yl]sulfonyl}hexahydro-2H-furo[2,3-c]pyrrol-2-yl)prop-2-enamide N-(5-{[4-(2-methyl-1,3-thiazol-4-yl)phenyl]sulfonyl}hexahydro-2H-furo[2,3-c]pyrrol-2-yl)prop-2-enamide N-(5-{[4-(pyridin-2-yloxy)phenyl]sulfonyl}hexahydro-2H-furo[2,3-c]pyrrol-2-yl)prop-2-enamide N-{5-[(2-oxo-1,2,3,4-tetrahydroquinolin-6-yl)sulfonyl]hexahydro-2H-furo[2,3-c]pyrrol-2-yl}prop-2-enamide N-{5-[(4-cyclohexylphenyl)sulfonyl]hexahydro-2H-thieno[2,3-c]pyrrol-2-yl}prop-2-enamide N-(4-{[2-(acryloylamino)hexahydro-5H-thieno[2,3-c]pyrrol-5-yl]sulfonyl}phenyl)cyclopropanecarboxamide N-(4-{[2-(acryloylamino)hexahydro-5H-thieno[2,3-c]pyrrol-5-yl]sulfonyl}phenyl)tricyclo[3.3.1.1~3,7~]decane-1-carboxamide benzyl(4-{[2-(acryloylamino)hexahydro-5H-thieno[2,3-c]pyrrol-5-yl]sulfonyl}phenyl)carbamate N-(5-{[4-(piperidin-1-ylcarbonyl)phenyl]sulfonyl}hexahydro-2H-thieno[2,3-c]pyrrol-2-yl)prop-2-enamide benzyl 4-{[2-(acryloylamino)hexahydro-5H-thieno[2,3-c]pyrrol-5-yl]sulfonyl}piperidine-1-carboxylate N-{5-[(4-nitrophenyl)sulfonyl]hexahydro-2H-thieno[2,3-c]pyrrol-2-yl}prop-2-enamide N-(4-{[2-(acryloylamino)hexahydro-5H-thieno[2,3-c]pyrrol-5-yl]sulfonyl}phenyl)tetrahydro-2H-pyran-4-carboxamide N-[5-({4-[(3-phenylpropanoyl)amino]phenyl}sulfonyl)hexahydro-2H-thieno[2,3-c]pyrrol-2-yl]prop-2-enamide N-(4-{[2-(acryloylamino)hexahydro-5H-thieno[2,3-c]pyrrol-5-yl]sulfonyl}phenyl)-2-phenylcyclopropanecarboxamide N-(4-{[2-(acryloylamino)hexahydro-5H-thieno[2,3-c]pyrrol-5-yl]sulfonyl}phenyl)-N-methyltetrahydro-2H-pyran-4-carboxamide 4-{[2-(acryloylamino)hexahydro-5H-thieno[2,3-c]pyrrol-5-yl]sulfonyl}-N-benzyl-N-methylbenzamide 4-{[2-(acryloylamino)hexahydro-5H-thieno[2,3-c]pyrrol-5-yl]sulfonyl}-N-(cyclopropylmethyl)benzamide N-(5-{[3-(piperidin-1-ylcarbonyl)phenyl]sulfonyl}hexahydro-2H-thieno[2,3-c]pyrrol-2-yl)prop-2-enamide N-(4-{[2-(acryloylamino)hexahydro-5H-thieno[2,3-c]pyrrol-5-yl]sulfonyl}phenyl)-N-methylcyclopropanecarboxamide N-{5-[(4-{[4-(6-methylpyridin-2-yl)piperazin-1-yl]carbonyl}phenyl)sulfonyl]hexahydro-2H-thieno[2,3-c]pyrrol-2-yl}prop-2-enamide 4-{[2-(acryloylamino)hexahydro-5H-thieno[2,3-c]pyrrol-5-yl]sulfonyl}-N-[2-(morpholin-4-yl)ethyl]benzamide 4-{[2-(acryloylamino)hexahydro-5H-thieno[2,3-c]pyrrol-5-yl]sulfonyl}-N-(2-phenylethyl)benzamide 4-{[2-(acryloylamino)hexahydro-5H-thieno[2,3-c]pyrrol-5-yl]sulfonyl}-N-methyl-N-(2-phenylethyl)benzamide N-(5-{[4-(3,4-dihydroisoquinolin-2(1H)-ylcarbonyl)phenyl]sulfonyl}hexahydro-2H-thieno[2,3-c]pyrrol-2-yl)prop-2-enamide 4-{[2-(acryloylamino)hexahydro-5H-thieno[2,3-c]pyrrol-5-yl]sulfonyl}-N-(2-cyclohexylethyl)benzamide 4-{[2-(acryloylamino)hexahydro-5H-thieno[2,3-c]pyrrol-5-yl]sulfonyl}-N-cyclohexylbenzamide N-{5-[(4-{[4-(pyrrolidin-1-ylcarbonyl)piperidin-1-yl]carbonyl}phenyl)sulfonyl]hexahydro-2H-thieno[2,3-c]pyrrol-2-yl}prop-2-enamide 4-{[2-(acryloylamino)hexahydro-5H-thieno[2,3-c]pyrrol-5-yl]sulfonyl}-N-(3,5-dimethylbenzyl)benzamide 4-{[2-(acryloylamino)hexahydro-5H-thieno[2,3-c]pyrrol-5-yl]sulfonyl}-N-benzylbenzamide 4-{[2-(acryloylamino)hexahydro-5H-thieno[2,3-c]pyrrol-5-yl]sulfonyl}-N-(3,4-difluorobenzyl)benzamide 4-{[2-(acryloylamino)hexahydro-5H-thieno[2,3-c]pyrrol-5-yl]sulfonyl}-N-[4-(trifluoromethyl)benzyl]benzamide 4-{[2-(acryloylamino)hexahydro-5H-thieno[2,3-c]pyrrol-5-yl]sulfonyl}-N-(naphthalen-1-ylmethyl)benzamide 4-{[2-(acryloylamino)hexahydro-5H-thieno[2,3-c]pyrrol-5-yl]sulfonyl}-N-[2-(3,4-dimethylphenyl)ethyl]benzamide 4-{[2-(acryloylamino)hexahydro-5H-thieno[2,3-c]pyrrol-5-yl]sulfonyl}-N-[2-(4-methoxyphenyl)ethyl]benzamide 4-{[2-(acryloylamino)hexahydro-5H-thieno[2,3-c]pyrrol-5-yl]sulfonyl}-N-(2,3-dihydro-1H-inden-2-yl)benzamide 4-{[2-(acryloylamino)hexahydro-5H-thieno[2,3-c]pyrrol-5-yl]sulfonyl}-N-[2-(3-methylphenyl)ethyl]benzamide N-[5-({4-[(acetylamino)methyl]phenyl}sulfonyl)hexahydro-2H-thieno[2,3-c]pyrrol-2-yl]prop-2-enamide N-{5-[(4-{[3-(naphthalen-1-yl)propanoyl]amino}phenyl)sulfonyl]hexahydro-2H-thieno[2,3-c]pyrrol-2-yl}prop-2-enamide N-[5-({4-[(3-cyclohexylpropanoyl)amino]phenyl}sulfonyl)hexahydro-2H-thieno[2,3-c]pyrrol-2-yl]prop-2-enamide N-{5-[(1-benzoylpiperidin-4-yl)sulfonyl]hexahydro-2H-thieno[2,3-c]pyrrol-2-yl}prop-2-enamide N-(5-{[1-(piperidin-1-ylcarbonyl)piperidin-4-yl]sulfonyl}hexahydro-2H-thieno[2,3-c]pyrrol-2-yl)prop-2-enamide N-(5-{[1-(pyridin-2-ylcarbonyl)piperidin-4-yl]sulfonyl}hexahydro-2H-thieno[2,3-c]pyrrol-2-yl)prop-2-enamide N-(4-{[2-(acryloylamino)hexahydro-5H-thieno[2,3-c]pyrrol-5-yl]sulfonyl}phenyl)-4-tert-butylcyclohexanecarboxamide N-(4-{[2-(acryloylamino)hexahydro-5H-thieno[2,3-c]pyrrol-5-yl]sulfonyl}phenyl)-1-benzofuran-2-carboxamide benzyl(3-{[2-(acryloylamino)hexahydro-5H-thieno[2,3-c]pyrrol-5-yl]sulfonyl}phenyl)carbamate N-[5-({3-[(3-phenylpropanoyl)amino]phenyl}sulfonyl)hexahydro-2H-thieno[2,3-c]pyrrol-2-yl]prop-2-enamide N-(3-{[2-(acryloylamino)hexahydro-5H-thieno[2,3-c]pyrrol-5-yl]sulfonyl}phenyl)tetrahydro-2H-pyran-4-carboxamide 4-{[2-(acryloylamino)hexahydro-5H-thieno[2,3-c]pyrrol-5-yl]sulfonyl}-N-(3-phenylpropyl)benzamide 4-{[2-(acryloylamino)hexahydro-5H-thieno[2,3-c]pyrrol-5-yl]sulfonyl}-N-[2-(3-chlorophenyl)ethyl]benzamide 4-{[2-(acryloylamino)hexahydro-5H-thieno[2,3-c]pyrrol-5-yl]sulfonyl}-N-[2-(2-methoxyphenyl)ethyl]benzamide 4-{[2-(acryloylamino)hexahydro-5H-thieno[2,3-c]pyrrol-5-yl]sulfonyl}-N-[2-(2,3-dihydro-1-benzofuran-7-yl)ethyl]benzamide 4-{[2-(acryloylamino)hexahydro-5H-thieno[2,3-c]pyrrol-5-yl]sulfonyl}-N-[2-(tetrahydro-2H-pyran-4-yl)ethyl]benzamide 4-{[2-(acryloylamino)hexahydro-5H-thieno[2,3-c]pyrrol-5-yl]sulfonyl}-N-[2-(4,4-difluoropiperidin-1-yl)ethyl]benzamide N-[5-({1-[3-(trifluoromethyl)benzoyl]piperidin-4-yl}sulfonyl)hexahydro-2H-thieno[2,3-c]pyrrol-2-yl]prop-2-enamide N-(5-{[1-(3-phenylpropanoyl)piperidin-4-yl]sulfonyl}hexahydro-2H-thieno[2,3-c]pyrrol-2-yl)prop-2-enamide N-[5-({4-[2-(benzylamino)-2-oxoethyl]phenyl}sulfonyl)hexahydro-2H-thieno[2,3-c]pyrrol-2-yl]prop-2-enamide 4-{[2-(acryloylamino)hexahydro-5H-thieno[2,3-c]pyrrol-5-yl]sulfonyl}-N-(4-tert-butylbenzyl)benzamide 4-{[2-(acryloylamino)hexahydro-5H-thieno[2,3-c]pyrrol-5-yl]sulfonyl}-N-(4-phenylbutyl)benzamide 4-{[2-(acryloylamino)hexahydro-5H-thieno[2,3-c]pyrrol-5-yl]sulfonyl}-N-[2-(4-chlorophenyl)ethyl]benzamide 4-{[2-(acryloylamino)hexahydro-5H-thieno[2,3-c]pyrrol-5-yl]sulfonyl}-N-[2-(quinolin-7-yl)ethyl]benzamide 4-{[2-(acryloylamino)hexahydro-5H-thieno[2,3-c]pyrrol-5-yl]sulfonyl}-N-[2-(naphthalen-2-yl)ethyl]benzamide 4-{[2-(acryloylamino)hexahydro-5H-thieno[2,3-c]pyrrol-5-yl]sulfonyl}-N-(3,4-dihydro-2H-chromen-6-ylmethyl)benzamide 4-{[2-(acryloylamino)hexahydro-5H-thieno[2,3-c]pyrrol-5-yl]sulfonyl}-N-[2-(4-tert-butylphenyl)ethyl]benzamide 4-{[2-(acryloylamino)hexahydro-5H-thieno[2,3-c]pyrrol-5-yl]sulfonyl}-N-[2-(biphenyl-4-yl)ethyl]benzamide 4-{[2-(acryloylamino)hexahydro-5H-thieno[2,3-c]pyrrol-5-yl]sulfonyl}-N-[2-(1,3-benzodioxol-5-yl)ethyl]benzamide 4-{[2-(acryloylamino)hexahydro-5H-thieno[2,3-c]pyrrol-5-yl]sulfonyl}-N-[(1R)-2-phenylcyclopropyl]benzamide benzyl(4-{[2-(acryloylamino)hexahydro-5H-thieno[2,3-c]pyrrol-5-yl]sulfonyl}phenyl)methylcarbamate 4-{[2-(acryloylamino)hexahydro-5H-thieno[2,3-c]pyrrol-5-yl]sulfonyl}-N-[2-(3,4-dimethoxyphenyl)ethyl]benzamide 4-{[2-(acryloylamino)hexahydro-5H-thieno[2,3-c]pyrrol-5-yl]sulfonyl}-N-{2-[4-(trifluoromethyl)phenyl]ethyl}benzamide 4-{[2-(acryloylamino)hexahydro-5H-thieno[2,3-c]pyrrol-5-yl]sulfonyl}-N-(2-phenylethyl)piperidine-1-carboxamide N-(4-{[2-(acryloylamino)hexahydro-5H-thieno[2,3-c]pyrrol-5-yl]sulfonyl}phenyl)furan-2-carboxamide N-{5-[(4-{[3-(tricyclo[3.3.1.1~3,7~]dec-1-yl)propanoyl]amino}phenyl)sulfonyl]hexahydro-2H-thieno[2,3-c]pyrrol-2-yl}prop-2-enamide 4-{[2-(acryloylamino)hexahydro-5H-thieno[2,3-c]pyrrol-5-yl]sulfonyl}-N-[2-(tricyclo[3.3.1.1~3,7~]dec-1-yl)ethyl]benzamide N-(5-{[1-(cyclopropylcarbonyl)-2,3-dihydro-1H-indol-5-yl]sulfonyl}hexahydro-2H-thieno[2,3-c]pyrrol-2-yl)prop-2-enamide N-[5-({2-chloro-4-[(3-phenylpropanoyl)amino]phenyl}sulfonyl)hexahydro-2H-thieno[2,3-c]pyrrol-2-yl]prop-2-enamide N-(4-{[2-(acryloylamino)hexahydro-5H-thieno[2,3-c]pyrrol-5-yl]sulfonyl}phenyl)-5,6-dihydro-4H-cyclopenta[b]thiophene-2-carboxamide N-(4-{[2-(acryloylamino)hexahydro-5H-thieno[2,3-c]pyrrol-5-yl]sulfonyl}phenyl)-4,5,6,7-tetrahydro-1H-indole-2-carboxamide N-[5-({2-methoxy-4-[(3-phenylpropanoyl)amino]phenyl}sulfonyl)hexahydro-2H-thieno[2,3-c]pyrrol-2-yl]prop-2-enamide N-(4-{[2-(acryloylamino)hexahydro-5H-thieno[2,3-c]pyrrol-5-yl]sulfonyl}phenyl)-5-(pyrrolidin-1-ylmethyl)furan-2-carboxamide N-(4-{[2-(acryloylamino)hexahydro-5H-thieno[2,3-c]pyrrol-5-yl]sulfonyl}phenyl)-1-benzothiophene-2-carboxamide N-(4-{[2-(acryloylamino)hexahydro-5H-thieno[2,3-c]pyrrol-5-yl]sulfonyl}phenyl)-3-methyl-1-benzofuran-2-carboxamide N-(4-{[2-(acryloylamino)hexahydro-5H-thieno[2,3-c]pyrrol-5-yl]sulfonyl}phenyl)-1H-indole-2-carboxamide 4-{[2-(acryloylamino)hexahydro-5H-thieno[2,3-c]pyrrol-5-yl]sulfonyl}-N-(tricyclo[3.3.1.1~3,7~]dec-1-ylmethyl)benzamide 4-{[2-(acryloylamino)hexahydro-5H-thieno[2,3-c]pyrrol-5-yl]sulfonyl}-N-(1,2,3,4-tetrahydronaphthalen-1-yl)benzamide N-(4-{[2-(acryloylamino)hexahydro-5H-thieno[2,3-c]pyrrol-5-yl]sulfonyl}phenyl)-4,5,6,7-tetrahydro-1-benzothiophene-2-carboxamide N-(4-{[2-(acryloylamino)hexahydro-5H-thieno[2,3-c]pyrrol-5-yl]sulfonyl}phenyl)-5-phenylfuran-2-carboxamide N-(4-{[2-(acryloylamino)hexahydro-5H-thieno[2,3-c]pyrrol-5-yl]sulfonyl}phenyl)-4-phenylthiophene-2-carboxamide N-[5-({5-[5-(trifluoromethyl)-1,2-oxazol-3-yl]thiophen-2-yl}sulfonyl)hexahydro-2H-thieno[2,3-c]pyrrol-2-yl]prop-2-enamide 5-{[2-(acryloylamino)hexahydro-5H-thieno[2,3-c]pyrrol-5-yl]sulfonyl}-N-(2-phenylethyl)furan-2-carboxamide N-{5-[(6-phenoxypyridin-3-yl)sulfonyl]hexahydro-2H-thieno[2,3-c]pyrrol-2-yl}prop-2-enamide N-(5-{[6-(morpholin-4-yl)pyridin-3-yl]sulfonyl}hexahydro-2H-thieno[2,3-c]pyrrol-2-yl)prop-2-enamide N-{5-[(6-phenylpyridin-3-yl)sulfonyl]hexahydro-2H-thieno[2,3-c]pyrrol-2-yl}prop-2-enamide N-[5-({3-chloro-4-[(3-phenylpropanoyl)amino]phenyl}sulfonyl)hexahydro-2H-thieno[2,3-c]pyrrol-2-yl]prop-2-enamide 4-{[2-(acryloylamino)hexahydro-5H-thieno[2,3-c]pyrrol-5-yl]sulfonyl}-2-fluoro-N-(2-phenylethyl)benzamide N-(5-{[5-(pyridin-2-yl)thiophen-2-yl]sulfonyl}hexahydro-2H-thieno[2,3-c]pyrrol-2-yl)prop-2-enamide 4-{[2-(acryloylamino)hexahydro-5H-thieno[2,3-c]pyrrol-5-yl]sulfonyl}-2-methoxy-N-(2-phenylethyl)benzamide N-[5-(1,3-benzothiazol-6-ylsulfonyl)hexahydro-2H-thieno[2,3-c]pyrrol-2-yl]prop-2-enamide N-{5-[(4-methyl-2-phenyl-1,3-thiazol-5-yl)sulfonyl]hexahydro-2H-thieno[2,3-c]pyrrol-2-yl}prop-2-enamide N-(5-{[5-(2-methyl-1,3-thiazol-4-yl)thiophen-2-yl]sulfonyl}hexahydro-2H-thieno[2,3-c]pyrrol-2-yl)prop-2-enamide N-(5-{[5-(1,2-oxazol-5-yl)thiophen-2-yl]sulfonyl}hexahydro-2H-thieno[2,3-c]pyrrol-2-yl)prop-2-enamide N-[5-(2,3-dihydro-1,4-benzodioxin-6-ylsulfonyl)hexahydro-2H-thieno[2,3-c]pyrrol-2-yl]prop-2-enamide 5-{[2-(acryloylamino)hexahydro-5H-thieno[2,3-c]pyrrol-5-yl]sulfonyl}-N-(2-phenylethyl)furan-3-carboxamide N-[5-({4-[(phenylacetyl)amino]benzyl}sulfonyl)hexahydro-2H-thieno[2,3-c]pyrrol-2-yl]prop-2-enamide N-(5-{[4-(morpholin-4-ylsulfonyl)phenyl]sulfonyl}hexahydro-2H-thieno[2,3-c]pyrrol-2-yl)prop-2-enamide N-(5-{[5-(1,3-oxazol-5-yl)thiophen-2-yl]
sulfonyl}hexahydro-2H-thieno[2,3-c]pyrrol-2-yl)prop-2-enamide
4-{[2-(acryloylamino)hexahydro-5H-thieno[2,3-c]pyrrol-5-yl]sulfonyl}-2-methyl-N-(2-phenylethyl)benzamide
N-{5-[(4-phenoxyphenyl)sulfonyl]hexahydro-2H-thieno[2,3-c]pyrrol-2-yl}prop-2-enamide
N-[5-({4-[(6-methylpyrazin-2-yl)oxy]phenyl}sulfonyl)hexahydro-2H-thieno[2,3-c]pyrrol-2-yl]prop-2-enamide
N-[5-({3-[(6-methylpyrazin-2-yl)oxy]phenyl}sulfonyl)hexahydro-2H-thieno[2,3-c]pyrrol-2-yl]prop-2-enamide
5-{[2-(acryloylamino)hexahydro-5H-thieno[2,3-c]pyrrol-5-yl]sulfonyl}-1-methyl-N-(2-phenylethyl)-1H-pyrrole-2-carboxamide
N-(5-{[4-(isoquinolin-3-ylamino)phenyl]
sulfonyl}hexahydro-2H-thieno[2,3-c]pyrrol-2-yl)prop-2-enamide
N-{5-[(3-chloro-4-methylphenyl)sulfonyl]hexahydro-2H-thieno[2,3-c]pyrrol-2-yl}prop-2-enamide
N-(5-{[5-(1,2-oxazol-5-yl)furan-2-yl]sulfonyl}hexahydro-2H-thieno[2,3-c]pyrrol-2-yl)prop-2-enamide
N-{5-[(4-{[3-chloro-5-(trifluoromethyl)pyridin-2-yl]oxy}phenyl)sulfonyl]hexahydro-2H-thieno[2,3-c]pyrrol-2-yl}prop-2-enamide
N-(5-{[4-(1H-pyrazol-1-yl)phenyl]sulfonyl}hexahydro-2H-thieno[2,3-c]pyrrol-2-yl)prop-2-enamide
N-{5-[(4-methoxy-3-methylphenyl)sulfonyl]hexahydro-2H-thieno[2,3-c]pyrrol-2-yl}prop-2-enamide
N-(5-{[6-(2-phenylethoxy)pyridin-3-yl]
sulfonyl}hexahydro-2H-thieno[2,3-c]pyrrol-2-yl)prop-2-enamide
N-[5-({5-[(acetylamino)methyl]thiophen-2-yl}sulfonyl)hexahydro-2H-thieno[2,3-c]pyrrol-2-yl]prop-2-enamide
N-{5-[(5-methyl-1-phenyl-1H-pyrazol-4-yl)sulfonyl]hexahydro-2H-thieno[2,3-c]pyrrol-2-yl}prop-2-enamide
N-(5-{[4-(1-methyl-1H-pyrazol-5-yl)phenyl]
sulfonyl}hexahydro-2H-thieno[2,3-c]pyrrol-2-yl)prop-2-enamide
N-(5-{[3-(1-methyl-1H-pyrazol-5-yl)phenyl]
sulfonyl}hexahydro-2H-thieno[2,3-c]pyrrol-2-yl)prop-2-enamide
N-{5-[(2,2-dimethyl-3,4-dihydro-2H-chromen-6-yl)sulfonyl]hexahydro-2H-thieno[2,3-c]pyrrol-2-yl}prop-2-enamide
N-{5-[(5-phenylthiophen-2-yl)sulfonyl]hexahydro-2H-thieno[2,3-c]pyrrol-2-yl}prop-2-enamide
N-(5-{[4-(cyclopentyloxy)phenyl]sulfonyl}hexahydro-2H-thieno[2,3-c]pyrrol-2-yl)prop-2-enamide
N-(5-{[5-(pyrrolidin-1-ylcarbonyl)-1H-pyrrol-3-yl]
sulfonyl}hexahydro-2H-thieno[2,3-c]pyrrol-2-yl)prop-2-enamide
N-(5-{[4-(2-methyl-1,3-thiazol-4-yl)phenyl]
sulfonyl}hexahydro-2H-thieno[2,3-c]pyrrol-2-yl)prop-2-enamide
N-(5-{[4-(pyridin-2-yloxy)phenyl]sulfonyl}hexahydro-2H-thieno[2,3-c]pyrrol-2-yl)prop-2-enamide
N-{5-[(2-oxo-1,2,3,4-tetrahydroquinolin-6-yl)sulfonyl]hexahydro-2H-thieno[2,3-c]pyrrol-2-yl}prop-2-enamide
N-{5-[(4-cyclohexylphenyl)sulfonyl]-5,6-dihydro-4H-furo[2,3-c]pyrrol-2-yl}prop-2-enamide
N-(4-{[2-(acryloylamino)-4,6-dihydro-5H-furo[2,3-c]pyrrol-5-yl]sulfonyl}phenyl)cyclopropanecarboxamide
N-(4-{[2-(acryloylamino)-4,6-dihydro-5H-furo[2,3-c]pyrrol-5-yl]sulfonyl}phenyl)tricyclo[3.3.1.1~3,7~]decane-1-carboxamide
benzyl(4-{[2-(acryloylamino)-4,6-dihydro-5H-furo[2,3-c]pyrrol-5-yl]sulfonyl}phenyl)carbamate
N-(5-{[4-(piperidin-1-ylcarbonyl)phenyl]sulfonyl}-5,6-dihydro-4H-furo[2,3-c]pyrrol-2-yl)prop-2-enamide
benzyl 4-{[2-(acryloylamino)-4,6-dihydro-5H-furo[2,3-c]pyrrol-5-yl]sulfonyl}piperidine-1-carboxylate
N-{5-[(4-nitrophenyl)sulfonyl]-5,6-dihydro-4H-furo[2,3-c]pyrrol-2-yl}prop-2-enamide
N-(4-{[2-(acryloylamino)-4,6-dihydro-5H-furo[2,3-c]pyrrol-5-yl]sulfonyl}phenyl)tetrahydro-2H-pyran-4-carboxamide
N-[5-({4-[(3-phenylpropanoyl)amino]phenyl}sulfonyl)-5,6-dihydro-4H-furo[2,3-c]pyrrol-2-yl]prop-2-enamide
N-(4-{[2-(acryloylamino)-4,6-dihydro-5H-furo[2,3-c]pyrrol-5-yl]sulfonyl}phenyl)-2-phenylcyclopropanecarboxamide
N-(4-{[2-(acryloylamino)-4,6-dihydro-5H-furo[2,3-c]pyrrol-5-yl]sulfonyl}phenyl)-N-methyltetrahydro-2H-pyran-4-carboxamide
4-{[2-(acryloylamino)-4,6-dihydro-5H-furo[2,3-c]pyrrol-5-yl]sulfonyl}-N-benzyl-N-methylbenzamide
4-{[2-(acryloylamino)-4,6-dihydro-5H-furo[2,3-c]pyrrol-5-yl]sulfonyl}-N-(cyclopropylmethyl)benzamide
N-(5-{[3-(piperidin-1-ylcarbonyl)phenyl]sulfonyl}-5,6-dihydro-4H-furo[2,3-c]pyrrol-2-yl)prop-2-enamide
N-(4-{[2-(acryloylamino)-4,6-dihydro-5H-furo[2,3-c]pyrrol-5-yl]sulfonyl}phenyl)-N-methylcyclopropanecarboxamide
N-{5-[(4-{[4-(6-methylpyridin-2-yl)piperazin-1-yl]
carbonyl}phenyl)sulfonyl]-5,6-dihydro-4H-furo[2,3-c]pyrrol-2-yl}prop-2-enamide
4-{[2-(acryloylamino)-4,6-dihydro-5H-furo[2,3-c]pyrrol-5-yl]sulfonyl}-N-[2-(morpholin-4-yl)ethyl]benzamide
4-{[2-(acryloylamino)-4,6-dihydro-5H-furo[2,3-c]pyrrol-5-yl]sulfonyl}-N-(2-phenylethyl)benzamide
4-{[2-(acryloylamino)-4,6-dihydro-5H-furo[2,3-c]pyrrol-5-yl]sulfonyl}-N-methyl-N-(2-phenylethyl)benzamide
N-(5-{[4-(3,4-dihydroisoquinolin-2(1H)-ylcarbonyl)phenyl]sulfonyl}-5,6-dihydro-4H-furo[2,3-c]pyrrol-2-yl)prop-2-enamide
4-{[2-(acryloylamino)-4,6-dihydro-5H-furo[2,3-c]pyrrol-5-yl]sulfonyl}-N-(2-cyclohexylethyl)benzamide
4-{[2-(acryloylamino)-4,6-dihydro-5H-furo[2,3-c]pyrrol-5-yl]sulfonyl}-N-cyclohexylbenzamide
N-{5-[(4-{[4-(pyrrolidin-1-ylcarbonyl)piperidin-1-yl]
carbonyl}phenyl)sulfonyl]-5,6-dihydro-4H-furo[2,3-c]pyrrol-2-yl}prop-2-enamide
4-{[2-(acryloylamino)-4,6-dihydro-5H-furo[2,3-c]pyrrol-5-yl]sulfonyl}-N-(3,5-dimethylbenzyl)benzamide
4-{[2-(acryloylamino)-4,6-dihydro-5H-furo[2,3-c]pyrrol-5-yl]sulfonyl}-N-benzylbenzamide
4-{[2-(acryloylamino)-4,6-dihydro-5H-furo[2,3-c]pyrrol-5-yl]sulfonyl}-N-(3,4-difluorobenzyl)benzamide
4-{[2-(acryloylamino)-4,6-dihydro-5H-furo[2,3-c]pyrrol-5-yl]sulfonyl}-N-[4-(trifluoromethyl)benzyl]benzamide
4-{[2-(acryloylamino)-4,6-dihydro-5H-furo[2,3-c]pyrrol-5-yl]sulfonyl}-N-(naphthalen-1-ylmethyl)benzamide
4-{[2-(acryloylamino)-4,6-dihydro-5H-furo[2,3-c]pyrrol-5-yl]sulfonyl}-N-[2-(3,4-dimethylphenyl)ethyl]benzamide
4-{[2-(acryloylamino)-4,6-dihydro-5H-furo[2,3-c]pyrrol-5-yl]sulfonyl}-N-[2-(4-methoxyphenyl)ethyl]benzamide
4-{[2-(acryloylamino)-4,6-dihydro-5H-furo[2,3-c]pyrrol-5-yl]sulfonyl}-N-(2,3-dihydro-1H-inden-2-yl)benzamide
4-{[2-(acryloylamino)-4,6-dihydro-5H-furo[2,3-c]pyrrol-5-yl]sulfonyl}-N-[2-(3-methylphenyl)ethyl]benzamide
N-[5-({4-[(acetylamino)methyl]phenyl}sulfonyl)-5,6-dihydro-4H-furo[2,3-c]pyrrol-2-yl]prop-2-enamide N-{5-[(4-{[3-(naphthalen-1-yl)propanoyl]amino}phenyl)sulfonyl]-5,6-dihydro-4H-furo[2,3-c]pyrrol-2-yl}prop-2-enamide N-[5-({4-[(3-cyclohexylpropanoyl)amino]phenyl}sulfonyl)-5,6-dihydro-4H-furo[2,3-c]pyrrol-2-yl]prop-2-enamide N-{5-[(1-benzoylpiperidin-4-yl)sulfonyl]-5,6-dihydro-4H-furo[2,3-c]pyrrol-2-yl}prop-2-enamide N-(5-{[1-(piperidin-1-ylcarbonyl)piperidin-4-yl]sulfonyl}-5,6-dihydro-4H-furo[2,3-c]pyrrol-2-yl)prop-2-enamide N-(5-{[1-(pyridin-2-ylcarbonyl)piperidin-4-yl]sulfonyl}-5,6-dihydro-4H-furo[2,3-c]pyrrol-2-yl)prop-2-enamide N-(4-{[2-(acryloylamino)-4,6-dihydro-5H-furo[2,3-c]pyrrol-5-yl]sulfonyl}phenyl)-4-tert-butylcyclohexanecarboxamide N-(4-{[2-(acryloylamino)-4,6-dihydro-5H-furo[2,3-c]pyrrol-5-yl]sulfonyl}phenyl)-1-benzofuran-2-carboxamide benzyl(3-{[2-(acryloylamino)-4,6-dihydro-5H-furo[2,3-c]pyrrol-5-yl]sulfonyl}phenyl)carbamate N-[5-({3-[(3-phenylpropanoyl)amino]phenyl}sulfonyl)-5,6-dihydro-4H-furo[2,3-c]pyrrol-2-yl]prop-2-enamide N-(3-{[2-(acryloylamino)-4,6-dihydro-5H-furo[2,3-c]pyrrol-5-yl]sulfonyl}phenyl)tetrahydro-2H-pyran-4-carboxamide 4-{[2-(acryloylamino)-4,6-dihydro-5H-furo[2,3-c]pyrrol-5-yl]sulfonyl}-N-(3-phenylpropyl)benzamide 4-{[2-(acryloylamino)-4,6-dihydro-5H-furo[2,3-c]pyrrol-5-yl]sulfonyl}-N-[2-(3-chlorophenyl)ethyl]benzamide 4-{[2-(acryloylamino)-4,6-dihydro-5H-furo[2,3-c]pyrrol-5-yl]sulfonyl}-N-[2-(2-methoxyphenyl)ethyl]benzamide 4-{[2-(acryloylamino)-4,6-dihydro-5H-furo[2,3-c]pyrrol-5-yl]sulfonyl}-N-[2-(2,3-dihydro-1-benzofuran-7-yl)ethyl]benzamide 4-{[2-(acryloylamino)-4,6-dihydro-5H-furo[2,3-c]pyrrol-5-yl]sulfonyl}-N-[2-(tetrahydro-2H-pyran-4-yl)ethyl]benzamide 4-{[2-(acryloylamino)-4,6-dihydro-5H-furo[2,3-c]pyrrol-5-yl]sulfonyl}-N-[2-(4,4-difluoropiperidin-1-yl)ethyl]benzamide N-[5-({1-[3-(trifluoromethyl)benzoyl]piperidin-4-yl}sulfonyl)-5,6-dihydro-4H-furo[2,3-c]pyrrol-2-yl]prop-2-enamide N-(5-{[1-(3-phenylpropanoyl)piperidin-4-yl]sulfonyl}-5,6-dihydro-4H-furo[2,3-c]pyrrol-2-yl)prop-2-enamide N-[5-({4-[2-(benzylamino)-2-oxoethyl]phenyl}sulfonyl)-5,6-dihydro-4H-furo[2,3-c]pyrrol-2-yl]prop-2-enamide 4-{[2-(acryloylamino)-4,6-dihydro-5H-furo[2,3-c]pyrrol-5-yl]sulfonyl}-N-(4-tert-butylbenzyl)benzamide 4-{[2-(acryloylamino)-4,6-dihydro-5H-furo[2,3-c]pyrrol-5-yl]sulfonyl}-N-(4-phenylbutyl)benzamide 4-{[2-(acryloylamino)-4,6-dihydro-5H-furo[2,3-c]pyrrol-5-yl]sulfonyl}-N-[2-(4-chlorophenyl)ethyl]benzamide 4-{[2-(acryloylamino)-4,6-dihydro-5H-furo[2,3-c]pyrrol-5-yl]sulfonyl}-N-[2-(quinolin-7-yl)ethyl]benzamide 4-{[2-(acryloylamino)-4,6-dihydro-5H-furo[2,3-c]pyrrol-5-yl]sulfonyl}-N-[2-(naphthalen-2-yl)ethyl]benzamide 4-{[2-(acryloylamino)-4,6-dihydro-5H-furo[2,3-c]pyrrol-5-yl]sulfonyl}-N-(3,4-dihydro-2H-chromen-6-ylmethyl)benzamide 4-{[2-(acryloylamino)-4,6-dihydro-5H-furo[2,3-c]pyrrol-5-yl]sulfonyl}-N-[2-(4-tert-butylphenyl)ethyl]benzamide 4-{[2-(acryloylamino)-4,6-dihydro-5H-furo[2,3-c]pyrrol-5-yl]sulfonyl}-N-[2-(biphenyl-4-yl)ethyl]benzamide 4-{[2-(acryloylamino)-4,6-dihydro-5H-furo[2,3-c]pyrrol-5-yl]sulfonyl}-N-[2-(1,3-benzodioxol-5-yl)ethyl]benzamide 4-{[2-(acryloylamino)-4,6-dihydro-5H-furo[2,3-c]pyrrol-5-yl]sulfonyl}-N-[(1R)-2-phenylcyclopropyl]benzamide benzyl(4-{[2-(acryloylamino)-4,6-dihydro-5H-furo[2,3-c]pyrrol-5-yl]sulfonyl}phenyl)methylcarbamate 4-{[2-(acryloylamino)-4,6-dihydro-5H-furo[2,3-c]pyrrol-5-yl]sulfonyl}-N-[2-(3,4-dimethoxyphenyl)ethyl]benzamide 4-{[2-(acryloylamino)-4,6-dihydro-5H-furo[2,3-c]pyrrol-5-yl]sulfonyl}-N-{2-[4-(trifluoromethyl)phenyl]ethyl}benzamide 4-{[2-(acryloylamino)-4,6-dihydro-5H-furo[2,3-c]pyrrol-5-yl]sulfonyl}-N-(2-phenylethyl)piperidine-1-carboxamide N-(4-{[2-(acryloylamino)-4,6-dihydro-5H-furo[2,3-c]pyrrol-5-yl]sulfonyl}phenyl)furan-2-carboxamide N-{5-[(4-{[3-(tricyclo[3.3.1.1~3,7~]dec-1-yl)propanoyl]amino}phenyl)sulfonyl]-5,6-dihydro-4H-furo[2,3-c]pyrrol-2-yl}prop-2-enamide 4-{[2-(acryloylamino)-4,6-dihydro-5H-furo[2,3-c]pyrrol-5-yl]sulfonyl}-N-[2-(tricyclo[3.3.1.1~3,7~]dec-1-yl)ethyl]benzamide N-(5-{[1-(cyclopropylcarbonyl)-2,3-dihydro-1H-indol-5-yl]sulfonyl}-5,6-dihydro-4H-furo[2,3-c]pyrrol-2-yl)prop-2-enamide N-[5-({2-chloro-4-[(3-phenylpropanoyl)amino]phenyl}sulfonyl)-5,6-dihydro-4H-furo[2,3-c]pyrrol-2-yl]prop-2-enamide N-(4-{[2-(acryloylamino)-4,6-dihydro-5H-furo[2,3-c]pyrrol-5-yl]sulfonyl}phenyl)-5,6-dihydro-4H-cyclopenta[b]thiophene-2-carboxamide N-(4-{[2-(acryloylamino)-4,6-dihydro-5H-furo[2,3-c]pyrrol-5-yl]sulfonyl}phenyl)-4,5,6,7-tetrahydro-1H-indole-2-carboxamide N-[5-({2-methoxy-4-[(3-phenylpropanoyl)amino]phenyl}sulfonyl)-5,6-dihydro-4H-furo[2,3-c]pyrrol-2-yl]prop-2-enamide N-(4-{[2-(acryloylamino)-4,6-dihydro-5H-furo[2,3-c]pyrrol-5-yl]sulfonyl}phenyl)-5-(pyrrolidin-1-ylmethyl)furan-2-carboxamide N-(4-{[2-(acryloylamino)-4,6-dihydro-5H-furo[2,3-c]pyrrol-5-yl]sulfonyl}phenyl)-1-benzothiophene-2-carboxamide N-(4-{[2-(acryloylamino)-4,6-dihydro-5H-furo[2,3-c]pyrrol-5-yl]sulfonyl}phenyl)-3-methyl-1-benzofuran-2-carboxamide N-(4-{[2-(acryloylamino)-4,6-dihydro-5H-furo[2,3-c]pyrrol-5-yl]sulfonyl}phenyl)-1H-indole-2-carboxamide 4-{[2-(acryloylamino)-4,6-dihydro-5H-furo[2,3-c]pyrrol-5-yl]sulfonyl}-N-(tricyclo[3.3.1.1~3,7~]dec-1-ylmethyl)benzamide 4-{[2-(acryloylamino)-4,6-dihydro-5H-furo[2,3-c]pyrrol-5-yl]sulfonyl}-N-(1,2,3,4-tetrahydronaphthalen-1-yl)benzamide N-(4-{[2-(acryloylamino)-4,6-dihydro-5H-furo[2,3-c]pyrrol-5-yl]sulfonyl}phenyl)-4,5,6,7-tetrahydro-1-benzothiophene-2-carboxamide N-(4-{[2-(acryloylamino)-4,6-dihydro-5H-furo[2,3-c]pyrrol-5-yl]sulfonyl}phenyl)-5-phenylfuran-2-carboxamide N-(4-{[2-(acryloylamino)-4,6-dihydro-5H-furo[2,3-c]pyrrol-5-yl]sulfonyl}phenyl)-4-phenylthiophene-2-carboxamide N-[5-({5-[5-(trifluoromethyl)-1,2-oxazol-3-yl]thiophen-2-yl}sulfonyl)-5,6-dihydro-4H-furo[2,3-c]pyrrol-2-yl]prop-2-enamide 5-{[2-(acryloylamino)-4,6-dihydro-5H-furo[2,3-c]pyrrol-5-yl]sulfonyl}-N-(2-phenylethyl)furan-2-carboxamide N-{5-[(6-phenoxypyridin-3-yl)sulfonyl]-5,6-dihydro-4H-furo[2,3-c]pyrrol-2-yl}prop-2-enamide N-(5-{[6-(morpholin-4-yl)pyridin-3-yl]sulfonyl}-5,6-dihydro-4H-furo[2,3-c]pyrrol-2-yl)prop-2-enamide N-{5-[(6-phenylpyridin-3-yl)sulfonyl]-5,6-dihydro-4H-furo[2,3-c]pyrrol-2-yl}prop-2-enamide N-[5-({3-chloro-4-[(3-phenylpropanoyl)amino]phenyl}sulfonyl)-5,6-dihydro-4H-furo[2,3-c]pyrrol-2-yl]prop-2-enamide 4-{[2-(acryloylamino)-4,6-dihydro-5H-furo[2,3-c]pyrrol-5-yl]sulfonyl}-2-fluoro-N-(2-phenylethyl)benzamide N-(5-{[5-(pyridin-2-yl)thiophen-2-yl]sulfonyl}-5,6-dihydro-4H-furo[2,3-c]pyrrol-2-yl)prop-2-enamide 4-{[2-(acryloylamino)-4,6-dihydro-5H-furo[2,3-c]pyrrol-5-yl]sulfonyl}-2-methoxy-N-(2-phenylethyl)benzamide N-[5-(1,3-benzothiazol-6-ylsulfonyl)-5,6-dihydro-4H-furo[2,3-c]pyrrol-2-yl]prop-2-enamide N-{5-[(4-methyl-2-phenyl-1,3-thiazol-5-yl)sulfonyl]-5,6-dihydro-4H-furo[2,3-c]pyrrol-2-yl}prop-2-enamide N-(5-{[5-(2-methyl-1,3-thiazol-4-yl)thiophen-2-yl]sulfonyl}-5,6-dihydro-4H-furo[2,3-c]pyrrol-2-yl)prop-2-enamide N-(5-{[5-(1,2-oxazol-5-yl)thiophen-2-yl]sulfonyl}-5,6-dihydro-4H-furo[2,3-c]pyrrol-2-yl)prop-2-enamide N-[5-(2,3-dihydro-1,4-benzodioxin-6-ylsulfonyl)-5,6-dihydro-4H-furo[2,3-c]pyrrol-2-yl]prop-2-enamide 5-{[2-(acryloylamino)-4,6-dihydro-5H-furo[2,3-c]pyrrol-5-yl]sulfonyl}-N-(2-phenylethyl)furan-3-carboxamide N-[5-({4-[(phenylacetyl)amino]benzyl}sulfonyl)-5,6-dihydro-4H-furo[2,3-c]pyrrol-2-yl]prop-2-enamide N-(5-{[4-(morpholin-4-ylsulfonyl)phenyl]sulfonyl}-5,6-dihydro-4H-furo[2,3-c]pyrrol-2-yl)prop-2-enamide N-(5-{[5-(1,3-oxazol-5-yl)thiophen-2-yl]sulfonyl}-5,6-dihydro-4H-furo[2,3-c]pyrrol-2-yl)prop-2-enamide 4-{[2-(acryloylamino)-4,6-dihydro-5H-furo[2,3-c]pyrrol-5-yl]sulfonyl}-2-methyl-N-(2-phenylethyl)benzamide N-{5-[(4-phenoxyphenyl)sulfonyl]-5,6-dihydro-4H-furo[2,3-c]pyrrol-2-yl}prop-2-enamide N-[5-({4-[(6-methylpyrazin-2-yl)oxy]phenyl}sulfonyl)-5,6-dihydro-4H-furo[2,3-c]pyrrol-2-yl]prop-2-enamide N-[5-({3-[(6-methylpyrazin-2-yl)oxy]phenyl}sulfonyl)-5,6-dihydro-4H-furo[2,3-c]pyrrol-2-yl]prop-2-enamide 5-{[2-(acryloylamino)-4,6-dihydro-5H-furo[2,3-c]pyrrol-5-yl]sulfonyl}-1-methyl-N-(2-phenylethyl)-1H-pyrrole-2-carboxamide N-(5-{[4-(isoquinolin-3-ylamino)phenyl]sulfonyl}-5,6-dihydro-4H-furo[2,3-c]pyrrol-2-yl)prop-2-enamide N-{5-[(3-chloro-4-methylphenyl)sulfonyl]-5,6-dihydro-4H-furo[2,3-c]pyrrol-2-yl}prop-2-enamide N-(5-{[5-(1,2-oxazol-5-yl)furan-2-yl]sulfonyl}-5,6-dihydro-4H-furo[2,3-c]pyrrol-2-yl)prop-2-enamide N-{5-[(4-{[3-chloro-5-(trifluoromethyl)pyridin-2-yl]oxy}phenyl)sulfonyl]-5,6-dihydro-4H-furo[2,3-c]pyrrol-2-yl}prop-2-enamide N-(5-{[4-(1H-pyrazol-1-yl)phenyl]sulfonyl}-5,6-dihydro-4H-furo[2,3-c]pyrrol-2-yl)prop-2-enamide N-{5-[(4-methoxy-3-methylphenyl)sulfonyl]-5,6-dihydro-4H-furo[2,3-c]pyrrol-2-yl}prop-2-enamide N-(5-{[6-(2-phenylethoxy)pyridin-3-yl]sulfonyl}-5,6-dihydro-4H-furo[2,3-c]pyrrol-2-yl)prop-2-enamide N-[5-({5-[(acetylamino)methyl]thiophen-2-yl}sulfonyl)-5,6-dihydro-4H-furo[2,3-c]pyrrol-2-yl]prop-2-enamide N-{5-[(5-methyl-1-phenyl-1H-pyrazol-4-yl)sulfonyl]-5,6-dihydro-4H-furo[2,3-c]pyrrol-2-yl}prop-2-enamide N-(5-{[4-(1-methyl-1H-pyrazol-5-yl)phenyl]sulfonyl}-5,6-dihydro-4H-furo[2,3-c]pyrrol-2-yl)prop-2-enamide N-(5-{[3-(1-methyl-1H-pyrazol-5-yl)phenyl]sulfonyl}-5,6-dihydro-4H-furo[2,3-c]pyrrol-2-yl)prop-2-enamide N-{5-[(2,2-dimethyl-3,4-dihydro-2H-chromen-6-yl)sulfonyl]-5,6-dihydro-4H-furo[2,3-c]pyrrol-2-yl}prop-2-enamide N-{5-[(5-phenylthiophen-2-yl)sulfonyl]-5,6-dihydro-4H-furo[2,3-c]pyrrol-2-yl}prop-2-enamide N-(5-{[4-(cyclopentyloxy)phenyl]sulfonyl}-5,6-dihydro-4H-furo[2,3-c]pyrrol-2-yl)prop-2-enamide N-(5-{[5-(pyrrolidin-1-ylcarbonyl)-1H-pyrrol-3-yl]sulfonyl}-5,6-dihydro-4H-furo[2,3-c]pyrrol-2-yl)prop-2-enamide N-(5-{[4-(2-methyl-1,3-thiazol-4-yl)phenyl]sulfonyl}-5,6-dihydro-4H-furo[2,3-c]pyrrol-2-yl)prop-2-enamide N-(5-{[4-(pyridin-2-yloxy)phenyl]sulfonyl}-5,6-dihydro-4H-furo[2,3-c]pyrrol-2-yl)prop-2-enamide N-{5-[(2-oxo-1,2,3,4-tetrahydroquinolin-6-yl)sulfonyl]-5,6-dihydro-4H-furo[2,3-c]pyrrol-2-yl}prop-2-enamide N-{5-[(4-cyclohexylphenyl)sulfonyl]-5,6-dihydro-4H-thieno[2,3-c]pyrrol-2-yl}prop-2-enamide N-(4-{[2-(acryloylamino)-4,6-dihydro-5H-thieno[2,3-c]pyrrol-5-yl]sulfonyl}phenyl)cyclopropanecarboxamide N-(4-{[2-(acryloylamino)-4,6-dihydro-5H-thieno[2,3-c]pyrrol-5-yl]sulfonyl}phenyl)tricyclo[3.3.1.1~3,7~]decane-1-carboxamide benzyl(4-{[2-(acryloylamino)-4,6-dihydro-5H-thieno[2,3-c]pyrrol-5-yl]sulfonyl}phenyl)carbamate N-(5-{[4-(piperidin-1-ylcarbonyl)phenyl]sulfonyl}-5,6-dihydro-4H-thieno[2,3-c]pyrrol-2-yl)prop-2-enamide benzyl 4-{[2-(acryloylamino)-4,6-dihydro-5H-thieno[2,3-c]pyrrol-5-yl]sulfonyl}piperidine-1-carboxylate N-{5-[(4-nitrophenyl)sulfonyl]-5,6-dihydro-4H-thieno[2,3-c]pyrrol-2-yl}prop-2-enamide N-(4-{[2-(acryloylamino)-4,6-dihydro-5H-thieno[2,3-c]pyrrol-5-yl]sulfonyl}phenyl)tetrahydro-2H-pyran-4-carboxamide N-[5-({4-[(3-phenylpropanoyl)amino]phenyl}sulfonyl)-5,6-dihydro-4H-thieno[2,3-c]pyrrol-2-yl]prop-2-enamide N-(4-{[2-(acryloylamino)-4,6-dihydro-5H-thieno[2,3-c]pyrrol-5-yl]sulfonyl}phenyl)-2-phenylcyclopropanecarboxamide N-(4-{[2-(acryloylamino)-4,6-dihydro-5H-thieno[2,3-c]pyrrol-5-yl]sulfonyl}phenyl)-N-methyltetrahydro-2H-pyran-4-carboxamide 4-{[2-(acryloylamino)-4,6-dihydro-5H-thieno[2,3-c]pyrrol-5-yl]sulfonyl}-N-benzyl-N-methylbenzamide 4-{[2-(acryloylamino)-4,6-dihydro-5H-thieno[2,3-c]pyrrol-5-yl]sulfonyl}-N-(cyclopropylmethyl)benzamide N-(5-{[3-(piperidin-1-ylcarbonyl)phenyl]sulfonyl}-5,6-dihydro-4H-thieno[2,3-c]pyrrol-2-yl)prop-2-enamide N-(4-{[2-(acryloylamino)-4,6-dihydro-5H-thieno[2,3-c]pyrrol-5-yl]sulfonyl}phenyl)-N-methylcyclopropanecarboxamide N-{5-[(4-{[4-(6-methylpyridin-2-yl)piperazin-1-yl]carbonyl}phenyl)sulfonyl]-5,6-dihydro-4H-thieno[2,3-c]pyrrol-2-yl}prop-2-enamide 4-{[2-(acryloylamino)-4,6-dihydro-5H-thieno[2,3-c]pyrrol-5-yl]sulfonyl}-N-[2-(morpholin-4-yl)ethyl]benzamide 4-{[2-(acryloylamino)-4,6-dihydro-5H-thieno[2,3-c]pyrrol-5-yl]sulfonyl}-N-(2-phenylethyl)benzamide 4-{[2-(acryloylamino)-4,6-dihydro-5H-thieno[2,3-c]pyrrol-5-yl]sulfonyl}-N-methyl-N-(2-phenylethyl)benzamide N-(5-{[4-(3,4-dihydroisoquinolin-2(1H)-ylcarbonyl)phenyl]sulfonyl}-5,6-dihydro-4H-thieno[2,3-c]pyrrol-2-yl)prop-2-enamide 4-{[2-(acryloylamino)-4,6-dihydro-5H-thieno[2,3-c]pyrrol-5-yl]sulfonyl}-N-(2-cyclohexylethyl)benzamide 4-{[2-(acryloylamino)-4,6-dihydro-5H-thieno[2,3-c]pyrrol-5-yl]sulfonyl}-N-cyclohexylbenzamide N-{5-[(4-{[4-(pyrrolidin-1-ylcarbonyl)piperidin-1-yl]carbonyl}phenyl)sulfonyl]-5,6-dihydro-4H-thieno[2,3-c]pyrrol-2-yl}prop-2-enamide 4-{[2-(acryloylamino)-4,6-dihydro-5H-thieno[2,3-c]pyrrol-5-yl]sulfonyl}-N-(3,5-dimethylbenzyl)benzamide 4-{[2-(acryloylamino)-4,6-dihydro-5H-thieno[2,3-c]pyrrol-5-yl]sulfonyl}-N-benzylbenzamide 4-{[2-(acryloylamino)-4,6-dihydro-5H-thieno[2,3-c]pyrrol-5-yl]sulfonyl}-N-(3,4-difluorobenzyl)benzamide 4-{[2-(acryloylamino)-4,6-dihydro-5H-thieno[2,3-c]pyrrol-5-yl]sulfonyl}-N-[4-(trifluoromethyl)benzyl]benzamide 4-{[2-(acryloylamino)-4,6-dihydro-5H-thieno[2,3-c]pyrrol-5-yl]sulfonyl}-N-(naphthalen-1-ylmethyl)benzamide 4-{[2-(acryloylamino)-4,6-dihydro-5H-thieno[2,3-c]pyrrol-5-yl]sulfonyl}-N-[2-(3,4-dimethylphenyl)ethyl]benzamide 4-{[2-(acryloylamino)-4,6-dihydro-5H-thieno[2,3-c]pyrrol-5-yl]sulfonyl}-N-[2-(4-methoxyphenyl)ethyl]benzamide 4-{[2-(acryloylamino)-4,6-dihydro-5H-thieno[2,3-c]pyrrol-5-yl]sulfonyl}-N-(2,3-dihydro-1H-inden-2-yl)benzamide 4-{[2-(acryloylamino)-4,6-dihydro-5H-thieno[2,3-c]pyrrol-5-yl]sulfonyl}-N-[2-(3-methylphenyl)ethyl]benzamide N-[5-({4-[(acetylamino)methyl]phenyl}sulfonyl)-5,6-dihydro-4H-thieno[2,3-c]pyrrol-2-yl]prop-2-enamide N-{5-[(4-{[3-(naphthalen-1-yl)propanoyl]amino}phenyl)sulfonyl]-5,6-dihydro-4H-thieno[2,3-c]pyrrol-2-yl}prop-2-enamide N-[5-({4-[(3-cyclohexylpropanoyl)amino]phenyl}sulfonyl)-5,6-dihydro-4H-thieno[2,3-c]pyrrol-2-yl]prop-2-enamide N-{5-[(1-benzoylpiperidin-4-yl)sulfonyl]-5,6-dihydro-4H-thieno[2,3-c]pyrrol-2-yl}prop-2-en amide N-(5-{[1-(piperidin-1-ylcarbonyl)piperidin-4-yl]sulfonyl}-5,6-dihydro-4H-thieno[2,3-c]pyrrol-2-yl)prop-2-enamide N-(5-{[1-(pyridin-2-ylcarbonyl)piperidin-4-yl]sulfonyl}-5,6-dihydro-4H-thieno[2,3-c]pyrrol-2-yl)prop-2-enamide N-(4-{[2-(acryloylamino)-4,6-dihydro-5H-thieno[2,3-c]pyrrol-5-yl]sulfonyl}phenyl)-4-tert-butylcyclohexanecarboxamide N-(4-{[2-(acryloylamino)-4,6-dihydro-5H-thieno[2,3-c]pyrrol-5-yl]sulfonyl}phenyl)-1-benzofuran-2-carboxamide benzyl(3-{[2-(acryloylamino)-4,6-dihydro-5H-thieno[2,3-c]pyrrol-5-yl]sulfonyl}phenyl)carbamate N-[5-({3-[(3-phenylpropanoyl)amino]phenyl}sulfonyl)-5,6-dihydro-4H-thieno[2,3-c]pyrrol-2-yl]prop-2-enamide N-(3-{[2-(acryloylamino)-4,6-dihydro-5H-thieno[2,3-c]pyrrol-5-yl]sulfonyl}phenyl)tetrahydro-2H-pyran-4-carboxamide 4-{[2-(acryloylamino)-4,6-dihydro-5H-thieno[2,3-c]pyrrol-5-yl]sulfonyl}-N-(3-phenylpropyl)benzamide 4-{[2-(acryloylamino)-4,6-dihydro-5H-thieno[2,3-c]pyrrol-5-yl]sulfonyl}-N-[2-(3-chlorophenyl)ethyl]benzamide 4-{[2-(acryloylamino)-4,6-dihydro-5H-thieno[2,3-c]pyrrol-5-yl]sulfonyl}-N-[2-(2-methoxyphenyl)ethyl]benzamide 4-{[2-(acryloylamino)-4,6-dihydro-5H-thieno[2,3-c]pyrrol-5-yl]sulfonyl}-N-[2-(2,3-dihydro-1-benzofuran-7-yl)ethyl]benzamide 4-{[2-(acryloylamino)-4,6-dihydro-5H-thieno[2,3-c]pyrrol-5-yl]sulfonyl}-N-[2-(tetrahydro-2H-pyran-4-yl)ethyl]benzamide 4-{[2-(acryloylamino)-4,6-dihydro-5H-thieno[2,3-c]pyrrol-5-yl]sulfonyl}-N-[2-(4,4-difluoropiperidin-1-yl)ethyl]benzamide N-[5-({1-[3-(trifluoromethyl)benzoyl]piperidin-4-yl}sulfonyl)-5,6-dihydro-4H-thieno[2,3-c]pyrrol-2-yl]prop-2-enamide N-(5-{[1-(3-phenylpropanoyl)piperidin-4-yl]sulfonyl}-5,6-dihydro-4H-thieno[2,3-c]pyrrol-2-yl)prop-2-enamide N-[5-({4-[2-(benzylamino)-2-oxoethyl]phenyl}sulfonyl)-5,6-dihydro-4H-thieno[2,3-c]pyrrol-2-yl]prop-2-enamide 4-{[2-(acryloylamino)-4,6-dihydro-5H-thieno[2,3-c]pyrrol-5-yl]sulfonyl}-N-(4-tert-butylbenzyl)benzamide 4-{[2-(acryloylamino)-4,6-dihydro-5H-thieno[2,3-c]pyrrol-5-yl]sulfonyl}-N-(4-phenylbutyl)benzamide 4-{[2-(acryloylamino)-4,6-dihydro-5H-thieno[2,3-c]pyrrol-5-yl]sulfonyl}-N-[2-(4-chlorophenyl)ethyl]benzamide 4-{[2-(acryloylamino)-4,6-dihydro-5H-thieno[2,3-c]pyrrol-5-yl]sulfonyl}-N-[2-(quinolin-7-yl)ethyl]benzamide 4-{[2-(acryloylamino)-4,6-dihydro-5H-thieno[2,3-c]pyrrol-5-yl]sulfonyl}-N-[2-(naphthalen-2-yl)ethyl]benzamide 4-{[2-(acryloylamino)-4,6-dihydro-5H-thieno[2,3-c]pyrrol-5-yl]sulfonyl}-N-(3,4-dihydro-2H-chromen-6-ylmethyl)benzamide 4-{[2-(acryloylamino)-4,6-dihydro-5H-thieno[2,3-c]pyrrol-5-yl]sulfonyl}-N-[2-(4-tert-butylphenyl)ethyl]benzamide 4-{[2-(acryloylamino)-4,6-dihydro-5H-thieno[2,3-c]pyrrol-5-yl]sulfonyl}-N-[2-(biphenyl-4-yl)ethyl]benzamide 4-{[2-(acryloylamino)-4,6-dihydro-5H-thieno[2,3-c]pyrrol-5-yl]sulfonyl}-N-[2-(1,3-benzodioxol-5-yl)ethyl]benzamide 4-{[2-(acryloylamino)-4,6-dihydro-5H-thieno[2,3-c]pyrrol-5-yl]sulfonyl}-N-[(1R)-2-phenylcyclopropyl]benzamide benzyl(4-{[2-(acryloylamino)-4,6-dihydro-5H-thieno[2,3-c]pyrrol-5-yl]sulfonyl}phenyl)methylcarbamate 4-{[2-(acryloylamino)-4,6-dihydro-5H-thieno[2,3-c]pyrrol-5-yl]sulfonyl}-N-[2-(3,4-dimethoxyphenyl)ethyl]benzamide 4-{[2-(acryloylamino)-4,6-dihydro-5H-thieno[2,3-c]pyrrol-5-yl]sulfonyl}-N-{2-[4-(trifluoromethyl)phenyl]ethyl}benzamide 4-{[2-(acryloylamino)-4,6-dihydro-5H-thieno[2,3-c]pyrrol-5-yl]sulfonyl}-N-(2-phenylethyl)piperidine-1-carboxamide N-(4-{[2-(acryloylamino)-4,6-dihydro-5H-thieno[2,3-c]pyrrol-5-yl]sulfonyl}phenyl)furan-2-carboxamide N-{5-[(4-{[3-(tricyclo[3.3.1.1~3,7~]dec-1-yl)propanoyl]amino}phenyl)sulfonyl]-5,6-dihydro-4H-thieno[2,3-c]pyrrol-2-yl}prop-2-enamide 4-{[2-(acryloylamino)-4,6-dihydro-5H-thieno[2,3-c]pyrrol-5-yl]sulfonyl}-N-[2-(tricyclo[3.3.1.1~3,7~]dec-1-yl)ethyl]benzamide N-(5-{[1-(cyclopropylcarbonyl)-2,3-dihydro-1H-indol-5-yl]sulfonyl}-5,6-dihydro-4H-thieno[2,3-c]pyrrol-2-yl)prop-2-enamide N-[5-({2-chloro-4-[(3-phenylpropanoyl)amino]phenyl}sulfonyl)-5,6-dihydro-4H-thieno[2,3-c]pyrrol-2-yl]prop-2-enamide N-(4-{[2-(acryloylamino)-4,6-dihydro-5H-thieno[2,3-c]pyrrol-5-yl]sulfonyl}phenyl)-5,6-dihydro-4H-cyclopenta[b]thiophene-2-carboxamide N-(4-{[2-(acryloylamino)-4,6-dihydro-5H-thieno[2,3-c]pyrrol-5-yl]sulfonyl}phenyl)-4,5,6,7-tetrahydro-1H-indole-2-carboxamide N-[5-({2-methoxy-4-[(3-phenylpropanoyl)amino]phenyl}sulfonyl)-5,6-dihydro-4H-thieno[2,3-c]pyrrol-2-yl]prop-2-enamide N-(4-{[2-(acryloylamino)-4,6-dihydro-5H-thieno[2,3-c]pyrrol-5-yl]sulfonyl}phenyl)-5-(pyrrolidin-1-ylmethyl)furan-2-carboxamide N-(4-{[2-(acryloylamino)-4,6-dihydro-5H-thieno[2,3-c]pyrrol-5-yl]sulfonyl}phenyl)-1-benzothiophene-2-carboxamide N-(4-{[2-(acryloylamino)-4,6-dihydro-5H-thieno[2,3-c]pyrrol-5-yl]sulfonyl}phenyl)-3-methyl-1-benzofuran-2-carboxamide
N-(4-{[2-(acryloylamino)-4,6-dihydro-5H-thieno[2,3-c]pyrrol-5-yl]sulfonyl}phenyl)-1H-indole-2-carboxamide
4-{[2-(acryloylamino)-4,6-dihydro-5H-thieno[2,3-c]pyrrol-5-yl]sulfonyl}-N-(tricyclo[3.3.1.1~3,7~]dec-1-ylmethyl)benzamide
4-{[2-(acryloylamino)-4,6-dihydro-5H-thieno[2,3-c]pyrrol-5-yl]sulfonyl}-N-(1,2,3,4-tetrahydronaphthalen-1-yl)benzamide
N-(4-{[2-(acryloylamino)-4,6-dihydro-5H-thieno[2,3-c]pyrrol-5-yl]sulfonyl}phenyl)-4,5,6,7-tetrahydro-1-benzothiophene-2-carboxamide
N-(4-{[2-(acryloylamino)-4,6-dihydro-5H-thieno[2,3-c]pyrrol-5-yl]sulfonyl}phenyl)-5-phenylfuran-2-carboxamide
N-(4-{[2-(acryloylamino)-4,6-dihydro-5H-thieno[2,3-c]pyrrol-5-yl]sulfonyl}phenyl)-4-phenylthiophene-2-carboxamide
N-[5-({5-[5-(trifluoromethyl)-1,2-oxazol-3-yl]thiophen-2-yl}sulfonyl)-5,6-dihydro-4H-thieno[2,3-c]pyrrol-2-yl]prop-2-enamide
5-{[2-(acryloylamino)-4,6-dihydro-5H-thieno[2,3-c]pyrrol-5-yl]sulfonyl}-N-(2-phenylethyl)furan-2-carboxamide
N-{5-[(6-phenoxypyridin-3-yl)sulfonyl]-5,6-dihydro-4H-thieno[2,3-c]pyrrol-2-yl}prop-2-enamide
N-(5-{[6-(morpholin-4-yl)pyridin-3-yl]sulfonyl}-5,6-dihydro-4H-thieno[2,3-c]pyrrol-2-yl)prop-2-enamide
N-{5-[(6-phenylpyridin-3-yl)sulfonyl]-5,6-dihydro-4H-thieno[2,3-c]pyrrol-2-yl}prop-2-enamide
N-[5-({3-chloro-4-[(3-phenylpropanoyl)amino]phenyl}sulfonyl)-5,6-dihydro-4H-thieno[2,3-c]pyrrol-2-yl]prop-2-enamide
4-{[2-(acryloylamino)-4,6-dihydro-5H-thieno[2,3-c]pyrrol-5-yl]sulfonyl}-2-fluoro-N-(2-phenylethyl)benzamide
N-(5-{[5-(pyridin-2-yl)thiophen-2-yl]sulfonyl}-5,6-dihydro-4H-thieno[2,3-c]pyrrol-2-yl)prop-2-enamide
4-{[2-(acryloylamino)-4,6-dihydro-5H-thieno[2,3-c]pyrrol-5-yl]sulfonyl}-2-methoxy-N-(2-phenylethyl)benzamide
N-[5-(1,3-benzothiazol-6-ylsulfonyl)-5,6-dihydro-4H-thieno[2,3-c]pyrrol-2-yl]prop-2-enamide
N-{5-[(4-methyl-2-phenyl-1,3-thiazol-5-yl)sulfonyl]-5,6-dihydro-4H-thieno[2,3-c]pyrrol-2-yl}prop-2-enamide
N-(5-{[5-(2-methyl-1,3-thiazol-4-yl)thiophen-2-yl]sulfonyl}-5,6-dihydro-4H-thieno[2,3-c]pyrrol-2-yl)prop-2-enamide
N-(5-{[5-(1,2-oxazol-5-yl)thiophen-2-yl]sulfonyl}-5,6-dihydro-4H-thieno[2,3-c]pyrrol-2-yl)prop-2-enamide
N-[5-(2,3-dihydro-1,4-benzodioxin-6-ylsulfonyl)-5,6-dihydro-4H-thieno[2,3-c]pyrrol-2-yl]prop-2-enamide
5-{[2-(acryloylamino)-4,6-dihydro-5H-thieno[2,3-c]pyrrol-5-yl]sulfonyl}-N-(2-phenylethyl)furan-3-carboxamide
N-[5-({4-[(phenylacetyl)amino]benzyl}sulfonyl)-5,6-dihydro-4H-thieno[2,3-c]pyrrol-2-yl]prop-2-enamide
N-(5-{[4-(morpholin-4-ylsulfonyl)phenyl]sulfonyl}-5,6-dihydro-4H-thieno[2,3-c]pyrrol-2-yl)prop-2-enamide
N-(5-{[5-(1,3-oxazol-5-yl)thiophen-2-yl]sulfonyl}-5,6-dihydro-4H-thieno[2,3-c]pyrrol-2-yl)prop-2-enamide
4-{[2-(acryloylamino)-4,6-dihydro-5H-thieno[2,3-c]pyrrol-5-yl]sulfonyl}-2-methyl-N-(2-phenylethyl)benzamide
N-{5-[(4-phenoxyphenyl)sulfonyl]-5,6-dihydro-4H-thieno[2,3-c]pyrrol-2-yl}prop-2-enamide
N-[5-({4-[(6-methylpyrazin-2-yl)oxy]phenyl}sulfonyl)-5,6-dihydro-4H-thieno[2,3-c]pyrrol-2-yl]prop-2-enamide
N-[5-({3-[(6-methylpyrazin-2-yl)oxy]phenyl}sulfonyl)-5,6-dihydro-4H-thieno[2,3-c]pyrrol-2-yl]prop-2-enamide
5-{[2-(acryloylamino)-4,6-dihydro-5H-thieno[2,3-c]pyrrol-5-yl]sulfonyl}-1-methyl-N-(2-phenylethyl)-1H-pyrrole-2-carboxamide
N-(5-{[4-(isoquinolin-3-ylamino)phenyl]sulfonyl}-5,6-dihydro-4H-thieno[2,3-c]pyrrol-2-yl)prop-2-enamide
N-{5-[(3-chloro-4-methylphenyl)sulfonyl]-5,6-dihydro-4H-thieno[2,3-c]pyrrol-2-yl}prop-2-enamide
N-(5-{[5-(1,2-oxazol-5-yl)furan-2-yl]sulfonyl}-5,6-dihydro-4H-thieno[2,3-c]pyrrol-2-yl)prop-2-enamide
N-{5-[(4-{[3-chloro-5-(trifluoromethyl)pyridin-2-yl]oxy}phenyl)sulfonyl]-5,6-dihydro-4H-thieno[2,3-c]pyrrol-2-yl}prop-2-enamide
N-(5-{[4-(1H-pyrazol-1-yl)phenyl]sulfonyl}-5,6-dihydro-4H-thieno[2,3-c]pyrrol-2-yl)prop-2-enamide
N-{5-[(4-methoxy-3-methylphenyl)sulfonyl]-5,6-dihydro-4H-thieno[2,3-c]pyrrol-2-yl}prop-2-enamide
N-(5-{[6-(2-phenylethoxy)pyridin-3-yl]sulfonyl}-5,6-dihydro-4H-thieno[2,3-c]pyrrol-2-yl)prop-2-enamide
N-[5-({5-[(acetylamino)methyl]thiophen-2-yl}sulfonyl)-5,6-dihydro-4H-thieno[2,3-c]pyrrol-2-yl]prop-2-enamide
N-{5-[(5-methyl-1-phenyl-1H-pyrazol-4-yl)sulfonyl]-5,6-dihydro-4H-thieno[2,3-c]pyrrol-2-yl}prop-2-enamide
N-(5-{[4-(1-methyl-1H-pyrazol-5-yl)phenyl]sulfonyl}-5,6-dihydro-4H-thieno[2,3-c]pyrrol-2-yl)prop-2-enamide
N-(5-{[3-(1-methyl-1H-pyrazol-5-yl)phenyl]sulfonyl}-5,6-dihydro-4H-thieno[2,3-c]pyrrol-2-yl)prop-2-enamide
N-{5-[(2,2-dimethyl-3,4-dihydro-2H-chromen-6-yl)sulfonyl]-5,6-dihydro-4H-thieno[2,3-c]pyrrol-2-yl}prop-2-enamide
N-{5-[(5-phenylthiophen-2-yl)sulfonyl]-5,6-dihydro-4H-thieno[2,3-c]pyrrol-2-yl}prop-2-enamide
N-(5-{[4-(cyclopentyloxy)phenyl]sulfonyl}-5,6-dihydro-4H-thieno[2,3-c]pyrrol-2-yl)prop-2-enamide
N-(5-{[5-(pyrrolidin-1-ylcarbonyl)-1H-pyrrol-3-yl]sulfonyl}-5,6-dihydro-4H-thieno[2,3-c]pyrrol-2-yl)prop-2-enamide
N-(5-{[4-(2-methyl-1,3-thiazol-4-yl)phenyl]sulfonyl}-5,6-dihydro-4H-thieno[2,3-c]pyrrol-2-yl)prop-2-enamide
N-(5-{[4-(pyridin-2-yloxy)phenyl]sulfonyl}-5,6-dihydro-4H-thieno[2,3-c]pyrrol-2-yl)prop-2-enamide
N-{5-[(2-oxo-1,2,3,4-tetrahydroquinolin-6-yl)sulfonyl]-5,6-dihydro-4H-thieno[2,3-c]pyrrol-2-yl}prop-2-enamide
N-{1-[(4-cyclohexylphenyl)sulfonyl]-2,2,5,5-tetramethylpyrrolidin-3-yl}prop-2-enamide
N-(4-{[3-(acryloylamino)-2,2,5,5-tetramethylpyrrolidin-1-yl]sulfonyl}phenyl)cyclopropanecarboxamide
N-(4-{[3-(acryloylamino)-2,2,5,5-tetramethylpyrrolidin-1-yl]sulfonyl}phenyl)tricyclo[3.3.1.1~3,7~]decane-1-carboxamide
benzyl(4-{[3-(acryloylamino)-2,2,5,5-tetramethylpyrrolidin-1-yl]sulfonyl}phenyl)carbamate
N-(2,2,5,5-tetramethyl-1-{[4-(piperidin-1-ylcarbonyl)phenyl]sulfonyl}pyrrolidin-3-yl)prop-2-enamide
benzyl 4-{[3-(acryloylamino)-2,2,5,5-tetramethylpyrrolidin-1-yl]sulfonyl}piperidine-1-carboxylate
N-{2,2,5,5-tetramethyl-1-[(4-nitrophenyl)sulfonyl]pyrrolidin-3-yl}prop-2-enamide
N-(4-{[3-(acryloylamino)-2,2,5,5-tetramethylpyrrolidin-1-yl]sulfonyl}phenyl)tetrahydro-2H-pyran-4-carboxamide
N-[2,2,5,5-tetramethyl-1-({4-[(3-phenylpropanoyl)amino]phenyl}sulfonyl)pyrrolidin-3-yl]prop-2-enamide
N-(4-{[3-(acryloylamino)-2,2,5,5-tetramethylpyrrolidin-1-yl]sulfonyl}phenyl)-2-phenylcyclopropanecarboxamide
N-(4-{[3-(acryloylamino)-2,2,5,5-tetramethylpyrrolidin-1-yl]sulfonyl}phenyl)-N-methyltetrahydro-2H-pyran-4-carboxamide 4-{[3-(acryloylamino)-2,2,5,5-tetramethylpyrrolidin-1-yl]sulfonyl}-N-benzyl-N-methylbenzamide
4-{[3-(acryloylamino)-2,2,5,5-tetramethylpyrrolidin-1-yl]sulfonyl}-N-(cyclopropylmethyl)benzamide
N-(2,2,5,5-tetramethyl-1-{[3-(piperidin-1-ylcarbonyl)phenyl]sulfonyl}pyrrolidin-3-yl)prop-2-enamide
N-(4-{[3-(acryloylamino)-2,2,5,5-tetramethylpyrrolidin-1-yl]sulfonyl}phenyl)-N-methylcyclopropanecarboxamide
N-{2,2,5,5-tetramethyl-1-[(4-{[4-(6-methylpyridin-2-yl)piperazin-1-yl]carbonyl}phenyl)sulfonyl]pyrrolidin-3-yl}prop-2-enamide
4-{[3-(acryloylamino)-2,2,5,5-tetramethylpyrrolidin-1-yl]sulfonyl}-N-[2-(morpholin-4-yl)ethyl]benzamide
4-{[3-(acryloylamino)-2,2,5,5-tetramethylpyrrolidin-1-yl]sulfonyl}-N-(2-phenylethyl)benzamide
4-{[3-(acryloylamino)-2,2,5,5-tetramethylpyrrolidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}-2,2,5,5-tetramethylpyrrolidin-3-yl)prop-2-enamide
4-{[3-(acryloylamino)-2,2,5,5-tetramethylpyrrolidin-1-yl]sulfonyl}-N-(2-cyclohexylethyl)benzamide
4-{[3-(acryloylamino)-2,2,5,5-tetramethylpyrrolidin-1-yl]sulfonyl}-N-cyclohexylbenzamide
N-{2,2,5,5-tetramethyl-1-[(4-{[4-(pyrrolidin-1-ylcarbonyl)piperidin-1-yl]carbonyl}phenyl)sulfonyl]pyrrolidin-3-yl}prop-2-enamide
4-{[3-(acryloylamino)-2,2,5,5-tetramethylpyrrolidin-1-yl]sulfonyl}-N-(3,5-dimethylbenzyl)benzamide
4-{[3-(acryloylamino)-2,2,5,5-tetramethylpyrrolidin-1-yl]sulfonyl}-N-benzylbenzamide
4-{[3-(acryloylamino)-2,2,5,5-tetramethylpyrrolidin-1-yl]sulfonyl}-N-(3,4-difluorobenzyl)benzamide
4-{[3-(acryloylamino)-2,2,5,5-tetramethylpyrrolidin-1-yl]sulfonyl}-N-[4-(trifluoromethyl)benzyl]benzamide
4-{[3-(acryloylamino)-2,2,5,5-tetramethylpyrrolidin-1-yl]sulfonyl}-N-(naphthalen-1-ylmethyl)benzamide
4-{[3-(acryloylamino)-2,2,5,5-tetramethylpyrrolidin-1-yl]sulfonyl}-N-[2-(3,4-dimethylphenyl)ethyl]benzamide
4-{[3-(acryloylamino)-2,2,5,5-tetramethylpyrrolidin-1-yl]sulfonyl}-N-[2-(4-methoxyphenyl)ethyl]benzamide
4-{[3-(acryloylamino)-2,2,5,5-tetramethylpyrrolidin-1-yl]sulfonyl}-N-(2,3-dihydro-1H-inden-2-yl)benzamide
4-{[3-(acryloylamino)-2,2,5,5-tetramethylpyrrolidin-1-yl]sulfonyl}-N-[2-(3-methylphenyl)ethyl]benzamide
N-[1-({4-[(acetylamino)methyl]phenyl}sulfonyl)-2,2,5,5-tetramethylpyrrolidin-3-yl]prop-2-enamide
N-{2,2,5,5-tetramethyl-1-[(4-{[3-(naphthalen-1-yl)propanoyl]amino}phenyl)sulfonyl]pyrrolidin-3-yl}prop-2-enamide
N-[1-({4-[(3-cyclohexylpropanoyl)amino]phenyl}sulfonyl)-2,2,5,5-tetramethylpyrrolidin-3-yl]prop-2-enamide
N-{1-[(1-benzoylpiperidin-4-yl)sulfonyl]-2,2,5,5-tetramethylpyrrolidin-3-yl}prop-2-enamide
N-(2,2,5,5-tetramethyl-1-{[1-(piperidin-1-ylcarbonyl)piperidin-4-yl]sulfonyl}pyrrolidin-3-yl)prop-2-enamide
N-(2,2,5,5-tetramethyl-1-{[1-(pyridin-2-ylcarbonyl)piperidin-4-yl]sulfonyl}pyrrolidin-3-yl)prop-2-enamide
N-(4-{[3-(acryloylamino)-2,2,5,5-tetramethylpyrrolidin-1-yl]sulfonyl}phenyl)-4-tert-butylcyclohexanecarboxamide
N-(4-{[3-(acryloylamino)-2,2,5,5-tetramethylpyrrolidin-1-yl]sulfonyl}phenyl)-1-benzofuran-2-carboxamide
benzyl(3-{[3-(acryloylamino)-2,2,5,5-tetramethylpyrrolidin-1-yl]sulfonyl}phenyl)carbamate
N-[2,2,5,5-tetramethyl-1-({3-[(3-phenylpropanoyl)amino]phenyl}sulfonyl)pyrrolidin-3-yl]prop-2-enamide
N-(3-{[3-(acryloylamino)-2,2,5,5-tetramethylpyrrolidin-1-yl]sulfonyl}phenyl)tetrahydro-2H-pyran-4-carboxamide
4-{[3-(acryloylamino)-2,2,5,5-tetramethylpyrrolidin-1-yl]sulfonyl}-N-(3-phenylpropyl)benzamide
4-{[3-(acryloylamino)-2,2,5,5-tetramethylpyrrolidin-1-yl]sulfonyl}-N-[2-(3-chlorophenyl)ethyl]benzamide
4-{[3-(acryloylamino)-2,2,5,5-tetramethylpyrrolidin-1-yl]sulfonyl}-N-[2-(2-methoxyphenyl)ethyl]benzamide
4-{[3-(acryloylamino)-2,2,5,5-tetramethylpyrrolidin-1-yl]sulfonyl}-N-[2-(2,3-dihydro-1-benzofuran-7-yl)ethyl]benzamide
4-{[3-(acryloylamino)-2,2,5,5-tetramethylpyrrolidin-1-yl]sulfonyl}-N-[2-(tetrahydro-2H-pyran-4-yl)ethyl]benzamide
4-{[3-(acryloylamino)-2,2,5,5-tetramethylpyrrolidin-1-yl]sulfonyl}-N-[2-(4,4-difluoropiperidin-1-yl)ethyl]benzamide
N-[2,2,5,5-tetramethyl-1-({1-[3-(trifluoromethyl)benzoyl]piperidin-4-yl}sulfonyl)pyrrolidin-3-yl]prop-2-enamide
N-(2,2,5,5-tetramethyl-1-{[1-(3-phenylpropanoyl)piperidin-4-yl]sulfonyl}pyrrolidin-3-yl)prop-2-enamide
N-[1-({4-[2-(benzylamino)-2-oxoethyl]phenyl}sulfonyl)-2,2,5,5-tetramethylpyrrolidin-3-yl]prop-2-enamide
4-{[3-(acryloylamino)-2,2,5,5-tetramethylpyrrolidin-1-yl]sulfonyl}-N-(4-tert-butylbenzyl)benzamide
4-{[3-(acryloylamino)-2,2,5,5-tetramethylpyrrolidin-1-yl]sulfonyl}-N-(4-phenylbutyl)benzamide
4-{[3-(acryloylamino)-2,2,5,5-tetramethylpyrrolidin-1-yl]sulfonyl}-N-[2-(4-chlorophenyl)ethyl]benzamide
4-{[3-(acryloylamino)-2,2,5,5-tetramethylpyrrolidin-1-yl]sulfonyl}-N-[2-(quinolin-7-yl)ethyl]benzamide
4-{[3-(acryloylamino)-2,2,5,5-tetramethylpyrrolidin-1-yl]sulfonyl}-N-[2-(naphthalen-2-yl)ethyl]benzamide
4-{[3-(acryloylamino)-2,2,5,5-tetramethylpyrrolidin-1-yl]sulfonyl}-N-(3,4-dihydro-2H-chromen-6-ylmethyl)benzamide
4-{[3-(acryloylamino)-2,2,5,5-tetramethylpyrrolidin-1-yl]sulfonyl}-N-[2-(4-tert-butylphenyl)ethyl]benzamide
4-{[3-(acryloylamino)-2,2,5,5-tetramethylpyrrolidin-1-yl]sulfonyl}-N-[2-(biphenyl-4-yl)ethyl]benzamide
4-{[3-(acryloylamino)-2,2,5,5-tetramethylpyrrolidin-1-yl]sulfonyl}-N-[2-(1,3-benzodioxol-5-yl)ethyl]benzamide
4-{[3-(acryloylamino)-2,2,5,5-tetramethylpyrrolidin-1-yl]sulfonyl}-N-[(1R)-2-phenylcyclopropyl]benzamide
benzyl(4-{[3-(acryloylamino)-2,2,5,5-tetramethylpyrrolidin-1-yl]sulfonyl}phenyl)methylcarbamate
4-{[3-(acryloylamino)-2,2,5,5-tetramethylpyrrolidin-1-yl]sulfonyl}-N-[2-(3,4-dimethoxyphenyl)ethyl]benzamide
4-{[3-(acryloylamino)-2,2,5,5-tetramethylpyrrolidin-1-yl]sulfonyl}-N-{2-[4-(trifluoromethyl)phenyl]ethyl}benzamide
4-{[3-(acryloylamino)-2,2,5,5-tetramethylpyrrolidin-1-yl]sulfonyl}-N-(2-phenylethyl)piperidine-1-carboxamide
N-(4-{[3-(acryloylamino)-2,2,5,5-tetramethylpyrrolidin-1-yl]sulfonyl}phenyl)furan-2-carboxamide
N-{2,2,5,5-tetramethyl-1-[(4-{[3-(tricyclo[3.3.1.1~3,7~]dec-1-yl)propanoyl]amino}phenyl)sulfonyl]pyrrolidin-3-yl}prop-2-enamide
4-{[3-(acryloylamino)-2,2,5,5-tetramethylpyrrolidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}-2,2,5,5-tetramethylpyrrolidin-3-yl)prop-2-enamide
N-[1-({2-chloro-4-[(3-phenylpropanoyl)amino]phenyl}sulfonyl)-2,2,5,5-tetramethylpyrrolidin-3-yl]prop-2-enamide N-(4-{[3-(acryloylamino)-2,2,5,5-tetramethylpyrrolidin-1-yl]sulfonyl}phenyl)-5,6-dihydro-4H-cyclopenta[b]thiophene-2-carboxamide
N-(4-{[3-(acryloylamino)-2,2,5,5-tetramethylpyrrolidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)-2,2,5,5-tetramethylpyrrolidin-3-yl]prop-2-enamide
N-(4-{[3-(acryloylamino)-2,2,5,5-tetramethylpyrrolidin-1-yl]sulfonyl}phenyl)-5-(pyrrolidin-1-ylmethyl)furan-2-carboxamide
N-(4-{[3-(acryloylamino)-2,2,5,5-tetramethylpyrrolidin-1-yl]sulfonyl}phenyl)-1-benzothiophene-2-carboxamide
N-(4-{[3-(acryloylamino)-2,2,5,5-tetramethylpyrrolidin-1-yl]sulfonyl}phenyl)-3-methyl-1-benzofuran-2-carboxamide
N-(4-{[3-(acryloylamino)-2,2,5,5-tetramethylpyrrolidin-1-yl]sulfonyl}phenyl)-1H-indole-2-carboxamide
4-{[3-(acryloylamino)-2,2,5,5-tetramethylpyrrolidin-1-yl]sulfonyl}-N-(tricyclo[3.3.1.1~3,7~]dec-1-ylmethyl)benzamide
4-{[3-(acryloylamino)-2,2,5,5-tetramethylpyrrolidin-1-yl]sulfonyl}-N-(1,2,3,4-tetrahydronaphthalen-1-yl)benzamide
N-(4-{[3-(acryloylamino)-2,2,5,5-tetramethylpyrrolidin-1-yl]sulfonyl}phenyl)-4,5,6,7-tetrahydro-1-benzothiophene-2-carboxamide
N-(4-{[3-(acryloylamino)-2,2,5,5-tetramethylpyrrolidin-1-yl]sulfonyl}phenyl)-5-phenylfuran-2-carboxamide
N-(4-{[3-(acryloylamino)-2,2,5,5-tetramethylpyrrolidin-1-yl]sulfonyl}phenyl)-4-phenylthiophene-2-carboxamide
N-[2,2,5,5-tetramethyl-1-({5-[5-(trifluoromethyl)-1,2-oxazol-3-yl]thiophen-2-yl}sulfonyl)pyrrolidin-3-yl]prop-2-enamide
5-{[3-(acryloylamino)-2,2,5,5-tetramethylpyrrolidin-1-yl]sulfonyl}-N-(2-phenylethyl)furan-2-carboxamide
N-{2,2,5,5-tetramethyl-1-[(6-phenoxypyridin-3-yl)sulfonyl]pyrrolidin-3-yl}prop-2-enamide
N-(2,2,5,5-tetramethyl-1-{[6-(morpholin-4-yl)pyridin-3-yl]sulfonyl}pyrrolidin-3-yl)prop-2-enamide
N-{2,2,5,5-tetramethyl-1-[(6-phenylpyridin-3-yl)sulfonyl]pyrrolidin-3-yl}prop-2-enamide
N-[1-({3-chloro-4-[(3-phenylpropanoyl)amino]phenyl}sulfonyl)-2,2,5,5-tetramethylpyrrolidin-3-yl]prop-2-enamide
4-{[3-(acryloylamino)-2,2,5,5-tetramethylpyrrolidin-1-yl]sulfonyl}-2-fluoro-N-(2-phenylethyl)benzamide
N-(2,2,5,5-tetramethyl-1-{[5-(pyridin-2-yl)thiophen-2-yl]sulfonyl}pyrrolidin-3-yl)prop-2-enamide
4-{[3-(acryloylamino)-2,2,5,5-tetramethylpyrrolidin-1-yl]sulfonyl}-2-methoxy-N-(2-phenylethyl)benzamide
N-[1-(1,3-benzothiazol-6-ylsulfonyl)-2,2,5,5-tetramethylpyrrolidin-3-yl]prop-2-enamide
N-{2,2,5,5-tetramethyl-1-[(4-methyl-2-phenyl-1,3-thiazol-5-yl)sulfonyl]pyrrolidin-3-yl}prop-2-enamide
N-(2,2,5,5-tetramethyl-1-{[5-(2-methyl-1,3-thiazol-4-yl)thiophen-2-yl]sulfonyl}pyrrolidin-3-yl)prop-2-enamide
N-(2,2,5,5-tetramethyl-1-{[5-(1,2-oxazol-5-yl)thiophen-2-yl]sulfonyl}pyrrolidin-3-yl)prop-2-enamide
N-[1-(2,3-dihydro-1,4-benzodioxin-6-ylsulfonyl)-2,2,5,5-tetramethylpyrrolidin-3-yl]prop-2-enamide
5-{[3-(acryloylamino)-2,2,5,5-tetramethylpyrrolidin-1-yl]sulfonyl}-N-(2-phenylethyl)furan-3-carboxamide
N-[2,2,5,5-tetramethyl-1-({4-[(phenylacetyl)amino]benzyl}sulfonyl)pyrrolidin-3-yl]prop-2-enamide
N-(2,2,5,5-tetramethyl-1-{[4-(morpholin-4-ylsulfonyl)phenyl]sulfonyl}pyrrolidin-3-yl)prop-2-enamide
N-(2,2,5,5-tetramethyl-1-{[5-(1,3-oxazol-5-yl)thiophen-2-yl]sulfonyl}pyrrolidin-3-yl)prop-2-enamide
4-{[3-(acryloylamino)-2,2,5,5-tetramethylpyrrolidin-1-yl]sulfonyl}-2-methyl-N-(2-phenylethyl)benzamide
N-{2,2,5,5-tetramethyl-1-[(4-phenoxyphenyl)sulfonyl]pyrrolidin-3-yl}prop-2-enamide
N-[2,2,5,5-tetramethyl-1-({4-[(6-methylpyrazin-2-yl)oxy]phenyl}sulfonyl)pyrrolidin-3-yl]prop-2-enamide
N-[2,2,5,5-tetramethyl-1-({3-[(6-methylpyrazin-2-yl)oxy]phenyl}sulfonyl)pyrrolidin-3-yl]prop-2-enamide
5-{[3-(acryloylamino)-2,2,5,5-tetramethylpyrrolidin-1-yl]sulfonyl}-1-methyl-N-(2-phenylethyl)-1H-pyrrole-2-carboxamide
N-(1-{[4-(isoquinolin-3-ylamino)phenyl]sulfonyl}-2,2,5,5-tetramethylpyrrolidin-3-yl)prop-2-enamide
N-{1-[(3-chloro-4-methylphenyl)sulfonyl]-2,2,5,5-tetramethylpyrrolidin-3-yl}prop-2-enamide
N-(2,2,5,5-tetramethyl-1-{[5-(1,2-oxazol-5-yl)furan-2-yl]sulfonyl}pyrrolidin-3-yl)prop-2-enamide
N-{1-[(4-{[3-chloro-5-(trifluoromethyl)pyridin-2-yl]oxy}phenyl)sulfonyl]-2,2,5,5-tetramethylpyrrolidin-3-yl}prop-2-enamide
N-(2,2,5,5-tetramethyl-1-{[4-(1H-pyrazol-1-yl)phenyl]sulfonyl}pyrrolidin-3-yl)prop-2-enamide
N-{1-[(4-methoxy-3-methylphenyl)sulfonyl]-2,2,5,5-tetramethylpyrrolidin-3-yl}prop-2-enamide
N-(2,2,5,5-tetramethyl-1-{[6-(2-phenylethoxy)pyridin-3-yl]sulfonyl}pyrrolidin-3-yl)prop-2-enamide
N-[1-({5-[(acetylamino)methyl]thiophen-2-yl}sulfonyl)-2,2,5,5-tetramethylpyrrolidin-3-yl]prop-2-enamide
N-{2,2,5,5-tetramethyl-1-[(5-methyl-1-phenyl-1H-pyrazol-4-yl)sulfonyl]pyrrolidin-3-yl}prop-2-enamide
N-(2,2,5,5-tetramethyl-1-{[4-(1-methyl-1H-pyrazol-5-yl)phenyl]sulfonyl}pyrrolidin-3-yl)prop-2-enamide
N-(2,2,5,5-tetramethyl-1-{[3-(1-methyl-1H-pyrazol-5-yl)phenyl]sulfonyl}pyrrolidin-3-yl)prop-2-enamide
N-{1-[(2,2-dimethyl-3,4-dihydro-2H-chromen-6-yl)sulfonyl]-2,2,5,5-tetramethylpyrrolidin-3-yl}prop-2-enamide
N-{2,2,5,5-tetramethyl-1-[(5-phenylthiophen-2-yl)sulfonyl]pyrrolidin-3-yl}prop-2-enamide
N-(1-{[4-(cyclopentyloxy)phenyl]sulfonyl}-2,2,5,5-tetramethylpyrrolidin-3-yl)prop-2-enamide
N-(2,2,5,5-tetramethyl-1-{[5-(pyrrolidin-1-ylcarbonyl)-1H-pyrrol-3-yl]sulfonyl}pyrrolidin-3-yl)prop-2-enamide
N-(2,2,5,5-tetramethyl-1-{[4-(2-methyl-1,3-thiazol-4-yl)phenyl]sulfonyl}pyrrolidin-3-yl)prop-2-enamide
N-(2,2,5,5-tetramethyl-1-{[4-(pyridin-2-yloxy)phenyl]sulfonyl}pyrrolidin-3-yl)prop-2-enamide
N-{2,2,5,5-tetramethyl-1-[(2-oxo-1,2,3,4-tetrahydroquinolin-6-yl)sulfonyl]pyrrolidin-3-yl}prop-2-enamide
N-{1-[(4-cyclohexylphenyl)sulfonyl]-5-(hydroxymethyl)pyrrolidin-3-yl}prop-2-enamide
N-(4-{[4-(acryloylamino)-2-(hydroxymethyl)pyrrolidin-1-yl]sulfonyl}phenyl)cyclopropanecarboxamide
N-(4-{[4-(acryloylamino)-2-(hydroxymethyl)pyrrolidin-1-yl]sulfonyl}phenyl)tricyclo[3.3.1.1~3,7~]decane-1-carboxamide
benzyl(4-{[4-(acryloylamino)-2-(hydroxymethyl)pyrrolidin-1-yl]sulfonyl}phenyl)carbamate
N-[5-(hydroxymethyl)-1-{[4-(piperidin-1-ylcarbonyl)phenyl]sulfonyl}pyrrolidin-3-yl]prop-2-enamide
benzyl 4-{[4-(acryloylamino)-2-(hydroxymethyl)pyrrolidin-1-yl]sulfonyl}piperidine-1-carboxylate
N-{5-(hydroxymethyl)-1-[(4-nitrophenyl)sulfonyl]pyrrolidin-3-yl}prop-2-enamide N-(4-{[4-(acryloylamino)-2-(hydroxymethyl)pyrrolidin-1-yl]sulfonyl}phenyl)tetrahydro-2H-pyran-4-carboxamide
N-[5-(hydroxymethyl)-1-({4-[(3-phenylpropanoyl)amino]phenyl}sulfonyl)pyrrolidin-3-yl]prop-2-enamide
N-(4-{[4-(acryloylamino)-2-(hydroxymethyl)pyrrolidin-1-yl]sulfonyl}phenyl)-2-phenylcyclopropanecarboxamide
N-(4-{[4-(acryloylamino)-2-(hydroxymethyl)pyrrolidin-1-yl]sulfonyl}phenyl)-N-methyltetrahydro-2H-pyran-4-carboxamide
4-{[4-(acryloylamino)-2-(hydroxymethyl)pyrrolidin-1-yl]sulfonyl}-N-benzyl-N-methylbenzamide
4-{[4-(acryloylamino)-2-(hydroxymethyl)pyrrolidin-1-yl]sulfonyl}-N-(cyclopropylmethyl)benzamide
N-[5-(hydroxymethyl)-1-{[3-(piperidin-1-ylcarbonyl)phenyl]sulfonyl}pyrrolidin-3-yl]prop-2-enamide
N-(4-{[4-(acryloylamino)-2-(hydroxymethyl)pyrrolidin-1-yl]sulfonyl}phenyl)-N-methylcyclopropanecarboxamide
N-{5-(hydroxymethyl)-1-[(4-{[4-(6-methylpyridin-2-yl)piperazin-1-yl]carbonyl}phenyl)sulfonyl]pyrrolidin-3-yl}prop-2-enamide
4-{[4-(acryloylamino)-2-(hydroxymethyl)pyrrolidin-1-yl]sulfonyl}-N-[2-(morpholin-4-yl)ethyl]benzamide
4-{[4-(acryloylamino)-2-(hydroxymethyl)pyrrolidin-1-yl]sulfonyl}-N-(2-phenylethyl)benzamide
4-{[4-(acryloylamino)-2-(hydroxymethyl)pyrrolidin-1-yl]sulfonyl}-N-methyl-N-(2-phenylethyl)benzamide
N-[1-{[4-(3,4-dihydroisoquinolin-2(1H)-ylcarbonyl)phenyl]sulfonyl}-5-(hydroxymethyl)pyrrolidin-3-yl]prop-2-enamide
4-{[4-(acryloylamino)-2-(hydroxymethyl)pyrrolidin-1-yl]sulfonyl}-N-(2-cyclohexylethyl)benzamide
4-{[4-(acryloylamino)-2-(hydroxymethyl)pyrrolidin-1-yl]sulfonyl}-N-cyclohexylbenzamide
N-{5-(hydroxymethyl)-1-[(4-{[4-(pyrrolidin-1-ylcarbonyl)piperidin-1-yl]carbonyl}phenyl)sulfonyl]pyrrolidin-3-yl}prop-2-enamide
4-{[4-(acryloylamino)-2-(hydroxymethyl)pyrrolidin-1-yl]sulfonyl}-N-(3,5-dimethylbenzyl)benzamide
4-{[4-(acryloylamino)-2-(hydroxymethyl)pyrrolidin-1-yl]sulfonyl}-N-benzylbenzamide
4-{[4-(acryloylamino)-2-(hydroxymethyl)pyrrolidin-1-yl]sulfonyl}-N-(3,4-difluorobenzyl)benzamide
4-{[4-(acryloylamino)-2-(hydroxymethyl)pyrrolidin-1-yl]sulfonyl}-N-[4-(trifluoromethyl)benzyl]benzamide
4-{[4-(acryloylamino)-2-(hydroxymethyl)pyrrolidin-1-yl]sulfonyl}-N-(naphthalen-1-ylmethyl)benzamide
4-{[4-(acryloylamino)-2-(hydroxymethyl)pyrrolidin-1-yl]sulfonyl}-N-[2-(3,4-dimethylphenyl)ethyl]benzamide
4-{[4-(acryloylamino)-2-(hydroxymethyl)pyrrolidin-1-yl]sulfonyl}-N-[2-(4-methoxyphenyl)ethyl]benzamide
4-{[4-(acryloylamino)-2-(hydroxymethyl)pyrrolidin-1-yl]sulfonyl}-N-(2,3-dihydro-1H-inden-2-yl)benzamide
4-{[4-(acryloylamino)-2-(hydroxymethyl)pyrrolidin-1-yl]sulfonyl}-N-[2-(3-methylphenyl)ethyl]benzamide
N-[1-({4-[(acetylamino)methyl]phenyl}sulfonyl)-5-(hydroxymethyl)pyrrolidin-3-yl]prop-2-enamide
N-{5-(hydroxymethyl)-1-[(4-{[3-(naphthalen-1-yl)propanoyl]amino}phenyl)sulfonyl]pyrrolidin-3-yl}prop-2-enamide
N-[1-({4-[(3-cyclohexylpropanoyl)amino]phenyl}sulfonyl)-5-(hydroxymethyl)pyrrolidin-3-yl]prop-2-enamide
N-{1-[(1-benzoylpiperidin-4-yl)sulfonyl]-5-(hydroxymethyl)pyrrolidin-3-yl}prop-2-enamide
N-[5-(hydroxymethyl)-1-{[1-(piperidin-1-ylcarbonyl)piperidin-4-yl]sulfonyl}pyrrolidin-3-yl]prop-2-enamide
N-[5-(hydroxymethyl)-1-{[1-(pyridin-2-ylcarbonyl)piperidin-4-yl]sulfonyl}pyrrolidin-3-yl]prop-2-enamide
N-(4-{[4-(acryloylamino)-2-(hydroxymethyl)pyrrolidin-1-yl]sulfonyl}phenyl)-4-tert-butylcyclohexanecarboxamide
N-(4-{[4-(acryloylamino)-2-(hydroxymethyl)pyrrolidin-1-yl]sulfonyl}phenyl)-1-benzofuran-2-carboxamide
benzyl(3-{[4-(acryloylamino)-2-(hydroxymethyl)pyrrolidin-1-yl]sulfonyl}phenyl)carbamate
N-[5-(hydroxymethyl)-1-({3-[(3-phenylpropanoyl)amino]phenyl}sulfonyl)pyrrolidin-3-yl]prop-2-enamide
N-(3-{[4-(acryloylamino)-2-(hydroxymethyl)pyrrolidin-1-yl]sulfonyl}phenyl)tetrahydro-2H-pyran-4-carboxamide
4-{[4-(acryloylamino)-2-(hydroxymethyl)pyrrolidin-1-yl]sulfonyl}-N-(3-phenylpropyl)benzamide
4-{[4-(acryloylamino)-2-(hydroxymethyl)pyrrolidin-1-yl]sulfonyl}-N-[2-(3-chlorophenyl)ethyl]benzamide
4-{[4-(acryloylamino)-2-(hydroxymethyl)pyrrolidin-1-yl]sulfonyl}-N-[2-(2-methoxyphenyl)ethyl]benzamide
4-{[4-(acryloylamino)-2-(hydroxymethyl)pyrrolidin-1-yl]sulfonyl}-N-[2-(2,3-dihydro-1-benzofuran-7-yl)ethyl]benzamide
4-{[4-(acryloylamino)-2-(hydroxymethyl)pyrrolidin-1-yl]sulfonyl}-N-[2-(tetrahydro-2H-pyran-4-yl)ethyl]benzamide
4-{[4-(acryloylamino)-2-(hydroxymethyl)pyrrolidin-1-yl]sulfonyl}-N-[2-(4,4-difluoropiperidin-1-yl)ethyl]benzamide
N-[5-(hydroxymethyl)-1-({1-[3-(trifluoromethyl)benzoyl]piperidin-4-yl}sulfonyl)pyrrolidin-3-yl]prop-2-enamide
N-[5-(hydroxymethyl)-1-{[1-(3-phenylpropanoyl)piperidin-4-yl]sulfonyl}pyrrolidin-3-yl]prop-2-enamide
N-[1-({4-[2-(benzylamino)-2-oxoethyl]phenyl}sulfonyl)-5-(hydroxymethyl)pyrrolidin-3-yl]prop-2-enamide
4-{[4-(acryloylamino)-2-(hydroxymethyl)pyrrolidin-1-yl]sulfonyl}-N-(4-tert-butylbenzyl)benzamide
4-{[4-(acryloylamino)-2-(hydroxymethyl)pyrrolidin-1-yl]sulfonyl}-N-(4-phenylbutyl)benzamide
4-{[4-(acryloylamino)-2-(hydroxymethyl)pyrrolidin-1-yl]sulfonyl}-N-[2-(4-chlorophenyl)ethyl]benzamide
4-{[4-(acryloylamino)-2-(hydroxymethyl)pyrrolidin-1-yl]sulfonyl}-N-[2-(quinolin-7-yl)ethyl]benzamide
4-{[4-(acryloylamino)-2-(hydroxymethyl)pyrrolidin-1-yl]sulfonyl}-N-[2-(naphthalen-2-yl)ethyl]benzamide
4-{[4-(acryloylamino)-2-(hydroxymethyl)pyrrolidin-1-yl]sulfonyl}-N-(3,4-dihydro-2H-chromen-6-ylmethyl)benzamide
4-{[4-(acryloylamino)-2-(hydroxymethyl)pyrrolidin-1-yl]sulfonyl}-N-[2-(4-tert-butylphenyl)ethyl]benzamide
4-{[4-(acryloylamino)-2-(hydroxymethyl)pyrrolidin-1-yl]sulfonyl}-N-[2-(biphenyl-4-yl)ethyl]benzamide
4-{[4-(acryloylamino)-2-(hydroxymethyl)pyrrolidin-1-yl]sulfonyl}-N-[2-(1,3-benzodioxol-5-yl)ethyl]benzamide
4-{[4-(acryloylamino)-2-(hydroxymethyl)pyrrolidin-1-yl]sulfonyl}-N-[(1R)-2-phenylcyclopropyl]benzamide
benzyl(4-{[4-(acryloylamino)-2-(hydroxymethyl)pyrrolidin-1-yl]sulfonyl}phenyl)methylcarbamate
4-{[4-(acryloylamino)-2-(hydroxymethyl)pyrrolidin-1-yl]sulfonyl}-N-[2-(3,4-dimethoxyphenyl)ethyl]benzamide
4-{[4-(acryloylamino)-2-(hydroxymethyl)pyrrolidin-1-yl]sulfonyl}-N-{2-[4-(trifluoromethyl)phenyl]ethyl}benzamide
4-{[4-(acryloylamino)-2-(hydroxymethyl)pyrrolidin-1-yl]sulfonyl}-N-(2-phenylethyl)piperidine-1-carboxamide
N-(4-{[4-(acryloylamino)-2-(hydroxymethyl)pyrrolidin-1-yl]sulfonyl}phenyl)furan-2-carboxamide N-{5-(hydroxymethyl)-1-[(4-{[3-(tricyclo[3.3.1.1~3,7~]dec-1-yl)propanoyl]amino}phenyl)sulfonyl]pyrrolidin-3-yl}prop-2-enamide 4-{[4-(acryloylamino)-2-(hydroxymethyl)pyrrolidin-1-yl]sulfonyl}-N-[2-(tricyclo[3.3.1.1~3,7~]dec-1-yl)ethyl]benzamide N-[1-{[1-(cyclopropylcarbonyl)-2,3-dihydro-1H-indol-5-yl]sulfonyl}-5-(hydroxymethyl)pyrrolidin-3-yl]prop-2-enamide N-[1-({2-chloro-4-[(3-phenylpropanoyl)amino]phenyl}sulfonyl)-5-(hydroxymethyl)pyrrolidin-3-yl]prop-2-enamide N-(4-{[4-(acryloylamino)-2-(hydroxymethyl)pyrrolidin-1-yl]sulfonyl}phenyl)-5,6-dihydro-4H-cyclopenta[b]thiophene-2-carboxamide N-(4-{[4-(acryloylamino)-2-(hydroxymethyl)pyrrolidin-1-yl]sulfonyl}phenyl)-4,5,6,7-tetrahydro-1H-indole-2-carboxamide N-[5-(hydroxymethyl)-1-({2-methoxy-4-[(3-phenylpropanoyl)amino]phenyl}sulfonyl)pyrrolidin-3-yl]prop-2-enamide N-(4-{[4-(acryloylamino)-2-(hydroxymethyl)pyrrolidin-1-yl]sulfonyl}phenyl)-5-(pyrrolidin-1-ylmethyl)furan-2-carboxamide N-(4-{[4-(acryloylamino)-2-(hydroxymethyl)pyrrolidin-1-yl]sulfonyl}phenyl)-1-benzothiophene-2-carboxamide N-(4-{[4-(acryloylamino)-2-(hydroxymethyl)pyrrolidin-1-yl]sulfonyl}phenyl)-3-methyl-1-benzofuran-2-carboxamide N-(4-{[4-(acryloylamino)-2-(hydroxymethyl)pyrrolidin-1-yl]sulfonyl}phenyl)-1H-indole-2-carboxamide 4-{[4-(acryloylamino)-2-(hydroxymethyl)pyrrolidin-1-yl]sulfonyl}-N-(tricyclo[3.3.1.1~3,7~]dec-1-ylmethyl)benzamide 4-{[4-(acryloylamino)-2-(hydroxymethyl)pyrrolidin-1-yl]sulfonyl}-N-(1,2,3,4-tetrahydronaphthalen-1-yl)benzamide N-(4-{[4-(acryloylamino)-2-(hydroxymethyl)pyrrolidin-1-yl]sulfonyl}phenyl)-4,5,6,7-tetrahydro-1-benzothiophene-2-carboxamide N-(4-{[4-(acryloylamino)-2-(hydroxymethyl)pyrrolidin-1-yl]sulfonyl}phenyl)-5-phenylfuran-2-carboxamide N-(4-{[4-(acryloylamino)-2-(hydroxymethyl)pyrrolidin-1-yl]sulfonyl}phenyl)-4-phenylthiophene-2-carboxamide N-[5-(hydroxymethyl)-1-({5-[5-(trifluoromethyl)-1,2-oxazol-3-yl]thiophen-2-yl}sulfonyl)pyrrolidin-3-yl]prop-2-enamide 5-{[4-(acryloylamino)-2-(hydroxymethyl)pyrrolidin-1-yl]sulfonyl}-N-(2-phenylethyl)furan-2-carboxamide N-{5-(hydroxymethyl)-1-[(6-phenoxypyridin-3-yl)sulfonyl]pyrrolidin-3-yl}prop-2-enamide N-[5-(hydroxymethyl)-1-{[6-(morpholin-4-yl)pyridin-3-yl]sulfonyl}pyrrolidin-3-yl]prop-2-enamide N-{5-(hydroxymethyl)-1-[(6-phenylpyridin-3-yl)sulfonyl]pyrrolidin-3-yl}prop-2-enamide N-[1-({3-chloro-4-[(3-phenylpropanoyl)amino]phenyl}sulfonyl)-5-(hydroxymethyl)pyrrolidin-3-yl]prop-2-enamide 4-{[4-(acryloylamino)-2-(hydroxymethyl)pyrrolidin-1-yl]sulfonyl}-2-fluoro-N-(2-phenylethyl)benzamide N-[5-(hydroxymethyl)-1-{[5-(pyridin-2-yl)thiophen-2-yl]sulfonyl}pyrrolidin-3-yl]prop-2-enamide 4-{[4-(acryloylamino)-2-(hydroxymethyl)pyrrolidin-1-yl]sulfonyl}-2-methoxy-N-(2-phenylethyl)benzamide N-[1-(1,3-benzothiazol-6-ylsulfonyl)-5-(hydroxymethyl)pyrrolidin-3-yl]prop-2-enamide N-{5-(hydroxymethyl)-1-[(4-methyl-2-phenyl-1,3-thiazol-5-yl)sulfonyl]pyrrolidin-3-yl}prop-2-enamide N-[5-(hydroxymethyl)-1-{[5-(2-methyl-1,3-thiazol-4-yl)thiophen-2-yl]sulfonyl}pyrrolidin-3-yl]prop-2-enamide N-[5-(hydroxymethyl)-1-{[5-(1,2-oxazol-5-yl)thiophen-2-yl]sulfonyl}pyrrolidin-3-yl]prop-2-enamide N-[1-(2,3-dihydro-1,4-benzodioxin-6-ylsulfonyl)-5-(hydroxymethyl)pyrrolidin-3-yl]prop-2-enamide 5-{[4-(acryloylamino)-2-(hydroxymethyl)pyrrolidin-1-yl]sulfonyl}-N-(2-phenylethyl)furan-3-carboxamide N-[5-(hydroxymethyl)-1-({4-[(phenylacetyl)amino]benzyl}sulfonyl)pyrrolidin-3-yl]prop-2-enamide N-[5-(hydroxymethyl)-1-{[4-(morpholin-4-ylsulfonyl)phenyl]sulfonyl}pyrrolidin-3-yl]prop-2-enamide N-[5-(hydroxymethyl)-1-{[5-(1,3-oxazol-5-yl)thiophen-2-yl]sulfonyl}pyrrolidin-3-yl]prop-2-enamide 4-{[4-(acryloylamino)-2-(hydroxymethyl)pyrrolidin-1-yl]sulfonyl}-2-methyl-N-(2-phenylethyl)benzamide N-{5-(hydroxymethyl)-1-[(4-phenoxyphenyl)sulfonyl]pyrrolidin-3-yl}prop-2-enamide N-[5-(hydroxymethyl)-1-({4-[(6-methylpyrazin-2-yl)oxy]phenyl}sulfonyl)pyrrolidin-3-yl]prop-2-enamide N-[5-(hydroxymethyl)-1-({3-[(6-methylpyrazin-2-yl)oxy]phenyl}sulfonyl)pyrrolidin-3-yl]prop-2-enamide 5-{[4-(acryloylamino)-2-(hydroxymethyl)pyrrolidin-1-yl]sulfonyl}-1-methyl-N-(2-phenylethyl)-1H-pyrrole-2-carboxamide N-[5-(hydroxymethyl)-1-{[4-(isoquinolin-3-ylamino)phenyl]sulfonyl}pyrrolidin-3-yl]prop-2-enamide N-{1-[(3-chloro-4-methylphenyl)sulfonyl]-5-(hydroxymethyl)pyrrolidin-3-yl}prop-2-enamide N-[5-(hydroxymethyl)-1-{[5-(1,2-oxazol-5-yl)furan-2-yl]sulfonyl}pyrrolidin-3-yl]prop-2-enamide N-{1-[(4-{[3-chloro-5-(trifluoromethyl)pyridin-2-yl]oxy}phenyl)sulfonyl]-5-(hydroxymethyl)pyrrolidin-3-yl}prop-2-enamide N-[5-(hydroxymethyl)-1-{[4-(1H-pyrazol-1-yl)phenyl]sulfonyl}pyrrolidin-3-yl]prop-2-enamide N-{5-(hydroxymethyl)-1-[(4-methoxy-3-methylphenyl)sulfonyl]pyrrolidin-3-yl}prop-2-enamide N-[5-(hydroxymethyl)-1-{[6-(2-phenylethoxy)pyridin-3-yl]sulfonyl}pyrrolidin-3-yl]prop-2-enamide N-[1-({5-[(acetylamino)methyl]thiophen-2-yl}sulfonyl)-5-(hydroxymethyl)pyrrolidin-3-yl]prop-2-enamide N-{5-(hydroxymethyl)-1-[(5-methyl-1-phenyl-1H-pyrazol-4-yl)sulfonyl]pyrrolidin-3-yl}prop-2-enamide N-[5-(hydroxymethyl)-1-{[4-(1-methyl-1H-pyrazol-5-yl)phenyl]sulfonyl}pyrrolidin-3-yl]prop-2-enamide N-[5-(hydroxymethyl)-1-{[3-(1-methyl-1H-pyrazol-5-yl)phenyl]sulfonyl}pyrrolidin-3-yl]prop-2-enamide N-{1-[(2,2-dimethyl-3,4-dihydro-2H-chromen-6-yl)sulfonyl]-5-(hydroxymethyl)pyrrolidin-3-yl}prop-2-enamide N-{5-(hydroxymethyl)-1-[(5-phenylthiophen-2-yl)sulfonyl]pyrrolidin-3-yl}prop-2-enamide N-[1-{[4-(cyclopentyloxy)phenyl]sulfonyl}-5-(hydroxymethyl)pyrrolidin-3-yl]prop-2-enamide N-[5-(hydroxymethyl)-1-{[5-(pyrrolidin-1-ylcarbonyl)-1H-pyrrol-3-yl]sulfonyl}pyrrolidin-3-yl]prop-2-enamide N-[5-(hydroxymethyl)-1-{[4-(2-methyl-1,3-thiazol-4-yl)phenyl]sulfonyl}pyrrolidin-3-yl]prop-2-enamide N-[5-(hydroxymethyl)-1-{[4-(pyridin-2-yloxy)phenyl]sulfonyl}pyrrolidin-3-yl]prop-2-enamide N-{5-(hydroxymethyl)-1-[(2-oxo-1,2,3,4-tetrahydroquinolin-6-yl)sulfonyl]pyrrolidin-3-yl}prop-2-enamide N-{1-[(4-cyclohexylphenyl)sulfonyl]azepan-4-yl}prop-2-enamide N-(4-{[4-(acryloylamino)azepan-1-yl]sulfonyl}phenyl)cyclopropanecarboxamide
N-(4-{[4-(acryloylamino)azepan-1-yl]sulfonyl}phenyl)tricyclo[3.3.1.1~3,7~]decane-1-carboxamide
benzyl(4-{[4-(acryloylamino)azepan-1-yl]sulfonyl}phenyl)carbamate
N-(1-{[4-(piperidin-1-ylcarbonyl)phenyl]sulfonyl}azepan-4-yl)prop-2-enamide
benzyl 4-{[4-(acryloylamino)azepan-1-yl]sulfonyl}piperidine-1-carboxylate
N-{1-[(4-nitrophenyl)sulfonyl]azepan-4-yl}prop-2-enamide
N-(4-{[4-(acryloylamino)azepan-1-yl]sulfonyl}phenyl)tetrahydro-2H-pyran-4-carboxamide
N-[1-({4-[(3-phenylpropanoyl)amino]phenyl}sulfonyl)azepan-4-yl]prop-2-enamide
N-(4-{[4-(acryloylamino)azepan-1-yl]sulfonyl}phenyl)-2-phenylcyclopropanecarboxamide
N-(4-{[4-(acryloylamino)azepan-1-yl]sulfonyl}phenyl)-N-methyltetrahydro-2H-pyran-4-carboxamide
4-{[4-(acryloylamino)azepan-1-yl]sulfonyl}-N-benzyl-N-methylbenzamide
4-{[4-(acryloylamino)azepan-1-yl]sulfonyl}-N-(cyclopropylmethyl)benzamide
N-(1-{[3-(piperidin-1-ylcarbonyl)phenyl]sulfonyl}azepan-4-yl)prop-2-enamide
N-(4-{[4-(acryloylamino)azepan-1-yl]sulfonyl}phenyl)-N-methylcyclopropanecarboxamide
N-{1-[(4-{[4-(6-methylpyridin-2-yl)piperazin-1-yl]carbonyl}phenyl)sulfonyl]azepan-4-yl}prop-2-enamide
4-{[4-(acryloylamino)azepan-1-yl]sulfonyl}-N-[2-(morpholin-4-yl)ethyl]benzamide
4-{[4-(acryloylamino)azepan-1-yl]sulfonyl}-N-(2-phenylethyl)benzamide
4-{[4-(acryloylamino)azepan-1-yl]sulfonyl}-N-methyl-N-(2-phenylethyl)benzamide
N-(1-{[4-(3,4-dihydroisoquinolin-2(1H)-ylcarbonyl)phenyl]sulfonyl}azepan-4-yl)prop-2-enamide
4-{[4-(acryloylamino)azepan-1-yl]sulfonyl}-N-(2-cyclohexylethyl)benzamide
4-{[4-(acryloylamino)azepan-1-yl]sulfonyl}-N-cyclohexylbenzamide
N-{1-[(4-{[4-(pyrrolidin-1-ylcarbonyl)piperidin-1-yl]carbonyl}phenyl)sulfonyl]azepan-4-yl}prop-2-enamide
4-{[4-(acryloylamino)azepan-1-yl]sulfonyl}-N-(3,5-dimethylbenzyl)benzamide
4-{[4-(acryloylamino)azepan-1-yl]sulfonyl}-N-benzylbenzamide
4-{[4-(acryloylamino)azepan-1-yl]sulfonyl}-N-(3,4-difluorobenzyl)benzamide
4-{[4-(acryloylamino)azepan-1-yl]sulfonyl}-N-[4-(trifluoromethyl)benzyl]benzamide
4-{[4-(acryloylamino)azepan-1-yl]sulfonyl}-N-(naphthalen-1-ylmethyl)benzamide
4-{[4-(acryloylamino)azepan-1-yl]sulfonyl}-N-[2-(3,4-dimethylphenyl)ethyl]benzamide
4-{[4-(acryloylamino)azepan-1-yl]sulfonyl}-N-[2-(4-methoxyphenyl)ethyl]benzamide
4-{[4-(acryloylamino)azepan-1-yl]sulfonyl}-N-(2,3-dihydro-1H-inden-2-yl)benzamide
4-{[4-(acryloylamino)azepan-1-yl]sulfonyl}-N-[2-(3-methylphenyl)ethyl]benzamide
N-[1-({4-[(acetylamino)methyl]phenyl}sulfonyl)azepan-4-yl]prop-2-enamide
N-{1-[(4-{[3-(naphthalen-1-yl)propanoyl]amino}phenyl)sulfonyl]azepan-4-yl}prop-2-enamide
N-[1-({4-[(3-cyclohexylpropanoyl)amino]phenyl}sulfonyl)azepan-4-yl]prop-2-enamide
N-{1-[(1-benzoylpiperidin-4-yl)sulfonyl]azepan-4-yl}prop-2-enamide
N-(1-{[1-(piperidin-1-ylcarbonyl)piperidin-4-yl]sulfonyl}azepan-4-yl)prop-2-enamide
N-(1-{[1-(pyridin-2-ylcarbonyl)piperidin-4-yl]sulfonyl}azepan-4-yl)prop-2-enamide
N-(4-{[4-(acryloylamino)azepan-1-yl]sulfonyl}phenyl)-4-tert-butylcyclohexanecarboxamide
N-(4-{[4-(acryloylamino)azepan-1-yl]sulfonyl}phenyl)-1-benzofuran-2-carboxamide
benzyl(3-{[4-(acryloylamino)azepan-1-yl]sulfonyl}phenyl)carbamate
N-[1-({3-[(3-phenylpropanoyl)amino]phenyl}sulfonyl)azepan-4-yl]prop-2-enamide
N-(3-{[4-(acryloylamino)azepan-1-yl]sulfonyl}phenyl)tetrahydro-2H-pyran-4-carboxamide
4-{[4-(acryloylamino)azepan-1-yl]sulfonyl}-N-(3-phenylpropyl)benzamide
4-{[4-(acryloylamino)azepan-1-yl]sulfonyl}-N-[2-(3-chlorophenyl)ethyl]benzamide
4-{[4-(acryloylamino)azepan-1-yl]sulfonyl}-N-[2-(2-methoxyphenyl)ethyl]benzamide
4-{[4-(acryloylamino)azepan-1-yl]sulfonyl}-N-[2-(2,3-dihydro-1-benzofuran-7-yl)ethyl]benzamide
4-{[4-(acryloylamino)azepan-1-yl]sulfonyl}-N-[2-(tetrahydro-2H-pyran-4-yl)ethyl]benzamide
4-{[4-(acryloylamino)azepan-1-yl]sulfonyl}-N-[2-(4,4-difluoropiperidin-1-yl)ethyl]benzamide
N-[1-({1-[3-(trifluoromethyl)benzoyl]piperidin-4-yl}sulfonyl)azepan-4-yl]prop-2-enamide
N-(1-{[1-(3-phenylpropanoyl)piperidin-4-yl]sulfonyl}azepan-4-yl)prop-2-enamide
N-[1-({4-[2-(benzylamino)-2-oxoethyl]phenyl}sulfonyl)azepan-4-yl]prop-2-enamide
4-{[4-(acryloylamino)azepan-1-yl]sulfonyl}-N-(4-tert-butylbenzyl)benzamide
4-{[4-(acryloylamino)azepan-1-yl]sulfonyl}-N-(4-phenylbutyl)benzamide
4-{[4-(acryloylamino)azepan-1-yl]sulfonyl}-N-[2-(4-chlorophenyl)ethyl]benzamide
4-{[4-(acryloylamino)azepan-1-yl]sulfonyl}-N-[2-(quinolin-7-yl)ethyl]benzamide
4-{[4-(acryloylamino)azepan-1-yl]sulfonyl}-N-[2-(naphthalen-2-yl)ethyl]benzamide
4-{[4-(acryloylamino)azepan-1-yl]sulfonyl}-N-(3,4-dihydro-2H-chromen-6-ylmethyl)benzamide
4-{[4-(acryloylamino)azepan-1-yl]sulfonyl}-N-[2-(4-tert-butylphenyl)ethyl]benzamide
4-{[4-(acryloylamino)azepan-1-yl]sulfonyl}-N-[2-(biphenyl-4-yl)ethyl]benzamide
4-{[4-(acryloylamino)azepan-1-yl]sulfonyl}-N-[2-(1,3-benzodioxol-5-yl)ethyl]benzamide
4-{[4-(acryloylamino)azepan-1-yl]sulfonyl}-N-[(1R)-2-phenylcyclopropyl]benzamide
benzyl(4-{[4-(acryloylamino)azepan-1-yl]sulfonyl}phenyl)methylcarbamate
4-{[4-(acryloylamino)azepan-1-yl]sulfonyl}-N-[2-(3,4-dimethoxyphenyl)ethyl]benzamide
4-{[4-(acryloylamino)azepan-1-yl]sulfonyl}-N-{2-[4-(trifluoromethyl)phenyl]ethyl}benzamide
4-{[4-(acryloylamino)azepan-1-yl]sulfonyl}-N-(2-phenylethyl)piperidine-1-carboxamide
N-(4-{[4-(acryloylamino)azepan-1-yl]sulfonyl}phenyl)furan-2-carboxamide
N-{1-[(4-{[3-(tricyclo[3.3.1.1~3,7~]dec-1-yl)propanoyl]amino}phenyl)sulfonyl]azepan-4-yl}prop-2-enamide 4-{[4-(acryloylamino)azepan-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}azepan-4-yl)prop-2-enamide
N-[1-({2-chloro-4-[(3-phenylpropanoyl)amino]phenyl}sulfonyl)azepan-4-yl]prop-2-enamide
N-(4-{[4-(acryloylamino)azepan-1-yl]sulfonyl}phenyl)-5,6-dihydro-4H-cyclopenta[b]thiophene-2-carboxamide
N-(4-{[4-(acryloylamino)azepan-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)azepan-4-yl]prop-2-enamide
N-(4-{[4-(acryloylamino)azepan-1-yl]sulfonyl}phenyl)-5-(pyrrolidin-1-ylmethyl)furan-2-carboxamide
N-(4-{[4-(acryloylamino)azepan-1-yl]sulfonyl}phenyl)-1-benzothiophene-2-carboxamide
N-(4-{[4-(acryloylamino)azepan-1-yl]sulfonyl}phenyl)-3-methyl-1-benzofuran-2-carboxamide
N-(4-{[4-(acryloylamino)azepan-1-yl]sulfonyl}phenyl)-1H-indole-2-carboxamide
4-{[4-(acryloylamino)azepan-1-yl]sulfonyl}-N-(tricyclo[3.3.1.1~3,7~]dec-1-ylmethyl)benzamide
4-{[4-(acryloylamino)azepan-1-yl]sulfonyl}-N-(1,2,3,4-tetrahydronaphthalen-1-yl)benzamide
N-(4-{[4-(acryloylamino)azepan-1-yl]sulfonyl}phenyl)-4,5,6,7-tetrahydro-1-benzothiophene-2-carboxamide
N-(4-{[4-(acryloylamino)azepan-1-yl]sulfonyl}phenyl)-5-phenylfuran-2-carboxamide
N-(4-{[4-(acryloylamino)azepan-1-yl]sulfonyl}phenyl)-4-phenylthiophene-2-carboxamide
N-[1-({5-[5-(trifluoromethyl)-1,2-oxazol-3-yl]thiophen-2-yl}sulfonyl)azepan-4-yl]prop-2-enamide
5-{[4-(acryloylamino)azepan-1-yl]sulfonyl}-N-(2-phenylethyl)furan-2-carboxamide
N-{1-[(6-phenoxypyridin-3-yl)sulfonyl]azepan-4-yl}prop-2-enamide
N-(1-{[6-(morpholin-4-yl)pyridin-3-yl]sulfonyl}azepan-4-yl)prop-2-enamide
N-{1-[(6-phenylpyridin-3-yl)sulfonyl]azepan-4-yl}prop-2-enamide
N-[1-({3-chloro-4-[(3-phenylpropanoyl)amino]phenyl}sulfonyl)azepan-4-yl]prop-2-enamide
4-{[4-(acryloylamino)azepan-1-yl]sulfonyl}-2-fluoro-N-(2-phenylethyl)benzamide
N-(1-{[5-(pyridin-2-yl)thiophen-2-yl]sulfonyl}azepan-4-yl)prop-2-enamide
4-{[4-(acryloylamino)azepan-1-yl]sulfonyl}-2-methoxy-N-(2-phenylethyl)benzamide
N-[1-(1,3-benzothiazol-6-ylsulfonyl)azepan-4-yl]prop-2-enamide
N-{1-[(4-methyl-2-phenyl-1,3-thiazol-5-yl)sulfonyl]azepan-4-yl}prop-2-enamide
N-(1-{[5-(2-methyl-1,3-thiazol-4-yl)thiophen-2-yl]sulfonyl}azepan-4-yl)prop-2-enamide
N-(1-{[5-(1,2-oxazol-5-yl)thiophen-2-yl]sulfonyl}azepan-4-yl)prop-2-enamide
N-[1-(2,3-dihydro-1,4-benzodioxin-6-ylsulfonyl)azepan-4-yl]prop-2-enamide
5-{[4-(acryloylamino)azepan-1-yl]sulfonyl}-N-(2-phenylethyl)furan-3-carboxamide
N-[1-({4-[(phenylacetyl)amino]benzyl}sulfonyl)azepan-4-yl]prop-2-enamide
N-(1-{[4-(morpholin-4-ylsulfonyl)phenyl]sulfonyl}azepan-4-yl)prop-2-enamide
N-(1-{[5-(1,3-oxazol-5-yl)thiophen-2-yl]sulfonyl}azepan-4-yl)prop-2-enamide
4-{[4-(acryloylamino)azepan-1-yl]sulfonyl}-2-methyl-N-(2-phenylethyl)benzamide
N-{1-[(4-phenoxyphenyl)sulfonyl]azepan-4-yl}prop-2-enamide
N-[1-({4-[(6-methylpyrazin-2-yl)oxy]phenyl}sulfonyl)azepan-4-yl]prop-2-enamide
N-[1-({3-[(6-methylpyrazin-2-yl)oxy]phenyl}sulfonyl)azepan-4-yl]prop-2-enamide
5-{[4-(acryloylamino)azepan-1-yl]sulfonyl}-1-methyl-N-(2-phenylethyl)-1H-pyrrole-2-carboxamide
N-(1-{[4-(isoquinolin-3-ylamino)phenyl]sulfonyl}azepan-4-yl)prop-2-enamide
N-{1-[(3-chloro-4-methylphenyl)sulfonyl]azepan-4-yl}prop-2-enamide
N-(1-{[5-(1,2-oxazol-5-yl)furan-2-yl]sulfonyl}azepan-4-yl)prop-2-enamide
N-{1-[(4-{[3-chloro-5-(trifluoromethyl)pyridin-2-yl]oxy}phenyl)sulfonyl]azepan-4-yl}prop-2-enamide
N-(1-{[4-(1H-pyrazol-1-yl)phenyl]sulfonyl}azepan-4-yl)prop-2-enamide
N-{1-[(4-methoxy-3-methylphenyl)sulfonyl]azepan-4-yl}prop-2-enamide
N-(1-{[6-(2-phenylethoxy)pyridin-3-yl]sulfonyl}azepan-4-yl)prop-2-enamide
N-[1-({5-[(acetylamino)methyl]thiophen-2-yl}sulfonyl)azepan-4-yl]prop-2-enamide
N-{1-[(5-methyl-1-phenyl-1H-pyrazol-4-yl)sulfonyl]azepan-4-yl}prop-2-enamide
N-(1-{[4-(1-methyl-1H-pyrazol-5-yl)phenyl]sulfonyl}azepan-4-yl)prop-2-enamide
N-(1-{[3-(1-methyl-1H-pyrazol-5-yl)phenyl]sulfonyl}azepan-4-yl)prop-2-enamide
N-{1-[(2,2-dimethyl-3,4-dihydro-2H-chromen-6-yl)sulfonyl]azepan-4-yl}prop-2-enamide
N-{1-[(5-phenylthiophen-2-yl)sulfonyl]azepan-4-yl}prop-2-enamide
N-(1-{[4-(cyclopentyloxy)phenyl]sulfonyl}azepan-4-yl)prop-2-enamide
N-(1-{[5-(pyrrolidin-1-ylcarbonyl)-1H-pyrrol-3-yl]sulfonyl}azepan-4-yl)prop-2-enamide
N-(1-{[4-(2-methyl-1,3-thiazol-4-yl)phenyl]sulfonyl}azepan-4-yl)prop-2-enamide
N-(1-{[4-(pyridin-2-yloxy)phenyl]sulfonyl}azepan-4-yl)prop-2-enamide
N-{1-[(2-oxo-1,2,3,4-tetrahydroquinolin-6-yl)sulfonyl]azepan-4-yl}prop-2-enamide
N-{1-[(4-cyclohexylphenyl)sulfonyl]azepan-3-yl}prop-2-enamide
N-(4-{[3-(acryloylamino)azepan-1-yl]sulfonyl}phenyl)cyclopropanecarboxamide
N-(4-{[3-(acryloylamino)azepan-1-yl]sulfonyl}phenyl)tricyclo[3.3.1.1~3,7~]decane-1-carboxamide
benzyl(4-{[3-(acryloylamino)azepan-1-yl]sulfonyl}phenyl)carbamate
N-(1-{[4-(piperidin-1-ylcarbonyl)phenyl]sulfonyl}azepan-3-yl)prop-2-enamide
benzyl 4-{[3-(acryloylamino)azepan-1-yl]sulfonyl}piperidine-1-carboxylate
N-{1-[(4-nitrophenyl)sulfonyl]azepan-3-yl}prop-2-enamide
N-(4-{[3-(acryloylamino)azepan-1-yl]sulfonyl}phenyl)tetrahydro-2H-pyran-4-carboxamide
N-[1-({4-[(3-phenylpropanoyl)amino]phenyl}sulfonyl)azepan-3-yl]prop-2-enamide
N-(4-{[3-(acryloylamino)azepan-1-yl]sulfonyl}phenyl)-2-phenylcyclopropanecarboxamide
N-(4-{[3-(acryloylamino)azepan-1-yl]sulfonyl}phenyl)-N-methyltetrahydro-2H-pyran-4-carboxamide 4-{[3-(acryloylamino)azepan-1-yl]sulfonyl}-N-benzyl-N-methylbenzamide 4-{[3-(acryloylamino)azepan-1-yl]sulfonyl}-N-(cyclopropylmethyl)benzamide N-(1-{[3-(piperidin-1-ylcarbonyl)phenyl]sulfonyl}azepan-3-yl)prop-2-enamide N-(4-{[3-(acryloylamino)azepan-1-yl]sulfonyl}phenyl)-N-methylcyclopropanecarboxamide N-{1-[(4-{[4-(6-methylpyridin-2-yl)piperazin-1-yl]carbonyl}phenyl)sulfonyl]azepan-3-yl}prop-2-enamide 4-{[3-(acryloylamino)azepan-1-yl]sulfonyl}-N-[2-(morpholin-4-yl)ethyl]benzamide 4-{[3-(acryloylamino)azepan-1-yl]sulfonyl}-N-(2-phenylethyl)benzamide 4-{[3-(acryloylamino)azepan-1-yl]sulfonyl}-N-methyl-N-(2-phenylethyl)benzamide N-(1-{[4-(3,4-dihydroisoquinolin-2(1H)-ylcarbonyl)phenyl]sulfonyl}azepan-3-yl)prop-2-enamide 4-{[3-(acryloylamino)azepan-1-yl]sulfonyl}-N-(2-cyclohexylethyl)benzamide 4-{[3-(acryloylamino)azepan-1-yl]sulfonyl}-N-cyclohexylbenzamide N-{1-[(4-{[4-(pyrrolidin-1-ylcarbonyl)piperidin-1-yl]carbonyl}phenyl)sulfonyl]azepan-3-yl}prop-2-enamide 4-{[3-(acryloylamino)azepan-1-yl]sulfonyl}-N-(3,5-dimethylbenzyl)benzamide 4-{[3-(acryloylamino)azepan-1-yl]sulfonyl}-N-benzylbenzamide 4-{[3-(acryloylamino)azepan-1-yl]sulfonyl}-N-(3,4-difluorobenzyl)benzamide 4-{[3-(acryloylamino)azepan-1-yl]sulfonyl}-N-[4-(trifluoromethyl)benzyl]benzamide 4-{[3-(acryloylamino)azepan-1-yl]sulfonyl}-N-(naphthalen-1-ylmethyl)benzamide 4-{[3-(acryloylamino)azepan-1-yl]sulfonyl}-N-[2-(3,4-dimethylphenyl)ethyl]benzamide 4-{[3-(acryloylamino)azepan-1-yl]sulfonyl}-N-[2-(4-methoxyphenyl)ethyl]benzamide 4-{[3-(acryloylamino)azepan-1-yl]sulfonyl}-N-(2,3-dihydro-1H-inden-2-yl)benzamide 4-{[3-(acryloylamino)azepan-1-yl]sulfonyl}-N-[2-(3-methylphenyl)ethyl]benzamide N-[1-({4-[(acetylamino)methyl]phenyl}sulfonyl)azepan-3-yl]prop-2-enamide N-{1-[(4-{[3-(naphthalen-1-yl)propanoyl]amino}phenyl)sulfonyl]azepan-3-yl}prop-2-enamide N-[1-({4-[(3-cyclohexylpropanoyl)amino]phenyl}sulfonyl)azepan-3-yl]prop-2-enamide N-{1-[(1-benzoylpiperidin-4-yl)sulfonyl]azepan-3-yl}prop-2-enamide N-(1-{[1-(piperidin-1-ylcarbonyl)piperidin-4-yl]sulfonyl}azepan-3-yl)prop-2-enamide N-(1-{[1-(pyridin-2-ylcarbonyl)piperidin-4-yl]sulfonyl}azepan-3-yl)prop-2-enamide N-(4-{[3-(acryloylamino)azepan-1-yl]sulfonyl}phenyl)-4-tert-butylcyclohexanecarboxamide N-(4-{[3-(acryloylamino)azepan-1-yl]sulfonyl}phenyl)-1-benzofuran-2-carboxamide benzyl(3-{[3-(acryloylamino)azepan-1-yl]sulfonyl}phenyl)carbamate N-[1-({3-[(3-phenylpropanoyl)amino]phenyl}sulfonyl)azepan-3-yl]prop-2-enamide N-(3-{[3-(acryloylamino)azepan-1-yl]sulfonyl}phenyl)tetrahydro-2H-pyran-4-carboxamide 4-{[3-(acryloylamino)azepan-1-yl]sulfonyl}-N-(3-phenylpropyl)benzamide 4-{[3-(acryloylamino)azepan-1-yl]sulfonyl}-N-[2-(3-chlorophenyl)ethyl]benzamide 4-{[3-(acryloylamino)azepan-1-yl]sulfonyl}-N-[2-(2-methoxyphenyl)ethyl]benzamide 4-{[3-(acryloylamino)azepan-1-yl]sulfonyl}-N-[2-(2,3-dihydro-1-benzofuran-7-yl)ethyl]benzamide 4-{[3-(acryloylamino)azepan-1-yl]sulfonyl}-N-[2-(tetrahydro-2H-pyran-4-yl)ethyl]benzamide 4-{[3-(acryloylamino)azepan-1-yl]sulfonyl}-N-[2-(4,4-difluoropiperidin-1-yl)ethyl]benzamide N-[1-({1-[3-(trifluoromethyl)benzoyl]piperidin-4-yl}sulfonyl)azepan-3-yl]prop-2-enamide N-(1-{[1-(3-phenylpropanoyl)piperidin-4-yl]sulfonyl}azepan-3-yl)prop-2-enamide N-[1-({4-[2-(benzylamino)-2-oxoethyl]phenyl}sulfonyl)azepan-3-yl]prop-2-enamide 4-{[3-(acryloylamino)azepan-1-yl]sulfonyl}-N-(4-tert-butylbenzyl)benzamide 4-{[3-(acryloylamino)azepan-1-yl]sulfonyl}-N-(4-phenylbutyl)benzamide 4-{[3-(acryloylamino)azepan-1-yl]sulfonyl}-N-[2-(4-chlorophenyl)ethyl]benzamide 4-{[3-(acryloylamino)azepan-1-yl]sulfonyl}-N-[2-(quinolin-7-yl)ethyl]benzamide 4-{[3-(acryloylamino)azepan-1-yl]sulfonyl}-N-[2-(naphthalen-2-yl)ethyl]benzamide 4-{[3-(acryloylamino)azepan-1-yl]sulfonyl}-N-(3,4-dihydro-2H-chromen-6-ylmethyl)benzamide 4-{[3-(acryloylamino)azepan-1-yl]sulfonyl}-N-[2-(4-tert-butylphenyl)ethyl]benzamide 4-{[3-(acryloylamino)azepan-1-yl]sulfonyl}-N-[2-(biphenyl-4-yl)ethyl]benzamide 4-{[3-(acryloylamino)azepan-1-yl]sulfonyl}-N-[2-(1,3-benzodioxol-5-yl)ethyl]benzamide 4-{[3-(acryloylamino)azepan-1-yl]sulfonyl}-N-[(1R)-2-phenylcyclopropyl]benzamide benzyl(4-{[3-(acryloylamino)azepan-1-yl]sulfonyl}phenyl)methylcarbamate 4-{[3-(acryloylamino)azepan-1-yl]sulfonyl}-N-[2-(3,4-dimethoxyphenyl)ethyl]benzamide 4-{[3-(acryloylamino)azepan-1-yl]sulfonyl}-N-{2-[4-(trifluoromethyl)phenyl]ethyl}benzamide 4-{[3-(acryloylamino)azepan-1-yl]sulfonyl}-N-(2-phenylethyl)piperidine-1-carboxamide N-(4-{[3-(acryloylamino)azepan-1-yl]sulfonyl}phenyl)furan-2-carboxamide N-{1-[(4-{[3-(tricyclo[3.3.1.1~3,7~]dec-1-yl)propanoyl]amino}phenyl)sulfonyl]azepan-3-yl}prop-2-enamide 4-{[3-(acryloylamino)azepan-1-yl]sulfonyl}-N-[2-(tricyclo[3.3.1.1~3,7~]dec-1-yl)ethyl]benzamide N-(1-{[1-(cyclopropylcarbonyl)-2,3-dihydro-1H-indol-5-yl]sulfonyl}azepan-3-yl)prop-2-enamide N-[1-({2-chloro-4-[(3-phenylpropanoyl)amino]phenyl}sulfonyl)azepan-3-yl]prop-2-enamide N-(4-{[3-(acryloylamino)azepan-1-yl]sulfonyl}phenyl)-5,6-dihydro-4H-cyclopenta[b]thiophene-2-carboxamide N-(4-{[3-(acryloylamino)azepan-1-yl]sulfonyl}phenyl)-4,5,6,7-tetrahydro-1H-indole-2-carboxamide N-[1-({2-methoxy-4-[(3-phenylpropanoyl)amino]phenyl}sulfonyl)azepan-3-yl]prop-2-enamide N-(4-{[3-(acryloylamino)azepan-1-yl]sulfonyl}phenyl)-5-(pyrrolidin-1-ylmethyl)furan-2-carboxamide N-(4-{[3-(acryloylamino)azepan-1-yl]sulfonyl}phenyl)-1-benzothiophene-2-carboxamide N-(4-{[3-(acryloylamino)azepan-1-yl]sulfonyl}phenyl)-3-methyl-1-benzofuran-2-carboxamide N-(4-{[3-(acryloylamino)azepan-1-yl]sulfonyl}phenyl)-1H-indole-2-carboxamide
4-{[3-(acryloylamino)azepan-1-yl]sulfonyl}-N-(tricyclo[3.3.1.1~3,7~]dec-1-ylmethyl)benzamide
4-{[3-(acryloylamino)azepan-1-yl]sulfonyl}-N-(1,2,3,4-tetrahydronaphthalen-1-yl)benzamide
N-(4-{[3-(acryloylamino)azepan-1-yl]sulfonyl}phenyl)-4,5,6,7-tetrahydro-1-benzothiophene-2-carboxamide
N-(4-{[3-(acryloylamino)azepan-1-yl]sulfonyl}phenyl)-5-phenylfuran-2-carboxamide
N-(4-{[3-(acryloylamino)azepan-1-yl]sulfonyl}phenyl)-4-phenylthiophene-2-carboxamide
N-[1-({5-[5-(trifluoromethyl)-1,2-oxazol-3-yl]thiophen-2-yl}sulfonyl)azepan-3-yl]prop-2-enamide
5-{[3-(acryloylamino)azepan-1-yl]sulfonyl}-N-(2-phenylethyl)furan-2-carboxamide
N-{1-[(6-phenoxypyridin-3-yl)sulfonyl]azepan-3-yl}prop-2-enamide
N-(1-{[6-(morpholin-4-yl)pyridin-3-yl]sulfonyl}azepan-3-yl)prop-2-enamide
N-{1-[(6-phenylpyridin-3-yl)sulfonyl]azepan-3-yl}prop-2-enamide
N-[1-({3-chloro-4-[(3-phenylpropanoyl)amino]phenyl}sulfonyl)azepan-3-yl]prop-2-enamide
4-{[3-(acryloylamino)azepan-1-yl]sulfonyl}-2-fluoro-N-(2-phenylethyl)benzamide
N-(1-{[5-(pyridin-2-yl)thiophen-2-yl]sulfonyl}azepan-3-yl)prop-2-enamide
4-{[3-(acryloylamino)azepan-1-yl]sulfonyl}-2-methoxy-N-(2-phenylethyl)benzamide
N-[1-(1,3-benzothiazol-6-ylsulfonyl)azepan-3-yl]prop-2-enamide
N-{1-[(4-methyl-2-phenyl-1,3-thiazol-5-yl)sulfonyl]azepan-3-yl}prop-2-enamide
N-(1-{[5-(2-methyl-1,3-thiazol-4-yl)thiophen-2-yl]sulfonyl}azepan-3-yl)prop-2-enamide
N-(1-{[5-(1,2-oxazol-5-yl)thiophen-2-yl]sulfonyl}azepan-3-yl)prop-2-enamide
N-[1-(2,3-dihydro-1,4-benzodioxin-6-ylsulfonyl)azepan-3-yl]prop-2-enamide
5-{[3-(acryloylamino)azepan-1-yl]sulfonyl}-N-(2-phenylethyl)furan-3-carboxamide
N-[1-({4-[(phenylacetyl)amino]benzyl}sulfonyl)azepan-3-yl]prop-2-enamide
N-(1-{[4-(morpholin-4-ylsulfonyl)phenyl]sulfonyl}azepan-3-yl)prop-2-enamide
N-(1-{[5-(1,3-oxazol-5-yl)thiophen-2-yl]sulfonyl}azepan-3-yl)prop-2-enamide
4-{[3-(acryloylamino)azepan-1-yl]sulfonyl}-2-methyl-N-(2-phenylethyl)benzamide
N-{1-[(4-phenoxyphenyl)sulfonyl]azepan-3-yl}prop-2-enamide
N-[1-({4-[(6-methylpyrazin-2-yl)oxy]phenyl}sulfonyl)azepan-3-yl]prop-2-enamide
N-[1-({3-[(6-methylpyrazin-2-yl)oxy]phenyl}sulfonyl)azepan-3-yl]prop-2-enamide
5-{[3-(acryloylamino)azepan-1-yl]sulfonyl}-1-methyl-N-(2-phenylethyl)-1H-pyrrole-2-carboxamide
N-(1-{[4-(isoquinolin-3-ylamino)phenyl]sulfonyl}azepan-3-yl)prop-2-enamide
N-{1-[(3-chloro-4-methylphenyl)sulfonyl]azepan-3-yl}prop-2-enamide
N-(1-{[5-(1,2-oxazol-5-yl)furan-2-yl]sulfonyl}azepan-3-yl)prop-2-enamide
N-{1-[(4-{[3-chloro-5-(trifluoromethyl)pyridin-2-yl]oxy}phenyl)sulfonyl]azepan-3-yl}prop-2-enamide
N-(1-{[4-(1H-pyrazol-1-yl)phenyl]sulfonyl}azepan-3-yl)prop-2-enamide
N-{1-[(4-methoxy-3-methylphenyl)sulfonyl]azepan-3-yl}prop-2-enamide
N-(1-{[6-(2-phenylethoxy)pyridin-3-yl]sulfonyl}azepan-3-yl)prop-2-enamide
N-[1-({5-[(acetylamino)methyl]thiophen-2-yl}sulfonyl)azepan-3-yl]prop-2-enamide
N-{1-[(5-methyl-1-phenyl-1H-pyrazol-4-yl)sulfonyl]azepan-3-yl}prop-2-enamide
N-(1-{[4-(1-methyl-1H-pyrazol-5-yl)phenyl]sulfonyl}azepan-3-yl)prop-2-enamide
N-(1-{[3-(1-methyl-1H-pyrazol-5-yl)phenyl]sulfonyl}azepan-3-yl)prop-2-enamide
N-{1-[(2,2-dimethyl-3,4-dihydro-2H-chromen-6-yl)sulfonyl]azepan-3-yl}prop-2-enamide
N-{1-[(5-phenylthiophen-2-yl)sulfonyl]azepan-3-yl}prop-2-enamide
N-(1-{[4-(cyclopentyloxy)phenyl]sulfonyl}azepan-3-yl)prop-2-enamide
N-(1-{[5-(pyrrolidin-1-ylcarbonyl)-1H-pyrrol-3-yl]sulfonyl}azepan-3-yl)prop-2-enamide
N-(1-{[4-(2-methyl-1,3-thiazol-4-yl)phenyl]sulfonyl}azepan-3-yl)prop-2-enamide
N-(1-{[4-(pyridin-2-yloxy)phenyl]sulfonyl}azepan-3-yl)prop-2-enamide
N-{1-[(2-oxo-1,2,3,4-tetrahydroquinolin-6-yl)sulfonyl]azepan-3-yl}prop-2-enamide
N-{6-[(4-cyclohexylphenyl)sulfonyl]octahydrofuro[2,3-c]pyridin-2-yl}prop-2-enamide
N-(4-{[2-(acryloylamino)hexahydrofuro[2,3-c]pyridin-6(2H)-yl]sulfonyl}phenyl)cyclopropanecarboxamide
N-(4-{[2-(acryloylamino)hexahydrofuro[2,3-c]pyridin-6(2H)-yl]sulfonyl}phenyl)tricyclo[3.3.1.1~3,7~]decane-1-carboxamide
benzyl(4-{[2-(acryloylamino)hexahydrofuro[2,3-c]pyridin-6(2H)-yl]sulfonyl}phenyl)carbamate
N-(6-{[4-(piperidin-1-ylcarbonyl)phenyl]sulfonyl}octahydrofuro[2,3-c]pyridin-2-yl)prop-2-enamide
benzyl 4-{[2-(acryloylamino)hexahydrofuro[2,3-c]pyridin-6(2H)-yl]sulfonyl}piperidine-1-carboxylate
N-{6-[(4-nitrophenyl)sulfonyl]octahydrofuro[2,3-c]pyridin-2-yl}prop-2-enamide
N-(4-{[2-(acryloylamino)hexahydrofuro[2,3-c]pyridin-6(2H)-yl]sulfonyl}phenyl)tetrahydro-2H-pyran-4-carboxamide
N-[6-({4-[(3-phenylpropanoyl)amino]phenyl}sulfonyl)octahydrofuro[2,3-c]pyridin-2-yl]prop-2-enamide
N-(4-{[2-(acryloylamino)hexahydrofuro[2,3-c]pyridin-6(2H)-yl]sulfonyl}phenyl)-2-phenylcyclopropanecarboxamide
N-(4-{[2-(acryloylamino)hexahydrofuro[2,3-c]pyridin-6(2H)-yl]sulfonyl}phenyl)-N-methyltetrahydro-2H-pyran-4-carboxamide
4-{[2-(acryloylamino)hexahydrofuro[2,3-c]pyridin-6(2H)-yl]sulfonyl}-N-benzyl-N-methylbenzamide
4-{[2-(acryloylamino)hexahydrofuro[2,3-c]pyridin-6(2H)-yl]sulfonyl}-N-(cyclopropylmethyl)benzamide
N-(6-{[3-(piperidin-1-ylcarbonyl)phenyl]sulfonyl}octahydrofuro[2,3-c]pyridin-2-yl)prop-2-enamide
N-(4-{[2-(acryloylamino)hexahydrofuro[2,3-c]pyridin-6(2H)-yl]sulfonyl}phenyl)-N-methylcyclopropanecarboxamide N-{6-[(4-{[4-(6-methylpyridin-2-yl)piperazin-1-yl]carbonyl}phenyl)sulfonyl]octahydrofuro[2,3-c]pyridin-2-yl}prop-2-enamide 4-{[2-(acryloylamino)hexahydrofuro[2,3-c]pyridin-6(2H)-yl]sulfonyl}-N-[2-(morpholin-4-yl)ethyl]benzamide 4-{[2-(acryloylamino)hexahydrofuro[2,3-c]pyridin-6(2H)-yl]sulfonyl}-N-(2-phenylethyl)benzamide 4-{[2-(acryloylamino)hexahydrofuro[2,3-c]pyridin-6(2H)-yl]sulfonyl}-N-methyl-N-(2-phenylethyl)benzamide N-(6-{[4-(3,4-dihydroisoquinolin-2(1H)-ylcarbonyl)phenyl]sulfonyl}octahydrofuro[2,3-c]pyridin-2-yl)prop-2-enamide 4-{[2-(acryloylamino)hexahydrofuro[2,3-c]pyridin-6(2H)-yl]sulfonyl}-N-(2-cyclohexylethyl)benzamide 4-{[2-(acryloylamino)hexahydrofuro[2,3-c]pyridin-6(2H)-yl]sulfonyl}-N-cyclohexylbenzamide N-{6-[(4-{[4-(pyrrolidin-1-ylcarbonyl)piperidin-1-yl]carbonyl}phenyl)sulfonyl]octahydrofuro[2,3-c]pyridin-2-yl}prop-2-enamide 4-{[2-(acryloylamino)hexahydrofuro[2,3-c]pyridin-6(2H)-yl]sulfonyl}-N-(3,5-dimethylbenzyl)benzamide 4-{[2-(acryloylamino)hexahydrofuro[2,3-c]pyridin-6(2H)-yl]sulfonyl}-N-benzylbenzamide 4-{[2-(acryloylamino)hexahydrofuro[2,3-c]pyridin-6(2H)-yl]sulfonyl}-N-(3,4-difluorobenzyl)benzamide 4-{[2-(acryloylamino)hexahydrofuro[2,3-c]pyridin-6(2H)-yl]sulfonyl}-N-[4-(trifluoromethyl)benzyl]benzamide 4-{[2-(acryloylamino)hexahydrofuro[2,3-c]pyridin-6(2H)-yl]sulfonyl}-N-(naphthalen-1-ylmethyl)benzamide 4-{[2-(acryloylamino)hexahydrofuro[2,3-c]pyridin-6(2H)-yl]sulfonyl}-N-[2-(3,4-dimethylphenyl)ethyl]benzamide 4-{[2-(acryloylamino)hexahydrofuro[2,3-c]pyridin-6(2H)-yl]sulfonyl}-N-[2-(4-methoxyphenyl)ethyl]benzamide 4-{[2-(acryloylamino)hexahydrofuro[2,3-c]pyridin-6(2H)-yl]sulfonyl}-N-(2,3-dihydro-1H-inden-2-yl)benzamide 4-{[2-(acryloylamino)hexahydrofuro[2,3-c]pyridin-6(2H)-yl]sulfonyl}-N-[2-(3-methylphenyl)ethyl]benzamide N-[6-({4-[(acetylamino)methyl]phenyl}sulfonyl)octahydrofuro[2,3-c]pyridin-2-yl]prop-2-enamide N-{6-[(4-{[3-(naphthalen-1-yl)propanoyl]amino}phenyl)sulfonyl]octahydrofuro[2,3-c]pyridin-2-yl}prop-2-enamide N-[6-({4-[(3-cyclohexylpropanoyl)amino]phenyl}sulfonyl)octahydrofuro[2,3-c]pyridin-2-yl]prop-2-enamide N-{6-[(1-benzoylpiperidin-4-yl)sulfonyl]octahydrofuro[2,3-c]pyridin-2-yl}prop-2-enamide N-(6-{[1-(piperidin-1-ylcarbonyl)piperidin-4-yl]sulfonyl}octahydrofuro[2,3-c]pyridin-2-yl)prop-2-enamide N-(6-{[1-(pyridin-2-ylcarbonyl)piperidin-4-yl]sulfonyl}octahydrofuro[2,3-c]pyridin-2-yl)prop-2-enamide N-(4-{[2-(acryloylamino)hexahydrofuro[2,3-c]pyridin-6(2H)-yl]sulfonyl}phenyl)-4-tert-butylcyclohexanecarboxamide N-(4-{[2-(acryloylamino)hexahydrofuro[2,3-c]pyridin-6(2H)-yl]sulfonyl}phenyl)-1-benzofuran-2-carboxamide benzyl(3-{[2-(acryloylamino)hexahydrofuro[2,3-c]pyridin-6(2H)-yl]sulfonyl}phenyl)carbamate N-[6-({3-[(3-phenylpropanoyl)amino]phenyl}sulfonyl)octahydrofuro[2,3-c]pyridin-2-yl]prop-2-enamide N-(3-{[2-(acryloylamino)hexahydrofuro[2,3-c]pyridin-6(2H)-yl]sulfonyl}phenyl)tetrahydro-2H-pyran-4-carboxamide 4-{[2-(acryloylamino)hexahydrofuro[2,3-c]pyridin-6(2H)-yl]sulfonyl}-N-(3-phenylpropyl)benzamide 4-{[2-(acryloylamino)hexahydrofuro[2,3-c]pyridin-6(2H)-yl]sulfonyl}-N-[2-(3-chlorophenyl)ethyl]benzamide 4-{[2-(acryloylamino)hexahydrofuro[2,3-c]pyridin-6(2H)-yl]sulfonyl}-N-[2-(2-methoxyphenyl)ethyl]benzamide 4-{[2-(acryloylamino)hexahydrofuro[2,3-c]pyridin-6(2H)-yl]sulfonyl}-N-[2-(2,3-dihydro-1-benzofuran-7-yl)ethyl]benzamide 4-{[2-(acryloylamino)hexahydrofuro[2,3-c]pyridin-6(2H)-yl]sulfonyl}-N-[2-(tetrahydro-2H-pyran-4-yl)ethyl]benzamide 4-{[2-(acryloylamino)hexahydrofuro[2,3-c]pyridin-6(2H)-yl]sulfonyl}-N-[2-(4,4-difluoropiperidin-1-yl)ethyl]benzamide N-[6-({1-[3-(trifluoromethyl)benzoyl]piperidin-4-yl}sulfonyl)octahydrofuro[2,3-c]pyridin-2-yl]prop-2-enamide N-(6-{[1-(3-phenylpropanoyl)piperidin-4-yl]sulfonyl}octahydrofuro[2,3-c]pyridin-2-yl)prop-2-enamide N-[6-({4-[2-(benzylamino)-2-oxoethyl]phenyl}sulfonyl)octahydrofuro[2,3-c]pyridin-2-yl]prop-2-enamide 4-{[2-(acryloylamino)hexahydrofuro[2,3-c]pyridin-6(2H)-yl]sulfonyl}-N-(4-tert-butylbenzyl)benzamide 4-{[2-(acryloylamino)hexahydrofuro[2,3-c]pyridin-6(2H)-yl]sulfonyl}-N-(4-phenylbutyl)benzamide 4-{[2-(acryloylamino)hexahydrofuro[2,3-c]pyridin-6(2H)-yl]sulfonyl}-N-[2-(4-chlorophenyl)ethyl]benzamide 4-{[2-(acryloylamino)hexahydrofuro[2,3-c]pyridin-6(2H)-yl]sulfonyl}-N-[2-(quinolin-7-yl)ethyl]benzamide 4-{[2-(acryloylamino)hexahydrofuro[2,3-c]pyridin-6(2H)-yl]sulfonyl}-N-[2-(naphthalen-2-yl)ethyl]benzamide 4-{[2-(acryloylamino)hexahydrofuro[2,3-c]pyridin-6(2H)-yl]sulfonyl}-N-(3,4-dihydro-2H-chromen-6-ylmethyl)benzamide 4-{[2-(acryloylamino)hexahydrofuro[2,3-c]pyridin-6(2H)-yl]sulfonyl}-N-[2-(4-tert-butylphenyl)ethyl]benzamide 4-{[2-(acryloylamino)hexahydrofuro[2,3-c]pyridin-6(2H)-yl]sulfonyl}-N-[2-(biphenyl-4-yl)ethyl]benzamide 4-{[2-(acryloylamino)hexahydrofuro[2,3-c]pyridin-6(2H)-yl]sulfonyl}-N-[2-(1,3-benzodioxol-5-yl)ethyl]benzamide 4-{[2-(acryloylamino)hexahydrofuro[2,3-c]pyridin-6(2H)-yl]sulfonyl}-N-[(1R)-2-phenylcyclopropyl]benzamide benzyl(4-{[2-(acryloylamino)hexahydrofuro[2,3-c]pyridin-6(2H)-yl]sulfonyl}phenyl)methylcarbamate 4-{[2-(acryloylamino)hexahydrofuro[2,3-c]pyridin-6(2H)-yl]sulfonyl}-N-[2-(3,4-dimethoxyphenyl)ethyl]benzamide 4-{[2-(acryloylamino)hexahydrofuro[2,3-c]pyridin-6(2H)-yl]sulfonyl}-N-{2-[4-(trifluoromethyl)phenyl]ethyl}benzamide 4-{[2-(acryloylamino)hexahydrofuro[2,3-c]pyridin-6(2H)-yl]sulfonyl}-N-(2-phenylethyl)piperidine-1-carboxamide N-(4-{[2-(acryloylamino)hexahydrofuro[2,3-c]pyridin-6(2H)-yl]sulfonyl}phenyl)furan-2-carboxamide N-{6-[(4-{[3-(tricyclo[3.3.1.1~3,7~]dec-1-yl)propanoyl]amino}phenyl)sulfonyl]octahydrofuro[2,3-c]pyridin-2-yl}prop-2-enamide 4-{[2-(acryloylamino)hexahydrofuro[2,3-c]pyridin-6(2H)-yl]sulfonyl}-N-[2-(tricyclo[3.3.1.1~3,7~]dec-1-yl)ethyl]benzamide N-(6-{[1-(cyclopropylcarbonyl)-2,3-dihydro-1H-indol-5-yl]sulfonyl}octahydrofuro[2,3-c]pyridin-2-yl)prop-2-enamide N-[6-({2-chloro-4-[(3-phenylpropanoyl)amino]phenyl}sulfonyl)octahydrofuro[2,3-c]pyridin-2-yl]prop-2-enamide N-(4-{[2-(acryloylamino)hexahydrofuro[2,3-c]pyridin-6(2H)-yl]sulfonyl}phenyl)-5,6-dihydro-4H-cyclopenta[b]thiophene-2-carboxamide N-(4-{[2-(acryloylamino)hexahydrofuro[2,3-c]pyridin-6(2H)-yl]sulfonyl}phenyl)-4,5,6,7-tetrahydro-1H-indole-2-carboxamide N-[6-({2-methoxy-4-[(3-phenylpropanoyl)amino]phenyl}sulfonyl)octahydrofuro[2,3-c]pyridin-2-yl]prop-2-enamide N-(4-{[2-(acryloylamino)hexahydrofuro[2,3-c]pyridin-6(2H)-yl]sulfonyl}phenyl)-5-(pyrrolidin-1-ylmethyl)furan-2-carboxamide N-(4-{[2-(acryloylamino)hexahydrofuro[2,3-c]pyridin-6(2H)-yl]sulfonyl}phenyl)-1-benzothiophene-2-carboxamide N-(4-{[2-(acryloylamino)hexahydrofuro[2,3-c]pyridin-6(2H)-yl]sulfonyl}phenyl)-3-methyl-1-benzofuran-2-carboxamide N-(4-{[2-(acryloylamino)hexahydrofuro[2,3-c]pyridin-6(2H)-yl]sulfonyl}phenyl)-1H-indole-2-carboxamide 4-{[2-(acryloylamino)hexahydrofuro[2,3-c]pyridin-6(2H)-yl]sulfonyl}-N-(tricyclo[3.3.1.1~3,7~]dec-1-ylmethyl)benzamide 4-{[2-(acryloylamino)hexahydrofuro[2,3-c]pyridin-6(2H)-yl]sulfonyl}-N-(1,2,3,4-tetrahydronaphthalen-1-yl)benzamide N-(4-{[2-(acryloylamino)hexahydrofuro[2,3-c]pyridin-6(2H)-yl]sulfonyl}phenyl)-4,5,6,7-tetrahydro-1-benzothiophene-2-carboxamide N-(4-{[2-(acryloylamino)hexahydrofuro[2,3-c]pyridin-6(2H)-yl]sulfonyl}phenyl)-5-phenylfuran-2-carboxamide N-(4-{[2-(acryloylamino)hexahydrofuro[2,3-c]pyridin-6(2H)-yl]sulfonyl}phenyl)-4-phenylthiophene-2-carboxamide N-[6-({5-[5-(trifluoromethyl)-1,2-oxazol-3-yl]thiophen-2-yl}sulfonyl)octahydrofuro[2,3-c]pyridin-2-yl]prop-2-enamide 5-{[2-(acryloylamino)hexahydrofuro[2,3-c]pyridin-6(2H)-yl]sulfonyl}-N-(2-phenylethyl)furan-2-carboxamide N-{6-[(6-phenoxypyridin-3-yl)sulfonyl]octahydrofuro[2,3-c]pyridin-2-yl}prop-2-enamide N-(6-{[6-(morpholin-4-yl)pyridin-3-yl]sulfonyl}octahydrofuro[2,3-c]pyridin-2-yl)prop-2-enamide N-{6-[(6-phenylpyridin-3-yl)sulfonyl]octahydrofuro[2,3-c]pyridin-2-yl}prop-2-enamide N-[6-({3-chloro-4-[(3-phenylpropanoyl)amino]phenyl}sulfonyl)octahydrofuro[2,3-c]pyridin-2-yl]prop-2-enamide 4-{[2-(acryloylamino)hexahydrofuro[2,3-c]pyridin-6(2H)-yl]sulfonyl}-2-fluoro-N-(2-phenylethyl)benzamide N-(6-{[5-(pyridin-2-yl)thiophen-2-yl]sulfonyl}octahydrofuro[2,3-c]pyridin-2-yl)prop-2-enamide 4-{[2-(acryloylamino)hexahydrofuro[2,3-c]pyridin-6(2H)-yl]sulfonyl}-2-methoxy-N-(2-phenylethyl)benzamide N-[6-(1,3-benzothiazol-6-ylsulfonyl)octahydrofuro[2,3-c]pyridin-2-yl]prop-2-enamide N-{6-[(4-methyl-2-phenyl-1,3-thiazol-5-yl)sulfonyl]octahydrofuro[2,3-c]pyridin-2-yl}prop-2-enamide N-(6-{[5-(2-methyl-1,3-thiazol-4-yl)thiophen-2-yl]sulfonyl}octahydrofuro[2,3-c]pyridin-2-yl)prop-2-enamide N-(6-{[5-(1,2-oxazol-5-yl)thiophen-2-yl]sulfonyl}octahydrofuro[2,3-c]pyridin-2-yl)prop-2-enamide N-[6-(2,3-dihydro-1,4-benzodioxin-6-ylsulfonyl)octahydrofuro[2,3-c]pyridin-2-yl]prop-2-enamide 5-{[2-(acryloylamino)hexahydrofuro[2,3-c]pyridin-6(2H)-yl]sulfonyl}-N-(2-phenylethyl)furan-3-carboxamide N-[6-({4-[(phenylacetyl)amino]benzyl}sulfonyl)octahydrofuro[2,3-c]pyridin-2-yl]prop-2-enamide N-(6-{[4-(morpholin-4-ylsulfonyl)phenyl]sulfonyl}octahydrofuro[2,3-c]pyridin-2-yl)prop-2-enamide N-(6-{[5-(1,3-oxazol-5-yl)thiophen-2-yl]sulfonyl}octahydrofuro[2,3-c]pyridin-2-yl)prop-2-enamide 4-{[2-(acryloylamino)hexahydrofuro[2,3-c]pyridin-6(2H)-yl]sulfonyl}-2-methyl-N-(2-phenylethyl)benzamide N-{6-[(4-phenoxyphenyl)sulfonyl]octahydrofuro[2,3-c]pyridin-2-yl}prop-2-enamide N-[6-({4-[(6-methylpyrazin-2-yl)oxy]phenyl}sulfonyl)octahydrofuro[2,3-c]pyridin-2-yl]prop-2-enamide N-[6-({3-[(6-methylpyrazin-2-yl)oxy]phenyl}sulfonyl)octahydrofuro[2,3-c]pyridin-2-yl]prop-2-enamide 5-{[2-(acryloylamino)hexahydrofuro[2,3-c]pyridin-6(2H)-yl]sulfonyl}-1-methyl-N-(2-phenylethyl)-1H-pyrrole-2-carboxamide N-(6-{[4-(isoquinolin-3-ylamino)phenyl]sulfonyl}octahydrofuro[2,3-c]pyridin-2-yl)prop-2-enamide N-{6-[(3-chloro-4-methylphenyl)sulfonyl]octahydrofuro[2,3-c]pyridin-2-yl}prop-2-enamide N-(6-{[5-(1,2-oxazol-5-yl)furan-2-yl]sulfonyl}octahydrofuro[2,3-c]pyridin-2-yl)prop-2-enamide N-{6-[(4-{[3-chloro-5-(trifluoromethyl)pyridin-2-yl]oxy}phenyl)sulfonyl]octahydrofuro[2,3-c]pyridin-2-yl}prop-2-enamide N-(6-{[4-(1H-pyrazol-1-yl)phenyl]sulfonyl}octahydrofuro[2,3-c]pyridin-2-yl)prop-2-enamide N-{6-[(4-methoxy-3-methylphenyl)sulfonyl]octahydrofuro[2,3-c]pyridin-2-yl}prop-2-enamide N-(6-{[6-(2-phenylethoxy)pyridin-3-yl]sulfonyl}octahydrofuro[2,3-c]pyridin-2-yl)prop-2-enamide N-[6-({5-[(acetylamino)methyl]thiophen-2-yl}sulfonyl)octahydrofuro[2,3-c]pyridin-2-yl]prop-2-enamide N-{6-[(5-methyl-1-phenyl-1H-pyrazol-4-yl)sulfonyl]octahydrofuro[2,3-c]pyridin-2-yl}prop-2-enamide N-(6-{[4-(1-methyl-1H-pyrazol-5-yl)phenyl]sulfonyl}octahydrofuro[2,3-c]pyridin-2-yl)prop-2-enamide N-(6-{[3-(1-methyl-1H-pyrazol-5-yl)phenyl]sulfonyl}octahydrofuro[2,3-c]pyridin-2-yl)prop-2-enamide N-{6-[(2,2-dimethyl-3,4-dihydro-2H-chromen-6-yl)sulfonyl]octahydrofuro[2,3-c]pyridin-2-yl}prop-2-enamide N-{6-[(5-phenylthiophen-2-yl)sulfonyl]octahydrofuro[2,3-c]pyridin-2-yl}prop-2-enamide N-(6-{[4-(cyclopentyloxy)phenyl]sulfonyl}octahydrofuro[2,3-c]pyridin-2-yl)prop-2-enamide N-(6-{[5-(pyrrolidin-1-ylcarbonyl)-1H-pyrrol-3-yl]sulfonyl}octahydrofuro[2,3-c]pyridin-2-yl)prop-2-enamide N-(6-{[4-(2-methyl-1,3-thiazol-4-yl)phenyl]sulfonyl}octahydrofuro[2,3-c]pyridin-2-yl)prop-2-enamide N-(6-{[4-(pyridin-2-yloxy)phenyl]sulfonyl}octahydrofuro[2,3-c]pyridin-2-yl)prop-2-enamide N-{6-[(2-oxo-1,2,3,4-tetrahydroquinolin-6-yl)sulfonyl]octahydrofuro[2,3-c]pyridin-2-yl}prop-2-enamide N-(3-{[(4-cyclohexylphenyl)sulfonyl](methyl) amino}propyl)prop-2-enamide
N-(4-{[3-(acryloylamino)propyl](methyl) sulfamoyl}phenyl)cyclopropanecarboxamide
N-(4-{[3-(acryloylamino)propyl](methyl) sulfamoyl}phenyl)tricyclo[3.3.1.1~3,7~]decane-1-carboxamide
benzyl(4-{[3-(acryloylamino)propyl](methyl) sulfamoyl}phenyl)carbamate
N-[3-(methyl{[4-(piperidin-1-ylcarbonyl)phenyl] sulfonyl}amino)propyl]prop-2-enamide
benzyl 4-{[3-(acryloylamino)propyl](methyl) sulfamoyl}piperidine-1-carboxylate
N-(3-{methyl[(4-nitrophenyl)sulfonyl]amino}propyl)prop-2-enamide
N-(4-{[3-(acryloylamino)propyl](methyl) sulfamoyl}phenyl)tetrahydro-2H-pyran-4-carboxamide
N-{3-[methyl({4-[(3-phenylpropanoyl)amino] phenyl}sulfonyl)amino]propyl}prop-2-enamide
N-(4-{[3-(acryloylamino)propyl](methyl) sulfamoyl}phenyl)-2-phenylcyclopropanecarboxamide
N-(4-{[3-(acryloylamino)propyl](methyl) sulfamoyl}phenyl)-N-methyltetrahydro-2H-pyran-4-carboxamide
4-{[3-(acryloylamino)propyl](methyl)sulfamoyl}-N-benzyl-N-methylbenzamide
4-{[3-(acryloylamino)propyl](methyl)sulfamoyl}-N-(cyclopropylmethyl)benzamide
N-[3-(methyl{[3-(piperidin-1-ylcarbonyl)phenyl] sulfonyl}amino)propyl]prop-2-enamide
N-(4-{[3-(acryloylamino)propyl](methyl) sulfamoyl}phenyl)-N-methylcyclopropanecarboxamide
N-(3-{methyl[(4-{[4-(6-methylpyridin-2-yl)piperazin-1-yl] carbonyl}phenyl)sulfonyl]amino}propyl)prop-2-enamide
4-{[3-(acryloylamino)propyl](methyl)sulfamoyl}-N-[2-(morpholin-4-yl)ethyl]benzamide
4-{[3-(acryloylamino)propyl](methyl)sulfamoyl}-N-(2-phenylethyl)benzamide
4-{[3-(acryloylamino)propyl](methyl)sulfamoyl}-N-methyl-N-(2-phenylethyl)benzamide
N-{3-[{[4-(3,4-dihydroisoquinolin-2(1H)-ylcarbonyl)phenyl]sulfonyl}(methyl)amino]propyl}prop-2-enamide
4-{[3-(acryloylamino)propyl](methyl)sulfamoyl}-N-(2-cyclohexylethyl)benzamide
4-{[3-(acryloylamino)propyl](methyl)sulfamoyl}-N-cyclohexylbenzamide
N-(3-{methyl[(4-{[4-(pyrrolidin-1-ylcarbonyl)piperidin-1-yl]carbonyl}phenyl)sulfonyl]amino}propyl)prop-2-enamide
4-{[3-(acryloylamino)propyl](methyl)sulfamoyl}-N-(3,5-dimethylbenzyl)benzamide
4-{[3-(acryloylamino)propyl](methyl)sulfamoyl}-N-benzylbenzamide
4-{[3-(acryloylamino)propyl](methyl)sulfamoyl}-N-(3,4-difluorobenzyl)benzamide
4-{[3-(acryloylamino)propyl](methyl)sulfamoyl}-N-[4-(trifluoromethyl)benzyl]benzamide
4-{[3-(acryloylamino)propyl](methyl)sulfamoyl}-N-(naphthalen-1-ylmethyl)benzamide
4-{[3-(acryloylamino)propyl](methyl)sulfamoyl}-N-[2-(3,4-dimethylphenyl)ethyl]benzamide
4-{[3-(acryloylamino)propyl](methyl)sulfamoyl}-N-[2-(4-methoxyphenyl)ethyl]benzamide
4-{[3-(acryloylamino)propyl](methyl)sulfamoyl}-N-(2,3-dihydro-1H-inden-2-yl)benzamide
4-{[3-(acryloylamino)propyl](methyl)sulfamoyl}-N-[2-(3-methylphenyl)ethyl]benzamide
N-{3-[({4-[(acetylamino)methyl]phenyl}sulfonyl)(methyl) amino]propyl}prop-2-enamide
N-(3-{methyl[(4-{[3-(naphthalen-1-yl)propanoyl] amino}phenyl)sulfonyl]amino}propyl)prop-2-enamide
N-{3-[({4-[(3-cyclohexylpropanoyl)amino] phenyl}sulfonyl)(methyl)amino]propyl}prop-2-enamide
N-(3-{[(1-benzoylpiperidin-4-yl)sulfonyl](methyl) amino}propyl)prop-2-enamide
N-[3-(methyl{[1-(piperidin-1-ylcarbonyl)piperidin-4-yl] sulfonyl}amino)propyl]prop-2-enamide
N-[3-(methyl{[1-(pyridin-2-ylcarbonyl)piperidin-4-yl] sulfonyl}amino)propyl]prop-2-enamide
N-(4-{[3-(acryloylamino)propyl](methyl) sulfamoyl}phenyl)-4-tert-butylcyclohexanecarboxamide
N-(4-{[3-(acryloylamino)propyl](methyl) sulfamoyl}phenyl)-1-benzofuran-2-carboxamide
benzyl(3-{[3-(acryloylamino)propyl](methyl) sulfamoyl}phenyl)carbamate
N-{3-[methyl({3-[(3-phenylpropanoyl)amino] phenyl}sulfonyl)amino]propyl}prop-2-enamide
N-(3-{[3-(acryloylamino)propyl](methyl) sulfamoyl}phenyl)tetrahydro-2H-pyran-4-carboxamide
4-{[3-(acryloylamino)propyl](methyl)sulfamoyl}-N-(3-phenylpropyl)benzamide
4-{[3-(acryloylamino)propyl](methyl)sulfamoyl}-N-[2-(3-chlorophenyl)ethyl]benzamide
4-{[3-(acryloylamino)propyl](methyl)sulfamoyl}-N-[2-(2-methoxyphenyl)ethyl]benzamide
4-{[3-(acryloylamino)propyl](methyl)sulfamoyl}-N-[2-(2,3-dihydro-1-benzofuran-7-yl)ethyl]benzamide
4-{[3-(acryloylamino)propyl](methyl)sulfamoyl}-N-[2-(tetrahydro-2H-pyran-4-yl)ethyl]benzamide
4-{[3-(acryloylamino)propyl](methyl)sulfamoyl}-N-[2-(4,4-difluoropiperidin-1-yl)ethyl]benzamide
N-{3-[methyl({1-[3-(trifluoromethyl)benzoyl]piperidin-4-yl}sulfonyl)amino]propyl}prop-2-enamide
N-[3-(methyl{[1-(3-phenylpropanoyl)piperidin-4-yl] sulfonyl}amino)propyl]prop-2-enamide
N-{3-[({4-[2-(benzylamino)-2-oxoethyl]phenyl}sulfonyl) (methyl)amino]propyl}prop-2-enamide
4-{[3-(acryloylamino)propyl](methyl)sulfamoyl}-N-(4-tert-butylbenzyl)benzamide
4-{[3-(acryloylamino)propyl](methyl)sulfamoyl}-N-(4-phenylbutyl)benzamide
4-{[3-(acryloylamino)propyl](methyl)sulfamoyl}-N-[2-(4-chlorophenyl)ethyl]benzamide
4-{[3-(acryloylamino)propyl](methyl)sulfamoyl}-N-[2-(quinolin-7-yl)ethyl]benzamide
4-{[3-(acryloylamino)propyl](methyl)sulfamoyl}-N-[2-(naphthalen-2-yl)ethyl]benzamide
4-{[3-(acryloylamino)propyl](methyl)sulfamoyl}-N-(3,4-dihydro-2H-chromen-6-ylmethyl)benzamide
4-{[3-(acryloylamino)propyl](methyl)sulfamoyl}-N-[2-(4-tert-butylphenyl)ethyl]benzamide
4-{[3-(acryloylamino)propyl](methyl)sulfamoyl}-N-[2-(biphenyl-4-yl)ethyl]benzamide
4-{[3-(acryloylamino)propyl](methyl)sulfamoyl}-N-[2-(1,3-benzodioxol-5-yl)ethyl]benzamide
4-{[3-(acryloylamino)propyl](methyl)sulfamoyl}-N-[(1R)-2-phenylcyclopropyl]benzamide
benzyl(4-{[3-(acryloylamino)propyl](methyl) sulfamoyl}phenyl)methylcarbamate
4-{[3-(acryloylamino)propyl](methyl)sulfamoyl}-N-[2-(3,4-dimethoxyphenyl)ethyl]benzamide
4-{[3-(acryloylamino)propyl](methyl)sulfamoyl}-N-{2-[4-(trifluoromethyl)phenyl]ethyl}benzamide 4-{[3-(acryloylamino)propyl](methyl)sulfamoyl}-N-(2-phenylethyl)piperidine-1-carboxamide
N-(4-{[3-(acryloylamino)propyl](methyl)sulfamoyl}phenyl)furan-2-carboxamide
N-(3-{methyl[(4-{[3-(tricyclo[3.3.1.1~3,7~]dec-1-yl)propanoyl]amino}phenyl)sulfonyl]amino}propyl)prop-2-enamide
4-{[3-(acryloylamino)propyl](methyl)sulfamoyl}-N-[2-(tricyclo[3.3.1.1~3,7~]dec-1-yl)ethyl]benzamide
N-{3-[{[1-(cyclopropylcarbonyl)-2,3-dihydro-1H-indol-5-yl]sulfonyl}(methyl)amino]propyl}prop-2-enamide
N-{3-[({2-chloro-4-[(3-phenylpropanoyl)amino]phenyl}sulfonyl)(methyl)amino]propyl}prop-2-enamide
N-(4-{[3-(acryloylamino)propyl](methyl)sulfamoyl}phenyl)-5,6-dihydro-4H-cyclopenta[b]thiophene-2-carboxamide
N-(4-{[3-(acryloylamino)propyl](methyl)sulfamoyl}phenyl)-4,5,6,7-tetrahydro-1H-indole-2-carboxamide
N-{3-[({2-methoxy-4-[(3-phenylpropanoyl)amino]phenyl}sulfonyl)(methyl)amino]propyl}prop-2-enamide
N-(4-{[3-(acryloylamino)propyl](methyl)sulfamoyl}phenyl)-5-(pyrrolidin-1-ylmethyl)furan-2-carboxamide
N-(4-{[3-(acryloylamino)propyl](methyl)sulfamoyl}phenyl)-1-benzothiophene-2-carboxamide
N-(4-{[3-(acryloylamino)propyl](methyl)sulfamoyl}phenyl)-3-methyl-1-benzofuran-2-carboxamide
N-(4-{[3-(acryloylamino)propyl](methyl)sulfamoyl}phenyl)-1H-indole-2-carboxamide
4-{[3-(acryloylamino)propyl](methyl)sulfamoyl}-N-(tricyclo[3.3.1.1~3,7~]dec-1-ylmethyl)benzamide
4-{[3-(acryloylamino)propyl](methyl)sulfamoyl}-N-(1,2,3,4-tetrahydronaphthalen-1-yl)benzamide
N-(4-{[3-(acryloylamino)propyl](methyl)sulfamoyl}phenyl)-4,5,6,7-tetrahydro-1-benzothiophene-2-carboxamide
N-(4-{[3-(acryloylamino)propyl](methyl)sulfamoyl}phenyl)-5-phenylfuran-2-carboxamide
N-(4-{[3-(acryloylamino)propyl](methyl)sulfamoyl}phenyl)-4-phenylthiophene-2-carboxamide
N-{3-[methyl({5-[5-(trifluoromethyl)-1,2-oxazol-3-yl]thiophen-2-yl}sulfonyl)amino]propyl}prop-2-enamide
5-{[3-(acryloylamino)propyl](methyl)sulfamoyl}-N-(2-phenylethyl)furan-2-carboxamide
N-(3-{methyl[(6-phenoxypyridin-3-yl)sulfonyl]amino}propyl)prop-2-enamide
N-[3-(methyl{[6-(morpholin-4-yl)pyridin-3-yl]sulfonyl}amino)propyl]prop-2-enamide
N-(3-{methyl[(6-phenylpyridin-3-yl)sulfonyl]amino}propyl)prop-2-enamide
N-{3-[({3-chloro-4-[(3-phenylpropanoyl)amino]phenyl}sulfonyl)(methyl)amino]propyl}prop-2-enamide
4-{[3-(acryloylamino)propyl](methyl)sulfamoyl}-2-fluoro-N-(2-phenylethyl)benzamide
N-[3-(methyl{[5-(pyridin-2-yl)thiophen-2-yl]sulfonyl}amino)propyl]prop-2-enamide
4-{[3-(acryloylamino)propyl](methyl)sulfamoyl}-2-methoxy-N-(2-phenylethyl)benzamide
N-{3-[(1,3-benzothiazol-6-ylsulfonyl)(methyl)amino]propyl}prop-2-enamide
N-(3-{methyl[(4-methyl-2-phenyl-1,3-thiazol-5-yl)sulfonyl]amino}propyl)prop-2-enamide
N-[3-(methyl{[5-(2-methyl-1,3-thiazol-4-yl)thiophen-2-yl]sulfonyl}amino)propyl]prop-2-enamide
N-[3-(methyl{[5-(1,2-oxazol-5-yl)thiophen-2-yl]sulfonyl}amino)propyl]prop-2-enamide
N-{3-[(2,3-dihydro-1,4-benzodioxin-6-ylsulfonyl)(methyl)amino]propyl}prop-2-enamide
5-{[3-(acryloylamino)propyl](methyl)sulfamoyl}-N-(2-phenylethyl)furan-3-carboxamide
N-{3-[methyl({4-[(phenylacetyl)amino]benzyl}sulfonyl)amino]propyl}prop-2-enamide
N-[3-(methyl{[4-(morpholin-4-ylsulfonyl)phenyl]sulfonyl}amino)propyl]prop-2-enamide
N-[3-(methyl{[5-(1,3-oxazol-5-yl)thiophen-2-yl]sulfonyl}amino)propyl]prop-2-enamide
4-{[3-(acryloylamino)propyl](methyl)sulfamoyl}-2-methyl-N-(2-phenylethyl)benzamide
N-(3-{methyl[(4-phenoxyphenyl)sulfonyl]amino}propyl)prop-2-enamide
N-{3-[methyl({4-[(6-methylpyrazin-2-yl)oxy]phenyl}sulfonyl)amino]propyl}prop-2-enamide
N-{3-[methyl({3-[(6-methylpyrazin-2-yl)oxy]phenyl}sulfonyl)amino]propyl}prop-2-enamide
5-{[3-(acryloylamino)propyl](methyl)sulfamoyl}-1-methyl-N-(2-phenylethyl)-1H-pyrrole-2-carboxamide
N-{3-[{[4-(isoquinolin-3-ylamino)phenyl]sulfonyl}(methyl)amino]propyl}prop-2-enamide
N-(3-{[(3-chloro-4-methylphenyl)sulfonyl](methyl)amino}propyl)prop-2-enamide
N-[3-(methyl{[5-(1,2-oxazol-5-yl)furan-2-yl]sulfonyl}amino)propyl]prop-2-enamide
N-(3-{[(4-{[3-chloro-5-(trifluoromethyl)pyridin-2-yl]oxy}phenyl)sulfonyl](methyl)amino}propyl)prop-2-enamide
N-[3-(methyl{[4-(1H-pyrazol-1-yl)phenyl]sulfonyl}amino)propyl]prop-2-enamide
N-(3-{[(4-methoxy-3-methylphenyl)sulfonyl](methyl)amino}propyl)prop-2-enamide
N-[3-(methyl{[6-(2-phenylethoxy)pyridin-3-yl]sulfonyl}amino)propyl]prop-2-enamide
N-{3-[({5-[(acetylamino)methyl]thiophen-2-yl}sulfonyl)(methyl)amino]propyl}prop-2-enamide
N-(3-{methyl[(5-methyl-1-phenyl-1H-pyrazol-4-yl)sulfonyl]amino}propyl)prop-2-enamide
N-[3-(methyl{[4-(1-methyl-1H-pyrazol-5-yl)phenyl]sulfonyl}amino)propyl]prop-2-enamide
N-[3-(methyl{[3-(1-methyl-1H-pyrazol-5-yl)phenyl]sulfonyl}amino)propyl]prop-2-enamide
N-(3-{[(2,2-dimethyl-3,4-dihydro-2H-chromen-6-yl)sulfonyl](methyl)amino}propyl)prop-2-enamide
N-(3-{methyl[(5-phenylthiophen-2-yl)sulfonyl]amino}propyl)prop-2-enamide
N-{3-[{[4-(cyclopentyloxy)phenyl]sulfonyl}(methyl)amino]propyl}prop-2-enamide
N-[3-(methyl{[5-(pyrrolidin-1-ylcarbonyl)-1H-pyrrol-3-yl]sulfonyl}amino)propyl]prop-2-enamide
N-[3-(methyl{[4-(2-methyl-1,3-thiazol-4-yl)phenyl]sulfonyl}amino)propyl]prop-2-enamide
N-[3-(methyl{[4-(pyridin-2-yloxy)phenyl]sulfonyl}amino)propyl]prop-2-enamide
N-(3-{methyl[(2-oxo-1,2,3,4-tetrahydroquinolin-6-yl)sulfonyl]amino}propyl)prop-2-enamide
N-{3-[(4-cyclohexylphenyl)sulfonyl]-3-azabicyclo[3.1.0]hex-6-yl}prop-2-enamide
N-(4-{[6-(acryloylamino)-3-azabicyclo[3.1.0]hex-3-yl]sulfonyl}phenyl)cyclopropanecarboxamide
N-(4-{[6-(acryloylamino)-3-azabicyclo[3.1.0]hex-3-yl]sulfonyl}phenyl)tricyclo[3.3.1.1~3,7~]decane-1-carboxamide benzyl(4-{[6-(acryloylamino)-3-azabicyclo[3.1.0]hex-3-yl]sulfonyl}phenyl)carbamate
N-(3-{[4-(piperidin-1-ylcarbonyl)phenyl]sulfonyl}-3-azabicyclo[3.1.0]hex-6-yl)prop-2-enamide
benzyl 4-{[6-(acryloylamino)-3-azabicyclo[3.1.0]hex-3-yl]sulfonyl}piperidine-1-carboxylate
N-{3-[(4-nitrophenyl)sulfonyl]-3-azabicyclo[3.1.0]hex-6-yl}prop-2-enamide
N-(4-{[6-(acryloylamino)-3-azabicyclo[3.1.0]hex-3-yl]sulfonyl}phenyl)tetrahydro-2H-pyran-4-carboxamide
N-[3-({4-[(3-phenylpropanoyl)amino]phenyl}sulfonyl)-3-azabicyclo[3.1.0]hex-6-yl]prop-2-enamide
N-(4-{[6-(acryloylamino)-3-azabicyclo[3.1.0]hex-3-yl]sulfonyl}phenyl)-2-phenylcyclopropanecarboxamide
N-(4-{[6-(acryloylamino)-3-azabicyclo[3.1.0]hex-3-yl]sulfonyl}phenyl)-N-methyltetrahydro-2H-pyran-4-carboxamide
4-{[6-(acryloylamino)-3-azabicyclo[3.1.0]hex-3-yl]sulfonyl}-N-benzyl-N-methylbenzamide
4-{[6-(acryloylamino)-3-azabicyclo[3.1.0]hex-3-yl]sulfonyl}-N-(cyclopropylmethyl)benzamide
N-(3-{[3-(piperidin-1-ylcarbonyl)phenyl]sulfonyl}-3-azabicyclo[3.1.0]hex-6-yl)prop-2-enamide
N-(4-{[6-(acryloylamino)-3-azabicyclo[3.1.0]hex-3-yl]sulfonyl}phenyl)-N-methylcyclopropanecarboxamide
N-{3-[(4-{[4-(6-methylpyridin-2-yl)piperazin-1-yl]carbonyl}phenyl)sulfonyl]-3-azabicyclo[3.1.0]hex-6-yl}prop-2-enamide
4-{[6-(acryloylamino)-3-azabicyclo[3.1.0]hex-3-yl]sulfonyl}-N-[2-(morpholin-4-yl)ethyl]benzamide
4-{[6-(acryloylamino)-3-azabicyclo[3.1.0]hex-3-yl]sulfonyl}-N-(2-phenylethyl)benzamide
4-{[6-(acryloylamino)-3-azabicyclo[3.1.0]hex-3-yl]sulfonyl}-N-methyl-N-(2-phenylethyl)benzamide
N-(3-{[4-(3,4-dihydroisoquinolin-2(1H)-ylcarbonyl)phenyl]sulfonyl}-3-azabicyclo[3.1.0]hex-6-yl)prop-2-enamide
4-{[6-(acryloylamino)-3-azabicyclo[3.1.0]hex-3-yl]sulfonyl}-N-(2-cyclohexylethyl)benzamide
4-{[6-(acryloylamino)-3-azabicyclo[3.1.0]hex-3-yl]sulfonyl}-N-cyclohexylbenzamide
N-{3-[(4-{[4-(pyrrolidin-1-ylcarbonyl)piperidin-1-yl]carbonyl}phenyl)sulfonyl]-3-azabicyclo[3.1.0]hex-6-yl}prop-2-enamide
4-{[6-(acryloylamino)-3-azabicyclo[3.1.0]hex-3-yl]sulfonyl}-N-(3,5-dimethylbenzyl)benzamide
4-{[6-(acryloylamino)-3-azabicyclo[3.1.0]hex-3-yl]sulfonyl}-N-benzylbenzamide
4-{[6-(acryloylamino)-3-azabicyclo[3.1.0]hex-3-yl]sulfonyl}-N-(3,4-difluorobenzyl)benzamide
4-{[6-(acryloylamino)-3-azabicyclo[3.1.0]hex-3-yl]sulfonyl}-N-[4-(trifluoromethyl)benzyl]benzamide
4-{[6-(acryloylamino)-3-azabicyclo[3.1.0]hex-3-yl]sulfonyl}-N-(naphthalen-1-ylmethyl)benzamide
4-{[6-(acryloylamino)-3-azabicyclo[3.1.0]hex-3-yl]sulfonyl}-N-[2-(3,4-dimethylphenyl)ethyl]benzamide
4-{[6-(acryloylamino)-3-azabicyclo[3.1.0]hex-3-yl]sulfonyl}-N-[2-(4-methoxyphenyl)ethyl]benzamide
4-{[6-(acryloylamino)-3-azabicyclo[3.1.0]hex-3-yl]sulfonyl}-N-(2,3-dihydro-1H-inden-2-yl)benzamide
4-{[6-(acryloylamino)-3-azabicyclo[3.1.0]hex-3-yl]sulfonyl}-N-[2-(3-methylphenyl)ethyl]benzamide
N-[3-({4-[(acetylamino)methyl]phenyl}sulfonyl)-3-azabicyclo[3.1.0]hex-6-yl]prop-2-enamide
N-{3-[(4-{[3-(naphthalen-1-yl)propanoyl]amino}phenyl)sulfonyl]-3-azabicyclo[3.1.0]hex-6-yl}prop-2-enamide
N-[3-({4-[(3-cyclohexylpropanoyl)amino]phenyl}sulfonyl)-3-azabicyclo[3.1.0]hex-6-yl]prop-2-enamide
N-{3-[(1-benzoylpiperidin-4-yl)sulfonyl]-3-azabicyclo[3.1.0]hex-6-yl}prop-2-enamide
N-(3-{[1-(piperidin-1-ylcarbonyl)piperidin-4-yl]sulfonyl}-3-azabicyclo[3.1.0]hex-6-yl)prop-2-enamide
N-(3-{[1-(pyridin-2-ylcarbonyl)piperidin-4-yl]sulfonyl}-3-azabicyclo[3.1.0]hex-6-yl)prop-2-enamide
N-(4-{[6-(acryloylamino)-3-azabicyclo[3.1.0]hex-3-yl]sulfonyl}phenyl)-4-tert-butylcyclohexanecarboxamide
N-(4-{[6-(acryloylamino)-3-azabicyclo[3.1.0]hex-3-yl]sulfonyl}phenyl)-1-benzofuran-2-carboxamide
benzyl(3-{[6-(acryloylamino)-3-azabicyclo[3.1.0]hex-3-yl]sulfonyl}phenyl)carbamate
N-[3-({3-[(3-phenylpropanoyl)amino]phenyl}sulfonyl)-3-azabicyclo[3.1.0]hex-6-yl]prop-2-enamide
N-(3-{[6-(acryloylamino)-3-azabicyclo[3.1.0]hex-3-yl]sulfonyl}phenyl)tetrahydro-2H-pyran-4-carboxamide
4-{[6-(acryloylamino)-3-azabicyclo[3.1.0]hex-3-yl]sulfonyl}-N-(3-phenylpropyl)benzamide
4-{[6-(acryloylamino)-3-azabicyclo[3.1.0]hex-3-yl]sulfonyl}-N-[2-(3-chlorophenyl)ethyl]benzamide
4-{[6-(acryloylamino)-3-azabicyclo[3.1.0]hex-3-yl]sulfonyl}-N-[2-(2-methoxyphenyl)ethyl]benzamide
4-{[6-(acryloylamino)-3-azabicyclo[3.1.0]hex-3-yl]sulfonyl}-N-[2-(2,3-dihydro-1-benzofuran-7-yl)ethyl]benzamide
4-{[6-(acryloylamino)-3-azabicyclo[3.1.0]hex-3-yl]sulfonyl}-N-[2-(tetrahydro-2H-pyran-4-yl)ethyl]benzamide
4-{[6-(acryloylamino)-3-azabicyclo[3.1.0]hex-3-yl]sulfonyl}-N-[2-(4,4-difluoropiperidin-1-yl)ethyl]benzamide
N-[3-({1-[3-(trifluoromethyl)benzoyl]piperidin-4-yl}sulfonyl)-3-azabicyclo[3.1.0]hex-6-yl]prop-2-enamide
N-(3-{[1-(3-phenylpropanoyl)piperidin-4-yl]sulfonyl}-3-azabicyclo[3.1.0]hex-6-yl)prop-2-enamide
N-[3-({4-[2-(benzylamino)-2-oxoethyl]phenyl}sulfonyl)-3-azabicyclo[3.1.0]hex-6-yl]prop-2-enamide
4-{[6-(acryloylamino)-3-azabicyclo[3.1.0]hex-3-yl]sulfonyl}-N-(4-tert-butylbenzyl)benzamide
4-{[6-(acryloylamino)-3-azabicyclo[3.1.0]hex-3-yl]sulfonyl}-N-(4-phenylbutyl)benzamide
4-{[6-(acryloylamino)-3-azabicyclo[3.1.0]hex-3-yl]sulfonyl}-N-[2-(4-chlorophenyl)ethyl]benzamide
4-{[6-(acryloylamino)-3-azabicyclo[3.1.0]hex-3-yl]sulfonyl}-N-[2-(quinolin-7-yl)ethyl]benzamide
4-{[6-(acryloylamino)-3-azabicyclo[3.1.0]hex-3-yl]sulfonyl}-N-[2-(naphthalen-2-yl)ethyl]benzamide
4-{[6-(acryloylamino)-3-azabicyclo[3.1.0]hex-3-yl]sulfonyl}-N-(3,4-dihydro-2H-chromen-6-ylmethyl)benzamide
4-{[6-(acryloylamino)-3-azabicyclo[3.1.0]hex-3-yl]sulfonyl}-N-[2-(4-tert-butylphenyl)ethyl]benzamide
4-{[6-(acryloylamino)-3-azabicyclo[3.1.0]hex-3-yl]sulfonyl}-N-[2-(biphenyl-4-yl)ethyl]benzamide
4-{[6-(acryloylamino)-3-azabicyclo[3.1.0]hex-3-yl]sulfonyl}-N-[2-(1,3-benzodioxol-5-yl)ethyl]benzamide
4-{[6-(acryloylamino)-3-azabicyclo[3.1.0]hex-3-yl]sulfonyl}-N-[(1R)-2-phenylcyclopropyl]benzamide
benzyl(4-{[6-(acryloylamino)-3-azabicyclo[3.1.0]hex-3-yl]sulfonyl}phenyl)methylcarbamate
4-{[6-(acryloylamino)-3-azabicyclo[3.1.0]hex-3-yl]sulfonyl}-N-[2-(3,4-dimethoxyphenyl)ethyl]benzamide
4-{[6-(acryloylamino)-3-azabicyclo[3.1.0]hex-3-yl]sulfonyl}-N-{2-[4-(trifluoromethyl)phenyl]ethyl}benzamide
4-{[6-(acryloylamino)-3-azabicyclo[3.1.0]hex-3-yl]sulfonyl}-N-(2-phenylethyl)piperidine-1-carboxamide N-(4-{[6-(acryloylamino)-3-azabicyclo[3.1.0]hex-3-yl]sulfonyl}phenyl)furan-2-carboxamide
N-{3-[(4-{[3-(tricyclo[3.3.1.1~3,7~]dec-1-yl)propanoyl]amino}phenyl)sulfonyl]-3-azabicyclo[3.1.0]hex-6-yl}prop-2-enamide
4-{[6-(acryloylamino)-3-azabicyclo[3.1.0]hex-3-yl]sulfonyl}-N-[2-(tricyclo[3.3.1.1~3,7~]dec-1-yl)ethyl]benzamide
N-(3-{[1-(cyclopropylcarbonyl)-2,3-dihydro-1H-indol-5-yl]sulfonyl}-3-azabicyclo[3.1.0]hex-6-yl)prop-2-enamide
N-[3-({2-chloro-4-[(3-phenylpropanoyl)amino]phenyl}sulfonyl)-3-azabicyclo[3.1.0]hex-6-yl]prop-2-enamide
N-(4-{[6-(acryloylamino)-3-azabicyclo[3.1.0]hex-3-yl]sulfonyl}phenyl)-5,6-dihydro-4H-cyclopenta[b]thiophene-2-carboxamide
N-(4-{[6-(acryloylamino)-3-azabicyclo[3.1.0]hex-3-yl]sulfonyl}phenyl)-4,5,6,7-tetrahydro-1H-indole-2-carboxamide
N-[3-({2-methoxy-4-[(3-phenylpropanoyl)amino]phenyl}sulfonyl)-3-azabicyclo[3.1.0]hex-6-yl]prop-2-enamide
N-(4-{[6-(acryloylamino)-3-azabicyclo[3.1.0]hex-3-yl]sulfonyl}phenyl)-5-(pyrrolidin-1-ylmethyl)furan-2-carboxamide
N-(4-{[6-(acryloylamino)-3-azabicyclo[3.1.0]hex-3-yl]sulfonyl}phenyl)-1-benzothiophene-2-carboxamide
N-(4-{[6-(acryloylamino)-3-azabicyclo[3.1.0]hex-3-yl]sulfonyl}phenyl)-3-methyl-1-benzofuran-2-carboxamide
N-(4-{[6-(acryloylamino)-3-azabicyclo[3.1.0]hex-3-yl]sulfonyl}phenyl)-1H-indole-2-carboxamide
4-{[6-(acryloylamino)-3-azabicyclo[3.1.0]hex-3-yl]sulfonyl}-N-(tricyclo[3.3.1.1~3,7~]dec-1-ylmethyl)benzamide
4-{[6-(acryloylamino)-3-azabicyclo[3.1.0]hex-3-yl]sulfonyl}-N-(1,2,3,4-tetrahydronaphthalen-1-yl)benzamide
N-(4-{[6-(acryloylamino)-3-azabicyclo[3.1.0]hex-3-yl]sulfonyl}phenyl)-4,5,6,7-tetrahydro-1-benzothiophene-2-carboxamide
N-(4-{[6-(acryloylamino)-3-azabicyclo[3.1.0]hex-3-yl]sulfonyl}phenyl)-5-phenylfuran-2-carboxamide
N-(4-{[6-(acryloylamino)-3-azabicyclo[3.1.0]hex-3-yl]sulfonyl}phenyl)-4-phenylthiophene-2-carboxamide
N-[3-({5-[5-(trifluoromethyl)-1,2-oxazol-3-yl]thiophen-2-yl}sulfonyl)-3-azabicyclo[3.1.0]hex-6-yl]prop-2-enamide
5-{[6-(acryloylamino)-3-azabicyclo[3.1.0]hex-3-yl]sulfonyl}-N-(2-phenylethyl)furan-2-carboxamide
N-{3-[(6-phenoxypyridin-3-yl)sulfonyl]-3-azabicyclo[3.1.0]hex-6-yl}prop-2-enamide
N-(3-{[6-(morpholin-4-yl)pyridin-3-yl]sulfonyl}-3-azabicyclo[3.1.0]hex-6-yl)prop-2-enamide
N-{3-[(6-phenylpyridin-3-yl)sulfonyl]-3-azabicyclo[3.1.0]hex-6-yl}prop-2-enamide
N-[3-({3-chloro-4-[(3-phenylpropanoyl)amino]phenyl}sulfonyl)-3-azabicyclo[3.1.0]hex-6-yl]prop-2-enamide
4-{[6-(acryloylamino)-3-azabicyclo[3.1.0]hex-3-yl]sulfonyl}-2-fluoro-N-(2-phenylethyl)benzamide
N-[3-({5-(pyridin-2-yl)thiophen-2-yl]sulfonyl}-3-azabicyclo[3.1.0]hex-6-yl)prop-2-enamide
4-{[6-(acryloylamino)-3-azabicyclo[3.1.0]hex-3-yl]sulfonyl}-2-methoxy-N-(2-phenylethyl)benzamide
N-[3-(1,3-benzothiazol-6-ylsulfonyl)-3-azabicyclo[3.1.0]hex-6-yl]prop-2-enamide
N-{3-[(4-methyl-2-phenyl-1,3-thiazol-5-yl)sulfonyl]-3-azabicyclo[3.1.0]hex-6-yl}prop-2-enamide
N-(3-{[5-(2-methyl-1,3-thiazol-4-yl)thiophen-2-yl]sulfonyl}-3-azabicyclo[3.1.0]hex-6-yl)prop-2-enamide
N-(3-{[5-(1,2-oxazol-5-yl)thiophen-2-yl]sulfonyl}-3-azabicyclo[3.1.0]hex-6-yl)prop-2-enamide
N-[3-(2,3-dihydro-1,4-benzodioxin-6-ylsulfonyl)-3-azabicyclo[3.1.0]hex-6-yl]prop-2-enamide
5-{[6-(acryloylamino)-3-azabicyclo[3.1.0]hex-3-yl]sulfonyl}-N-(2-phenylethyl)furan-3-carboxamide
N-[3-({4-[(phenylacetyl)amino]benzyl}sulfonyl)-3-azabicyclo[3.1.0]hex-6-yl]prop-2-enamide
N-(3-{[4-(morpholin-4-ylsulfonyl)phenyl]sulfonyl}-3-azabicyclo[3.1.0]hex-6-yl)prop-2-enamide
N-(3-{[5-(1,3-oxazol-5-yl)thiophen-2-yl]sulfonyl}-3-azabicyclo[3.1.0]hex-6-yl)prop-2-enamide
4-{[6-(acryloylamino)-3-azabicyclo[3.1.0]hex-3-yl]sulfonyl}-2-methyl-N-(2-phenylethyl)benzamide
N-{3-[(4-phenoxyphenyl)sulfonyl]-3-azabicyclo[3.1.0]hex-6-yl}prop-2-enamide
N-[3-({4-[(6-methylpyrazin-2-yl)oxy]phenyl}sulfonyl)-3-azabicyclo[3.1.0]hex-6-yl]prop-2-enamide
N-[3-({3-[(6-methylpyrazin-2-yl)oxy]phenyl}sulfonyl)-3-azabicyclo[3.1.0]hex-6-yl]prop-2-enamide
5-{[6-(acryloylamino)-3-azabicyclo[3.1.0]hex-3-yl]sulfonyl}-1-methyl-N-(2-phenylethyl)-1H-pyrrole-2-carboxamide
N-(3-{[4-(isoquinolin-3-ylamino)phenyl]sulfonyl}-3-azabicyclo[3.1.0]hex-6-yl)prop-2-enamide
N-{3-[(3-chloro-4-methylphenyl)sulfonyl]-3-azabicyclo[3.1.0]hex-6-yl}prop-2-enamide
N-(3-{[5-(1,2-oxazol-5-yl)furan-2-yl]sulfonyl}-3-azabicyclo[3.1.0]hex-6-yl)prop-2-enamide
N-{3-[(4-{[3-chloro-5-(trifluoromethyl)pyridin-2-yl]oxy}phenyl)sulfonyl]-3-azabicyclo[3.1.0]hex-6-yl}prop-2-enamide
N-(3-{[4-(1H-pyrazol-1-yl)phenyl]sulfonyl}-3-azabicyclo[3.1.0]hex-6-yl)prop-2-enamide
N-{3-[(4-methoxy-3-methylphenyl)sulfonyl]-3-azabicyclo[3.1.0]hex-6-yl}prop-2-enamide
N-(3-{[6-(2-phenylethoxy)pyridin-3-yl]sulfonyl}-3-azabicyclo[3.1.0]hex-6-yl)prop-2-enamide
N-[3-({5-[(acetylamino)methyl]thiophen-2-yl}sulfonyl)-3-azabicyclo[3.1.0]hex-6-yl]prop-2-enamide
N-{3-[(5-methyl-1-phenyl-1H-pyrazol-4-yl)sulfonyl]-3-azabicyclo[3.1.0]hex-6-yl}prop-2-enamide
N-(3-{[4-(1-methyl-1H-pyrazol-5-yl)phenyl]sulfonyl}-3-azabicyclo[3.1.0]hex-6-yl)prop-2-enamide
N-(3-{[3-(1-methyl-1H-pyrazol-5-yl)phenyl]sulfonyl}-3-azabicyclo[3.1.0]hex-6-yl)prop-2-enamide
N-{3-[(2,2-dimethyl-3,4-dihydro-2H-chromen-6-yl)sulfonyl]-3-azabicyclo[3.1.0]hex-6-yl}prop-2-enamide
N-{3-[(5-phenylthiophen-2-yl)sulfonyl]-3-azabicyclo[3.1.0]hex-6-yl}prop-2-enamide
N-(3-{[4-(cyclopentyloxy)phenyl]sulfonyl}-3-azabicyclo[3.1.0]hex-6-yl)prop-2-enamide
N-(3-{[5-(pyrrolidin-1-ylcarbonyl)-1H-pyrrol-3-yl]sulfonyl}-3-azabicyclo[3.1.0]hex-6-yl)prop-2-enamide
N-(3-{[4-(2-methyl-1,3-thiazol-4-yl)phenyl]sulfonyl}-3-azabicyclo[3.1.0]hex-6-yl)prop-2-enamide
N-(3-{[4-(pyridin-2-yloxy)phenyl]sulfonyl}-3-azabicyclo[3.1.0]hex-6-yl)prop-2-enamide
N-{3-[(2-oxo-1,2,3,4-tetrahydroquinolin-6-yl)sulfonyl]-3-azabicyclo[3.1.0]hex-6-yl}prop-2-enamide
N-{1-[(4-cyclohexylphenyl)sulfonyl]azetidin-3-yl}prop-2-enamide N-(4-{[3-(acryloylamino)azetidin-1-yl]sulfonyl}phenyl)cyclopropanecarboxamide
N-(4-{[3-(acryloylamino)azetidin-1-yl]sulfonyl}phenyl)tricyclo[3.3.1.1~3,7~]decane-1-carboxamide
benzyl(4-{[3-(acryloylamino)azetidin-1-yl]sulfonyl}phenyl)carbamate
N-(1-{[4-(piperidin-1-ylcarbonyl)phenyl]sulfonyl}azetidin-3-yl)prop-2-enamide
benzyl 4-{[3-(acryloylamino)azetidin-1-yl]sulfonyl}piperidine-1-carboxylate
N-{1-[(4-nitrophenyl)sulfonyl]azetidin-3-yl}prop-2-enamide
N-(4-{[3-(acryloylamino)azetidin-1-yl]sulfonyl}phenyl)tetrahydro-2H-pyran-4-carboxamide
N-[1-({4-[(3-phenylpropanoyl)amino]phenyl}sulfonyl)azetidin-3-yl]prop-2-enamide
N-(4-{[3-(acryloylamino)azetidin-1-yl]sulfonyl}phenyl)-2-phenylcyclopropanecarboxamide
N-(4-{[3-(acryloylamino)azetidin-1-yl]sulfonyl}phenyl)-N-methyltetrahydro-2H-pyran-4-carboxamide
4-{[3-(acryloylamino)azetidin-1-yl]sulfonyl}-N-benzyl-N-methylbenzamide
4-{[3-(acryloylamino)azetidin-1-yl]sulfonyl}-N-(cyclopropylmethyl)benzamide
N-(1-{[3-(piperidin-1-ylcarbonyl)phenyl]sulfonyl}azetidin-3-yl)prop-2-enamide
N-(4-{[3-(acryloylamino)azetidin-1-yl]sulfonyl}phenyl)-N-methylcyclopropanecarboxamide
N-{1-[(4-{[4-(6-methylpyridin-2-yl)piperazin-1-yl]carbonyl}phenyl)sulfonyl]azetidin-3-yl}prop-2-enamide
4-{[3-(acryloylamino)azetidin-1-yl]sulfonyl}-N-[2-(morpholin-4-yl)ethyl]benzamide
4-{[3-(acryloylamino)azetidin-1-yl]sulfonyl}-N-(2-phenylethyl)benzamide
4-{[3-(acryloylamino)azetidin-1-yl]sulfonyl}-N-methyl-N-(2-phenylethyl)benzamide
N-(1-{[4-(3,4-dihydroisoquinolin-2(1H)-ylcarbonyl)phenyl]sulfonyl}azetidin-3-yl)prop-2-enamide
4-{[3-(acryloylamino)azetidin-1-yl]sulfonyl}-N-(2-cyclohexylethyl)benzamide
4-{[3-(acryloylamino)azetidin-1-yl]sulfonyl}-N-cyclohexylbenzamide
N-{1-[(4-{[4-(pyrrolidin-1-ylcarbonyl)piperidin-1-yl]carbonyl}phenyl)sulfonyl]azetidin-3-yl}prop-2-enamide
4-{[3-(acryloylamino)azetidin-1-yl]sulfonyl}-N-(3,5-dimethylbenzyl)benzamide
4-{[3-(acryloylamino)azetidin-1-yl]sulfonyl}-N-benzylbenzamide
4-{[3-(acryloylamino)azetidin-1-yl]sulfonyl}-N-(3,4-difluorobenzyl)benzamide
4-{[3-(acryloylamino)azetidin-1-yl]sulfonyl}-N-[4-(trifluoromethyl)benzyl]benzamide
4-{[3-(acryloylamino)azetidin-1-yl]sulfonyl}-N-(naphthalen-1-ylmethyl)benzamide
4-{[3-(acryloylamino)azetidin-1-yl]sulfonyl}-N-[2-(3,4-dimethylphenyl)ethyl]benzamide
4-{[3-(acryloylamino)azetidin-1-yl]sulfonyl}-N-[2-(4-methoxyphenyl)ethyl]benzamide
4-{[3-(acryloylamino)azetidin-1-yl]sulfonyl}-N-(2,3-dihydro-1H-inden-2-yl)benzamide
4-{[3-(acryloylamino)azetidin-1-yl]sulfonyl}-N-[2-(3-methylphenyl)ethyl]benzamide
N-[1-({4-[(acetylamino)methyl]phenyl}sulfonyl)azetidin-3-yl]prop-2-enamide
N-{1-[(4-{[3-(naphthalen-1-yl)propanoyl]amino}phenyl)sulfonyl]azetidin-3-yl}prop-2-enamide
N-[1-({4-[(3-cyclohexylpropanoyl)amino]phenyl}sulfonyl)azetidin-3-yl]prop-2-enamide
N-{1-[(1-benzoylpiperidin-4-yl)sulfonyl]azetidin-3-yl}prop-2-enamide
N-(1-{[1-(piperidin-1-ylcarbonyl)piperidin-4-yl]sulfonyl}azetidin-3-yl)prop-2-enamide
N-(1-{[1-(pyridin-2-ylcarbonyl)piperidin-4-yl]sulfonyl}azetidin-3-yl)prop-2-enamide
N-(4-{[3-(acryloylamino)azetidin-1-yl]sulfonyl}phenyl)-4-tert-butylcyclohexanecarboxamide
N-(4-{[3-(acryloylamino)azetidin-1-yl]sulfonyl}phenyl)-1-benzofuran-2-carboxamide
benzyl(3-{[3-(acryloylamino)azetidin-1-yl]sulfonyl}phenyl)carbamate
N-[1-({3-[(3-phenylpropanoyl)amino]phenyl}sulfonyl)azetidin-3-yl]prop-2-enamide
N-(3-{[3-(acryloylamino)azetidin-1-yl]sulfonyl}phenyl)tetrahydro-2H-pyran-4-carboxamide
4-{[3-(acryloylamino)azetidin-1-yl]sulfonyl}-N-(3-phenylpropyl)benzamide
4-{[3-(acryloylamino)azetidin-1-yl]sulfonyl}-N-[2-(3-chlorophenyl)ethyl]benzamide
4-{[3-(acryloylamino)azetidin-1-yl]sulfonyl}-N-[2-(2-methoxyphenyl)ethyl]benzamide
4-{[3-(acryloylamino)azetidin-1-yl]sulfonyl}-N-[2-(2,3-dihydro-1-benzofuran-7-yl)ethyl]benzamide
4-{[3-(acryloylamino)azetidin-1-yl]sulfonyl}-N-[2-(tetrahydro-2H-pyran-4-yl)ethyl]benzamide
4-{[3-(acryloylamino)azetidin-1-yl]sulfonyl}-N-[2-(4,4-difluoropiperidin-1-yl)ethyl]benzamide
N-[1-({1-[3-(trifluoromethyl)benzoyl]piperidin-4-yl}sulfonyl)azetidin-3-yl]prop-2-enamide
N-(1-{[1-(3-phenylpropanoyl)piperidin-4-yl]sulfonyl}azetidin-3-yl)prop-2-enamide
N-[1-({4-[2-(benzylamino)-2-oxoethyl]phenyl}sulfonyl)azetidin-3-yl]prop-2-enamide
4-{[3-(acryloylamino)azetidin-1-yl]sulfonyl}-N-(4-tert-butylbenzyl)benzamide
4-{[3-(acryloylamino)azetidin-1-yl]sulfonyl}-N-(4-phenylbutyl)benzamide
4-{[3-(acryloylamino)azetidin-1-yl]sulfonyl}-N-[2-(4-chlorophenyl)ethyl]benzamide
4-{[3-(acryloylamino)azetidin-1-yl]sulfonyl}-N-[2-(quinolin-7-yl)ethyl]benzamide
4-{[3-(acryloylamino)azetidin-1-yl]sulfonyl}-N-[2-(naphthalen-2-yl)ethyl]benzamide
4-{[3-(acryloylamino)azetidin-1-yl]sulfonyl}-N-(3,4-dihydro-2H-chromen-6-ylmethyl)benzamide
4-{[3-(acryloylamino)azetidin-1-yl]sulfonyl}-N-[2-(4-tert-butylphenyl)ethyl]benzamide
4-{[3-(acryloylamino)azetidin-1-yl]sulfonyl}-N-[2-(biphenyl-4-yl)ethyl]benzamide
4-{[3-(acryloylamino)azetidin-1-yl]sulfonyl}-N-[2-(1,3-benzodioxol-5-yl)ethyl]benzamide
4-{[3-(acryloylamino)azetidin-1-yl]sulfonyl}-N-[(1R)-2-phenylcyclopropyl]benzamide
benzyl(4-{[3-(acryloylamino)azetidin-1-yl]sulfonyl}phenyl)methylcarbamate
4-{[3-(acryloylamino)azetidin-1-yl]sulfonyl}-N-[2-(3,4-dimethoxyphenyl)ethyl]benzamide
4-{[3-(acryloylamino)azetidin-1-yl]sulfonyl}-N-{2-[4-(trifluoromethyl)phenyl]ethyl}benzamide
4-{[3-(acryloylamino)azetidin-1-yl]sulfonyl}-N-(2-phenylethyl)piperidine-1-carboxamide
N-(4-{[3-(acryloylamino)azetidin-1-yl]sulfonyl}phenyl)furan-2-carboxamide N-{1-[(4-{[3-(tricyclo[3.3.1.1~3,7~]dec-1-yl)propanoyl]amino}phenyl)sulfonyl]azetidin-3-yl}prop-2-enamide
4-{[3-(acryloylamino)azetidin-1-yl]sulfonyl}-N-[2-(tricyclo[3.3.1.1~3,7~]dec-1-yl)ethyl]benzamide
N-(1-{[1-(cyclopropylcarbonyl)-2,3-dihydro-1H-indol-5-yl]sulfonyl}azetidin-3-yl)prop-2-enamide
N-[1-({2-chloro-4-[(3-phenylpropanoyl)amino]phenyl}sulfonyl)azetidin-3-yl]prop-2-enamide
N-(4-{[3-(acryloylamino)azetidin-1-yl]sulfonyl}phenyl)-5,6-dihydro-4H-cyclopenta[b]thiophene-2-carboxamide
N-(4-{[3-(acryloylamino)azetidin-1-yl]sulfonyl}phenyl)-4,5,6,7-tetrahydro-1H-indole-2-carboxamide
N-[1-({2-methoxy-4-[(3-phenylpropanoyl)amino]phenyl}sulfonyl)azetidin-3-yl]prop-2-enamide
N-(4-{[3-(acryloylamino)azetidin-1-yl]sulfonyl}phenyl)-5-(pyrrolidin-1-ylmethyl)furan-2-carboxamide
N-(4-{[3-(acryloylamino)azetidin-1-yl]sulfonyl}phenyl)-1-benzothiophene-2-carboxamide
N-(4-{[3-(acryloylamino)azetidin-1-yl]sulfonyl}phenyl)-3-methyl-1-benzofuran-2-carboxamide
N-(4-{[3-(acryloylamino)azetidin-1-yl]sulfonyl}phenyl)-1H-indole-2-carboxamide
4-{[3-(acryloylamino)azetidin-1-yl]sulfonyl}-N-(tricyclo[3.3.1.1~3,7~]dec-1-ylmethyl)benzamide
4-{[3-(acryloylamino)azetidin-1-yl]sulfonyl}-N-(1,2,3,4-tetrahydronaphthalen-1-yl)benzamide
N-(4-{[3-(acryloylamino)azetidin-1-yl]sulfonyl}phenyl)-4,5,6,7-tetrahydro-1-benzothiophene-2-carboxamide
N-(4-{[3-(acryloylamino)azetidin-1-yl]sulfonyl}phenyl)-5-phenylfuran-2-carboxamide
N-(4-{[3-(acryloylamino)azetidin-1-yl]sulfonyl}phenyl)-4-phenylthiophene-2-carboxamide
N-[1-({5-[5-(trifluoromethyl)-1,2-oxazol-3-yl]thiophen-2-yl}sulfonyl)azetidin-3-yl]prop-2-enamide
5-{[3-(acryloylamino)azetidin-1-yl]sulfonyl}-N-(2-phenylethyl)furan-2-carboxamide
N-{1-[(6-phenoxypyridin-3-yl)sulfonyl]azetidin-3-yl}prop-2-enamide
N-(1-{[6-(morpholin-4-yl)pyridin-3-yl]sulfonyl}azetidin-3-yl)prop-2-enamide
N-{1-[(6-phenylpyridin-3-yl)sulfonyl]azetidin-3-yl}prop-2-enamide
N-[1-({3-chloro-4-[(3-phenylpropanoyl)amino]phenyl}sulfonyl)azetidin-3-yl]prop-2-enamide
4-{[3-(acryloylamino)azetidin-1-yl]sulfonyl}-2-fluoro-N-(2-phenylethyl)benzamide
N-(1-{[5-(pyridin-2-yl)thiophen-2-yl]sulfonyl}azetidin-3-yl)prop-2-enamide
4-{[3-(acryloylamino)azetidin-1-yl]sulfonyl}-2-methoxy-N-(2-phenylethyl)benzamide
N-[1-(1,3-benzothiazol-6-ylsulfonyl)azetidin-3-yl]prop-2-enamide
N-{1-[(4-methyl-2-phenyl-1,3-thiazol-5-yl)sulfonyl]azetidin-3-yl}prop-2-enamide
N-(1-{[5-(2-methyl-1,3-thiazol-4-yl)thiophen-2-yl]sulfonyl}azetidin-3-yl)prop-2-enamide
N-(1-{[5-(1,2-oxazol-5-yl)thiophen-2-yl]sulfonyl}azetidin-3-yl)prop-2-enamide
N-[1-(2,3-dihydro-1,4-benzodioxin-6-ylsulfonyl)azetidin-3-yl]prop-2-enamide
5-{[3-(acryloylamino)azetidin-1-yl]sulfonyl}-N-(2-phenylethyl)furan-3-carboxamide
N-[1-({4-[(phenylacetyl)amino]benzyl}sulfonyl)azetidin-3-yl]prop-2-enamide
N-(1-{[4-(morpholin-4-ylsulfonyl)phenyl]sulfonyl}azetidin-3-yl)prop-2-enamide
N-(1-{[5-(1,3-oxazol-5-yl)thiophen-2-yl]sulfonyl}azetidin-3-yl)prop-2-enamide
4-{[3-(acryloylamino)azetidin-1-yl]sulfonyl}-2-methyl-N-(2-phenylethyl)benzamide
N-{1-[(4-phenoxyphenyl)sulfonyl]azetidin-3-yl}prop-2-enamide
N-[1-({4-[(6-methylpyrazin-2-yl)oxy]phenyl}sulfonyl)azetidin-3-yl]prop-2-enamide
N-[1-({3-[(6-methylpyrazin-2-yl)oxy]phenyl}sulfonyl)azetidin-3-yl]prop-2-enamide
5-{[3-(acryloylamino)azetidin-1-yl]sulfonyl}-1-methyl-N-(2-phenylethyl)-1H-pyrrole-2-carboxamide
N-(1-{[4-(isoquinolin-3-ylamino)phenyl]sulfonyl}azetidin-3-yl)prop-2-enamide
N-{1-[(3-chloro-4-methylphenyl)sulfonyl]azetidin-3-yl}prop-2-enamide
N-(1-{[5-(1,2-oxazol-5-yl)furan-2-yl]sulfonyl}azetidin-3-yl)prop-2-enamide
N-{1-[(4-{[3-chloro-5-(trifluoromethyl)pyridin-2-yl]oxy}phenyl)sulfonyl]azetidin-3-yl}prop-2-enamide
N-(1-{[4-(1H-pyrazol-1-yl)phenyl]sulfonyl}azetidin-3-yl)prop-2-enamide
N-{1-[(4-methoxy-3-methylphenyl)sulfonyl]azetidin-3-yl}prop-2-enamide
N-(1-{[6-(2-phenylethoxy)pyridin-3-yl]sulfonyl}azetidin-3-yl)prop-2-enamide
N-[1-({5-[(acetylamino)methyl]thiophen-2-yl}sulfonyl)azetidin-3-yl]prop-2-enamide
N-{1-[(5-methyl-1-phenyl-1H-pyrazol-4-yl)sulfonyl]azetidin-3-yl}prop-2-enamide
N-(1-{[4-(1-methyl-1H-pyrazol-5-yl)phenyl]sulfonyl}azetidin-3-yl)prop-2-enamide
N-(1-{[3-(1-methyl-1H-pyrazol-5-yl)phenyl]sulfonyl}azetidin-3-yl)prop-2-enamide
N-{1-[(2,2-dimethyl-3,4-dihydro-2H-chromen-6-yl)sulfonyl]azetidin-3-yl}prop-2-enamide
N-{1-[(5-phenylthiophen-2-yl)sulfonyl]azetidin-3-yl}prop-2-enamide
N-(1-{[4-(cyclopentyloxy)phenyl]sulfonyl}azetidin-3-yl)prop-2-enamide
N-(1-{[5-(pyrrolidin-1-ylcarbonyl)-1H-pyrrol-3-yl]sulfonyl}azetidin-3-yl)prop-2-enamide
N-(1-{[4-(2-methyl-1,3-thiazol-4-yl)phenyl]sulfonyl}azetidin-3-yl)prop-2-enamide
N-(1-{[4-(pyridin-2-yloxy)phenyl]sulfonyl}azetidin-3-yl)prop-2-enamide and
N-{1-[(2-oxo-1,2,3,4-tetrahydroquinolin-6-yl)sulfonyl]azetidin-3-yl}prop-2-enamide.

Also provided is a compound, or pharmaceutically acceptable salt thereof, chosen from:
N-[1-(4-Cyclohexyl-benzenesulfonyl)-piperidin-4-yl]-acrylamide
N-[1-(4-Cyclohexyl-benzenesulfonyl)-piperidin-4-ylmethyl]-acrylamide
Cyclopropanecarboxylic acid {4-[4-(acryloylamino-methyl)-piperidine-1-sulfonyl]-phenyl}-amide
Adamantane-1-carboxylic acid {4-[4-(acryloylamino-methyl)-piperidine-1-sulfonyl]-phenyl}-amide
{4-[4-(Acryloylamino-methyl)-piperidine-1-sulfonyl]-phenyl}-carbamic acid benzyl ester
4-[4-(Acryloylamino-methyl)-benzenesulfonyl]-piperazine-1-carboxylic acid benzyl ester
N-{1-[4-(Piperidine-1-carbonyl)-benzenesulfonyl]-piperidin-4-ylmethyl}-acrylamide
4-[4-(Acryloylamino-methyl)-piperidine-1-sulfonyl]-piperidine-1-carboxylic acid benzyl ester
N-[1-(4-Nitro-benzenesulfonyl)-piperidin-4-yl]-acrylamide

[4-(4-Acryloylamino-piperidine-1-sulfonyl)-phenyl]-carbamic acid benzyl ester
N-{1-[4-(Piperidine-1-carbonyl)-benzenesulfonyl]-piperidin-4-yl}-acrylamide
4-(4-Acryloylamino-piperidine-1-sulfonyl)-piperidine-1-carboxylic acid benzyl ester
Cyclopropanecarboxylic acid [4-(4-acryloylamino-piperidine-1-sulfonyl)-phenyl]-amide
Adamantane-1-carboxylic acid [4-(4-acryloylamino-piperidine-1-sulfonyl)-phenyl]-amide
Tetrahydro-pyran-4-carboxylic acid [4-(4-acryloylamino-piperidine-1-sulfonyl)-phenyl]-amide
{4-[(3-Acryloylamino-propyl)-methyl-sulfamoyl]-phenyl}-carbamic acid benzyl ester
N-{1-[4-(3-Phenyl-propionylamino)-benzenesulfonyl]-piperidin-4-yl}-acrylamide
2-Phenyl-cyclopropanecarboxylic acid [4-(4-acryloylamino-piperidine-1-sulfonyl)-phenyl]-amide
Tetrahydro-pyran-4-carboxylic acid [4-(4-acryloylamino-piperidine-1-sulfonyl)-phenyl]-methyl-amide
4-(4-Acryloylamino-piperidine-1-sulfonyl)-N-benzyl-N-methyl-benzamide
4-(4-Acryloylamino-piperidine-1-sulfonyl)-N-cyclopropyl-methyl-benzamide
N-{1-[3-(Piperidine-1-carbonyl)-benzenesulfonyl]-piperidin-4-yl}-acrylamide
4-(3-Acryloylamino-pyrrolidine-1-sulfonyl)-piperidine-1-carboxylic acid benzyl ester
4-(3-Acryloylamino-pyrrolidine-1-sulfonyl)-piperidine-1-carboxylic acid benzyl ester
Cyclopropanecarboxylic acid [4-(4-acryloylamino-piperidine-1-sulfonyl)-phenyl]-methyl-amide
N-(1-{4-[4-(6-Methyl-pyridin-2-yl)-piperazine-1-carbonyl]-benzenesulfonyl}-piperidin-4-yl)-acrylamide
4-(4-Acryloylamino-piperidine-1-sulfonyl)-N-(2-morpholin-4-yl-ethyl)-benzamide
4-(4-Acryloylamino-piperidine-1-sulfonyl)-N-phenethyl-benzamide
4-(4-Acryloylamino-piperidine-1-sulfonyl)-N-methyl-N-phenethyl-benzamide
N-{1-[4-(3,4-Dihydro-1H-isoquinoline-2-carbonyl)-benzenesulfonyl]-piperidin-4-yl}-acrylamide
[4-(3-Acryloylamino-pyrrolidine-1-sulfonyl)-phenyl]-carbamic acid benzyl ester
[4-(3-Acryloylamino-pyrrolidine-1-sulfonyl)-phenyl]-carbamic acid benzyl ester
4-(4-Acryloylamino-piperidine-1-sulfonyl)-N-(2-cyclohexyl-ethyl)-benzamide
4-(4-Acryloylamino-piperidine-1-sulfonyl)-N-cyclohexyl-benzamide
N-(1-{4-[4-(Pyrrolidine-1-carbonyl)-piperidine-1-carbonyl]-benzenesulfonyl}-piperidin-4-yl)-acrylamide
4-(4-Acryloylamino-piperidine-1-sulfonyl)-N-(3,5-dimethyl-benzyl)-benzamide
4-(4-Acryloylamino-piperidine-1-sulfonyl)-N-benzyl-benzamide
4-(4-Acryloylamino-piperidine-1-sulfonyl)-N-(3,4-difluoro-benzyl)-benzamide
4-(4-Acryloylamino-piperidine-1-sulfonyl)-N-(4-trifluoromethyl-benzyl)-benzamide
4-(4-Acryloylamino-piperidine-1-sulfonyl)-N-naphthalen-1-ylmethyl-benzamide
4-(4-Acryloylamino-piperidine-1-sulfonyl)-N-[2-(3,4-dimethyl-phenyl)-ethyl]-benzamide
4-(4-Acryloylamino-piperidine-1-sulfonyl)-N-[2-(4-methoxy-phenyl)-ethyl]-benzamide
4-(4-Acryloylamino-piperidine-1-sulfonyl)-N-indan-2-yl-benzamide
4-(4-Acryloylamino-piperidine-1-sulfonyl)-N-(2-m-tolyl-ethyl)-benzamide
N-{1-[4-(Acetylamino-methyl)-benzenesulfonyl]-piperidin-4-yl}-acrylamide
N-{1-[4-(3-Naphthalen-1-yl-propionylamino)-benzenesulfonyl]-piperidin-4-yl}-acrylamide
N-{1-[4-(3-Cyclohexyl-propionylamino)-benzenesulfonyl]-piperidin-4-yl}-acrylamide
N-[1-(1-Benzoyl-piperidine-4-sulfonyl)-piperidin-4-yl]-acrylamide
N-{1-[1-(Piperidine-1-carbonyl)-piperidine-4-sulfonyl]-piperidin-4-yl}-acrylamide
N-{1-[1-(Pyridine-2-carbonyl)-piperidine-4-sulfonyl]-piperidin-4-yl}-acrylamide
4-tert-Butyl-cyclohexanecarboxylic acid [4-(4-acryloylamino-piperidine-1-sulfonyl)-phenyl]-amide
Benzofuran-2-carboxylic acid [4-(4-acryloylamino-piperidine-1-sulfonyl)-phenyl]-amide
[3-(4-Acryloylamino-piperidine-1-sulfonyl)-phenyl]-carbamic acid benzyl ester
N-{1-[3-(3-Phenyl-propionylamino)-benzenesulfonyl]-piperidin-4-yl}-acrylamide
Tetrahydro-pyran-4-carboxylic acid [3-(4-acryloylamino-piperidine-1-sulfonyl)-phenyl]-amide
4-(4-Acryloylamino-piperidine-1-sulfonyl)-N-(3-phenyl-propyl)-benzamide
4-(4-Acryloylamino-piperidine-1-sulfonyl)-N-[2-(3-chloro-phenyl)-ethyl]-benzamide
4-(4-Acryloylamino-piperidine-1-sulfonyl)-N-[2-(2-methoxy-phenyl)-ethyl]-benzamide
4-(4-Acryloylamino-piperidine-1-sulfonyl)-N-[2-(2,3-dihydro-benzofuran-7-yl)-ethyl]-benzamide
4-(4-Acryloylamino-piperidine-1-sulfonyl)-N-[2-(tetrahydro-pyran-4-yl)-ethyl]-benzamide
4-(4-Acryloylamino-piperidine-1-sulfonyl)-N-[2-(4,4-difluoro-piperidin-1-yl)-ethyl]-benzamide
N-{1-[1-(3-Trifluoromethyl-benzoyl)-piperidine-4-sulfonyl]-piperidin-4-yl}-acrylamide
N-{1-[1-(3-Phenyl-propionyl)-piperidine-4-sulfonyl]-piperidin-4-yl}-acrylamide
N-{1-[4-(Benzylcarbamoyl-methyl)-benzenesulfonyl]-piperidin-4-yl}-acrylamide
4-(4-Acryloylamino-piperidine-1-sulfonyl)-N-(4-tert-butyl-benzyl)-benzamide
4-(4-Acryloylamino-piperidine-1-sulfonyl)-N-(4-phenyl-butyl)-benzamide
4-(4-Acryloylamino-piperidine-1-sulfonyl)-N-[2-(4-chloro-phenyl)-ethyl]-benzamide
4-(4-Acryloylamino-piperidine-1-sulfonyl)-N-(2-quinolin-7-yl-ethyl)-benzamide
4-(4-Acryloylamino-piperidine-1-sulfonyl)-N-(2-naphthalen-2-yl-ethyl)-benzamide
4-(4-Acryloylamino-piperidine-1-sulfonyl)-N-(2-chroman-6-yl-ethyl)-benzamide
4-(4-Acryloylamino-piperidine-1-sulfonyl)-N-[2-(4-tert-butyl-phenyl)-ethyl]-benzamide
4-(4-Acryloylamino-piperidine-1-sulfonyl)-N-(2-biphenyl-4-yl-ethyl)-benzamide
4-(4-Acryloylamino-piperidine-1-sulfonyl)-N-(2-benzo[1,3]dioxol-5-yl-ethyl)-benzamide
4-(4-Acryloylamino-piperidine-1-sulfonyl)-N-(2-phenyl-cyclopropyl)-benzamide
4-(4-Acryloylamino-piperidine-1-sulfonyl)-2-chloro-benzoic acid methyl ester

[4-(4-Acryloylamino-piperidine-1-sulfonyl)-phenyl]-methyl-carbamic acid benzyl ester
4-(4-Acryloylamino-piperidine-1-sulfonyl)-N-[2-(3,4-dimethoxy-phenyl)-ethyl]-benzamide
4-(4-Acryloylamino-piperidine-1-sulfonyl)-N-[2-(4-trifluoromethyl-phenyl)-ethyl]-benzamide
4-(4-Acryloylamino-piperidine-1-sulfonyl)-piperidine-1-carboxylic acid phenethyl-amide
[4-(4-Acryloylamino-piperidin-1-ylmethyl)-phenyl]-carbamic acid benzyl ester
Furan-2-carboxylic acid [4-(4-acryloylamino-piperidine-1-sulfonyl)-phenyl]-amide
N-{1-[4-(Phenylacetylamino-methyl)-benzenesulfonyl]-piperidin-4-yl}-acrylamide
N-{1-[4-(3-Adamantan-1-yl-propionylamino)-benzenesulfonyl]-piperidin-4-yl}-acrylamide
4-(4-Acryloylamino-piperidine-1-sulfonyl)-N-(2-adamantan-1-yl-ethyl)-benzamide
N-[1-(1-Cyclopropanecarbonyl-2,3-dihydro-1H-indole-5-sulfonyl)-piperidin-4-yl]-acrylamide
N-{1-[2-Chloro-4-(3-phenyl-propionylamino)-benzenesulfonyl]-piperidin-4-yl}-acrylamide
5,6-Dihydro-4H-cyclopenta[b]thiophene-2-carboxylic acid [4-(4-acryloylamino-piperidine-1-sulfonyl)-phenyl]-amide
(R)-[4-(3-Acryloylamino-piperidine-1-sulfonyl)-phenyl]-carbamic acid benzyl ester
(S)-[4-(3-Acryloylamino-piperidine-1-sulfonyl)-phenyl]-carbamic acid benzyl ester
4,5,6,7-Tetrahydro-1H-indole-2-carboxylic acid [4-(4-acryloylamino-piperidine-1-sulfonyl)-phenyl]-amide
N-{1-[2-Methoxy-4-(3-phenyl-propionylamino)-benzenesulfonyl]-piperidin-4-yl}-acrylamide
5-Pyrrolidin-1-ylmethyl-furan-2-carboxylic acid [4-(4-acryloylamino-piperidine-1-sulfonyl)-phenyl]-amide
Benzo[b]thiophene-2-carboxylic acid [4-(4-acryloylamino-piperidine-1-sulfonyl)-phenyl]-amide
3-Methyl-benzofuran-2-carboxylic acid [4-(4-acryloylamino-piperidine-1-sulfonyl)-phenyl]-amide
1H-Indole-2-carboxylic acid [4-(4-acryloylamino-piperidine-1-sulfonyl)-phenyl]-amide
4-(4-Acryloylamino-piperidine-1-sulfonyl)-N-adamantan-1-ylmethyl-benzamide
4-(4-Acryloylamino-piperidine-1-sulfonyl)-N-(1,2,3,4-tetrahydro-naphthalen-1-yl)-benzamide
4,5,6,7-Tetrahydro-benzo[b]thiophene-2-carboxylic acid [4-(4-acryloylamino-piperidine-1-sulfonyl)-phenyl]-amide
5-Phenyl-furan-2-carboxylic acid [4-(4-acryloylamino-piperidine-1-sulfonyl)-phenyl]-amide
4-Phenyl-thiophene-2-carboxylic acid [4-(4-acryloylamino-piperidine-1-sulfonyl)-phenyl]-amide
N-{1-[5-(5-Trifluoromethyl-isoxazol-3-yl)-thiophene-2-sulfonyl]-piperidin-4-yl}-acrylamide
5-(4-Acryloylamino-piperidine-1-sulfonyl)-furan-2-carboxylic acid phenethyl-amide
[4-(3-Acryloylamino-azetidine-1-sulfonyl)-phenyl]-carbamic acid benzyl ester
N-[1-(6-Phenoxy-pyridine-3-sulfonyl)-piperidin-4-yl]-acrylamide
N-[1-(6-Morpholin-4-yl-pyridine-3-sulfonyl)-piperidin-4-yl]-acrylamide
N-[1-(6-Phenyl-pyridine-3-sulfonyl)-piperidin-4-yl]-acrylamide
N-{1-[3-Chloro-4-(3-phenyl-propionylamino)-benzenesulfonyl]-piperidin-4-yl}-acrylamide
4-(4-Acryloylamino-piperidine-1-sulfonyl)-2-fluoro-N-phenethyl-benzamide
N-[1-(5-Pyridin-2-yl-thiophene-2-sulfonyl)-piperidin-4-yl]-acrylamide
4-(4-Acryloylamino-piperidine-1-sulfonyl)-2-methoxy-N-phenethyl-benzamide
N-[1-(Benzothiazole-6-sulfonyl)-piperidin-4-yl]-acrylamide
N-[1-(4-Methyl-2-phenyl-thiazole-5-sulfonyl)-piperidin-4-yl]-acrylamide
N-{1-[5-(2-Methyl-thiazol-4-yl)-thiophene-2-sulfonyl]-piperidin-4-yl}-acrylamide
N-[1-(5-Isoxazol-5-yl-thiophene-2-sulfonyl)-piperidin-4-yl]-acrylamide
N-[1-(2,3-Dihydro-benzo[1,4]dioxine-6-sulfonyl)-piperidin-4-yl]-acrylamide
5-(4-Acryloylamino-piperidine-1-sulfonyl)-furan-3-carboxylic acid phenethyl-amide
N-[1-(4-Phenylacetylamino-phenylmethanesulfonyl)-piperidin-4-yl]-acrylamide
N-{1-[4-(Morpholine-4-sulfonyl)-benzenesulfonyl]-piperidin-4-yl}-acrylamide
N-[1-(5-Oxazol-5-yl-thiophene-2-sulfonyl)-piperidin-4-yl]-acrylamide
4-(4-Acryloylamino-piperidine-1-sulfonyl)-2-methyl-N-phenethyl-benzamide
N-[1-(4-Phenoxy-benzenesulfonyl)-piperidin-4-yl]-acrylamide
N-{1-[4-(6-Methyl-pyrazin-2-yloxy)-benzenesulfonyl]-piperidin-4-yl}-acrylamide
N-{1-[3-(6-Methyl-pyrazin-2-yloxy)-benzenesulfonyl]-piperidin-4-yl}-acrylamide
5-(4-Acryloylamino-piperidine-1-sulfonyl)-1-methyl-1H-pyrrole-2-carboxylic acid phenethyl-amide
N-{1-[4-(Isoquinolin-3-ylamino)-benzenesulfonyl]-piperidin-4-yl}-acrylamide
N-[1-(3-Chloro-4-methyl-benzenesulfonyl)-piperidin-4-yl]-acrylamide
N-[1-(5-Isoxazol-5-yl-furan-2-sulfonyl)-piperidin-4-yl]-acrylamide
N-{1-[4-(3-Chloro-5-trifluoromethyl-pyridin-2-yloxy)-benzenesulfonyl]-piperidin-4-yl}-acrylamide
N-[1-(4-Pyrazol-1-yl-benzenesulfonyl)-piperidin-4-yl]-acrylamide
N-[1-(4-Methoxy-3-methyl-benzenesulfonyl)-piperidin-4-yl]-acrylamide
N-[1-(6-Phenethyloxy-pyridine-3-sulfonyl)-piperidin-4-yl]-acrylamide
N-{1-[5-(Acetylamino-methyl)-thiophene-2-sulfonyl]-piperidin-4-yl}-acrylamide
N-[1-(5-Methyl-1-phenyl-1H-pyrazole-4-sulfonyl)-piperidin-4-yl]-acrylamide
N-{1-[4-(2-Methyl-2H-pyrazol-3-yl)-benzenesulfonyl]-piperidin-4-yl}-acrylamide
N-{1-[3-(2-Methyl-2H-pyrazol-3-yl)-benzenesulfonyl]-piperidin-4-yl}-acrylamide
N-[1-(2,2-Dimethyl-chroman-6-sulfonyl)-piperidin-4-yl]-acrylamide
N-[1-(5-Phenyl-thiophene-2-sulfonyl)-piperidin-4-yl]-acrylamide
N-[1-(4-Cyclopentyloxy-benzenesulfonyl)-piperidin-4-yl]-acrylamide
N-{1-[5-(Pyrrolidine-1-carbonyl)-1H-pyrrole-3-sulfonyl]-piperidin-4-yl}-acrylamide
N-{1-[4-(2-Methyl-thiazol-4-yl)-benzenesulfonyl]-piperidin-4-yl}-acrylamide
N-{1-[4-(Pyridin-2-yloxy)-benzenesulfonyl]-piperidin-4-yl}-acrylamide and N-[1-(2-Oxo-1,2,3,4-tetrahydro-quinoline-6-sulfonyl)-piperidin-4-yl]-acrylamide.

Methods for obtaining the compounds and pharmaceutically acceptable salts thereof described herein will be apparent to those of ordinary skill in the art, suitable procedures being described, for example, in the reaction schemes and examples below, and in the references cited herein.

The acrylamide derivatives of the general Formula I, or a pharmaceutically acceptable salt thereof, may be prepared by any process known to be applicable for the preparation of chemically-related compounds by one skilled in the art. Such processes, when used to prepare the acrylamide derivatives of Formulas I, and II-VII, or a pharmaceutically-acceptable salt thereof, are provided as a further feature of the invention and are illustrated by the following schemes 1-11, in which, unless otherwise stated, $R^1$, etc., and n, have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

Scheme 1 (Method A):

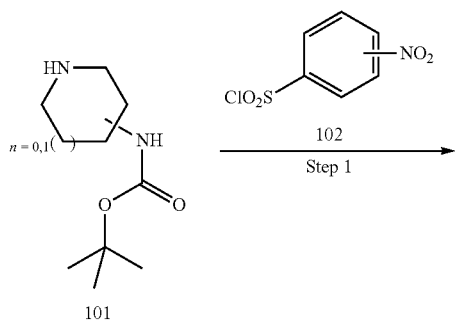

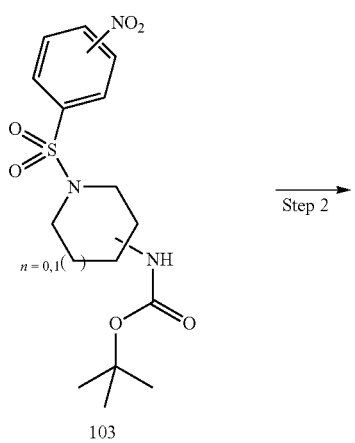

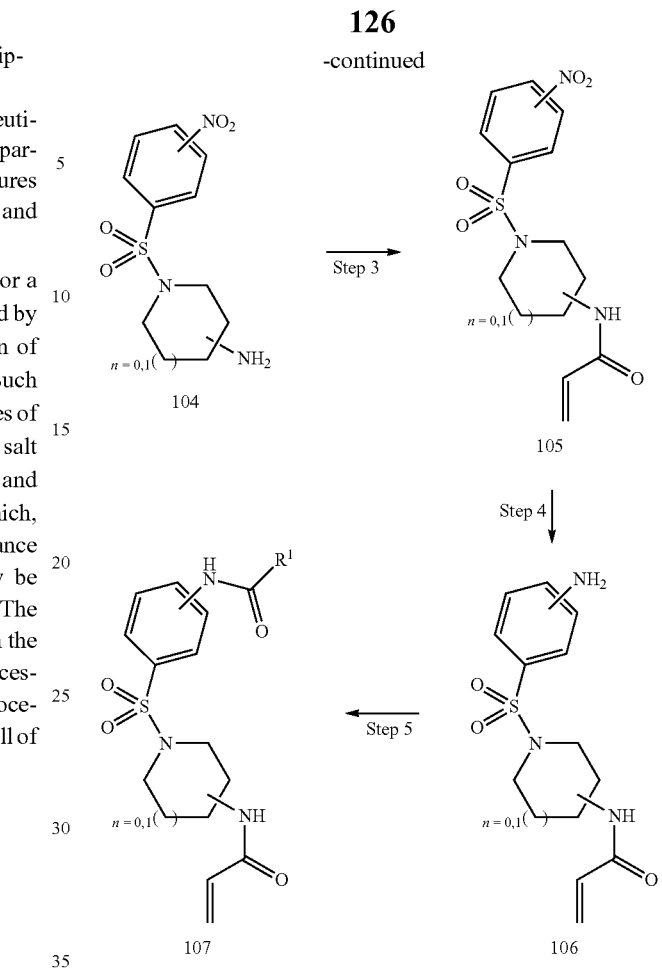

In step 1, scheme 1 the secondary amines of formula 101 are converted into their corresponding sulfonamides of formula 103, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 1 the sulfonamide of formula 103 are converted into their corresponding amines of formula 104, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 3, scheme 1 the amine derivatives of formula 104 are converted into their corresponding acrylamide of formula 105 using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

In step 4, scheme 1 the acrylamides of formula 105 are converted into their corresponding anilines of formula 106, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 5, scheme 1 the anilines of formula 106 are converted into their corresponding amides of formula 107, which are compounds of Formula I, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as acetyl chloride. Alternatively, anilines of formula 106 can be converted into amides of formula 107 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

Scheme 2 (Method B)

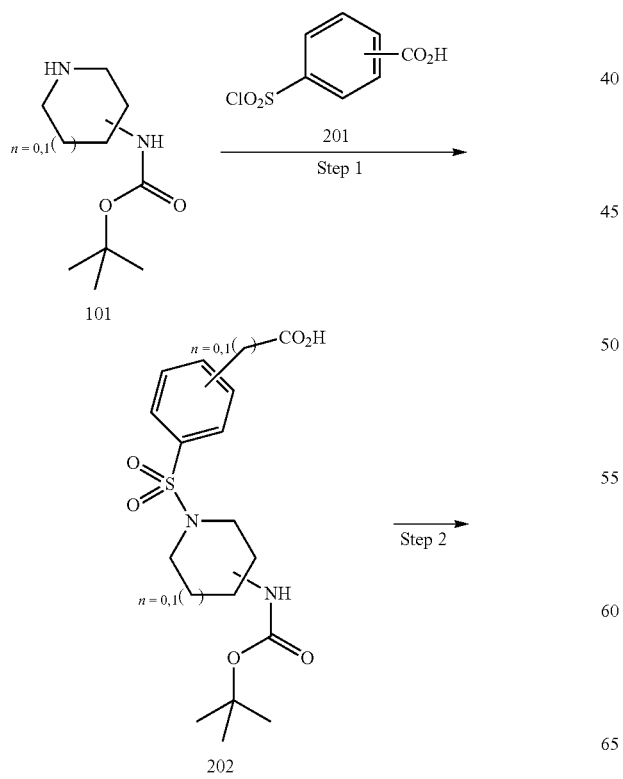

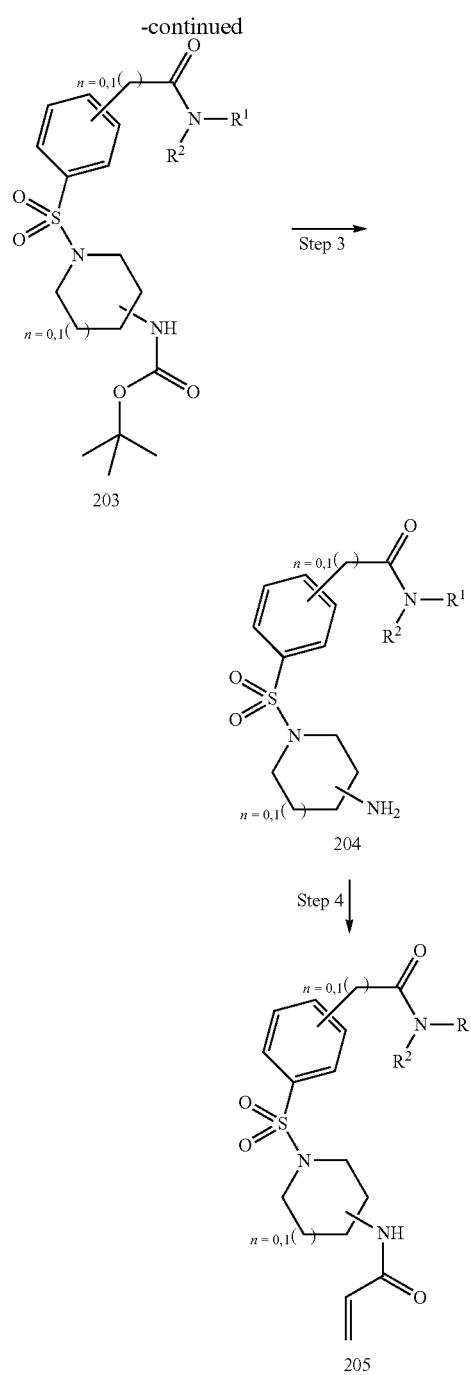

In step 1, scheme 2 the secondary amines of formula 101 are converted into their corresponding sulfonamides of formula 202, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 2 the functionalized carboxylic acids of formula 202 can be converted into amides of formula 203 using methods well known to someone skilled in the art, e.g.

carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 3, scheme 2 the functionalized amides of formula 203 are converted into their corresponding amines of formula 204, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 4, scheme 2 the amine derivatives of formula 204 are converted into their corresponding acrylamides of formula 205, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 3 (Method C):

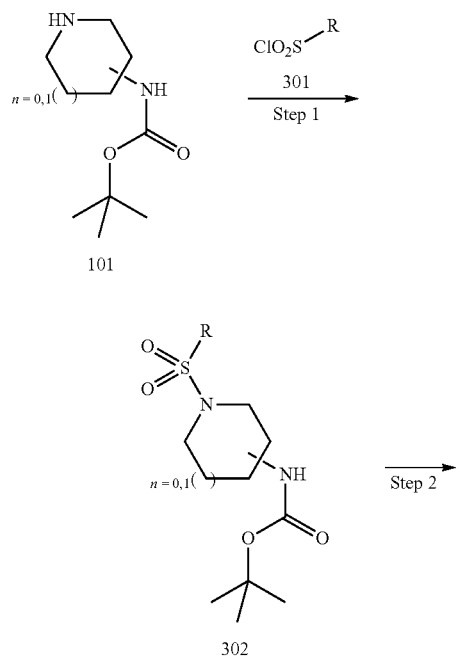

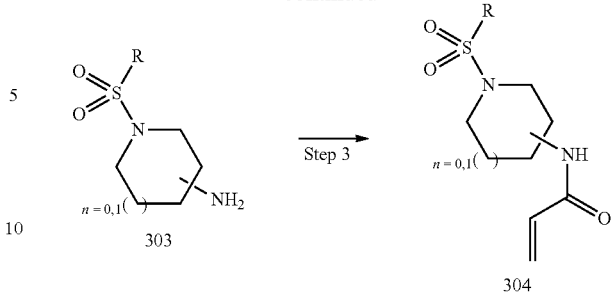

In step 1, scheme 2 the secondary amines of formula 101 are converted into their corresponding sulfonamides of formula 302, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 3 the functionalized amides of formula 302 are converted into their corresponding amines of formula 303, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 3, scheme 3 the amine derivatives of formula 303 are converted into their corresponding acrylamides of formula 304, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 4 (Method D):

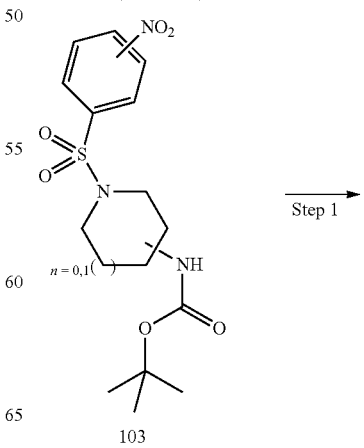

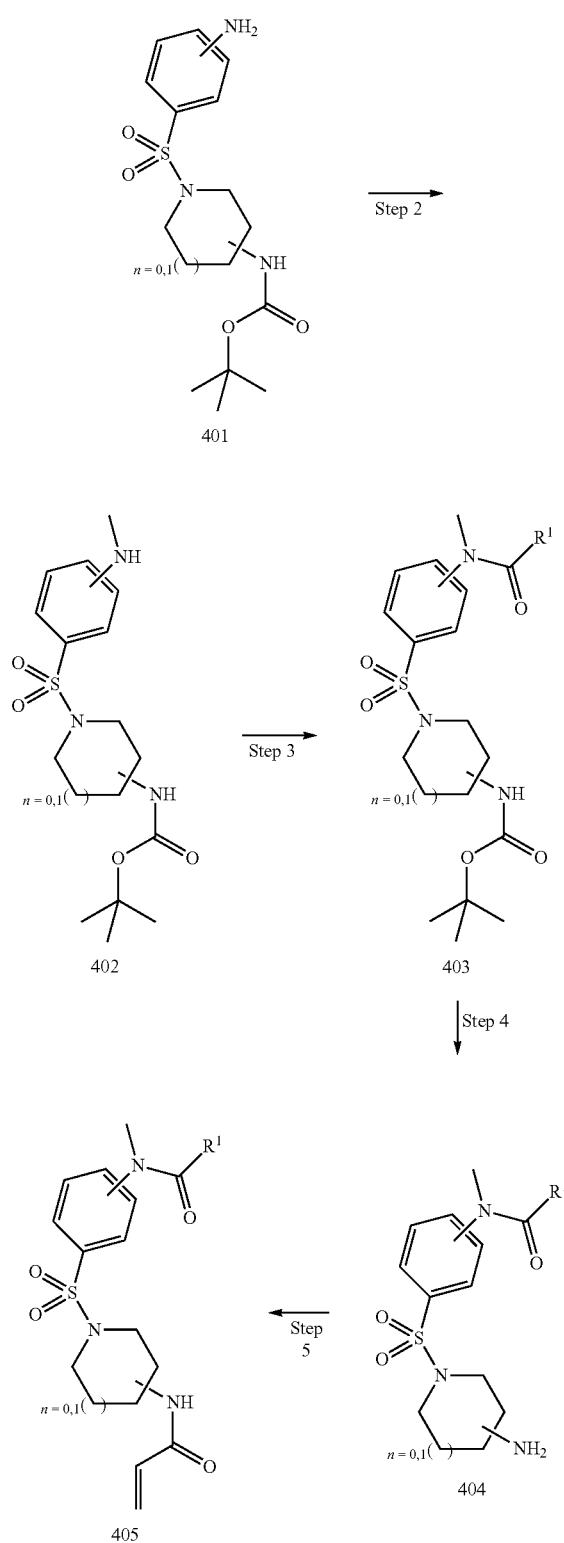

In step 1, scheme 4 the nitro-benzene sulfonamides of formula 103 are converted into their corresponding anilines of formula 401, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 2, scheme 4 the anilines of formula 401 are converted into their corresponding secondary amines of formula 402, using methods well known to someone skilled in the art, e.g. alkylation of amines. The reaction is typically carried out in solvents like N,N-dimethylformamide, N-methylpyrrolidinone, acetonitrile, dichloromethane and dichloroethane at temperatures between 0° C. and 100° C. Typically used bases are potassium carbonate, sodium hydride, lithium hexamethyldisilazide, sodium hexamethyldisilazide and potassium hexamethyldisilazide with alkylating agents such as alkyl halides, alkyl mesylates and alkyl triflates.

In step 3, scheme 4 the amines of formula 402 are converted into their corresponding amides of formula 403, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as acetyl chloride. Alternatively, the amines of formula 402 can be converted into amides of formula 403 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 4, scheme 4 the functionalized amides of formula 403 are converted into their corresponding amines of formula 404, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 5, scheme 4 the amine derivatives of formula 404 are converted into their corresponding acrylamides of formula 405, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 5 (Method E):

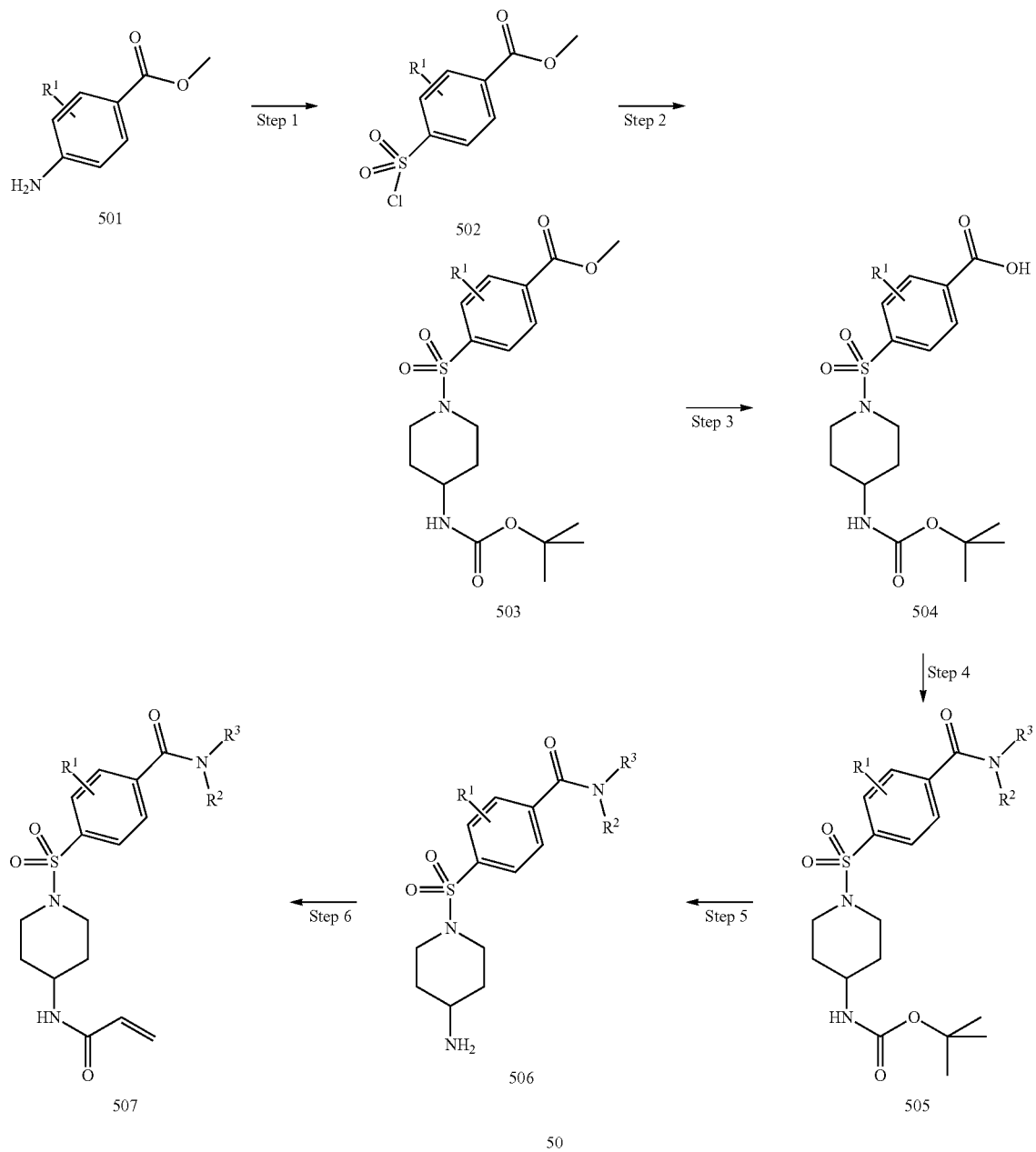

In step 1, scheme 5 the functionalized anilines of formula 501 are converted into their corresponding sulfonyl chlorides of formula 502, using methods well known to someone skilled in the art, e.g. diazotization followed by nucleophilic displacement. The reaction is typically carried out with solvents such as acetic acid, sulfuric acid, hydrochloric acid, water and mixtures thereof, at temperatures between −78° C. and 100° C.

In step 2, scheme 5 the sulfonyl chlorides of formula 502 are converted into their corresponding sulfonamides of formula 503, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 3, scheme 5 the functionalized sulfonamides of formula 503 are converted into the corresponding carboxylic acids of formula 504, using methods well known to someone skilled in the art, e.g. hydrolysis of an ester. The reaction is typically carried out with solvents such as tetrahydrofuran, acetonitrile, ethanol and water or mixtures thereof at temperatures between 0° C. and 100° C. Typically used bases are sodium hydroxide, lithium hydroxide and potassium hydroxide.

In step 4, scheme 5 the carboxylic acids of formula 504 are converted into amides of formula 505 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 5, scheme 5 the functionalized amides of formula 505 are converted into their corresponding amines of formula 506, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 6, scheme 5 the amine derivatives of formula 506 are converted into their corresponding acrylamides of formula 507, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 6 (Method F):

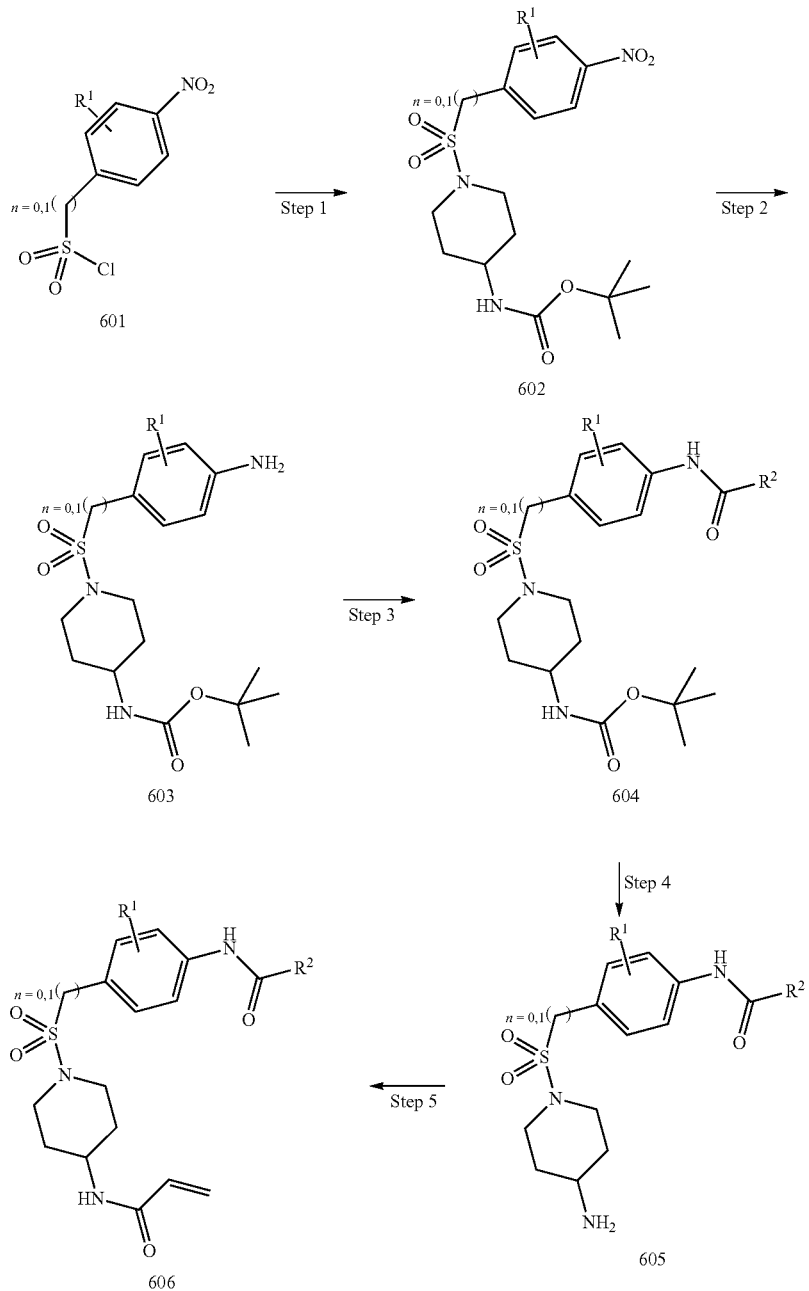

In step 1, scheme 6 the sulfonyl chlorides of formula 601 are converted into their corresponding sulfonamides of formula 602, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 6 the nitro-benzene sulfonamides of formula 602 are converted into their corresponding anilines of formula 603, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride and iron powder.

In step 3, scheme 6 the amines of formula 603 are converted into their corresponding amides of formula 604, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as acetyl chloride. Alternatively, the amines of formula 603 can be converted into amides of formula 604 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 4, scheme 6 the functionalized amides of formula 604 are converted into their corresponding amines of formula 605, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 5, scheme 6 the amine derivatives of formula 605 are converted into their corresponding acrylamides of formula 606, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 7 (Method G):

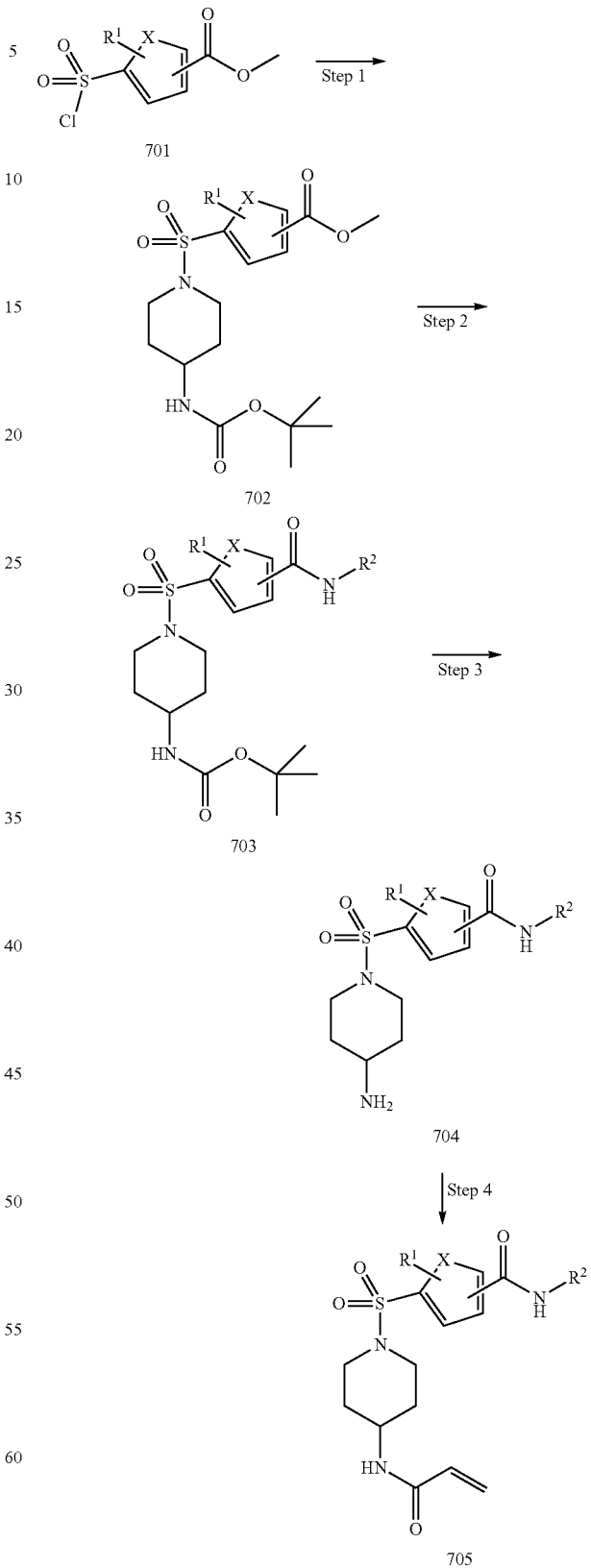

wherein x is O, S, NH, N-alkyl, and the like.

In step 1, scheme 7 the sulfonyl chlorides of formula 701 are converted into their corresponding sulfonamide esters of formula 702, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 7 the sulfonamide esters of formula 702 are converted into their corresponding amides of formula 703, using methods well known to someone skilled in the art, e.g. nucleophilic displacement of esters. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 3, scheme 7 the functionalized amides of formula 703 are converted into their corresponding amines of formula 704, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 4, scheme 7 the amine derivatives of formula 704 are converted into their corresponding acrylamides of formula 705, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 8 (Method H):

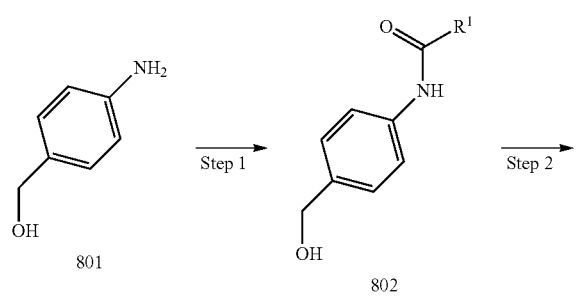

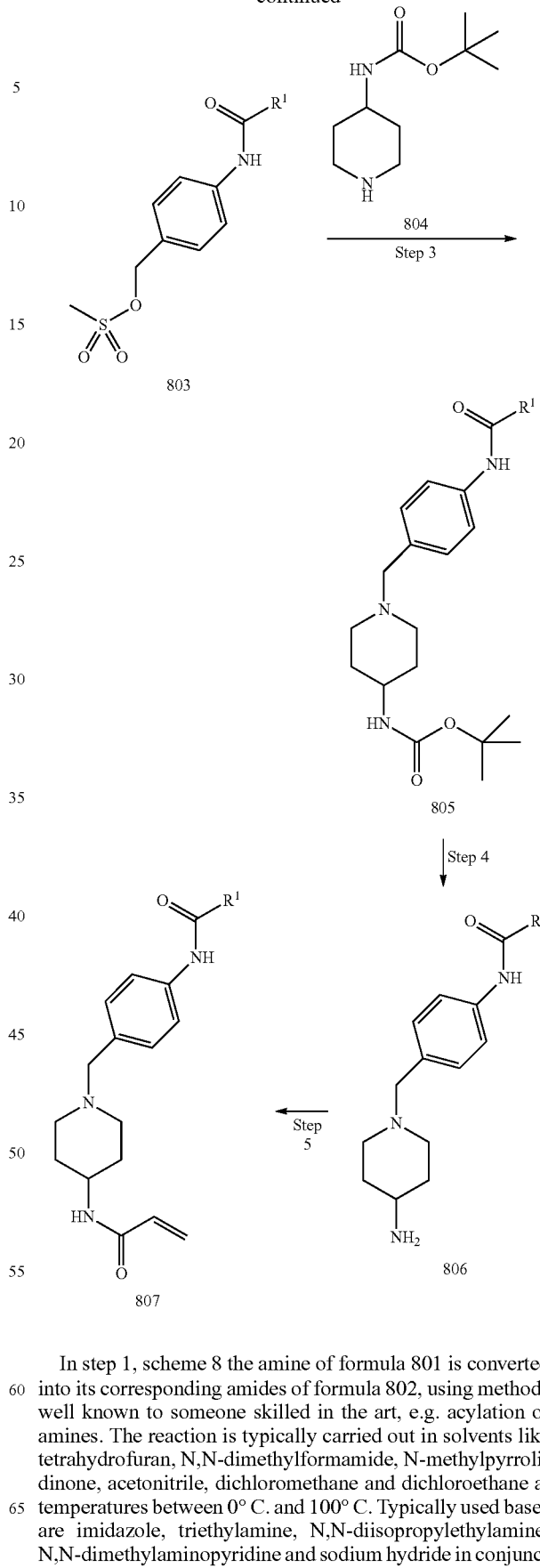

In step 1, scheme 8 the amine of formula 801 is converted into its corresponding amides of formula 802, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as acetyl chloride. Alternatively, the amine of formula 801 is converted into amides of formula 802 using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 2, scheme 8 the functionalized alcohols of formula 802 are converted into the corresponding mesylates of formula 803, using methods well known to someone skilled in the art, e.g. activation of an alcohol. The reaction is typically carried out with solvents such as tetrahydrofuran, acetonitrile, dichloromethane, dichloroethane and N,N-dimethylformamide or mixtures thereof at temperatures between 0° C. and 20° C. Typically used bases are pyridine, imidazole, triethylamine, N,N-diisopropylethylamine, N,N-dimethylaminopyridine and sodium hydride in conjunction with reagents such as methane sulfonyl chloride.

In step 3, scheme 8 the activated alcohols of formula 803 are converted into the corresponding amides of formula 805 using methods well known to someone skilled in the art, e.g. nucleophilic displacement of a sulfonate with an amine. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with amines.

In step 4, scheme 8 the functionalized amides of formula 805 are converted into their corresponding amines of formula 806, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 5, scheme 8 the amine derivatives of formula 806 are converted into their corresponding acrylamides of formula 807, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 9 (Method I):

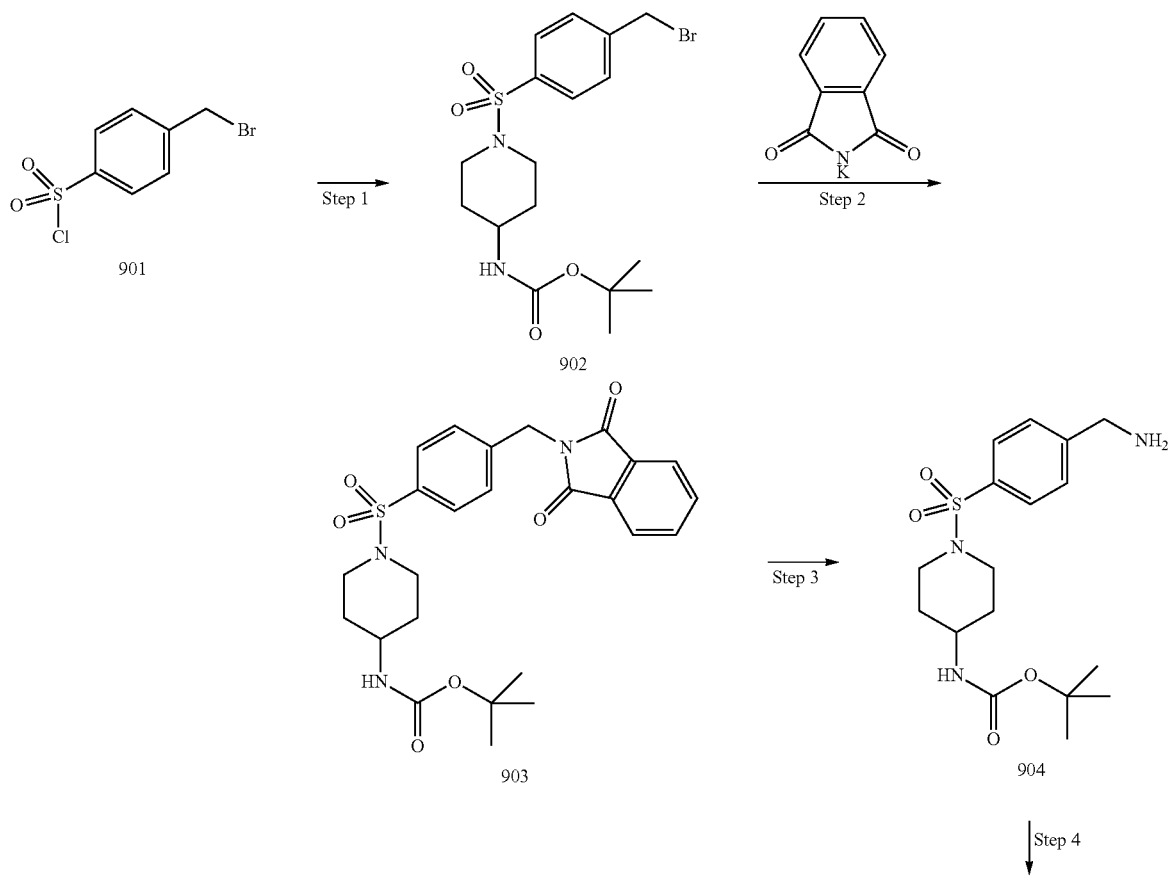

-continued

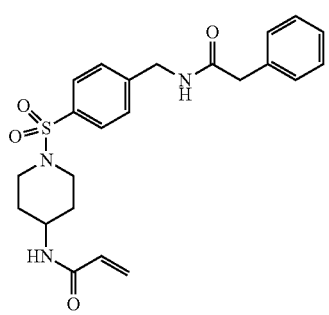
907

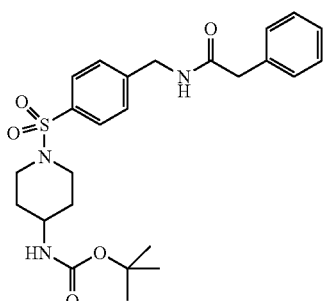
905

906

In step 1, scheme 9 the sulfonyl chloride of formula 901 is converted into its corresponding sulfonamide of formula 902, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 9 the benzyl halide of formula 902 is converted into the corresponding protected amine of formula 903 using methods well known to someone skilled in the art, e.g. nucleophilic displacement of an alkyl halide with an imide. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. A typically used imide is potassium phthalimide.

In step 3, scheme 9 the protected amine of formula 903 is converted into its corresponding amine of formula 904, using methods well known to someone skilled in the art, e.g. deprotection of phthalamides. The reaction is typically carried out without solvent or in solvents like diethyl ether, dioxane, tetrahydrofuran, dichloromethane and dichloroethane or mixtures thereof, at temperatures between 0° C. and 40° C. A typically used reagent is hydrazine.

In step 4, scheme 9 the amine of formula 904 is converted into its corresponding amide of formula 905, using methods well known to someone skilled in the art, e.g. acylation of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine, N,N-dimethylaminopyridine and sodium hydride in conjunction with reagents such as phenyl acetyl chloride. Alternatively, the amine of formula 904 is converted into amides of formula X using methods well known to someone skilled in the art, e.g. carboxylic acid couplings of amines. The reaction is typically carried out in solvents like tetrahydrofuran, N,N-dimethylformamide, N-methylpyrrolidinone, acetonitrile, dichloromethane and dichloroethane at temperatures between 0° C. and 100° C. Typically used bases are imidazole, triethylamine, N,N-diisopropylethylamine and N,N-dimethylaminopyridine in conjunction with reagents such as N,N-diisopropylcarbodiimide, N,N-dicyclohexylcarbodiimide or N-(3-dimethylaminopropyl)-N'-ethylcarbodiimide hydrochloride and benzoic acid.

In step 5, scheme 8 the functionalized amide of formula 905 is converted into its corresponding amine of formula 906, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 6, scheme 8 the amine derivative of formula 906 is converted into its corresponding acrylamide of formula 907, which is a compound of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Scheme 10 (Method J):

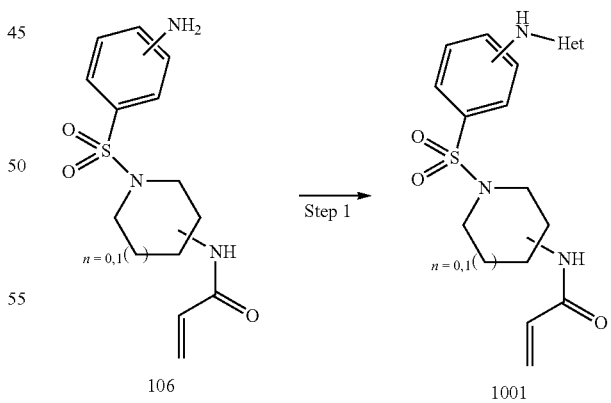

106                    1001

In step 1, scheme 10 the anilines of formula 106 are converted into the corresponding amines of formula 1001, which are compounds of Formula I, using methods well known to someone skilled in the art, e.g. nucleophilic displacement of a halo-heteroycle with an amine. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine in conjunction with halo-substituted heterocycles.

Scheme 11 (Method K):

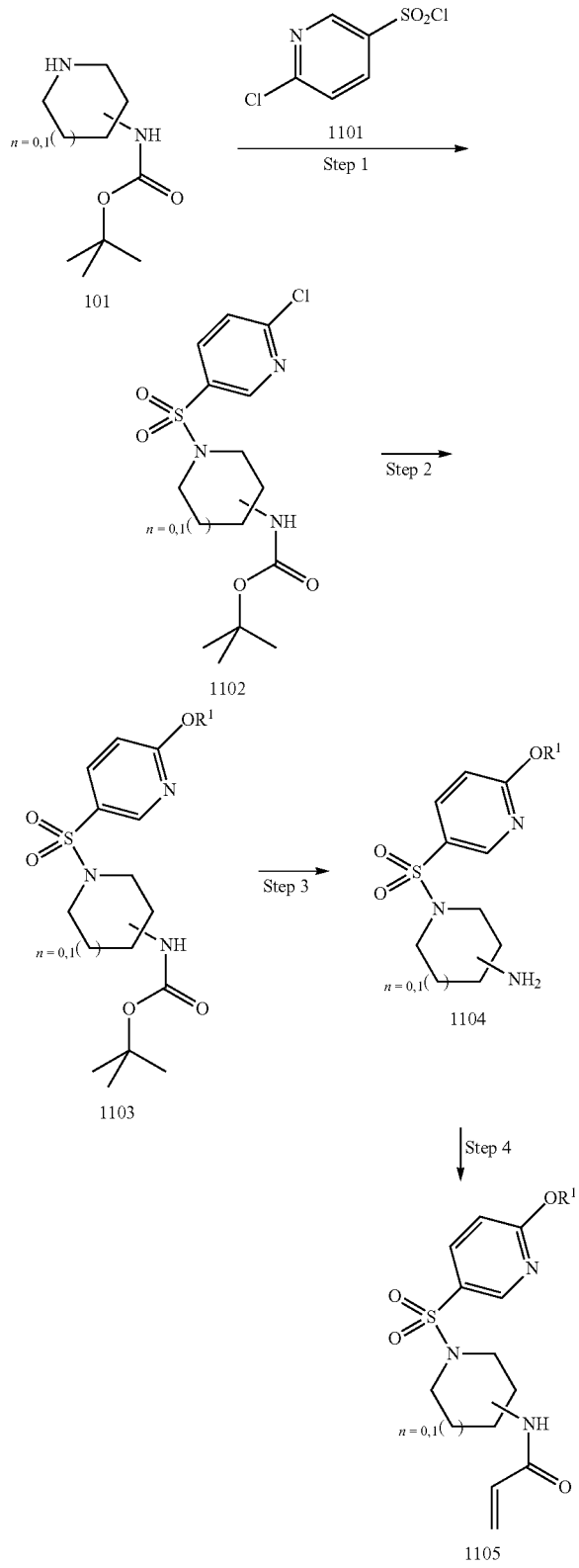

In step 1, scheme 11 the sulfonyl chloride of formula X1101 is converted into its corresponding sulfonamides of formula 1102, using methods well known to someone skilled in the art, e.g. sulfonylation of secondary amines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and N,N-dimethylaminopyridine.

In step 2, scheme 11, the halo-substituted heterocycles of formula 1102 are converted into their corresponding s of formula 1103 using methods well known to someone skilled in the art, e.g. nucleophilic displacement of a halo-heteroycle with an alcohol. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are NaH, triethylamine, N,N-diisopropyl ethylamine, pyridine, potassium carbonate and N,N-dimethylaminopyridine in conjunction with alcohols.

In step 3, scheme 11, the functionalized amides of formula 1103 are converted into their corresponding amines of formula 1104, using methods well known to someone skilled in the art, e.g. deprotection of acid labile protecting groups such as a tert-butoxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 4, scheme 11, the amine derivatives of formula 1104 are converted into their corresponding acrylamides of formula 1105, which are compounds of Formula I, using methods well known to someone skilled in the art, e.g. acylation of amines, coupling of amines with carboxylic acids or acetylation. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropylethylamine, pyridine, potassium carbonate and N,N-dimethylaminopyridine in conjunction with reagents such as acryloyl chloride.

Provided is a method of inhibiting the activity of transglutaminase TG2, comprising contacting said transglutaminase TG2 with an effective amount of at least one compound or pharmaceutically acceptable salt thereof described herein.

Also provided is a method of treating a disease state mediated by transglutaminase TG2 activity in a subject in need of such a treatment, comprising administering to the subject a therapeutically effective amount of at least one compound or pharmaceutically acceptable salt thereof described herein.

Also provided is a method of treating a neurodegenerative pathology mediated by transglutaminase TG2 activity in a subject in need of such a treatment, comprising administering to the subject a therapeutically effective amount of at least one compound or pharmaceutically acceptable salt thereof described herein. Also provided is a method for treating disease states mediated by (or at least in part by) the presence of transglutaminase TG2. Such disease states include, for example, neurodegenerative diseases, gluten sensitivity diseases such as Celiac disease, protein misfolding disorders, hepatic and renal injury, kidney disease, renal failure, neuropathy, cancer metastasis, leukemia, melanoma, autoimmune diseases, inflammatory diseases, degenerative joint disease such as osteoarthritis, psoriasis, cardiovascular disorders, ischemia, atherosclerosis, fibrosis, diabetes, lamellar ichthyosis, supranuclear palsey, Hb Koln and sickle cell disorders, acne, cataracts, myopia, immune system diseases, diabetic nephropathy, muscular dystrophies, wound remodelling and repair, and multiple sclerosis. In some embodiments, the disease state is chosen from acne, cataracts, immune system diseases, psoriasis, neuropathy, neurodegenerative disease, such as Alzheimer's disease, Huntington's disease, and Parkinson's disease, Celiac disease, cancer metastasis, inflammation, fibrosis, diabetes, autoimmune diseases, lamellar ichthyosis, psoriasis, supranuclear palsy, and renal failure. In some embodiments, the disease state is a gluten sensitivity disease. In some embodiments, the disease state is Celiac disease. In some embodiments, the neurodegenerative disease is chosen from Alzheimer's disease, amyotrophic lateral sclerosis, Huntington's disease, Parkinson's' disease, Prion disease and spinocerebellar ataxias. In some embodiments, the neurodegenerative disease is Huntington's disease.

Also provided are methods of treatment in which at least one compound or pharmaceutically acceptable salt thereof described herein is the only active agent given to the subject and also includes methods of treatment in which at least one compound or pharmaceutically acceptable salt thereof described herein is given to the subject in combination with one or more additional active agents.

In general, the compounds and pharmaceutically acceptable salts thereof described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the compounds and pharmaceutically acceptable salts thereof described herein are administered as a pharmaceutical composition. Accordingly, provided are pharmaceutical compositions comprising at least one compound or pharmaceutically acceptable salt thereof described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or pharmaceutically acceptable salt thereof is sufficient to provide a practical quantity of material for administration per unit dose of the compound or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or pharmaceutically acceptable salt thereof described herein.

Effective concentrations of at least one compound or pharmaceutically acceptable salt thereof described herein are mixed with a suitable pharmaceutically acceptable vehicle. In instances in which the compound or pharmaceutically acceptable salt thereof exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound or pharmaceutically acceptable salt thereof described herein, the resulting mixture may be a solution, suspension, emulsion or the like. The form of the resulting mixture depends upon a number of factors, including the intended mode of administration and the solubility of the compound or pharmaceutically acceptable salt thereof in the chosen vehicle. The effective concentration sufficient for ameliorating the symptoms of the disease treated may be empirically determined.

The compounds and pharmaceutically acceptable salts thereof described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound or pharmaceutically acceptable salt thereof described herein. In some embodiments, oral pharmaceutical compositions contain at least 5% (weight %) of at least one compound or pharmaceutically acceptable salt thereof described herein. Some embodiments contain from 25% to 50% or from 5% to 75% of at least one compound or pharmaceutically acceptable salt thereof described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compounds and pharmaceutically acceptable salts thereof described herein can be incorporated into oral liquid preparations such as aqueous or oily suspensions, solutions, emulsions, syrups, or elixirs, for example. Moreover, pharmaceutical compositions containing these compounds and pharmaceutically acceptable salts thereof can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound or pharmaceutically acceptable salt thereof is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compounds and pharmaceutically acceptable salts thereof described herein may be administered parenterally in a sterile medium. Parenteral administration includes subcutaneous injections, intravenous, intramuscular, intrathecal injection or infusion techniques. The compounds and pharmaceutically acceptable salts thereof described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compounds and pharmaceutically acceptable salts thereof described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compounds and pharmaceutically acceptable salts thereof described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compounds and pharmaceutically acceptable salts thereof described herein may also be formulated for transdermal administration as a transdermal patch.

Topical pharmaceutical compositions comprising at least one compound or pharmaceutically acceptable salt thereof described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds and pharmaceutically acceptable salts thereof described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound or pharmaceutically acceptable salt thereof include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compounds and pharmaceutically acceptable salts thereof described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound or pharmaceutically acceptable salt thereof described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound or pharmaceutically acceptable salt thereof described herein, and instructions for using the composition to treat a subject (typically a human patient). In some embodiments, the instructions are for using the pharmaceutical composition to treat a subject suffering a disease state mediated by transglutaminase TG2 activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compounds or pharmaceutically acceptable salts thereof can be administered alone, as mixtures, or in combination with other active agents.

Also provided are methods for treating Celiac disease comprising administering to a subject, at least one compound or pharmaceutically acceptable salt thereof described herein. In some embodiments, the at least one compound or pharmaceutically acceptable salt thereof is administered, either simultaneously or sequentially, in combination with one or more additional agents used in the treatment of Celiac disease. In some embodiments, the at least one compound or pharmaceutically acceptable salt thereof and the one or more additional agents are present in a combined composition. In some embodiments, the at least one compound or pharmaceutically acceptable salt thereof and the one or more additional agents are administered separately.

Also provided are pharmaceutical compositions comprising at least one compound or pharmaceutically acceptable salt thereof described herein and one or more additional pharmaceutical agents used in the treatment of Celiac disease. Similarly, also provided are packaged pharmaceutical compositions containing a first pharmaceutical composition comprising at least one compound or pharmaceutically acceptable salt thereof described herein, and another composition comprising one or more additional pharmaceutical agents used in the treatment of Celiac disease.

The methods for treating Celiac disease, as provided herein, may be useful for both prophylactic and therapeutic purposes. Evidence of therapeutic effect may be any diminution in the severity of disease, particularly diminution of the severity of such symptoms as fatigue, chronic diarrhea, malabsorption of nutrients, weight loss, abdominal distension, and anemia. Other indicators of Celiac disease include the presence of antibodies specific for glutens, antibodies specific for tissue transglutaminase, the presence of pro-inflammatory T cells and cytokines, and degradation of the villus structure of the small intestine. Application of the methods and compositions provided herein can result in the improvement of any or all of these indicators of Celiac disease.

Subjects suitable for prophylaxis in accordance with the Celiac disease treatment methods provided herein may be identified by genetic testing for predisposition, e.g., by human leukocyte antigen (HLA) typing; by family history, and by other methods known in the art.

Patients who may benefit from the Celiac disease treatment methods provided herein include both adults and children. As is known in the art for other medications, and in accordance with the treatment method herein, dosages of the compounds and pharmaceutically acceptable salts thereof provided herein can be adjusted for pediatric use.

The methods described herein include methods for treating Huntington's disease, including treating memory and/or cognitive impairment associated with Huntington's disease, comprising administering to a subject, simultaneously or sequentially, at least one compound or pharmaceutically acceptable salt thereof described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound or pharmaceutically acceptable salt thereof described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one compound or pharmaceutically acceptable salt thereof described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one compound or pharmaceutically acceptable salt thereof described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one compound or pharmaceutically acceptable salt thereof described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one compound or pharmaceutically acceptable salt thereof described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one compound or pharmaceutically acceptable salt thereof described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds and pharmaceutically acceptable salts thereof described herein are typically administered at dosage levels and in a manner customary for transglutaminase TG2 inhibitors. For example, the compounds and pharmaceutically acceptable salts thereof can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound or pharmaceutically acceptable salt thereof described herein, for example, 0.1-50 mg of at least one compound or pharmaceutically acceptable salt thereof described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/ day. Unit dosage forms can contain, for example, 0.1-10 mg of at least one compound or pharmaceutically acceptable salt thereof described herein.

A labeled form of a compound or pharmaceutically acceptable salt thereof described herein can be used as a diagnostic for identifying and/or obtaining compounds that have the function of modulating an activity of transglutaminase TG2 as described herein. The compounds and pharmaceutically acceptable salts thereof described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds and pharmaceutically acceptable salts thereof, compositions, and methods described herein are further illustrated by the following non-limiting examples.

As used herein, the following abbreviations have the following meanings. If an abbreviation is not defined, it has its generally accepted meaning.
CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=tert-butyl alcohol
LiHMDS=lithium hexamethyl-disilazide
LC/MS=liquid chromatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate
μL=microliter
μM=micromolar

EXPERIMENTAL

Commercially available reagents and solvents (HPLC grade) were used without further purification.

$^1$H NMR spectra were recorded on a Bruker DRX 500 MHz spectrometer or Bruker DPX 250 MHz spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical HPLC-MS was performed on Shimadzu LCMS-2010EV systems using reverse phase Atlantis dC18 columns (3 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2788 dual wavelength UV detector. Mass spectra were obtained over the range m/z 150 to 850 at a sampling rate of 2 scans per second using Waters LCT or analytical HPLC-MS on Shimadzu LCMS-2010EV systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array. Data were integrated and reported using Shimadzu psiport software.

Method A

Example A-1

[4-(4-Acryloylamino-piperidine-1-sulfonyl)-phenyl]carbamic acid benzyl ester

[1-(4-Nitro-benzenesulfonyl)-piperidin-4-yl]carbamic acid tert-butyl ester

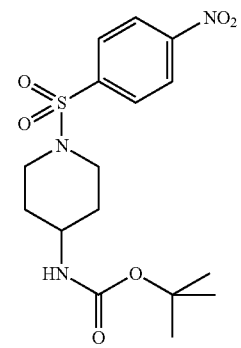 [SMILES: CC(C)(C)OC(=O)NC1CCN(S(=O)(=O)c2ccc([N+](=O)[O-])cc2)CC1]

Diisopropylethylamine (4.5 ml, 27.0 mmol) was added in one portion to a stirred solution of piperidin-4-yl-carbamic acid tert-butyl ester (5.0 g, 20.0 mmol) in DCM (40 ml) at room temperature. To this mixture was added 4-nitrophenyl sulfonyl chloride (6.0 g, 27.0 mmol) in one portion and the mixture was stirred at room temperature under a nitrogen atmosphere for 1 hour. After this time the mixture was diluted with DCM (100 ml) and washed sequentially with HCl (1M solution, 50 ml), NaOH (1M solution, 50 ml) and brine (50 ml). The organic layer was separated, dried (MgSO$_4$), filtered and concentrated. The resulting solid was collected by filtration, dried with diethyl ether and dried under vacuum give the title compound (7.14 g, 74% yield) as a pale yellow solid. Tr=2.07 min m/z (ES$^+$) (M+Na$^+$) 408.

1-(4-Nitro-benzenesulfonyl)-piperidin-4-ylamine

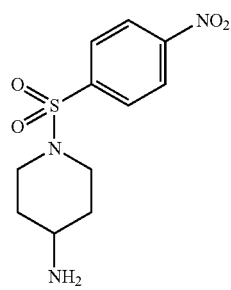 [SMILES: NC1CCN(S(=O)(=O)c2ccc([N+](=O)[O-])cc2)CC1]

[1-(4-Nitro-benzenesulfonyl)-piperidin-4-yl]-carbamic acid tert-butyl ester (3.5 g, 9.0 mmol) was suspended in a 4M solution of HCl in Dioxane (100 ml). The resulting suspension was stirred at room temperature for 3 hours. After this time the solution was concentrated under vacuum, then azeotroped with methanol and suspended in diethyl ether. The resulting solid precipitate was then collected by filtration, washed with diethyl ether and dried under vacuum to afford the title compound (2.3 g, 86% yield) as a white solid. Tr=1.10 min, m/z (ES$^+$) (M+H)$^+$ 286.

N-[1-(4-Nitro-benzenesulfonyl)-piperidin-4-yl]-acrylamide

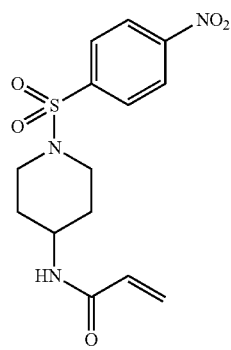 [SMILES: C=CC(=O)NC1CCN(S(=O)(=O)c2ccc([N+](=O)[O-])cc2)CC1]

Diisopropylethylamine (6.8 ml, 41.5 mmol) was added in one portion to a stirred solution of 1-(4-nitro-benzenesulfonyl)-piperidin-4-ylamine (2.36 g, 8.3 mmol) in DCM (10 ml) followed by the drop wise addition of acryloyl chloride (0.78 ml, 9.1 mmol) and the mixture was stirred at room temperature under a nitrogen atmosphere for 3 hours. After this time the resulting precipitate was collected by filtration, washed with water and dried under vacuum to give the title compound (2.80 g, 98% yield) as a white solid. δ$_H$ (500 MHz, DMSO) 8.39-8.51 (m, 2 H) 7.95-8.10 (m, 3 H) 6.11-6.21 (m, 1 H) 6.01-6.10 (m, 1 H) 5.56 (dd, J=10.09, 2.20 Hz, 1 H) 3.61-3.68 (m, 1 H) 3.52-3.60 (m, 2 H) 2.56-2.66 (m, 2 H) 1.83 (dd, J=13.20, 3.30 Hz, 2 H) 1.36-1.47 (m, 2 H). Tr=1.63 min, m/z (ES$^+$) (M+H)$^+$ 340.

N-[1-(4-Amino-benzenesulfonyl)-piperidin-4-yl]-acrylamide

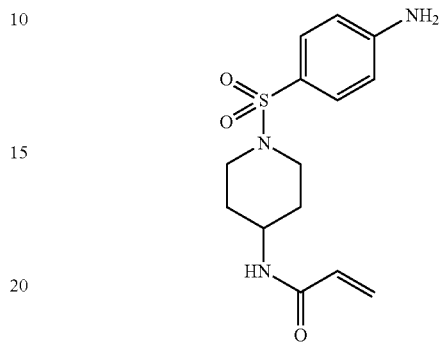

N-[1-(4-Nitro-benzenesulfonyl)-piperidin-4-yl]-acrylamide (2.80 g, 8.3 mmol) was suspended in a 5:1 mixture of ethanol and water (30 ml). To this solution was added iron powder (1.20 g, 21.0 mmol) followed by saturated ammonium chloride solution (3 ml) and the mixture was heated to 80° C. for three hours. After this time, the reaction mixture was cooled to room temperature and filtered through a pad of celite, the celite was washed with ethanol (10 ml) and EtOAc (50 ml) and the solution was concentrated under vacuum. The resulting residue was suspended in water (10 ml) and the solid precipitate collected by filtration and dried under vacuum to give the title compound (1.3 g, 51% yield) as a white solid. Tr=1.30 min, m/z (ES$^+$) (M+H)$^+$ 310.

[4-(4-Acryloylamino-piperidine-1-sulfonyl)-phenyl] carbamic acid benzyl ester

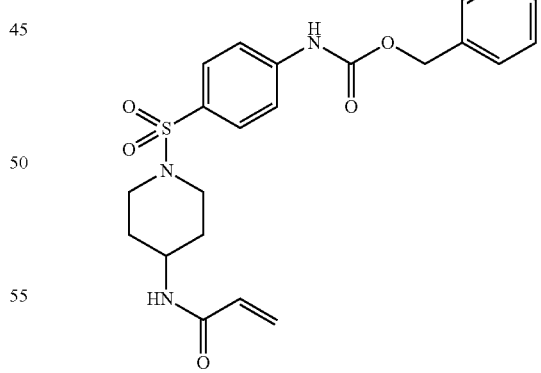

N-[1-(4-Amino-benzenesulfonyl)-piperidin-4-yl]-acrylamide (0.09 g, 0.3 mmol) was dissolved in THF (5 ml). To this was added diisopropylethylamine (0.1 ml, 0.6 mmol) in one portion followed by the drop wise addition of benzyl chloroformate (0.05 ml, 0.33 mmol) and the mixture was stirred at room temperature under a nitrogen atmosphere for 3 hours. After this time the mixture was diluted with DCM (100 ml) and washed sequentially with HCl (1M solution, 50 ml), NaOH (1M solution, 50 ml) and brine (50 ml). The organic layer was separated, dried (MgSO$_4$), filtered and concentrated. The resulting residue was purified by flash column chromatography (elution: 100% EtOAc) to give the title compound (0.04 g, 34% yield) as a white powder.

Example A-1

[4-(4-Acryloylamino-piperidine-1-sulfonyl)-phenyl]-carbamic acid benzyl ester $\delta_H$ (500 MHz, DMSO) 10.32 (s, 1 H) 8.05 (d, J=7.52 Hz, 1 H) 7.57-7.79 (m, 4 H) 7.25-7.50 (m, 5 H) 6.11-6.24 (m, 1 H) 5.98-6.10 (m, 1 H) 5.56 (dd, J=10.09, 2.38 Hz, 1 H) 5.20 (s, 2 H) 3.53-3.64 (m, 1 H) 3.43-3.52 (m, 2 H) 2.42-2.50 (m, 2 H) 1.81 (dd, J=13.11, 3.03 Hz, 2 H) 1.32-1.51 (m, 2 H). Tr=3.93 min, m/z (ES$^+$) (M+H)$^+$ 444.

Example A-2

N-[1-(4-Cyclohexyl-benzenesulfonyl)-piperidin-4-yl]acrylamide $\delta_H$ (500 MHz, MeOD) 7.71 (d, J=8.39 Hz, 2 H) 7.49 (d, J=8.24 Hz, 2 H) 6.21 (d, J=6.10 Hz, 2 H) 5.58-5.70 (m, 1 H) 3.62-3.76 (m, 3 H) 2.58-2.72 (m, 1 H) 2.49 (td, J=11.79, 2.37 Hz, 2 H) 1.85-1.99 (m, 6 H) 1.80 (d, J=12.82 Hz, 1 H) 1.42-1.65 (m, 6 H) 1.25-1.40 (m, 1 H). Tr=4.76 min, m/z (ES$^+$) (M+H)$^+$ 377.

Example A-3

Cyclopropanecarboxylic acid [4-(4-acryloylamino-piperidine-1-sulfonyl)-phenyl]-amide $\delta_H$ (500 MHz, DMSO) 10.66 (s, 1 H) 8.02-8.11 (m, 1 H) 7.79-7.88 (m, 2 H) 7.62-7.71 (m, 2 H) 6.12-6.22 (m, 1 H) 5.99-6.09 (m, 1 H) 5.56 (dd, J=10.09, 2.20 Hz, 1 H) 3.54-3.65 (m, 1 H) 3.53 (br. s., 1 H) 3.39-3.53 (m, 2 H) 2.40-2.47 (m, 2 H) 1.74-1.91 (m, 3 H) 1.30-1.50 (m, 2 H) 0.81-0.93 (m, 4 H). Tr=3.24 min, m/z (ES$^+$) (M+H)$^+$ 378.

Example A-4

Adamantane-1-carboxylic acid [4-(4-acryloylamino-piperidine-1-sulfonyl)-phenyl]-amide $\delta_H$ (500 MHz, DMSO) 9.56 (s, 1 H) 8.06 (d, J=7.34 Hz, 1 H) 7.96 (d, J=8.99 Hz, 2 H) 7.67 (d, J=8.80 Hz, 2 H) 6.10-6.24 (m, 1 H) 5.98-6.09 (m, 1 H) 5.56 (dd, J=10.09, 2.20 Hz, 1 H) 3.56-3.65 (m, 1 H) 3.42-3.51 (m, 2 H) 2.40-2.50 (m, 2 H) 2.03 (br. s., 6 H) 1.89-1.98 (m, 3 H) 1.74-1.88 (m, 2 H) 1.66-1.75 (m, 6 H) 1.34-1.51 (m, 2 H). Tr=4.33 min, m/z (ES$^+$) (M+H)$^+$ 472.

Example A-5

Tetrahydro-pyran-4-carboxylic acid [4-(4-acryloylamino-piperidine-1-sulfonyl)-phenyl]-amide $\delta_H$ (500 MHz, DMSO) 10.36 (s, 1 H) 8.06 (d, J=7.52 Hz, 1 H) 7.86 (d, J=8.80 Hz, 2 H) 7.68 (d, J=8.80 Hz, 2 H) 6.10-6.22 (m, 1 H) 5.99-6.09 (m, 1 H) 5.56 (dd, J=10.18, 2.29 Hz, 1 H) 3.84-3.96 (m, 2 H) 3.53-3.66 (m, 1 H) 3.42-3.53 (m, 2 H) 2.56-2.69 (m, 2 H) 2.41-2.49 (m, 2 H) 1.82 (dd, J=13.20, 3.30 Hz, 2 H) 1.58-1.76 (m, 4 H) 1.30-1.47 (m, 2 H). Tr=3.19 min, m/z (ES$^+$) (M+H)$^+$ 422.

Example A-6

N-{1-[4-(3-Phenyl-propionylamino)-benzenesulfonyl]-piperidin-4-yl}-acrylamide $\delta_H$ (500 MHz, DMSO) 10.38 (s, 1 H) 8.06 (d, J=7.34 Hz, 1 H) 7.83 (d, J=8.80 Hz, 2 H) 7.67 (d, J=8.80 Hz, 2 H) 7.05-7.34 (m, 5 H) 6.11-6.22 (m, 1 H) 5.97-6.09 (m, 1 H) 5.56 (dd, J=10.18, 2.29 Hz, 1 H) 3.53-3.66 (m, 1 H) 3.46 (d, J=11.92 Hz, 2 H) 2.93 (t, J=7.70 Hz, 2 H) 2.61-2.76 (m, 2 H) 2.37-2.48 (m, 2 H) 1.82 (dd, J=13.02, 3.12 Hz, 2 H) 1.30-1.49 (m, 2 H). Tr=3.79 min, m/z (ES$^+$) (M+H)$^+$ 442.

Example A-7

2-Phenyl-cyclopropanecarboxylic acid [4-(4-acryloylamino-piperidine-1-sulfonyl)-phenyl]-amide $\delta_H$ (500 MHz, DMSO) 10.72 (s, 1 H) 7.99-8.12 (m, 1 H) 7.84 (d, J=8.99 Hz, 2 H) 7.68 (d, J=8.99 Hz, 2 H) 7.13-7.39 (m, 5 H) 6.11-6.22 (m, 1 H) 5.98-6.09 (m, 1 H) 5.47-5.62 (m, 1 H) 3.54-3.66 (m, 1 H) 3.42-3.52 (m, 2 H) 2.34-2.45 (m, 2 H) 2.06-2.22 (m, 1 H) 1.75-1.88 (m, 2 H) 1.49-1.60 (m, 1 H) 1.34-1.48 (m, 3 H). Tr=3.94 min, m/z (ES$^+$) (M+H)$^+$ 454.

Example A-8

[4-(3-Acryloylamino-pyrrolidine-1-sulfonyl)-phenyl]-carbamic acid benzyl ester $\delta_H$ (500 MHz, CDCl$_3$) 7.70 (d, J=8.70 Hz, 2 H) 7.51 (d, J=8.54 Hz, 2 H) 7.25-7.39 (m, 5 H) 6.98 (s, 1 H) 6.17 (d, J=16.94 Hz, 1 H) 5.89 (dd, J=16.94, 10.38 Hz, 1 H) 5.49-5.66 (m, 2 H) 5.16 (s, 2 H) 4.24-4.45 (m, 1 H) 3.32-3.46 (m, 1 H) 3.21 (d, J=4.42 Hz, 2 H) 3.09 (td, J=9.38, 5.34 Hz, 1 H) 1.94-2.08 (m, 1 H) 1.70-1.85 (m, 1 H). Tr=4.05 min, m/z (ES$^+$) (M+H)$^+$ 430.

Example A-9

N-{1-[4-(3-Naphthalen-1-yl-propionylamino)-benzenesulfonyl]-piperidin-4-yl}-acrylamide $\delta_H$ (500 MHz, DMSO) 10.41 (s, 1 H) 8.12-8.21 (m, 1 H) 8.02-8.11 (m, 1 H) 7.94 (d, J=7.93 Hz, 1 H) 7.76-7.87 (m, 3 H) 7.64-7.73 (m, 2 H) 7.50-7.64 (m, 2 H) 7.34-7.49 (m, 2 H) 6.11-6.24 (m, 1 H) 5.98-6.11 (m, 1 H) 3.53-3.64 (m, 1 H) 3.46-3.52 (m, 2 H) 2.81 (t, J=7.71 Hz, 2 H) 2.42-2.47 (m, 2 H) 1.78-1.91 (m, 2 H) 1.36-1.50 (m, 2 H). Tr=4.15 min, m/z (ES$^+$) (M+H)$^+$ 492.

Example A-10

N-{1-[4-(3-Cyclohexyl-propionylamino)-benzenesulfonyl]-piperidin-4-yl}-acrylamide $\delta_H$ (500 MHz, DMSO) 10.31 (s, 1 H) 8.04 (d, J=7.02 Hz, 1 H) 7.83 (d, J=8.70 Hz, 2 H) 7.67 (d, J=8.70 Hz, 2 H) 6.12-6.23 (m, 1 H) 5.99-6.09 (m, 1 H) 5.56 (d, J=9.92 Hz, 1 H) 3.55-3.64 (m, 1 H) 3.48 (d, J=11.60 Hz, 2 H) 2.44-2.48 (m, 2 H) 2.37 (t, J=7.55 Hz, 2 H) 1.82 (d, J=12.51 Hz, 1 H) 1.58-1.75 (m, 5 H)

1.37-1.55 (m, 4 H) 1.06-1.28 (m, 5 H) 0.77-0.99 (m, 2 H). Tr=4.20 min, m/z (ES$^+$) (M+H)$^+$ 448.

Example A-11

4-tert-Butyl-cyclohexanecarboxylic acid [4-(4-acryloylamino-piperidine-1-sulfonyl)-phenyl]-amide $\delta_H$ (500 MHz, DMSO) 10.25 (s, 1 H) 8.04 (d, J=7.17 Hz, 1 H) 7.85 (d, J=8.70 Hz, 2 H) 7.66 (d, J=8.70 Hz, 2 H) 6.11-6.23 (m, 1 H) 5.98-6.10 (m, 1 H) 5.56 (d, J=10.22 Hz, 1 H) 3.61 (d, J=2.29 Hz, 1 H) 3.47 (d, J=11.90 Hz, 2 H) 2.42-2.48 (m, 2 H) 2.21-2.33 (m, 1 H) 1.88-1.96 (m, 2 H) 1.74-1.87 (m, 4 H) 1.33-1.51 (m, 4 H) 0.95-1.09 (m, 3 H) 0.86 (s, 9 H). Tr=4.52 min, m/z (ES$^+$) (M+H)$^+$ 476.

Example A-12

Benzofuran-2-carboxylic acid [4-(4-acryloylamino-piperidine-1-sulfonyl)-phenyl]-amide $\delta_H$ (500 MHz, DMSO) 10.93 (s, 1 H) 8.00-8.17 (m, 3 H) 7.82-7.93 (m, 2 H) 7.69-7.81 (m, 3 H) 7.54 (t, J=7.78 Hz, 1 H) 7.32-7.45 (m, 1 H) 6.11-6.24 (m, 1 H) 5.96-6.11 (m, 1 H) 5.56 (d, J=10.22 Hz, 1 H) 3.64 (br. s., 1 H) 3.51 (d, J=12.05 Hz, 2 H) 2.53-2.60 (m, 2 H) 1.84 (d, J=11.14 Hz, 2 H) 1.38-1.51 (m, 2 H). Tr=3.89 min, m/z (ES$^+$) (M+H)$^+$ 454.

Example A-13

[3-(4-Acryloylamino-piperidine-1-sulfonyl)-phenyl]-carbamic acid benzyl ester $\delta_H$ (500 MHz, DMSO) 10.17 (br. s., 1 H) 8.05 (d, J=7.32 Hz, 1 H) 7.98 (s, 1 H) 7.71 (d, J=7.93 Hz, 1 H) 7.56 (t, J=7.93 Hz, 1 H) 7.29-7.47 (m, 6 H) 6.12-6.23 (m, 1 H) 5.99-6.10 (m, 1 H) 5.50-5.61 (m, 1 H) 5.19 (s, 2 H) 3.61 (br. s., 1 H) 3.42-3.54 (m, 2 H) 2.53-2.59 (m, 2 H) 1.74-1.94 (m, 2 H) 1.35-1.51 (m, 2 H). Tr=3.86 min, m/z (ES$^+$) (M+H)$^+$ 444.

Example A-14

N-{1-[3-(3-Phenyl-propionylamino)-benzenesulfonyl]-piperidin-4-yl}-acrylamide $\delta_H$ (500 MHz, DMSO) 10.29 (s, 1 H) 8.01-8.11 (m, 2 H) 7.86 (d, J=8.09 Hz, 1 H) 7.57 (t, J=8.01 Hz, 1 H) 7.39 (d, J=7.63 Hz, 1 H) 7.11-7.33 (m, 5 H) 6.12-6.24 (m, 1 H) 6.00-6.11 (m, 1 H) 5.49-5.64 (m, 1 H) 3.56-3.70 (m, 1 H) 3.43-3.54 (m, 2 H) 2.85-3.00 (m, 2 H) 2.66 (t, J=7.78 Hz, 2 H) 1.76-1.93 (m, 2 H) 1.44 (q, J=10.33 Hz, 2 H). Tr=3.97 min, m/z (ES$^+$) (M+H)$^+$ 442.

Example A-15

Tetrahydro-pyran-4-carboxylic acid [3-(4-acryloylamino-piperidine-1-sulfonyl)-phenyl]-amide $\delta_H$ (500 MHz, DMSO) 10.26 (s, 1 H) 8.01-8.16 (m, 2 H) 7.87 (d, J=8.24 Hz, 1 H) 7.57 (t, J=8.01 Hz, 1 H) 7.39 (d, J=7.78 Hz, 1 H) 6.11-6.22 (m, 1 H) 5.98-6.10 (m, 1 H) 5.56 (d, J=10.22 Hz, 1 H) 3.92 (d, J=11.44 Hz, 2 H) 3.55-3.69 (m, 1 H) 3.49 (d, J=11.60 Hz, 2 H) 2.58-2.65 (m, 2 H) 1.79-1.90 (m, 2 H) 1.58-1.80 (m, 4 H) 1.36-1.53 (m, 2 H). Tr=3.11 min, m/z (ES$^+$) (M+H)$^+$ 422.

Example A-16

Furan-2-carboxylic acid [4-(4-acryloylamino-piperidine-1-sulfonyl)-phenyl]-amide $\delta_H$ (500 MHz, DMSO) 10.62 (br. s., 1 H) 7.93-8.13 (m, 4 H) 7.64-7.81 (m, 2 H) 7.42 (br. s., 1 H) 6.73 (br. s., 1 H) 6.09-6.25 (m, 1 H) 5.97-6.12 (m, 1 H) 5.55 (d, J=9.46 Hz, 1 H) 3.62 (br. s., 1 H) 3.43-3.54 (m, 2 H) 1.73-1.94 (m, 2 H) 1.31-1.58 (m, 2 H). Tr=3.31 min, m/z (ES$^+$) (M+H)$^+$ 404.

Example A-17

N-{1-[4-(3-Adamantan-1-yl-propionylamino)-benzenesulfonyl]-piperidin-4-yl}-acrylamide $\delta_H$ (500 MHz, DMSO) 10.34 (s, 1 H) 8.06 (d, J=7.57 Hz, 1 H) 7.83 (d, J=8.83 Hz, 2 H) 7.67 (d, J=8.83 Hz, 2 H) 6.11-6.23 (m, 1 H) 5.99-6.10 (m, 1 H) 5.56 (dd, J=10.17, 2.29 Hz, 1 H) 3.54-3.65 (m, 1 H) 3.47 (d, J=11.82 Hz, 2 H) 2.40-2.49 (m, 2 H) 2.25-2.35 (m, 2 H) 1.94 (br. s., 3 H) 1.82 (dd, J=13.00, 3.07 Hz, 2 H) 1.56-1.72 (m, 6 H) 1.34-1.50 (m, 10 H). Tr=4.70 min, m/z (ES$^+$) (M+H)$^+$ 500.

Example A-18

5,6-Dihydro-4H-cyclopenta[b]thiophene-2-carboxylic acid [4-(4-acryloylamino-piperidine-1-sulfonyl)-phenyl]-amide $\delta_H$ (500 MHz, DMSO) 10.46 (s, 1 H) 8.07 (d, J=7.41 Hz, 1 H) 8.00 (d, J=8.67 Hz, 2 H) 7.88 (s, 1 H) 7.73 (d, J=8.83 Hz, 2 H) 6.11-6.24 (m, 1 H) 6.00-6.10 (m, 1 H) 5.56 (dd, J=10.17, 1.97 Hz, 1 H) 3.55-3.64 (m, 1 H) 3.49 (d, J=11.82 Hz, 2 H) 2.92 (t, J=7.25 Hz, 2 H) 2.76 (t, J=7.17 Hz, 2 H) 2.35-2.45 (m, 2 H) 1.83 (d, J=10.09 Hz, 2 H) 1.35-1.54 (m, 2 H). Tr=4.22 min, m/z (ES$^+$) (M+H)$^+$ 461.

Example A-19

[4-(3-Acryloylamino-piperidine-1-sulfonyl)-phenyl]-carbamic acid benzyl ester $\delta_H$ (500 MHz, DMSO) 10.32 (s, 1 H) 8.07 (d, J=7.78 Hz, 1 H) 7.61-7.75 (m, 4 H) 7.29-7.50 (m, 5 H) 6.17-6.29 (m, 1 H) 6.05-6.16 (m, 1 H) 5.61 (dd, J=10.07, 2.14 Hz, 1 H) 5.11-5.24 (m, 2 H) 3.71-3.88 (m, 1 H) 3.37-3.46 (m, 1 H) 3.25 (br. s., 1 H) 2.37 (br. s., 1 H) 2.05-2.23 (m, 1 H) 1.61-1.82 (m, 2 H) 1.40-1.57 (m, 1 H) 1.01-1.26 (m, 1 H). Tr=4.04 min, m/z (ES$^+$) (M+H)$^+$ 445.

Example A-20

4,5,6,7-Tetrahydro-1H-indole-2-carboxylic acid [4-(4-acryloylamino-piperidine-1-sulfonyl)-phenyl]-amide $\delta_H$ (500 MHz, DMSO) 11.29 (s, 1 H) 9.93 (s, 1 H) 8.03-8.10 (m, 1 H) 8.01 (d, J=8.85 Hz, 2 H) 7.68 (d, J=8.85 Hz, 2 H) 6.88 (d, J=2.14 Hz, 1 H) 6.09-6.23 (m, 1 H) 5.98-6.09 (m, 1 H) 5.56 (dd, J=10.07, 2.14 Hz, 1 H) 3.54-3.70 (m, 1 H) 3.48 (d, J=11.90 Hz, 2 H) 2.56-2.60 (m, 2 H) 2.43-2.48 (m, 2 H) 1.76-1.93 (m, 2 H) 1.62-1.77 (m, 4 H) 1.34-1.51 (m, 2 H). Tr=3.92 min, m/z (ES$^+$) (M+H)$^+$ 457.

Example A-21

5-Pyrrolidin-1-ylmethyl-furan-2-carboxylic acid [4-(4-acryloylamino-piperidine-1-sulfonyl)-phenyl]-amide $\delta_H$ (500 MHz, DMSO) 10.50 (s, 1 H) 8.06-8.11 (m, 1 H) 8.02 (d, J=8.67 Hz, 2 H) 7.73 (d, J=8.83 Hz, 2 H) 7.39 (d, J=3.31 Hz, 1 H) 6.54 (d, J=3.31 Hz, 1 H) 6.13-6.22 (m, 1 H) 5.98-6.10 (m, 1 H) 5.56 (dd, J=10.09, 1.89 Hz, 1 H) 3.67-3.73 (m, 2 H) 3.57-3.64 (m, 1 H) 3.43-3.53 (m, 2 H) 1.83 (d, J=10.40 Hz, 2 H) 1.63-1.77 (m, 4 H) 1.33-1.51 (m, 2 H). Tr=2.68 min, m/z (ES$^+$) (M+H)$^+$ 487.

Example A-22

Benzo[b]thiophene-2-carboxylic acid [4-(4-acryloylamino-piperidine-1-sulfonyl)-phenyl]-amide $\delta_H$ (500 MHz, DMSO) 10.92 (s, 1 H) 8.44 (s, 1 H) 7.97-8.15 (m, 5 H) 7.78 (d, J=8.83 Hz, 2 H) 7.43-7.60 (m, 2 H) 6.12-6.22 (m, 1 H) 5.99-6.11 (m, 1 H) 5.56 (dd, J=10.09, 2.05 Hz, 1 H) 3.56-3.67 (m, 1 H) 3.51 (d, J=11.82 Hz, 2 H) 2.52-2.58 (m, 2 H) 1.74-1.92 (m, 2 H) 1.26-1.52 (m, 2 H). Tr=4.10 min, m/z (ES$^+$) (M+H)$^+$ 470.

Example A-23

3-Methyl-benzofuran-2-carboxylic acid [4-(4-acryloylamino-piperidine-1-sulfonyl)-phenyl]-amide $\delta_H$ (500 MHz, DMSO) 10.86 (s, 1 H) 8.14 (d, J=8.83 Hz, 2 H) 8.08 (d, J=7.41 Hz, 1 H) 7.83 (d, J=7.72 Hz, 1 H) 7.66-7.79 (m, 3 H) 7.51-7.59 (m, 1 H) 7.41 (t, J=7.49 Hz, 1 H) 6.10-6.23 (m, 1 H) 5.96-6.12 (m, 1 H) 5.56 (dd, J=10.01, 2.13 Hz, 1 H) 3.57-3.71 (m, 1 H) 3.51 (d, J=11.98 Hz, 2 H) 2.64 (s, 3 H) 2.51-2.56 (m, 2 H) 1.84 (dd, J=12.93, 2.84 Hz, 2 H) 1.32-1.52 (m, 2H). Tr=4.27 min, m/z (ES$^+$) (M+H)$^+$ 468.

Example A-24

1H-Indole-2-carboxylic acid [4-(4-acryloylamino-piperidine-1-sulfonyl)-phenyl]-amide $\delta_H$ (500 MHz, DMSO) 11.91 (s, 1 H) 10.67 (s, 1 H) 8.08-8.19 (m, 3 H) 7.70-7.90 (m, 3 H) 7.45-7.63 (m, 2 H) 7.27-7.37 (m, 1 H) 7.15 (t, J=7.49 Hz, 1 H) 6.16-6.32 (m, 1 H) 6.02-6.15 (m, 1 H) 5.62 (dd, J=10.09, 2.21 Hz, 1 H) 3.61-3.74 (m, 1 H) 3.57 (d, J=12.14 Hz, 2 H) 2.59-2.66 (m, 2 H) 1.90 (dd, J=13.00, 3.07 Hz, 2 H) 1.36-1.60 (m, 2 H). Tr=3.89 min, m/z (ES$^+$) (M+H)$^+$ 453.

Example A-25

4,5,6,7-Tetrahydro-benzo[b]thiophene-2-carboxylic acid [4-(4-acryloylamino-piperidine-1-sulfonyl)-phenyl]-amide $\delta_H$ (500 MHz, DMSO) 10.45 (s, 1 H) 8.07 (d, J=7.41 Hz, 1 H) 7.99 (d, J=8.67 Hz, 2 H) 7.78 (s, 1 H) 7.71 (d, J=8.83 Hz, 2 H) 6.09-6.24 (m, 1 H) 5.97-6.07 (m, 1 H) 5.55 (dd, J=10.17, 2.13 Hz, 1 H) 3.55-3.66 (m, 1 H) 3.48 (d, J=11.82 Hz, 2 H) 2.77 (t, J=5.60 Hz, 2 H) 2.59-2.67 (m, 2 H) 1.70-1.87 (m, 6 H) 1.35-1.51 (m, 2 H). Tr=4.31 min, m/z (ES$^+$) (M+H)$^+$ 474.

Example A-26

5-Phenyl-furan-2-carboxylic acid [4-(4-acryloylamino-piperidine-1-sulfonyl)-phenyl]-amide $\delta_H$ (500 MHz, DMSO) 10.57 (s, 1 H) 8.02-8.11 (m, 3 H) 7.98 (d, J=7.48 Hz, 2 H) 7.76 (d, J=8.70 Hz, 2 H) 7.47-7.57 (m, 3 H) 7.37-7.46 (m, 1 H) 7.23 (d, J=3.51 Hz, 1 H) 6.12-6.21 (m, 1 H) 5.98-6.08 (m, 1 H) 5.55 (dd, J=10.15, 2.06 Hz, 1 H) 3.56-3.68 (m, 1 H) 3.50 (d, J=11.75 Hz, 2 H) 1.83 (d, J=10.38 Hz, 2 H) 1.44 (q, J=10.22 Hz, 2 H). Tr=4.21 min, m/z (ES$^+$) (M+H)$^+$ 480.

Example A-27

4-Phenyl-thiophene-2-carboxylic acid [4-(4-acryloylamino-piperidine-1-sulfonyl)-phenyl]-amide $\delta_H$ (500 MHz, DMSO) 10.65 (s, 1 H) 8.53 (d, J=1.22 Hz, 1 H) 8.25 (d, J=1.07 Hz, 1 H) 8.07 (d, J=7.32 Hz, 1 H) 8.02 (d, J=8.85 Hz, 2 H) 7.76 (dd, J=7.93, 5.19 Hz, 4 H) 7.49 (t, J=7.71 Hz, 2 H) 7.31-7.39 (m, 1 H) 6.11-6.23 (m, 1 H) 5.99-6.09 (m, 1 H) 5.55 (dd, J=9.99, 2.21 Hz, 1 H) 3.56-3.66 (m, 1 H) 3.50 (d, J=12.05 Hz, 2 H) 1.77-1.92 (m, 2 H) 1.39-1.52 (m, 2 H). Tr=4.43 min, m/z (ES$^+$) (M+H)$^+$ 496.

Example A-28

[4-(3-Acryloylamino-azetidine-1-sulfonyl)-phenyl]-carbamic acid benzyl ester $\delta_H$ (500 MHz, DMSO) 10.39 (s, 1 H) 8.62 (d, J=6.71 Hz, 1 H) 7.67-7.81 (m, 4 H) 7.29-7.51 (m, 5 H) 5.97-6.16 (m, 2 H) 5.60 (dd, J=9.23, 2.98 Hz, 1 H) 5.21 (s, 2 H) 4.22-4.44 (m, 1 H) 3.90 (t, J=8.09 Hz, 2 H) 3.41-3.53 (m, 2 H). Tr=3.88 min, m/z (ES$^+$) (M+H)$^+$ 416.

Method B

Example B-1

N-{1-[4-(Piperidine-1-carbonyl)-benzenesulfonyl]-piperidin-4-yl}-acrylamide 4-(4-tert-Butoxycarbonylamino-piperidine-1-sulfonyl)-benzoic acid

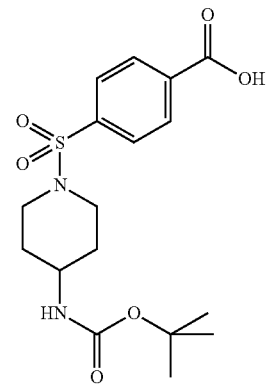 [SMILES: CC(C)(C)OC(=O)NC1CCN(S(=O)(=O)c2ccc(C(=O)O)cc2)CC1]

Diisopropylethylamine (10.9 ml, 62.4 mmol) was added in one portion to a stirred solution of piperidin-4-yl-carbamic acid tert-butyl ester (5.0 g, 20.0 mmol) in THF (150 ml) at room temperature. To this mixture was added 4-(chlorosulfonyl)benzoic acid (5.52 g, 25.0 mmol) portion wise and the mixture was stirred at room temperature under a nitrogen atmosphere for 1 hour. After this time the mixture was concentrated and the resulting residue suspended in HCl (1M solution, 100 ml), the resulting solid precipitate was collected by filtration, washed with water and dried under vacuum give the title compound (9.2 g, 96% yield) as a white solid. Tr=1.28 min m/z (ES+) (M+Na+) 407.

{1-[4-(Piperidine-1-carbonyl)-benzenesulfonyl]-piperidin-4-yl}-carbamic acid tert-butyl ester

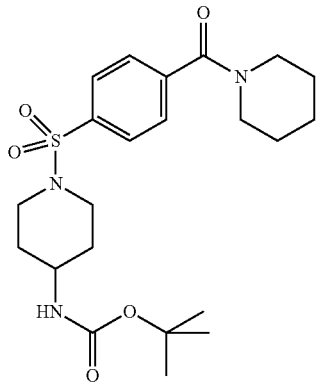 [SMILES: CC(C)(C)OC(=O)NC1CCN(S(=O)(=O)c2ccc(C(=O)N3CCCCC3)cc2)CC1]

Diisopropylethylamine (0.36 ml, 2.1 mmol) was added in one portion to a stirred solution of 4-(4-tert-butoxycarbonylamino-piperidine-1-sulfonyl)-benzoic acid (0.2 g, 0.52 mmol), EDC (0.2 g, 1.04 mmol) and HOBT (0.16 g, 1.04 mmol) in DCM (5 ml) at room temperature. The mixture was stirred at room temperature for 10 minutes before piperidine (0.07 ml, 0.78 mmol) was added in one portion and stirring continued for 24 hours. After this time the mixture was diluted with DCM (50 ml), washed sequentially with saturated sodium bicarbonate (20 ml), water (20 ml) and brine (20 ml). The organic layer was separated, dired (MgSO$_4$), filtered and concentrated. The resulting residue was purified by flash column chromatography (elution: 0 to 2% MeOH in DCM) to give the title compound (0.17 g, 74% yield) as a white powder. $\delta_H$ (250 MHz, MeOD) 7.89-8.06 (m, 2 H) 7.67-7.82 (m, 2 H) 3.68-3.93 (m, 4 H) 2.54-2.75 (m, 2 H) 2.02 (dd, J=12.94, 3.35 Hz, 2 H) 1.76-1.91 (m, 4 H) 1.56-1.75 (m, 4 H) 1.53 (s, 9 H). Tr=1.94 min m/z (ES+) (M+Na+) 474.

[4-(4-Amino-piperidine-1-sulfonyl)-phenyl]-piperidin-1-yl-methanone

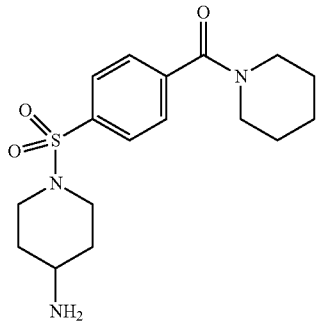 [SMILES: NC1CCN(S(=O)(=O)c2ccc(C(=O)N3CCCCC3)cc2)CC1]

{1-[4-(Piperidine-1-carbonyl)-benzenesulfonyl]-piperidin-4-yl}-carbamic acid tert-butyl ester (0.17 g, 0.39 mmol) was suspended in a 4M solution of HCl in Dioxane (10 ml). The resulting suspension was stirred at room temperature for 3 hours. After this time the solution was concentrated under vacuum, then azeotroped with methanol and suspended in diethyl ether. The resulting solid precipitate was then collected by filtration, washed with diethyl ether and dried under vacuum to afford the title compound (0.13 g, 100% yield) as a white solid. Tr=1.19 min, m/z (ES+) (M+H)+ 352.

N-{1-[4-(Piperidine-1-carbonyl)-benzenesulfonyl]-piperidin-4-yl}-acrylamide

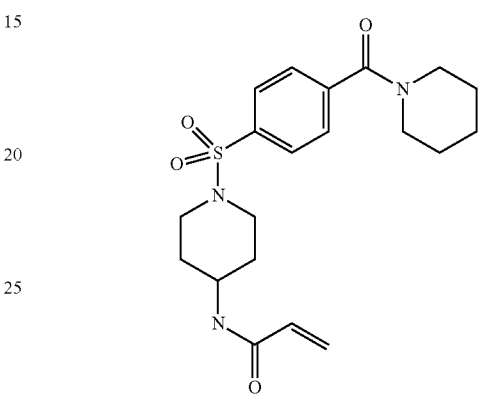

Diisopropylethylamine (0.33 ml, 1.9 mmol) was added in one portion to a stirred solution of [4-(4-amino-piperidine-1-sulfonyl)-phenyl]-piperidin-1-yl-methanone (0.13 g, 0.39 mmol) in THF (7 ml) followed by the drop wise addition of acryloyl chloride (0.03 ml, 0.43 mmol) and the mixture was stirred at room temperature under a nitrogen atmosphere for 3 hours. After this time the mixture was diluted with DCM (100 ml) and washed sequentially with HCl (1M solution, 50 ml), NaOH (1M solution, 50 ml) and brine (50 ml). The organic layer was separated, dried (MgSO$_4$), filtered and concentrated. The resulting residue was purified by flash column chromatography (elution: 100% EtOAc) to give the title compound (0.09 g, 58% yield) as a white powder.

Example B-1

N-{1-[4-(Piperidine-1-carbonyl)-benzenesulfonyl]-piperidin-4-yl}-acrylamide $\delta_H$ (500 MHz, MeOD) 7.89 (d, J=8.39 Hz, 2 H) 7.65 (d, J=8.39 Hz, 2 H) 6.16-6.27 (m, 2 H) 5.59-5.72 (m, 1 H) 3.64-3.82 (m, 5 H) 3.32-3.41 (m, 2 H) 2.58 (td, J=11.83, 2.29 Hz, 2 H) 1.90-2.01 (m, 2 H) 1.66-1.81 (m, 4 H) 1.45-1.65 (m, 4 H). Tr=3.42 min, m/z (ES+) (M+H)+ 406.

Example B-2

4-(4-Acryloylamino-piperidine-1-sulfonyl)-N-benzyl-N-methyl-benzamide $\delta_H$ (500 MHz, DMSO) 8.07 (d, J=7.25 Hz, 1 H) 7.63-7.86 (m, 4 H) 7.25-7.45 (m, 4 H) 7.18 (d, J=7.41 Hz, 1 H) 6.11-6.21 (m, 1 H) 5.99-6.10 (m, 1 H) 5.56 (d, J=9.93 Hz, 1 H) 4.35-4.76 (m, 2 H) 3.41-3.78 (m, 5 H) 2.77-2.99 (m, 3 H) 2.53-2.59 (m, 2 H) 1.82 (br. s., 2 H) 1.35-1.53 (m, 2H). Tr=3.68 min, m/z (ES+) (M+H)+ 442.

Example B-3

4-(4-Acryloylamino-piperidine-1-sulfonyl)-N-cyclopropylmethyl-benzamide $\delta_H$ (500 MHz, DMSO) 8.62 (t, J=5.60 Hz, 1 H) 7.77-7.91 (m, 3 H) 7.60 (d, J=8.51 Hz, 2 H) 5.86-6.00 (m, 1 H) 5.72-5.85 (m, 1 H) 5.32 (dd, J=10.01, 2.29 Hz, 1 H) 3.33-3.42 (m, 1 H) 3.24-3.34 (m, 2 H) 2.94 (d, J=6.31 Hz, 2 H) 2.29-2.35 (m, 2 H) 1.59 (dd, J=13.00, 3.23 Hz, 2 H) 1.08-1.28 (m, 2 H) 0.74-0.88 (m, 1 H) 0.15-0.28 (m, 2 H) -0.07-0.08 (m, 2 H). Tr=3.29 min, m/z (ES$^+$) (M+H)$^+$ 392.

Example B-4

N-{1-[3-(Piperidine-1-carbonyl)-benzenesulfonyl]-piperidin-4-yl}-acrylamide $\delta_H$ (500 MHz, DMSO) 8.07 (d, J=7.52 Hz, 1 H) 7.78-7.85 (m, 1 H) 7.69-7.76 (m, 2 H) 7.66 (s, 1 H) 6.10-6.21 (m, 1 H) 6.01-6.09 (m, 1 H) 5.56 (dd, J=10.00, 2.29 Hz, 1 H) 3.47-3.70 (m, 5 H) 2.52-2.57 (m, 2 H) 1.83 (dd, J=13.02, 3.30 Hz, 2 H) 1.61 (br. s., 4 H) 1.36-1.51 (m, 4 H). Tr=3.39 min, m/z (ES$^+$) (M+H)$^+$ 406.

Example B-5

N-(1-{4-[4-(6-Methyl-pyridin-2-yl)-piperazine-1-carbonyl]-benzenesulfonyl}-piperidin-4-yl)-acrylamide $\delta_H$ (500 MHz, DMSO) 8.10 (d, J=7.41 Hz, 1 H) 7.82 (d, J=8.51 Hz, 2 H) 7.70 (d, J=8.51 Hz, 2 H) 7.46 (dd, J=8.35, 7.41 Hz, 1 H) 6.64 (d, J=8.51 Hz, 1 H) 6.55 (d, J=7.25 Hz, 1 H) 6.12-6.23 (m, 1 H) 5.99-6.10 (m, 1 H) 5.52-5.62 (m, 1 H) 3.74 (br. s., 2 H) 3.57-3.68 (m, 4 H) 3.46-3.57 (m, 5 H) 2.54-2.61 (m, 2 H) 1.85 (dd, J=13.08, 3.15 Hz, 2 H) 1.37-1.54 (m, 2 H). Tr=2.68 min, m/z (ES$^+$) (M+H)$^+$ 498.

Example B-6

4-(4-Acryloylamino-piperidine-1-sulfonyl)-N-(2-morpholin-4-yl-ethyl)-benzamide $\delta_H$ (500 MHz, DMSO) 8.71 (t, J=5.67 Hz, 1 H) 8.00-8.12 (m, 3 H) 7.84 (d, J=8.51 Hz, 2 H) 6.10-6.22 (m, 1 H) 5.99-6.09 (m, 1 H) 5.56 (dd, J=10.01, 2.29 Hz, 1 H) 3.48-3.68 (m, 8 H) 3.39-3.46 (m, 2 H) 2.45-2.50 (m, 2 H) 2.42 (br. s., 3 H) 1.82 (dd, J=13.16, 3.23 Hz, 2 H) 1.35-1.49 (m, 2 H). Tr=2.31 min, m/z (ES$^+$) (M+H)$^+$ 451.

Example B-7

4-(4-Acryloylamino-piperidine-1-sulfonyl)-N-phenethyl-benzamide $\delta_H$ (500 MHz, DMSO) 8.86 (t, J=5.52 Hz, 1 H) 7.97-8.12 (m, 3 H) 7.84 (d, J=8.51 Hz, 2 H) 7.14-7.37 (m, 5 H) 6.10-6.24 (m, 1 H) 6.00-6.09 (m, 1 H) 5.56 (dd, J=10.01, 2.29 Hz, 1 H) 3.58-3.68 (m, 1 H) 3.45-3.57 (m, 4 H) 2.86 (t, J=7.41 Hz, 2 H) 2.52-2.57 (m, 2 H) 1.82 (dd, J=13.16, 3.23 Hz, 2 H) 1.34-1.48 (m, 2 H). Tr=3.63 min, m/z (ES$^+$) (M+H)$^+$ 442.

Example B-8

4-(4-Acryloylamino-piperidine-1-sulfonyl)-N-methyl-N-phenethyl-benzamide $\delta_H$ (500 MHz, DMSO) 8.00-8.16 (m, 1 H) 7.73-7.85 (m, 1 H) 7.66 (d, J=8.20 Hz, 1 H) 7.54 (d, J=8.20 Hz, 1 H) 7.16-7.40 (m, 5 H) 6.90-7.04 (m, 1 H) 6.11-6.25 (m, 1 H) 5.97-6.14 (m, 1 H) 5.57 (dd, J=10.09, 2.21 Hz, 1 H) 3.41-3.77 (m, 5 H) 2.71-3.11 (m, 5 H) 1.77-1.93 (m, 2 H) 1.38-1.54 (m, 2 H). Tr=3.67 min, m/z (ES$^+$) (M+H)$^+$ 456.

Example B-9

N-{1-[4-(3,4-Dihydro-1H-isoquinoline-2-carbonyl)-benzenesulfonyl]-piperidin-4-yl}-acrylamide $\delta_H$ (500 MHz, DMSO) 8.09 (d, J=7.41 Hz, 1 H) 7.78-7.90 (m, 2 H) 7.65-7.78 (m, 2 H) 6.98-7.34 (m, 4 H) 6.13-6.24 (m, 1 H) 6.02-6.11 (m, 1 H) 5.57 (dd, J=10.17, 2.29 Hz, 1 H) 4.48-4.84 (m, 2 H) 3.41-3.95 (m, 6 H) 2.80-2.96 (m, 2 H) 2.55-2.68 (m, 2 H) 1.85 (d, J=10.56 Hz, 2 H) 1.35-1.53 (m, 2 H). Tr=3.73 min, m/z (ES$^+$) (M+H)$^+$ 454.

Example B-10

4-(4-Acryloylamino-piperidine-1-sulfonyl)-N-(2-cyclohexyl-ethyl)-benzamide $\delta_H$ (500 MHz, DMSO) 8.71 (t, J=5.60 Hz, 1 H) 8.00-8.12 (m, 3 H) 7.83 (d, J=8.51 Hz, 2 H) 6.10-6.23 (m, 1 H) 5.98-6.09 (m, 1 H) 5.56 (dd, J=10.01, 2.29 Hz, 1 H) 3.58-3.66 (m, 1 H) 3.47-3.58 (m, 2 H) 3.25-3.34 (m, 2 H) 1.82 (dd, J=13.08, 3.15 Hz, 2 H) 1.56-1.79 (m, 5 H) 1.37-1.51 (m, 4 H) 1.25-1.35 (m, 1 H) 1.07-1.24 (m, 3 H) 0.81-0.96 (m, 2 H). Tr=4.06 min, m/z (ES$^+$) (M+H)$^+$ 448.

Example B-11

4-(4-Acryloylamino-piperidine-1-sulfonyl)-N-cyclohexyl-benzamide $\delta_H$ (500 MHz, CDCl$_3$) 7.92 (d, J=8.35 Hz, 2 H) 7.82 (d, J=8.35 Hz, 2 H) 6.29 (dd, J=16.87, 1.26 Hz, 1 H) 5.99-6.14 (m, 2 H) 5.67 (dd, J=10.25, 1.26 Hz, 1 H) 5.56 (d, J=8.04 Hz, 1 H) 3.94-4.10 (m, 1 H) 3.65-3.89 (m, 3 H) 2.48 (td, J=11.94, 2.29 Hz, 2 H) 1.95-2.14 (m, 4 H) 1.80 (dt, J=13.64, 3.59 Hz, 2 H) 1.69-1.74 (m, 1 H) 1.56 (qd, J=11.98, 4.10 Hz, 2 H) 1.37-1.51 (m, 2 H) 1.06-1.36 (m, 3 H). Tr=3.62 min, m/z (ES$^+$) (M+H)$^+$ 420.

Example B-12

N-(1-{4-[4-(Pyrrolidine-1-carbonyl)-piperidine-1-carbonyl]-benzenesulfonyl}-piperidin-4-yl)-acrylamide $\delta_H$ (500 MHz, CDCl$_3$) 7.83 (d, J=8.20 Hz, 2 H) 7.59 (d, J=8.35 Hz, 2 H) 6.29 (dd, J=16.87, 1.26 Hz, 1 H) 6.02-6.12 (m, 1 H) 5.60-5.71 (m, 2 H) 4.72 (br. s., 1 H) 3.81-3.94 (m, 1 H) 3.75 (d, J=12.30 Hz, 3 H) 3.35-3.57 (m, 4 H) 2.89-3.17 (m, 2 H) 2.64-2.75 (m, 1 H) 2.58 (td, J=11.70, 2.13 Hz, 2 H) 1.96-2.12 (m, 4 H) 1.44-1.92 (m, 11 H). Tr=3.28 min, m/z (ES$^+$) (M+H)$^+$ 503.

Example B-13

4-(4-Acryloylamino-piperidine-1-sulfonyl)-N-(3,5-dimethyl-benzyl)-benzamide $\delta_H$ (500 MHz, DMSO) 9.27 (t, J=5.99 Hz, 1 H) 8.01-8.20 (m, 3 H) 7.85 (d, J=8.51 Hz, 2 H) 6.84-6.98 (m, 3 H) 6.11-6.21 (m, 1 H) 5.99-6.09 (m, 1 H) 5.56 (dd, J=10.01, 2.29 Hz, 1 H) 4.43 (d, J=5.83 Hz, 2 H) 3.56-3.67 (m, 1 H) 3.54 (d, J=12.14

Hz, 2 H) 2.54-2.58 (m, 2 H) 2.25 (s, 6 H) 1.83 (dd, J=13.08, 3.31 Hz, 2 H) 1.36-1.53 (m, 2 H). Tr=3.82 min, m/z (ES$^+$) (M+H)$^+$ 456.

Example B-14

4-(4-Acryloylamino-piperidine-1-sulfonyl)-N-benzyl-benzamide $\delta_H$ (500 MHz, DMSO) 9.34 (t, J=5.99 Hz, 1 H) 8.13 (d, J=8.35 Hz, 2 H) 8.07 (d, J=7.57 Hz, 1 H) 7.85 (d, J=8.51 Hz, 2 H) 7.20-7.39 (m, 5 H) 6.12-6.22 (m, 1 H) 5.99-6.10 (m, 1 H) 5.56 (dd, J=10.09, 2.21 Hz, 1 H) 4.51 (d, J=5.99 Hz, 2 H) 3.57-3.67 (m, 1 H) 3.54 (d, J=12.14 Hz, 2 H) 2.53-2.59 (m, 2 H) 1.82 (dd, J=13.00, 3.23 Hz, 2 H) 1.34-1.51 (m, 2 H). Tr=3.55 min, m/z (ES$^+$) (M+H)$^+$ 428.

Example B-15

4-(4-Acryloylamino-piperidine-1-sulfonyl)-N-(3,4-difluoro-benzyl)-benzamide $\delta_H$ (500 MHz, DMSO) 9.36 (t, J=5.91 Hz, 1 H) 8.12 (d, J=8.51 Hz, 2 H) 8.07 (d, J=7.57 Hz, 1 H) 7.86 (d, J=8.51 Hz, 2 H) 7.33-7.47 (m, 2 H) 7.19 (ddd, J=6.07, 4.02, 2.21 Hz, 1 H) 6.11-6.22 (m, 1 H) 6.00-6.11 (m, 1 H) 5.56 (dd, J=10.09, 2.36 Hz, 1 H) 4.49 (d, J=5.83 Hz, 2 H) 3.58-3.68 (m, 1 H) 3.47-3.58 (m, 2 H) 2.54-2.60 (m, 2 H) 1.83 (dd, J=13.08, 3.15 Hz, 2 H) 1.33-1.50 (m, 2 H). Tr=3.61 min, m/z (ES$^+$) (M+H)$^+$ 464.

Example B-16

4-(4-Acryloylamino-piperidine-1-sulfonyl)-N-(4-trifluoromethyl-benzyl)-benzamide $\delta_H$ (500 MHz, DMSO) 9.44 (t, J=5.91 Hz, 1H) 8.13 (d, J=8.51 Hz, 2 H) 8.07 (d, J=7.57 Hz, 1 H) 7.87 (d, J=8.51 Hz, 2 H) 7.72 (d, J=8.20 Hz, 2 H) 7.56 (d, J=8.04 Hz, 2 H) 6.12-6.22 (m, 1 H) 6.00-6.09 (m, 1 H) 5.56 (dd, J=10.01, 2.29 Hz, 1 H) 4.59 (d, J=5.83 Hz, 2 H) 3.57-3.69 (m, 1 H) 3.48-3.59 (m, 2 H) 2.53-2.58 (m, 2 H) 1.83 (dd, J=13.00, 3.23 Hz, 2 H) 1.34-1.50 (m, 2 H). Tr=4.10 min, m/z (ES$^+$) (M+H)$^+$ 496.

Example B-17

4-(4-Acryloylamino-piperidine-1-sulfonyl)-N-naphthalen-1-ylmethyl-benzamide $\delta_H$ (500 MHz, DMSO) 9.36 (t, J=5.67 Hz, 1 H) 8.19 (d, J=8.20 Hz, 1 H) 8.14 (d, J=8.51 Hz, 2 H) 8.06 (d, J=7.57 Hz, 1 H) 7.93-8.01 (m, 1 H) 7.81-7.92 (m, 3 H) 7.42-7.63 (m, 4 H) 6.10-6.20 (m, 1 H) 5.99-6.10 (m, 1 H) 5.56 (dd, J=10.01, 2.29 Hz, 1 H) 4.98 (d, J=5.67 Hz, 2 H) 3.58-3.66 (m, 1 H) 3.49-3.58 (m, 2 H) 2.54-2.58 (m, 2 H) 1.82 (dd, J=12.93, 3.00 Hz, 2 H) 1.34-1.51 (m, 2 H). Tr=4.08 min, m/z (ES$^+$) (M+H)$^+$ 478.

Example B-18

4-(4-Acryloylamino-piperidine-1-sulfonyl)-N-[2-(3,4-dimethyl-phenyl)-ethyl]-benzamide $\delta_H$ (500 MHz, DMSO) 8.84 (t, J=5.57 Hz, 1 H) 7.98-8.10 (m, 3 H) 7.84 (d, J=8.39 Hz, 2 H) 7.00-7.09 (m, 2 H) 6.95 (d, J=7.48 Hz, 1 H) 6.11-6.22 (m, 1 H) 6.00-6.08 (m, 1 H) 5.56 (dd, J=9.99, 2.21 Hz, 1 H) 3.41-3.67 (m, 6 H) 2.77 (t, J=7.48 Hz, 2 H) 2.54-2.57 (m, 2 H) 2.18 (d, J=8.09 Hz, 6 H) 1.78-1.89 (m, 2 H) 1.37-1.48 (m, 2 H). Tr=3.96 min, m/z (ES$^+$) (M+H)$^+$ 470.

Example B-19

4-(4-Acryloylamino-piperidine-1-sulfonyl)-N-[2-(4-methoxy-phenyl)-ethyl]-benzamide $\delta_H$ (500 MHz, DMSO) 8.75-8.89 (m, 1 H) 7.99-8.14 (m, 3 H) 7.84 (d, J=8.39 Hz, 2 H) 7.07-7.25 (m, 2 H) 6.79-6.95 (m, 2 H) 6.12-6.23 (m, 1 H) 5.97-6.09 (m, 1 H) 5.56 (dd, J=10.07, 2.29 Hz, 1 H) 3.73 (s, 3 H) 3.59-3.65 (m, 1 H) 3.42-3.57 (m, 4 H) 2.79 (t, J=7.40 Hz, 2 H) 1.83 (dd, J=12.97, 3.66 Hz, 2 H) 1.37-1.52 (m, 2 H). Tr=3.62 min, m/z (ES$^+$) (M+H)$^+$ 472.

Example B-20

4-(4-Acryloylamino-piperidine-1-sulfonyl)-N-indan-2-yl-benzamide $\delta_H$ (500 MHz, DMSO) 8.85-9.00 (m, 1 H) 8.01-8.15 (m, 3 H) 7.83 (d, J=8.54 Hz, 2 H) 7.22-7.31 (m, 2 H) 7.11-7.21 (m, 2 H) 6.10-6.23 (m, 1 H) 5.98-6.09 (m, 1 H) 5.56 (dd, J=10.07, 2.29 Hz, 1 H) 4.64-4.81 (m, 1 H) 3.59 (br. s., 1 H) 3.47-3.58 (m, 2 H) 3.21-3.31 (m, 2 H) 2.97 (dd, J=15.87, 6.56 Hz, 2 H) 1.73-1.89 (m, 2 H) 1.34-1.46 (m, 2 H). Tr=3.75 min, m/z (ES$^+$) (M+H)$^+$ 454.

Example B-21

4-(4-Acryloylamino-piperidine-1-sulfonyl)-N-(2-m-tolyl-ethyl)-benzamide $\delta_H$ (500 MHz, DMSO) 8.86 (t, J=5.49 Hz, 1 H) 8.01-8.14 (m, 3 H) 7.84 (d, J=8.54 Hz, 2 H) 7.14-7.25 (m, 1 H) 6.95-7.11 (m, 3 H) 6.11-6.20 (m, 1 H) 5.98-6.10 (m, 1 H) 5.56 (dd, J=9.99, 2.21 Hz, 1 H) 3.57-3.66 (m, 1 H) 3.44-3.58 (m, 4 H) 2.82 (t, J=7.48 Hz, 2 H) 2.54-2.59 (m, 2 H) 2.28 (s, 3 H) 1.82 (dd, J=13.35, 3.13 Hz, 2 H) 1.32-1.49 (m, 2 H). Tr=3.82 min, m/z (ES$^+$) (M+H)$^+$ 456.

Example B-22

4-(4-Acryloylamino-piperidine-1-sulfonyl)-N-(3-phenyl-propyl)-benzamide $\delta_H$ (500 MHz, DMSO) 8.75 (t, J=5.52 Hz, 1 H) 8.00-8.11 (m, 3 H) 7.83 (d, J=8.35 Hz, 2 H) 7.13-7.36 (m, 5 H) 6.11-6.20 (m, 1 H) 6.00-6.09 (m, 1 H) 5.56 (dd, J=10.01, 2.13 Hz, 1 H) 3.57-3.68 (m, 1 H) 3.54 (d, J=12.14 Hz, 2 H) 3.22-3.32 (m, 2 H) 2.59-2.69 (m, 2 H) 2.52-2.58 (m, 2 H) 1.75-1.92 (m, 4 H) 1.37-1.48 (m, 2 H). Tr=3.79 min, m/z (ES$^+$) (M+H)$^+$ 456.

Example B-23

4-(4-Acryloylamino-piperidine-1-sulfonyl)-N-[2-(3-chloro-phenyl)-ethyl]-benzamide $\delta_H$ (500 MHz, DMSO) 8.73-8.87 (m, 1 H) 7.97-8.09 (m, 3 H) 7.78-7.88 (m, 2 H) 7.15-7.40 (m, 4 H) 6.11-6.21 (m, 1 H) 5.99-6.10 (m, 1 H) 5.56 (dd, J=10.01, 2.13 Hz, 1 H) 3.57-3.70 (m, 1 H) 3.46-3.58 (m, 4 H) 2.88 (t, J=7.09 Hz, 2 H) 2.53-2.59 (m, 2 H) 1.83 (dd, J=13.00, 2.92 Hz, 2 H) 1.31-1.51 (m, 2 H). Tr=4.10 min, m/z (ES$^+$) (M+H)$^+$ 476.

Example B-24

4-(4-Acryloylamino-piperidine-1-sulfonyl)-N-[2-(2-methoxy-phenyl)-ethyl]-benzamide $\delta_H$ (500 MHz, DMSO) 8.79 (t, J=5.60 Hz, 1 H) 7.98-8.08 (m, 3 H) 7.83 (d, J=8.35 Hz, 2 H) 7.11-7.27 (m, 2 H) 6.98 (d, J=8.04 Hz, 1 H) 6.88 (t, J=7.33 Hz, 1 H) 6.12-6.23 (m, 1 H) 5.98-6.11 (m, 1 H) 5.56 (dd, J=10.17, 2.29 Hz, 1 H) 3.79 (s, 3 H) 3.57-3.70 (m, 1 H) 3.43-3.58 (m, 4 H) 2.85 (t, J=7.41 Hz, 2 H) 2.54-2.59 (m, 2 H) 1.83 (dd, J=13.08, 3.31 Hz, 2 H) 1.33-1.49 (m, 2 H). Tr=3.96 min, m/z (ES$^+$) (M+H)$^+$ 472.

Example B-25

4-(4-Acryloylamino-piperidine-1-sulfonyl)-N-[2-(2,3-dihydro-benzofuran-7-yl)-ethyl-]benzamide $\delta_H$ (500 MHz, DMSO) 8.81 (t, J=5.60 Hz, 1 H) 7.99-8.11 (m, 3 H) 7.84 (d, J=8.51 Hz, 2 H) 7.09 (dd, J=7.33, 0.87 Hz, 1 H) 6.96 (d, J=7.57 Hz, 1 H) 6.76 (t, J=7.41 Hz, 1 H) 6.11-6.24 (m, 1 H) 6.00-6.09 (m, 1 H) 5.56 (dd, J=10.17, 2.29 Hz, 1 H) 4.51 (t, J=8.75 Hz, 2 H) 3.57-3.70 (m, 1 H) 3.42-3.59 (m, 4 H) 3.18 (t, J=8.67 Hz, 2 H) 2.79 (t, J=7.41 Hz, 2 H) 2.54-2.61 (m, 2 H) 1.83 (dd, J=13.08, 3.31 Hz, 2 H) 1.31-1.52 (m, 2 H). Tr=3.73 min, m/z (ES$^+$) (M+H)$^+$ 484.

Example B-26

4-(4-Acryloylamino-piperidine-1-sulfonyl)-N-[2-(tetrahydro-pyran-4-yl)-ethyl]-benzamide $\delta_H$ (500 MHz, DMSO) 8.70 (t, J=5.60 Hz, 1 H) 7.99-8.10 (m, 3 H) 7.83 (d, J=8.51 Hz, 2 H) 6.10-6.21 (m, 1 H) 6.00-6.10 (m, 1 H) 5.56 (dd, J=10.01, 2.29 Hz, 1 H) 3.83 (dd, J=11.27, 2.92 Hz, 2 H) 3.57-3.68 (m, 1 H) 3.54 (d, J=12.14 Hz, 2 H) 3.19-3.32 (m, 2 H) 2.53-2.57 (m, 2 H) 1.83 (dd, J=13.16, 3.23 Hz, 2 H) 1.32-1.67 (m, 7 H) 1.09-1.24 (m, 2 H). Tr=3.40 min, m/z (ES$^+$) (M+H)$^+$ 450.

Example B-27

4-(4-Acryloylamino-piperidine-1-sulfonyl)-N-[2-(4,4-difluoro-piperidin-1-yl)-ethyl]-benzamide $\delta_H$ (500 MHz, DMSO) 8.68 (t, J=5.60 Hz, 1 H) 8.05 (d, J=8.51 Hz, 3 H) 7.84 (d, J=8.51 Hz, 2 H) 6.11-6.23 (m, 1 H) 5.99-6.10 (m, 1 H) 5.56 (dd, J=10.09, 2.21 Hz, 1 H) 3.58-3.68 (m, 1 H) 3.49-3.58 (m, 2 H) 3.38-3.46 (m, 2 H) 2.53-2.60 (m, 7 H) 1.88-2.02 (m, 4 H) 1.83 (dd, J=13.16, 3.39 Hz, 2 H) 1.33-1.50 (m, 2 H). Tr=2.65 min, m/z (ES$^+$) (M+H)$^+$ 485.

Example B-28

4-(4-Acryloylamino-piperidine-1-sulfonyl)-N-(4-tert-butyl-benzyl)-benzamide $\delta_H$ (500 MHz, DMSO) 9.26 (t, J=5.91 Hz, 1 H) 8.11 (d, J=8.67 Hz, 2 H) 8.04 (d, J=7.57 Hz, 1 H) 7.85 (d, J=8.51 Hz, 2 H) 7.32-7.41 (m, 2 H) 7.26 (d, J=8.35 Hz, 2 H) 6.09-6.22 (m, 1 H) 5.98-6.08 (m, 1 H) 5.56 (dd, J=10.17, 2.29 Hz, 1 H) 4.46 (d, J=5.99 Hz, 2 H) 3.56-3.68 (m, 1 H) 3.47-3.58 (m, 2 H) 2.53-2.59 (m, 2 H) 1.82 (dd, J=13.16, 3.23 Hz, 2 H) 1.35-1.52 (m, 2 H) 1.28 (s, 9 H). Tr=4.21 min, m/z (ES$^+$) (M+H)$^+$ 484.

Example B-29

4-(4-Acryloylamino-piperidine-1-sulfonyl)-N-(4-phenyl-butyl)-benzamide $\delta_H$ (500 MHz, DMSO) 8.72 (t, J=5.60 Hz, 1 H) 8.05 (d, J=8.35 Hz, 3 H) 7.83 (d, J=8.20 Hz, 2 H) 7.13-7.33 (m, 5 H) 6.11-6.24 (m, 1 H) 6.00-6.11 (m, 1 H) 5.56 (dd, J=10.01, 2.13 Hz, 1 H) 3.56-3.67 (m, 1 H) 3.53 (d, J=11.98 Hz, 2 H) 3.32 (q, J=6.52 Hz, 2 H) 2.58-2.67 (m, 2 H) 2.52-2.58 (m, 2 H) 1.83 (dd, J=12.93, 2.84 Hz, 2 H) 1.51-1.69 (m, 4 H) 1.35-1.51 (m, 2 H). Tr=4.01 min, m/z (ES$^+$) (M+H)$^+$ 470.

Example B-30

4-(4-Acryloylamino-piperidine-1-sulfonyl)-N-[2-(4-chloro-phenyl)-ethyl-]benzamide $\delta_H$ (500 MHz, DMSO) 8.81 (t, J=5.52 Hz, 1 H) 7.97-8.09 (m, 3 H) 7.83 (d, J=8.51 Hz, 2 H) 7.20-7.40 (m, 4 H) 6.12-6.22 (m, 1 H) 5.97-6.10 (m, 1 H) 5.56 (dd, J=10.17, 2.29 Hz, 1 H) 3.58-3.68 (m, 1 H) 3.46-3.57 (m, 4 H) 2.86 (t, J=7.17 Hz, 2 H) 2.53-2.58 (m, 2 H) 1.83 (dd, J=13.16, 3.23 Hz, 2 H) 1.35-1.52 (m, 2 H). Tr=4.07 min, m/z (ES$^+$) (M+H)$^+$ 476.

Example B-31

4-(4-Acryloylamino-piperidine-1-sulfonyl)-N-(2-quinolin-7-yl-ethyl)-benzamide $\delta_H$ (500 MHz, DMSO) 9.02 (dd, J=4.12, 1.83 Hz, 1 H) 8.94 (t, J=5.42 Hz, 1 H) 8.43 (dd, J=8.24, 1.68 Hz, 1 H) 8.05-8.16 (m, 3 H) 7.83-7.96 (m, 3 H) 7.71 (d, J=6.41 Hz, 1 H) 7.54-7.67 (m, 2 H) 6.17-6.28 (m, 1 H) 6.06-6.15 (m, 1 H) 5.62 (dd, J=10.07, 2.29 Hz, 1 H) 3.71-3.79 (m, 2 H) 3.64-3.73 (m, 1 H) 3.49-3.64 (m, 4 H) 2.61-2.64 (m, 2 H) 1.89 (dd, J=12.97, 3.05 Hz, 2 H) 1.41-1.57 (m, 2 H). Tr=3.36 min, m/z (ES$^+$) (M+H)$^+$ 493.

Example B-32

4-(4-Acryloylamino-piperidine-1-sulfonyl)-N-(2-naphthalen-2-yl-ethyl)-benzamide $\delta_H$ (500 MHz, DMSO) 8.90-9.06 (m, 1 H) 8.27 (d, J=8.24 Hz, 1 H) 8.00-8.13 (m, 3 H) 7.94 (d, J=7.93 Hz, 1 H) 7.76-7.90 (m, 3 H) 7.49-7.65 (m, 2 H) 7.33-7.49 (m, 2 H) 6.11-6.23 (m, 1 H) 5.99-6.11 (m, 1 H) 5.56 (d, J=10.22 Hz, 1 H) 3.49-3.67 (m, 5 H) 2.53-2.60 (m, 2 H) 1.82 (br. s., 2 H) 1.32-1.54 (m, 2 H). Tr=4.02 min, m/z (ES$^+$) (M+H)$^+$ 492.

Example B-33

4-(4-Acryloylamino-piperidine-1-sulfonyl)-N-(2-chroman-6-yl-ethyl)-benzamide $\delta_H$ (500 MHz, DMSO) 9.25 (t, J=5.87 Hz, 1 H) 8.05-8.19 (m, 3 H) 7.89 (d, J=8.24 Hz, 2 H) 7.03-7.14 (m, 2 H) 6.74 (d, J=8.85 Hz, 1 H) 6.15-6.28 (m, 1 H) 6.05-6.15 (m, 1 H) 5.62 (dd, J=10.07, 2.14 Hz, 1 H) 4.43 (d, J=5.80 Hz, 2 H) 4.10-4.22 (m, 2 H) 3.64-3.74 (m, 1 H) 3.52-3.64 (m, 2 H) 2.77 (t, J=6.41 Hz, 2 H) 2.58-2.66 (m, 2 H) 1.91-2.00 (m, 2 H) 1.88 (dd, J=12.82, 2.75 Hz, 2 H) 1.39-1.60 (m, 2 H). Tr=3.69 min, m/z (ES$^+$) (M+H)$^+$ 484.

Example B-34

4-(4-Acryloylamino-piperidine-1-sulfonyl)-N-[2-(4-tert-butyl-phenyl)-ethyl-]benzamide $\delta_H$ (500 MHz, DMSO) 8.85 (t, J=5.52 Hz, 1 H) 7.99-8.10 (m, 3 H) 7.84 (d, J=8.51 Hz, 2 H) 7.33 (d, J=8.20 Hz, 2 H) 7.18 (d, J=8.35 Hz, 2 H) 6.11-6.24 (m, 1 H) 6.00-6.10 (m, 1 H) 5.56 (dd, J=10.09, 2.21 Hz, 1 H) 3.58-3.69 (m, 1 H) 3.44-3.58 (m, 4 H) 2.82 (t, J=7.49 Hz, 2 H) 2.55-2.59 (m, 2 H) 1.83 (dd, J=13.08, 3.15 Hz, 2 H) 1.37-1.51 (m, 2 H) 1.27 (s, 9 H). Tr=4.36 min, m/z (ES$^+$) (M+H)$^+$ 498.

Example B-35

4-(4-Acryloylamino-piperidine-1-sulfonyl)-N-(2-biphenyl-4-yl-ethyl)-benzamide $\delta_H$ (500 MHz, DMSO) 8.87 (t, J=5.52 Hz, 1 H) 7.99-8.10 (m, 3 H) 7.84 (d, J=8.51 Hz, 2 H) 7.56-7.70 (m, 4 H) 7.46 (t, J=7.72 Hz, 2 H) 7.27-7.40 (m, 3 H) 6.11-6.22 (m, 1 H) 6.00-6.09 (m, 1 H) 5.55 (dd, J=10.01, 2.29 Hz, 1 H) 3.46-3.72 (m, 5 H) 2.92 (t, J=7.25 Hz, 2 H) 2.55-2.59 (m, 2 H) 1.83 (dd, J=13.00, 3.07 Hz, 2 H) 1.35-1.51 (m, 2 H). Tr=4.35 min, m/z (ES$^+$) (M+H)$^+$ 518.

Example B-36

4-(4-Acryloylamino-piperidine-1-sulfonyl)-N-(2-benzo[1,3]dioxol-5-yl-ethyl)-benzamide $\delta_H$ (500 MHz, DMSO) 8.78 (t, J=5.52 Hz, 1 H) 7.98-8.11 (m, 3 H) 7.83 (d, J=8.35 Hz, 2 H) 6.78-6.87 (m, 2 H) 6.70 (dd, J=7.96, 1.50 Hz, 1 H) 6.12-6.24 (m, 1 H) 5.99-6.10 (m, 1 H) 5.97 (s, 2 H) 5.56 (dd, J=10.17, 2.29 Hz, 1 H) 3.56-3.69 (m, 1 H) 3.40-3.58 (m, 4 H) 2.78 (t, J=7.33 Hz, 2 H) 2.54-2.60 (m, 2 H) 1.83 (dd, J=13.00, 3.23 Hz, 2 H) 1.33-1.52 (m, 2 H). Tr=3.61 min, m/z (ES$^+$) (M+H)$^+$ 486.

Example B-37

4-(4-Acryloylamino-piperidine-1-sulfonyl)-N-(2-phenyl-cyclopropyl)-benzamide $\delta_H$ (500 MHz, DMSO) 8.95 (d, J=4.41 Hz, 1 H) 7.96-8.15 (m, 3 H) 7.84 (d, J=8.51 Hz, 2 H) 7.24-7.37 (m, 2 H) 7.08-7.24 (m, 3 H) 6.11-6.24 (m, 1 H) 5.97-6.10 (m, 1 H) 5.56 (dd, J=10.01, 2.29 Hz, 1 H) 3.58-3.68 (m, 1 H) 3.47-3.58 (m, 2 H) 2.98-3.13 (m, 1 H) 2.53-2.59 (m, 2 H) 2.11 (ddd, J=9.46, 6.23, 3.39 Hz, 1 H) 1.83 (dd, J=13.16, 3.23 Hz, 2 H) 1.33-1.50 (m, 3 H) 1.27 (dt, J=7.72, 5.99 Hz, 1 H). Tr=3.93 min, m/z (ES$^+$) (M+H)$^+$ 454.

Example B-38

4-(4-Acryloylamino-piperidine-1-sulfonyl)-N-[2-(3,4-dimethoxy-phenyl)-ethyl]-benzamide $\delta_H$ (500 MHz, DMSO) 8.79 (t, J=5.60 Hz, 1 H) 8.04 (d, J=8.51 Hz, 3 H) 7.84 (d, J=8.35 Hz, 2 H) 6.80-6.91 (m, 2 H) 6.76 (dd, J=8.20, 1.89 Hz, 1 H) 6.10-6.23 (m, 1 H) 5.95-6.09 (m, 1 H) 5.56 (dd, J=10.01, 2.29 Hz, 1 H) 3.71 (s, 6 H) 3.57-3.66 (m, 1 H) 3.44-3.57 (m, 4 H) 2.80 (t, J=7.41 Hz, 2 H) 2.53-2.60 (m, 2 H) 1.83 (dd, J=13.08, 3.15 Hz, 2 H) 1.34-1.53 (m, 2 H). Tr=3.50 min, m/z (ES$^+$) (M+H)$^+$ 502.

Example B-39

4-(4-Acryloylamino-piperidine-1-sulfonyl)-N-[2-(4-trifluoromethyl-phenyl)-ethyl-]-benzamide $\delta_H$ (500 MHz, DMSO) 8.84 (t, J=5.52 Hz, 1 H) 7.98-8.11 (m, 3 H) 7.84 (d, J=8.35 Hz, 2 H) 7.67 (d, J=8.20 Hz, 2 H) 7.49 (d, J=8.04 Hz, 2 H) 6.11-6.22 (m, 1 H) 5.97-6.10 (m, 1 H) 5.56 (dd, J=10.09, 2.21 Hz, 1 H) 3.44-3.67 (m, 5 H) 2.97 (t, J=7.01 Hz, 2 H) 2.52-2.59 (m, 2 H) 1.73-1.91 (m, 2 H) 1.32-1.52 (m, 2 H). Tr=4.00 min, m/z (ES$^+$) (M+H)$^+$ 510.

Example B-40

4-(4-Acryloylamino-piperidine-1-sulfonyl)-N-(2-adamantan-1-yl-ethyl)-benzamide $\delta_H$ (500 MHz, DMSO) 8.66 (t, J=5.42 Hz, 1 H) 7.99-8.11 (m, 3 H) 7.82 (d, J=8.39 Hz, 2 H) 6.09-6.23 (m, 1 H) 5.99-6.09 (m, 1 H) 5.56 (dd, J=10.15, 2.06 Hz, 1 H) 3.56-3.67 (m, 1 H) 3.53 (d, J=12.05 Hz, 2 H) 3.23-3.32 (m, 2 H) 2.54-2.59 (m, 2 H) 1.88-1.96 (m, 3 H) 1.82 (d, J=10.22 Hz, 2 H) 1.57-1.72 (m, 6 H) 1.53 (br. s., 6 H) 1.38-1.46 (m, 2 H) 1.30-1.39 (m, 2 H). Tr=4.56 min, m/z (ES$^+$) (M+H)$^+$ 500.

Example B-41

4-(4-Acryloylamino-piperidine-1-sulfonyl)-N-adamantan-1-ylmethyl-benzamide $\delta_H$ (500 MHz, DMSO) 8.58 (t, J=6.31 Hz, 1 H) 7.98-8.10 (m, 3 H) 7.83 (d, J=8.35 Hz, 2 H) 6.11-6.23 (m, 1 H) 6.00-6.10 (m, 1 H) 5.56 (dd, J=10.09, 2.21 Hz, 1 H) 3.58-3.66 (m, 1 H) 3.47-3.59 (m, 2 H) 3.01 (d, J=6.31 Hz, 2 H) 2.54-2.58 (m, 2 H) 1.88-1.98 (m, 3 H) 1.77-1.87 (m, 2 H) 1.47-1.73 (m, 12 H) 1.35-1.48 (m, 2 H). Tr=4.38 min, m/z (ES$^+$) (M+H)$^+$ 486.

Example B-42

4-(4-Acryloylamino-piperidine-1-sulfonyl)-N-(1,2,3,4-tetrahydro-naphthalen-1-yl)-benzamide $\delta_H$ (500 MHz, DMSO) 9.02-9.14 (m, 1 H) 8.14 (d, J=8.35 Hz, 2 H) 8.07 (d, J=7.57 Hz, 1 H) 7.83 (d, J=8.51 Hz, 2 H) 7.09-7.23 (m, 4 H) 6.11-6.21 (m, 1 H) 5.97-6.09 (m, 1 H) 5.56 (dd, J=10.09, 2.21 Hz, 1 H) 5.19-5.33 (m, 1 H) 3.57-3.68 (m, 1 H) 3.46-3.57 (m, 2 H) 2.68-2.88 (m, 2 H) 2.52-2.60 (m, 2 H) 1.90-2.06 (m, 2 H) 1.70-1.91 (m, 4 H) 1.32-1.52 (m, 2 H). Tr=3.99 min, m/z (ES$^+$) (M+H)$^+$ 468.

Example B-43

N-{1-[4-(Benzylcarbamoyl-methyl)-benzenesulfonyl]-piperidin-4-yl}-acrylamide $\delta_H$ (500 MHz, DMSO) 8.65 (t, J=5.72 Hz, 1 H) 8.06 (d, J=7.32 Hz, 1 H) 7.63-7.75 (m, 2 H) 7.49-7.58 (m, 2 H) 7.15-7.40 (m, 5 H) 6.13-6.24 (m, 1 H) 5.98-6.10 (m, 1 H) 5.56 (dd, J=10.15, 2.21 Hz, 1 H) 4.23-4.36 (m, 2 H) 3.61 (s, 3 H) 3.44-3.55 (m, 2 H) 1.78-1.89 (m, 2 H) 1.33-1.54 (m, 2 H). Tr=3.46 min, m/z (ES$^+$) (M+H)$^+$ 442.

Method C

Example C-1

N-[1-(1-Cyclopropanecarbonyl-2,3-dihydro-1H-indole-5-sulfonyl)-piperidin-4-yl]-acrylamide

[1-(1-Cyclopropanecarbonyl-2,3-dihydro-1H-indole-5-sulfonyl)-piperidin-4-yl]-carbamic acid tert-butyl ester

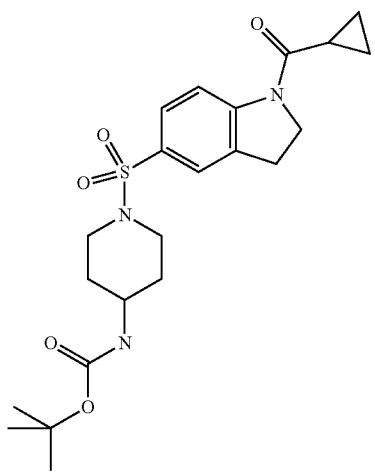 [SMILES: CC(C)(C)OC(=O)NC1CCN(S(=O)(=O)c2ccc3c(c2)CCN3C(=O)C2CC2)CC1]

Diisopropylethylamine (0.33 ml, 2.0 mmol) was added in one portion to a stirred solution of piperidin-4-yl-carbamic acid tert-butyl ester (0.2 g, 1.0 mmol) in DCM (5 ml) at room temperature. To this mixture was added 1-cyclopropanecarbonyl-2,3-dihydro-1H-indole-5-sulfonyl chloride (0.29 g, 1.0 mmol) in one portion and the mixture was stirred at room temperature under a nitrogen atmosphere for 1 hour. After this time the mixture was diluted with DCM (100 ml) and washed sequentially with HCl (1M solution, 50 ml), NaOH (1M solution, 50 ml) and brine (50 ml). The organic layer was separated, dried (MgSO$_4$), filtered and concentrated. The resulting solid was collected by filtration, dried with diethyl ether and dried under vacuum give the title compound (0.36 g, 73% yield) as a pale yellow solid. Tr=2.02 min m/z (ES$^+$) (M+Na$^+$) 472.

[5-(4-Amino-piperidine-1-sulfonyl)-2,3-dihydro-indol-1-yl]-cyclopropyl-methanone

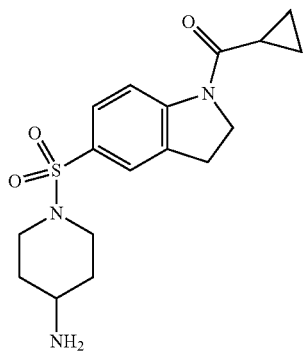 [SMILES: NC1CCN(S(=O)(=O)c2ccc3c(c2)CCN3C(=O)C2CC2)CC1]

[1-(1-Cyclopropanecarbonyl-2,3-dihydro-1H-indole-5-sulfonyl)-piperidin-4-yl]-carbamic acid tert-butyl ester (0.36 g, 0.8 mmol) was suspended in a 4M solution of HCl in Dioxane (10 ml). The resulting suspension was stirred at room temperature for 3 hours. After this time the solution was concentrated under vacuum, then azeotroped with methanol and suspended in diethyl ether. The resulting solid precipitate was then collected by filtration, washed with diethyl ether and dried under vacuum to afford the title compound (0.09 g, 32% yield) as a white solid. Tr=1.36 min, m/z (ES$^+$) (M+H)$^+$ 350.

N-[1-(1-Cyclopropanecarbonyl-2,3-dihydro-1H-indole-5-sulfonyl)-piperidin-4-yl]-acrylamide

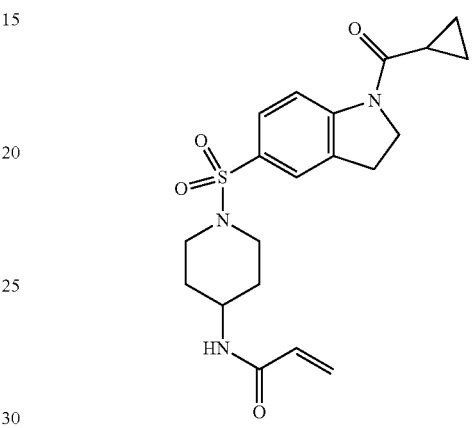

[5-(4-Amino-piperidine-1-sulfonyl)-2,3-dihydro-indol-1-yl]-cyclopropyl-methanone (0.09 g, 0.25 mmol) was dissolved in THF (5 ml). To this was added diisopropylethylamine (0.2 ml, 1.0 mmol) in one portion followed by the drop wise addition of acryloyl chloride (0.02 ml, 0.27 mmol) and the mixture was stirred at room temperature under a nitrogen atmosphere for 3 hours. After this time the mixture was diluted with EtOAc (50 ml) and washed sequentially with HCl (1M solution, 20 ml), NaOH (1M solution, 20 ml) and brine (20 ml), the organic layer was separated, dried (MgSO$_4$), filtered and concentrated. The resulting residue was purified by flash column chromatography (elution: 100% EtOAc) to give the title compound (0.035 g, 35% yield) as a white powder.

Example C-1

N-[1-(1-Cyclopropanecarbonyl-2,3-dihydro-1H-indole-5-sulfonyl)-piperidin-4-yl]-acrylamide $\delta_H$ (500 MHz, DMSO) 8.18 (br. s., 1 H) 8.07 (d, J=7.48 Hz, 1 H) 7.47-7.61 (m, 2 H) 6.10-6.26 (m, 1 H) 5.96-6.10 (m, 1 H) 5.56 (dd, J=10.15, 2.21 Hz, 1 H) 4.26-4.45 (m, 2 H) 3.51-3.64 (m, 1 H) 3.48 (d, J=12.05 Hz, 2 H) 3.27 (t, J=8.47 Hz, 2 H) 2.39-2.48 (m, 2 H) 1.98-2.05 (m, 1 H) 1.77-1.90 (m, 2 H) 1.39-1.48 (m, 2 H) 1.21-1.29 (m, 1 H) 0.91 (d, J=6.10 Hz, 4 H). Tr=3.47 min, m/z (ES$^+$) (M+H)$^+$ 404.

Example C-2

N-{1-[5-(5-Trifluoromethyl-isoxazol-3-yl)-thiophene-2-sulfonyl]-piperidin-4-yl}-acrylamide $\delta_H$ (500 MHz, DMSO) 8.22 (s, 1 H) 8.10 (d, J=7.41 Hz, 1 H) 8.01 (d, J=3.94 Hz, 1 H) 7.82 (d, J=3.94 Hz, 1 H) 6.02-6.21 (m, 2 H) 5.57 (dd, J=10.01, 2.29 Hz, 1 H) 3.64-3.75 (m, 1 H)

Example C-3

N-[1-(6-Phenoxy-pyridine-3-sulfonyl)-piperidin-4-yl]-acrylamide $\delta_H$ (500 MHz, DMSO) 8.49 (d, J=2.44 Hz, 1 H) 8.15 (dd, J=8.77, 2.52 Hz, 1 H) 8.08 (d, J=7.48 Hz, 1 H) 7.41-7.51 (m, 2 H) 7.26-7.33 (m, 1 H) 7.24 (t, J=7.55 Hz, 3 H) 6.13-6.24 (m, 1 H) 6.01-6.10 (m, 1 H) 5.57 (dd, J=10.07, 2.29 Hz, 1 H) 3.61-3.71 (m, 1 H) 3.51 (d, J=12.05 Hz, 2 H) 2.52-2.61 (m, 2 H) 1.83 (dd, J=13.05, 2.98 Hz, 2 H) 1.35-1.52 (m, 2 H). Tr=3.92 min, m/z (ES⁺) (M+H)⁺ 388.

Example C-4

N-[1-(6-Morpholin-4-yl-pyridine-3-sulfonyl)-piperidin-4-yl]-acrylamide $\delta_H$ (500 MHz, DMSO) 8.38 (d, J=2.44 Hz, 1 H) 8.07 (d, J=7.48 Hz, 1 H) 7.76 (dd, J=9.16, 2.44 Hz, 1 H) 6.96 (d, J=9.16 Hz, 1 H) 6.11-6.21 (m, 1 H) 5.97-6.10 (m, 1 H) 5.56 (dd, J=10.15, 2.21 Hz, 1 H) 3.66-3.74 (m, 4 H) 3.56-3.64 (m, 5 H) 3.44 (d, J=11.90 Hz, 2 H) 1.82 (dd, J=13.12, 3.05 Hz, 2 H) 1.32-1.51 (m, 2 H). Tr=3.25 min, m/z (ES⁺) (M+H)⁺ 381.

Example C-5

N-[1-(6-Phenyl-pyridine-3-sulfonyl)-piperidin-4-yl] acrylamide $\delta_H$ (500 MHz, DMSO) 8.98 (d, J=1.83 Hz, 1 H) 8.15-8.29 (m, 4 H) 8.07 (d, J=7.48 Hz, 1 H) 7.48-7.64 (m, 3 H) 6.09-6.21 (m, 1 H) 5.97-6.09 (m, 1 H) 5.55 (dd, J=10.07, 2.29 Hz, 1 H) 3.62-3.72 (m, 1 H) 3.57 (d, J=12.05 Hz, 2 H) 2.59-2.74 (m, 2 H) 1.84 (dd, J=13.20, 3.13 Hz, 2 H) 1.38-1.53 (m, 2 H). Tr=3.94 min, m/z (ES⁺) (M+H)⁺ 372.

Example C-6

N-[1-(5-Pyridin-2-yl-thiophene-2-sulfonyl)-piperidin-4-yl]-acrylamide $\delta_H$ (500 MHz, DMSO) 8.58 (d, J=4.73 Hz, 1 H) 8.09 (dd, J=7.65, 3.55 Hz, 2 H) 7.88-7.99 (m, 2 H) 7.66 (d, J=3.94 Hz, 1 H) 7.40 (dd, J=7.41, 4.89 Hz, 1 H) 6.11-6.23 (m, 1 H) 5.99-6.09 (m, 1 H) 5.56 (dd, J=10.17, 2.13 Hz, 1 H) 3.62-3.73 (m, 1 H) 3.53 (d, J=11.98 Hz, 2 H) 2.67 (t, J=10.56 Hz, 2 H) 1.87 (dd, J=13.08, 3.00 Hz, 2 H) 1.38-1.57 (m, 2 H). Tr=3.62 min, m/z (ES⁺) (M+H)⁺ 378.

Example C-7

N-[1-(Benzothiazole-6-sulfonyl)-piperidin-4-yl]acrylamide $\delta_H$ (500 MHz, DMSO) 9.65 (s, 1 H) 8.72 (d, J=1.58 Hz, 1 H) 8.30 (d, J=8.67 Hz, 1 H) 8.04 (d, J=7.41 Hz, 1 H) 7.86 (dd, J=8.59, 1.81 Hz, 1 H) 6.10-6.19 (m, 1 H) 5.98-6.07 (m, 1 H) 5.54 (dd, J=10.01, 2.29 Hz, 1 H) 3.58-3.66 (m, 1 H) 3.54 (d, J=12.14 Hz, 2 H) 2.53-2.60 (m, 2 H) 1.82 (dd, J=13.16, 3.23 Hz, 2 H) 1.36-1.55 (m, 2 H). Tr=3.31 min, m/z (ES⁺) (M+H)⁺ 352.

Example C-8

N-[1-(4-Methyl-2-phenyl-thiazole-5-sulfonyl)-piperidin-4-yl]-acrylamide $\delta_H$ (500 MHz, DMSO) 8.10 (d, J=7.57 Hz, 1 H) 8.00 (dd, J=8.12, 1.34 Hz, 2 H) 7.51-7.61 (m, 3 H) 6.13-6.21 (m, 1 H) 6.02-6.09 (m, 1 H) 5.56 (dd, J=10.01, 2.29 Hz, 1 H) 3.68-3.78 (m, 1 H) 3.55-3.62 (m, 2 H) 2.79-2.88 (m, 2 H) 2.65 (s, 3 H) 1.88 (dd, J=13.16, 3.23 Hz, 2 H) 1.37-1.58 (m, 2 H). Tr=4.29 min, m/z (ES⁺) (M+H)⁺ 392.

Example C-9

N-{1-[5-(2-Methyl-thiazol-4-yl)-thiophene-2-sulfonyl]-piperidin-4-yl}-acrylamide $\delta_H$ (500 MHz, DMSO) 8.04-8.15 (m, 2 H) 7.70 (d, J=3.94 Hz, 1 H) 7.61 (d, J=3.94 Hz, 1 H) 6.12-6.21 (m, 1 H) 5.99-6.08 (m, 1 H) 5.56 (dd, J=10.17, 2.29 Hz, 1 H) 3.60-3.71 (m, 1 H) 3.46-3.56 (m, 2 H) 2.70 (s, 3 H) 2.59-2.67 (m, 2 H) 1.87 (dd, J=13.08, 3.31 Hz, 2 H) 1.40-1.54 (m, 2 H). Tr=3.85 min, m/z (ES⁺) (M+H)⁺ 398.

Example C-10

N-[1-(5-Isoxazol-5-yl-thiophene-2-sulfonyl)-piperidin-4-yl]-acrylamide $\delta_H$ (500 MHz, DMSO) 8.76 (d, J=1.89 Hz, 1 H) 8.09 (d, J=7.57 Hz, 1 H) 7.86 (d, J=4.10 Hz, 1 H) 7.75 (d, J=3.94 Hz, 1 H) 7.16 (d, J=2.05 Hz, 1 H) 6.12-6.21 (m, 1 H) 6.01-6.09 (m, 1 H) 5.56 (dd, J=10.01, 2.29 Hz, 1 H) 3.64-3.74 (m, 1 H) 3.50-3.58 (m, 2 H) 2.71 (td, J=11.51, 2.21 Hz, 2 H) 1.87 (dd, J=13.24, 3.31 Hz, 2 H) 1.42-1.53 (m, 2 H). Tr=3.60 min, m/z (ES⁺) (M+H)⁺ 368.

Example C-11

N-{1-[4-(Morpholine-4-sulfonyl)-benzenesulfonyl]-piperidin-4-yl}-acrylamide $\delta_H$ (500 MHz, DMSO) 8.07 (d, J=7.48 Hz, 1 H) 7.93-8.05 (m, 4 H) 6.12-6.21 (m, 1 H) 6.00-6.10 (m, 1 H) 5.56 (dd, J=10.07, 2.29 Hz, 1 H) 3.59-3.72 (m, 5 H) 3.54 (br. s., 2 H) 2.89-2.99 (m, 4 H) 2.56-2.62 (m, 2 H) 1.84 (d, J=9.46 Hz, 2 H) 1.45 (br. s., 2 H). Tr=3.45 min, m/z (ES⁺) (M+H)⁺ 444.

Example C-12

N-[1-(5-Oxazol-5-yl-thiophene-2-sulfonyl)-piperidin-4-yl]-acrylamide $\delta_H$ (500 MHz, DMSO) 8.56 (s, 1 H) 8.10 (d, J=7.48 Hz, 1 H) 7.82 (s, 1 H) 7.69 (d, J=3.97 Hz, 1 H) 7.64 (d, J=3.97 Hz, 1 H) 6.12-6.24 (m, 1 H) 6.00-6.11 (m, 1 H) 5.57 (dd, J=10.07, 2.29 Hz, 1 H) 3.61-3.75 (m, 1 H) 3.53 (d, J=12.05 Hz, 2 H) 2.66-2.74 (m, 2 H) 1.80-1.94 (m, 2 H) 1.48 (dd, J=12.97, 3.20 Hz, 2 H). Tr=3.50 min, m/z (ES⁺) (M+H)⁺ 368.

Example C-13

N-[1-(4-Phenoxy-benzenesulfonyl)-piperidin-4-yl]-acrylamide $\delta_H$ (500 MHz, DMSO) 8.08 (d, J=7.48 Hz, 1 H) 7.67-7.80 (m, 2 H) 7.44-7.53 (m, 2 H) 7.23-7.35 (m, 1 H) 7.08-7.21 (m, 4 H) 6.12-6.23 (m, 1 H) 6.00-6.10 (m, 1 H) 5.57 (dd, J=10.15, 2.21 Hz, 1 H) 3.55-3.68 (m, 1 H) 3.49 (d, J=11.90 Hz, 2 H) 2.40-2.48 (m, 2 H) 1.83 (dd, J=13.12, 3.05 Hz, 2 H) 1.38-1.50 (m, 2 H). Tr=4.19 min, m/z (ES$^+$) (M+H)$^+$ 387.

Example C-14

N-{1-[4-(6-Methyl-pyrazin-2-yloxy)-benzenesulfonyl]-piperidin-4-yl}-acrylamide $\delta_H$ (500 MHz, DMSO) 8.40 (d, J=12.67 Hz, 2 H) 8.08 (d, J=7.32 Hz, 1 H) 7.74-7.83 (m, 2 H) 7.39-7.50 (m, 2 H) 6.13-6.22 (m, 1 H) 5.98-6.10 (m, 1 H) 5.56 (dd, J=10.07, 2.29 Hz, 1 H) 3.58-3.70 (m, 1 H) 3.53 (d, J=12.05 Hz, 2 H) 2.51-2.57 (m, 2 H) 2.38 (s, 3 H) 1.84 (dd, J=13.12, 3.20 Hz, 2 H) 1.39-1.51 (m, 2 H). Tr=3.54 min, m/z (ES$^+$) (M+H)$^+$ 403.

Example C-15

N-{1-[3-(6-Methyl-pyrazin-2-yloxy)-benzenesulfonyl]-piperidin-4-yl}-acrylamide $\delta_H$ (500 MHz, DMSO) 8.40 (s, 1 H) 8.33 (s, 1 H) 8.09 (d, J=7.48 Hz, 1 H) 7.67-7.80 (m, 1 H) 7.52-7.65 (m, 3 H) 6.11-6.23 (m, 1 H) 5.97-6.10 (m, 1 H) 5.56 (dd, J=9.99, 2.21 Hz, 1 H) 3.58-3.70 (m, 1 H) 3.53 (d, J=12.05 Hz, 2 H) 2.32 (s, 3 H) 1.83 (dd, J=13.05, 2.98 Hz, 2 H) 1.37-1.51 (m, 2H). Tr=3.54 min, m/z (ES$^+$) (M+H)$^+$ 403.

Example C-16

N-[1-(3-Chloro-4-methyl-benzenesulfonyl)-piperidin-4-yl]-acrylamide $\delta_H$ (500 MHz, DMSO) 8.04 (d, J=7.48 Hz, 1 H) 7.72 (d, J=1.53 Hz, 1 H) 7.57-7.68 (m, 2 H) 6.12-6.22 (m, 1 H) 5.99-6.10 (m, 1 H) 5.56 (dd, J=10.07, 2.29 Hz, 1 H) 3.57-3.71 (m, 1 H) 3.41-3.56 (m, 2 H) 2.54-2.62 (m, 2 H) 2.44 (s, 3 H) 1.83 (dd, J=13.12, 3.51 Hz, 2 H) 1.34-1.51 (m, 2 H). Tr=3.86 min, m/z (ES$^+$) (M+H)$^+$ 343.

Example C-17

N-[1-(5-Isoxazol-5-yl-furan-2-sulfonyl)-piperidin-4-yl]-acrylamide $\delta_H$ (500 MHz, DMSO) 8.79 (d, J=1.98 Hz, 1 H) 8.07 (d, J=7.48 Hz, 1 H) 7.26-7.49 (m, 2 H) 7.06 (d, J=1.98 Hz, 1 H) 6.12-6.24 (m, 1 H) 6.00-6.12 (m, 1 H) 5.57 (dd, J=9.99, 2.21 Hz, 1 H) 3.69-3.81 (m, 1 H) 3.54-3.69 (m, 2 H) 2.83-2.97 (m, 2 H) 1.86 (dd, J=13.20, 3.28 Hz, 2 H) 1.33-1.50 (m, 2 H). Tr=3.51 min, m/z (ES$^+$) (M+H)$^+$ 352.

Example C-18

N-{1-[4-(3-Chloro-5-trifluoromethyl-pyridin-2-yloxy)-benzenesulfonyl]-piperidin-4-yl}-acrylamide $\delta_H$ (500 MHz, DMSO) 8.64 (d, J=2.14 Hz, 1 H) 8.56 (d, J=1.07 Hz, 1 H) 8.07 (d, J=7.32 Hz, 1 H) 7.76-7.91 (m, 2 H) 7.49-7.60 (m, 2 H) 6.12-6.26 (m, 1 H) 6.01-6.10 (m, 1 H) 5.56 (dd, J=10.15, 2.21 Hz, 1 H) 3.59-3.69 (m, 1 H) 3.43-3.58 (m, 2 H) 1.85 (dd, J=13.20, 3.13 Hz, 2 H) 1.36-1.58 (m, 2H). Tr=4.43 min, m/z (ES$^+$) (M+H)$^+$ 490.

Example C-19

N-[1-(4-Pyrazol-1-yl-benzenesulfonyl)-piperidin-4-yl]-acrylamide $\delta_H$ (500 MHz, DMSO) 8.69 (d, J=2.59 Hz, 1 H) 8.13 (d, J=8.85 Hz, 2 H) 8.04 (d, J=7.48 Hz, 1 H) 7.81-7.92 (m, 3 H) 6.64 (t, J=2.06 Hz, 1 H) 6.11-6.21 (m, 1 H) 5.98-6.09 (m, 1 H) 5.55 (dd, J=10.07, 2.29 Hz, 1 H) 3.63 (dt, J=7.32, 3.66 Hz, 1 H) 3.54 (d, J=12.05 Hz, 2 H) 2.54-2.61 (m, 2 H) 1.83 (dd, J=13.20, 3.28 Hz, 2 H) 1.33-1.52 (m, 2 H). Tr=3.45 min, m/z (ES$^+$) (M+H)$^+$ 361.

Example C-20

N-[1-(4-Methoxy-3-methyl-benzenesulfonyl)-piperidin-4-yl]-acrylamide $\delta_H$ (500 MHz, DMSO) 8.04 (d, J=7.57 Hz, 1 H) 7.57 (dd, J=8.51, 2.21 Hz, 1 H) 7.51 (d, J=1.58 Hz, 1 H) 7.15 (d, J=8.67 Hz, 1 H) 6.12-6.20 (m, 2 H) 6.01-6.07 (m, 1 H) 5.53-5.57 (m, 2 H) 3.88 (s, 3 H) 3.54-3.62 (m, 1 H) 3.47 (d, J=12.14 Hz, 2 H) 2.42 (td, J=11.47, 2.13 Hz, 2 H) 2.22 (s, 3 H) 1.82 (m, J=13.20, 3.20 Hz, 2 H) 1.38-1.47 (m, 2 H). Tr=3.66 min, m/z (ES$^+$) (M+H)$^+$ 339.

Example C-21

N-{1-[5-(Acetylamino-methyl)-thiophene-2-sulfonyl]-piperidin-4-yl}-acrylamide $\delta_H$ (500 MHz, DMSO) 8.60 (t, J=5.75 Hz, 1 H) 8.09 (d, J=7.57 Hz, 1 H) 7.40-7.52 (m, 1 H) 7.11 (d, J=3.78 Hz, 1 H) 6.11-6.25 (m, 1 H) 6.00-6.09 (m, 1 H) 5.57 (dd, J=10.01, 2.29 Hz, 1 H) 4.45 (d, J=5.83 Hz, 2 H) 3.59-3.69 (m, 1 H) 3.43-3.55 (m, 2 H) 1.80-1.94 (m, 5 H) 1.40-1.55 (m, 2 H). Tr=2.83 min, m/z (ES$^+$) (M+H)$^+$ 372.

Example C-22

N-[1-(5-Methyl-1-phenyl-1H-pyrazole-4-sulfonyl)-piperidin-4-yl]-acrylamide $\delta_H$ (500 MHz, DMSO) 8.09 (d, J=7.48 Hz, 1 H) 7.89-8.00 (m, 1 H) 7.57-7.62 (m, 4 H) 7.49-7.55 (m, 1 H) 6.14-6.23 (m, 1 H) 5.99-6.12 (m, 1 H) 5.57 (dd, J=9.99, 2.21 Hz, 1 H) 3.61-3.73 (m, 1 H) 3.48-3.58 (m, 2 H) 2.58 (td, J=11.52, 2.14 Hz, 2 H) 2.45 (s, 3 H) 1.88 (dd, J=13.05, 3.13 Hz, 2 H) 1.43-1.55 (m, 2 H). Tr=3.69 min, m/z (ES$^+$) (M+H)$^+$ 375.

Example C-23

N-{1-[4-(2-Methyl-2H-pyrazol-3-yl)-benzenesulfonyl]-piperidin-4-yl}-acrylamide $\delta_H$ (500 MHz, DMSO) 7.97-8.08 (m, 3 H) 7.80 (d, J=2.14 Hz, 1 H) 7.74 (d, J=8.54 Hz, 2 H) 6.85 (d, J=2.29 Hz, 1 H) 6.10-6.18 (m, 1 H) 5.97-6.07 (m, 1 H) 5.50-5.57 (m, 1 H) 3.92

(s, 3 H) 3.55-3.65 (m, 1 H) 3.45-3.55 (m, 2 H) 1.83 (dd, J=13.12, 3.20 Hz, 2 H) 1.34-1.50 (m, 2 H). Tr=3.53 min, m/z (ES$^+$) (M+H)$^+$ 375.

Example C-24

N-{1-[4-(Acetylamino-methyl)-benzenesulfonyl]-piperidin-4-yl}-acrylamide $\delta_H$ (500 MHz, DMSO) 8.50 (t, J=5.99 Hz, 1 H) 8.08 (d, J=7.41 Hz, 1 H) 7.66-7.74 (m, 2 H) 7.50 (d, J=8.35 Hz, 2 H) 6.12-6.23 (m, 1 H) 5.99-6.10 (m, 1 H) 5.56 (dd, J=10.01, 2.29 Hz, 1 H) 4.30-4.42 (m, 2 H) 3.53-3.63 (m, 1 H) 3.44-3.53 (m, 2 H) 2.42-2.49 (m, 2 H) 1.91 (s, 3 H) 1.77-1.87 (m, 2 H) 1.34-1.51 (m, 2 H). Tr=2.79 min, m/z (ES$^+$) (M+H)$^+$ 366.

Example C-25

N-[1-(2,3-Dihydro-benzo[1,4]dioxine-6-sulfonyl)-piperidin-4-yl]-acrylamide $\delta_H$ (500 MHz, DMSO) 8.07 (d, J=7.48 Hz, 1 H) 7.15-7.26 (m, 2 H) 7.10 (d, J=8.39 Hz, 1 H) 6.12-6.22 (m, 1 H) 6.00-6.10 (m, 1 H) 5.57 (dd, J=9.99, 2.21 Hz, 1 H) 4.34 (dd, J=12.66, 5.04 Hz, 4 H) 3.54-3.67 (m, 1 H) 3.47 (d, J=12.05 Hz, 2 H) 2.40-2.49 (m, 2 H) 1.83 (dd, J=13.12, 3.36 Hz, 2 H) 1.34-1.51 (m, 2 H). Tr=3.51 min, m/z (ES$^+$) (M+H)$^+$ 353.

Example C-26

N-{1-[5-(Acetylamino-methyl)-thiophene-2-sulfonyl]-piperidin-4-yl}-acrylamide $\delta_H$ (500 MHz, DMSO) 8.60 (t, J=5.75 Hz, 1 H) 8.09 (d, J=7.57 Hz, 1 H) 7.40-7.52 (m, 1 H) 7.11 (d, J=3.78 Hz, 1 H) 6.11-6.25 (m, 1 H) 6.00-6.09 (m, 1 H) 5.57 (dd, J=10.01, 2.29 Hz, 1 H) 4.45 (d, J=5.83 Hz, 2 H) 3.59-3.69 (m, 1 H) 3.43-3.55 (m, 2 H) 1.80-1.94 (m, 5 H) 1.40-1.55 (m, 2 H). Tr=2.83 min, m/z (ES$^+$) (M+H)$^+$ 372.

Example C-27

N-[1-(5-Methyl-1-phenyl-1H-pyrazole-4-sulfonyl)-piperidin-4-yl]-acrylamide $\delta_H$ (500 MHz, DMSO) 8.09 (d, J=7.48 Hz, 1 H) 7.89-8.00 (m, 1 H) 7.57-7.62 (m, 4 H) 7.49-7.55 (m, 1 H) 6.14-6.23 (m, 1 H) 5.99-6.12 (m, 1 H) 5.57 (dd, J=9.99, 2.21 Hz, 1 H) 3.61-3.73 (m, 1 H) 3.48-3.58 (m, 2 H) 2.58 (td, J=11.52, 2.14 Hz, 2 H) 2.45 (s, 3 H) 1.88 (dd, J=13.05, 3.13 Hz, 2 H) 1.43-1.55 (m, 2 H). Tr=3.69 min, m/z (ES$^+$) (M+H)$^+$ 375.

Example C-28

N-{1-[4-(1-Methyl-1H-pyrazol-3-yl)-benzenesulfonyl]-piperidin-4-yl}-acrylamide $\delta_H$ (500 MHz, DMSO) 7.97-8.08 (m, 3 H) 7.80 (d, J=2.14 Hz, 1 H) 7.74 (d, J=8.54 Hz, 2 H) 6.85 (d, J=2.29 Hz, 1 H) 6.10-6.18 (m, 1 H) 5.97-6.07 (m, 1 H) 5.50-5.57 (m, 1 H) 3.92 (s, 3 H) 3.55-3.65 (m, 1 H) 3.45-3.55 (m, 2 H) 1.83 (dd, J=13.12, 3.20 Hz, 2 H) 1.34-1.50 (m, 2 H). Tr=3.53 min, m/z (ES$^+$) (M+H)$^+$ 375.

Example C-29

N-{1-[3-(2-Methyl-2H-pyrazol-3-yl)-benzenesulfonyl]-piperidin-4-yl}-acrylamide $\delta_H$ (500 MHz, DMSO) 8.07 (d, J=7.48 Hz, 1 H) 7.90 (dt, J=6.94, 1.72 Hz, 1 H) 7.71-7.83 (m, 3 H) 7.52 (d, J=1.98 Hz, 1 H) 6.56 (d, J=1.83 Hz, 1 H) 6.09-6.22 (m, 1 H) 5.98-6.08 (m, 1 H) 5.56 (dd, J=10.15, 2.21 Hz, 1 H) 3.89 (s, 3 H) 3.64 (d, J=7.40, 3.74 Hz, 1 H) 3.57 (d, J=12.05 Hz, 2 H) 1.83 (dd, J=12.97, 3.05 Hz, 2 H) 1.35-1.53 (m, 2 H). Tr=3.46 min, m/z (ES$^+$) (M+H)$^+$ 375.

Example C-30

N-[1-(2,2-Dimethyl-chroman-6-sulfonyl)-piperidin-4-yl]-acrylamide $\delta_H$ (500 MHz, DMSO) 8.07 (d, J=7.48 Hz, 1 H) 7.48 (d, J=1.98 Hz, 1 H) 7.40 (dd, J=8.54, 2.29 Hz, 1 H) 6.90 (d, J=8.70 Hz, 1 H) 6.11-6.20 (m, 1 H) 6.00-6.08 (m, 1 H) 5.56 (dd, J=10.07, 2.29 Hz, 1 H) 3.53-3.64 (m, 1 H) 3.47 (d, J=12.05 Hz, 2 H) 2.82 (t, J=6.64 Hz, 2 H) 2.36-2.46 (m, 2 H) 1.77-1.88 (m, 4 H) 1.37-1.49 (m, 2 H) 1.31 (s, 6 H). Tr=4.14 min, m/z (ES$^+$) (M+H)$^+$ 379.

Example C-31

N-[1-(5-Phenyl-thiophene-2-sulfonyl)-piperidin-4-yl]-acrylamide $\delta_H$ (500 MHz, DMSO) 8.08 (d, J=7.57 Hz, 1 H) 7.73-7.79 (m, 2 H) 7.69 (d, J=3.94 Hz, 1 H) 7.64 (d, J=3.94 Hz, 1 H) 7.46-7.53 (m, 2 H) 7.39-7.45 (m, 1 H) 6.10-6.27 (m, 1 H) 5.98-6.08 (m, 1 H) 5.56 (dd, J=10.17, 2.29 Hz, 1 H) 3.62-3.78 (m, 1 H) 3.45-3.60 (m, 2 H) 2.68 (td, J=11.51, 2.36 Hz, 2 H) 1.88 (dd, J=13.16, 3.39 Hz, 2 H) 1.39-1.56 (m, 2 H). Tr=4.16 min, m/z (ES$^+$) (M+H)$^+$ 377.

Example C-32

N-[1-(4-Cyclopentyloxy-benzenesulfonyl)-piperidin-4-yl]-acrylamide $\delta_H$ (500 MHz, DMSO) 8.04 (d, J=7.41 Hz, 1 H) 7.63 (d, J=8.83 Hz, 2 H) 7.10 (d, J=8.67 Hz, 2 H) 6.09-6.26 (m, 1 H) 5.97-6.09 (m, 1 H) 5.56 (dd, J=10.09, 2.05 Hz, 1 H) 4.92 (t, J=5.83 Hz, 1 H) 3.54-3.67 (m, 1 H) 3.47 (d, J=11.98 Hz, 2 H) 2.42 (t, J=10.64 Hz, 2 H) 1.91-2.03 (m, 2 H) 1.78-1.87 (m, 2 H) 1.65-1.77 (m, 4 H) 1.52-1.64 (m, 2 H) 1.32-1.51 (m, 2 H). Tr=4.21 min, m/z (ES$^+$) (M+H)$^+$ 379.

Example C-33

N-{1-[5-(Pyrrolidine-1-carbonyl)-1H-pyrrole-3-sulfonyl]-piperidin-4-yl}-acrylamide $\delta_H$ (500 MHz, DMSO) 12.37 (br. s., 1 H) 8.05 (d, J=7.41 Hz, 1 H) 7.33 (s, 1 H) 6.76 (s, 1 H) 6.12-6.23 (m, 1 H) 5.98-6.09 (m, 1 H) 5.56 (dd, J=10.09, 2.21 Hz, 1 H) 3.71 (t, J=6.62 Hz, 2 H) 3.55-3.64 (m, 1 H) 3.48 (t, J=6.78 Hz, 2 H) 3.42 (br. s., 2 H) 2.41 (t, J=10.48 Hz, 2 H) 1.95 (quin, J=6.62 Hz, 2 H) 1.76-1.89 (m, 4 H) 1.38-1.54 (m, 2 H). Tr=2.99 min, m/z (ES$^+$) (M+H)$^+$ 391.

Example C-34

N-{1-[4-(2-Methyl-thiazol-4-yl)-benzenesulfonyl]-piperidin-4-yl}-acrylamide $\delta_H$ (500 MHz, DMSO) 8.13-8.23 (m, 3 H) 8.04 (d, J=7.41 Hz, 1 H) 7.79 (d, J=8.51 Hz, 2 H) 6.10-6.22 (m, 1 H) 5.97-6.09 (m, 1 H) 5.55 (dd, J=10.09, 2.21 Hz, 1 H) 3.58-3.69 (m, 1 H) 3.53 (d, J=12.14 Hz, 2 H) 2.74 (s, 3 H) 1.83 (dd, J=12.93, 2.84 Hz, 2 H) 1.36-1.51 (m, 2 H). Tr=3.75 min, m/z (ES+) (M+H)+ 392.

Example C-35

N-{1-[4-(Pyridin-2-yloxy)-benzenesulfonyl]-piperidin-4-yl}-acrylamide $\delta_H$ (500 MHz, DMSO) 8.23 (dd, J=4.89, 1.26 Hz, 1 H) 8.09 (d, J=7.57 Hz, 1 H) 7.88-7.99 (m, 1 H) 7.77 (d, J=8.67 Hz, 2 H) 7.36 (d, J=8.67 Hz, 2 H) 7.24 (dd, J=6.86, 5.28 Hz, 1 H) 7.17 (d, J=8.20 Hz, 1 H) 6.13-6.23 (m, 1 H) 5.99-6.10 (m, 1 H) 5.56 (dd, J=10.09, 2.05 Hz, 1 H) 3.58-3.72 (m, 1 H) 3.52 (d, J=11.82 Hz, 2 H) 1.71-1.93 (m, 2 H) 1.37-1.54 (m, 2 H). Tr=3.71 min, m/z (ES+) (M+H)+ 388.

Example C-36

N-[1-(2-Oxo-1,2,3,4-tetrahydro-quinoline-6-sulfonyl)-piperidin-4-yl]-acrylamide $\delta_H$ (500 MHz, DMSO) 10.49 (s, 1 H) 8.05 (d, J=7.41 Hz, 1 H) 7.55 (s, 1 H) 7.52 (dd, J=8.28, 1.81 Hz, 1 H) 7.03 (d, J=8.35 Hz, 1 H) 6.12-6.21 (m, 1 H) 6.01-6.08 (m, 1 H) 5.56 (dd, J=10.09, 2.21 Hz, 1 H) 3.54-3.64 (m, 1 H) 3.48 (d, J=11.98 Hz, 2 H) 2.98 (t, J=7.65 Hz, 2 H) 2.44 (t, J=10.56 Hz, 2 H) 1.82 (dd, J=13.08, 3.00 Hz, 2 H) 1.37-1.50 (m, 2 H). Tr=3.02 min, m/z (ES+) (M+H)+ 364.

Method D

Example D-1

Tetrahydro-pyran-4-carboxylic acid [4-(4-acryloylamino-piperidine-1-sulfonyl)-phenyl]-methyl-amide

[1-(4-Amino-benzenesulfonyl)-piperidin-4-yl]carbamic acid tert-butyl ester

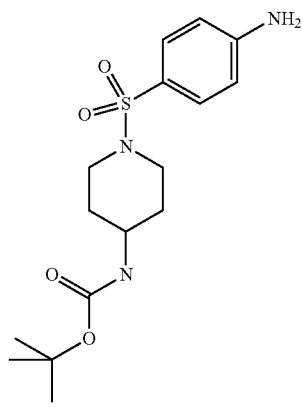 [SMILES: CC(C)(C)OC(=O)NC1CCN(S(=O)(=O)c2ccc(N)cc2)CC1]

[1-(4-Nitro-benzenesulfonyl)-piperidin-4-yl]-carbamic acid tert-butyl ester (0.5 g, 1.3 mmol) was suspended in a 5:1 mixture of ethanol and water (20 ml). To this solution was added iron powder (0.22 g, 3.4 mmol) followed by saturated ammonium chloride solution (3 ml) and the mixture was heated to 80° C. for three hours. After this time, the reaction mixture was cooled to room temperature and filtered through a pad of celite, the celite was washed with ethanol (10 ml) and EtOAc (50 ml) and the solution was concentrated under vacuum. The resulting residue was suspended in water (10 ml) and the solid precipitate collected by filtration and dried under vacuum to give the title compound (0.38 g, 78% yield) as a white solid. Tr=1.84 min, m/z (ES+) (M+Na)+ 378.

[1-(4-Methylamino-benzenesulfonyl)-piperidin-4-yl]-carbamic acid tert-butyl ester

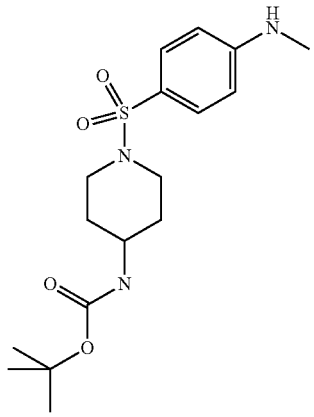 [SMILES: CNc1ccc(S(=O)(=O)N2CCC(NC(=O)OC(C)(C)C)CC2)cc1]

Paraformaldehyde (0.15 g, 0.5 mmol) was added in one portion to pressure vessel containing [1-(4-amino-benzenesulfonyl)-piperidin-4-yl]-carbamic acid tert-butyl ester (0.12 g, 0.34 mmol) in Methanol (5 ml) at room temperature. To this mixture was added sodium methoxide (0.055 g, 1.02 mmol) in one portion, the pressure vessel was sealed and heated at 70° C. for 12 hours. After this time the reaction was cooled to room temperature and sodium borohydride (0.031 g, 0.82 mmol) added in one portion, the pressure vessel was re-sealed and heated at 70° C. for 1 hour. The reaction was then cooled to room temperature, diluted with DCM (20 ml) and washed with water (20 ml). The organic layer was separated, dried (MgSO4), filtered and concentrated to give the title compound (0.13 g, 99% yield) as a white solid which was taken on without further purification. Tr=1.96 min m/z (ES+) (M+Na+) 392.

[(1-{4-[Methyl-(tetrahydro-pyran-4-carbonyl)-amino]-benzenesulfonyl}-piperidin-4-yl)-carbamic acid tert-butyl ester

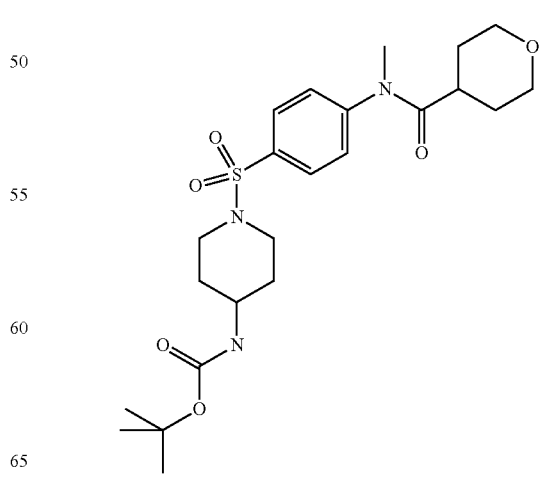

[1-(4-Methylamino-benzenesulfonyl)-piperidin-4-yl]-carbamic acid tert-butyl ester (0.13 g, 0.35 mmol) was dissolved in THF (5 ml). To this was added diisopropylethylamine (0.18 ml, 0.7 mmol) in one portion followed by the drop wise addition of tetrahydro-2H-pyran-4-carbonyl chloride (0.06 ml, 0.38 mmol) and the mixture was stirred at room temperature under a nitrogen atmosphere for 3 hours. After this time the mixture was concentrated, diluted with DCM (200 ml) and washed sequentially with HCl (1M solution, 10 ml), NaOH (1M solution, 10 ml) and brine (10 ml). The organic layer was separated, dried (MgSO₄), filtered and concentrated to give the title compound (0.17 g, 98% yield) as a white powder which was taken on without further purification. Tr=1.89 min m/z (ES⁺) (M+Na⁺) 504.

Tetrahydro-pyran-4-carboxylic acid [4-(4-amino-piperidine-1-sulfonyl)-phenyl]-methyl-amide

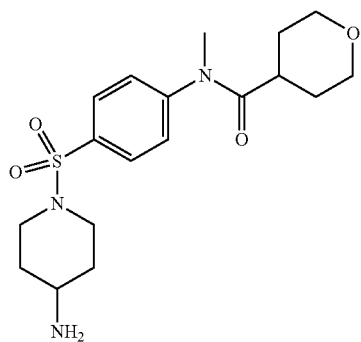 [SMILES: CN(C(=O)C1CCOCC1)c1ccc(S(=O)(=O)N2CCC(N)CC2)cc1]

[(1-{4-[Methyl-(tetrahydro-pyran-4-carbonyl)-amino]-benzenesulfonyl}-piperidin-4-yl)-carbamic acid tert-butyl ester (0.17 g, 0.4 mmol) was suspended in a 4M solution of HCl in Dioxane (5 ml). The resulting suspension was stirred at room temperature for 3 hours. After this time the solution was concentrated under vacuum, then azeotroped with methanol and suspended in diethyl ether. The resulting solid precipitate was then collected by filtration, washed with diethyl ether and dried under vacuum to afford the title compound (0.17 g, Quantitative yield) as a white solid. Tr=1.20 min, m/z (ES⁺) (M+H)⁺ 382.

Tetrahydro-pyran-4-carboxylic acid [4-(4-acryloylamino-piperidine-1-sulfonyl)-phenyl]-methyl-amide

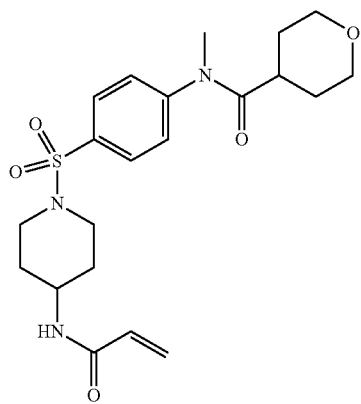 [SMILES: C=CC(=O)NC1CCN(S(=O)(=O)c2ccc(N(C)C(=O)C3CCOCC3)cc2)CC1]

Diisopropylethylamine (0.34 ml, 2.1 mmol) was added in one portion to a stirred solution of tetrahydro-pyran-4-carboxylic acid [4-(4-amino-piperidine-1-sulfonyl)-phenyl]-methyl-amide (0.17 g, 0.4 mmol) in DCM (10 ml), followed by the drop wise addition of acryloyl chloride (0.04 ml, 0.42 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO₄), filtered, concentrated and the resulting residue was purified by flash column chromatography (elution: 97% EtOAc, 3% Methanol) to give the title compound (0.032 g, 18% yield) as a white solid.

Example D-1

Tetrahydro-pyran-4-carboxylic acid [4-(4-acryloylamino-piperidine-1-sulfonyl)-phenyl]-methyl-amide δ$_H$ (500 MHz, DMSO) 8.09 (d, J=7.52 Hz, 1 H) 7.81 (d, J=8.44 Hz, 2 H) 7.63 (d, J=8.44 Hz, 2 H) 6.11-6.21 (m, 1 H) 6.01-6.09 (m, 1 H) 5.56 (dd, J=10.09, 2.20 Hz, 1 H) 3.78 (d, J=10.82 Hz, 2 H) 3.57-3.67 (m, 1 H) 3.49-3.58 (m, 2 H) 3.25 (s, 3 H) 3.12 (br. s., 2 H) 2.44-2.50 (m, 2 H) 1.84 (dd, J=13.20, 3.30 Hz, 2 H) 1.56-1.65 (m, 2 H) 1.39-1.53 (m, 4 H). Tr=3.32 min, m/z (ES⁺) (M+H)⁺ 436.

Example D-2

Cyclopropanecarboxylic acid [4-(4-acryloylamino-piperidine-1-sulfonyl)-phenyl]-methyl-amide δ$_H$ (250 MHz, DMSO) 8.02 (d, J=7.31 Hz, 1 H) 7.71-7.82 (m, 2 H) 7.49-7.63 (m, 2 H) 5.90-6.19 (m, 2 H) 5.50 (dd, J=9.59, 2.74 Hz, 1 H) 3.39-3.63 (m, 4 H) 3.21 (s, 3 H) 1.76 (br. s., 2 H) 1.28-1.50 (m, 3 H) 0.71-0.85 (m, 2 H) 0.56-0.71 (m, 2 H). Tr=3.29 min, m/z (ES⁺) (M+H)⁺ 392.

Example D-3

[4-(4-Acryloylamino-piperidine-1-sulfonyl)-phenyl]-methyl-carbamic acid benzyl ester δ$_H$ (500 MHz, DMSO) 8.06 (d, J=7.41 Hz, 1 H) 7.69-7.78 (m, 2 H) 7.57-7.67 (m, 2 H) 7.24-7.47 (m, 5 H) 6.12-6.22 (m, 1 H) 5.98-6.08 (m, 1 H) 5.56 (dd, J=10.09, 2.21 Hz, 1 H) 5.17 (s, 2 H) 3.57-3.68 (m, 1 H) 3.46-3.57 (m, 2 H) 2.42-2.49 (m, 2 H) 1.84 (dd, J=13.16, 3.23 Hz, 2 H) 1.34-1.53 (m, 2 H). Tr=3.95 min, m/z (ES⁺) (M+H)⁺ 458.

Method E

Example E-1

4-(4-Acryloylamino-piperidine-1-sulfonyl)-2-fluoro-N-phenethyl-benzamide

4-Chlorosulfonyl-2-fluoro-benzoic acid methyl ester

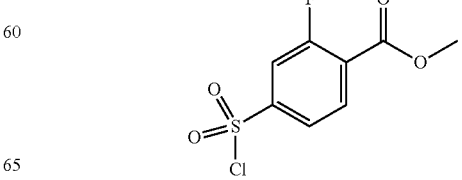

Sodium nitrite (0.54 g, 8.0 mmol) was added portion wise to a stirred solution of methyl 4-amino-2-fluorobenzoate (1.0 g, 6.0 mmol) in acetic acid (7 ml) and HCl (concentrated, 2.5 ml) while maintaining the temperature below 15° C. This solution was then added drop wise to a stirred solution of saturated sulfur dioxide, copper (II) chloride (0.25 g, 1.0 mmol) and water (0.5 ml) in acetic acid (5 ml) at 5° C. The reaction mixture was allowed to warm to room temperature and poured over ice water and stirred for a further 15 minutes. The resulting precipitate was collected by filtration, washed with water and dried overnight in a vacuum oven to give the title compound (1.5 g, 55% yield) as a pale brown solid which was used without further purification.

4-(4-tert-Butoxycarbonylamino-piperidine-1-sulfonyl)-2-fluoro-benzoic acid methyl ester

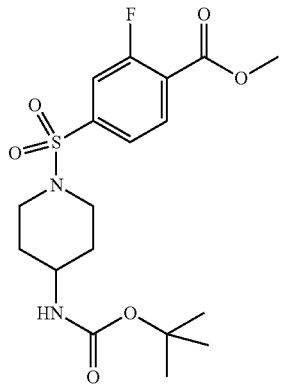 [SMILES: COC(=O)c1ccc(S(=O)(=O)N2CCC(NC(=O)OC(C)(C)C)CC2)cc1F]

Diisopropylethylamine (3.2 ml, 18.5 mmol) was added in one portion to a stirred solution of piperidin-4-yl-carbamic acid tert-butyl ester (0.5 g, 2.5 mmol) in DCM (10 ml) at room temperature. To this mixture was added 4-chlorosulfonyl-2-fluoro-benzoic acid methyl ester (0.6 g, 2.5 mmol) in one portion and the mixture was stirred at room temperature under a nitrogen atmosphere for 1 hour. After this time the mixture was diluted with DCM (50 ml) and washed sequentially with HCl (1M solution, 10 ml), NaOH (1M solution, 10 ml) and brine (10 ml). The organic layer was separated, dried (MgSO$_4$), filtered and concentrated. The resulting residue was purified by flash column chromatography (elution: 98% DCM, 2% Methanol) to give the title compound (0.98 g, 87% yield) as a white solid. Tr=2.08 min m/z (ES$^+$) (M+Na$^+$) 439.

4-(4-tert-Butoxycarbonylamino-piperidine-1-sulfonyl)-2-fluoro-benzoic acid

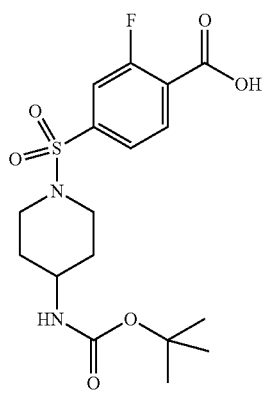 [SMILES: CC(C)(C)OC(=O)NC1CCN(S(=O)(=O)c2ccc(C(=O)O)c(F)c2)CC1]

4-(4-Tert-Butoxycarbonylamino-piperidine-1-sulfonyl)-2-fluoro-benzoic acid methyl ester (0.8 g, 2.0 mmol) was added to a 1:1 mixture of water and tetrahydrofuran (20 ml) containing lithium hydroxide (0.8 g, 20.4 mmol) and the mixture was stirred at room temperature for 2 hours. After this time the mixture was concentrated to half the original volume and the remaining solution was acidified to pH 1 with 1M HCl. The resulting precipitate was collected by filtration, washed with water (10 ml) and dried under vacuum to give the title compound (0.82 g, 99% yield) as a white solid. Tr=1.80 min m/z (ES$^+$) (M+Na$^+$) 425.

[1-(3-Fluoro-4-phenethylcarbamoyl-benzenesulfonyl)-piperidin-4-yl]-carbamic acid tert-butyl ester

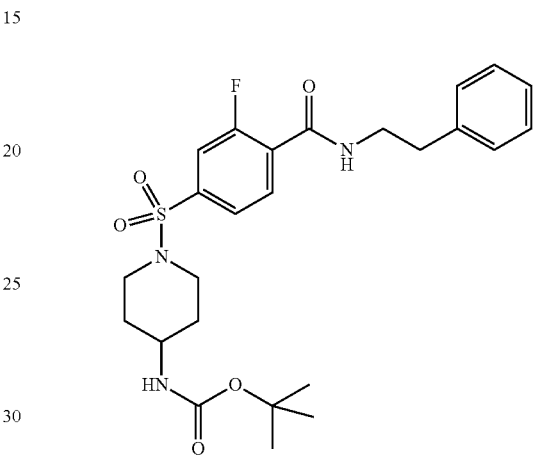

Thionyl chloride (0.16 g, 2.2 mmol) was added dropwise to a stirred solution of 4-(4-tert-butoxycarbonylamino-piperidine-1-sulfonyl)-2-fluoro-benzoic acid (0.3 g, 0.75 mmol) and pyridine (0.36 ml, 4.5 mmol) in DCM (10 ml). The reaction mixture was stirred at room temperature under a nitrogen atmosphere for 4 hours, after this time phenethylamine (0.19 ml, 1.5 mmol) was added in one portion and stirring was continued for a further 12 hours. The mixture was then diluted with DCM (10 ml) before being washed sequentially with HCl (1M solution, 10 ml) and NaOH (1M solution, 10 ml). The organic layer was separated, dried (MgSO$_4$), filtered and concentrated to give the title compound (0.38 g, 74%) as a white foam which was taken on without further purification. Tr=2.16 min m/z (ES$^+$) (M+Na$^+$) 528.

4-(4-Amino-piperidine-1-sulfonyl)-2-fluoro-N-phenethyl-benzamide

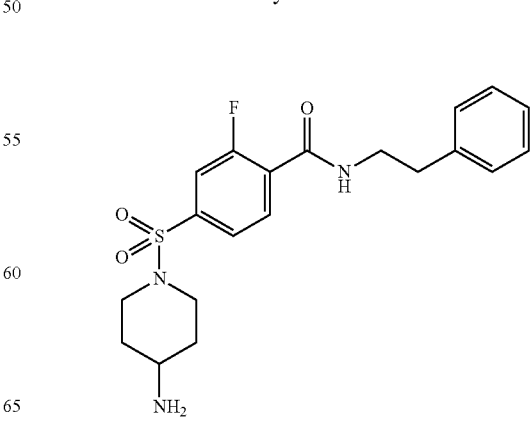

[1-(3-Fluoro-4-phenethylcarbamoyl-benzenesulfonyl)-piperidin-4-yl]-carbamic acid tert-butyl ester (0.38 g, 0.7 mmol) was suspended in a 4M solution of HCl in Dioxane (5 ml). The resulting suspension was stirred at room temperature for 3 hours. After this time the solution was concentrated under vacuum, then azeotroped with methanol and suspended in diethyl ether. The resulting solid precipitate was then collected by filtration, washed with diethyl ether and dried under vacuum to afford the title compound (0.24 g, 80% yield) as a white solid. Tr=1.20 min, m/z (ES+) (M+H)+ 406.

4-(4-Acryloylamino-piperidine-1-sulfonyl)-2-fluoro-N-phenethyl-benzamide

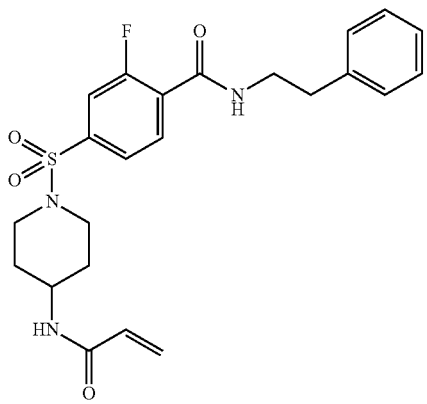 [SMILES: C=CC(=O)NC1CCN(S(=O)(=O)c2ccc(C(=O)NCCc3ccccc3)c(F)c2)CC1]

Diisopropylethylamine (0.51 ml, 3.0 mmol) was added in one portion to a stirred solution of 4-(4-Amino-piperidine-1-sulfonyl)-2-fluoro-N-phenethyl-benzamide (0.24 g, 0.6 mmol) in THF (10 ml), followed by the drop wise addition of acryloyl chloride (0.05 ml, 0.66 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO4), filtered, concentrated and the resulting residue was purified by flash column chromatography (elution: 98% DCM, 2% Methanol) to give the title compound (0.06 g, 25% yield) as a white solid.

Example E-1

4-(4-Acryloylamino-piperidine-1-sulfonyl)-2-fluoro-N-phenethyl-benzamide $\delta_H$ (500 MHz, DMSO) 8.66 (t, J=5.52 Hz, 1 H) 8.08 (d, J=7.57 Hz, 1 H) 7.76 (t, J=7.33 Hz, 1 H) 7.65 (ddd, J=15.80, 8.55, 1.50 Hz, 2 H) 7.18-7.35 (m, 5 H) 6.10-6.22 (m, 1 H) 5.98-6.10 (m, 1 H) 5.56 (dd, J=10.09, 2.21 Hz, 1 H) 3.59-3.70 (m, 1 H) 3.45-3.59 (m, 4 H) 2.84 (t, J=7.25 Hz, 2 H) 2.59 (t, J=10.48 Hz, 2 H) 1.76-1.89 (m, 2 H) 1.35-1.50 (m, 2 H). Tr=3.89 min, m/z (ES+) (M+H)+ 460.

Example E-2

4-(4-Acryloylamino-piperidine-1-sulfonyl)-2-methoxy-N-phenethyl-benzamide $\delta_H$ (500 MHz, DMSO) 8.36 (t, J=5.52 Hz, 1 H) 8.08 (d, J=7.57 Hz, 1 H) 7.82 (d, J=7.88 Hz, 1 H) 7.17-7.44 (m, 7 H) 6.11-6.23 (m, 1 H) 5.98-6.11 (m, 1 H) 5.56 (dd, J=10.09, 2.21 Hz, 1 H) 3.90 (s, 3 H) 3.57-3.67 (m, 1 H) 3.47-3.58 (m, 4 H) 2.84 (t, J=7.25 Hz, 2 H) 2.53-2.60 (m, 2 H) 1.83 (dd, J=13.00, 3.07 Hz, 2 H) 1.35-1.49 (m, 2 H). Tr=3.98 min, m/z (ES+) (M+H)+ 472.

Example E-3

4-(4-Acryloylamino-piperidine-1-sulfonyl)-2-methyl-N-phenethyl-benzamide $\delta_H$ (500 MHz, DMSO) 8.77 (t, J=5.52 Hz, 1 H) 8.09 (d, J=7.57 Hz, 1 H) 7.82-7.95 (m, 2 H) 7.79 (d, J=8.20 Hz, 1 H) 7.13-7.38 (m, 5 H) 6.11-6.27 (m, 1 H) 5.96-6.10 (m, 1 H) 5.57 (dd, J=10.01, 2.29 Hz, 1 H) 3.65-3.84 (m, 1 H) 3.42-3.62 (m, 4 H) 2.76-2.93 (m, 4 H) 2.56-2.62 (m, 3 H) 1.82 (dd, J=12.85, 2.92 Hz, 2 H) 1.26-1.52 (m, 2 H). Tr=3.85 min, m/z (ES+) (M+H)+ 456.

Method F

Example F-1

N-{1-[3-Chloro-4-(3-phenyl-propionylamino)-benzenesulfonyl]-piperidin-4-yl}-acrylamide

[1-(3-Chloro-4-nitro-benzenesulfonyl)-piperidin-4-yl]carbamic acid tert-butyl ester

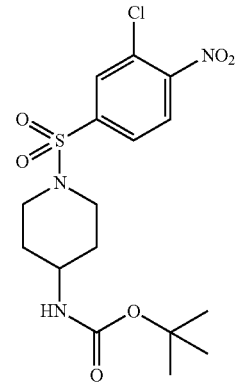 [SMILES: CC(C)(C)OC(=O)NC1CCN(S(=O)(=O)c2ccc([N+](=O)[O-])c(Cl)c2)CC1]

Diisopropylethylamine (1.74 ml, 9.98 mmol) was added in one portion to a stirred solution of piperidin-4-yl-carbamic acid tert-butyl ester (0.25 g, 1.25 mmol) in DCM (5 ml) at room temperature. To this mixture was added 3-chloro-4-nitrobenzene sulfonyl chloride (0.32 g, 1.25 mmol) in one portion and the mixture was stirred at room temperature under a nitrogen atmosphere for 1 hour. After this time the mixture was diluted with DCM (100 ml) and washed sequentially with HCl (1M solution, 50 ml), NaOH (1M solution, 50 ml) and brine (50 ml), the organic layer was separated, dried (MgSO4), filtered and concentrated. The resulting residue was purified by flash column chromatography (elution: % EtOAc: % Heptane) to give the title compound (0.44 g, 84% yield) as a white solid. $\delta_H$ (500 MHz, DMSO) 7.97-8.12 (m, 3 H) 6.93 (d, J=7.72 Hz, 1 H) 3.64 (d, J=12.77 Hz, 2 H) 3.43

(d, J=3.94 Hz, 2 H) 2.88-3.00 (m, 2 H) 1.78 (d, J=10.40 Hz, 2 H) 1.25-1.46 (m, 11 H). Tr=2.22 min, m/z (ES⁺) (M+Na)⁺ 442.

[1-(4-Amino-3-chloro-benzenesulfonyl)-piperidin-4-yl]carbamic acid tert-butyl ester

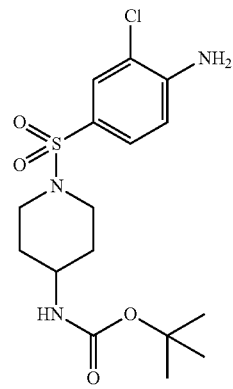

[1-(3-Chloro-4-nitro-benzenesulfonyl)-piperidin-4-yl]-carbamic acid tert-butyl ester (0.44 g, 1.05 mmol) was suspended in a 5:1 mixture of ethanol and water (30 ml). To this solution was added iron powder (0.29 g, 5.24 mmol) followed by saturated ammonium chloride solution (3 ml) and the mixture was heated to 80° C. for three hours. After this time, the reaction mixture was cooled to room temperature and filtered through a pad of celite, the celite was washed with ethanol (10 ml) and EtOAc (50 ml) and the solution was concentrated under vacuum. The resulting residue was suspended in water (10 ml) and the solid precipitate collected by filtration and dried under vacuum to give the title compound (0.11 g, 18% yield) as a white solid. Tr=2.12 min, m/z (ES⁺) (M+Na)⁺ 412.

{1-[3-Chloro-4-(3-phenyl-propionylamino)-benzenesulfonyl]-piperidin-4-yl}-carbamic acid tert-butyl ester

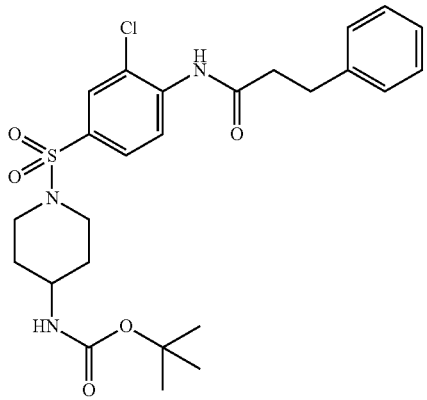 [SMILES: CC(C)(C)OC(=O)NC1CCN(S(=O)(=O)c2ccc(NC(=O)CCc3ccccc3)c(Cl)c2)CC1]

3-Phenyl propionyl chloride (0.29 g, 1.76 mmol) was added in one portion to a solution of [1-(4-amino-3-chloro-benzenesulfonyl)-piperidin-4-yl]-carbamic acid tert-butyl ester (0.57 g, 1.4 mmol) in Pyridine (5 ml) and the mixture was heated to 60° C. The mixture was stirred at this temperature under a nitrogen atmosphere for 12 hours. After this time the mixture was diluted with DCM (100 ml) and washed sequentially with HCl (1M solution, 50 ml), NaOH (1M solution, 50 ml) and brine (50 ml). The organic layer was separated, dried (MgSO₄), filtered and concentrated. The resulting residue was purified by flash column chromatography (elution: 98% DCM, 2% Methanol) to give the title compound (0.09 g, 8% yield) as a white powder. Tr=2.41 min, m/z (ES⁺) (M+Na)⁺ 545.

N-[4-(4-Amino-piperidine-1-sulfonyl)-2-chloro-phenyl]-3-phenyl-propionamide

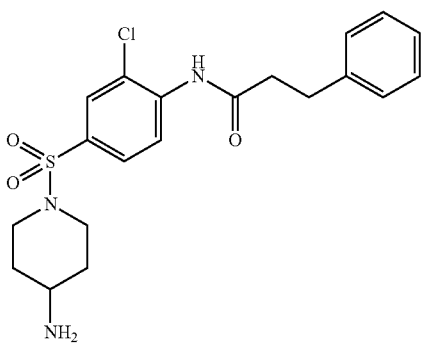 [SMILES: NC1CCN(S(=O)(=O)c2ccc(NC(=O)CCc3ccccc3)c(Cl)c2)CC1]

{1-[3-Chloro-4-(3-phenyl-propionylamino)-benzenesulfonyl]-piperidin-4-yl}-carbamic acid tert-butyl ester (0.09 g, 0.1 mmol) was suspended in a 4M solution of HCl in Dioxane (5 ml). The resulting suspension was stirred at room temperature for 3 hours. After this time the solution was concentrated under vacuum to give the title compound (0.048 g, 99% yield) as a colourless oil which was taken on directly without further purification. Tr=1.71 min, m/z (ES⁺) (M+H)⁺ 422.

N-{1-[3-Chloro-4-(3-phenyl-propionylamino)-benzenesulfonyl]-piperidin-4-yl}-acrylamide

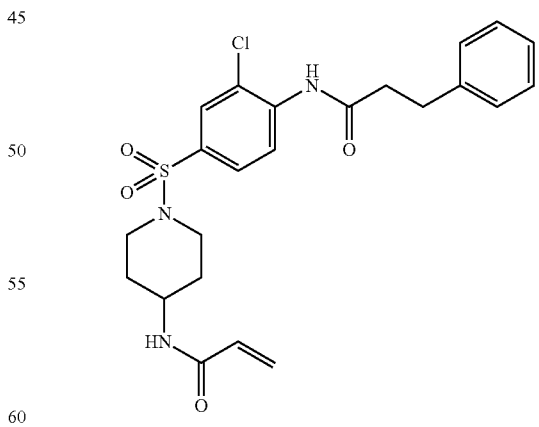

Diisopropylethylamine (0.09 ml, 0.56 mmol) was added in one portion to a stirred solution of N-[4-(4-Amino-piperidine-1-sulfonyl)-2-chloro-phenyl]-3-phenyl-propionamide (0.05 g, 0.1 mmol) in THF (5 ml), followed by the drop wise addition of acryloyl chloride (0.01 ml, 0.12 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO$_4$), filtered, concentrated and the resulting residue was purified by flash column chromatography (elution: 2% Methanol, 98% DCM) to give the title compound (0.002 g, 4% yield) as a white solid.

Example F-1

N-{1-[3-Chloro-4-(3-phenyl-propionylamino)-benzenesulfonyl]-piperidin-4-yl}-acrylamide δ$_H$ (500 MHz, DMSO) 9.46 (s, 1 H) 8.15 (d, J=8.85 Hz, 1 H) 8.08 (d, J=7.48 Hz, 1 H) 7.77 (dd, J=8.85, 2.59 Hz, 1 H) 7.74 (d, J=2.59 Hz, 1 H) 7.22-7.34 (m, 4 H) 7.14-7.22 (m, 1 H) 6.12-6.23 (m, 1 H) 6.01-6.12 (m, 1 H) 5.58 (dd, J=10.07, 2.29 Hz, 1 H) 3.60-3.72 (m, 1 H) 3.48 (d, J=12.36 Hz, 2 H) 2.87-2.97 (m, 2 H) 2.72-2.81 (m, 2 H) 2.60-2.71 (m, 2 H) 1.79 (dd, J=13.12, 3.20 Hz, 2 H) 1.27-1.42 (m, 2 H). Tr=4.49 min, m/z (ES$^+$) (M+H)$^+$ 476.

Example F-2

N-{1-[2-Chloro-4-(3-phenyl-propionylamino)-benzenesulfonyl]-piperidin-4-yl}-acrylamide δ$_H$ (500 MHz, DMSO) 10.50 (s, 1 H) 8.09 (d, J=7.63 Hz, 1 H) 8.01 (d, J=1.98 Hz, 1 H) 7.90 (d, J=8.70 Hz, 1 H) 7.61 (dd, J=8.77, 2.06 Hz, 1 H) 7.14-7.36 (m, 5 H) 6.11-6.24 (m, 1 H) 6.02-6.11 (m, 1 H) 5.57 (dd, J=9.99, 2.21 Hz, 1 H) 3.70-3.81 (m, 1 H) 3.59 (d, J=12.82 Hz, 2 H) 2.81-2.97 (m, 4 H) 2.63-2.74 (m, 2 H) 1.98-2.15 (m, 2 H) 1.80 (dd, J=13.12, 3.20 Hz, 2 H) 1.28-1.45 (m, 2 H). Tr=4.02 min, m/z (ES$^+$) (M+H)$^+$ 476.

Example F-3

N-{1-[2-Methoxy-4-(3-phenyl-propionylamino)-benzenesulfonyl]-piperidin-4-yl}-acrylamide δ$_H$ (500 MHz, DMSO) 10.34 (s, 1 H) 8.07 (d, J=7.63 Hz, 1 H) 7.53-7.69 (m, 2 H) 7.09-7.36 (m, 6 H) 6.13-6.22 (m, 1 H) 6.00-6.12 (m, 1 H) 5.57 (dd, J=10.07, 2.29 Hz, 1 H) 3.84 (s, 3 H) 3.61-3.76 (m, 1 H) 3.55 (d, J=12.66 Hz, 2 H) 2.92 (t, J=7.63 Hz, 2 H) 2.60-2.77 (m, 5 H) 1.78 (dd, J=12.74, 2.82 Hz, 2 H) 1.20-1.45 (m, 2 H). Tr=3.93 min, m/z (ES$^+$) (M+H)$^+$ 473.

Example F-4

N-[1-(4-Phenylacetylamino-phenylmethanesulfonyl)-piperidin-4-yl]-acrylamide

δ$_H$ (500 MHz, DMSO) 10.26 (s, 1 H) 8.10 (d, J=7.63 Hz, 1 H) 7.60 (d, J=8.54 Hz, 2 H) 7.29-7.37 (m, 6 H) 7.21-7.28 (m, 1 H) 6.14-6.23 (m, 1 H) 6.03-6.11 (m, 1 H) 5.58 (dd, J=9.99, 2.21 Hz, 1 H) 4.34 (s, 2 H) 3.66-3.76 (m, 1 H) 3.64 (s, 2 H) 3.47 (d, J=12.51 Hz, 2 H) 2.81 (t, J=10.99 Hz, 2 H) 1.72-1.84 (m, 2 H) 1.28-1.39 (m, 2 H). Tr=3.60 min, m/z (ES$^+$) (M+H)$^+$ 442.

Method G

Example G-1

5-(4-tert-Butoxycarbonylamino-piperidine-1-sulfonyl)-furan-2-carboxylic acid methyl ester 5-(4-tert-Butoxycarbonylamino-piperidine-1-sulfonyl)-furan-2-carboxylic acid methyl ester

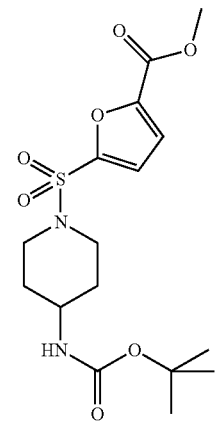 [SMILES: COC(=O)c1ccc(S(=O)(=O)N2CCC(NC(=O)OC(C)(C)C)CC2)o1]

Diisopropylethylamine (0.75 ml, 4.45 mmol) was added in one portion to a stirred solution of piperidin-4-yl-carbamic acid tert-butyl ester (0.45 g, 2.26 mmol) in DCM (5 ml) at room temperature. To this mixture was added 5-chlorosulfonyl-furan-2-carboxylic acid methyl ester (0.5 g, 2.26 mmol) in one portion and the mixture was stirred at room temperature under a nitrogen atmosphere for 1 hour. After this time the mixture was diluted with DCM (100 ml) and washed sequentially with HCl (1M solution, 50 ml), NaOH (1M solution, 50 ml) and brine (50 ml). The organic layer was separated, dried (MgSO$_4$), filtered and concentrated. The resulting solid was collected by filtration, washed with diethyl ether and dried under vacuum to give the title compound (0.76 g, 88% yield) as an off-white solid. Tr=1.98 min, m/z (ES$^+$) (M+Na)$^+$ 411.

[1-(5-Phenethylcarbamoyl-furan-2-sulfonyl)-piperidin-4-yl]-carbamic acid tert-butyl ester

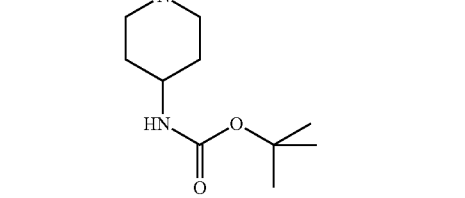

Phenethylamine (0.5 g, 4.1 mmol) was added in one portion to a stirred solution of 5-(4-tert-butoxycarbonylamino-piperidine-1-sulfonyl)-furan-2-carboxylic acid methyl ester (0.4 g, 1.0 mmol) in methanol (10 ml) at room temperature. The reaction mixture was then heated to 45° C. and stirred at this temperature overnight, after which time the mixture was concentrated. The resulting residue was dissolved in DCM (100 ml), washed sequentially with HCl (1M solution, 50 ml), NaOH (1M solution, 50 ml) and brine (50 ml). The organic layer was separated, dried (MgSO$_4$), filtered and concentrated to give the title compound (0.46 g, 94% yield) as a light brown solid which was taken on without further purification. δ$_H$ (500 MHz, DMSO) 8.71 (t, J=5.79 Hz, 1 H) 7.13-7.38 (m, 8 H) 6.93 (d, J=7.61 Hz, 1 H) 5.75 (s, 1 H) 3.41-3.63 (m, 5 H) 2.66-2.91 (m, 5 H) 1.66-1.87 (m, 2 H) 1.25-1.47 (m, 12 H).

5-(4-tert-Butoxycarbonylamino-piperidine-1-sulfonyl)-furan-2-carboxylic acid methyl ester

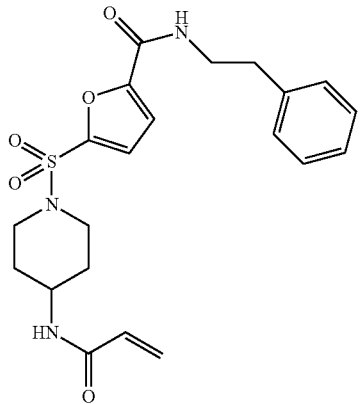 [SMILES: C=CC(=O)NC1CCN(S(=O)(=O)c2ccc(C(=O)NCCc3ccccc3)o2)CC1]

[1-(5-Phenethylcarbamoyl-furan-2-sulfonyl)-piperidin-4-yl]-carbamic acid tert-butyl ester (0.15 g, 0.3 mmol) was suspended in a 4M solution of HCl in Dioxane (5 ml). The resulting suspension was stirred at room temperature for 3 hours. After this time the solution was concentrated under vacuum and the resulting residue dissolved in THF (10 ml). To this solution was added diisopropylethylamine (0.3 ml, 1.6 mmol) was added in one portion, followed by the drop wise addition of acryloyl chloride (0.03 ml, 0.38 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO$_4$), filtered, concentrated and the resulting residue was purified by flash column chromatography (elution: 50% EtOAc, 50% heptane) to give the title compound (0.01 g, 2% yield) as a white solid.

Example G-1

5-(4-Acryloylamino-piperidine-1-sulfonyl)-furan-2-carboxylic acid phenethyl-amide δ$_H$ (500 MHz, DMSO) 8.72 (t, J=5.75 Hz, 1 H) 8.11 (d, J=7.41 Hz, 1 H) 7.12-7.36 (m, 7 H) 6.01-6.24 (m, 2 H) 5.44-5.61 (m, 1 H) 3.67-3.80 (m, 1 H) 3.60 (d, J=12.30 Hz, 2 H) 3.41-3.51 (m, 2 H) 2.75-2.92 (m, 4 H) 1.71-1.90 (m, 2 H) 1.32-1.49 (m, 2 H). Tr=3.82 min, m/z (ES$^+$) (M+H)$^+$ 432.

Example G-2

5-(4-Acryloylamino-piperidine-1-sulfonyl)-furan-3-carboxylic acid phenethyl-amide δ$_H$ (500 MHz, DMSO) 8.53 (t, J=5.60 Hz, 1 H) 8.47 (s, 1 H) 8.10 (d, J=7.57 Hz, 1 H) 7.55 (s, 1 H) 7.17-7.33 (m, 5 H) 6.02-6.21 (m, 2 H) 5.57 (dd, J=10.01, 2.13 Hz, 1 H) 3.68-3.77 (m, 1 H) 3.56 (d, J=12.45 Hz, 2 H) 3.40-3.47 (m, 2 H) 2.77-2.89 (m, 4 H) 1.84 (dd, J=13.00, 3.07 Hz, 2 H) 1.32-1.44 (m, 2 H). Tr=3.71 min, m/z (ES$^+$) (M+H)$^+$ 432.

Example G-3

5-(4-Acryloylamino-piperidine-1-sulfonyl)-1-methyl-1H-pyrrole-2-carboxylic acid phenethyl-amide δ$_H$ (500 MHz, DMSO) 8.42 (t, J=5.60 Hz, 1 H) 8.09 (d, J=7.41 Hz, 1 H) 7.52 (d, J=1.58 Hz, 1 H) 7.17-7.32 (m, 5 H) 7.01 (d, J=1.73 Hz, 1 H) 5.98-6.22 (m, 2 H) 5.57 (dd, J=10.09, 2.21 Hz, 1 H) 3.87 (s, 3 H) 3.52-3.66 (m, 1 H) 3.37-3.43 (m, 4 H) 2.80 (t, J=7.41 Hz, 2 H) 2.38-2.46 (m, 2 H) 1.85 (d, J=9.93 Hz, 2 H) 1.38-1.55 (m, 2 H). Tr=3.67 min, m/z (ES$^+$) (M+H)$^+$ 445.

Method H

Example H-1

[4-(4-Acryloylamino-piperidin-1-ylmethyl)-phenyl]carbamic acid benzyl ester (4-Hydroxymethyl-phenyl)-carbamic acid benzyl ester

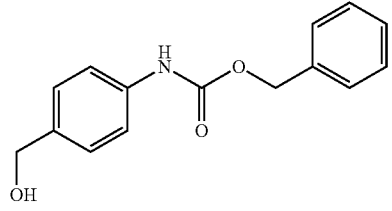 [SMILES: O=C(Nc1ccc(CO)cc1)OCc1ccccc1]

Sodium bicarbonate (1.0 g, 12.2 mmol) was added portionwise to a stirred solution of (4-amino-phenyl)-methanol (0.5 g, 4.06 mmol) in a 1:1 mixture of THF:H$_2$O (16 ml) and the mixture was stirred at room temperature for 5 minutes. After this time, benzyl carbonyl chloride (0.69 g, 4.06 mmol) was added dropwise, followed by a further portion of sodium bicarbonate (0.5 g, 6.1 mmol) and stirring was continued for 1 hour. The reaction mixture was then diluted with DCM (50 ml) and washed sequentially with HCl (1M solution, 10 ml) then NaOH (1M solution, 10 ml). The organic layer was separated, dried (MgSO$_4$), filtered and concentrated. The resulting residue was purified by flash column chromatography (elution: 50% EtOAc, 50% heptane) to give the title compound (0.6 g, 57% yield) as an off-white solid. δ$_H$ (500 MHz, DMSO) 9.63 (s, 1 H) 7.01-7.39 (m, 9 H) 4.90-5.11 (m, 3 H) 4.30 (d, J=5.63 Hz, 2 H).

Methanesulfonic acid 4-benzyloxycarbonylamino-benzyl ester

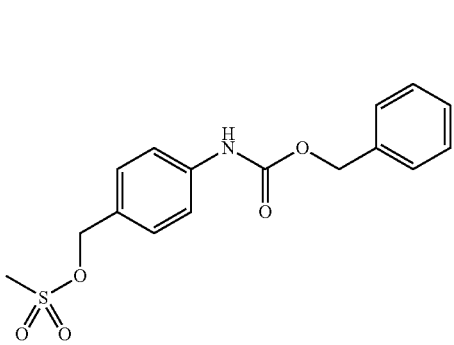 [SMILES: CS(=O)(=O)OCc1ccc(NC(=O)OCc2ccccc2)cc1]

Diisopropylethylamine (0.19 ml, 1.17 mmol) was added to a cool (0° C.) solution of (4-Hydroxymethyl-phenyl)-carbamic acid benzyl ester (0.25 g, 0.97 mmol) in DCM (8 ml) and the reaction stirred at this temperature for 5 minutes. After this time, methane sulfonyl chloride (0.09 ml, 1.07 mmol) was added dropwise and the mixture was allowed to warm to room temperature and stirred for 1 hour. The reaction mixture was then diluted with DCM (20 ml) and washed sequentially with saturated sodium bicarbonate solution (10 ml), saturated ammonium chloride (10 ml) and brine (10 ml). The organic layer was separated, dried (MgSO$_4$), filtered and concentrated to afford the title compound (0.29 g, 89% yield) as a yellow oil which was taken forward without further purification.

[1-(4-Benzyloxycarbonylamino-benzyl)-piperidin-4-yl]-carbamic acid tert-butyl ester

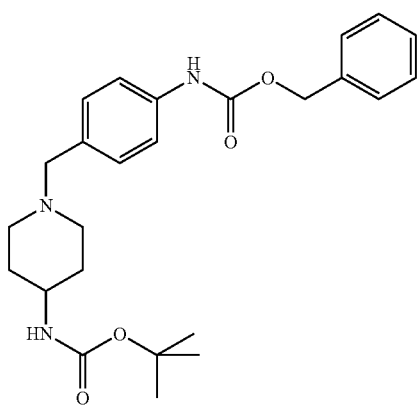 [SMILES: CC(C)(C)OC(=O)NC1CCN(Cc2ccc(NC(=O)OCc3ccccc3)cc2)CC1]

Methanesulfonic acid 4-benzyloxycarbonylamino-benzyl ester (0.35 g, 2.5 mmol) was added to a suspension of piperidin-4-yl-carbamic acid tert-butyl ester (0.15 g, 0.76 mmol) and potassium bicarbonate (0.35 g, 2.5 mmol) in DMF (10 ml) and the reaction heated to 60° C. and stirred at this temperature for 16 hours under a nitrogen atmosphere. After this time, the reaction mixture was cooled to room temperature and the solvent removed. The resulting residue was diluted with EtOAc (50 ml) and washed with water (10 ml). The organic layer was separated, dried (MgSO$_4$), filtered and concentrated and the resulting residue was triturated with EtOAc, the resulting precipitate collected by filtration and dried under vacuum to give the title compound (0.14 g, 37% yield) as a white solid. Tr=1.58 min, m/z (ES$^+$) (M+H)$^+$ 440.

[4-(4-Acryloylamino-piperidin-1-ylmethyl)-phenyl] carbamic acid benzyl ester

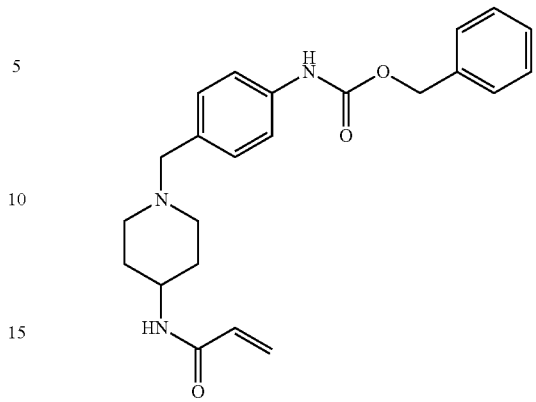

[1-(4-Benzyloxycarbonylamino-benzyl)piperidin-4-yl]-carbamic acid tert-butyl ester (0.14 g, 0.32 mmol) was suspended in a 4M solution of HCl in Dioxane (5 ml). The resulting suspension was stirred at room temperature for 3 hours. After this time the solution was concentrated under vacuum and the resulting residue dissolved in THF (10 ml). To this solution was added diisopropylethylamine (0.28 ml, 1.6 mmol) was added in one portion, followed by the drop wise addition of acryloyl chloride (0.03 ml, 0.38 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO$_4$), filtered, concentrated and the resulting residue was purified by flash column chromatography (elution: 100% DCM to 90% DCM, 10% Methanol) to give the title compound (0.012 g, 10% yield) as a white solid.

Example H-1

[4-(4-Acryloylamino-piperidin-1-ylmethyl)-phenyl]-carbamic acid benzyl ester $\delta_H$ (500 MHz, DMSO) 9.71 (br. s., 1 H) 7.99 (br. s., 1 H) 7.30-7.47 (m, 6 H) 7.19 (br. s., 2 H) 6.15-6.25 (m, 1 H) 6.02-6.10 (m, 1 H) 5.56 (dd, J=9.99, 1.60 Hz, 1 H) 5.15 (s, 2 H) 3.59 (br. s., 1 H) 3.35-3.42 (m, 2H) 2.67-2.81 (m, 2H) 1.88-2.05 (m, 2 H) 1.64-1.78 (m, 2 H) 1.33-1.45 (m, 2 H). Tr=2.96 min, m/z (ES$^+$) (M+H)$^+$ 394.

Method I

Example I-1

N-{1-[4-(Phenylacetylamino-methyl)-benzenesulfonyl]-piperidin-4-yl}-acrylamide

[1-(4-Bromomethyl-benzenesulfonyl)-piperidin-4-yl] carbamic acid tert-butyl ester

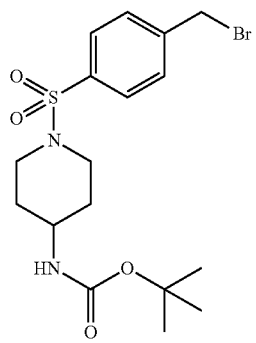 [SMILES: CC(C)(C)OC(=O)NC1CCN(S(=O)(=O)c2ccc(CBr)cc2)CC1]

Diisopropylethylamine (0.99 ml, 5.6 mmol) was added in one portion to a stirred solution of piperidin-4-yl-carbamic acid tert-butyl ester (0.37 g, 1.85 mmol) in DCM (20 ml) at room temperature. To this mixture was added 4-bromomethyl-benzenesulfonyl chloride (0.5 g, 1.85 mmol) in one portion and the mixture was stirred at room temperature under a nitrogen atmosphere for 1 hour. After this time the mixture was diluted with DCM (50 ml) and washed sequentially with HCl (1M solution, 20 ml), NaOH (1M solution, 20 ml) and brine (20 ml). The organic layer was separated, dried (MgSO$_4$), filtered and concentrated. The resulting solid was collected by filtration, washed with diethyl ether and dried under vacuum to give the title compound (0.56 g, 70% yield) as an off-white solid. Tr=2.12 min, m/z (ES$^+$) (M+Na)$^+$ 457.

{1-[4-(1,3-Dioxo-1,3-dihydro-isoindol-2-ylmethyl)-benzenesulfonyl]-piperidin-4-yl}-carbamic acid tert-butyl ester

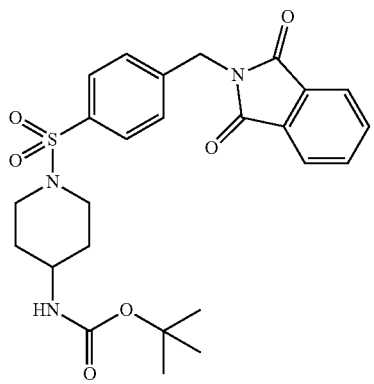 [SMILES: CC(C)(C)OC(=O)NC1CCN(S(=O)(=O)c2ccc(CN3C(=O)c4ccccc4C3=O)cc2)CC1]

Potassium phthalimide (0.11 g, 0.58 mmol) was added to a solution of 1-(4-bromomethyl-benzenesulfonyl)-piperidin-4-yl]-carbamic acid tert-butyl ester (0.15 g, 0.76 mmol) in DMF (10 ml) and the reaction heated to 60° C. and stirred at this temperature for 20 hours under a nitrogen atmosphere. After this time, the reaction mixture was cooled to room temperature and the solvent removed. The resulting residue was diluted with EtOAc (50 ml) and washed with water (10 ml). The organic layer was separated, dried (MgSO$_4$), filtered and concentrated and the resulting residue was purified by flash column chromatography (elution: 50% EtOAc, 50% heptane) to give the title compound (0.2 g, 71% yield) as a white solid. δ$_H$ (500 MHz, DMSO) 7.81-7.99 (m, 4 H) 7.69 (d, J=8.35 Hz, 2 H) 7.57 (d, J=8.35 Hz, 2 H) 6.84 (d, J=7.41 Hz, 1 H) 4.89 (s, 2 H) 3.45 (d, J=11.98 Hz, 2 H) 3.23 (br. s., 1 H) 2.36-2.47 (m, 2 H) 1.75 (d, J=10.25 Hz, 2 H) 1.21-1.45 (m, 13 H).

[1-(4-Aminomethyl-benzenesulfonyl)-piperidin-4-yl]-carbamic acid tert-butyl ester

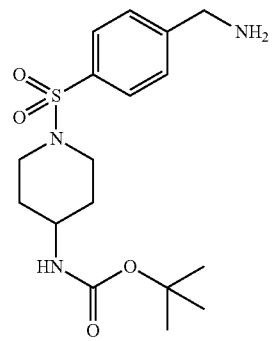 [SMILES: CC(C)(C)OC(=O)NC1CCN(S(=O)(=O)c2ccc(CN)cc2)CC1]

Hydrazine monohydrate (0.11 ml, 2.4 mmol) was added to a stirred solution of {1-[4-(1,3-dioxo-1,3-dihydro-isoindol-2-ylmethyl)-benzenesulfonyl]-piperidin-4-yl}-carbamic acid tert-butyl ester (0.4 g, 0.8 mmol) in ethanol (10 ml), the mixture was heated to 70° C. and stirred at this temperature for 4 hours. After this time, the precipitate was removed by filtration and the filtrate was concentrated. The resulting residue was triturated with DCM and the resulting precipitate was collected by filtration and dried under vacuum to give the title compound (0.29 g, 98% yield) as a white solid. Tr=1.38 min, m/z (ES$^+$) (M+Na)$^+$ 392.

{1-[4-(Phenylacetylamino-methyl)-benzenesulfonyl]-piperidin-4-yl}-carbamic acid tert-butyl ester

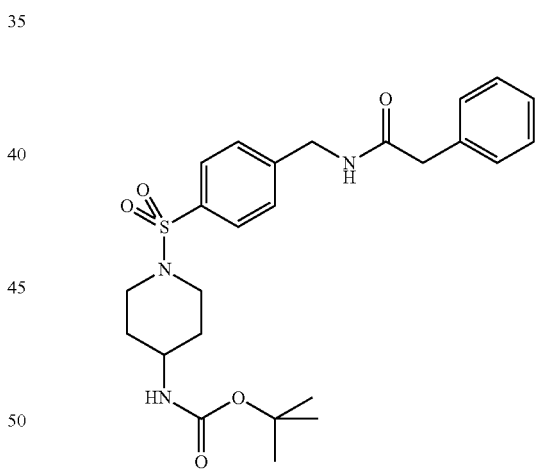

Diisopropylethylamine (0.17 ml, 1.02 mmol) was added in one portion to a stirred solution of [1-(4-aminomethyl-benzenesulfonyl)-piperidin-4-yl]-carbamic acid tert-butyl ester (0.25 g, 0.68 mmol) in DCM (10 ml) at room temperature. To this mixture was added benzyl carbonyl chloride (0.1 g, 0.68 mmol) in one portion and the mixture was stirred at room temperature under a nitrogen atmosphere for 1 hour. After this time the mixture was diluted with DCM (50 ml) and washed sequentially with HCl (1M solution, 20 ml), NaOH (1M solution, 20 ml) and brine (20 ml). The organic layer was separated, dried (MgSO$_4$), filtered and concentrated to give the title compound (0.32 g, 97% yield) as a white solid. δ$_H$ (500 MHz, DMSO) 8.67 (t, J=5.99 Hz, 1 H) 7.66 (d, J=8.20 Hz, 2 H) 7.47 (d, J=8.35 Hz, 2 H) 7.19-7.36 (m, 5 H) 6.85 (d, J=7.25 Hz, 1 H) 4.38 (d, J=5.99 Hz, 2 H) 3.51 (s, 2 H) 3.46 (d, J=11.82 Hz, 2 H) 3.21 (br. s., 1 H) 2.33-2.43 (m, 3 H) 1.76 (d, J=10.56 Hz, 2 H) 1.30-1.45 (m, 12 H).

N-{1-[4-(Phenylacetylamino-methyl)-benzenesulfonyl]-piperidin-4-yl}-acrylamide

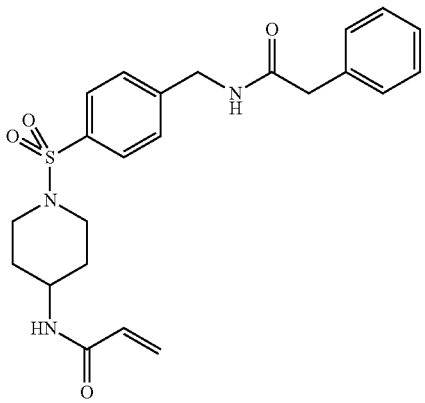 [SMILES: C=CC(=O)NC1CCN(S(=O)(=O)c2ccc(CNC(=O)Cc3ccccc3)cc2)CC1]

{1-[4-(Phenylacetylamino-methyl)-benzenesulfonyl]-piperidin-4-yl}-carbamic acid tert-butyl ester (0.15 g, 0.31 mmol) was suspended in a 4M solution of HCl in Dioxane (10 ml). The resulting suspension was stirred at room temperature for 3 hours. After this time the solution was concentrated under vacuum and the resulting residue dissolved in THF (10 ml). To this solution was added diisopropylethylamine (0.25 ml, 1.54 mmol) was added in one portion, followed by the drop wise addition of acryloyl chloride (0.03 ml, 0.38 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO$_4$), filtered, concentrated and the resulting residue was purified by flash column chromatography (elution: 100% DCM to 95% DCM, 5% Methanol) to give the title compound (0.025 g, 18% yield) as a white solid.

Example I-1

N-{1-[4-(Phenylacetylamino-methyl)-benzenesulfonyl]-piperidin-4-yl}-acrylamide $\delta_H$ (500 MHz, DMSO) 8.67 (t, J=5.83 Hz, 1 H) 8.05 (d, J=7.41 Hz, 1 H) 7.68 (d, J=8.20 Hz, 2 H) 7.47 (d, J=8.35 Hz, 2 H) 7.17-7.38 (m, 5 H) 6.10-6.23 (m, 1 H) 6.00-6.08 (m, 1 H) 5.56 (dd, J=10.09, 2.36 Hz, 1 H) 4.38 (d, J=5.99 Hz, 2 H) 3.55-3.65 (m, 1 H) 3.51 (s, 3 H) 2.44-2.49 (m, 2 H) 1.76-1.88 (m, 2 H) 1.30-1.53 (m, 2 H). Tr=3.58 min, m/z (ES$^+$) (M+H)$^+$ 442.

Method J

Example J-1

N-{1-[4-(Isoquinolin-3-ylamino)-benzenesulfonyl]-piperidin-4-yl}-acrylamide

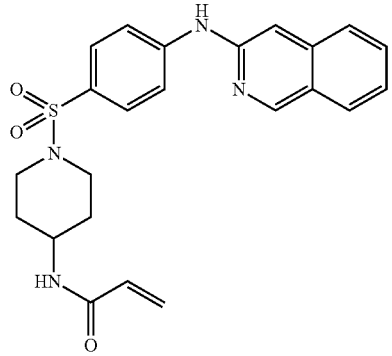 [SMILES: C=CC(=O)NC1CCN(S(=O)(=O)c2ccc(Nc3cc4ccccc4cn3)cc2)CC1]

Tris(dibenzylideneacetone)dipalladium (0) (0.05 g, 0.06 mmol), 4,5-bis(diphenylphosphino)-9,9-dimethylxanthene (0.015 g, 0.03 mmol), cesium carbonate (0.5 g, 2.0 mmol) and 2-chloroquinoline (0.085 g, 0.52 mmol) were added sequentially to a stirred solution of N-[1-(4-amino-benzenesulfonyl)-piperidin-4-yl]-acrylamide in dry dioxane (5 ml) under a nitrogen atmosphere. The mixture was heated to 110° C. for 12 hours. After this time the mixture was cooled to room temperature, filtered through a pad of celite, the celite was washed with EtOAc (50 ml) and the filtrate was washed sequentially with citric acid (10% solution, 20 ml) and brine (20 ml). The organic layer was separated, dried (MgSO$_4$), filtered and concentrated. The resulting residue was purified by prep HPLC to give the title compound (0.002 g, 0.5% yield) as a white solid.

Example J-1

N-{1-[4-(Isoquinolin-3-ylamino)-benzenesulfonyl]-piperidin-4-yl}-acrylamide $\delta_H$ (500 MHz, DMSO) 9.99 (s, 1 H) 8.26 (d, J=8.98 Hz, 2 H) 8.16 (d, J=8.98 Hz, 1 H) 8.07 (d, J=7.41 Hz, 1 H) 7.74-7.82 (m, 2 H) 7.69 (d, J=8.83 Hz, 2 H) 7.57-7.66 (m, 1 H) 7.33-7.44 (m, 1 H) 7.14 (d, J=8.83 Hz, 1 H) 6.11-6.24 (m, 1 H) 5.97-6.08 (m, 1 H) 5.54 (dd, J=10.17, 2.13 Hz, 1 H) 3.55-3.66 (m, 1 H) 3.50 (d, J=11.82 Hz, 2 H) 1.78-1.90 (m, 2 H) 1.38-1.54 (m, 2 H). Tr=3.69 min, m/z (ES$^+$) (M+H)$^+$ 437.

Method K

Example K-1

N-[1-(6-Phenethyloxy-pyridine-3-sulfonyl)-piperidin-4-yl]-acrylamide

[1-(6-Chloro-pyridine-3-sulfonyl)-piperidin-4-yl]-carbamic acid tert-butyl ester

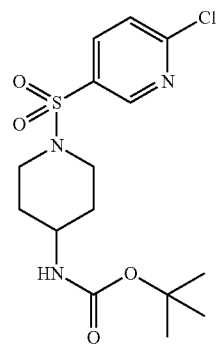 [SMILES: CC(C)(C)OC(=O)NC1CCN(S(=O)(=O)c2ccc(Cl)nc2)CC1]

Diisopropylethylamine (1.34 ml, 8.14 mmol) was added in one portion to a stirred solution of piperidin-4-yl-carbamic acid tert-butyl ester (0.5 g, 2.70 mmol) in DCM (20 ml) at room temperature. To this mixture was added 6-chloro-pyridine-3-sulfonyl chloride (0.57 g, 2.70 mmol) in one portion and the mixture was stirred at room temperature under a nitrogen atmosphere for 1 hour. After this time the mixture was diluted with DCM (50 ml) and washed sequentially with HCl (1M solution, 20 ml), NaOH (1M solution, 20 ml) and brine (20 ml). The organic layer was separated, dried (MgSO$_4$), filtered and concentrated to give the title compound (0.64 g, 65% yield) as a white solid. $\delta_H$ (500 MHz, DMSO) 8.76 (d, J=2.20 Hz, 1 H) 8.19 (dd, J=8.44, 2.57 Hz, 1 H) 7.82 (d, J=8.44 Hz, 1 H) 6.89 (d, J=7.70 Hz, 1 H) 3.48 (d, J=11.92 Hz, 2 H) 3.31 (br. s., 1 H) 2.59-2.68 (m, 2 H) 1.76 (d, J=10.27 Hz, 2 H) 1.30-1.46 (m, 11 H).

[1-(6-Phenethyloxy-pyridine-3-sulfonyl)-piperidin-4-yl]-carbamic acid tert-butyl ester

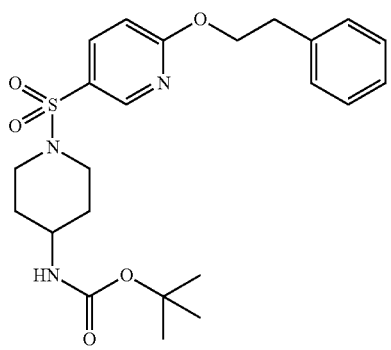 [SMILES: CC(C)(C)OC(=O)NC1CCN(S(=O)(=O)c2ccc(OCCc3ccccc3)nc2)CC1]

Sodium hydride (0.03 g, 1.15 mmol, 60% suspension in mineral oil) was added in portionwise to a cool (0° C.), stirred solution of phenethyl alcohol (0.08 g, 0.64 mmol) in DMF (5 ml) and the mixture was stirred at this temperature for 5 minutes. After this time, [1-(6-chloro-pyridine-3-sulfonyl)piperidin-4-yl]-carbamic acid tert-butyl ester (0.2 g, 0.5 mmol) was added in one portion and the mixture was warmed to room temperature stirred at this temperature under a nitrogen atmosphere for 12 hours. After this time the mixture was cooled to room temperature, concentrated and the resulting residue was diluted with DCM (50 ml) and washed sequentially with HCl (1M solution, 20 ml), NaOH (1M solution, 20 ml) and brine (20 ml). The organic layer was separated, dried (MgSO$_4$), filtered and concentrated to give the title compound (0.18 g, 75% yield) as a white solid. Tr=2.32 min, m/z (ES$^+$) (M+H)$^+$ 462.

N-[1-(6-Phenethyloxy-pyridine-3-sulfonyl)-piperidin-4-yl]-acrylamide

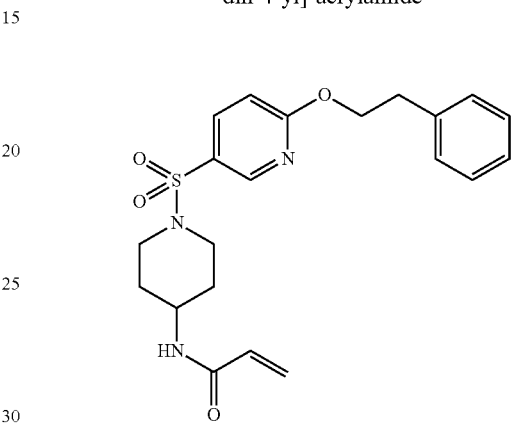

[1-(6-Phenethyloxy-pyridine-3-sulfonyl)-piperidin-4-yl]-carbamic acid tert-butyl ester (0.18 g, 0.39 mmol) was suspended in a 4M solution of HCl in Dioxane (10 ml). The resulting suspension was stirred at room temperature for 3 hours. After this time the solution was concentrated under vacuum and the resulting residue dissolved in THF (10 ml). To this solution was added diisopropylethylamine (0.34 ml, 1.99 mmol) was added in one portion, followed by the drop wise addition of acryloyl chloride (0.03 ml, 0.38 mmol) and the mixture was stirred at room temperature under a nitrogen atmosphere for 3 hours. After this time the mixture was diluted with DCM (20 ml) and washed sequentially with HCl (1M solution, 10 ml), NaOH (1M solution, 10 ml) and brine (10 ml). The organic layer was separated, dried (MgSO$_4$), filtered, concentrated and the resulting residue was purified by flash column chromatography (elution: 50% DCM, 50% EtOAc) to give the title compound (0.032 g, 19% yield) as a white solid.

Example K-1

N-[1-(6-Phenethyloxy-pyridine-3-sulfonyl)-piperidin-4-yl]-acrylamide $\delta_H$ (500 MHz, DMSO) 8.51 (d, J=2.05 Hz, 1 H) 8.04 (d, J=7.57 Hz, 1 H) 7.98 (dd, J=8.83, 2.52 Hz, 1 H) 7.31 (m, J=4.60 Hz, 4 H) 7.19-7.26 (m, 1 H) 7.00 (d, J=9.14 Hz, 1 H) 6.01-6.21 (m, 2 H) 5.50-5.59 (m, 1 H) 4.57 (t, J=6.86 Hz, 2 H) 3.59-3.70 (m, 1 H) 3.49 (d, J=11.98 Hz, 2 H) 3.06 (t, J=6.86 Hz, 2 H) 2.53-2.59 (m, 2 H) 1.82 (dd, J=13.08, 3.31 Hz, 2 H) 1.35-1.48 (m, 2 H). Tr=4.35 min, m/z (ES$^+$) (M+H)$^+$ 416.

Example L

Using procedures similar to those described above, the following compounds were prepared and tested.

| Structure | IUPAC Name | Molecular weight | Mass Spectrum |
|---|---|---|---|
| 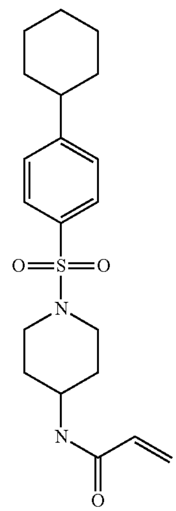 [SMILES: C=CC(=O)NC1CCN(S(=O)(=O)c2ccc(C3CCCCC3)cc2)CC1] | N-[1-(4-Cyclohexyl-benzenesulfonyl)-piperidin-4-yl]-acrylamide | 376 | Tr = 4.76 min, m/z (ES+) (M + H)+ 377 |
| 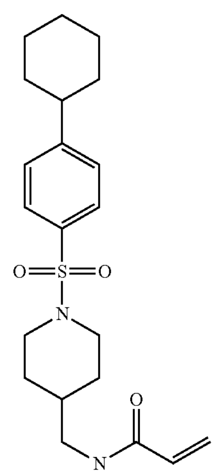 [SMILES: C=CC(=O)NCC1CCN(S(=O)(=O)c2ccc(C3CCCCC3)cc2)CC1] | N-[1-(4-Cyclohexyl-benzenesulfonyl)-piperidin-4-ylmethyl]-acrylamide | 390.55 | Tr = 4.53 min, m/z (ES+) (M + H)+ 391 |
| 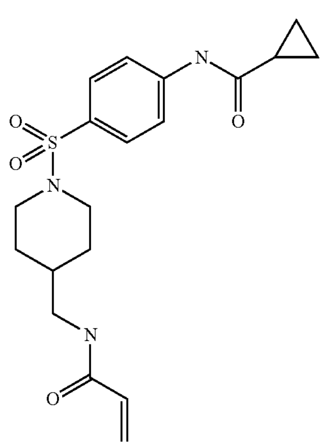 [SMILES: C=CC(=O)NCC1CCN(S(=O)(=O)c2ccc(NC(=O)C3CC3)cc2)CC1] | Cyclopropanecarboxylic acid{4-[4-(acryloylamino-methyl)-piperidine-1-sulfonyl]-phenyl}-amide | 391 | Tr = 3.31 min, m/z (ES+) (M + H)+ 392 |

-continued

| Structure | IUPAC Name | Molecular weight | Mass Spectrum |
|---|---|---|---|
| 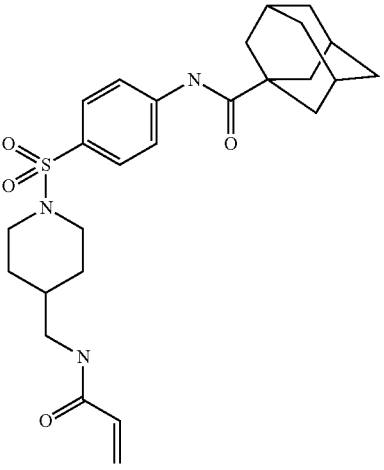 [SMILES: C=CC(=O)NCC1CCN(S(=O)(=O)c2ccc(NC(=O)C34CC5CC(CC(C5)C3)C4)cc2)CC1] | Adamantane-1-carboxylic acid{4-[4-(acryloylamino-methyl)-piperidine-1-sulfonyl]-phenyl}-amide | 485 | Tr = 4.36 min, m/z (ES+) (M + H)+ 486 |
| 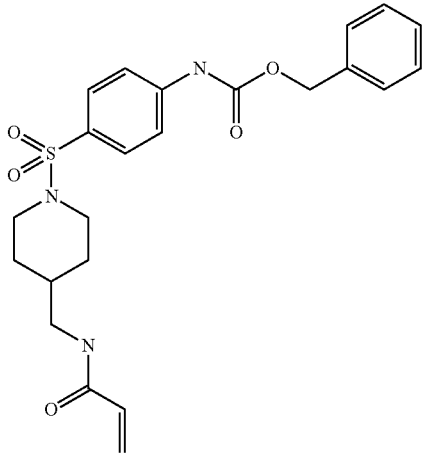 [SMILES: C=CC(=O)NCC1CCN(S(=O)(=O)c2ccc(NC(=O)OCc3ccccc3)cc2)CC1] | {4-[4-(Acryloylamino-methyl)-piperidine-1-sulfonyl]-phenyl}-carbamic acid benzyl ester | 457 | Tr = 3.94 min, m/z (ES+) (M + H)+ 458 |
| 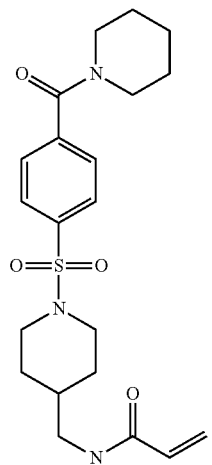 [SMILES: C=CC(=O)NCC1CCN(S(=O)(=O)c2ccc(C(=O)N3CCCCC3)cc2)CC1] | N-{1-[4-(Piperidine-1-carbonyl)-benzenesulfonyl]-piperidin-4-ylmethyl}-acrylamide | 419 | Tr = 3.46 min, m/z (ES+) (M + H)+ 420 |

-continued

| Structure | IUPAC Name | Molecular weight | Mass Spectrum |
|---|---|---|---|
| 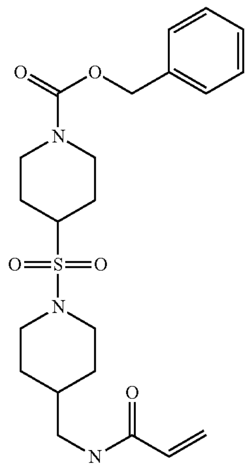 [SMILES: C=CC(=O)NCC1CCN(S(=O)(=O)C2CCN(C(=O)OCc3ccccc3)CC2)CC1] | 4-[4-(Acryloylamino-methyl)-piperidine-1-sulfonyl]-piperidine-1-carboxylic acid benzyl ester | 449 | Tr = 3.73 min, m/z (ES+) (M + H)+ 450 |
| 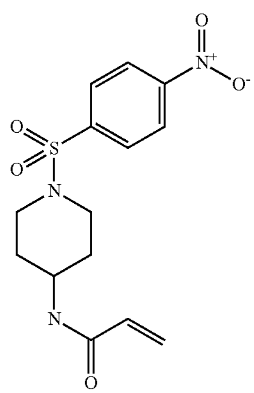 [SMILES: C=CC(=O)NC1CCN(S(=O)(=O)c2ccc([N+](=O)[O-])cc2)CC1] | N-[1-(4-Nitro-benzenesulfonyl)-piperidin-4-yl]-acrylamide | 339 | Tr = 3.84 min, m/z (ES+) (M + H)+ 340 |
| 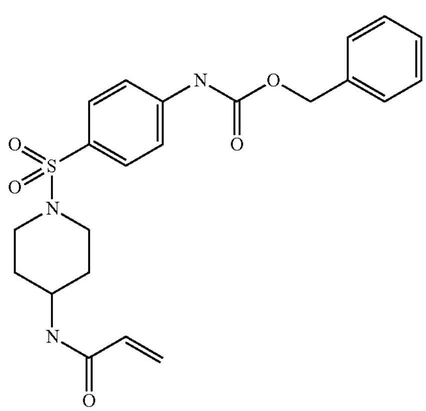 [SMILES: C=CC(=O)NC1CCN(S(=O)(=O)c2ccc(NC(=O)OCc3ccccc3)cc2)CC1] | [4-(4-Acryloylamino-piperidine-1-sulfonyl)-phenyl]-carbamic acid benzyl ester | 443 | Tr = 3.93 min, m/z (ES+) (M + H)+ 444 |

-continued

| Structure | IUPAC Name | Molecular weight | Mass Spectrum |
|---|---|---|---|
| 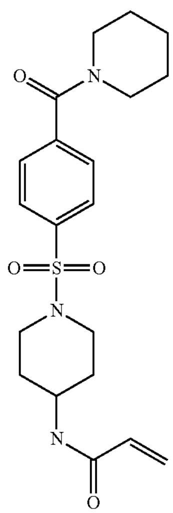 [SMILES: C=CC(=O)NC1CCN(S(=O)(=O)c2ccc(C(=O)N3CCCCC3)cc2)CC1] | N-{1-[4-(Piperidine-1-carbonyl)-benzenesulfonyl]-piperidin-4-yl}-acrylamide | 405 | Tr = 3.42 min, m/z (ES+) (M + H)+ 406 |
| 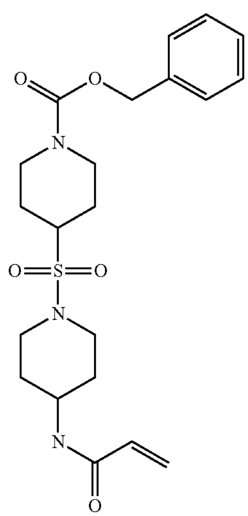 [SMILES: C=CC(=O)NC1CCN(S(=O)(=O)C2CCN(C(=O)OCc3ccccc3)CC2)CC1] | 4-(4-Acryloylamino-piperidine-1-sulfonyl)-piperidine-1-carboxylic acid benzyl ester | 435 | Tr = 3.70 min, m/z (ES+) (M + H)+ 436 |
| 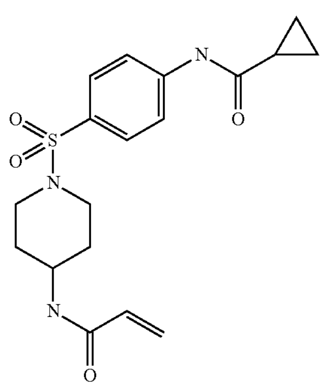 [SMILES: C=CC(=O)NC1CCN(S(=O)(=O)c2ccc(NC(=O)C3CC3)cc2)CC1] | Cyclopropanecarboxylic acid[4-(4-acryloylamino-piperidine-1-sulfonyl)-phenyl]-amide | 377 | Tr = 3.24 min, m/z (ES+) (M + H)+ 378 |

| Structure | IUPAC Name | Molecular weight | Mass Spectrum |
|---|---|---|---|
| 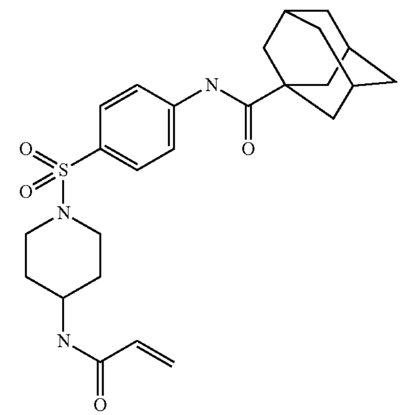 [SMILES: C=CC(=O)NC1CCN(S(=O)(=O)c2ccc(NC(=O)C34CC5CC(CC(C5)C3)C4)cc2)CC1] | Adamantane-1-carboxylic acid[4-(4-acryloylamino-piperidine-1-sulfonyl)-phenyl]-amide | 471 | Tr = 4.33 min, m/z (ES+) (M + H)+ 472 |
| 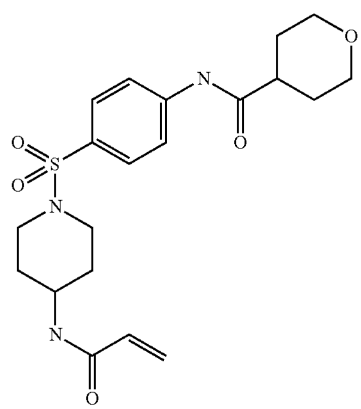 [SMILES: C=CC(=O)NC1CCN(S(=O)(=O)c2ccc(NC(=O)C3CCOCC3)cc2)CC1] | Tetrahydro-pyran-4-carboxylic acid[4-(4-acryloylamino-piperidine-1-sulfonyl)-phenyl]-amide | 421 | Tr = 3.19 min, m/z (ES+) (M + H)+ 422 |
| 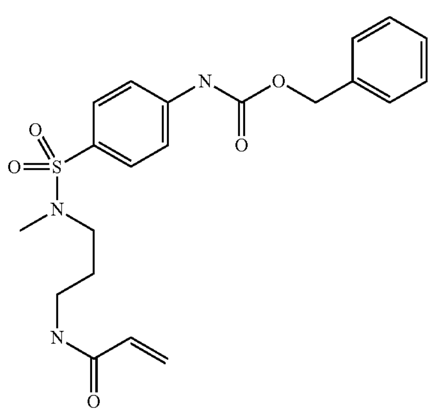 [SMILES: C=CC(=O)NCCCN(C)S(=O)(=O)c1ccc(NC(=O)OCc2ccccc2)cc1] | {4-[(3-Acryloylamino-propyl)-methyl-sulfamoyl]-phenyl}-carbamic acid benzyl ester | 431 | Tr = 4.07 min, m/z (ES+) (M + H)+ 432 |

-continued

| Structure | IUPAC Name | Molecular weight | Mass Spectrum |
|---|---|---|---|
| 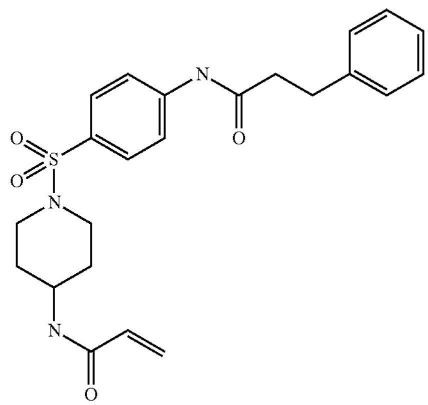 [SMILES: C=CC(=O)NC1CCN(S(=O)(=O)c2ccc(NC(=O)CCc3ccccc3)cc2)CC1] | N-{1-[4-(3-Phenyl-propionylamino)-benzenesulfonyl]-piperidin-4-yl}-acrylamide | 441 | Tr = 3.79 min, m/z (ES$^+$) (M + H)$^+$ 442 |
| 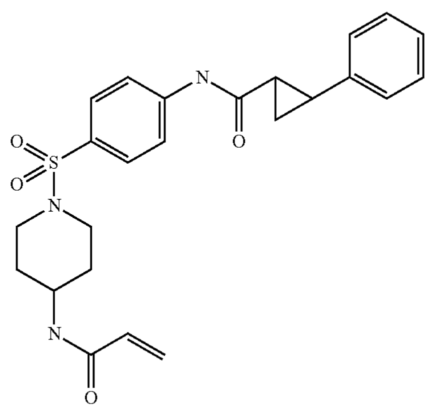 [SMILES: C=CC(=O)NC1CCN(S(=O)(=O)c2ccc(NC(=O)C3CC3c3ccccc3)cc2)CC1] | 2-Phenyl-cyclopropanecarboxylic acid[4-(4-acryloylamino-piperidine-1-sulfonyl)-phenyl]-amide | 453 | Tr = 3.94 min, m/z (ES$^+$) (M + H)$^+$ 454 |
| 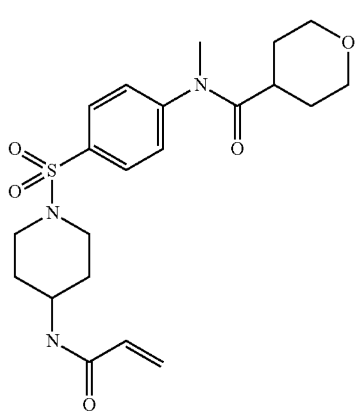 [SMILES: C=CC(=O)NC1CCN(S(=O)(=O)c2ccc(N(C)C(=O)C3CCOCC3)cc2)CC1] | Tetrahydro-pyran-4-carboxylic acid[4-(4-acryloylamino-piperidine-1-sulfonyl)-phenyl]-methyl-amide | 435 | Tr = 3.32 min, m/z (ES$^+$) (M + H)$^+$ 436 |

-continued

| Structure | IUPAC Name | Molecular weight | Mass Spectrum |
|---|---|---|---|
| 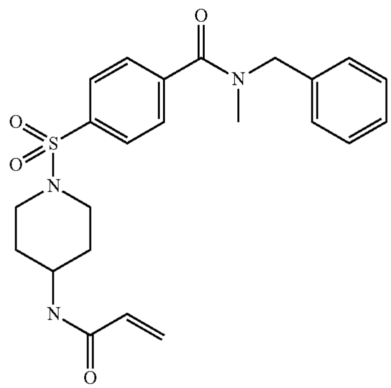 [SMILES: C=CC(=O)NC1CCN(S(=O)(=O)c2ccc(C(=O)N(C)Cc3ccccc3)cc2)CC1] | 4-(4-Acryloylamino-piperidine-1-sulfonyl)-N-benzyl-N-methyl-benzamide | 441 | Tr = 3.68 min, m/z (ES+) (M + H)+ 442 |
| 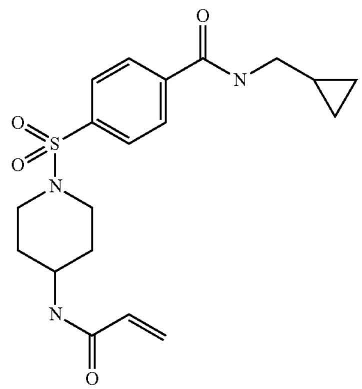 [SMILES: C=CC(=O)NC1CCN(S(=O)(=O)c2ccc(C(=O)NCC3CC3)cc2)CC1] | 4-(4-Acryloylamino-piperidine-1-sulfonyl)-N-cyclopropylmethyl-benzamide | 391 | Tr = 3.29 min, m/z (ES+) (M + H)+ 392 |
| 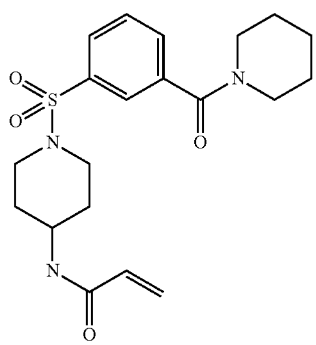 [SMILES: C=CC(=O)NC1CCN(S(=O)(=O)c2cccc(C(=O)N3CCCCC3)c2)CC1] | N-{1-[3-(Piperidine-1-carbonyl)-benzenesulfonyl]-piperidin-4-yl}-acrylamide | 405 | Tr = 3.39 min, m/z (ES+) (M + H)+ 406 |
| 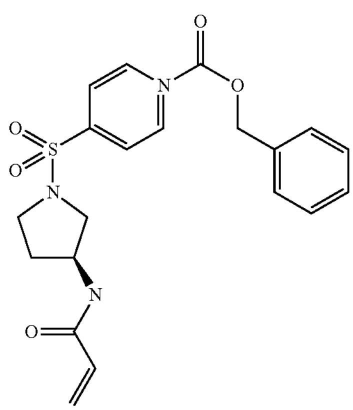 | 4-(3-Acryloylamino-pyrrolidine-1-sulfonyl)-piperidine-1-carboxylic acid benzyl ester | 421 | Tr = 3.62 min, m/z (ES+) (M + H)+ 422 |

-continued

| Structure | IUPAC Name | Molecular weight | Mass Spectrum |
|---|---|---|---|
| 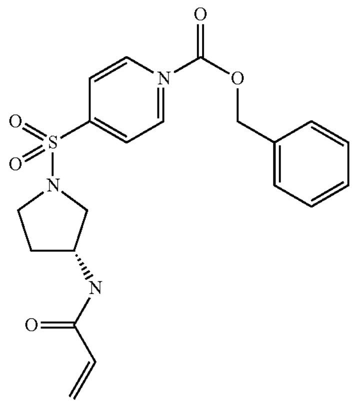 | 4-(3-Acryloylamino-pyrrolidine-1-sulfonyl)-piperidine-1-carboxylic acid benzyl ester | 421 | Tr = 3.62 min, m/z (ES+) (M + H)+ 422 |
| 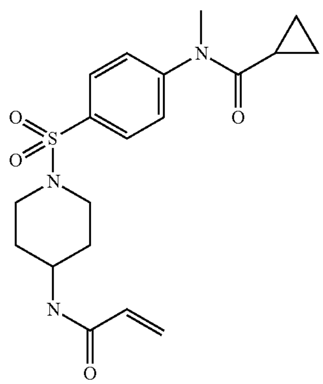 [SMILES: C=CC(=O)NC1CCN(S(=O)(=O)c2ccc(N(C)C(=O)C3CC3)cc2)CC1] | Cyclopropanecarboxylic acid[4-(4-acryloylamino-piperidine-1-sulfonyl)-phenyl]-methyl-amide | 391 | Tr = 3.29 min, m/z (ES+) (M + H)+ 392 |
| 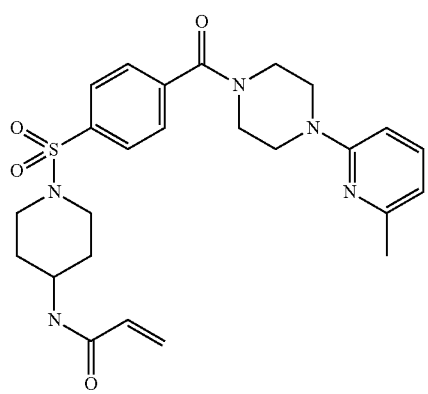 [SMILES: C=CC(=O)NC1CCN(S(=O)(=O)c2ccc(C(=O)N3CCN(c4cccc(C)n4)CC3)cc2)CC1] | N-(1-{4-[4-(6-Methyl-pyridin-2-yl)-piperazine-1-carbonyl]-benzenesulfonyl}-piperidin-4-yl)-acrylamide | 497 | Tr = 2.68 min, m/z (ES+) (M + H)+ 498 |
| 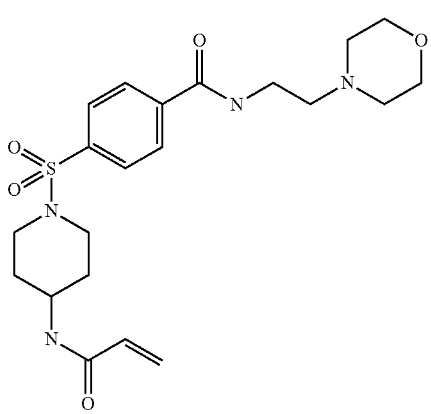 [SMILES: C=CC(=O)NC1CCN(S(=O)(=O)c2ccc(C(=O)NCCN3CCOCC3)cc2)CC1] | 4-(4-Acryloylamino-piperidine-1-sulfonyl)-N-(2-morpholin-4-yl-ethyl)-benzamide | 450 | Tr = 2.31 min, m/z (ES+) (M + H)+ 451 |

| Structure | IUPAC Name | Molecular weight | Mass Spectrum |
|---|---|---|---|
| 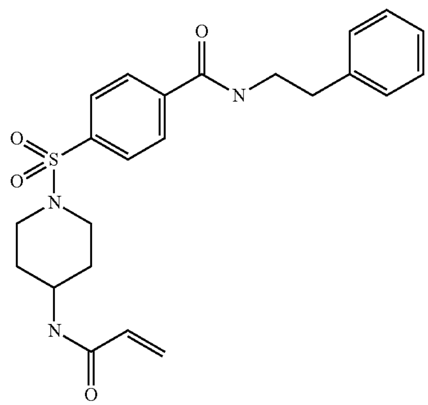 [SMILES: C=CC(=O)NC1CCN(S(=O)(=O)c2ccc(C(=O)NCCc3ccccc3)cc2)CC1] | 4-(4-Acryloylamino-piperidine-1-sulfonyl)-N-phenethyl-benzamide | 441 | Tr = 3.63 min, m/z (ES⁺) (M + H)⁺ 442 |
| 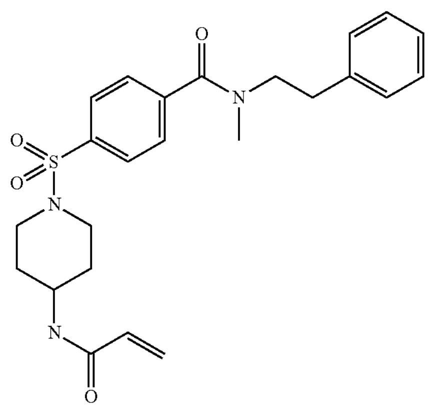 [SMILES: C=CC(=O)NC1CCN(S(=O)(=O)c2ccc(C(=O)N(C)CCc3ccccc3)cc2)CC1] | 4-(4-Acryloylamino-piperidine-1-sulfonyl)-N-methyl-N-phenethyl-benzamide | 455 | Tr = 3.67 min, m/z (ES⁺) (M + H)⁺ 456 |
| 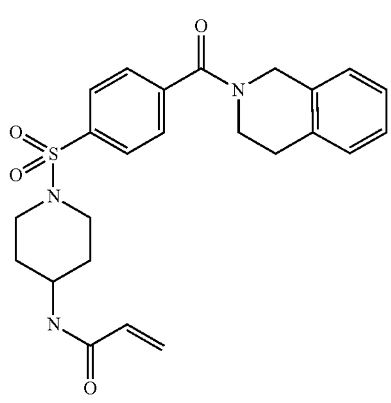 [SMILES: C=CC(=O)NC1CCN(S(=O)(=O)c2ccc(C(=O)N3CCc4ccccc4C3)cc2)CC1] | N-{1-[4-(3,4-Dihydro-1H-isoquinoline-2-carbonyl)-benzenesulfonyl]-piperidin-4-yl}-acrylamide | 453 | Tr = 3.73 min, m/z (ES⁺) (M + H)⁺ 454 |

-continued

| Structure | IUPAC Name | Molecular weight | Mass Spectrum |
|---|---|---|---|
| | [4-(3-Acryloylamino-pyrrolidine-1-sulfonyl)-phenyl]-carbamic acid benzyl ester | 429 | Tr = 4.05 min, m/z (ES$^+$) (M + H)$^+$ 430 |
| | [4-(3-Acryloylamino-pyrrolidine-1-sulfonyl)-phenyl]-carbamic acid benzyl ester | 429 | Tr = 4.06 min, m/z (ES$^+$) (M + H)$^+$ 430 |
| 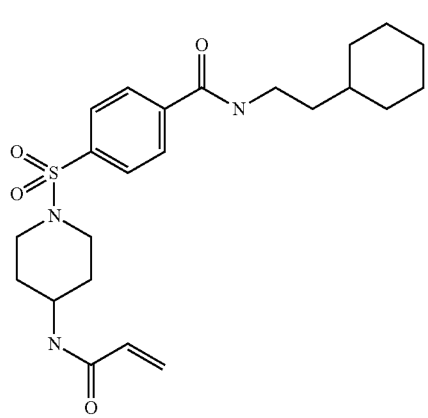 [SMILES: C=CC(=O)NC1CCN(S(=O)(=O)c2ccc(C(=O)NCCC3CCCCC3)cc2)CC1] | 4-(4-Acryloylamino-piperidine-1-sulfonyl)-N-(2-cyclohexyl-ethyl)-benzamide | 447 | Tr = 4.06 min, m/z (ES$^+$) (M + H)$^+$ 448 |

-continued

| Structure | IUPAC Name | Molecular weight | Mass Spectrum |
|---|---|---|---|
| 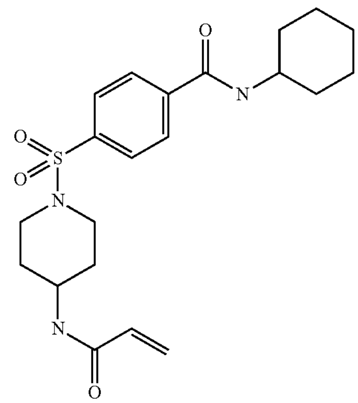 [SMILES: C=CC(=O)NC1CCN(S(=O)(=O)c2ccc(C(=O)NC3CCCCC3)cc2)CC1] | 4-(4-Acryloylamino-piperidine-1-sulfonyl)-N-cyclohexyl-benzamide | 419 | Tr = 3.62 min, m/z (ES+) (M + H)+ 420 |
| 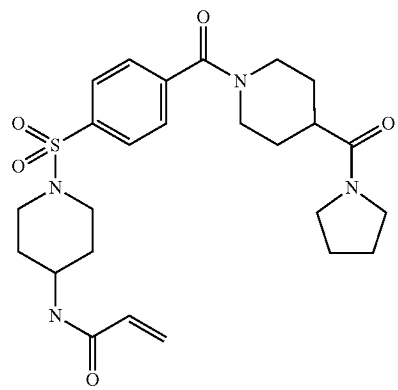 [SMILES: C=CC(=O)NC1CCN(S(=O)(=O)c2ccc(C(=O)N3CCC(C(=O)N4CCCC4)CC3)cc2)CC1] | N-(1-{4-[4-(Pyrrolidine-1-carbonyl)-piperidine-1-carbonyl]-benzenesulfonyl}-piperidin-4-yl)-acrylamide | 502 | Tr = 3.28 min, m/z (ES+) (M + H)+ 503 |
| 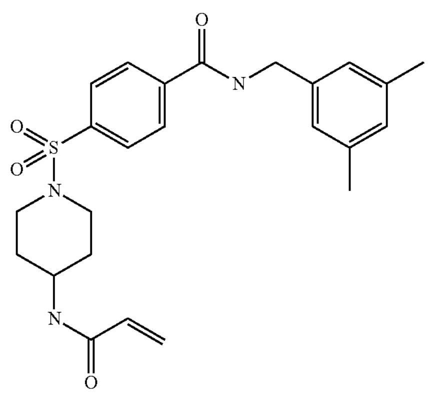 [SMILES: C=CC(=O)NC1CCN(S(=O)(=O)c2ccc(C(=O)NCc3cc(C)cc(C)c3)cc2)CC1] | 4-(4-Acryloylamino-piperidine-1-sulfonyl)-N-(3,5-dimethyl-benzyl)-benzamide | 455 | Tr = 3.82 min, m/z (ES+) (M + H)+ 456 |
| 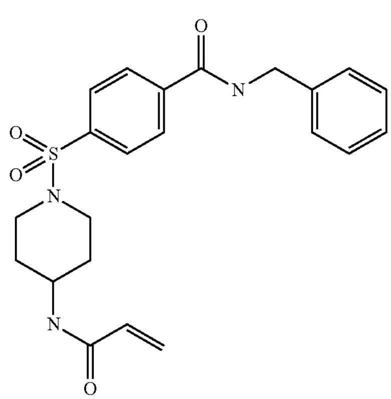 [SMILES: C=CC(=O)NC1CCN(S(=O)(=O)c2ccc(C(=O)NCc3ccccc3)cc2)CC1] | 4-(4-Acryloylamino-piperidine-1-sulfonyl)-N-benzyl-benzamide | 427 | Tr = 3.55 min, m/z (ES+) (M + H)+ 428 |

-continued

| Structure | IUPAC Name | Molecular weight | Mass Spectrum |
|---|---|---|---|
| 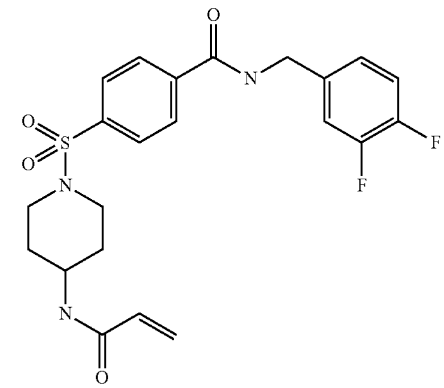 [SMILES: C=CC(=O)NC1CCN(S(=O)(=O)c2ccc(C(=O)NCc3ccc(F)c(F)c3)cc2)CC1] | 4-(4-Acryloylamino-piperidine-1-sulfonyl)-N-(3,4-difluoro-benzyl)-benzamide | 463 | Tr = 3.61 min, m/z (ES+) (M + H)+ 464 |
| 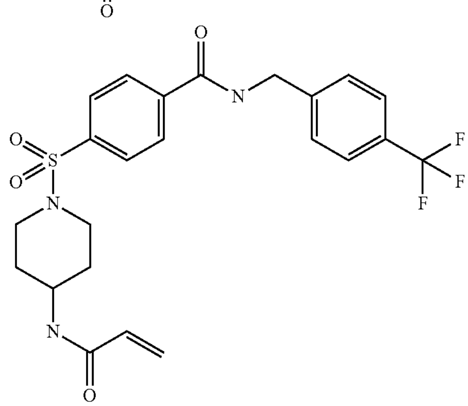 | 4-(4-Acryloylamino-piperidine-1-sulfonyl)-N-(4-trifluoromethyl-benzyl)-benzamide | 495 | Tr = 4.10 min, m/z (ES+) (M + H)+ 496 |
| 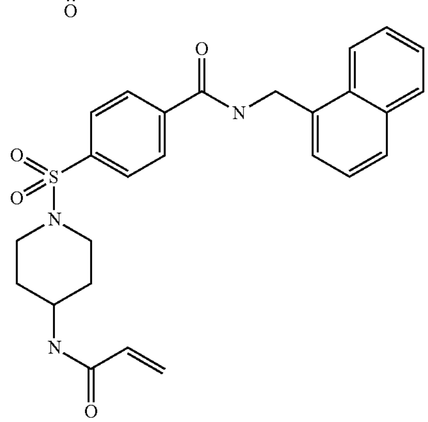 | 4-(4-Acryloylamino-piperidine-1-sulfonyl)-N-naphthalen-1-ylmethyl-benzamide | 477 | Tr = 4.08 min, m/z (ES+) (M + H)+ 478 |
| 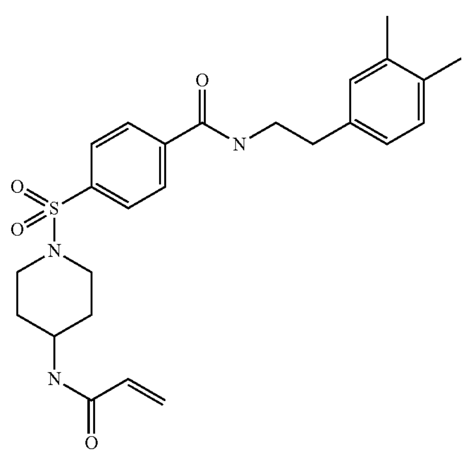 [SMILES: C=CC(=O)NC1CCN(S(=O)(=O)c2ccc(C(=O)NCCc3ccc(C)c(C)c3)cc2)CC1] | 4-(4-Acryloylamino-piperidine-1-sulfonyl)-N-[2-(3,4-dimethyl-phenyl)-ethyl]-benzamide | 469 | Tr = 3.96 min, m/z (ES+) (M + H)+ 470 |

| Structure | IUPAC Name | Molecular weight | Mass Spectrum |
|---|---|---|---|
| 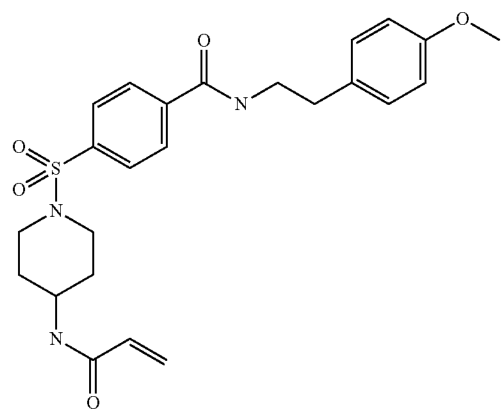 [SMILES: C=CC(=O)NC1CCN(S(=O)(=O)c2ccc(C(=O)NCCc3ccc(OC)cc3)cc2)CC1] | 4-(4-Acryloylamino-piperidine-1-sulfonyl)-N-[2-(4-methoxy-phenyl)-ethyl]-benzamide | 471 | Tr = 3.62 min, m/z (ES+) (M + H)+ 472 |
| 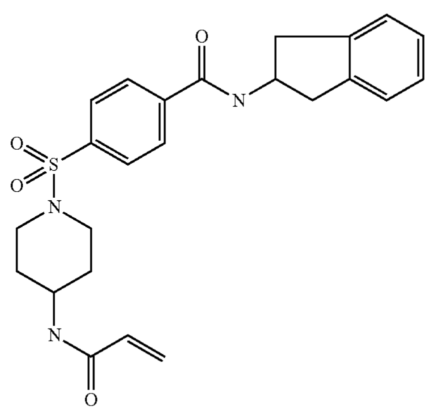 [SMILES: C=CC(=O)NC1CCN(S(=O)(=O)c2ccc(C(=O)NC3Cc4ccccc4C3)cc2)CC1] | 4-(4-Acryloylamino-piperidine-1-sulfonyl)-N-indan-2-yl-benzamide | 453 | Tr = 3.75 min, m/z (ES+) (M + H)+ 454 |
| 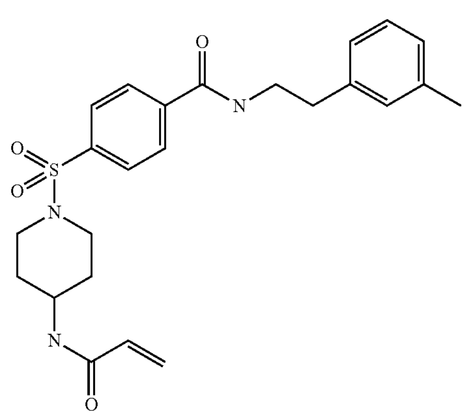 [SMILES: C=CC(=O)NC1CCN(S(=O)(=O)c2ccc(C(=O)NCCc3cccc(C)c3)cc2)CC1] | 4-(4-Acryloylamino-piperidine-1-sulfonyl)-N-(2-m-tolyl-ethyl)-benzamide | 455 | Tr = 3.82 min, m/z (ES+) (M + H)+ 456 |

-continued

| Structure | IUPAC Name | Molecular weight | Mass Spectrum |
|---|---|---|---|
| 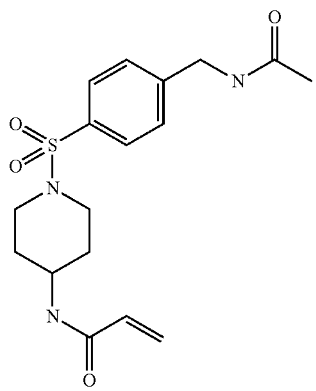 [SMILES: C=CC(=O)NC1CCN(S(=O)(=O)c2ccc(CNC(C)=O)cc2)CC1] | N-{1-[4-(Acetylamino-methyl)-benzenesulfonyl]-piperidin-4-yl}-acrylamide | 365 | Tr = 2.79 min, m/z (ES+) (M + H)+ 366 |
| 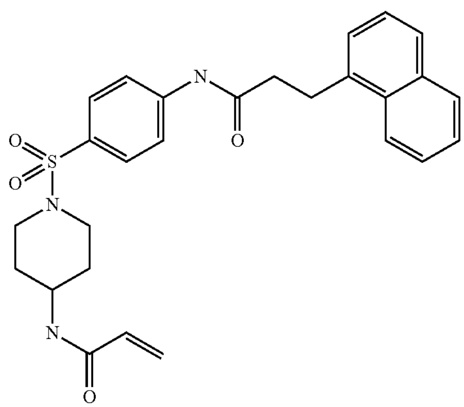 [SMILES: C=CC(=O)NC1CCN(S(=O)(=O)c2ccc(NC(=O)CCc3cccc4ccccc34)cc2)CC1] | N-{1-[4-(3-Naphthalen-1-yl-propionylamino)-benzenesulfonyl]-piperidin-4-yl}-acrylamide | 491 | Tr = 4.15 min, m/z (ES+) (M + H)+ 492 |
| 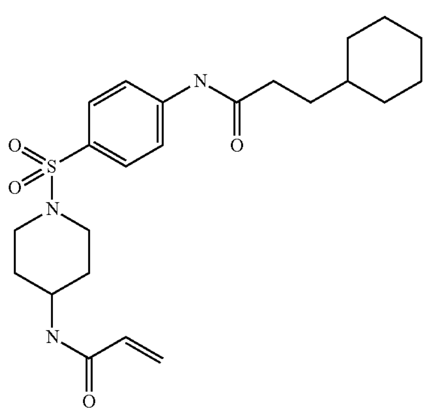 [SMILES: C=CC(=O)NC1CCN(S(=O)(=O)c2ccc(NC(=O)CCC3CCCCC3)cc2)CC1] | N-{1-[4-(3-Cyclohexyl-propionylamino)-benzenesulfonyl]-piperidin-4-yl}-acrylamide | 447 | Tr = 4.20 min, m/z (ES+) (M + H)+ 448 |

-continued

| Structure | IUPAC Name | Molecular weight | Mass Spectrum |
|---|---|---|---|
| 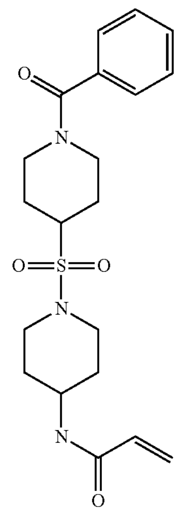 [SMILES: C=CC(=O)NC1CCN(S(=O)(=O)C2CCN(C(=O)c3ccccc3)CC2)CC1] | N-[1-(1-Benzoyl-piperidine-4-sulfonyl)-piperidin-4-yl]-acrylamide | 405 | Tr = 3.13 min, m/z (ES⁺) (M + H)⁺ 406 |
| 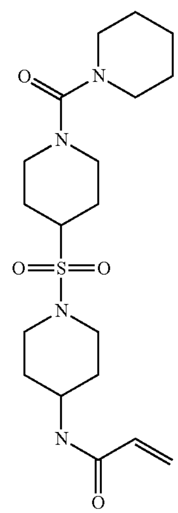 [SMILES: C=CC(=O)NC1CCN(S(=O)(=O)C2CCN(C(=O)N3CCCCC3)CC2)CC1] | N-{1-[1-(Piperidine-1-carbonyl)-piperidine-4-sulfonyl]-piperidin-4-yl}-acrylamide | 412 | Tr = 3.26 min, m/z (ES⁺) (M + H)⁺ 413 |
| 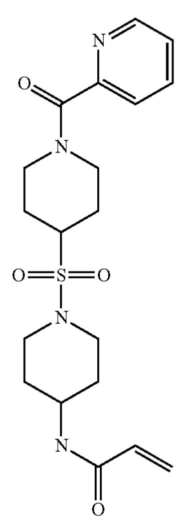 [SMILES: C=CC(=O)NC1CCN(S(=O)(=O)C2CCN(C(=O)c3ccccn3)CC2)CC1] | N-{1-[1-(Pyridine-2-carbonyl)-piperidine-4-sulfonyl]-piperidin-4-yl}-acrylamide | 406 | Tr = 2.75 min, m/z (ES⁺) (M + H)⁺ 407 |

-continued

| Structure | IUPAC Name | Molecular weight | Mass Spectrum |
|---|---|---|---|
| 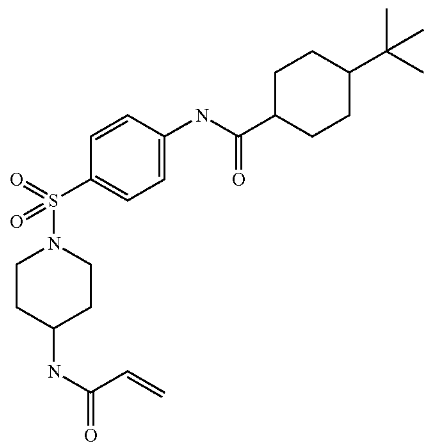 [SMILES: C=CC(=O)NC1CCN(S(=O)(=O)c2ccc(NC(=O)C3CCC(C(C)(C)C)CC3)cc2)CC1] | 4-tert-Butyl-cyclohexanecarboxylic acid[4-(4-acryloylamino-piperidine-1-sulfonyl)-phenyl]-amide | 475 | Tr = 4.52 min, m/z (ES+) (M + H)+ 476 |
| 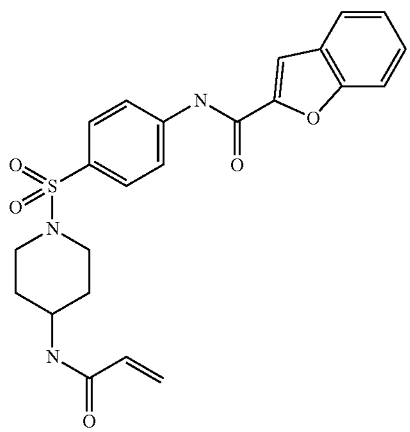 [SMILES: C=CC(=O)NC1CCN(S(=O)(=O)c2ccc(NC(=O)c3cc4ccccc4o3)cc2)CC1] | Benzofuran-2-carboxylic acid[4-(4-acryloylamino-piperidine-1-sulfonyl)-phenyl]-amide | 453 | Tr = 3.89 min, m/z (ES+) (M + H)+ 454 |
| 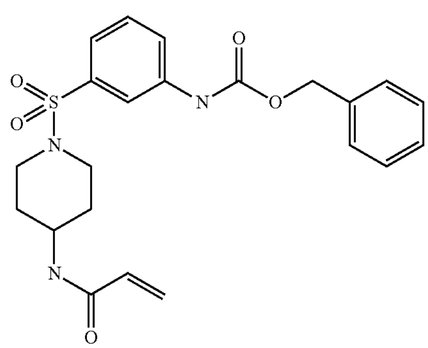 [SMILES: C=CC(=O)NC1CCN(S(=O)(=O)c2cccc(NC(=O)OCc3ccccc3)c2)CC1] | [3-(4-Acryloylamino-piperidine-1-sulfonyl)-phenyl]-carbamic acid benzyl ester | 443 | Tr = 3.86 min, m/z (ES+) (M + H)+ 444 |
| 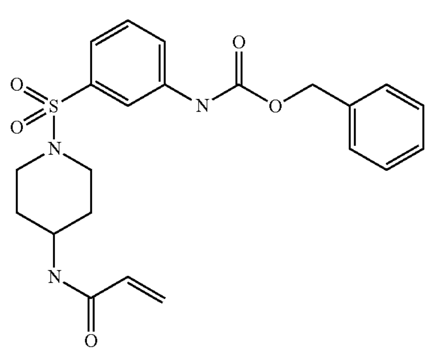 [SMILES: C=CC(=O)NC1CCN(S(=O)(=O)c2cccc(NC(=O)OCc3ccccc3)c2)CC1] | N-{1-[3-(3-Phenyl-propionylamino)-benzenesulfonyl]-piperidin-4-yl}-acrylamide | | |

-continued

| Structure | IUPAC Name | Molecular weight | Mass Spectrum |
|---|---|---|---|
| 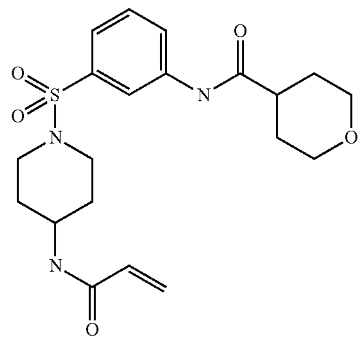 [SMILES: C=CC(=O)NC1CCN(S(=O)(=O)c2cccc(NC(=O)C3CCOCC3)c2)CC1] | Tetrahydro-pyran-4-carboxylic acid[3-(4-acryloylamino-piperidine-1-sulfonyl)-phenyl]-amide | 421 | Tr = 3.11 min, m/z (ES$^+$) (M + H)$^+$ 422 |
| 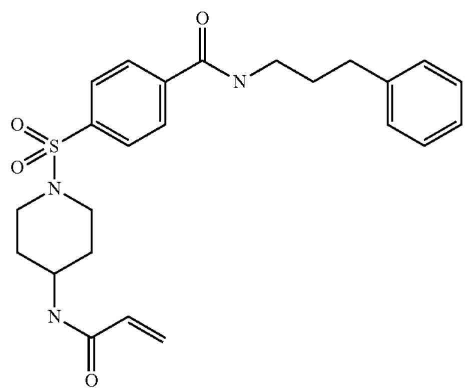 [SMILES: C=CC(=O)NC1CCN(S(=O)(=O)c2ccc(C(=O)NCCCc3ccccc3)cc2)CC1] | 4-(4-Acryloylamino-piperidine-1-sulfonyl)-N-(3-phenyl-propyl)-benzamide | 455 | Tr = 3.79 min, m/z (ES$^+$) (M + H)$^+$ 456 |
| 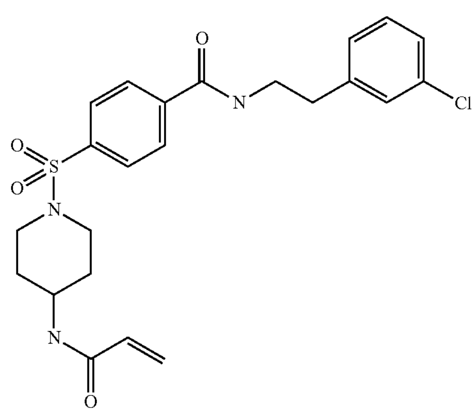 [SMILES: C=CC(=O)NC1CCN(S(=O)(=O)c2ccc(C(=O)NCCc3cccc(Cl)c3)cc2)CC1] | 4-(4-Acryloylamino-piperidine-1-sulfonyl)-N-[2-(3-chloro-phenyl)-ethyl]-benzamide | 476 | Tr = 4.10 min, m/z (ES$^+$) (M + H)$^+$ 476 |
| 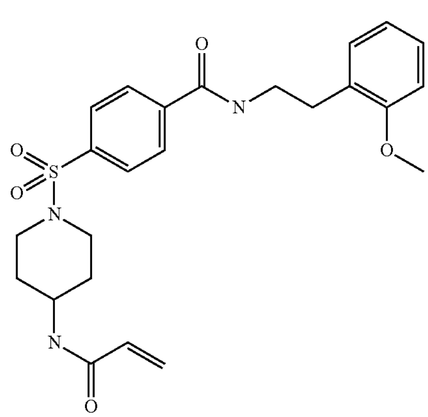 [SMILES: C=CC(=O)NC1CCN(S(=O)(=O)c2ccc(C(=O)NCCc3ccccc3OC)cc2)CC1] | 4-(4-Acryloylamino-piperidine-1-sulfonyl)-N-[2-(2-methoxy-phenyl)-ethyl]-benzamide | 471 | Tr = 3.96 min, m/z (ES$^+$) (M + H)$^+$ 472 |

-continued

| Structure | IUPAC Name | Molecular weight | Mass Spectrum |
|---|---|---|---|
| 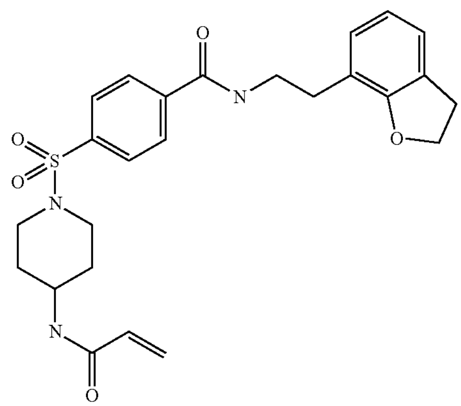 [SMILES: C=CC(=O)NC1CCN(S(=O)(=O)c2ccc(C(=O)NCCc3cccc4c3OCC4)cc2)CC1] | 4-(4-Acryloylamino-piperidine-1-sulfonyl)-N-[2-(2,3-dihydro-benzofuran-7-yl)-ethyl]-benzamide | 483 | Tr = 3.73 min, m/z (ES$^+$) (M + H)$^+$ 484 |
| | 4-(4-Acryloylamino-piperidine-1-sulfonyl)-N-[2-(tetrahydro-pyran-4-yl)-ethyl]-benzamide | 449 | Tr = 3.40 min, m/z (ES$^+$) (M + H)$^+$ 450 |
| 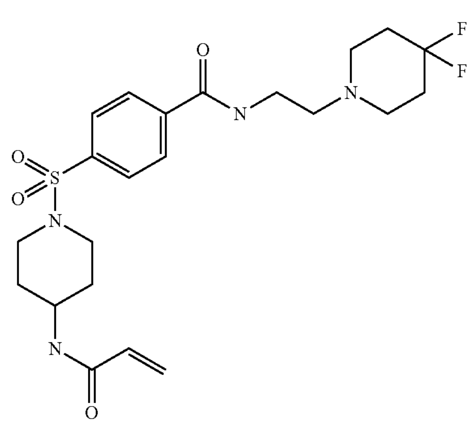 [SMILES: C=CC(=O)NC1CCN(S(=O)(=O)c2ccc(C(=O)NCCN3CCC(F)(F)CC3)cc2)CC1] | 4-(4-Acryloylamino-piperidine-1-sulfonyl)-N-[2-(4,4-difluoro-piperidin-1-yl)-ethyl]-benzamide | 484 | Tr = 2.65 min, m/z (ES$^+$) (M + H)$^+$ 485 |

-continued
| Structure | IUPAC Name | Molecular weight | Mass Spectrum |
|---|---|---|---|
| 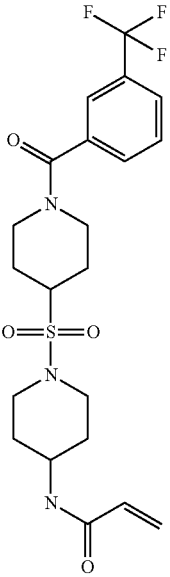 [SMILES: C=CC(=O)NC1CCN(S(=O)(=O)C2CCN(C(=O)c3cccc(C(F)(F)F)c3)CC2)CC1] | N-{1-[1-(3-Trifluoromethyl-benzoyl)-piperidine-4-sulfonyl]-piperidin-4-yl}-acrylamide | 473 | Tr = 3.58 min, m/z (ES$^+$) (M + H)$^+$ 474 |
| 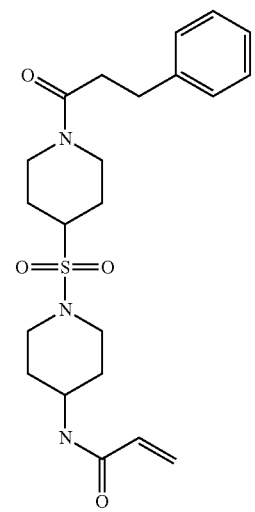 [SMILES: C=CC(=O)NC1CCN(S(=O)(=O)C2CCN(C(=O)CCc3ccccc3)CC2)CC1] | N-{1-[1-(3-Phenyl-propionyl)-piperidine-4-sulfonyl]-piperidin-4-yl}-acrylamide | 433 | Tr = 3.42 min, m/z (ES$^+$) (M + H)$^+$ 434 |
| 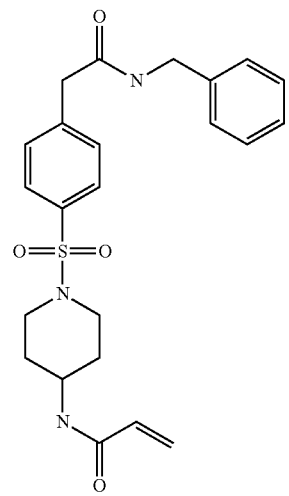 [SMILES: C=CC(=O)NC1CCN(S(=O)(=O)c2ccc(CC(=O)NCc3ccccc3)cc2)CC1] | N-{1-[4-(Benzylcarbamoyl-methyl)-benzenesulfonyl]-piperidin-4-yl}-acrylamide | 441 | Tr = 3.46 min, m/z (ES$^+$) (M + H)$^+$ 442 |

-continued

| Structure | IUPAC Name | Molecular weight | Mass Spectrum |
|---|---|---|---|
| 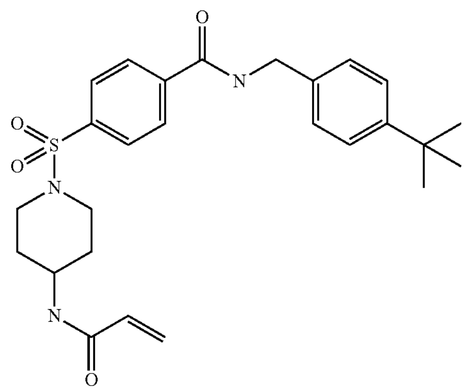 [SMILES: C=CC(=O)NC1CCN(S(=O)(=O)c2ccc(C(=O)NCc3ccc(C(C)(C)C)cc3)cc2)CC1] | 4-(4-Acryloylamino-piperidine-1-sulfonyl)-N-(4-tert-butyl-benzyl)-benzamide | 483 | Tr = 4.21 min, m/z (ES$^+$) (M + H)$^+$ 484 |
| 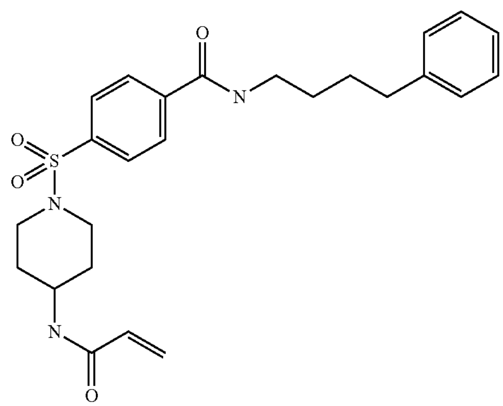 [SMILES: C=CC(=O)NC1CCN(S(=O)(=O)c2ccc(C(=O)NCCCCc3ccccc3)cc2)CC1] | 4-(4-Acryloylammo-piperidine-1-sulfonyl)-N-(4-phenyl-butyl)-benzamide | 469 | Tr = 4.01 min, m/z (ES$^+$) (M + H)$^+$ 470 |
| 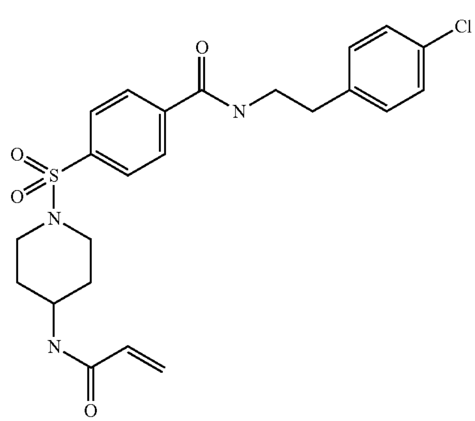 [SMILES: C=CC(=O)NC1CCN(S(=O)(=O)c2ccc(C(=O)NCCc3ccc(Cl)cc3)cc2)CC1] | 4-(4-Acryloylamino-piperidine-1-sulfonyl)-N-[2-(4-chloro-phenyl)-ethyl]-benzamide | 476 | Tr = 4.07 min, m/z (ES$^+$) (M + H)$^+$ 476 |

-continued

| Structure | IUPAC Name | Molecular weight | Mass Spectrum |
|---|---|---|---|
| 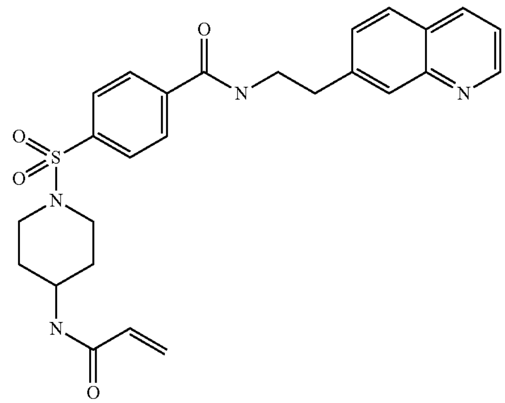 [SMILES: C=CC(=O)NC1CCN(S(=O)(=O)c2ccc(C(=O)NCCc3ccc4cccnc4c3)cc2)CC1] | 4-(4-Acryloylamino-piperidine-1-sulfonyl)-N-(2-quinolin-7-yl-ethyl)-benzamide | 492 | Tr = 3.36 min, m/z (ES+) (M + H)+ 493 |
| 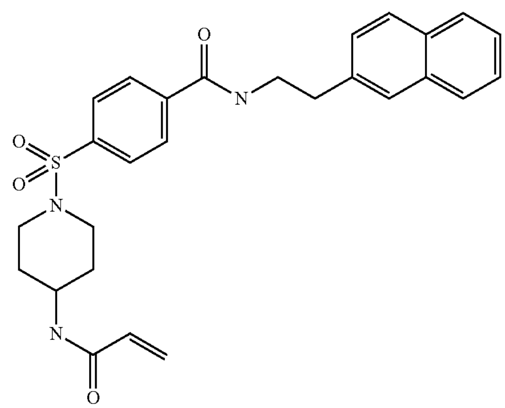 | 4-(4-Acryloylamino-piperidine-1-sulfonyl)-N-(2-naphthalen-2-yl-ethyl)-benzamide | 491 | Tr = 4.02 min, m/z (ES+) (M + H)+ 492 |
| 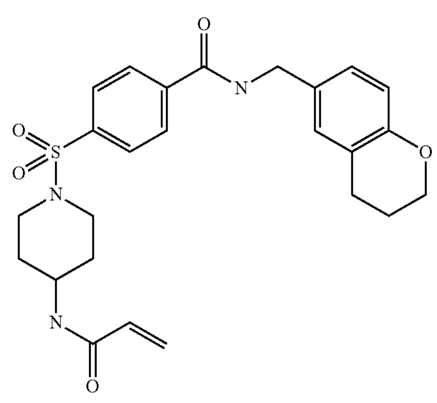 | 4-(4-Acryloylamino-piperidine-1-sulfonyl)-N-(2-chroman-6-yl-ethyl)-benzamide | 497 | Tr = 3.69 min, m/z (ES+) (M + H)+ 498 |

-continued

| Structure | IUPAC Name | Molecular weight | Mass Spectrum |
|---|---|---|---|
| 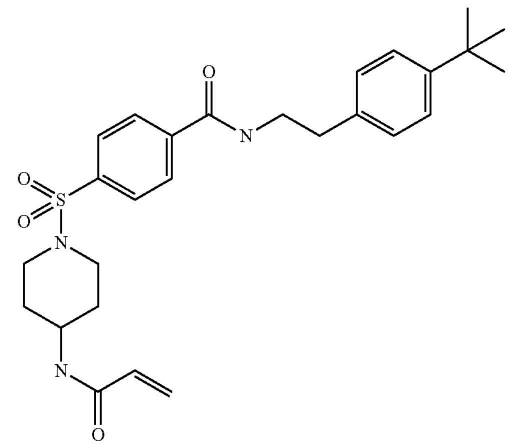 [SMILES: C=CC(=O)NC1CCN(S(=O)(=O)c2ccc(C(=O)NCCc3ccc(C(C)(C)C)cc3)cc2)CC1] | 4-(4-Acryloylamino-piperidine-1-sulfonyl)-N-[2-(4-tert-butyl-phenyl)-ethyl]-benzamide | 497 | Tr = 4.36 min, m/z (ES+) (M + H)+ 498 |
| 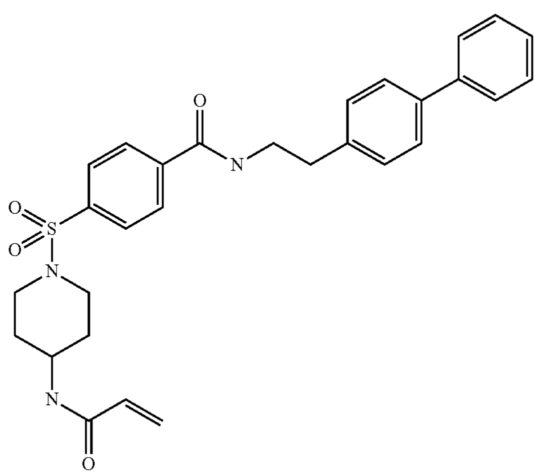 [SMILES: C=CC(=O)NC1CCN(S(=O)(=O)c2ccc(C(=O)NCCc3ccc(-c4ccccc4)cc3)cc2)CC1] | 4-(4-Acryloylamino-piperidine-1-sulfonyl)-N-(2-biphenyl-4-yl-ethyl)-benzamide | 517 | Tr = 4.35 min, m/z (ES+) (M + H)+ 518 |
| 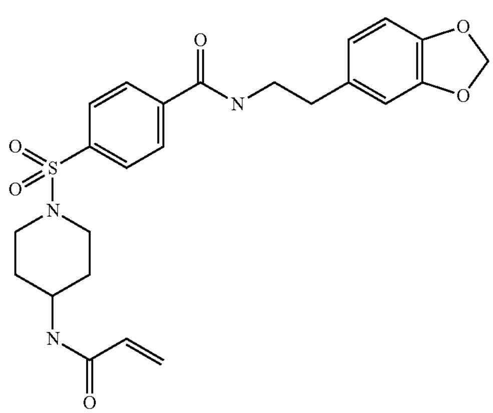 [SMILES: C=CC(=O)NC1CCN(S(=O)(=O)c2ccc(C(=O)NCCc3ccc4c(c3)OCO4)cc2)CC1] | 4-(4-Acryloylamino-piperidine-1-sulfonyl)-N-(2-benzo[1,3]dioxol-5-yl-ethyl)-benzamide | 485 | Tr = 3.61 min, m/z (ES+) (M + H)+ 486 |

| Structure | IUPAC Name | Molecular weight | Mass Spectrum |
|---|---|---|---|
| 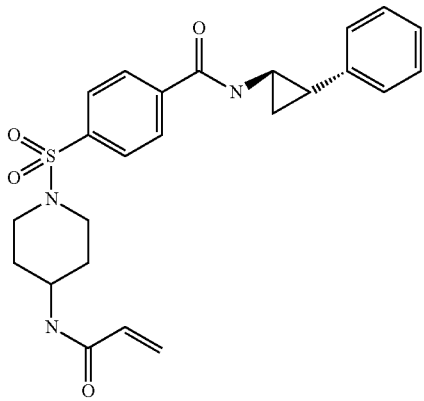 | 4-(4-Acryloylamino-piperidine-1-sulfonyl)-N-(2-phenyl-cyclopropyl)-benzamide | 453 | Tr = 3.93 min, m/z (ES+) (M + H)+ 454 |
| 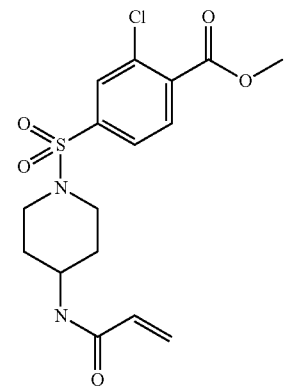 [SMILES: C=CC(=O)NC1CCN(S(=O)(=O)c2ccc(C(=O)OC)c(Cl)c2)CC1] | 4-(4-Acryloylamino-piperidine-1-sulfonyl)-2-chloro-benzoic acid methyl ester | 386 | Tr = 3.80 min, m/z (ES+) (M + H)+ 387 |
| 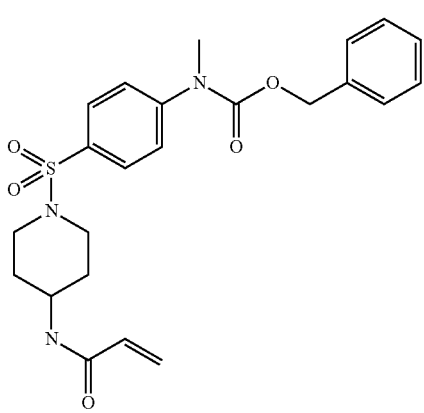 [SMILES: C=CC(=O)NC1CCN(S(=O)(=O)c2ccc(N(C)C(=O)OCc3ccccc3)cc2)CC1] | [4-(4-Acryloylamino-piperidine-1-sulfonyl)-phenyl]-methyl-carbamic acid benzyl ester | 457 | Tr = 3.95 min, m/z (ES+) (M + H)+ 458 |

-continued

| Structure | IUPAC Name | Molecular weight | Mass Spectrum |
|---|---|---|---|
| 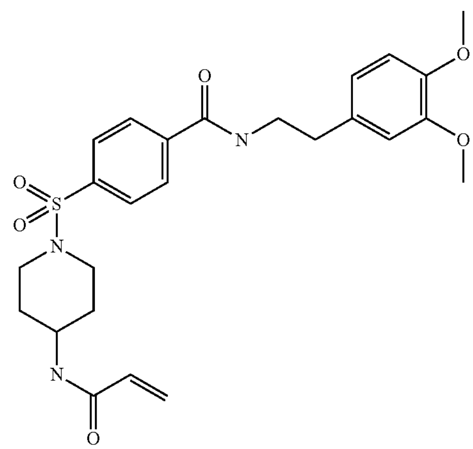 [SMILES: C=CC(=O)NC1CCN(S(=O)(=O)c2ccc(C(=O)NCCc3ccc(OC)c(OC)c3)cc2)CC1] | 4-(4-Acryloylamino-piperidine-1-sulfonyl)-N-[2-(3,4-dimethoxy-phenyl)-ethyl]-benzamide | 501 | Tr = 3.5 min, m/z (ES$^+$) (M + H)$^+$ 502 |
| 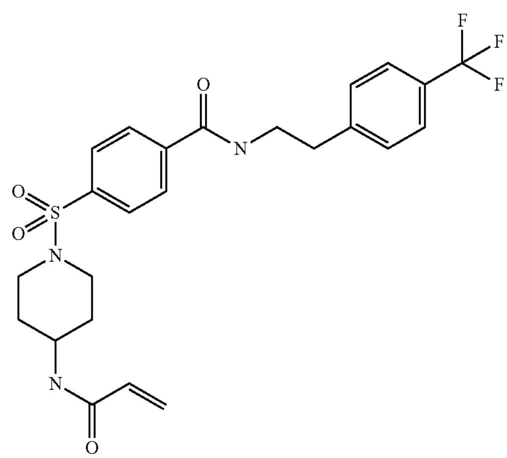 [SMILES: C=CC(=O)NC1CCN(S(=O)(=O)c2ccc(C(=O)NCCc3ccc(C(F)(F)F)cc3)cc2)CC1] | 4-(4-Acryloylamino-piperidine-1-sulfonyl)-N-[2-(4-trifluoromethyl-phenyl)-ethyl]-benzamide | 509 | Tr = 4.00 min, m/z (ES$^+$) (M + H)$^+$ 510 |
| 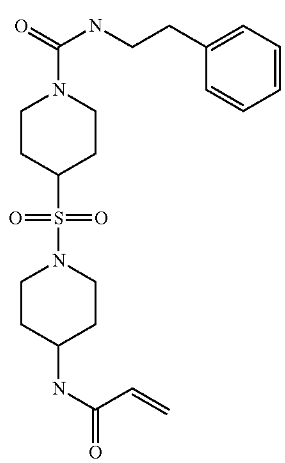 [SMILES: C=CC(=O)NC1CCN(S(=O)(=O)C2CCN(C(=O)NCCc3ccccc3)CC2)CC1] | 4-(4-Acryloylamino-piperidine-1-sulfonyl)-piperidine-1-carboxylic acid phenethyl-amide | 448 | Tr = 3.36 min, m/z (ES$^+$) (M + H)$^+$ 449 |

-continued

| Structure | IUPAC Name | Molecular weight | Mass Spectrum |
|---|---|---|---|
| 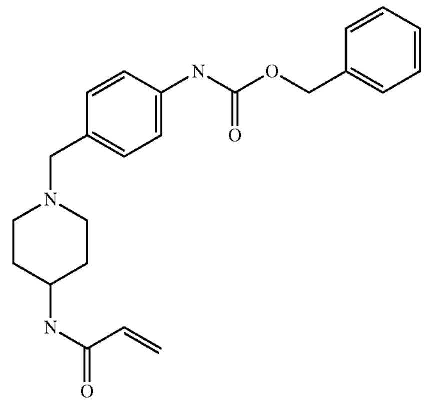 [SMILES: C=CC(=O)NC1CCN(Cc2ccc(NC(=O)OCc3ccccc3)cc2)CC1] | [4-(4-Acryloylamino-piperidin-1-ylmethyl)-phenyl]-carbamic acid benzyl ester | 393 | Tr = 2.96 min, m/z (ES+) (M + H)+ 394 |
| 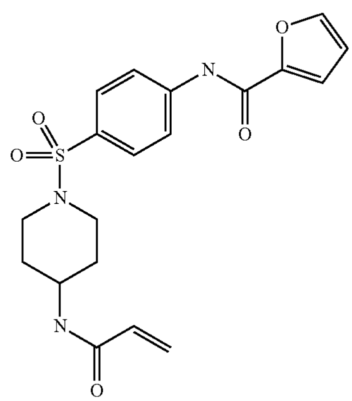 [SMILES: C=CC(=O)NC1CCN(S(=O)(=O)c2ccc(NC(=O)c3ccco3)cc2)CC1] | Furan-2-carboxylic acid [4-(4-acryloylamino-piperidine-1-sulfonyl)-phenyl]-amide | 403 | Tr = 3.31 min, m/z (ES+) (M + H)+ 404 |
| 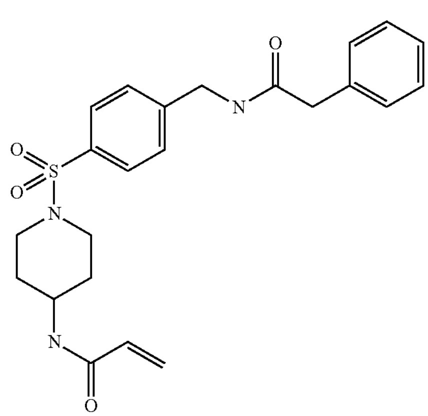 [SMILES: C=CC(=O)NC1CCN(S(=O)(=O)c2ccc(CNC(=O)Cc3ccccc3)cc2)CC1] | N-{1-[4-(Phenylacetylamino-methyl)-benzenesulfonyl]-piperidin-4-yl}-acrylamide | 442 | Tr = 3.58 min, m/z (ES+) (M + H)+ 442 |

| Structure | IUPAC Name | Molecular weight | Mass Spectrum |
|---|---|---|---|
| 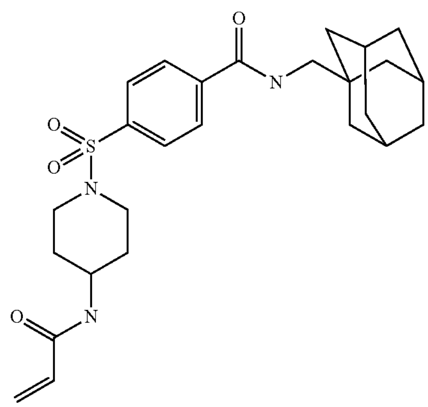 | N-{1-[4-(3-Adamantan-1-yl-propionylamino)-benzenesulfonyl]-piperidin-4-yl}-acrylamide | 499 | Tr = 4.70 min, m/z (ES$^+$) (M + H)$^+$ 500 |
| 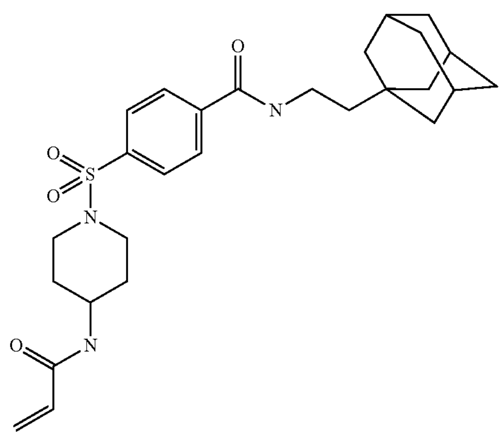 [SMILES: C=CC(=O)NC1CCN(S(=O)(=O)c2ccc(C(=O)NCCC34CC5CC(CC(C5)C3)C4)cc2)CC1] | 4-(4-Acryloylamino-piperidine-1-sulfonyl)-N-(2-adamantan-1-yl-ethyl)-benzamide | 499 | Tr = 4.56 min, m/z (ES$^+$) (M + H)$^+$ 500 |
| 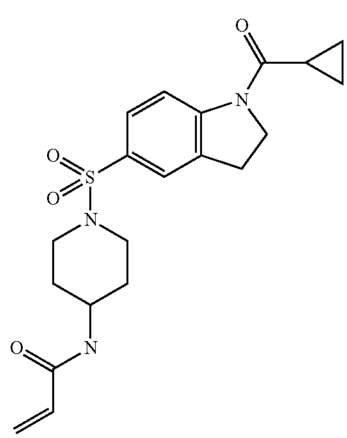 [SMILES: C=CC(=O)NC1CCN(S(=O)(=O)c2ccc3c(c2)CCN3C(=O)C2CC2)CC1] | N-[1-(1-Cyclopropanecarbonyl-2,3-dihydro-1H-indole-5-sulfonyl)-piperidin-4-yl]-acrylamide | 403 | Tr = 3.47 min, m/z (ES$^+$) (M + H)$^+$ 404 |

-continued

| Structure | IUPAC Name | Molecular weight | Mass Spectrum |
|---|---|---|---|
| 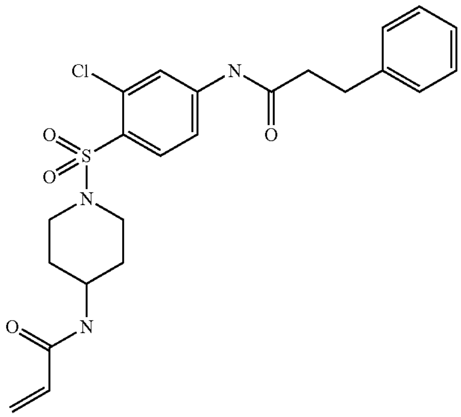 [SMILES: C=CC(=O)NC1CCN(S(=O)(=O)c2ccc(NC(=O)CCc3ccccc3)cc2Cl)CC1] | N-{1-[2-Chloro-4-(3-phenyl-propionylamino)-benzenesulfonyl]-piperidin-4-yl}-acrylamide | 476 | Tr = 4.02 min, m/z (ES$^+$) (M + H)$^+$ 476 |
| 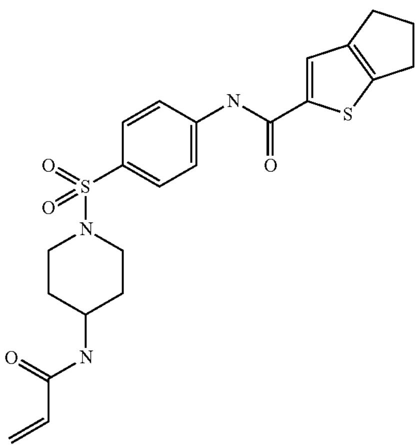 [SMILES: C=CC(=O)NC1CCN(S(=O)(=O)c2ccc(NC(=O)c3cc4c(s3)CCC4)cc2)CC1] | 5,6-Dihydro-4H-cyclopenta[b]thiophene-2-carboxylic acid[4-(4-acryloylamino-piperidine-1-sulfonyl)-phenyl]-amide | 460 | Tr = 4.22 min, m/z (ES$^+$) (M + H)$^+$ 461 |
| 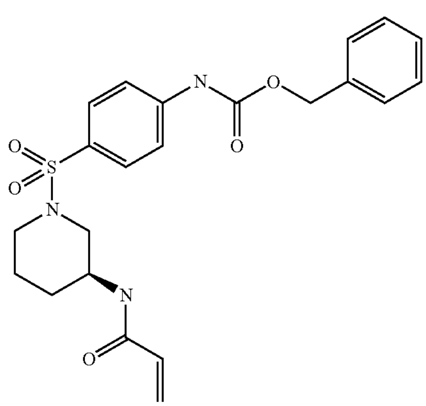 [SMILES: C=CC(=O)N[C@H]1CCCN(S(=O)(=O)c2ccc(NC(=O)OCc3ccccc3)cc2)C1] | (R)-[4-(3-Acryloylamino-piperidine-1-sulfonyl)-phenyl]-carbamic acid benzyl ester | 444 | Tr = 4.04 min, m/z (ES$^+$) (M + H)$^+$ 445 |

-continued

| Structure | IUPAC Name | Molecular weight | Mass Spectrum |
|---|---|---|---|
| 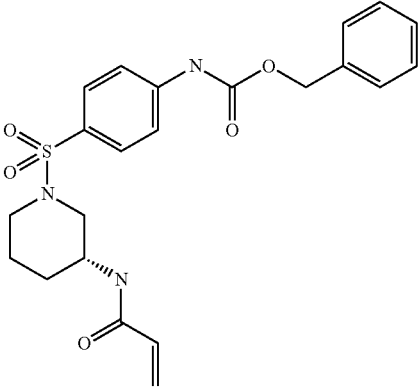 [SMILES: C=CC(=O)N[C@@H]1CCCN(S(=O)(=O)c2ccc(NC(=O)OCc3ccccc3)cc2)C1] | (S)-[4-(3-Acryloylamino-piperidine-1-sulfonyl)-phenyl]-carbamic acid benzyl ester | 444 | Tr = 3.98 min, m/z (ES+) (M + H)+ 445 |
| 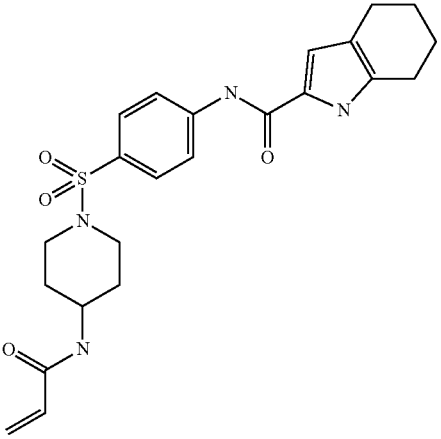 [SMILES: C=CC(=O)NC1CCN(S(=O)(=O)c2ccc(NC(=O)c3cc4c([nH]3)CCCC4)cc2)CC1] | 4,5,6,7-Tetrahydro-1H-indole-2-carboxylic acid [4-(4-acryloylamino-piperidine-1-sulfonyl)-phenyl]-amide | 456 | Tr = 3.92 min, m/z (ES+) (M + H)+ 457 |
| 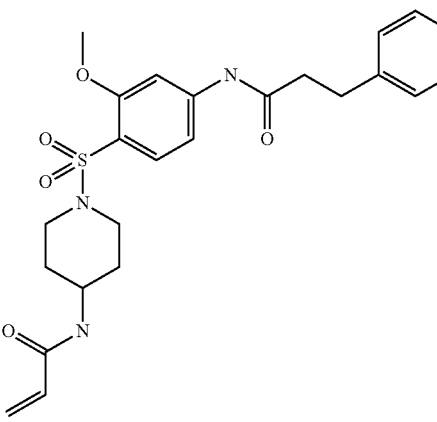 | N-{1-[2-Methoxy-4-(3-phenyl-propionylamino)-benzenesulfonyl]-piperidin-4-yl}-acrylamide | 471 | Tr = 3.93 min, m/z (ES+) (M + H)+ 473 |

-continued

| Structure | IUPAC Name | Molecular weight | Mass Spectrum |
|---|---|---|---|
| 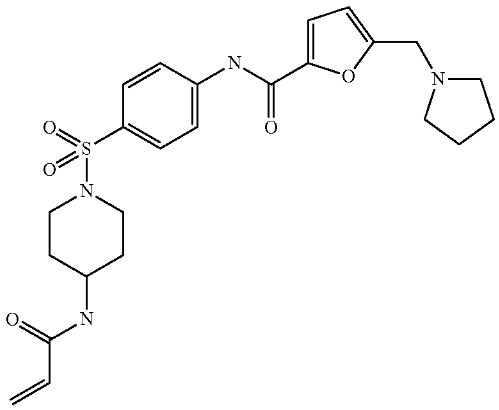 [SMILES: C=CC(=O)NC1CCN(S(=O)(=O)c2ccc(NC(=O)c3ccc(CN4CCCC4)o3)cc2)CC1] | 5-Pyrrolidin-1-ylmethyl-furan-2-carboxylic acid [4-(4-acryloylamino-piperidine-1-sulfonyl)-phenyl]-amide | 486 | Tr = 2.68 min, m/z (ES$^+$) (M + H)$^+$ 487 |
| 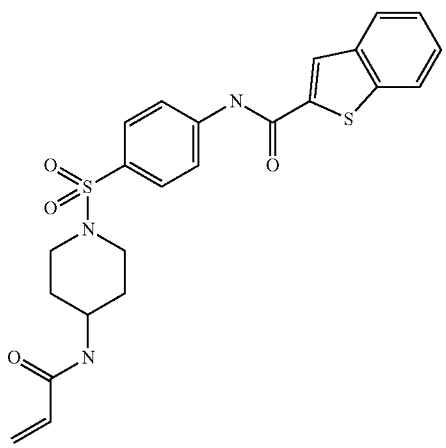 [SMILES: C=CC(=O)NC1CCN(S(=O)(=O)c2ccc(NC(=O)c3cc4ccccc4s3)cc2)CC1] | Benzo[b]thiophene-2-carboxylic acid[4-(4-acryloylamino-piperidine-1-sulfonyl)-phenyl]-amide | 469 | Tr = 4.10 min, m/z (ES$^+$) (M + H)$^+$ 470 |
| 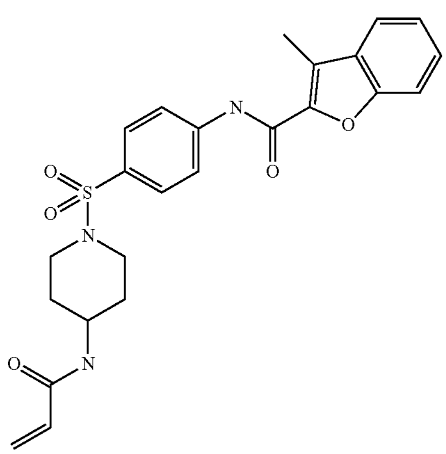 [SMILES: C=CC(=O)NC1CCN(S(=O)(=O)c2ccc(NC(=O)c3oc4ccccc4c3C)cc2)CC1] | 3-Methyl-benzofuran-2-carboxylic acid[4-(4-acryloylamino-piperidine-1-sulfonyl)-phenyl]-amide | 467 | Tr = 4.27 min, m/z (ES$^+$) (M + H)$^+$ 468 |

-continued

| Structure | IUPAC Name | Molecular weight | Mass Spectrum |
|---|---|---|---|
| 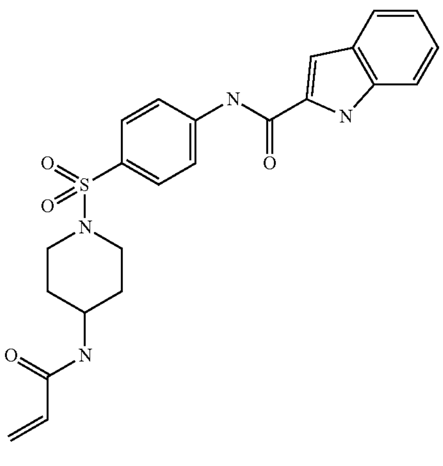 | 1H-Indole-2-carboxylic acid[4-(4-acryloylamino-piperidine-1-sulfonyl)-phenyl]-amide | 452 | Tr = 3.89 min, m/z (ES+) (M + H)+ 453 |
| 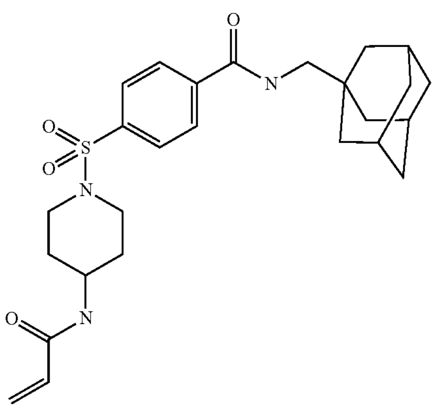 [SMILES: C=CC(=O)NC1CCN(S(=O)(=O)c2ccc(C(=O)NCC34CC5CC(CC(C5)C3)C4)cc2)CC1] | 4-(4-Acryloylamino-piperidine-1-sulfonyl)-N-adamantan-1-ylmethyl-benzamide | 485 | Tr = 4.38 min, m/z (ES+) (M + H)+ 486 |
| 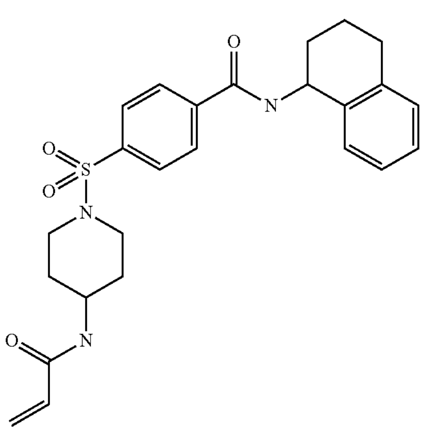 [SMILES: C=CC(=O)NC1CCN(S(=O)(=O)c2ccc(C(=O)NC3CCCc4ccccc43)cc2)CC1] | 4-(4-Acryloylamino-piperidine-1-sulfonyl)-N-(1,2,3,4-tetrahydro-naphthalen-1-yl)-benzamide | 467 | Tr = 3.99 min, m/z (ES+) (M + H)+ 468 |

| Structure | IUPAC Name | Molecular weight | Mass Spectrum |
|---|---|---|---|
| 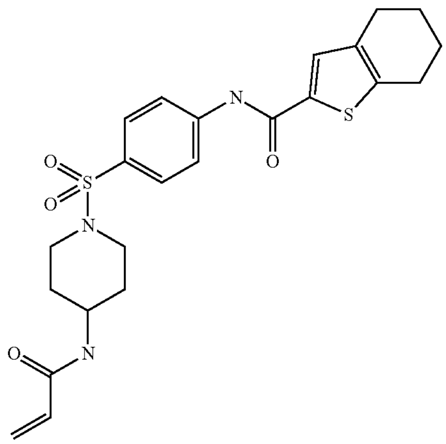 | 4,5,6,7-Tetrahydro-benzo[b]thiophene-2-carboxylic acid[4-(4-acryloylamino-piperidine-1-sulfonyl)-phenyl]-amide | 473 | Tr = 4.31 min, m/z (ES+) (M + H)+ 474 |
| 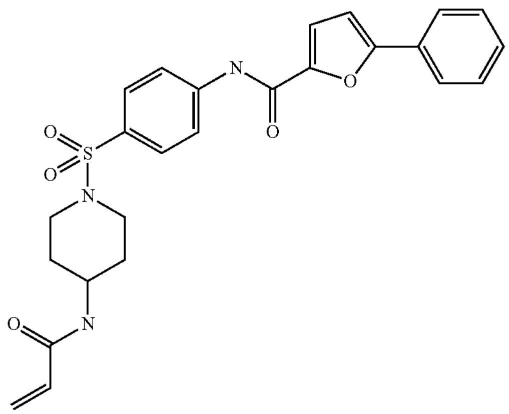 [SMILES: C=CC(=O)NC1CCN(S(=O)(=O)c2ccc(NC(=O)c3ccc(-c4ccccc4)o3)cc2)CC1] | 5-Phenyl-furan-2-carboxylic acid[4-(4-acryloylamino-piperidine-1-sulfonyl)-phenyl]-amide | 479.56 | Tr = 4.28, m/z (ES+) [M + H]+ = 480.00 |
| 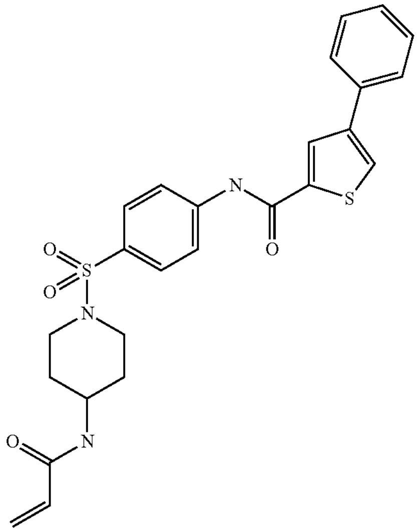 [SMILES: C=CC(=O)NC1CCN(S(=O)(=O)c2ccc(NC(=O)c3cc(-c4ccccc4)cs3)cc2)CC1] | 4-Phenyl-thiophene-2-carboxylic acid[4-(4-acryloylamino-piperidine-1-sulfonyl)-phenyl]-amide | 495 | Tr = 4.43, m/z (ES+) [M + H]+ = 496 |

-continued

| Structure | IUPAC Name | Molecular weight | Mass Spectrum |
|---|---|---|---|
| 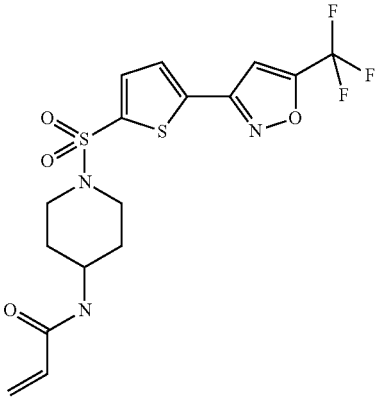 [SMILES: C=CC(=O)NC1CCN(S(=O)(=O)c2ccc(-c3cc(C(F)(F)F)on3)s2)CC1] | N-{1-[5-(5-Trifluoromethyl-isoxazol-3-yl)-thiophene-2-sulfonyl]-piperidin-4-yl}-acrylamide | 435.45 | Tr = 4.22, m/z (ES+) [M + H]+ = 436 |
| 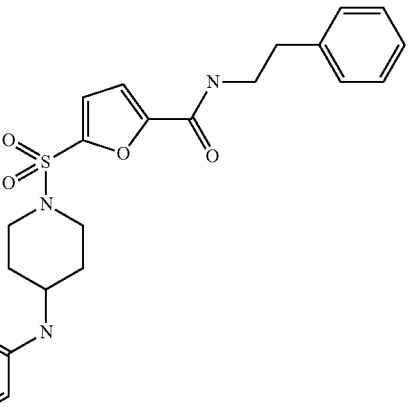 | 5-(4-Acryloylamino-piperidine-1-sulfonyl)-furan-2-carboxylic acid phenethyl-amide | 431 | Tr = 3.82, m/z (ES+) [M + H]+ = 432 |
| 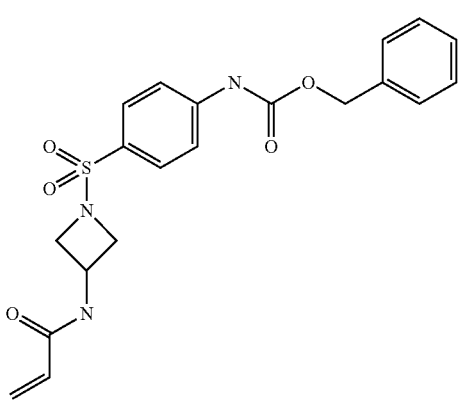 [SMILES: C=CC(=O)NC1CN(S(=O)(=O)c2ccc(NC(=O)OCc3ccccc3)cc2)C1] | [4-(3-Acryloylamino-azetidine-1-sulfonyl)-phenyl]-carbamic acid benzyl ester | 415 | Tr = 3.88, m/z (ES+) [M + H]+ = 416 |
| 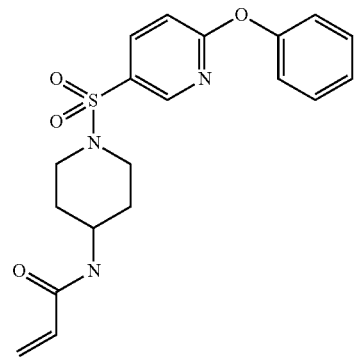 [SMILES: C=CC(=O)NC1CCN(S(=O)(=O)c2ccc(Oc3ccccc3)nc2)CC1] | N-[1-(6-Phenoxy-pyridine-3-sulfonyl)-piperidin-4-yl]-acrylamide | 387 | Tr = 3.92, m/z (ES+) [M + H]+ = 388 |

-continued

| Structure | IUPAC Name | Molecular weight | Mass Spectrum |
|---|---|---|---|
| 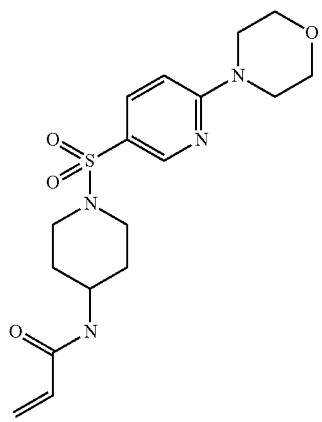 [SMILES: C=CC(=O)NC1CCN(S(=O)(=O)c2ccc(N3CCOCC3)nc2)CC1] | N-[1-(6-Morpholin-4-yl-pyridine-3-sulfonyl)-piperidin-4-yl]-acrylamide | 380 | Tr = 3.25, m/z (ES+) [M + H]+ = 381 |
| 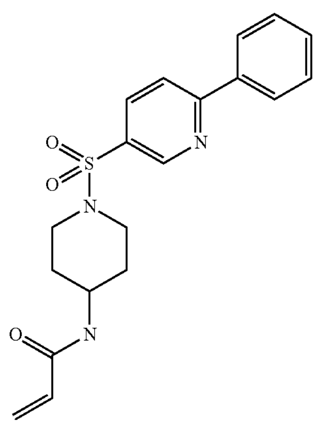 [SMILES: C=CC(=O)NC1CCN(S(=O)(=O)c2ccc(-c3ccccc3)nc2)CC1] | N-[1-(6-Phenyl-pyridine-3-sulfonyl)-piperidin-4-yl]-acrylamide | 371.46 | Tr = 3.94, m/z (ES+) [M + H]+ = 372 |
| 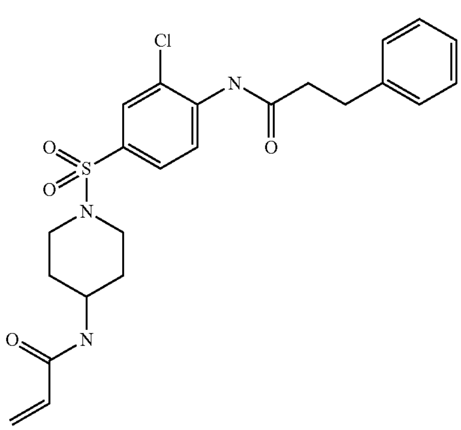 [SMILES: C=CC(=O)NC1CCN(S(=O)(=O)c2ccc(NC(=O)CCc3ccccc3)c(Cl)c2)CC1] | N-{1-[3-Chloro-4-(3-phenyl-propionylamino)-benzenesulfonyl]-piperidin-4-yl}-acrylamide | 476 | Tr = 4.49, m/z (ES+) [M + H]+ = 476 |

-continued

| Structure | IUPAC Name | Molecular weight | Mass Spectrum |
|---|---|---|---|
| 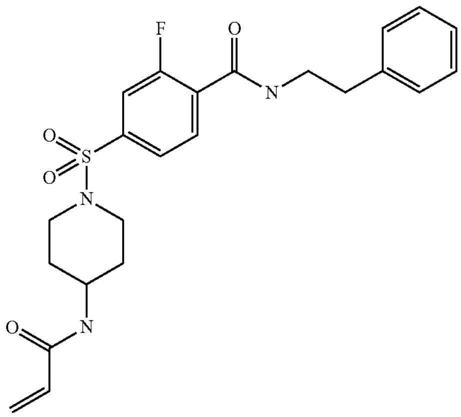 [SMILES: C=CC(=O)NC1CCN(S(=O)(=O)c2ccc(C(=O)NCCc3ccccc3)c(F)c2)CC1] | 4-(4-Acryloylamino-piperidine-1-sulfonyl)-2-fluoro-N-phenethyl-benzamide | 459.54 | Tr = 3.89, m/z (ES+) [M + H]+ = 460 |
| 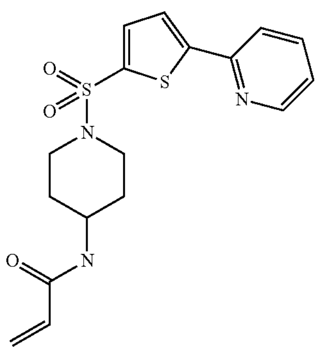 [SMILES: C=CC(=O)NC1CCN(S(=O)(=O)c2ccc(-c3ccccn3)s2)CC1] | N-[1-(5-Pyridin-2-yl-thiophene-2-sulfonyl)-piperidin-4-yl]-acrylamide | 377 | Tr = 3.62, m/z (ES+) [M + H]+ = 378 |
| 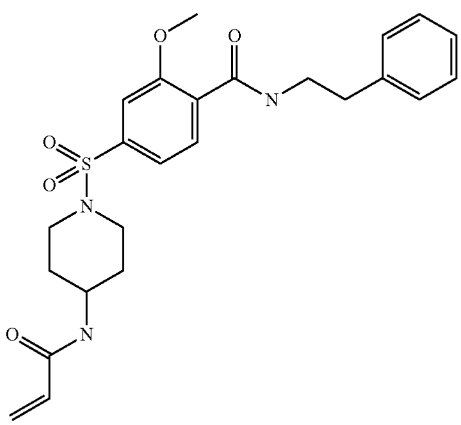 [SMILES: C=CC(=O)NC1CCN(S(=O)(=O)c2ccc(C(=O)NCCc3ccccc3)c(OC)c2)CC1] | 4-(4-Acryloylamino-piperidine-1-sulfonyl)-2-methoxy-N-phenethyl-benzamide | 471 | Tr = 3.98, m/z (ES+) [M + H]+ = 472 |
| 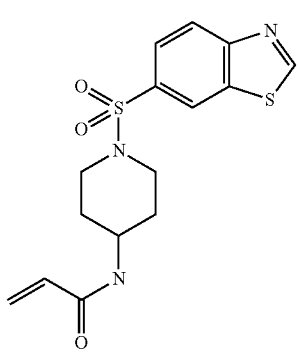 [SMILES: C=CC(=O)NC1CCN(S(=O)(=O)c2ccc3ncsc3c2)CC1] | N-[1-(Benzothiazole-6-sulfonyl)-piperidin-4-yl]-acrylamide | 351 | Tr = 3.31, m/z (ES+) [M + H]+ = 351 |

-continued

| Structure | IUPAC Name | Molecular weight | Mass Spectrum |
|---|---|---|---|
| 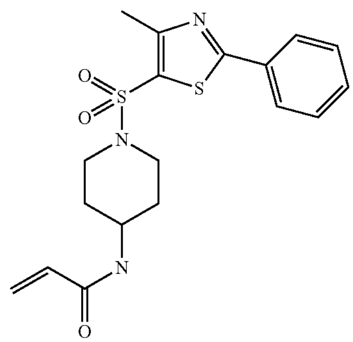 [SMILES: C=CC(=O)NC1CCN(S(=O)(=O)c2sc(-c3ccccc3)nc2C)CC1] | N-[1-(4-Methyl-2-phenyl-thiazole-5-sulfonyl)-piperidin-4-yl]-acrylamide | 391 | Tr = 4.29, m/z (ES+) [M + H]+ = 392 |
| 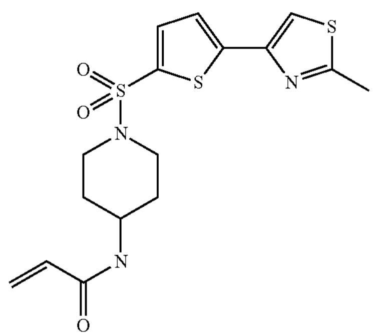 [SMILES: C=CC(=O)NC1CCN(S(=O)(=O)c2ccc(-c3csc(C)n3)s2)CC1] | N-{1-[5-(2-Methyl-thiazol-4-yl)-thiophene-2-sulfonyl]-piperidin-4-yl}-acrylamide | 397 | Tr = 3.85, m/z (ES+) [M + H]+ = 398 |
| 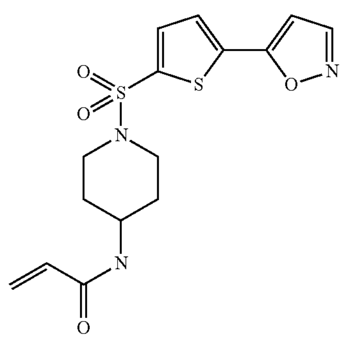 [SMILES: C=CC(=O)NC1CCN(S(=O)(=O)c2ccc(-c3ccno3)s2)CC1] | N-[1-(5-Isoxazol-5-yl-thiophene-2-sulfonyl)-piperidin-4-yl]-acrylamide | 367 | Tr = 3.60, m/z (ES+) [M + H]+ = 368 |
| 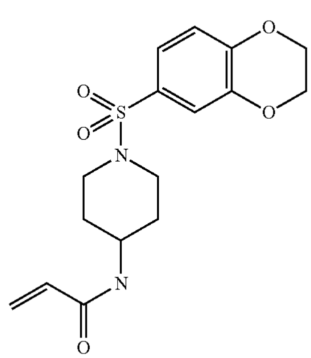 [SMILES: C=CC(=O)NC1CCN(S(=O)(=O)c2ccc3c(c2)OCCO3)CC1] | N-[1-(2,3-Dihydro-benzo[1,4]dioxine-6-sulfonyl)-piperidin-4-yl]-acrylamide | 352 | Tr = 3.51, m/z (ES+) [M + H]+ = 353 |

-continued

| Structure | IUPAC Name | Molecular weight | Mass Spectrum |
|---|---|---|---|
| 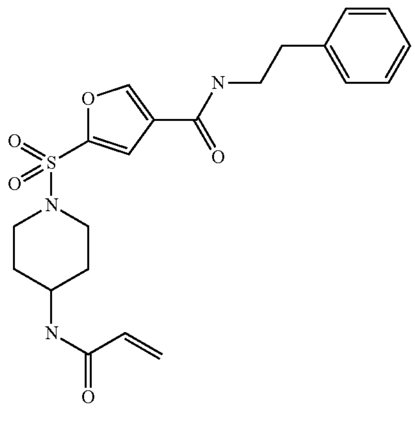 [SMILES: C=CC(=O)NC1CCN(S(=O)(=O)c2cc(C(=O)NCCc3ccccc3)co2)CC1] | 5-(4-Acryloylamino-piperidine-1-sulfonyl)-furan-3-carboxylic acid phenethyl-amide | 431 | Tr = 3.71, m/z (ES+) [M + H]+ = 432 |
| 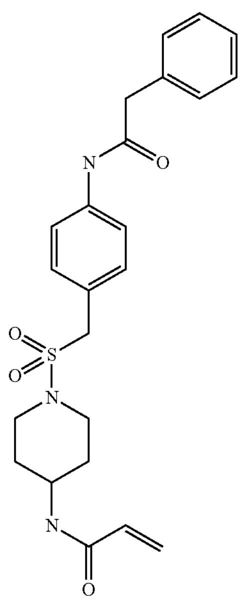 [SMILES: C=CC(=O)NC1CCN(S(=O)(=O)Cc2ccc(NC(=O)Cc3ccccc3)cc2)CC1] | N-[1-(4-Phenylacetylamino-phenylmethanesulfonyl)-piperidin-4-yl]-acrylamide | 441 | Tr = 3.60, m/z (ES+) [M + H]+ = 442 |
| 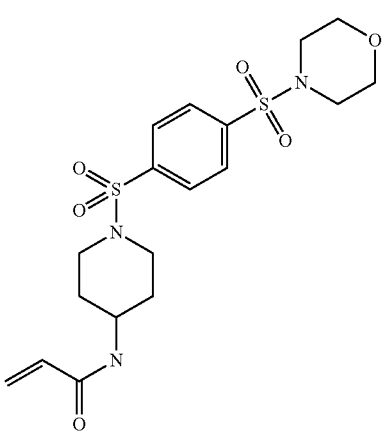 [SMILES: C=CC(=O)NC1CCN(S(=O)(=O)c2ccc(S(=O)(=O)N3CCOCC3)cc2)CC1] | N-{1-[4-(Morpholine-4-sulfonyl)-benzenesulfonyl]-piperidin-4-yl}-acrylamide | 443 | Tr = 3.45, m/z (ES+) [M + H]+ = 444 |

-continued

| Structure | IUPAC Name | Molecular weight | Mass Spectrum |
|---|---|---|---|
| 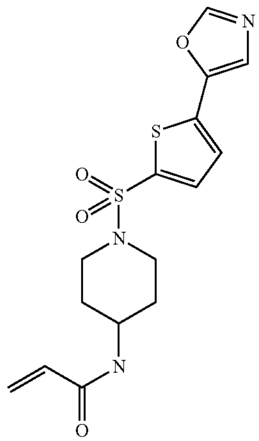 [SMILES: C=CC(=O)NC1CCN(S(=O)(=O)c2ccc(-c3cnco3)s2)CC1] | N-[1-(5-Oxazol-5-yl-thiophene-2-sulfonyl)-piperidin-4-yl]-acrylamide | 367 | Tr = 3.50, m/z (ES+) [M + H]+ = 368 |
| 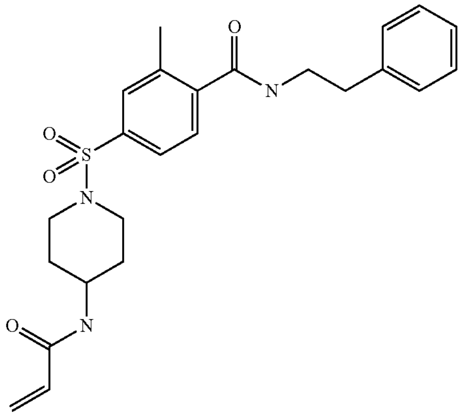 [SMILES: C=CC(=O)NC1CCN(S(=O)(=O)c2ccc(C(=O)NCCc3ccccc3)c(C)c2)CC1] | 4-(4-Acryloylamino-piperidine-1-sulfonyl)-2-methyl-N-phenethyl-benzamide | 455 | Tr = 3.85, m/z (ES+) [M + H]+ = 456 |
| 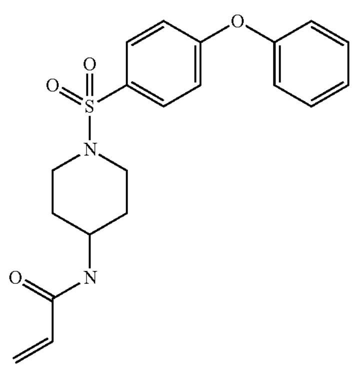 [SMILES: C=CC(=O)NC1CCN(S(=O)(=O)c2ccc(Oc3ccccc3)cc2)CC1] | N-[1-(4-Phenoxy-benzenesulfonyl)-piperidin-4-yl]-acrylamide | 386 | Tr = 4.19, m/z (ES+) [M + H]+ = 387 |
| 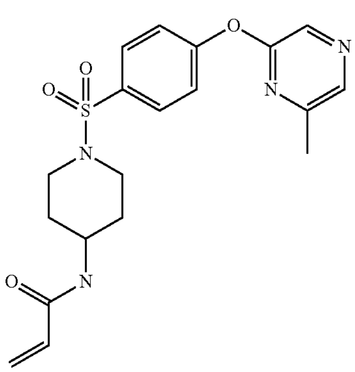 [SMILES: C=CC(=O)NC1CCN(S(=O)(=O)c2ccc(Oc3cncc(C)n3)cc2)CC1] | N-{1-[4-(6-Methyl-pyrazin-2-yloxy)-benzenesulfonyl]-piperidin-4-yl}-acrylamide | 402 | Tr = 3.54, m/z (ES+) [M + H]+ = 403 |

-continued

| Structure | IUPAC Name | Molecular weight | Mass Spectrum |
|---|---|---|---|
| 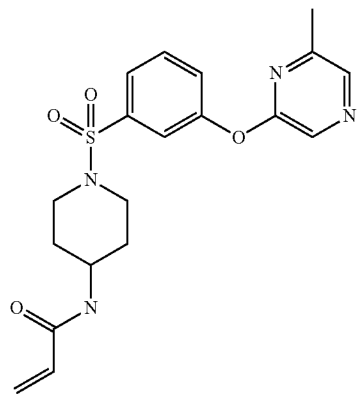 [SMILES: C=CC(=O)NC1CCN(S(=O)(=O)c2cccc(Oc3cncc(C)n3)c2)CC1] | N-{1-[3-(6-Methyl-pyrazin-2-yloxy)-benzenesulfonyl]-piperidin-4-yl}-acrylamide | 402 | Tr = 3.54, m/z (ES+) [M + H]+ = 403 |
| 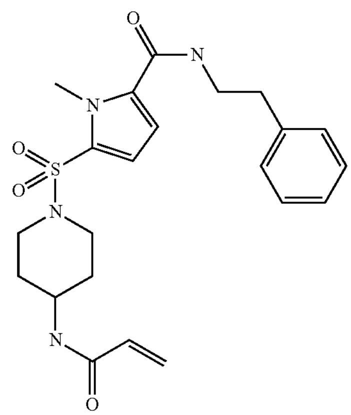 [SMILES: C=CC(=O)NC1CCN(S(=O)(=O)c2ccc(C(=O)NCCc3ccccc3)n2C)CC1] | 5-(4-Acryloylamino-piperidine-1-sulfonyl)-1-methyl-1H-pyrrole-2-carboxylic acid phenethyl-amide | 444 | Tr = 3.67, m/z (ES+) [M + H]+ = 445 |
| 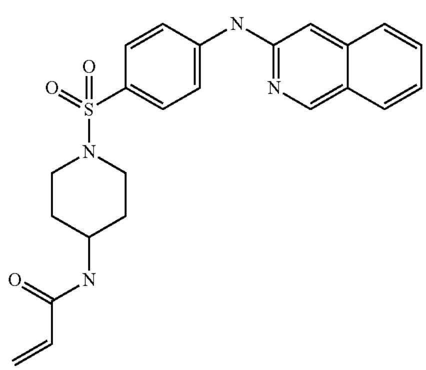 [SMILES: C=CC(=O)NC1CCN(S(=O)(=O)c2ccc(Nc3cc4ccccc4cn3)cc2)CC1] | N-{1-[4-(Isoquinolin-3-ylamino)-benzenesulfonyl]-piperidin-4-yl}-acrylamide | 436 | Tr = 3.69, m/z (ES+) [M + H]+ = 437 |
| 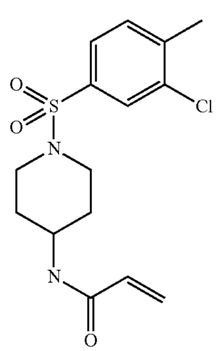 [SMILES: C=CC(=O)NC1CCN(S(=O)(=O)c2ccc(C)c(Cl)c2)CC1] | N-[1-(3-Chloro-4-methyl-benzenesulfonyl)-piperidin-4-yl]-acrylamide | 342 | Tr = 3.86, m/z (ES+) [M + H]+ = 343 |

-continued

| Structure | IUPAC Name | Molecular weight | Mass Spectrum |
|---|---|---|---|
| 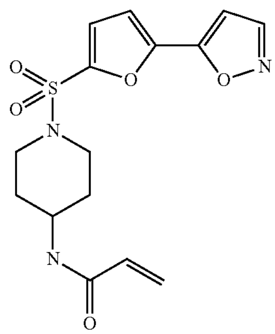 [SMILES: C=CC(=O)NC1CCN(S(=O)(=O)c2ccc(-c3ccno3)o2)CC1] | N-[1-(5-Isoxazol-5-yl-furan-2-sulfonyl)-piperidin-4-yl]-acrylamide | 351 | Tr = 3.51 m/z (ES+) [M + H]+ = 352 |
| 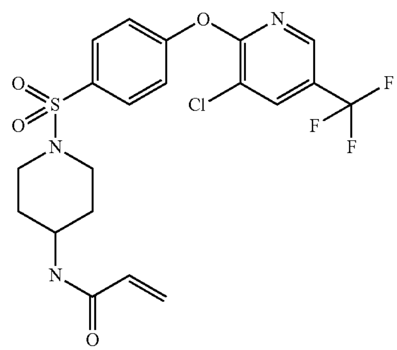 [SMILES: C=CC(=O)NC1CCN(S(=O)(=O)c2ccc(Oc3ncc(C(F)(F)F)cc3Cl)cc2)CC1] | N-{1-[4-(3-Chloro-5-trifluoromethyl-pyridin-2-yloxy)-benzenesulfonyl]-piperidin-4-yl}-acrylamide | 489 | Tr = 4.43 m/z (ES+) [M + H]+ = 490 |
| 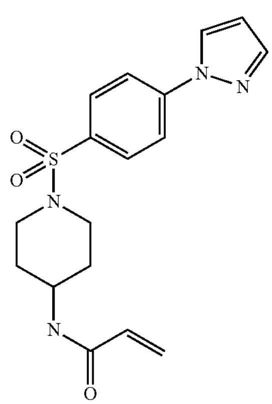 [SMILES: C=CC(=O)NC1CCN(S(=O)(=O)c2ccc(-n3cccn3)cc2)CC1] | N-[1-(4-Pyrazol-1-yl-benzenesulfonyl)-piperidin-4-yl]-acrylamide | 360 | Tr = 3.45 m/z (ES+) [M + H]+ = 361 |
| 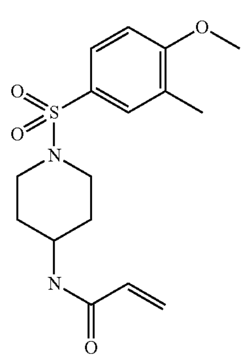 [SMILES: C=CC(=O)NC1CCN(S(=O)(=O)c2ccc(OC)c(C)c2)CC1] | N-[1-(4-Methoxy-3-methyl-benzenesulfonyl)-piperidin-4-yl]-acrylamide | 338 | Tr = 3.66 m/z (ES+) [M + H]+ = 339 |

-continued

| Structure | IUPAC Name | Molecular weight | Mass Spectrum |
|---|---|---|---|
| 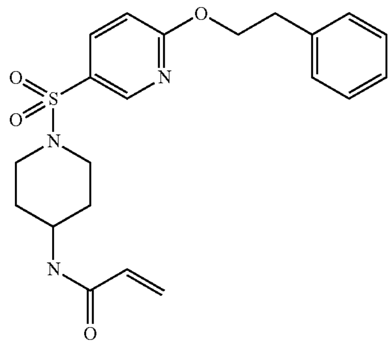 [SMILES: C=CC(=O)NC1CCN(S(=O)(=O)c2ccc(OCCc3ccccc3)nc2)CC1] | N-[1-(6-Phenethyloxy-pyridine-3-sulfonyl)-piperidin-4-yl]-acrylamide | 415 | Tr = 4.35 m/z (ES+) [M + H]+ = 416 |
| 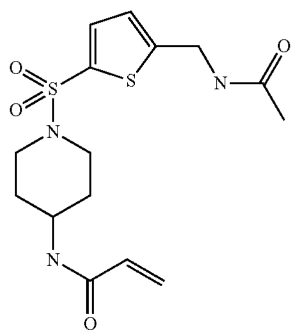 [SMILES: C=CC(=O)NC1CCN(S(=O)(=O)c2ccc(CNC(C)=O)s2)CC1] | N-{1-[5-(Acetylamino-methyl)-thiophene-2-sulfonyl]-piperidin-4-yl}-acrylamide | 371 | Tr = 2.83 m/z (ES+) [M + H]+ = 372 |
| 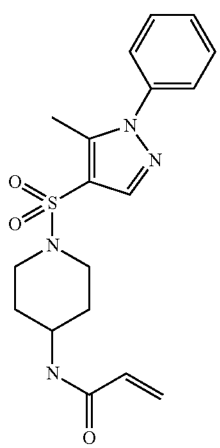 [SMILES: C=CC(=O)NC1CCN(S(=O)(=O)c2cnn(-c3ccccc3)c2C)CC1] | N-[1-(5-Methyl-1-phenyl-1H-pyrazole-4-sulfonyl)-piperidin-4-yl]-acrylamide | 374 | Tr = 3.69 m/z (ES+) [M + H]+ = 375 |
| 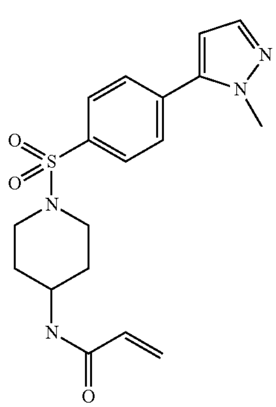 [SMILES: C=CC(=O)NC1CCN(S(=O)(=O)c2ccc(-c3ccnn3C)cc2)CC1] | N-{1-[4-(2-Methyl-2H-pyrazol-3-yl)-benzenesulfonyl]-piperidin-4-yl}-acrylamide | 374 | Tr = 3.53 m/z (ES+) [M + H]+ = 375 |

-continued

| Structure | IUPAC Name | Molecular weight | Mass Spectrum |
|---|---|---|---|
| 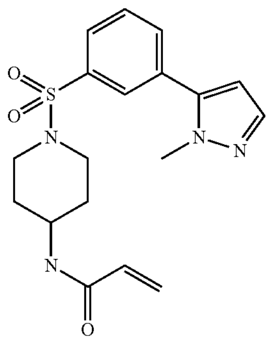 [SMILES: C=CC(=O)NC1CCN(S(=O)(=O)c2cccc(-c3ccnn3C)c2)CC1] | N-{1-[3-(2-Methyl-2H-pyrazol-3-yl)-benzenesulfonyl]-piperidin-4-yl}-acrylamide | 374 | Tr = 3.46 m/z (ES+) [M + H]+ = 375 |
| 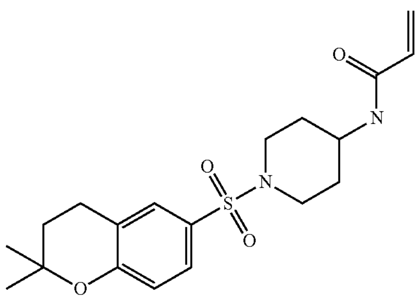 [SMILES: C=CC(=O)NC1CCN(S(=O)(=O)c2ccc3c(c2)CCC(C)(C)O3)CC1] | N-[1-(2,2-Dimethyl-chroman-6-sulfonyl)-piperidin-4-yl]-acrylamide | 378 | Tr = 4.14 m/z (ES+) [M + H]+ = 379 |
| 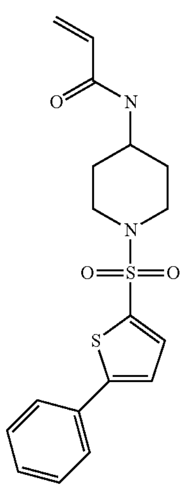 [SMILES: C=CC(=O)NC1CCN(S(=O)(=O)c2ccc(-c3ccccc3)s2)CC1] | N-[1-(5-Phenyl-thiophene-2-sulfonyl)-piperidin-4-yl]-acrylamide | 376 | Tr = 4.16 m/z (ES+) [M + H]+ = 377 |
| 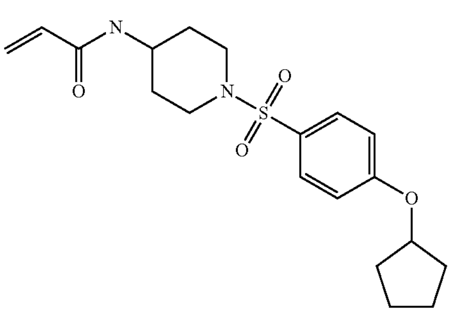 [SMILES: C=CC(=O)NC1CCN(S(=O)(=O)c2ccc(OC3CCCC3)cc2)CC1] | N-[1-(4-Cyclopentyloxy-benzenesulfonyl)-piperidin-4-yl]-acrylamide | 378 | Tr = 4.21 m/z (ES+) [M + H]+ = 379 |

-continued

| Structure | IUPAC Name | Molecular weight | Mass Spectrum |
|---|---|---|---|
| 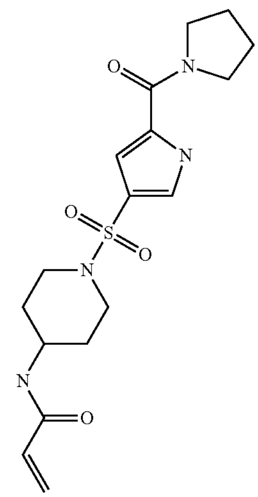 [SMILES: C=CC(=O)NC1CCN(S(=O)(=O)c2c[nH]c(C(=O)N3CCCC3)c2)CC1] | N-{1-[5-(Pyrrolidine-1-carbonyl)-1H-pyrrole-3-sulfonyl]-piperidin-4-yl}-acrylamide | 380 | Tr = 2.99 m/z (ES+) [M + H]+ = 381 |
| 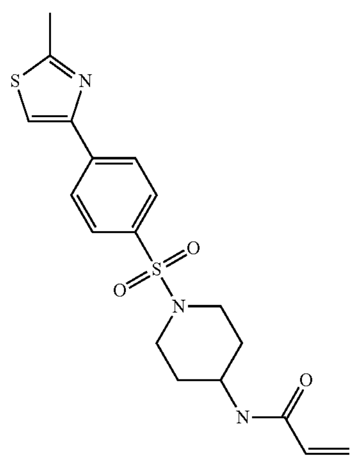 [SMILES: C=CC(=O)NC1CCN(S(=O)(=O)c2ccc(-c3csc(C)n3)cc2)CC1] | N-{1-[4-(2-Methyl thiazol-4-yl)-benzenesulfonyl]-piperidin-4-yl}-acrylamide | 391 | Tr = 3.75 m/z (ES+) [M + H]+ = 392 |
| 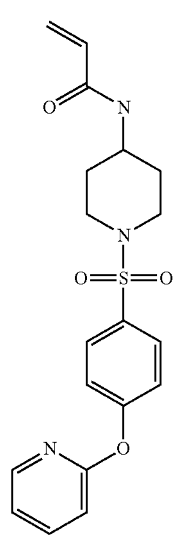 [SMILES: C=CC(=O)NC1CCN(S(=O)(=O)c2ccc(Oc3ccccn3)cc2)CC1] | N-{1-[4-(Pyridin-2-yloxy)-benzenesulfonyl]-piperidin-4-yl}-acrylamide | 387 | Tr = 3.71 m/z (ES+) [M + H]+ = 388 |

-continued

| Structure | IUPAC Name | Molecular weight | Mass Spectrum |
|---|---|---|---|
| 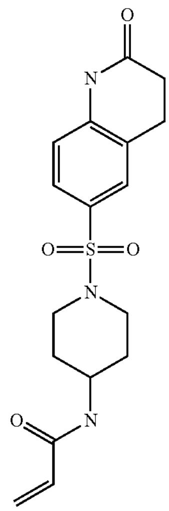 [SMILES: C=CC(=O)NC1CCN(S(=O)(=O)c2ccc3c(c2)CCC(=O)N3)CC1] | N-[1-(2-Oxo-1,2,3,4-tetrahydro-quinoline-6-sulfonyl)-piperidin-4-yl]-acrylamide | 363 | Tr = 3.02 m/z (ES+) [M + H]+ = 364 |

Biology Example 1

The fluorescent screening assay for human TG2 was performed as described herein: Assay conditions were 20 nM TG2, 8 μM N,N-dimethylated Casein (NMC) and 16 μM K×D (used for all transglutaminase assays) in 25 mM Hepes, pH 7.4, 250 mM NaCl, 2 mM $MgCl_2$, 0.5 mM $CaCl_2$, 0.2 mM DTT, 0.05% Pluronic F-127 at 37° C. A time point was taken with a microplate reader (Safire or Ultra, Tecan; ex: 350 nm, em: 535 nm) every 3 minutes for up to 2 hours and the initial linear reaction progress was used to determine the reaction velocity as a measure for enzyme activity. Assay conditions were identical for human TG6 and similar for human TG1 and mouse TG2 apart from enzyme concentration (mTG2 at 5 nM; TG1 at 10 nM) and $CaCl_2$ concentration (0.2 mM for mTG2; 0.05 mM for TG1). Factor XIIIa was activated using 0.1 μg/μl thrombin (Sigma) in 35 mM Tris pH 8.0 for 20 min at 30° C. and the transamidation reaction was performed with 20 nM Factor XIIIa in 50 mM Tris pH 8.0, 1.25 mM $CaCl_2$, 0.05% Pluronic, 0.2 mM DTT. TG3 was activated with 0.02 μg/μl thrombin under the same conditions as Factor XIIIa and assay conditions were 10 nM TG3 in 50 mM Hepes, pH 8, 20 mM $CaCl_2$, 0.2 mM DTT, 0.05% Pluronic F-127.

Certain compounds described herein were tested and found to have $IC_{50}$ value less than 100 nanomolar. Certain compounds described herein were tested and found to have an $IC_{50}$ value from 100 nanomolar to 1 micromolar. Certain compounds described herein were tested and found to have an $IC_{50}$ value from 1 to 25 micromolar.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula II

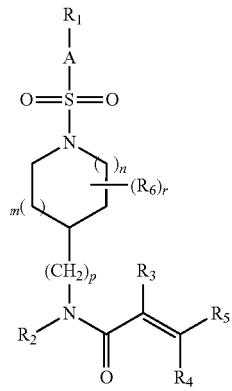

Formula II or a pharmaceutically acceptable salt thereof, wherein
A is optionally substituted phenylene;
$R^1$ is chosen from —$(CH_2)_x CONR^c R^d$, wherein
  $R^c$ is independently chosen from H and optionally substituted $C_1$-$C_6$ alkyl;
  $R^d$ is chosen from H, optionally substituted $C_1$-$C_6$ alkyl, optionally substituted cycloalkyl, optionally substituted aryl, optionally substituted aralkyl, optionally substituted heterocycloalkyl, and optionally substituted heteroaryl;
  x is 0, 1, or 2;
$R_2$ is chosen from H and optionally substituted alkyl;
$R_3$, $R_4$, and $R_5$ are H;
p is chosen from 0, 1, 2, and 3;
m is 1, and n is 1,
for each occurrence, $R_6$ is independently chosen from optionally substituted lower alkyl and
r is chosen from 0, 1, 2, 3, and 4.

2. The compound of claim 1, or a pharmaceutically acceptable salt thereof, wherein r is 0 or 1.

3. The compound of claim 1, or a pharmaceutically acceptable salt thereof, wherein for each occurrence, $R_6$ is independently chosen from methyl and hydroxymethyl.

4. The compound of claim 1, or a pharmaceutically acceptable salt thereof, wherein p is 1.

5. The compound of claim 1, or a pharmaceutically acceptable salt thereof, wherein p is 2.

6. The compound of claim 1, or a pharmaceutically acceptable salt thereof, wherein p is 3.

7. The compound of claim 1, or a pharmaceutically acceptable salt thereof, wherein A is phenylene substituted with one or more groups chosen from lower alkyl, lower alkoxy, and halo.

8. The compound of claim 7, or a pharmaceutically acceptable salt thereof, wherein A is phenylene.

9. The compound of claim 8, or a pharmaceutically acceptable salt thereof, wherein A is para-phenylene.

10. The compound of claim 1, or a pharmaceutically acceptable salt thereof, wherein A is chosen from 2-oxo-1,2,3,4-tetrahydroquinolindiyl, chromanediyl, and indolinediyl, each of which is optionally substituted.

11. The compound of claim 1, or a pharmaceutically acceptable salt thereof, wherein $R^c$ is H or methyl.

12. The compound of claim 11, or a pharmaceutically acceptable salt thereof, wherein $R^d$ is cyclopropyl, cyclohexyl, indanyl, cyclopropylmethyl, cyclohexylethyl, benzyl, phenylethyl, naphthalenylmethyl, naphthalenylethyl, quinolinylethyl, dihydrobenzofuranylethyl, chromanylethyl, benzo[1,3]dioxolylethyl, phenylpropyl, biphenylethyl, piperidylethyl, pyranylethyl, morpholinylethyl, or benzofuranyl, each of which is optionally substituted.

13. The compound of claim 1, or a pharmaceutically acceptable salt thereof, wherein $R_2$ is H.

14. A pharmaceutical composition comprising a compound of claim 1, or a pharmaceutically acceptable salt thereof, and a pharmaceutically acceptable excipient.

* * * * *

UNITED STATES PATENT AND TRADEMARK OFFICE
CERTIFICATE OF CORRECTION

Page 1 of 1

PATENT NO. : 8,889,716 B2
APPLICATION NO. : 13/466018
DATED : November 18, 2014
INVENTOR(S) : Michael Prime et al.

It is certified that error appears in the above-identified patent and that said Letters Patent is hereby corrected as shown below:

Title Page, item (75),

Please delete:

"Douglas MacDonald"

And substitute the following:

Douglas Macdonald

Signed and Sealed this
Seventeenth Day of March, 2015

Michelle K. Lee
*Director of the United States Patent and Trademark Office*